US012673933B2

(12) United States Patent
Li et al.

(10) Patent No.: US 12,673,933 B2
(45) Date of Patent: Jul. 7, 2026

(54) AMINOPYRAZINE COMPOUNDS AS HPK1 INHIBITOR AND THE USE THEREOF

(71) Applicant: BEIGENE, LTD., Camana Bay (KY)

(72) Inventors: Jing Li, Beijing (CN); Zhiwei Wang, Beijing (CN); Sanjia Xu, Beijing (CN); Hanzi Sun, Beijing (CN); Ye Liu, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 1173 days.

(21) Appl. No.: 17/636,473

(22) PCT Filed: Aug. 20, 2020

(86) PCT No.: PCT/CN2020/110171

§ 371 (c)(1),
(2) Date: Feb. 18, 2022

(87) PCT Pub. No.: WO2021/032148

PCT Pub. Date: Feb. 25, 2021

(65) Prior Publication Data

US 2022/0289712 A1 Sep. 15, 2022

(30) Foreign Application Priority Data

| | | |
|---|---|---|
| Aug. 21, 2019 | (WO) | PCT/CN2019/101820 |
| Sep. 25, 2019 | (WO) | PCT/CN2019/107971 |
| Dec. 3, 2019 | (WO) | PCT/CN2019/122733 |
| Jul. 10, 2020 | (WO) | PCT/CN2020/101287 |

(51) Int. Cl.

| | |
|---|---|
| ***C07D 401/14*** | (2006.01) |
| ***C07D 401/04*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |
| ***C07D 491/048*** | (2006.01) |
| ***C07D 491/052*** | (2006.01) |
| ***C07D 495/04*** | (2006.01) |
| ***C07D 498/04*** | (2006.01) |

(52) U.S. Cl.

CPC ......... *C07D 401/14* (2013.01); *C07D 401/04* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 491/048* (2013.01); *C07D 491/052* (2013.01); *C07D 495/04* (2013.01); *C07D 498/04* (2013.01); *C07B 2200/05* (2013.01)

(58) Field of Classification Search

CPC .. C07D 401/14; C07D 405/14; C07D 409/14; C07D 413/14; C07D 417/14; C07D 471/04; C07D 487/04; C07D 491/048; C07D 491/052; C07D 495/04; C07D 498/04; C07B 2200/05

USPC ..................................................... 514/210.21

See application file for complete search history.

(56) References Cited

U.S. PATENT DOCUMENTS

| | | | |
|---|---|---|---|
| 5,942,532 | A | 8/1999 | Ohemeng |
| 10,239,873 | B2 | 3/2019 | Choi et al. |
| 11,566,003 | B2 | 1/2023 | Chan |
| 2006/0122185 | A1 | 6/2006 | Green et al. |
| 2006/0258662 | A1 | 11/2006 | Binch et al. |
| 2007/0087988 | A1 | 4/2007 | Sawasdikosol et al. |
| 2011/0081364 | A1 | 4/2011 | Binch et al. |
| 2016/0214996 | A1 | 7/2016 | Song |
| 2016/0297815 | A1 | 10/2016 | Choi et al. |

(Continued)

FOREIGN PATENT DOCUMENTS

| | | | |
|---|---|---|---|
| CN | 101098872 | A | 1/2008 |
| CN | 101851237 | A | 10/2010 |

(Continued)

OTHER PUBLICATIONS

Alzabin, S. et al., "Hematopoietic progenitor kinase 1 is a critical component of prostaglandin E2-mediated suppression of the anti-tumor immune response," Cancer Immunol Immunother, Mar. 2010, 59(3):419-429.

(Continued)

*Primary Examiner* — Kortney L. Klinkel
*Assistant Examiner* — Grace Ching Hsu
(74) *Attorney, Agent, or Firm* — McNeill PLLC

(57) ABSTRACT

Disclosed herein is an aminopyrazine compound of Formula (I), or a stereoisomer thereof, or a pharmaceutically acceptable salt thereof, and pharmaceutical compositions comprising thereof. Also disclosed is a method of treating HPK1 related disorders or diseases by using the compound disclosed herein.

(I)

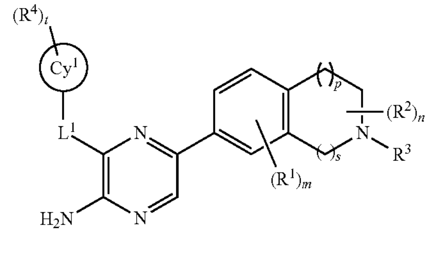

18 Claims, No Drawings

(56) References Cited

U.S. PATENT DOCUMENTS

| | | | |
|---|---|---|---|
| 2018/0072720 A1 | 3/2018 | Vechorkin et al. | |
| 2018/0298009 A1 | 10/2018 | Ford | |
| 2019/0106419 A1 | 4/2019 | Vechorkin et al. | |
| 2021/0380581 A1 | 12/2021 | Vechorkin et al. | |
| 2022/0331435 A1 | 10/2022 | Liao | |

FOREIGN PATENT DOCUMENTS

| | | | | |
|---|---|---|---|---|
| CN | 106336413 A | 1/2017 | | |
| CN | 106432246 A | 2/2017 | | |
| CN | 108440532 | 8/2018 | | |
| CN | 109923114 A | 6/2019 | | |
| CN | 112654609 | 4/2021 | | |
| JP | 2012012332 A | 1/2012 | | |
| WO | WO-2005028475 A2 | 3/2005 | | |
| WO | 2006015123 A1 | 2/2006 | | |
| WO | WO-2006015124 A2 | 2/2006 | | |
| WO | WO-2006058074 A1 | 6/2006 | | |
| WO | WO-2008124849 A2 | 10/2008 | | |
| WO | WO-2010049173 A1 | 5/2010 | | |
| WO | 2011149950 A2 | 12/2011 | | |
| WO | WO-2014006554 A1 | 1/2014 | | |
| WO | WO-2014085795 A1 | 6/2014 | | |
| WO | WO-2014093383 A1 | 6/2014 | | |
| WO | 2016000615 | 1/2016 | | |
| WO | WO-2016164641 A1 | 10/2016 | | |
| WO | WO-2016205942 A1 | 12/2016 | | |
| WO | WO-2018049152 A1 | 3/2018 | | |
| WO | WO-2018049191 A1 | 3/2018 | | |
| WO | WO-2018049200 A1 | 3/2018 | | |
| WO | WO-2018049214 A1 | 3/2018 | | |
| WO | WO-2018167147 A1 | 9/2018 | | |
| WO | 2018183965 | 10/2018 | | |
| WO | WO-2018183956 A1 | 10/2018 | | |
| WO | WO-2019167000 A1 | 9/2019 | | |
| WO | WO-2019227059 A1 * | 11/2019 | .......... | C07D 401/14 |
| WO | WO-2019238067 A1 | 12/2019 | | |
| WO | WO-2020103896 A1 | 5/2020 | | |
| WO | 2020227325 A1 | 11/2020 | | |
| WO | WO-2021000925 A1 | 1/2021 | | |
| WO | WO-2021013083 A1 | 1/2021 | | |
| WO | WO-2021032148 A1 | 2/2021 | | |
| WO | 2021057872 A1 | 4/2021 | | |

OTHER PUBLICATIONS

Alzabin, S. et al., "Hematopoietic progenitor kinase 1 is a negative regulator of dendritic cell activation," J Immunol, May 2009, 182(10):6187-6194.

Batliwalla, F. M. et al., "Microarray Analyses of Peripheral Blood Cells Identifies Unique Gene Expression Signature in Psoriatic Arthritis," Molecular Medicine, vol. 11, No. 1-12, Jan.-Dec. 2005, pp. 21-29.

Ikegami, R. et al., "The Expression of Prostaglandin E Receptors EP2 and EP4 and Their Different Regulation by Lipopolysaccharide in C3H/HeN Peritoneal Macrophages," J Immunol, Apr. 2001, vol. 166, No. 7, pp. 4689-4696.

International Search Report and Written Opinion for International Application No. PCT/CN2019/090922, mailed Sep. 19, 2019, 12 pages.

International Search Report and Written Opinion for International Application No. PCT/CN2019/119896, mailed Feb. 26, 2020, 8 pages.

International Search Report and Written Opinion for International Application No. PCT/CN2020/100037, mailed Oct. 10, 2020, 15 pages.

International Search Report and Written Opinion for International Application No. PCT/CN2020/102647, mailed Sep. 22, 2020, 9 pages.

International Search Report and Written Opinion for International Application No. PCT/CN2020/110171, mailed Nov. 23, 2020, 12 pages.

Liou, J. et al., "HPK1 is activated by lymphocyte antigen receptors and negatively regulates AP-1," Immunity, Apr. 2000, 12(4):399-408.

Sawasdikosol, S. et al., "HPK1 as a novel target for cancer immunotherapy," Immunol Res., Dec. 2012, vol. 54, No. 1-3, pp. 262-265.

Wang, W. et al., "Activation of the Hematopoietic Progenitor Kinase-1 (HPK1)-dependent, Stress-activated c-Jun N-terminal Kinase (JNK) Pathway by Transforming Growth Factor β (TGF-β)-activated Kinase (TAK1), a Kinase Mediator of TGF β Signal Transduction," J. Biol. Chem., Sep. 1997, vol. 272, No. 36, pp. 22771-22775.

Zhou, G. et al., "Hematopoietic Progenitor Kinase 1 Is a Component of Transforming Growth Factor β-induced c-Jun N-terminal Kinase Signaling Cascade," J. Biol. Chem., May 1999, vol. 274, No. 19, pp. 13133-13138.

"Find ETDs Home >> Thesis Resources Find ETDs" Online: "https://ndltd.org/thesis-resources/find-etds/", 7 pages, Accessed Jan. 31, 2023.

Cannon, J. G. et al., "Analog Design," Chapter Nineteen in Burger's Medicinal Chemistry and Drug Discovery, 5th Edition, vol. I: Principles and Practice, Wiley-Interscience, 783-802, 1995.

Dorwald F. A., "Side Reactions in Organic Synthesis," Wiley: VCH, Weinheim p. IX of Preface, 37 pages, 2005.

Irwin, J. J. et al., "ZINC—A Free Database of Commercially Available Compounds for Virtual Screening," J. Chem. Inf. Model., 45:177-182, 2005.

Kelly, A. H. et al., "Azaindoles I. preparation of 7-azaindoles by thermal indolization of 2-pyridylhydrazones," Canadian Journal of Chemistry, 44:2455-2459, 1966.

Kim, S. et al., "PubChem in 2021: new data content and improved web interfaces," Nucleic Acids Research, 49:D1388-D1395, 2021.

Lochmuller, C. H. et al., "Chromatographic Resolution of Enantiomers," Journal of Chromatography, 113:283-302, 1975.

Paul A Bartlett and Michael Entzeroth, "Exploiting Chemical Diversity for Drug Discovery", The Royal Society of Chemistry, pp. 113-118, 2006.

STN Registry/Zregistry (CAS Registrysm), 2 pages, Sep. 2016.

US Final Office Action for U.S. Appl. No. 17/623,732, dated Apr. 17, 2025, (15 pages).

US Non-Final Office Action for U.S. Appl. No. 17/623,732, dated Jan. 10, 2025, (31 pages).

US Non-Final Office Action for U.S. Appl. No. 17/627,885, dated Mar. 6, 2025, (29 pages).

Venkatesh, S. et al., "Role of the development scientist in compound lead selection and optimization," Journal of Pharmaceutical Sciences, 89(2):145-154, 2000.

Wang, Y. et al., "Pharmacological inhibition of hematopoietic progenitor kinase 1 positively regulates T-cell function," PLOS One, 15(12):1-19, 2020.

Cao Gao et al., "Suzuki coupling reaction catalyzed by aniline-β-imine/PdCI2" p. 342,344.

* cited by examiner

AMINOPYRAZINE COMPOUNDS AS HPK1 INHIBITOR AND THE USE THEREOF

CROSS-REFERENCE TO RELATED APPLICATIONS

This application is a U.S. National Stage Application under 35 U.S.C. § 371 of International Application No. PCT/CN2020/110171, filed Aug. 20, 2020, which claims priority to Patent Application Nos. PCT/CN2020/101287 (CN), filed on Jul. 10, 2020, PCT/CN2019/122733 (CN), filed on Dec. 3, 2019, PCT/CN2019/107971 (CN), filed on Sep. 25, 2019, and PCT/CN2019/101820 (CN), filed on Aug. 21, 2019.

FIELD OF THE INVENTION

The disclosure herein provides aminopyrazine compounds as well as their compositions and methods of use. The compounds disclosed herein modulate, e.g., inhibit, hematopoietic progenitor kinase 1 (HPK1) activity and are useful in the treatment of various diseases including cancer.

BACKGROUND OF THE INVENTION

HPK1 regulates diverse functions of various immune cells and its kinase activity has been shown to be induced upon activation of T cell receptors (TCR) [Liou J., et al., *Immunity,* 2000. 12 (4): pp. 399-408], B cell receptors (BCR) [Liou J., et al., *Immunity,* 2000. 12 (4): pp. 399-408], transforming growth factor receptor (TGF-βR) [Wang, W., et al., *J Biol Chem,* 1997. 272 (36): pp. 22771-5; Zhou, G., et al., *J Biol Chem,* 1999. 274 (19): pp. 13133-8], and Gs-coupled PGE2 receptors (EP2 and EP4) [Ikegami, R., et al., *J Immunol,* 2001. 166 (7): pp. 4689-96]. Overexpression of HPK1 suppresses TCR-induced activation of AP-1-dependent gene transcription in a kinase-dependent manner, suggesting that HPK1 is required to inhibit the Erk MAPK pathway [Liou J., et al., *Immunity,* 2000. 12 (4): pp. 399-408] and this blockage is thought to be the inhibitory mechanism that negatively regulates TCR-induced IL-2 gene transcription [S. Sawasdikosol., et al., *Immunol Res,* 2012. 54: pp. 262-265].

In vitro HPK1−/− T cells have a lower TCR activation threshold, proliferate robustly, produce enhanced amounts of Th1 cytokines, the HPK1−/− mice experience more severe autoimmune symptoms [S. Sawasdikosol., et al., *Immunol Res,* 2012. 54: pp. 262-265]. In humans, HPK1 was downregulated in peripheral blood mononuclear cells of psoriatic arthritis patients or T cells of systemic lupus erythematosus (SLE) patients [Batliwalla F. M., et al., *Mol Med,* 2005. 11 (1-12): pp. 21-9], which indicated that attenuation of HPK1 activity may contribute to autoimmunity in patients. Furthermore, HPK1 may also control anti-tumor immunity via T cell-dependent mechanisms. In the PGE2-producing Lewis lung carcinoma tumor model, the tumors developed more slowly in HPK1 knockout mice as compared to wild-type mice [US patent application No. 2007/0087988]. HPK1 deficient T cells were more effective in controlling tumor growth and metastasis than wild-type T cells [Alzabin, S., et al., *Cancer Immunol Immunother,* 2010. 59 (3): pp. 419-29]. Similarly, BMDCs from HPK1 knockout mice were more efficient to mount a T cell response to eradicate Lewis lung carcinoma as compared to wild-type BMDCs [Alzabin, S., et al., *J Immunol,* 2009. 182 (10): pp. 6187-94]. In all, HPK1 may be a good target for enhancing antitumor immunity.

As HPK1 modulators, WO2016205942 discloses benzoimidazoles, WO2018049152A1 discloses pyrazolopyrmidines, WO2018049191A1 discloses pyrazolopyridones, and WO2008124849, WO2018049200A1 and WO2018049214A1 disclose pyrazolopyridines.

However, there is a need to provide new HPK1 kinase inhibitors useful in treating cancer.

SUMMARY OF THE INVENTION

In the first aspect, disclosed herein are aminopyrazine compounds of Formula (I), and the methods of use. The first embodiment comprises the following aspects:

Aspect 1: A compound of Formula (I)

(I)

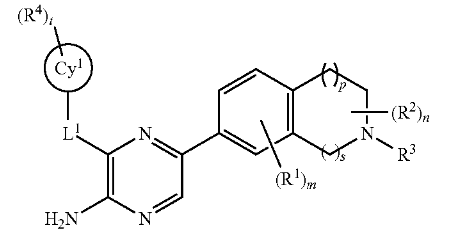

or a pharmaceutically acceptable salt thereof, or a stereoisomer thereof, wherein $Cy^1$ is cycloalkyl, aryl, monocyclic heterocyclyl or monocyclic heteroaryl or bicyclic fused heteroaryl or bicyclic fused heterocyclyl;

$L^1$ is selected from a single bond, alkylene (preferably —$CR^aR^b$—), —O—, —$NR^a$—, —S—, —S(O)—, —$S(O)_2$—, -cycloalkylene, $*^1$—O-alkylene-$**^1$ (preferably $*^1$—O—$CR^aR^b$—$**^1$) $*^1$-alkylene-O—$**^1$ (preferably $*^1$—$CR^aR^b$—O—$**^1$), $*^1$—$NR^c$-alkylene-$**^1$ (preferably $*^1$—$NR^c$—$CR^aR^b$—$**^1$) $*^1$-alkylene-$NR^c$—$**^1$ (preferably $*^1$—$CR^aR^b$—$NR^c$—$**^1$), $*^1$—$NR^cC(O)$—$**^1$, $*^1$—$C(O)NR^c$—$**^1$, alkenylene, or alkynylene; wherein $*^1$ refers to the position attached to the $Cy^1$ moiety, and $**^1$ refers to the position attached to the aminopyrazine moiety;

$R^1$, $R^2$, or $R^4$ at each of their occurrences, are independently hydrogen, halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^a$, —$SO_2R^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one $R^d$;

$R^3$ is hydrogen, halogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with at least one $R^d$;

$R^a$, $R^b$, and $R^c$ are each independently hydrogen, deuterium, halogen, —$C_{1-8}$alkyl, —$C_{2-8}$alkenyl, —$C_{2-8}$alkynyl, cycloalkyl, heterocyclyl, aryl, or heteroaryl; each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent $R^e$; or ($R^a$ and $R^b$), ($R^b$ and $R^c$), or ($R^c$ and $R^a$), together with the atom(s) to which they are attached, form a 3- to 12-membered ring, said ring comprising 0, 1 or 2 additional heteroatom(s) independently selected from nitrogen, oxygen or optionally oxidized sulfur as ring member(s), said ring is optionally substituted with at least one substituent $R^e$;

$R^d$ and $R^e$ are each independently halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^f$, —$SO_2R^f$, —$SO_2NR^fR^g$, —$COR^f$, —$CO_2R^f$, —$CONR^fR^g$, —C(=$NR^f$)$NR^gR^h$, —$NR^fR^g$, —$NR^fCOR^g$, —$NR^fCONR^gR^h$, —$NR^fCO_2R^f$, —$NR^f$-$SONR^fR^g$, —$NR^fSO_2NR^gR^h$ or —$NR^fSO_2R^g$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent selected from halogen, —$C_{1-8}$alkyl, —$OR^i$, —$NR^iR^j$, —CO—$NR^iR^j$, cycloalkyl, heterocyclyl, aryl, or heteroaryl;

$R^f$, $R^g$, $R^h$, $R^i$, and $R^j$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl;

m, n and t are each independently 0, 1, 2, 3 or 4; and p and s are each independently 0, 1, 2, 3, or 4.

Aspect 2: The compound according to Aspect 1, wherein $L^1$ is a single bond, —$CR^aR^b$—, —O—, —$NR^a$, $*^1$—$CR^aR^b$—$NR^c$—$**^1$, $*^1$—O—$CR^aR^b$—$**^1$, $*^1$—$CR^aR^b$—O—$**^1$, $*^1$—C(O)NH—$**^1$, $*^1$—NHC(O)—$**^1$, or —S—; $R^a$, $R^b$, and $R^c$ are each independently hydrogen, deuterium, halogen, —$C_{1-8}$alkyl or $C_{3-8}$cycloalkyl, each of such —$C_{1-8}$alkyl or $C_{3-8}$cycloalkyl are optionally substituted with $OR^f$; $R^f$ is each independently hydrogen, or —$C_{1-8}$alkyl; or $R^a$ and $R^b$ together with the carbon atom to which they are attached, form a 3- to 5-membered ring.

Aspect 3: The compound according to Aspect 2, wherein $R^a$, $R^b$ and $R^c$ are each independently hydrogen, deuterium, F, Cl, Br, I, methyl, ethyl, propyl, isopropyl, 2-methylpropyl, butyl, pentyl or hexyl, each methyl, ethyl, propyl, isopropyl, 2-methylpropyl, butyl, pentyl or hexyl is optionally substituted by OH.

Aspect 4: The compound according to any one of Aspects 1-3, wherein $L^1$ is selected from a single bond, —O—, $*^1$—$CH_2$—O—$**^1$, $*^1$—NHC(O)—$**^1$, $*^1$—$CHCH_3$—O—$**^1$, $*^1$—$CH_2$—NH—$**^1$, $*^1$—$CH_2$—N($CH_3$)—$**^1$, $*^1$—C$(CH_3)_2$—O—$**^1$, or $*^1$—$CF_2$—O—$**^1$.

Aspect 5: The compound according to any one of Aspects 1-4, wherein m=1; $R^1$ is selected from hydrogen, —$C_{1-8}$alkyl (preferably methyl), $OR^a$, —$NR^aR^b$, or halogen, said —$C_{1-8}$alkyl is optionally substituted with at least one halogen; $R^a$ and $R^b$ are each independently hydrogen, or —$C_{1-8}$alkyl.

Aspect 6: The compound according to any one of Aspects 1-5, wherein p=1, and s=1; or p=0, and s=2.

Aspect 7: The compound according to any one of Aspects 1-6, wherein n=0.

Aspect 8: The compound according to any one of Aspects 1-7, wherein $R^3$ is selected from —$C_{1-8}$alkyl (preferably methyl, ethyl, propyl, 2-methylpropyl, butyl, pentyl or hexyl) or $C_{4-8}$heterocyclyl(preferably piperidinyl), said —$C_{1-8}$alkyl and $C_{4-8}$heterocyclyl(preferably piperidinyl) are optionally substituted with $R^d$, $R^d$ is selected from —$C_{1-8}$alkyl (preferably methyl), —$NR^fR^g$ or —$CONR^fR^g$, $R^f$ and $R^g$ are each independently hydrogen, or —$C_{1-8}$alkyl (preferably methyl or butyl).

Aspect 9: The compound according to Aspect 1, wherein Formula (I) is Formula (Ia) or Formula (Ib)

(Ia)

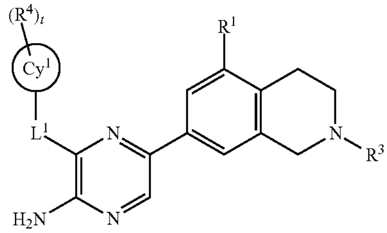

or (Ib)

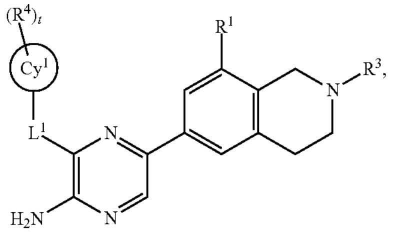

$R^1$, $R^4$, $R^3$, t, $Cy^1$, $L^1$ are as defined in Formula (I).

Aspect 10: The compound according to Aspect 9, wherein $R^1$ and $R^3$ are each independently selected from hydrogen, —$CH_3$, $OCH_3$, halogen (such as F or Cl), —$NHCH_3$, —$NHCH_2CH_3$,

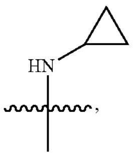

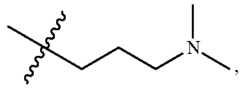

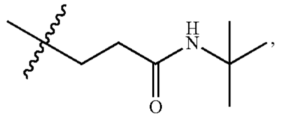

$CHF_2$, —$CF_3$ or

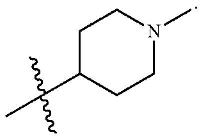 [SMILES: *C1CCN(C)CC1]

Aspect 11: The compound according to Aspect 9, wherein Formula (I) is Formula (Ic) or (Id)

(Ic)

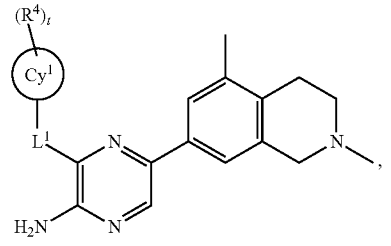

-continued
(Id)
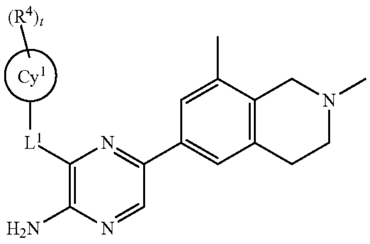
,
(Ie)
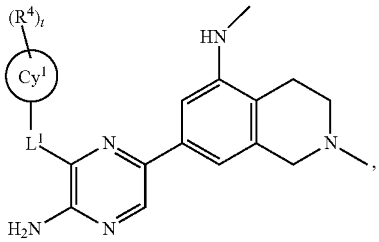
,
(If)
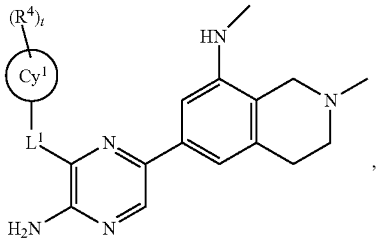
,
(Ig)
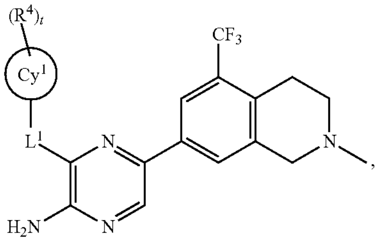
,
(Ih)
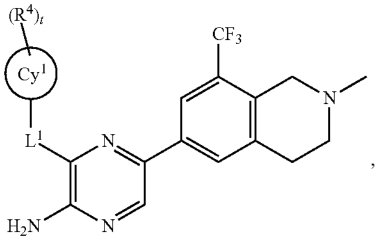
,
(Ii)
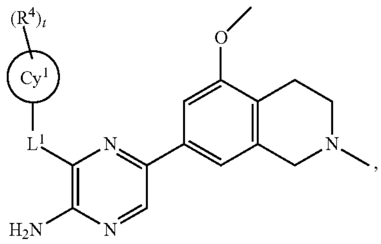
,
-continued
(Ij)
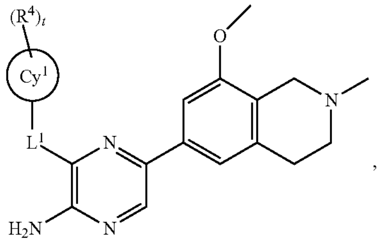
,
(Ik)
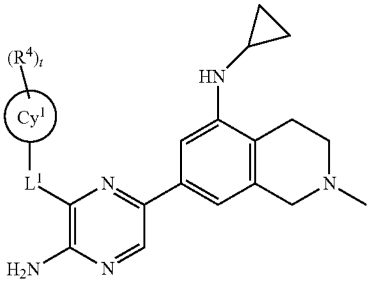
,
(Il)
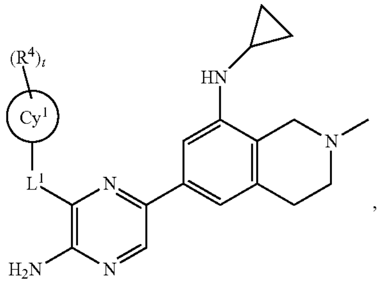
,
(Im)
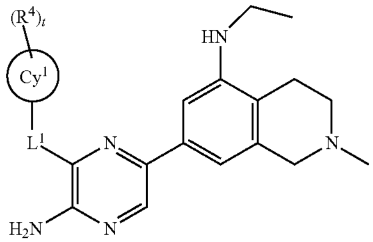
,
(In)
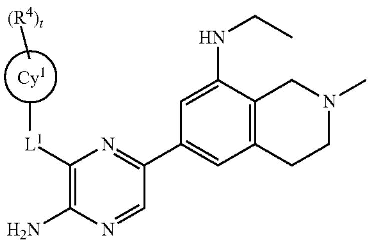
.
Aspect 12: The compound according to Aspect 11, wherein Formula (Ic) is selected from (Ic1)
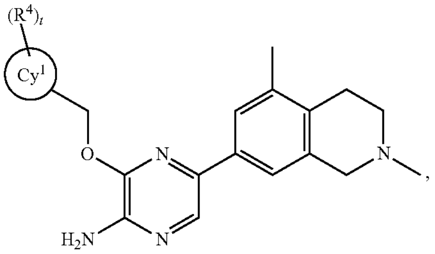
(Ic2)
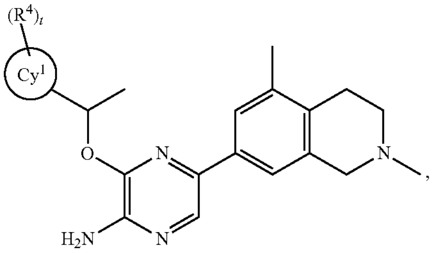
(Ic3)
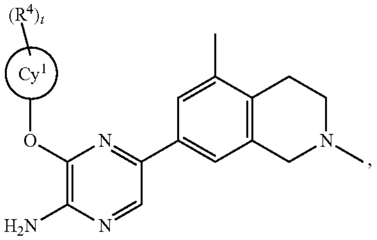
(Ic4)
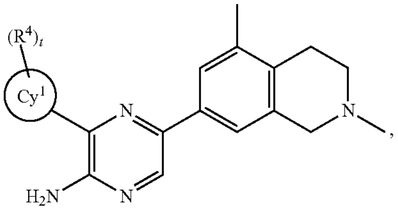
(Ic5)
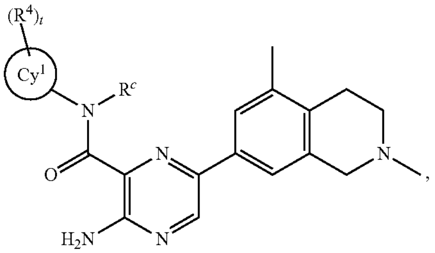
(Ic6)
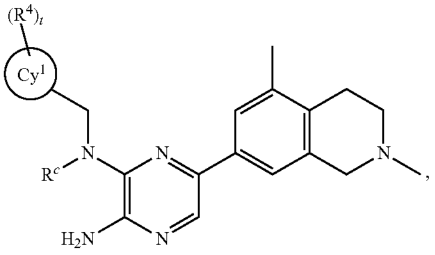
-continued
(Ic7)
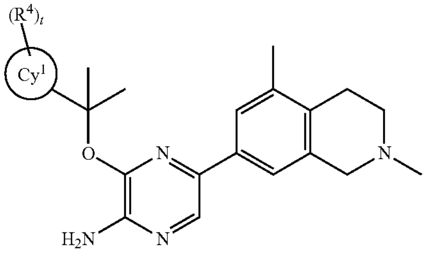
or
(Ic8)
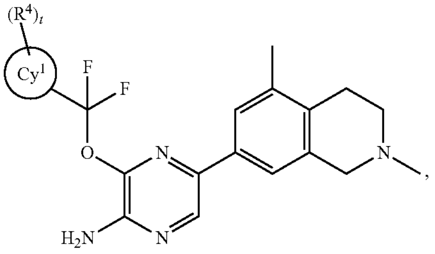
(Ic9)
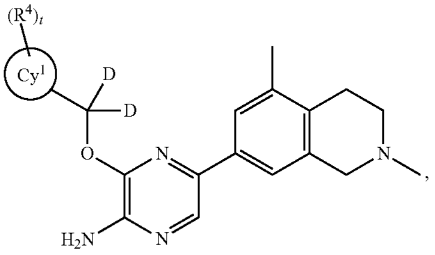
(Ic10)
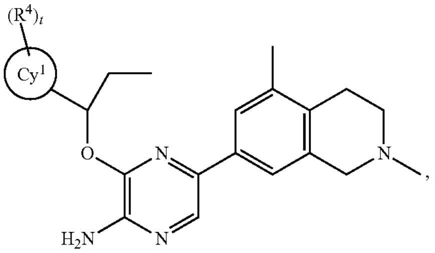
(Ic11)
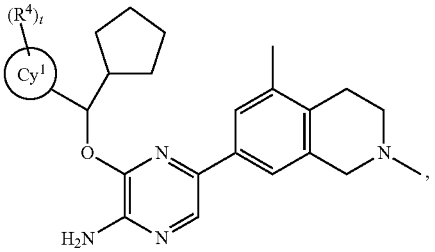
(Ic12)
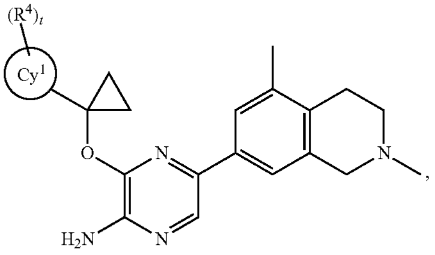

-continued (Ic13)

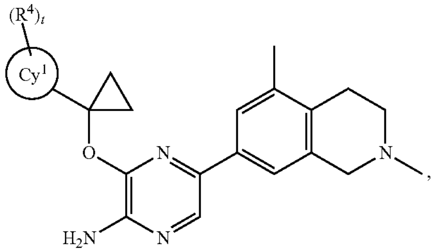

(Ic14)

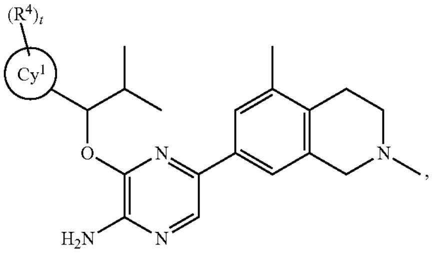

or (Ic15)

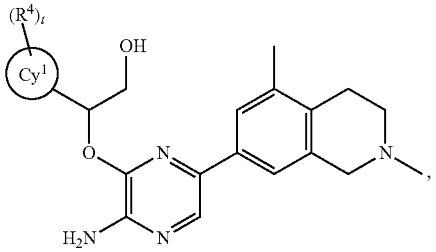

(Ie1)

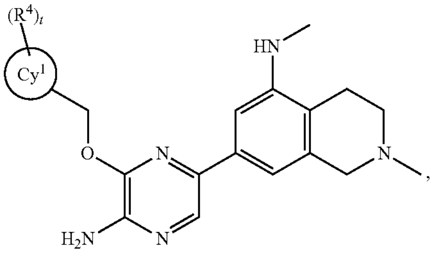

(Id1)

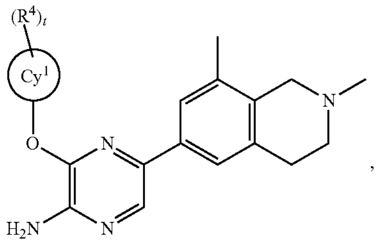

(Ih1)

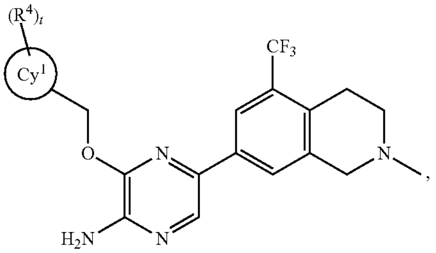

-continued (Ii1)

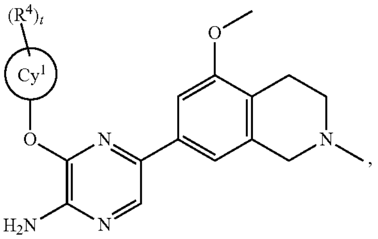

(Ie2)

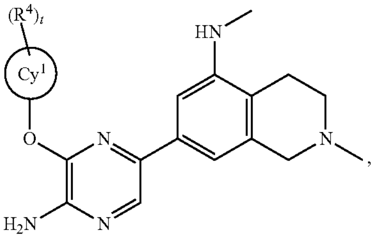

(Ik1)

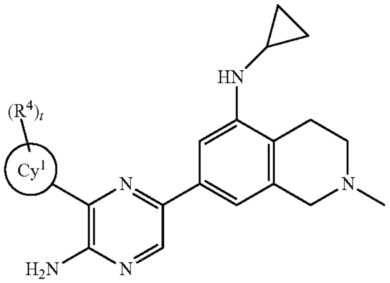

wherein $R^4$, t, $Cy^1$, are as defined in Formula (I); and $R^c$ is hydrogen or —$C_{1-8}$alkyl (preferably methyl).

Aspect 13: The compound according to any one of Aspects 1-12, wherein $Cy^1$ is selected from 3- to 8-membered monocyclic heterocyclyl comprising one or two heteroatoms independently selected from nitrogen, oxygen, or optionally oxidized sulfur as ring member(s), wherein $Cy^1$ is optionally substituted with —$(R^4)_t$ as defined in Formula (I).

Aspect 14: The compound according to Aspect 13, wherein $Cy^1$ is selected from oxiranyl, aziridinyl, thiiranyl, azetidinyl, oxetanyl, thietanyl, pyrrolidinyl (pyrrolidin-1-yl, pyrrolidin-2-yl, pyrrolidin-3-yl), imidazolidinyl (imidazolidin-2-yl, imidazolidin-4-yl), pyrazolidinyl, piperidinyl, tetrahydropyranyl, morpholinyl, thiomorpholinyl, thioxanyl, piperazinyl, azocanyl, azetidinyl, dihydropyridinyl, tetrahydropyridinyl, pyranyl, homopiperidinyl, homopiperazinyl, azepanyl, oxepanyl, thiepanyl, oxathianyl, 1,4-oxathianyl, 1,4-dioxepanyl, 1,4-oxathiepanyl, 1,4-oxaazepanyl, 1,4-dithiepanyl, 1,4-thiazepanyl, 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl, wherein $Cy^1$ is optionally substituted with —$(R^4)_t$ as defined in Formula (I).

Aspect 15: The compound according to Aspect 14, wherein $Cy^1$ is selected from piperidinyl, dihydropyridinyl, or pyrrolidinyl (pyrrolidin-1-yl, pyrrolidin-2-yl, or pyrrolidin-3-yl); t=0 or 1, each $R^4$ is selected from hydrogen, oxo, or —$C_{1-8}$alkyl (preferably methyl).

Aspect 16: The compound according to Aspect 15, wherein

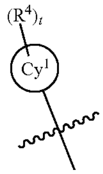

is selected from

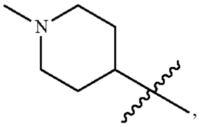,
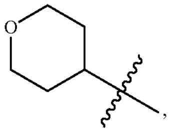,
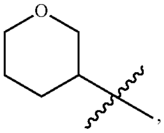,
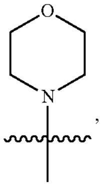,
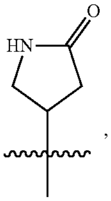,
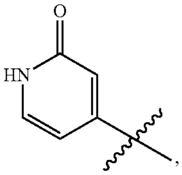, or
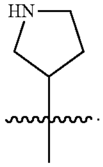.

Aspect 17: The compound according to any one of Aspects 1-12, wherein $Cy^1$ is monocyclic or bicyclic aryl group optionally substituted with —$(R^4)_t$ as defined in Formula (I).

Aspect 18: The compound according to Aspect 17, wherein $Cy^1$ is naphthyl, or phenyl; t=0, 1, 2 or 3; each $R^4$ is independently selected from hydrogen, halogen, —$C_{1-8}$alkyl optionally substituted with halogen or —$OR^f$, —CN, —$COOR^a$, —$OR^a$, —$CONR^aR^b$, or —$NR^aR^b$, wherein $R^a$, $R^b$ and $R^f$ are each independently hydrogen, —$C_{1-8}$alkyl, —$C_{3-6}$cycloalkyl, or —$C_{3-6}$heterocyclyl, or $R^a$ and $R^b$, together with the nitrogen atom to which they are attached, form a 3- to 12-membered ring, said ring comprising 0, 1 or 2 additional heteroatom(s) independently selected from nitrogen, oxygen or optionally oxidized sulfur as ring member(s); preferably each $R^4$ is hydrogen, chloro, fluoro, methoxy, —COOH, —$CON(CH_3)_2$, —$CF_3$, —$CH_2$—$OCH_3$, —CN, pyrrolidin-1-ylcarbonyl, morpholinocarbonyl, or N-cyclopropyaminocarbonyl.

Aspect 19: The compound according to Aspect 18, wherein

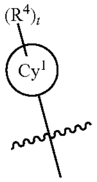

is selected from

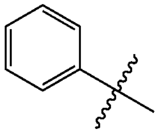,
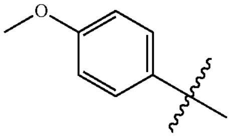,
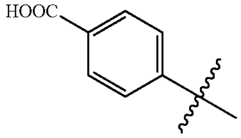,
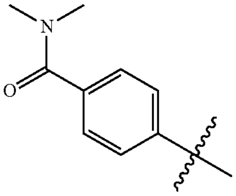,
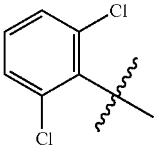,
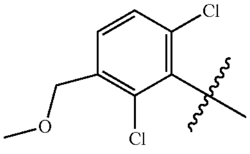,
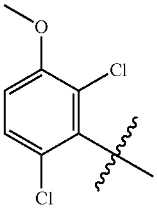,
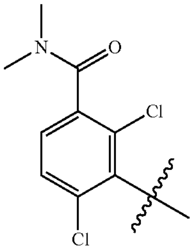,
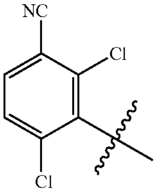,
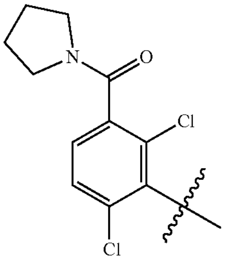,
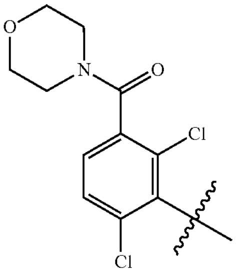,
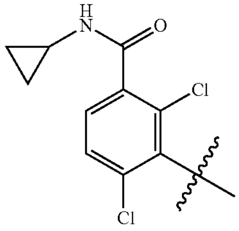, or
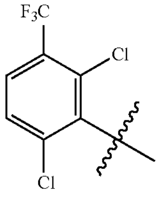.

Aspect 20: The compound according to any one of Aspects 1-12, wherein $Cy^1$ is 5- or 6-membered heteroaryl optionally substituted with —$(R^4)_t$ as defined in Formula (I).

Aspect 21: The compound according to Aspect 20, wherein $Cy^1$ is selected from pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1,2,3-oxadiazolyl, 1,2,4-oxadiazolyl, or 1,3,4-oxadiazolyl), phthalazinyl, pyrazolyl, pyrazinyl, pyridazinyl, pyrrolyl, triazolyl (such as 1,2,3-triazolyl, 1,2,4-triazolyl, or 1,3,4-triazolyl), wherein $Cy^1$ is optionally substituted with —$(R^4)_t$ as defined in Formula (I).

Aspect 22: The compound according to Aspect 21, wherein $Cy^1$ is selected from

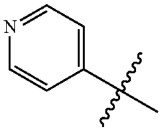, 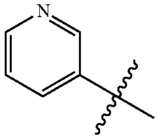, 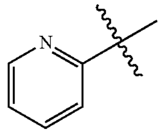, 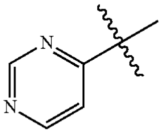, 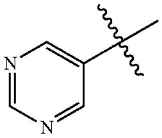, 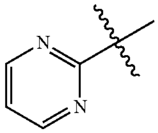, 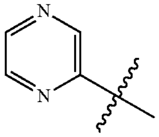, 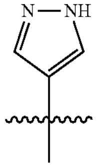, 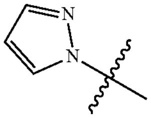, 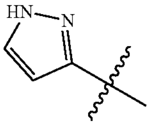, 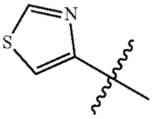, 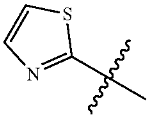, 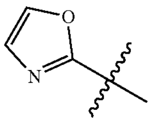, wherein $Cy^1$ is optionally substituted with —$(R^4)_t$ as defined in Formula (I); preferably, t=0, 1, 2 or 3, provided that the valency theory is met; more preferably, t=1 or 2; each $R^4$ is independently selected from hydrogen, halogen, —$C_{1-8}$alkyl, —$C_{2-8}$alkynyl (preferably ethynyl), cycloalkyl, heterocyclyl, oxo, —CN, —$OR^a$, —$CONR^aR^b$, —$NR^aCOR^b$, or —$NR^aR^b$, each of said —$C_{1-8}$alkyl, —$C_{2-8}$alkynyl, cycloalkyl or heterocyclyl is optionally substituted with at least one $R^d$; more preferably, each $R^4$ is —$C_{1-8}$alkyl optionally substituted with at least one halogen, e.g., fluoro or cyano; or each $R^4$ is cycloalkyl optionally substituted with cyano, —$C_{1-8}$alkyl or hydroxy; or each $R^4$ is heterocyclyl optionally substituted with halogen or —$C_{1-8}$alkyl; or each $R^4$ is —$C_{2-8}$alkynyl (e.g., ethynyl) optionally substituted with at least one $R^d$, wherein $R^d$ is independently —$C_{1-8}$alkyl, cycloalkyl (preferably cyclopropyl or cyclohexyl), aryl, heteroaryl (preferably pyridyl (e.g, pyrid-3-yl or pyrid-4-yl), pyrazlyl (e.g., 1H-pyrazol-3-yl or 1H-pyrazol-5-yl), or thiazolyl), —$SO_2R^f$ or —$CONR^fR^g$, each of said —$C_{1-8}$alkyl, cycloalkyl, aryl, or heteroaryl is optionally substituted with at least one substituent selected from halogen, —$C_{1-8}$alkyl, —$OR^f$, or —$NR^iR^j$; and wherein $R^f$, $R^g$, $R^i$, and $R^j$ are each independently hydrogen or —$C_{1-8}$alkyl; or each $R^4$ is —$OR^a$, —$CONR^aR^b$, or —$NR^aR^b$, wherein $R^a$ and $R^b$ are each hydrogen, —$C_{1-8}$alkyl, cycloalkyl, aryl or heterocyclyl, wherein said —$C_{1-8}$alkyl is optionally substituted with $R^e$ which is selected from cycloalkyl, aryl or heterocyclyl, each of cycloalkyl, aryl or heterocyclyl is optionally substituted with at least one —CO—$NR^iR^j$, wherein $R^i$, and $R^j$ are each independently hydrogen, or —$C_{1-8}$alkyl; or $R^a$ and $R^b$ together with the nitrogen atom to which they are attached, form a 3- to 12-membered ring, said ring comprising 0, 1 or 2 additional heteroatom(s) independently selected from nitrogen, oxygen or optionally oxidized sulfur as ring member(s), said ring is optionally substituted with at least one substituent $R^e$.

Aspect 23: The compound according to Aspect 22, wherein

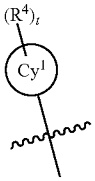

is selected from,

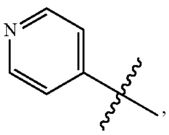, 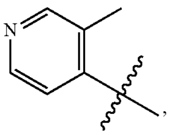, 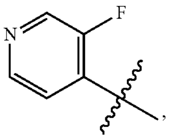, 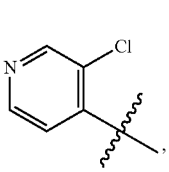, 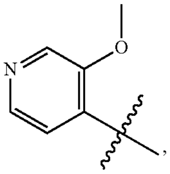, 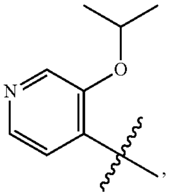, 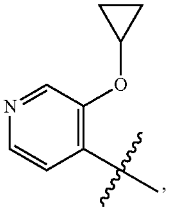, 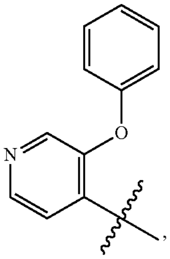, 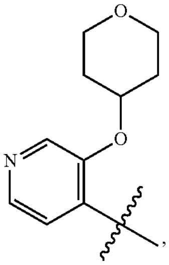, 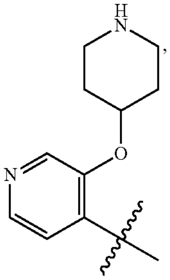 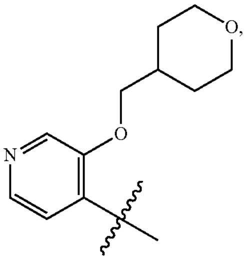 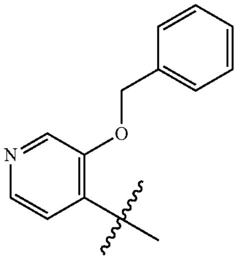, 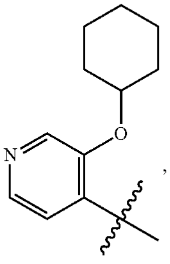, 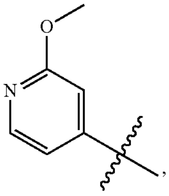, 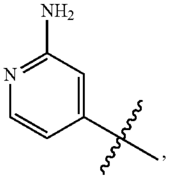, 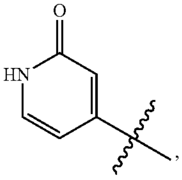, -continued
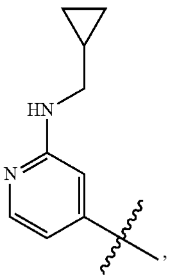,
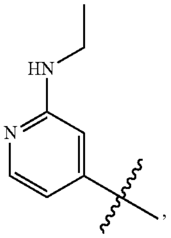,
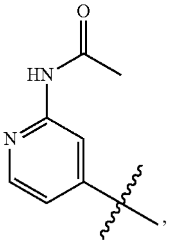,
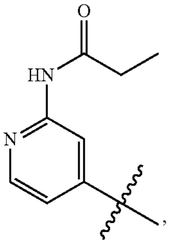,
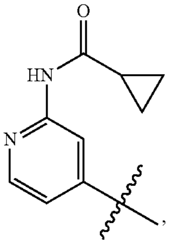,
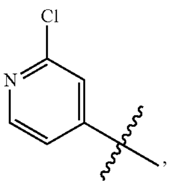,
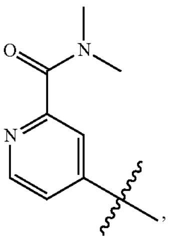,
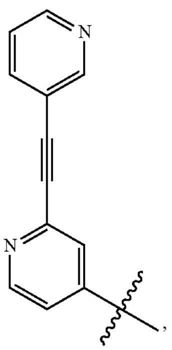,
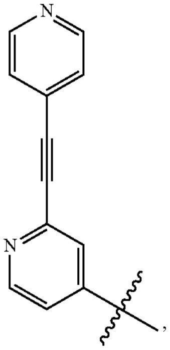,
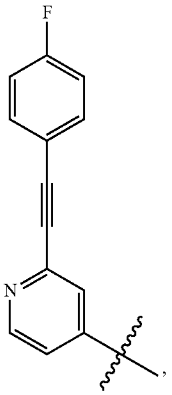,
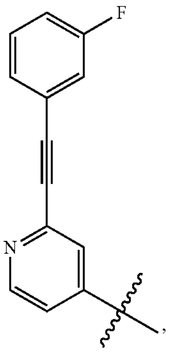,
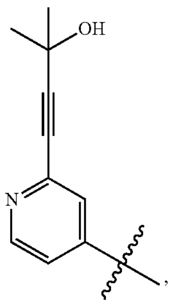,
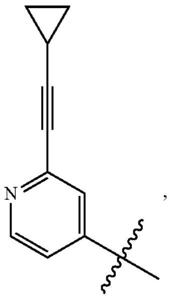,
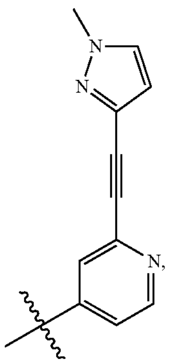
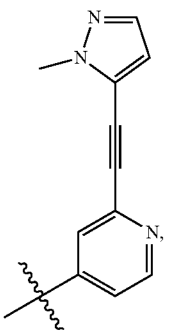
-continued
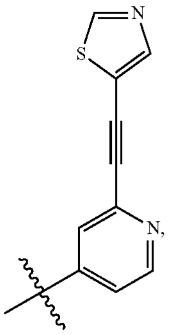
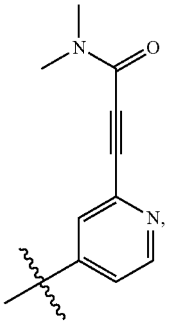
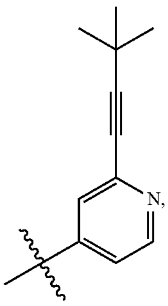
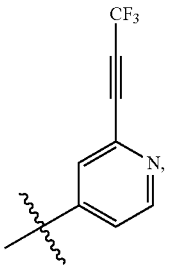
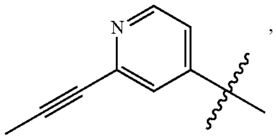,
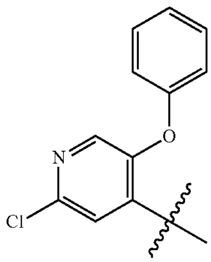,
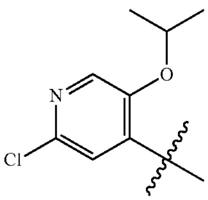,
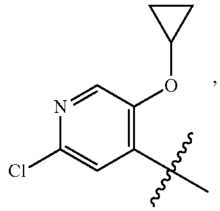,
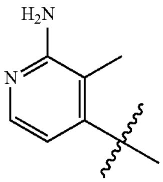,
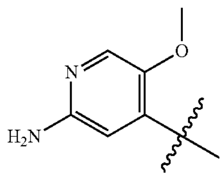,
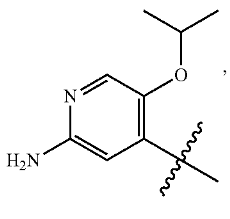,
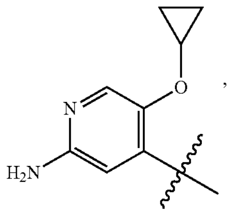,
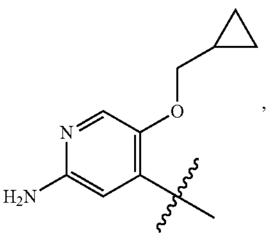, -continued
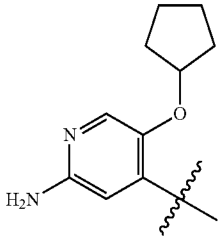 , 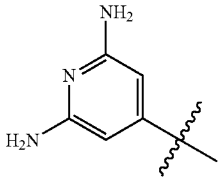 ,
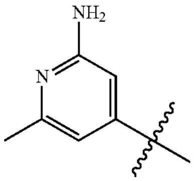 , 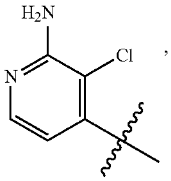 , 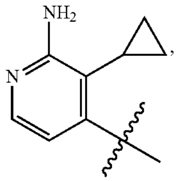
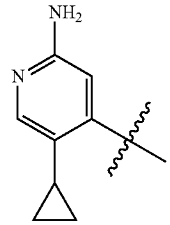 , 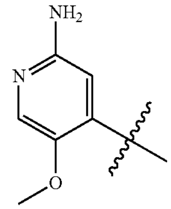 , 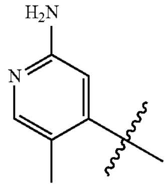 ,
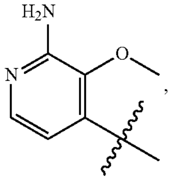 , 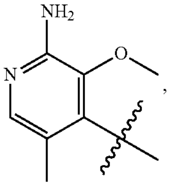 , 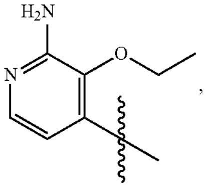 ,
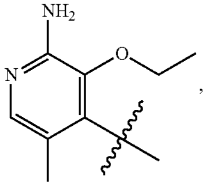 , 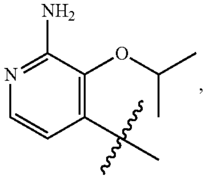 ,
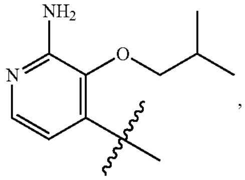 , 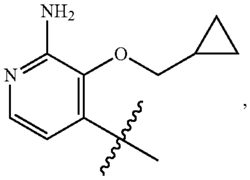 ,
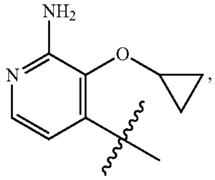 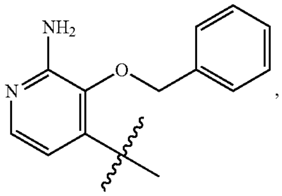 ,
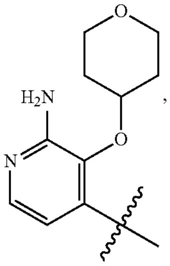 , 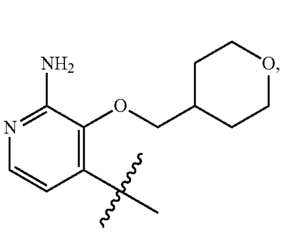
-continued
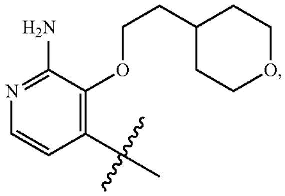 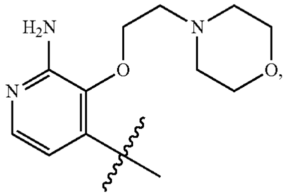
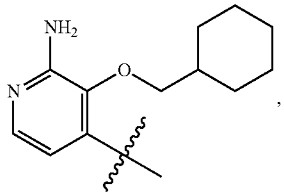 , 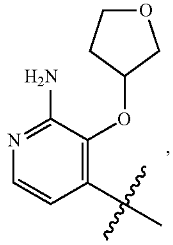 ,
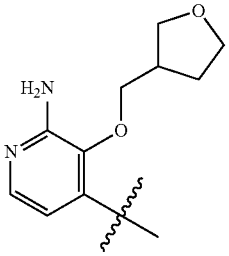 , 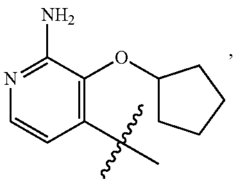 ,
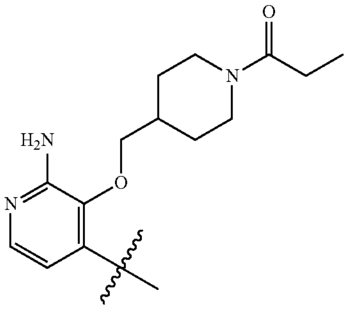 , 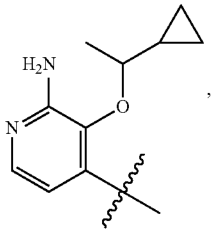 ,
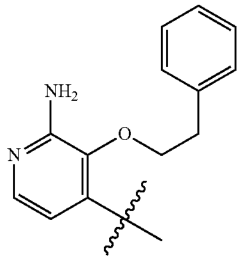 , 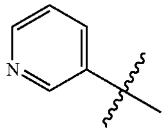 ,
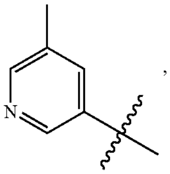 , 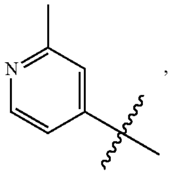 , 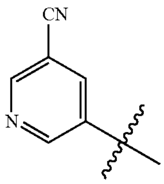 ,
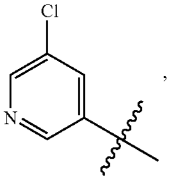 , 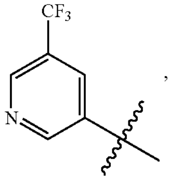 , 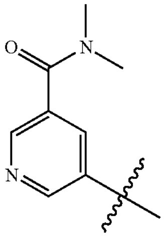 ,

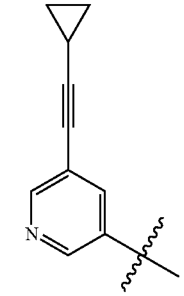, 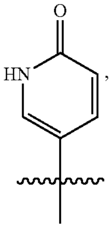, 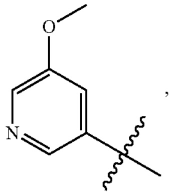,
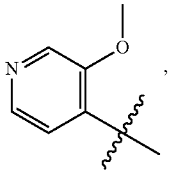, 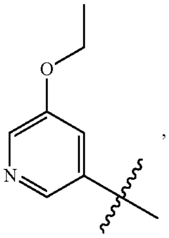, 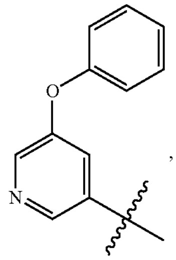,
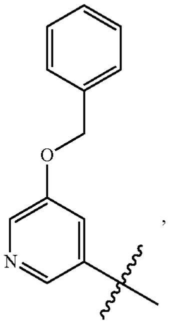, 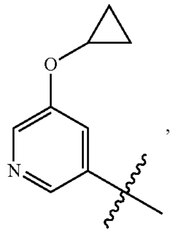,
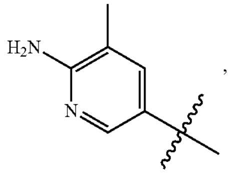, 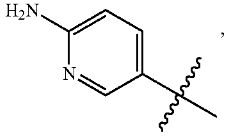,
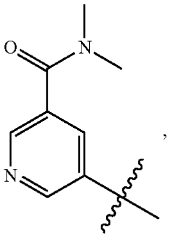, 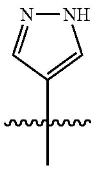, 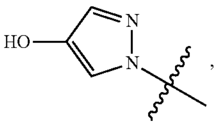,
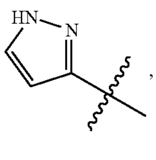, 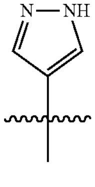, 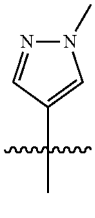, 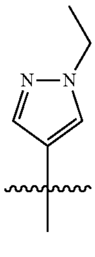,
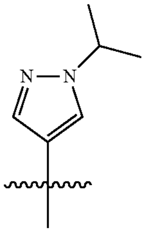, 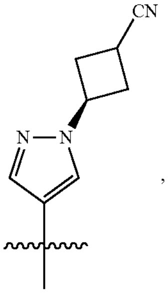, 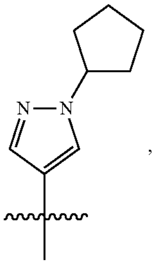,
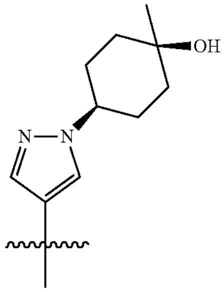, 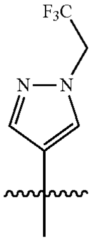, 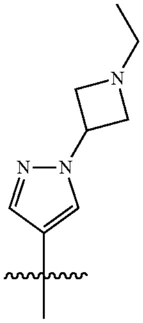,
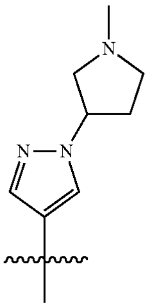, 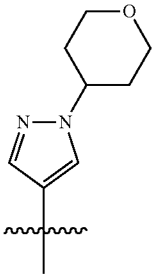, 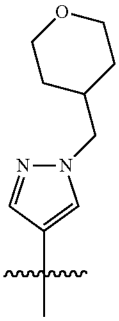,
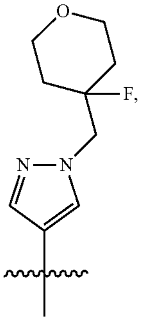 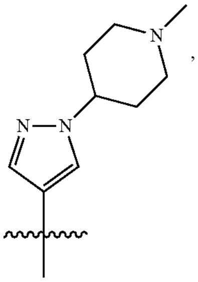, 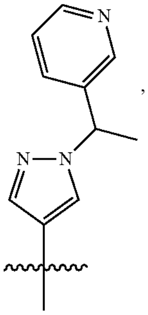,
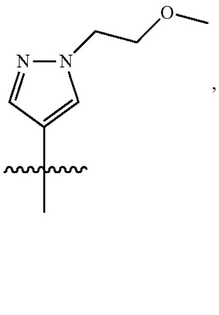, 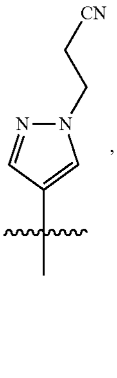, 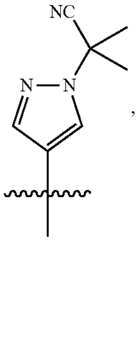, -continued
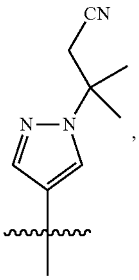 , 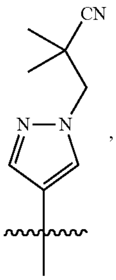 , 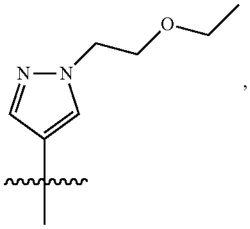 ,
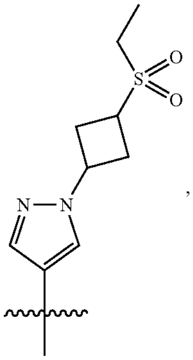 , 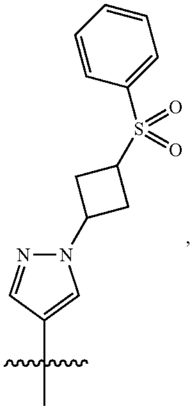 , 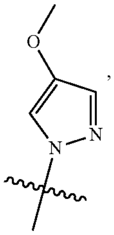 ,
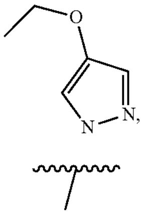
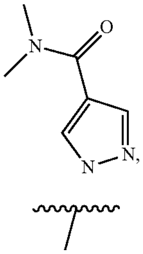
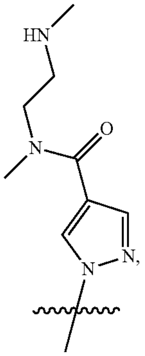
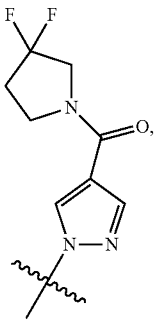 , 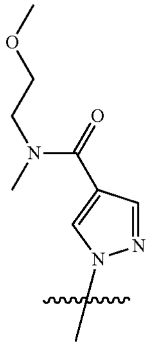 , 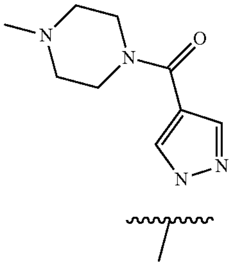 ,
-continued
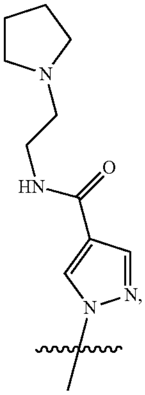
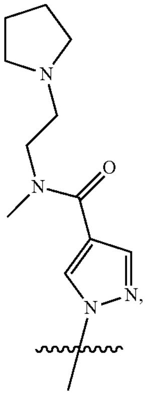
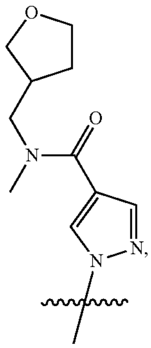
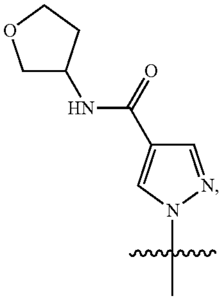
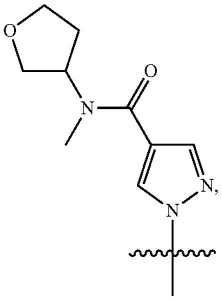
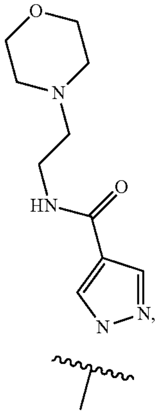
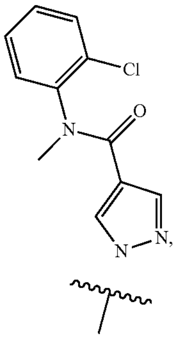
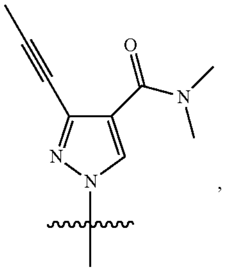 ,
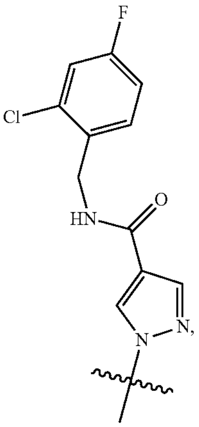
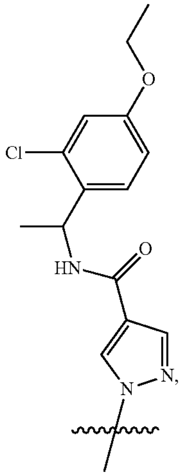

-continued

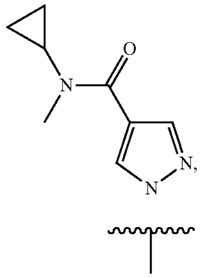 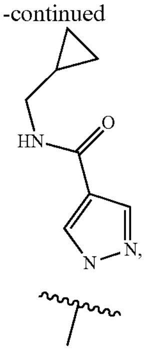 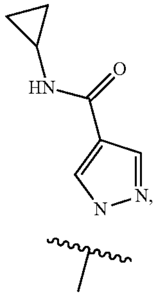

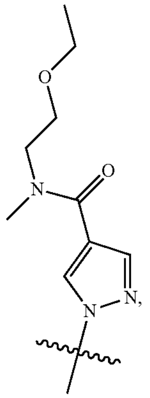 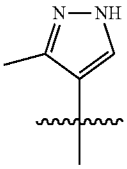 , 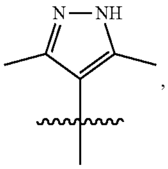 ,

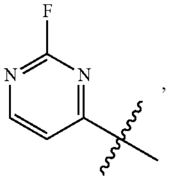 , 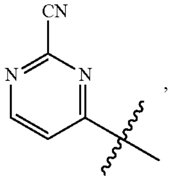 , 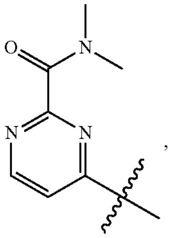 ,

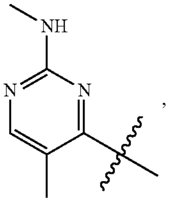 , 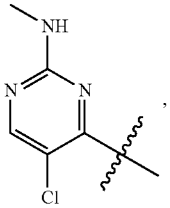 ,

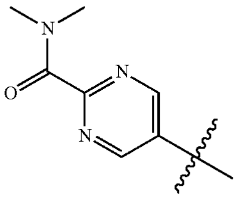 , 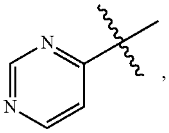 ,

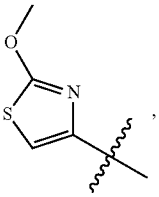 , or 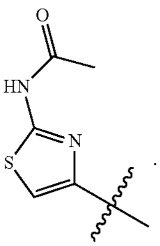 .

Aspect 24: The compound according to any one of Aspects 1-12, wherein $Cy^1$ is selected from 7 to 12-membered bicyclic fused heteroaryl or heterocyclyl comprising one or two or three heteroatoms independently selected from nitrogen, oxygen, or optionally oxidized sulfur as ring member(s), wherein $Cy^1$ is optionally substituted with $—(R^4)_t$ as defined in Formula (I).

Aspect 25: The compound according to Aspect 24, wherein $Cy^1$ is selected from indazole, benzoimidazole, quinoline, pyridooxazine, pyrrolopyridine, isoquinoline, benzoxazine, quinoxaline, Isochromene, pyranopyrazole, pyranopyridine, benzodioxole, quinazoline, benzoxazole, indole, pyrrolopyrazine, pyrrolopyrimidine, imidazopyrimidine, or thienopyridine, wherein one or two carbon-carbon double bond or carbon-nitrogen double bond is optionally hydrogenated, and, wherein $Cy^1$ is optionally substituted with $—(R^4)_t$ as defined in Formula (I). preferably t is 0, 1 or 2; each $R^4$ is halogen, $—C_{1-8}$alkyl, oxo, or $—OR^a$, said $—C_{1-8}$alkyl is optionally substituted with halogen, hydroxy or alkoxy, and wherein $R^a$ is hydrogen or $—C^{1-8}$alkyl.

Aspect 26: The compound according to Aspect 24, wherein $Cy^1$ is selected from

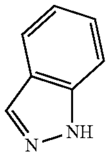 , 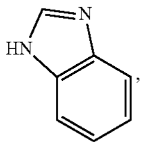 , 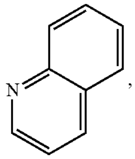 , 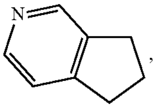 ,

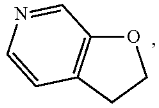 , 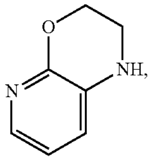 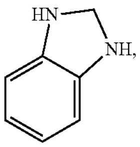

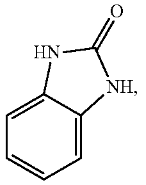 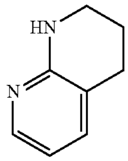 , 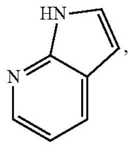 , 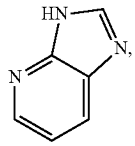

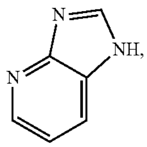 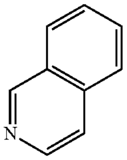 , 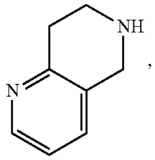 ,

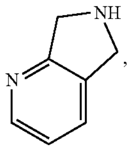 , 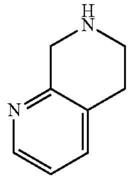 , 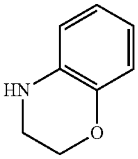 , 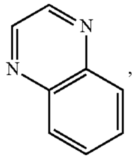 ,

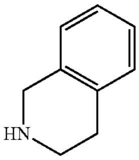 , 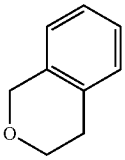 , 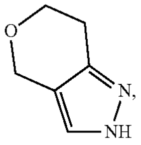

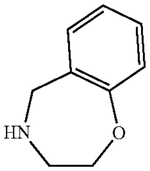 , 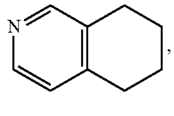 , 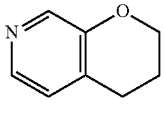 ,

-continued
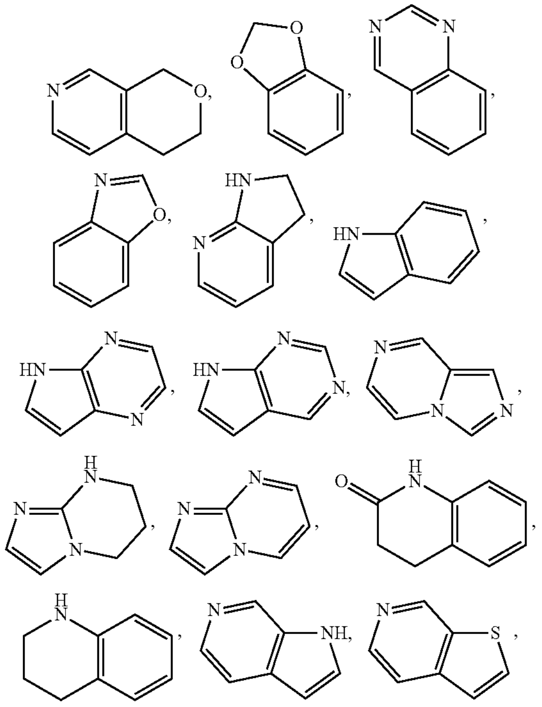
, or
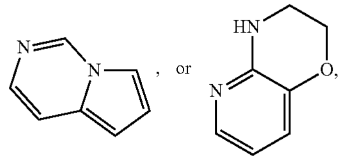
wherein $Cy^1$ is optionally substituted with —$(R^4)_t$ as defined in Formula (I).
Aspect 27: The compound according to Aspect 26, wherein
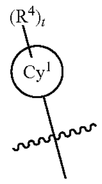
is selected from
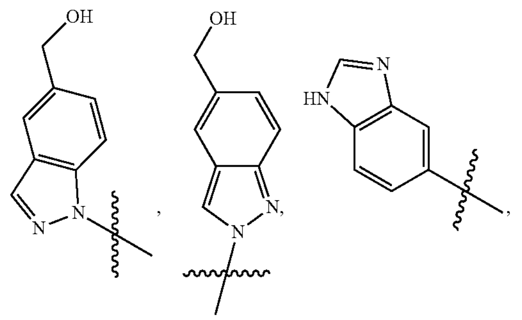
-continued
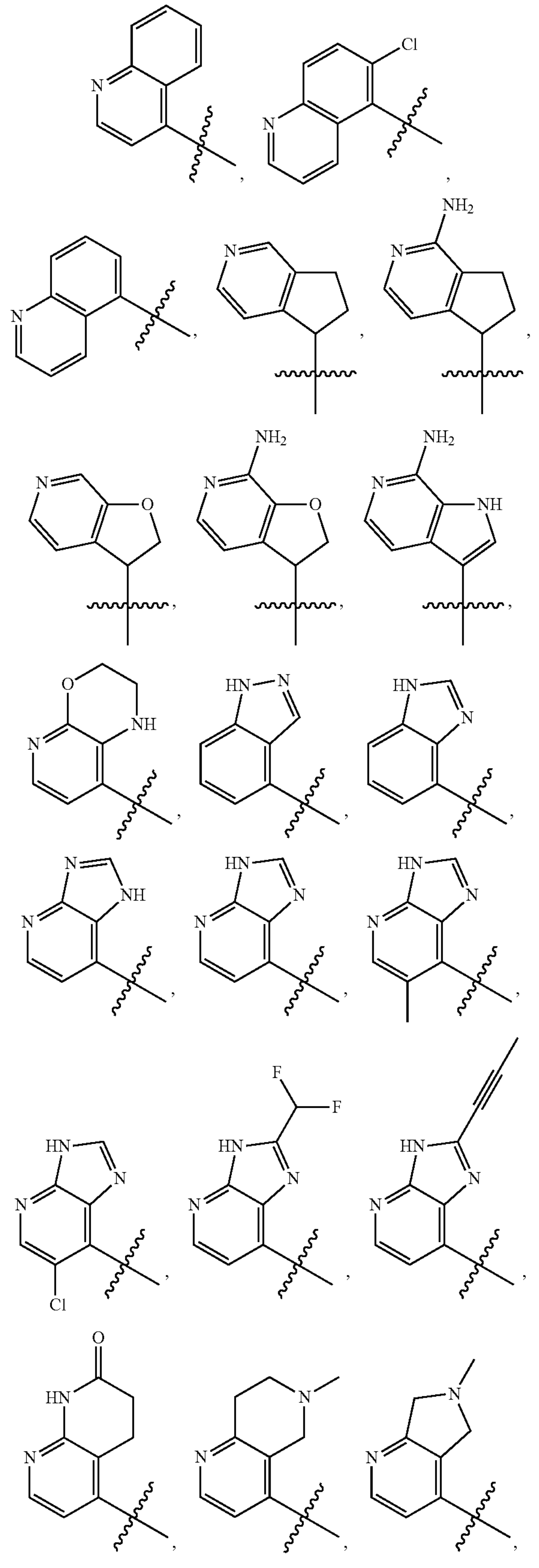

-continued
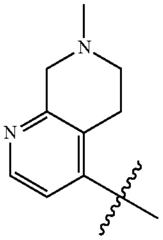, 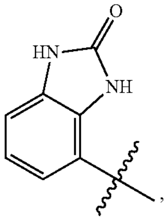, 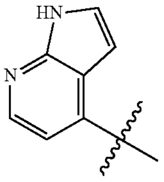,
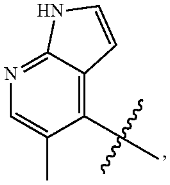, 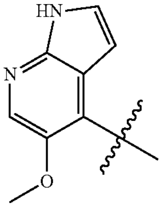, 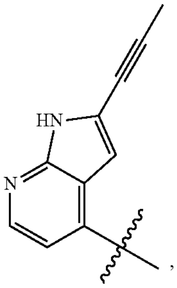,
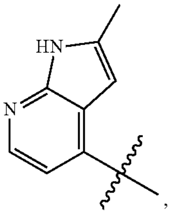, 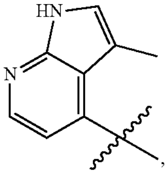, 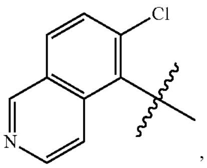,
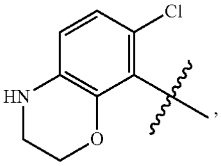, 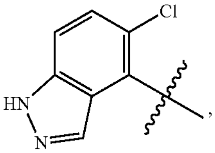,
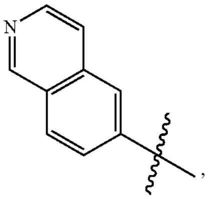, 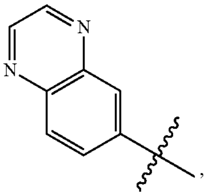,
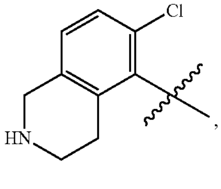, 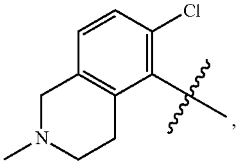,
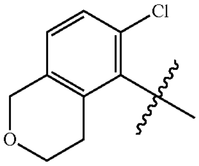, 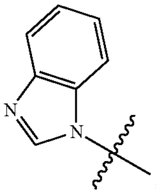, 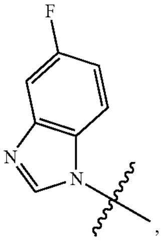,
-continued
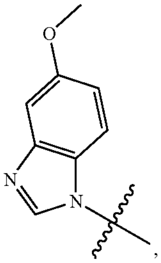, 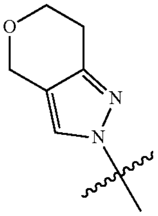,
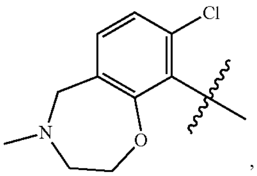, 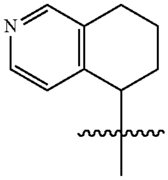,
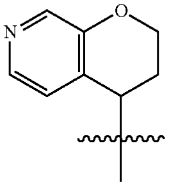, 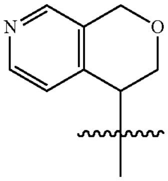, 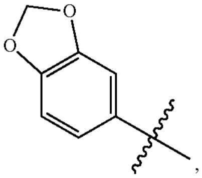,
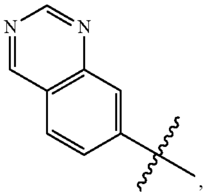, 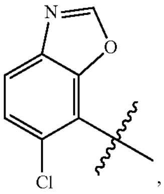, 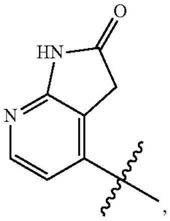,
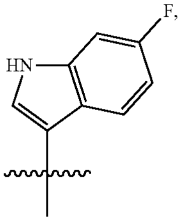 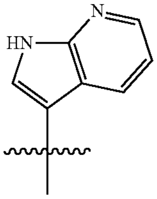, 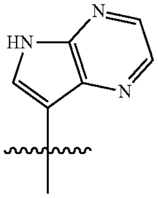,
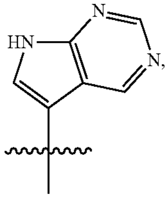 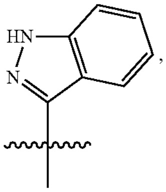, 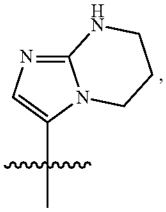,
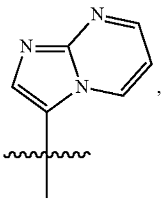, 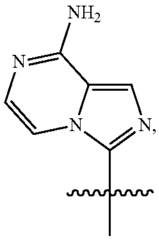 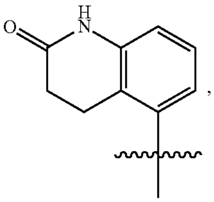, -continued
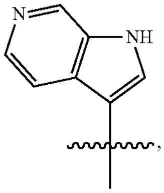, 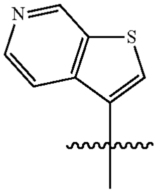, 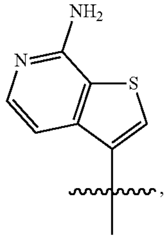,
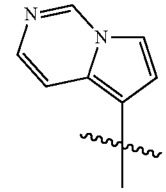 or 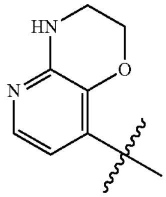.
Aspect 28: The compound selected from
1
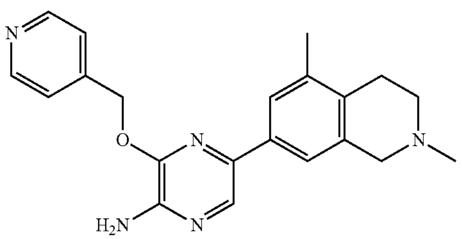
2
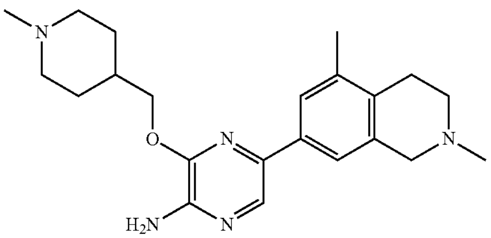
3
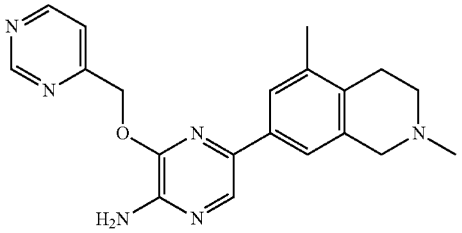
4
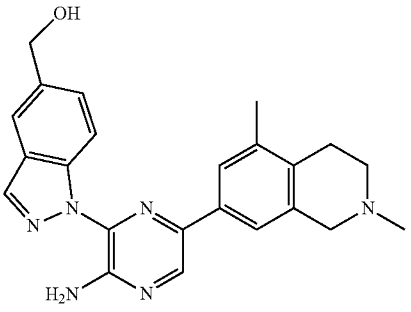
-continued
5
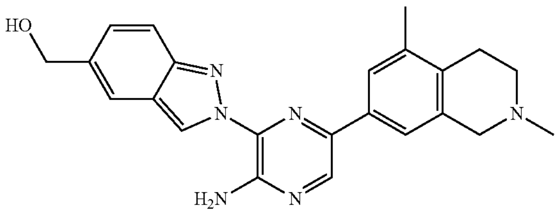
6
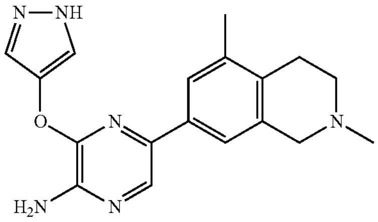
7
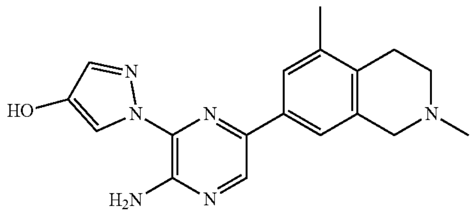
8
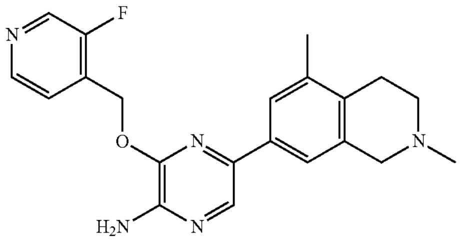
9
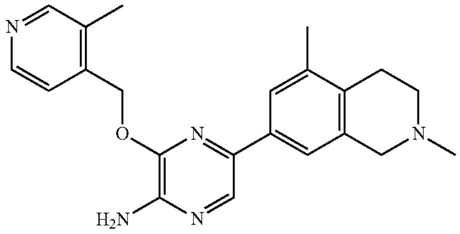
10
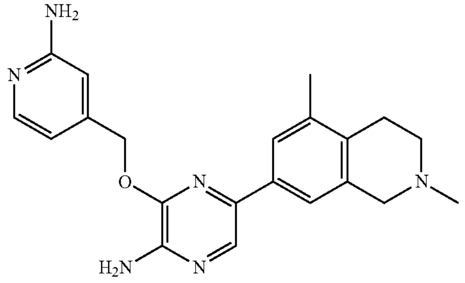

-continued
11
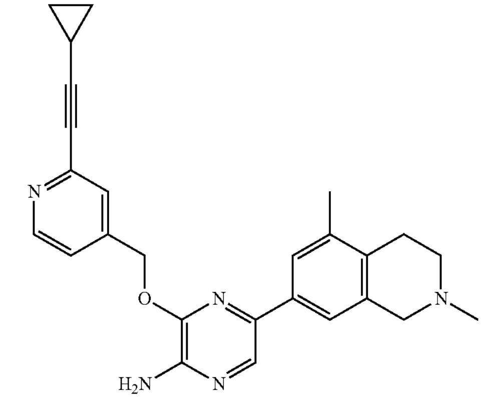
12
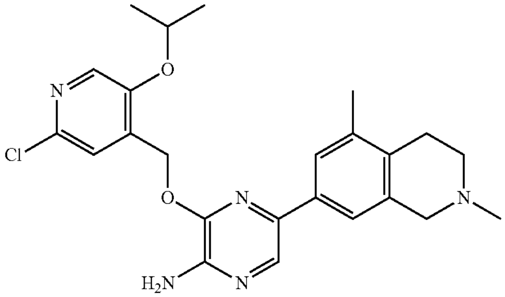
13
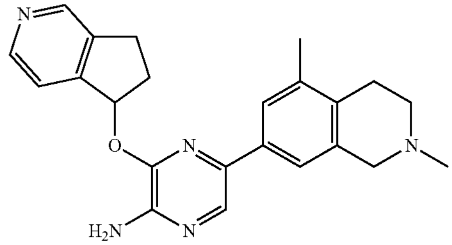
14
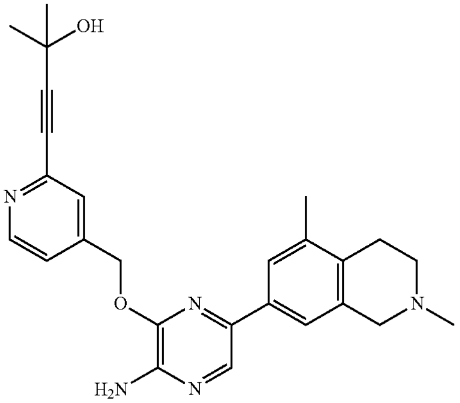
15
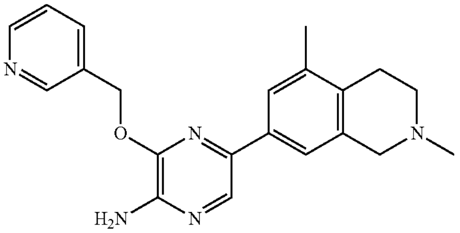
-continued
16
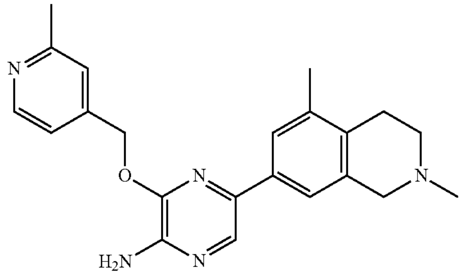
17
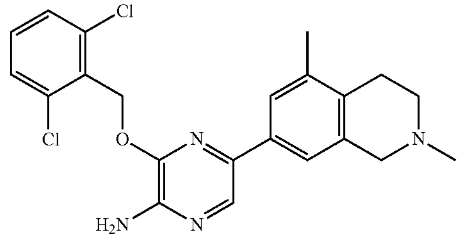
18
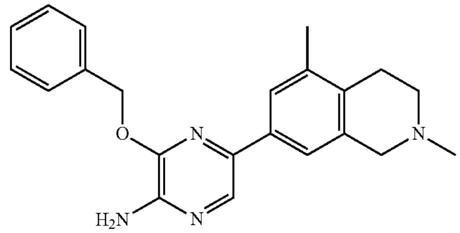
19
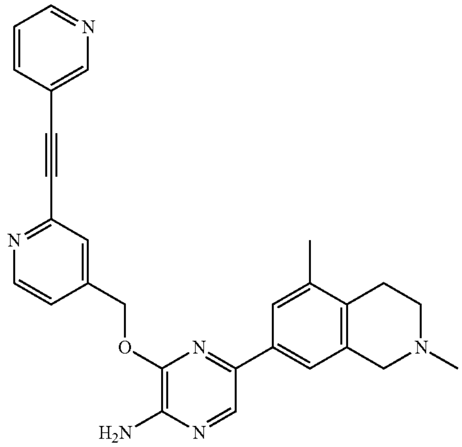

-continued
20
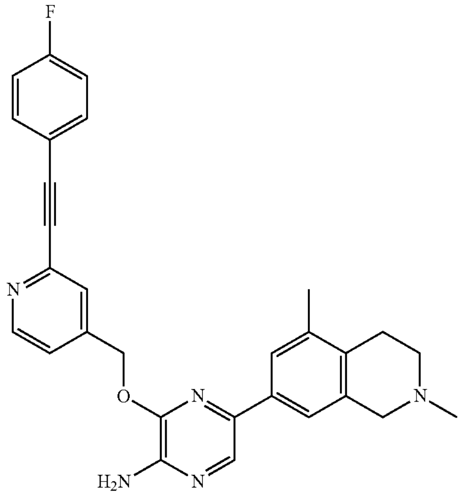
21
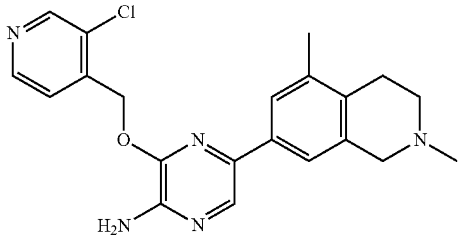
22
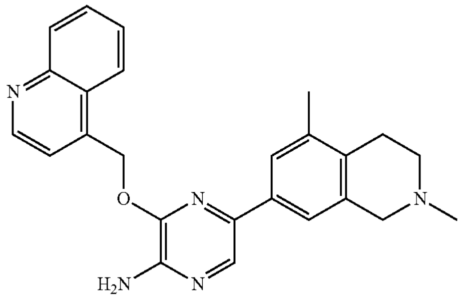
23
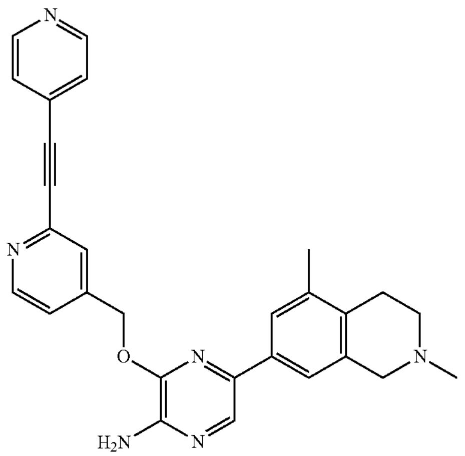
-continued
24
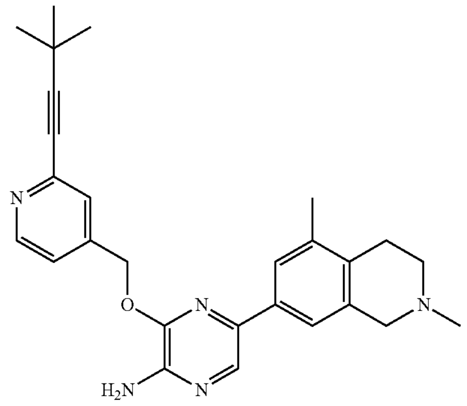
25
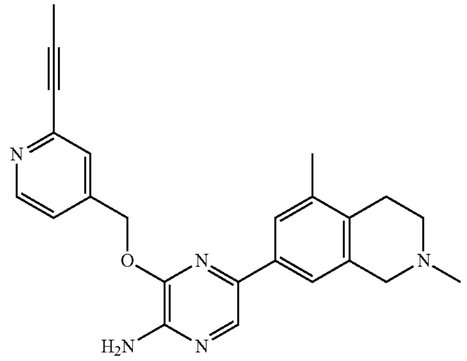
26
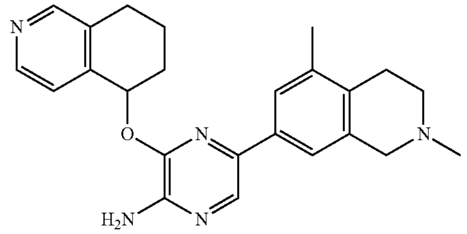
27
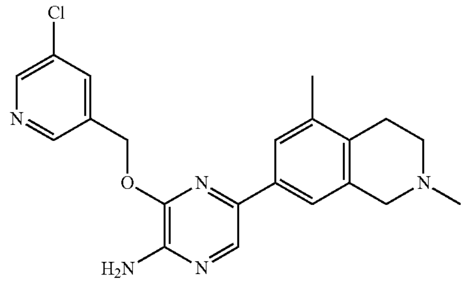
28
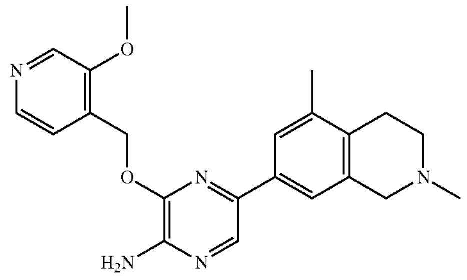

-continued
29
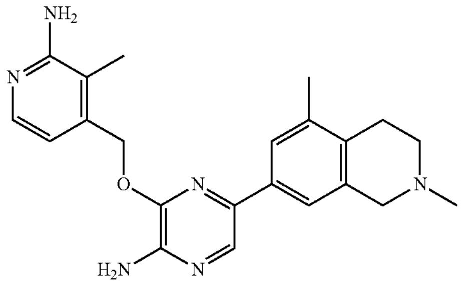
30
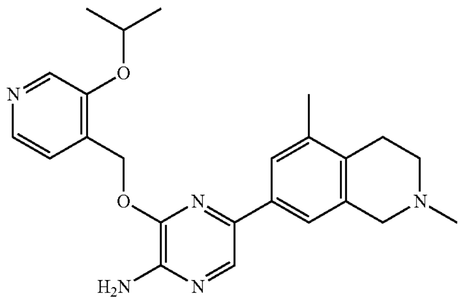
31
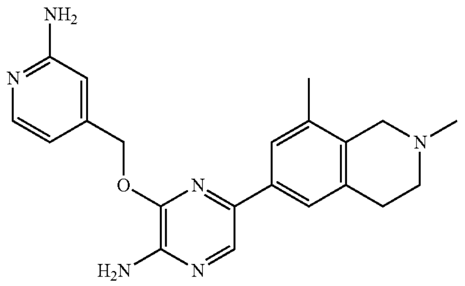
32
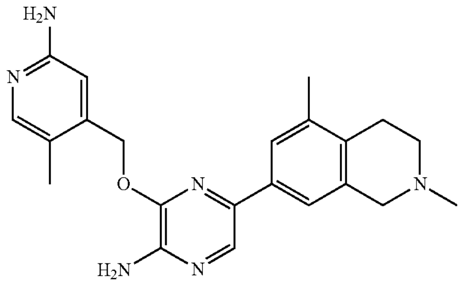
33
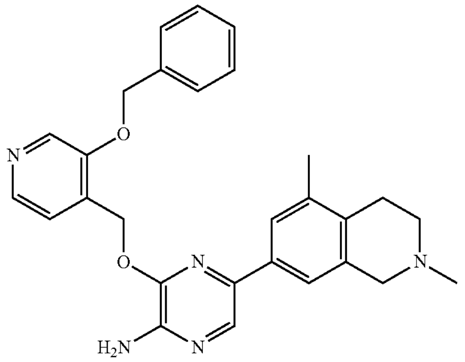
-continued
34
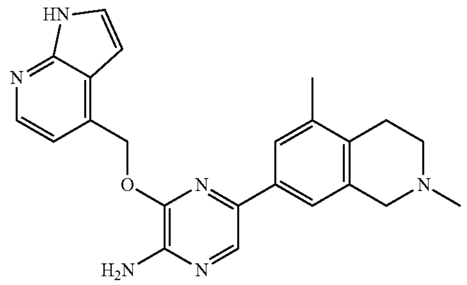
35
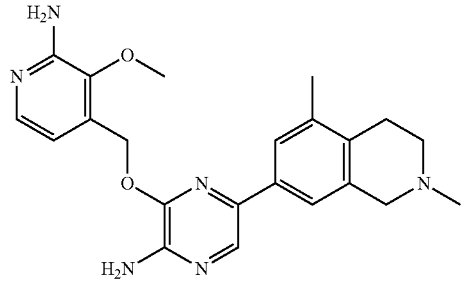
36
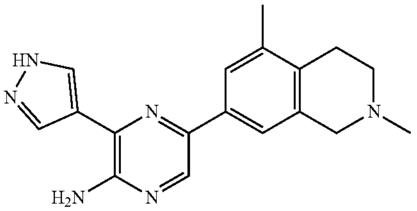
37(141)
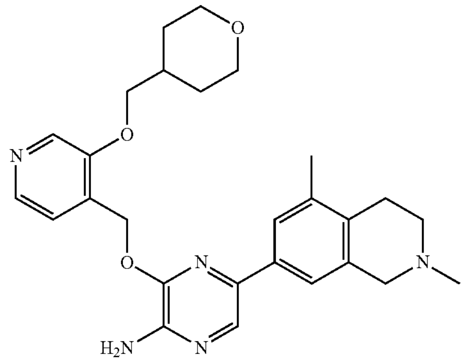
38
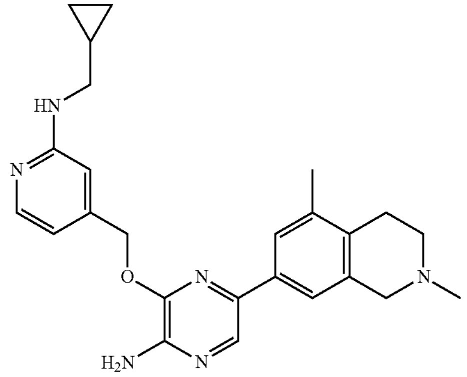

39
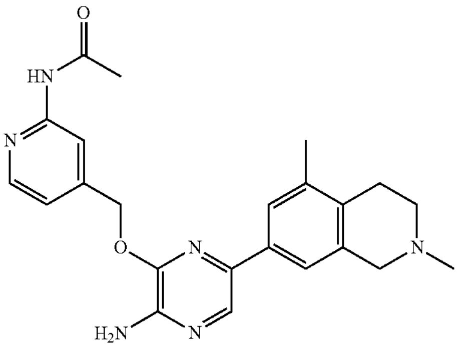
40
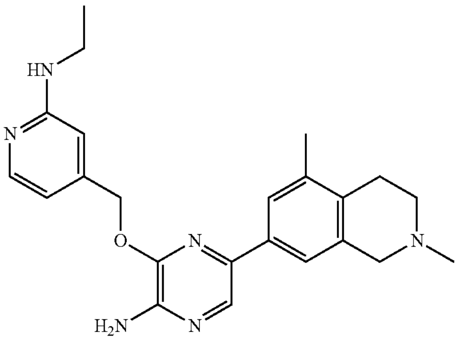
41
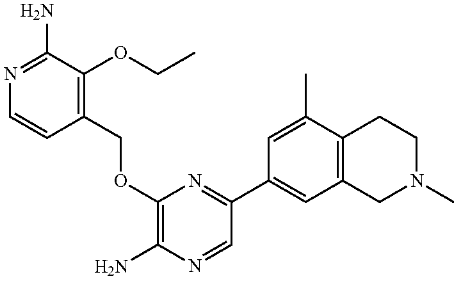
42
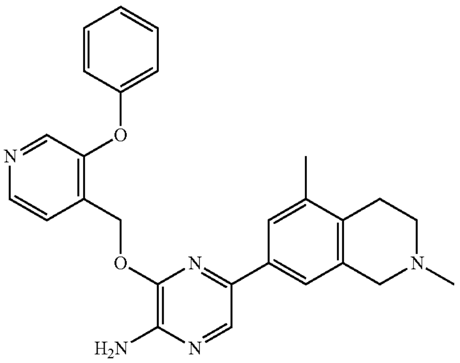
43
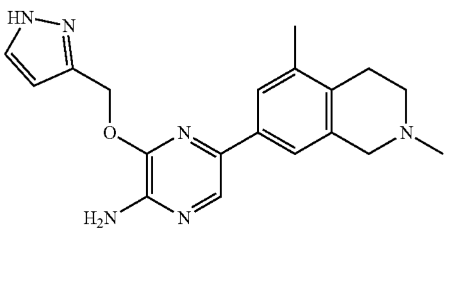
44
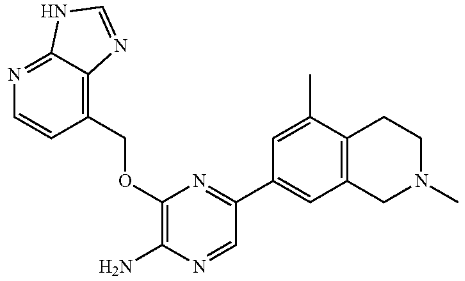
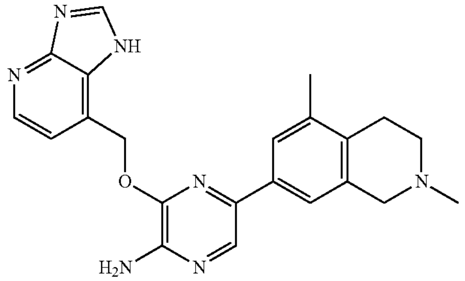
45
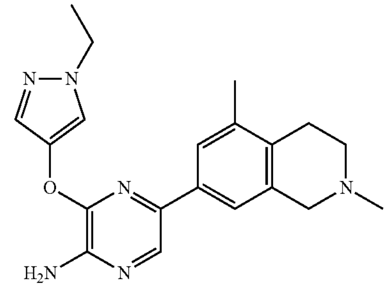
46
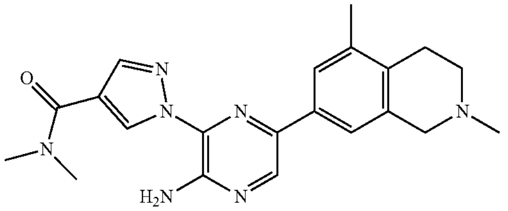
47A
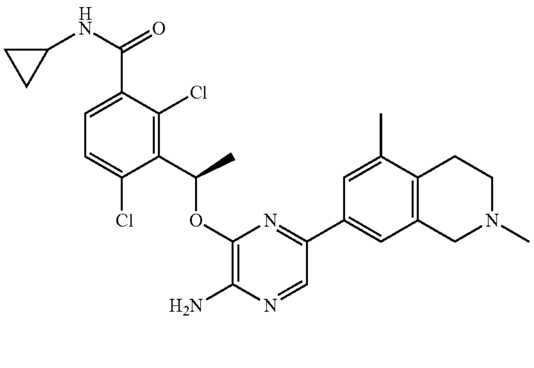

-continued
47B
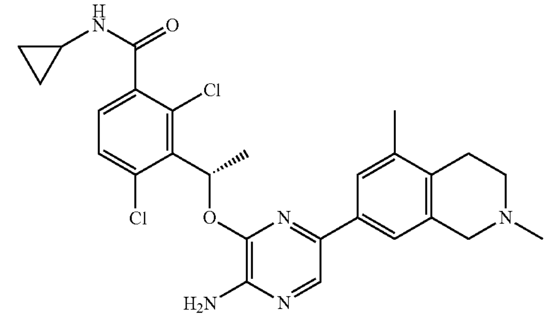
48
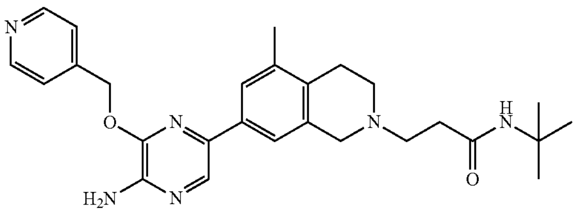
49
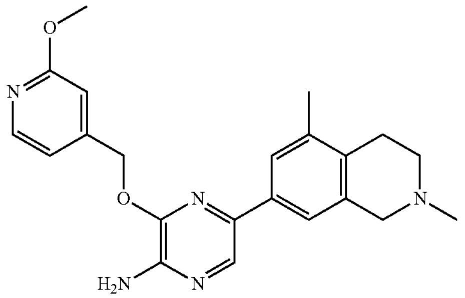
50
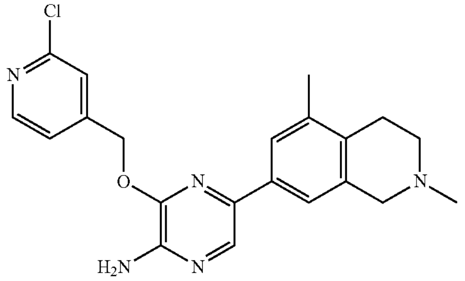
51
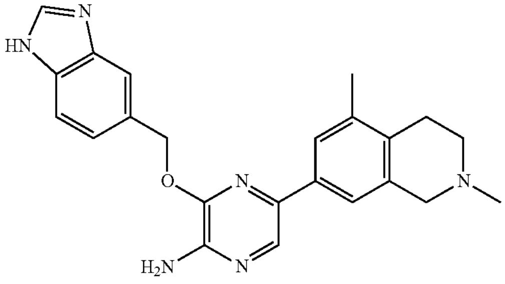
-continued
52
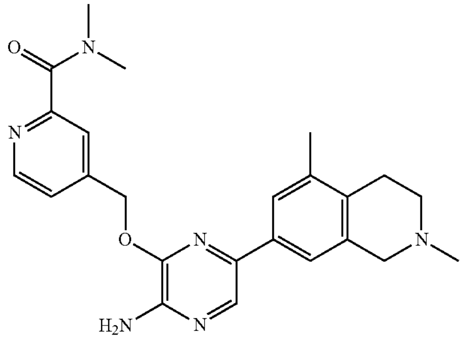
53
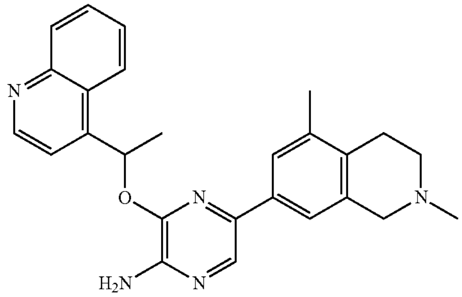
54
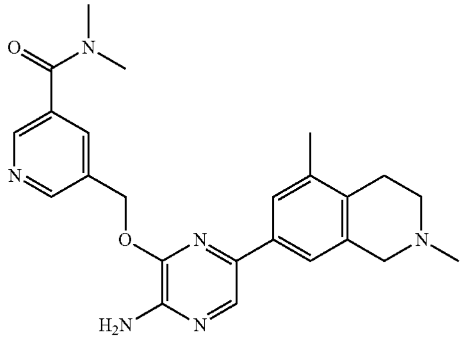
55
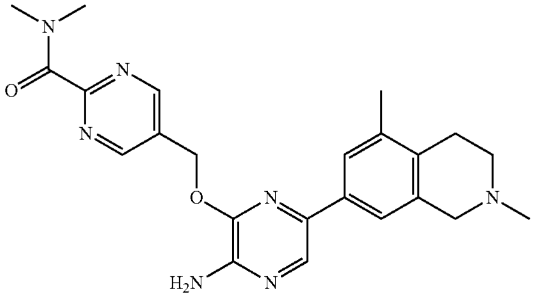
56
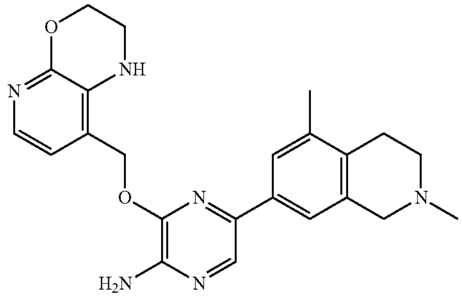

-continued
57
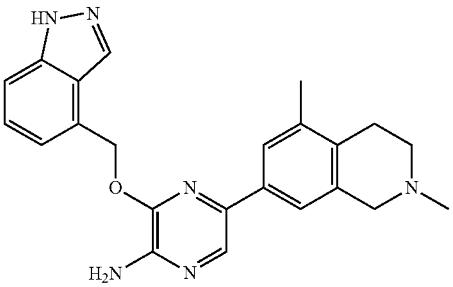
58
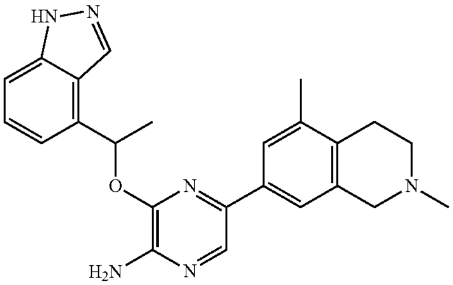
59
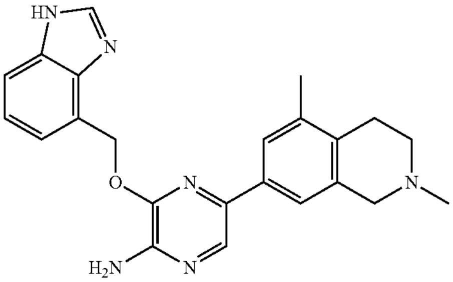
60
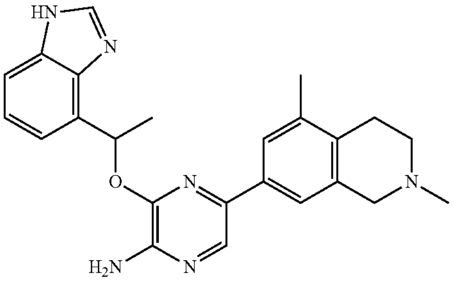
61
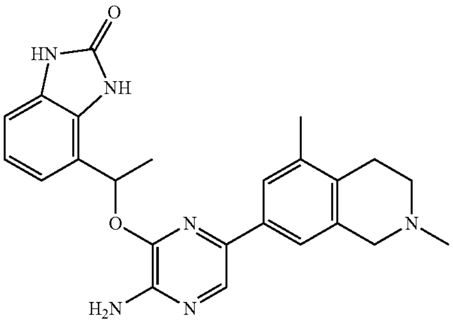
-continued
62
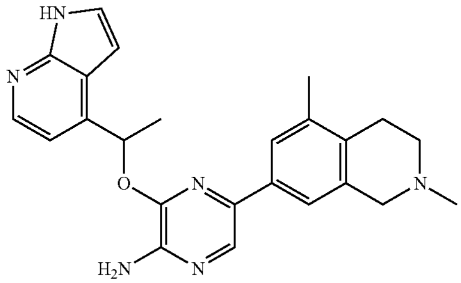
63
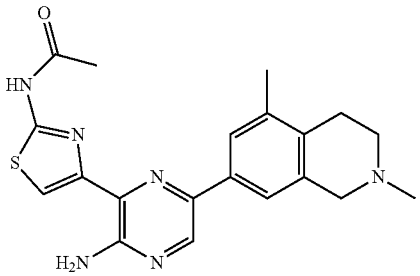
64
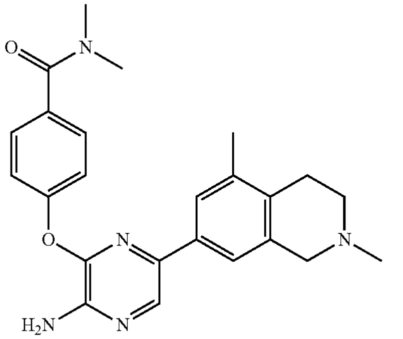
65
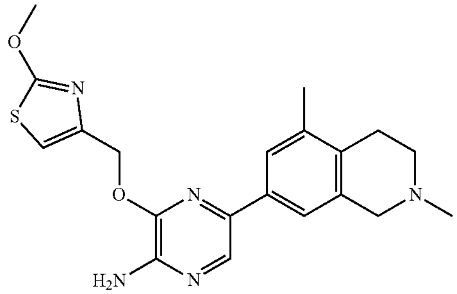
66
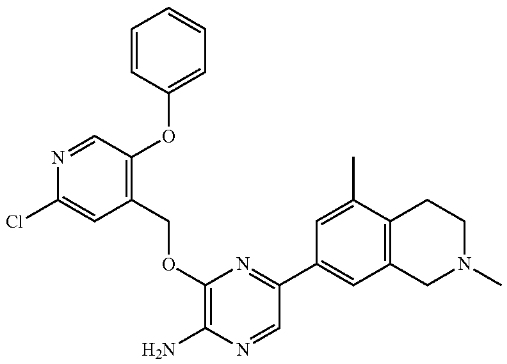

-continued
67
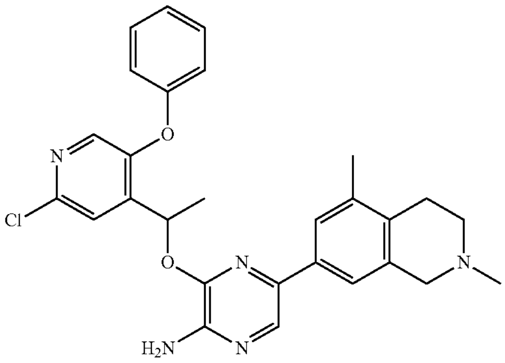
68
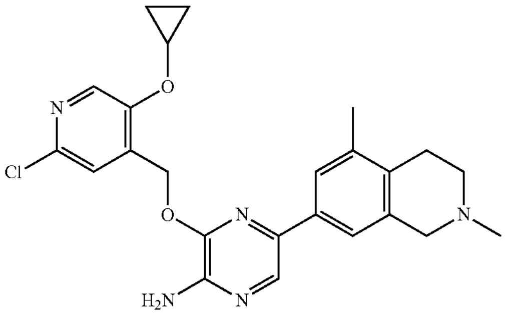
69
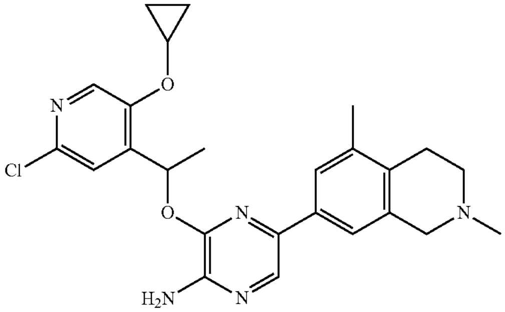
70
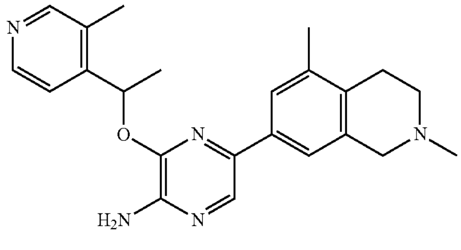
71
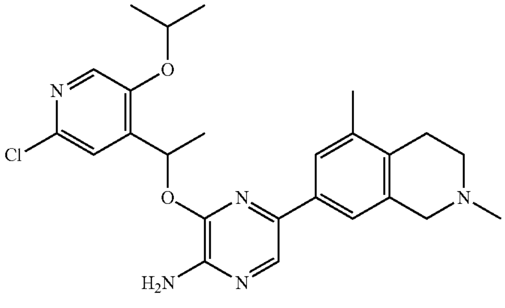
-continued
72
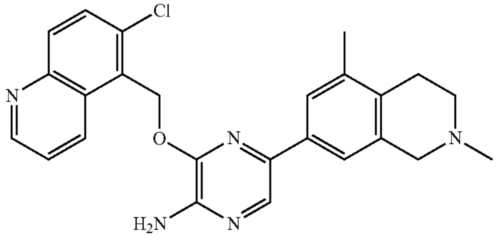
73
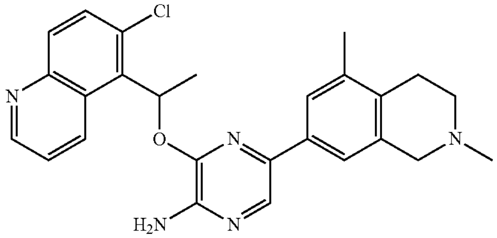
74
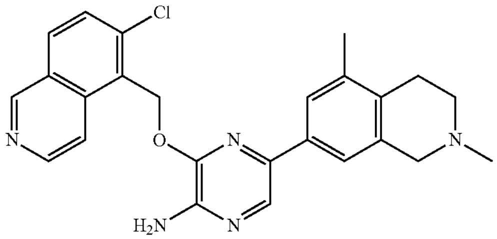
75
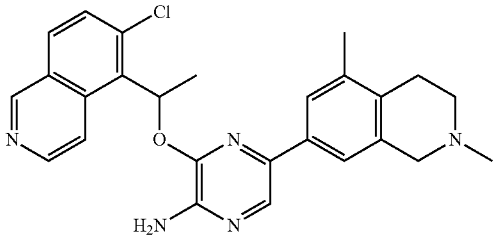
76
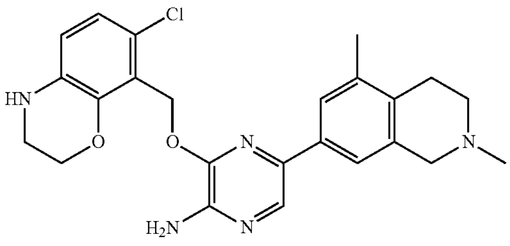
77
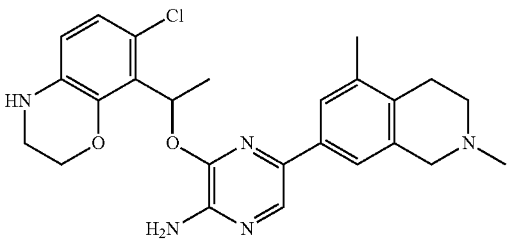

-continued
78
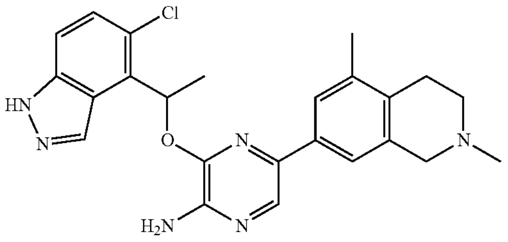
79
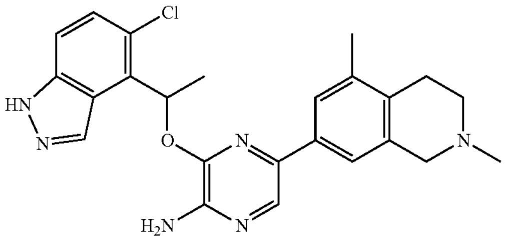
80
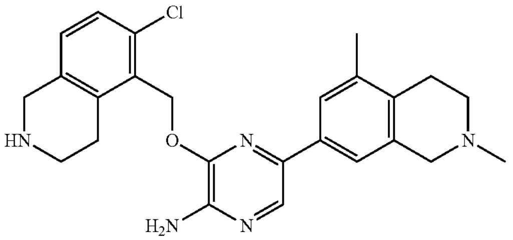
81
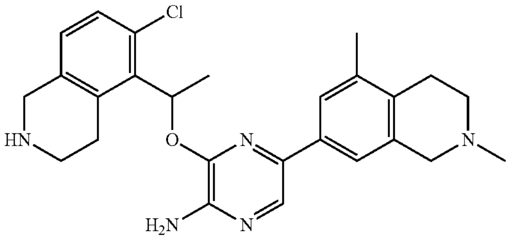
82
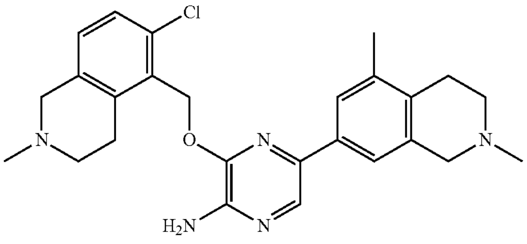
83
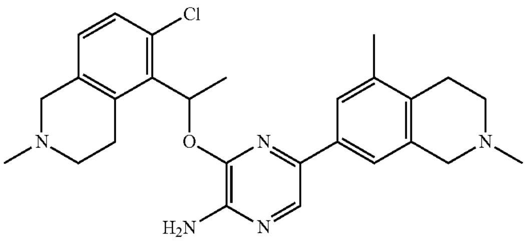
-continued
84
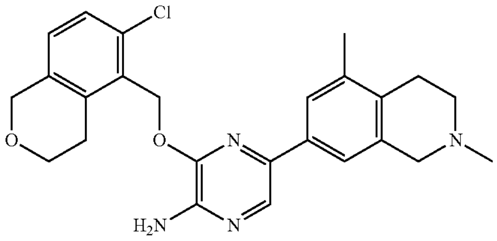
85
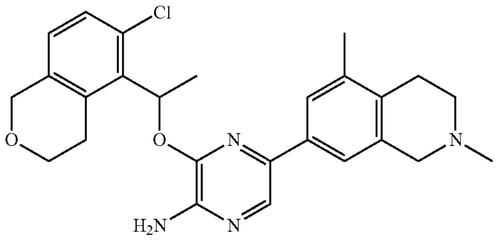
86
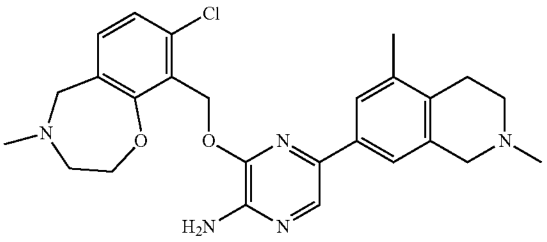
87
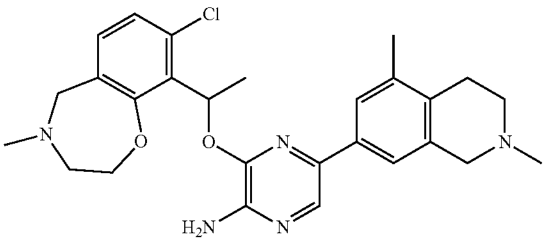
88
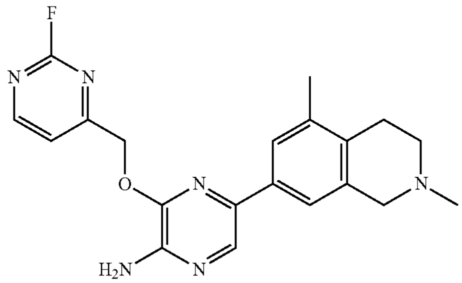
89
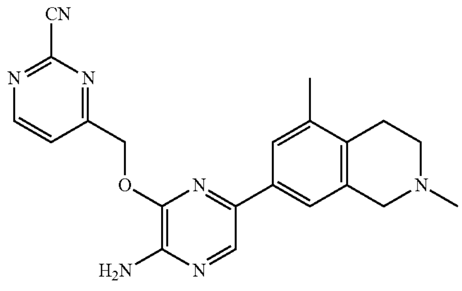

-continued
90
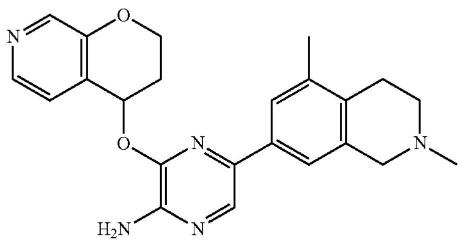
91
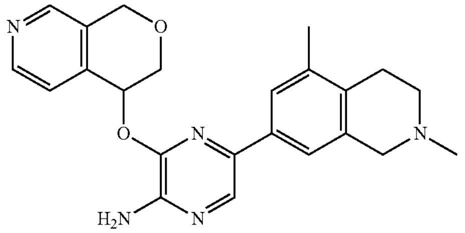
92
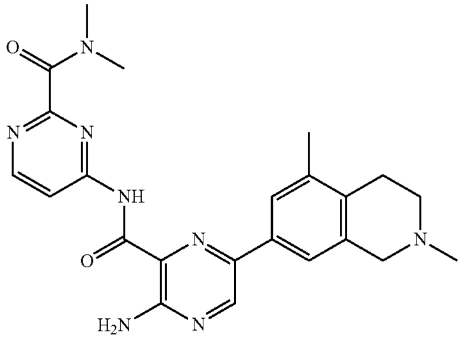
93
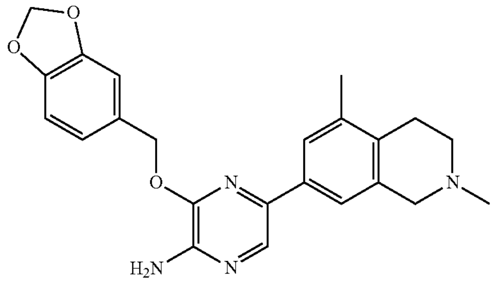
94
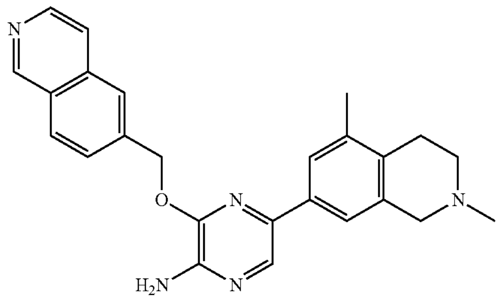
-continued
95
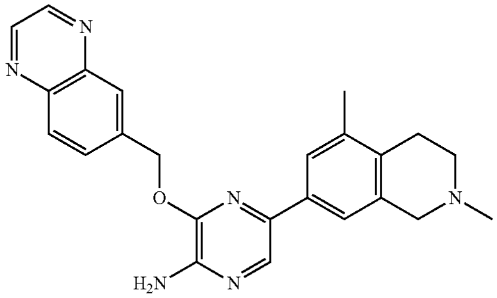
96
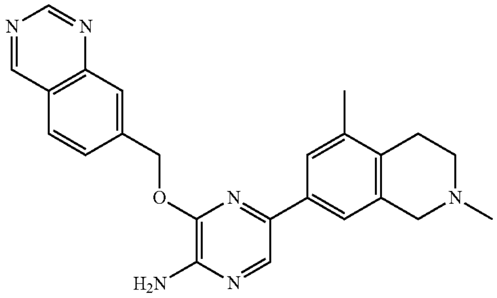
97
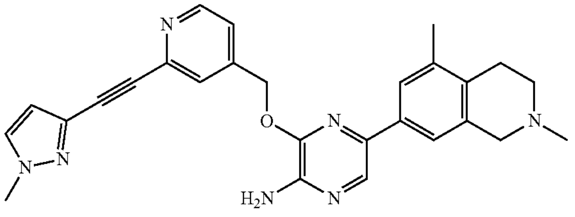
98
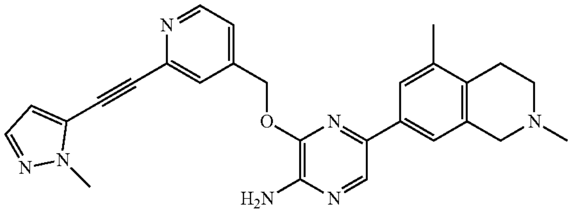
99
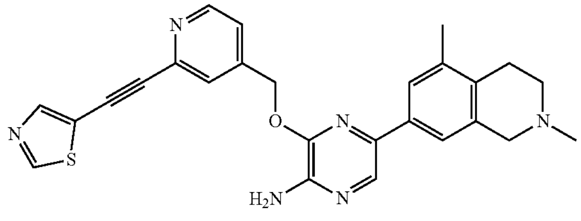
100
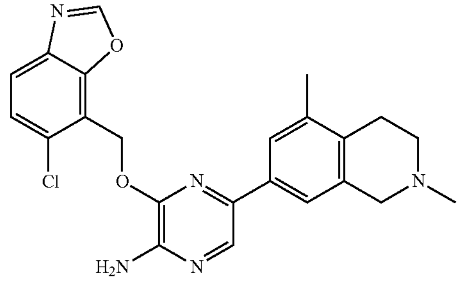

-continued
101
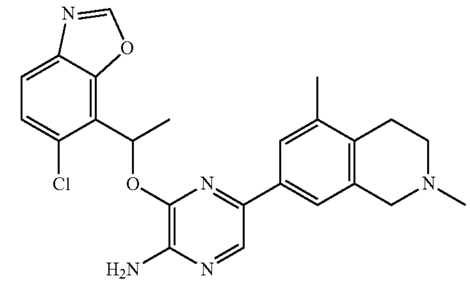
102
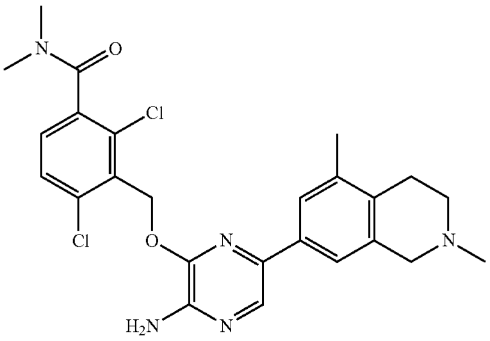
103
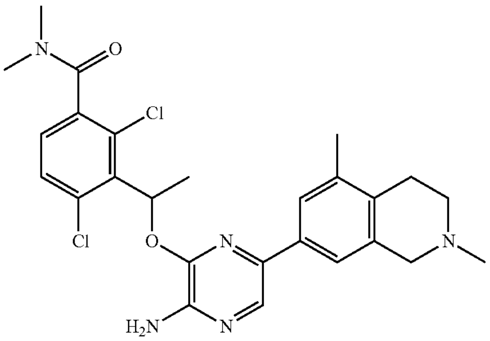
104
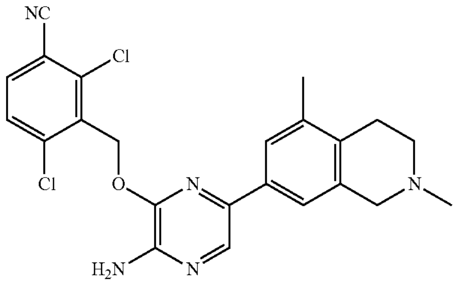
105
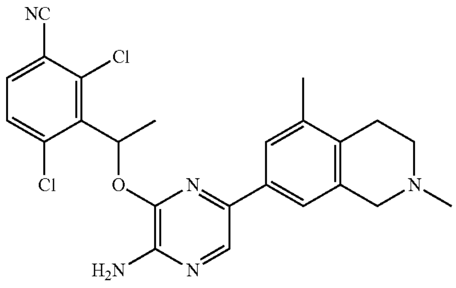
-continued
106
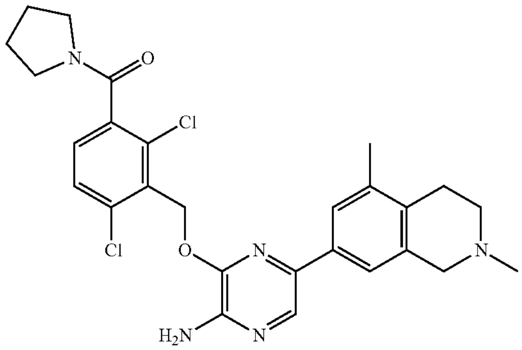
107
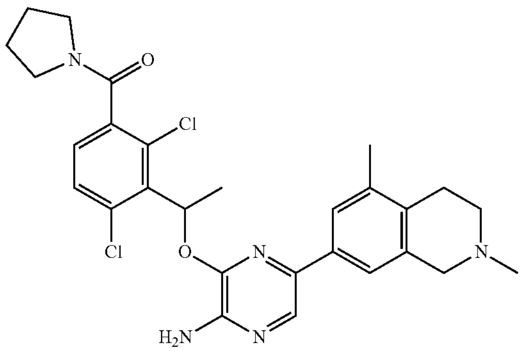
108
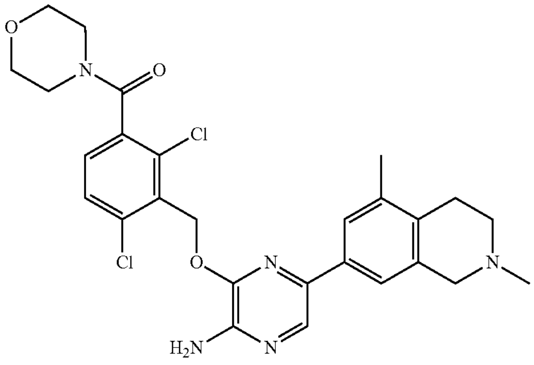
109
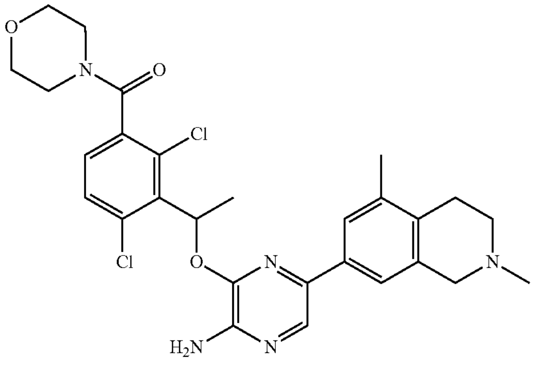

-continued
110
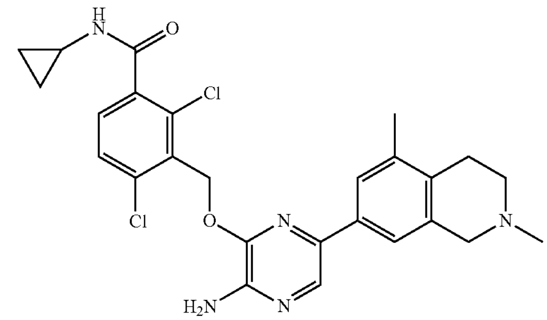
111
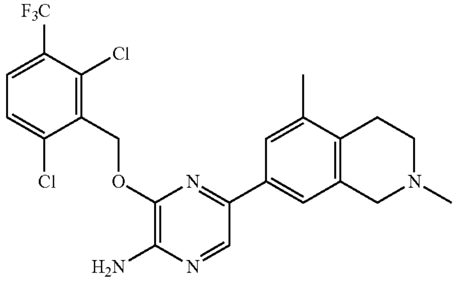
112
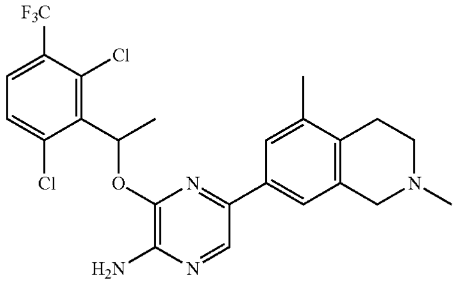
113
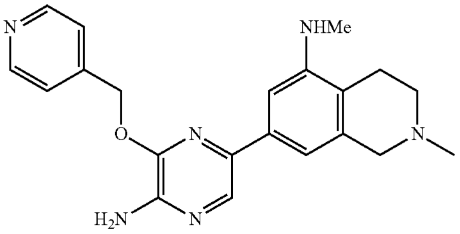
114
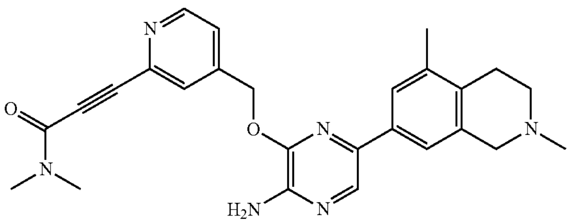
-continued
115
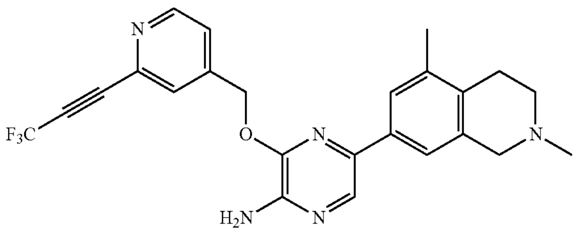
116
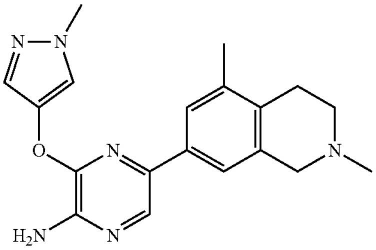
117
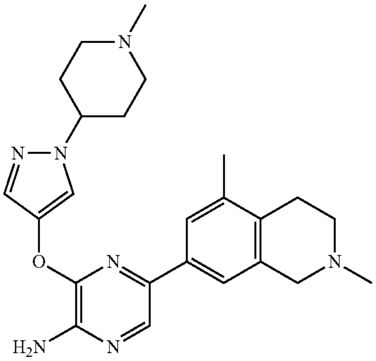
118
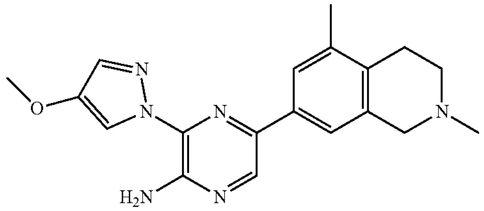
119
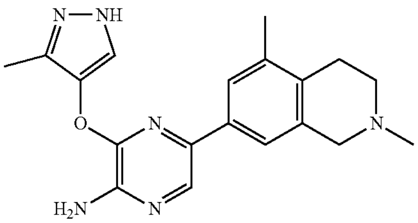
120
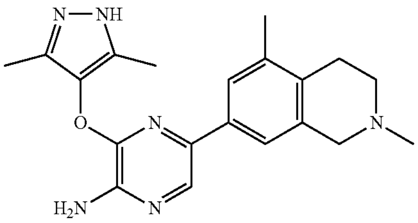

-continued
121
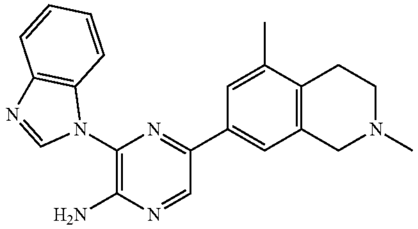
122
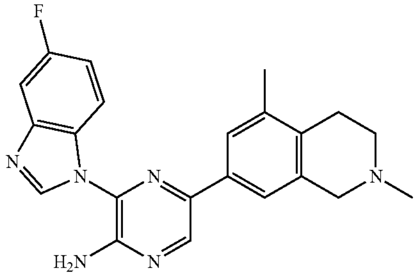
123
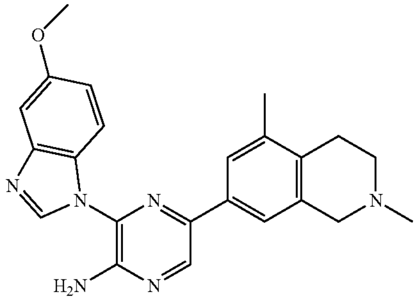
124
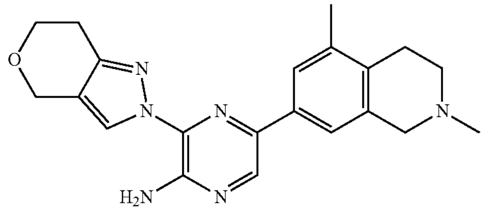
125
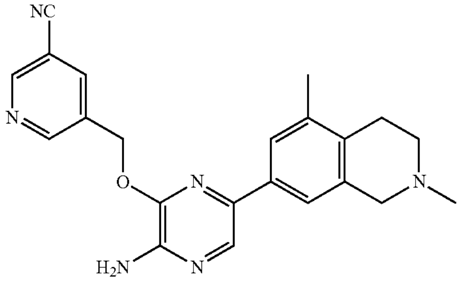
126
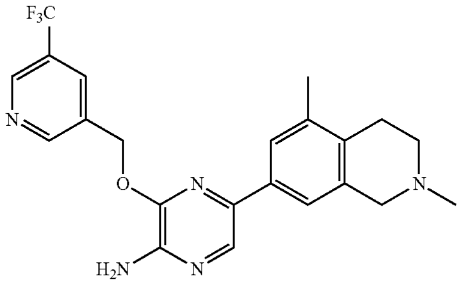
-continued
127
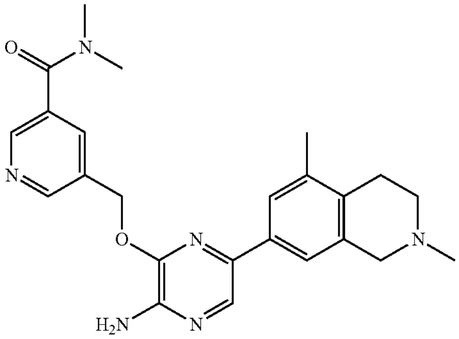
128
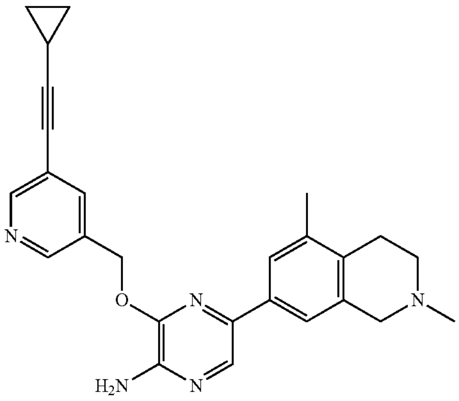
129
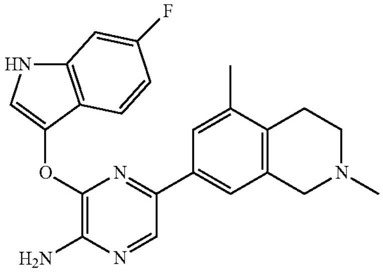
130
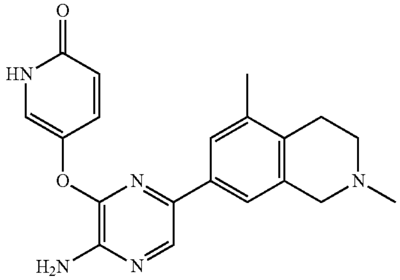
131
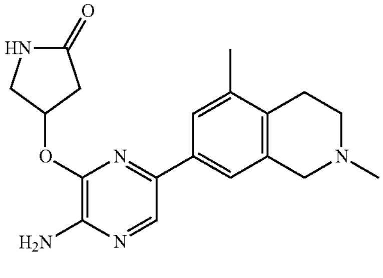

-continued
132
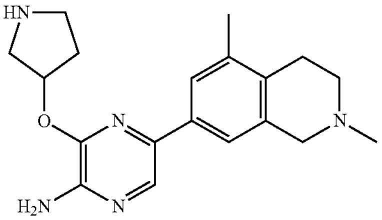
133
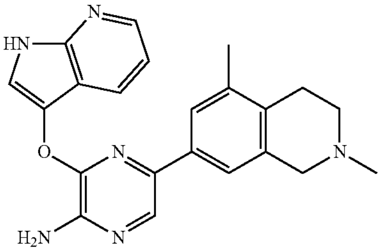
134
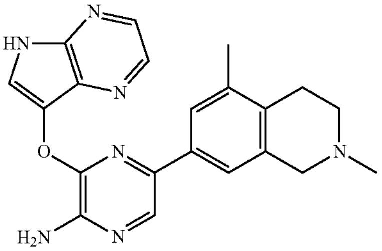
135
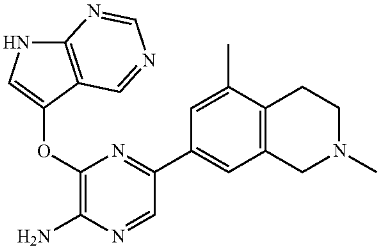
136
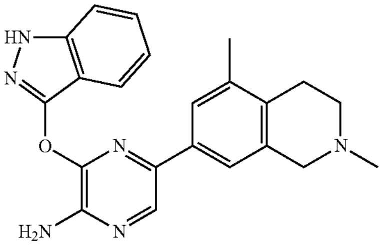
137
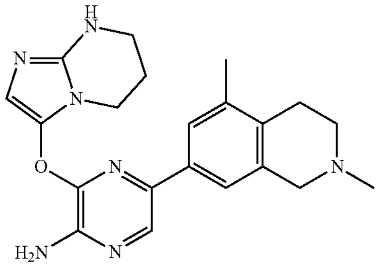
-continued
138
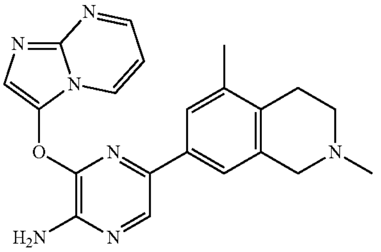
139
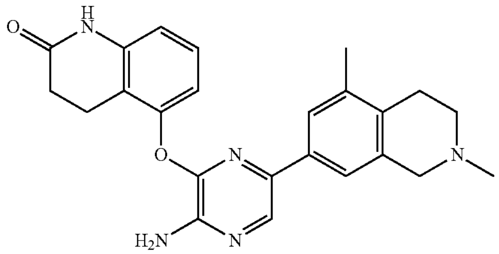
140
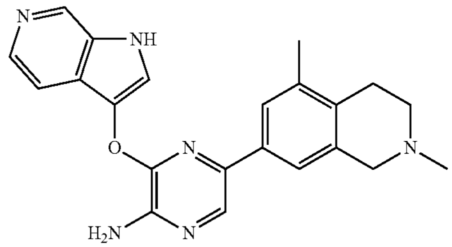
141
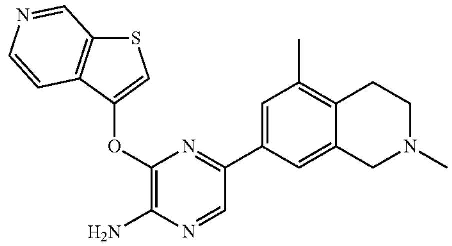
142
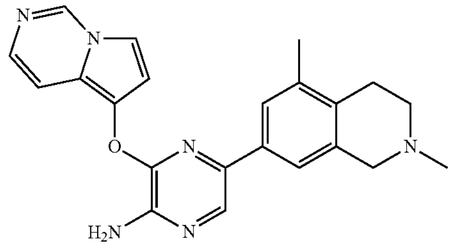
143
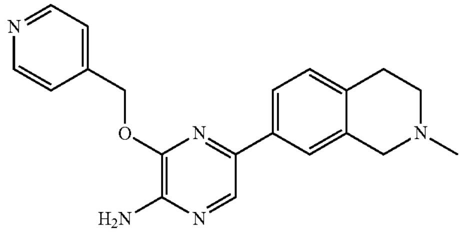

-continued
144
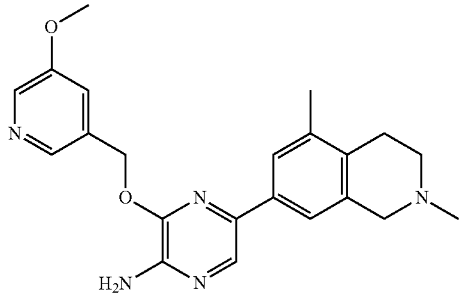
145
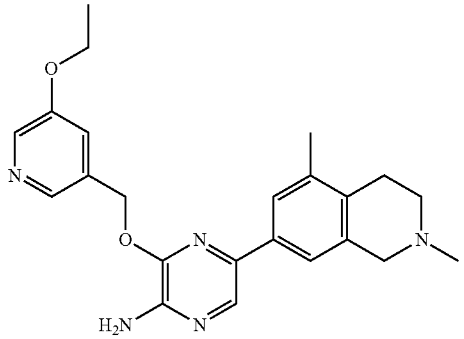
146
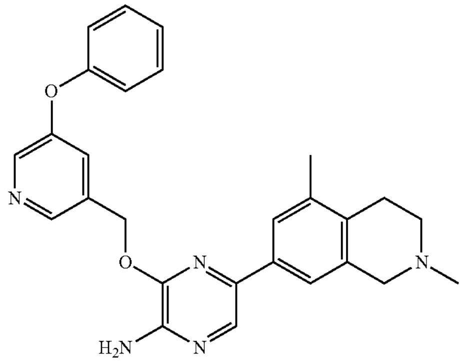
147
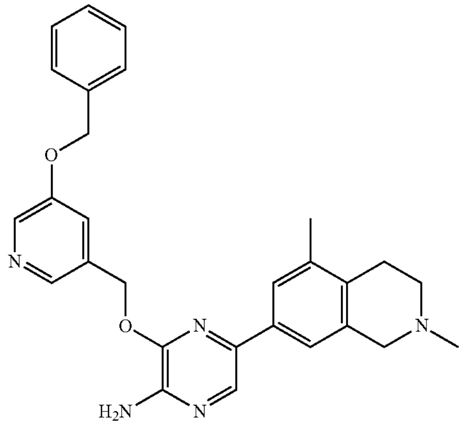
-continued
148
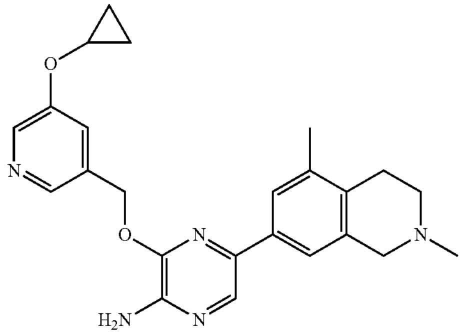
149
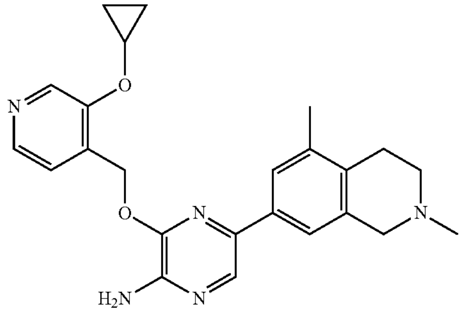
150
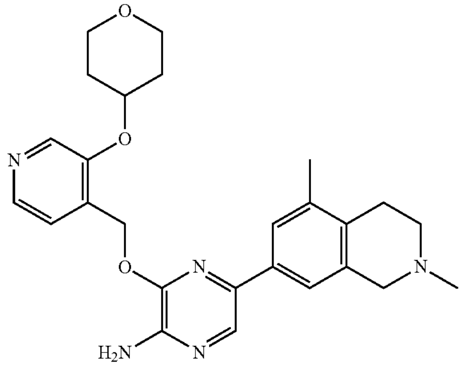
151
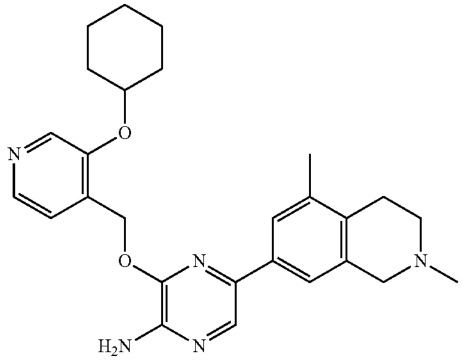

-continued
152
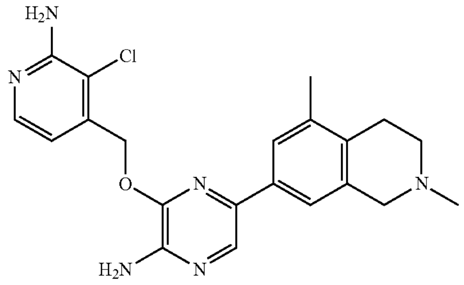
153
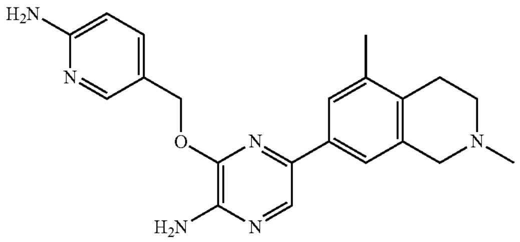
154
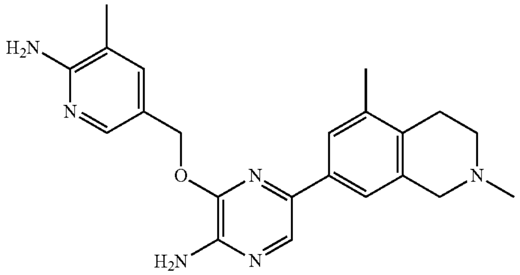
155
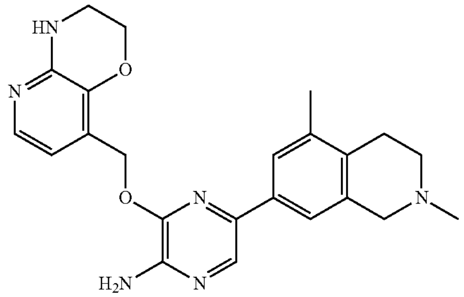
156
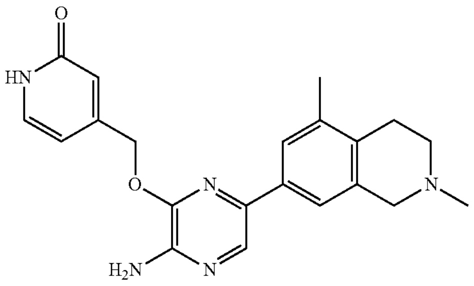
-continued
157
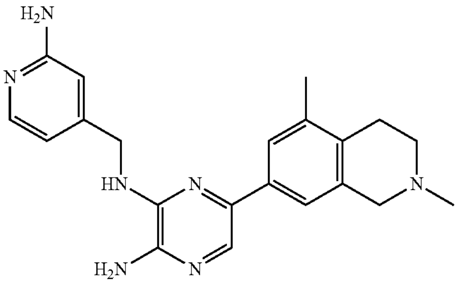
158
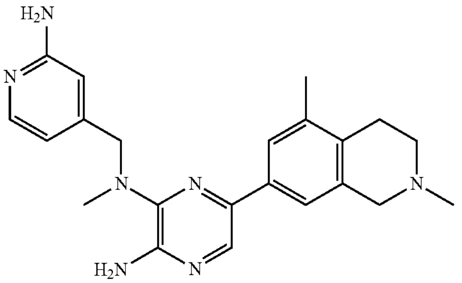
159
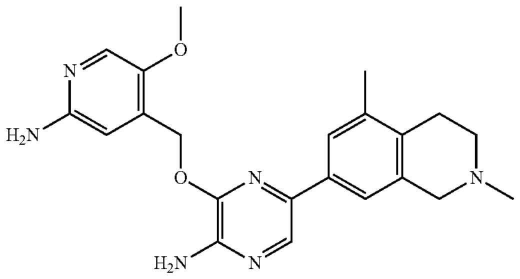
160
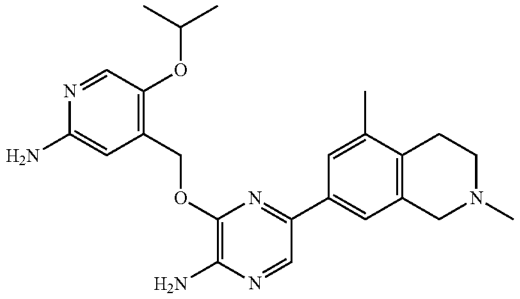
161
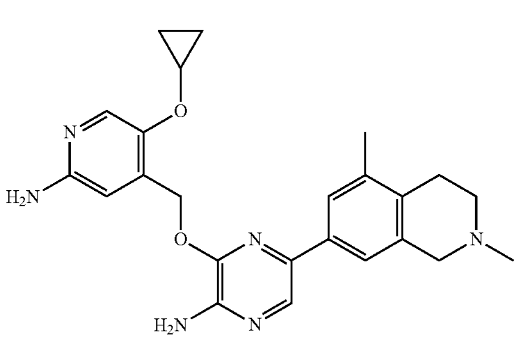

-continued
162
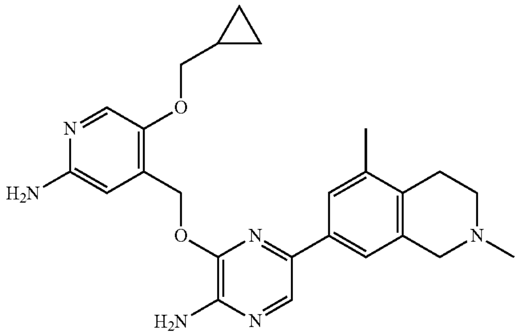
163
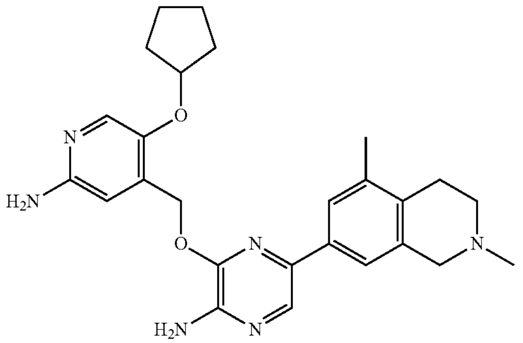
164
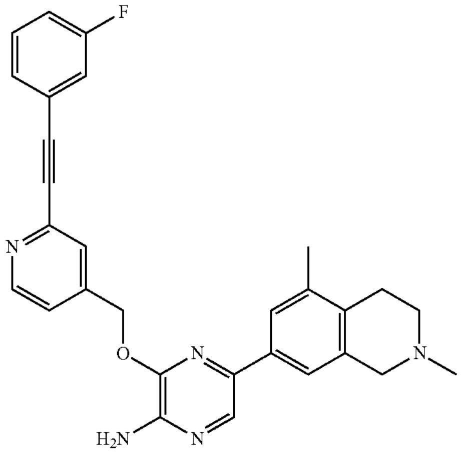
165
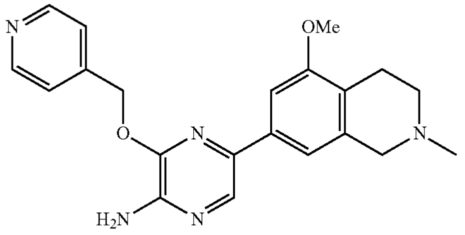
-continued
166
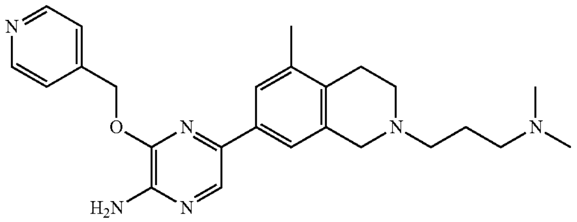
167
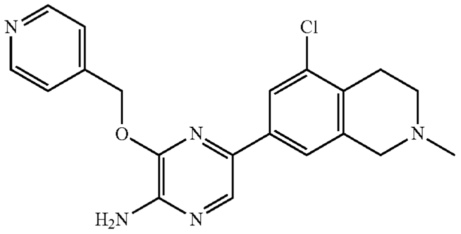
168
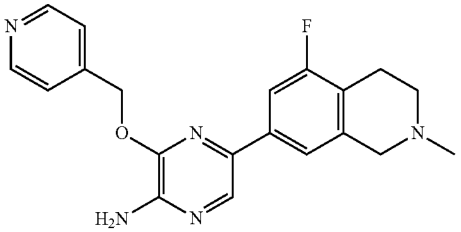
169
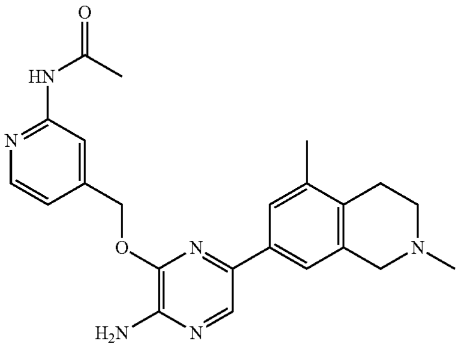
170
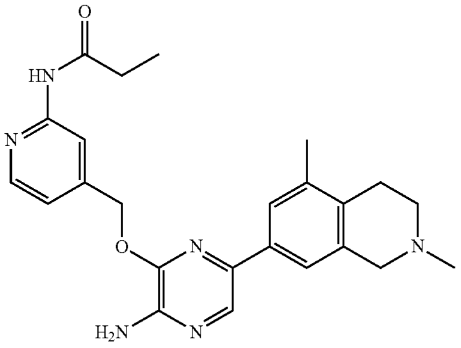

-continued
171
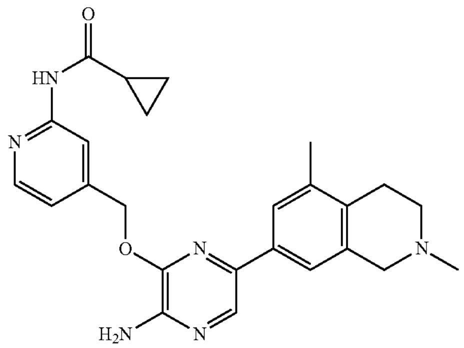
172
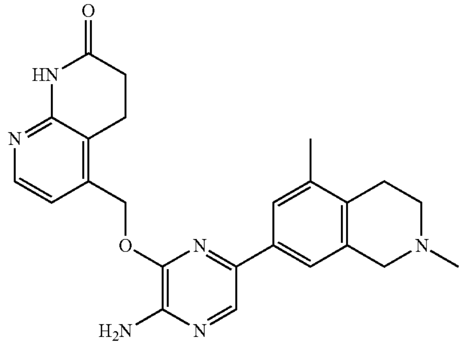
173
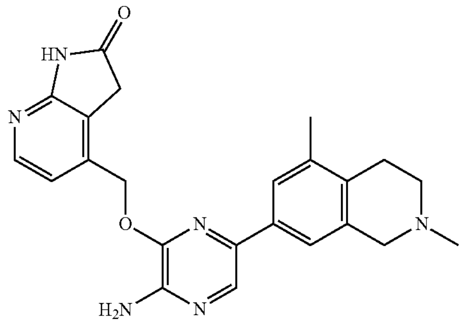
174
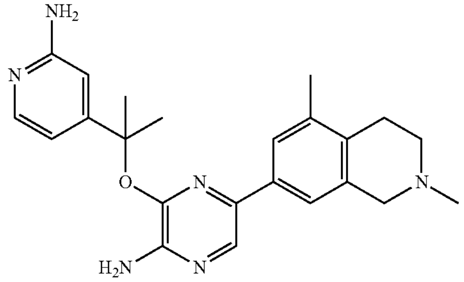
175
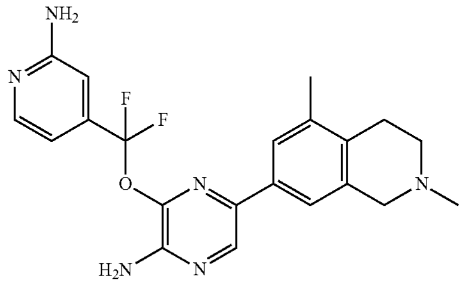
-continued
176
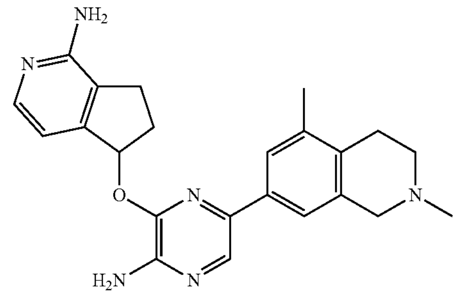
177
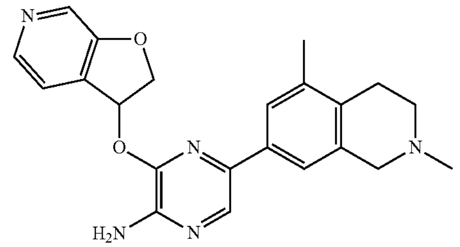
178
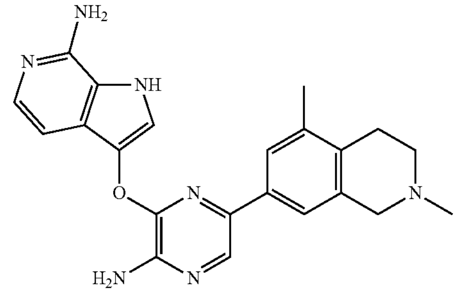
179
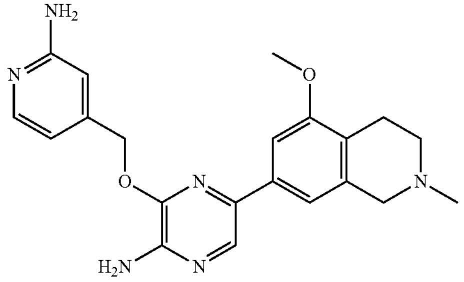
180
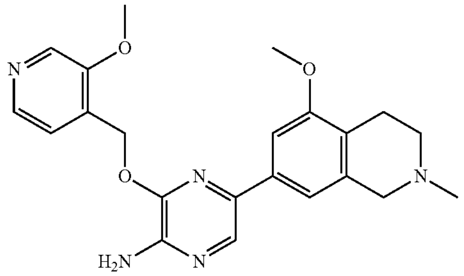

-continued
181
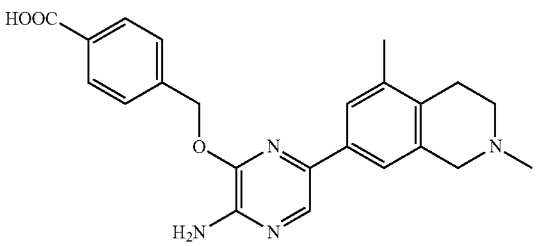
182
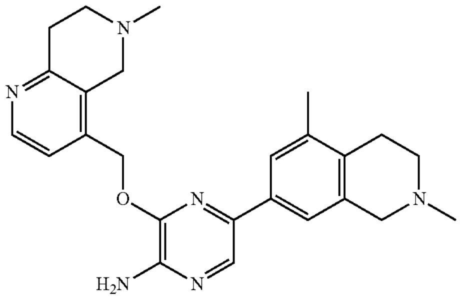
183
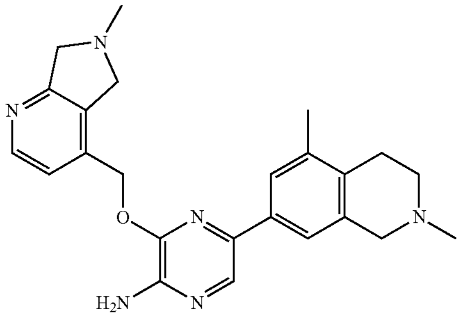
184
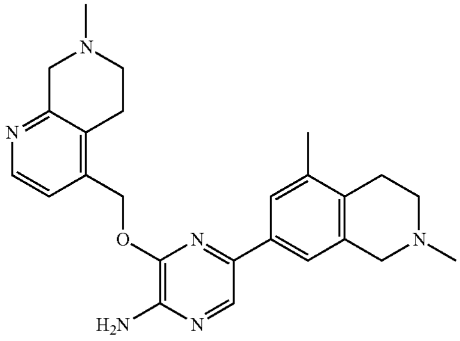
185
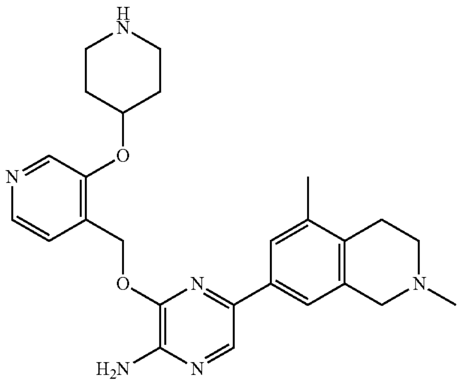
-continued
186
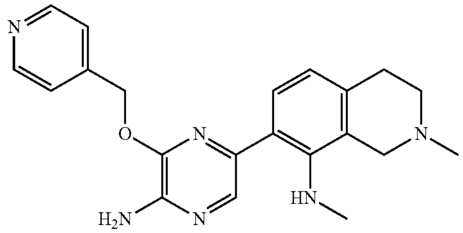
187
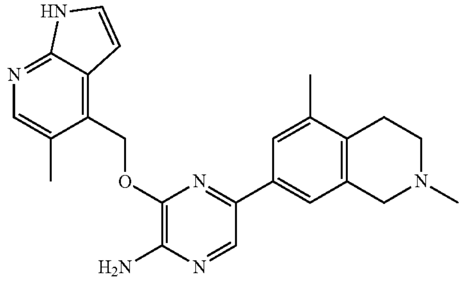
188
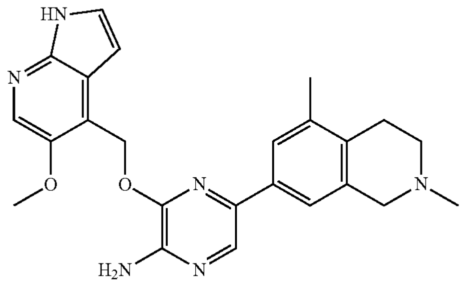
189
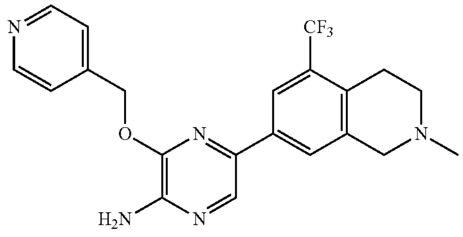
190
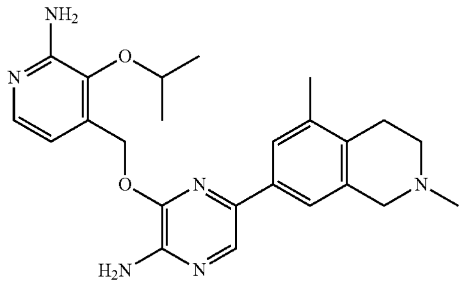

-continued
191
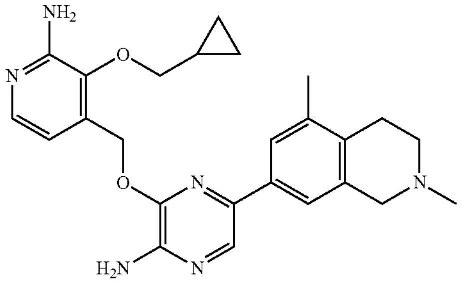
192
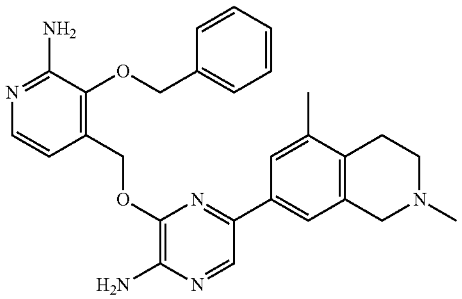
193
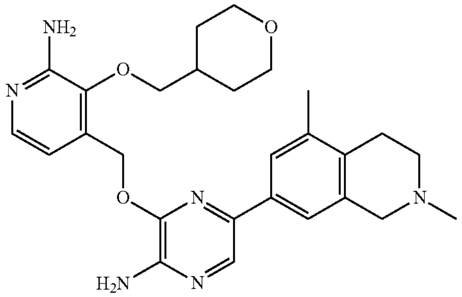
194
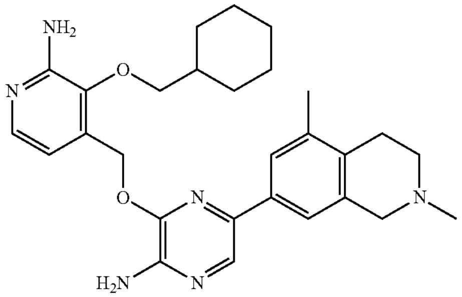
195
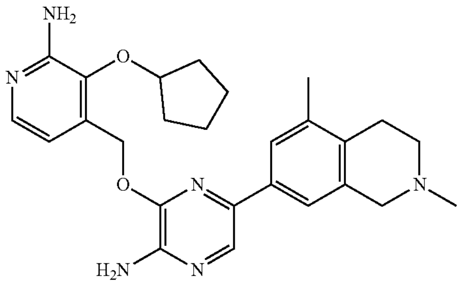
-continued
196
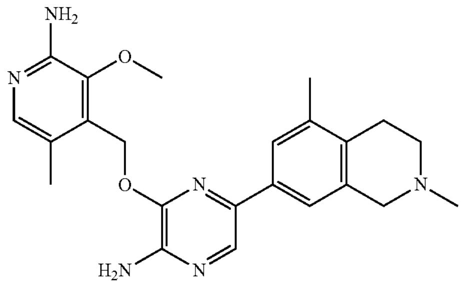
197
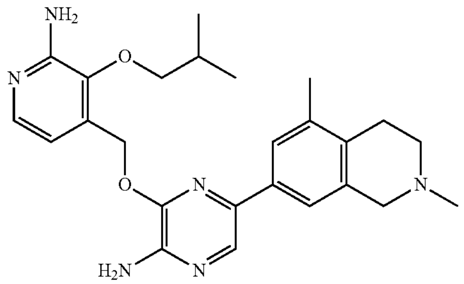
198
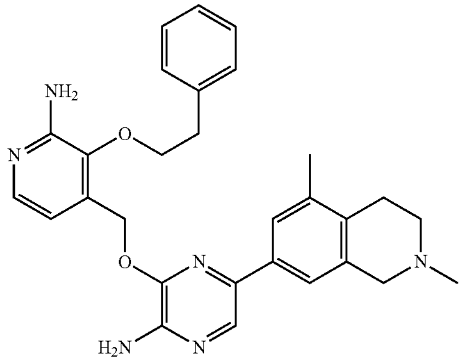
199
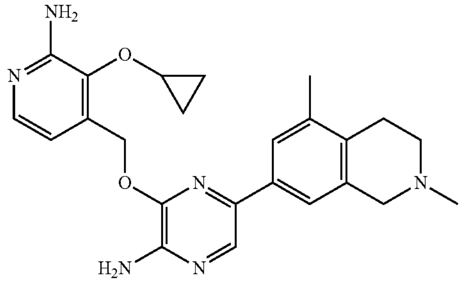
200
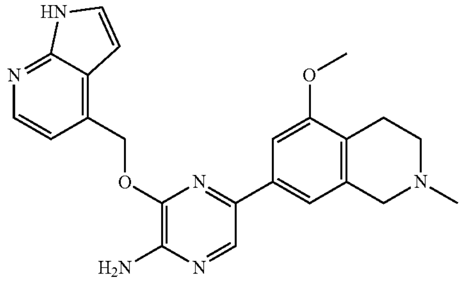

-continued
201
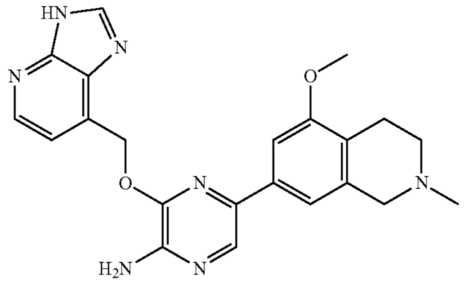
202
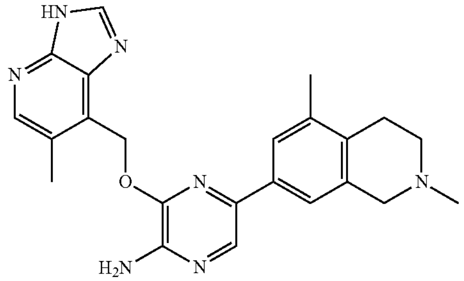
203
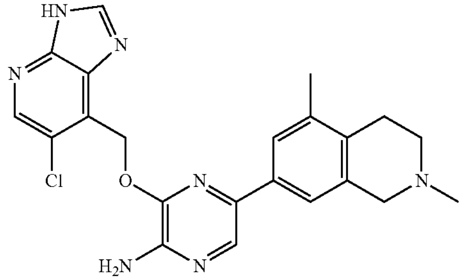
204
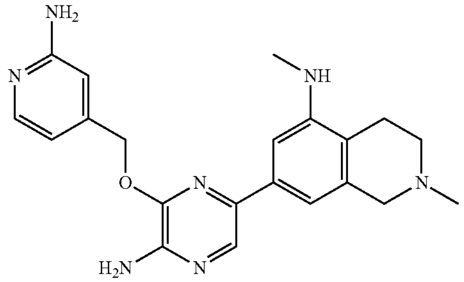
205
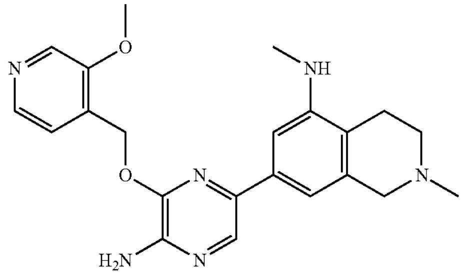
-continued
206
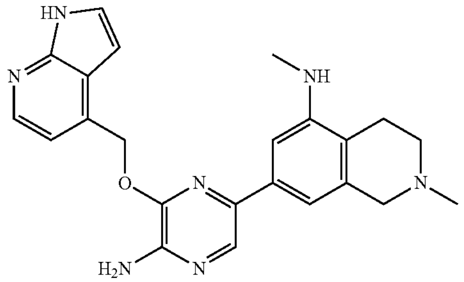
207
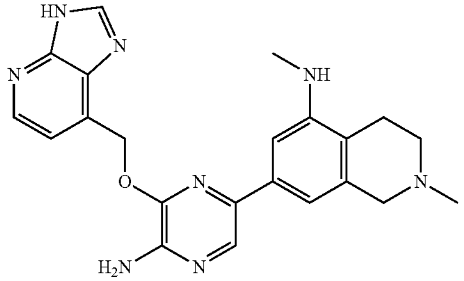
208
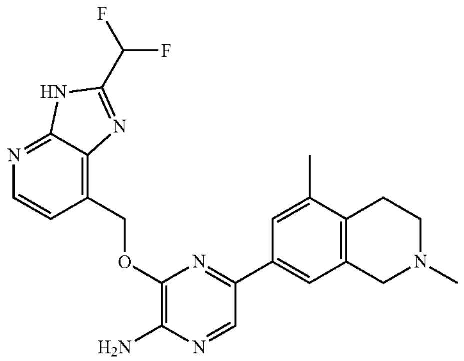
209
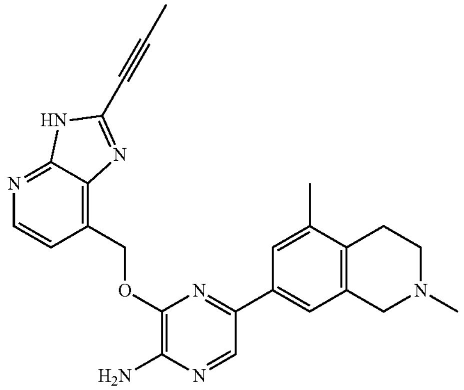

-continued
210
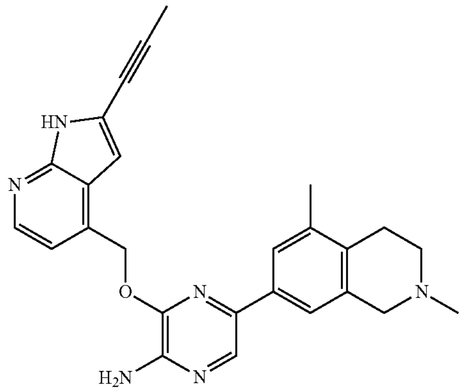
221
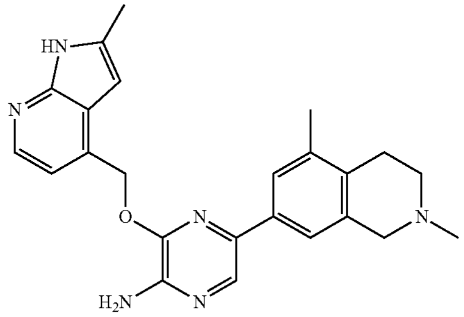
222
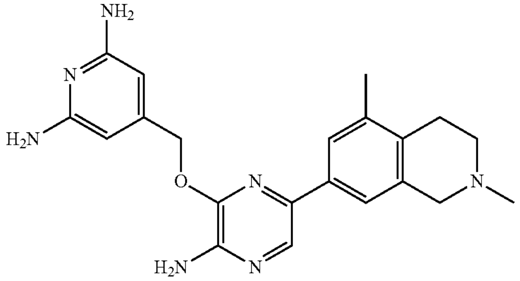
223
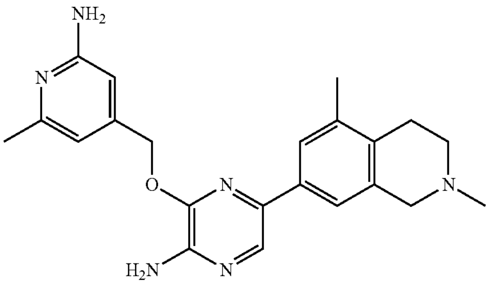
224
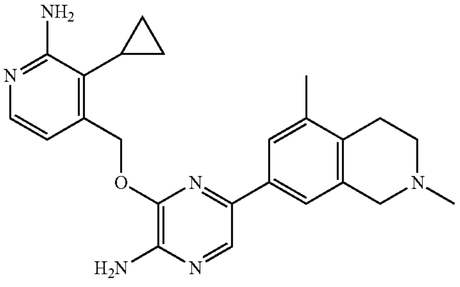
-continued
225
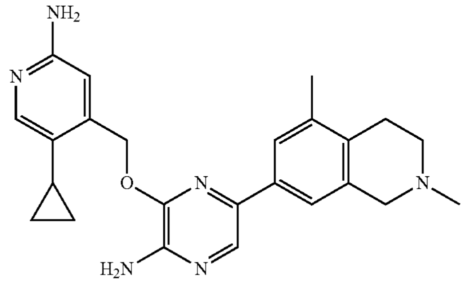
226
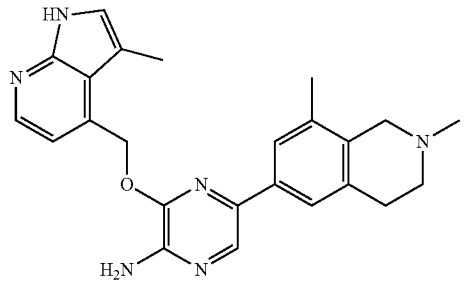
227
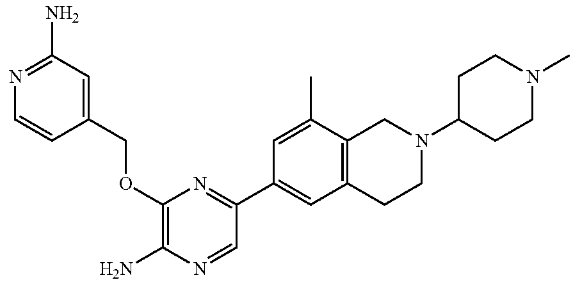
228
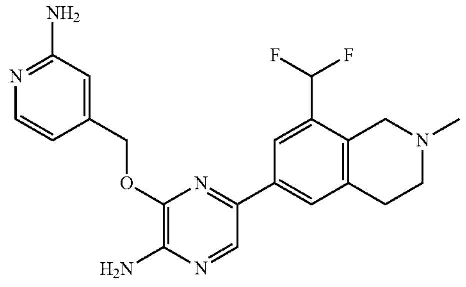
229
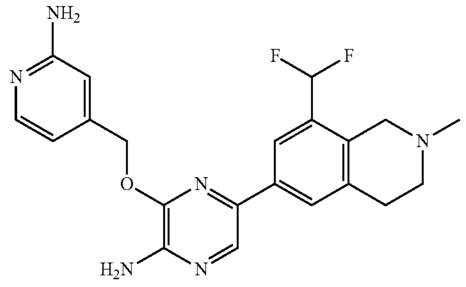

230
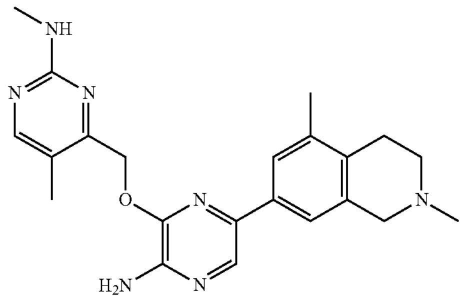
231
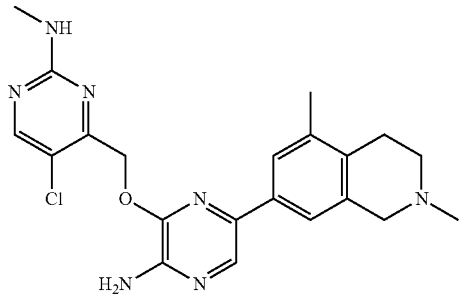
232
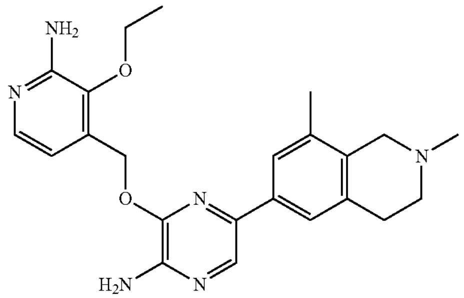
233
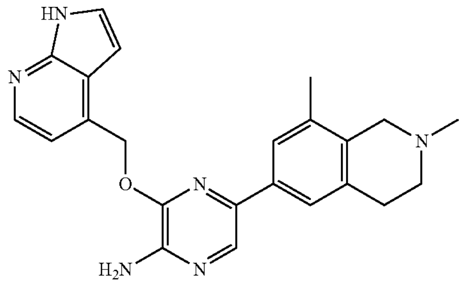
234
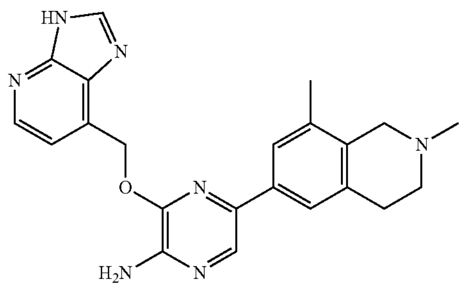
235
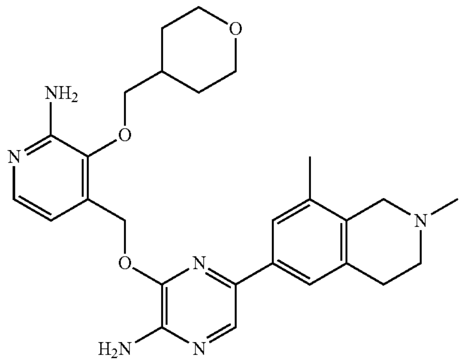
236
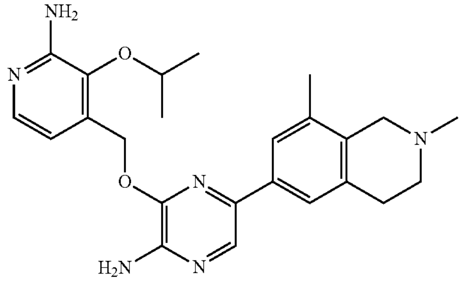
237
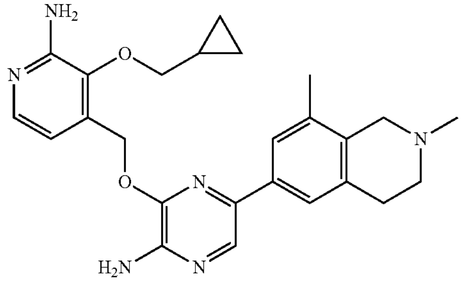
238
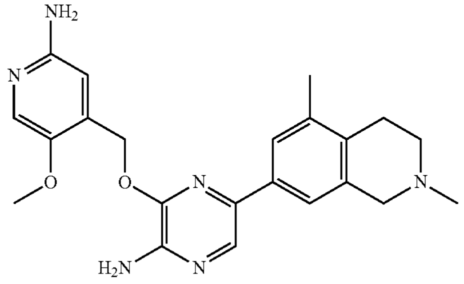
239
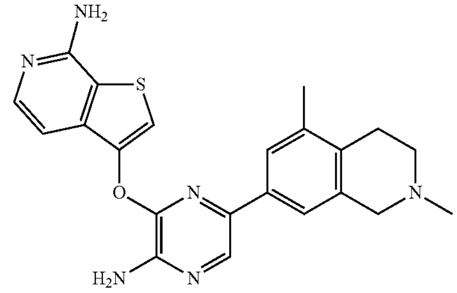

-continued
240
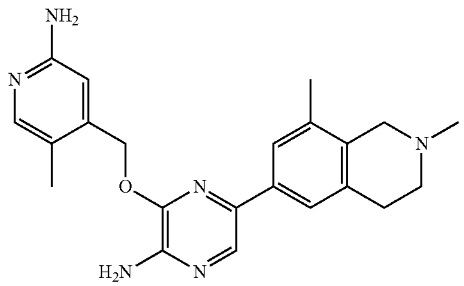
241
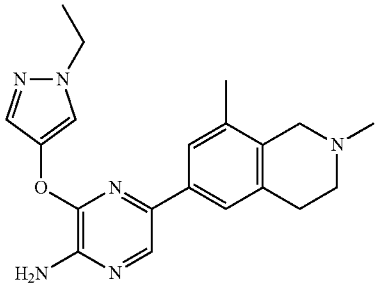
242
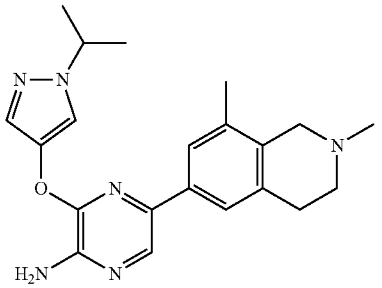
243
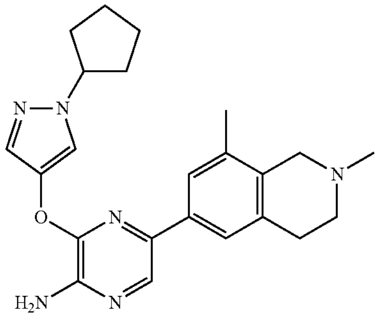
244
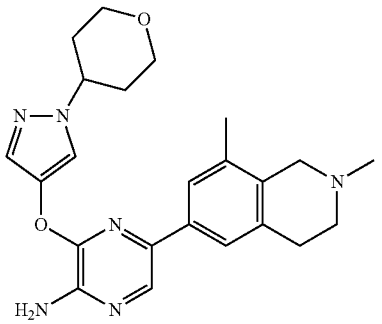
-continued
245
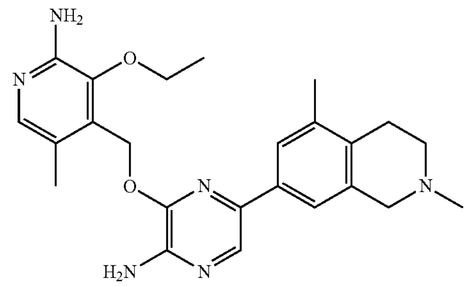
246
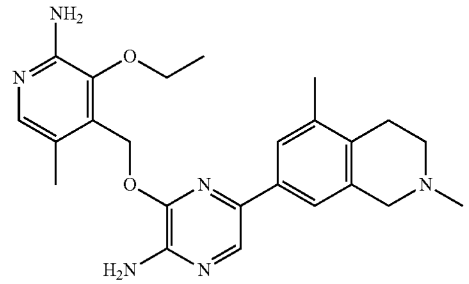
247
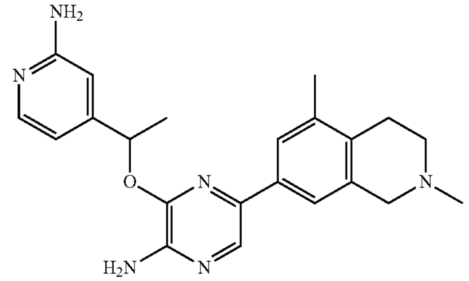
248
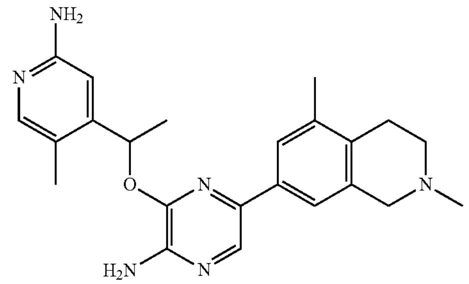
249
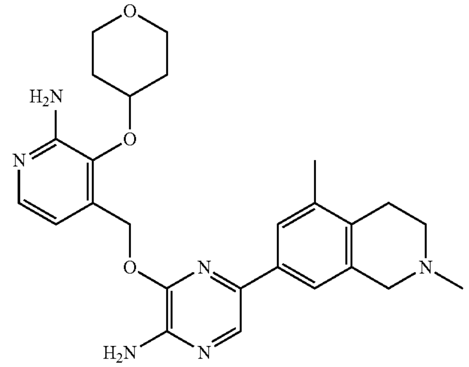

-continued
250
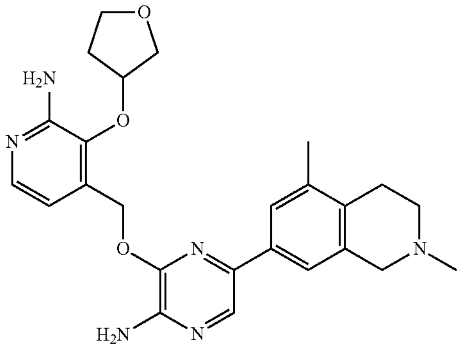
251
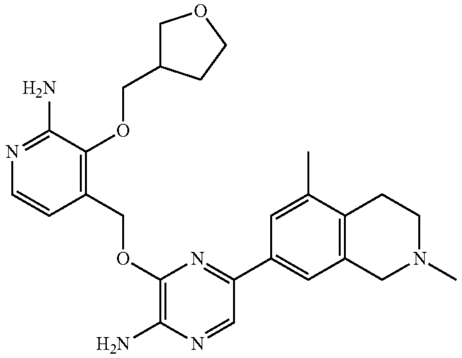
252
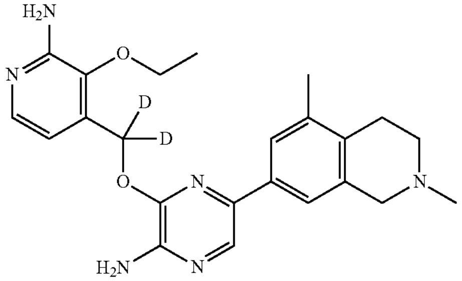
253
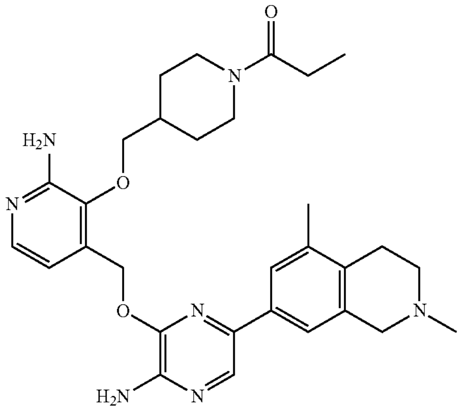
-continued
254
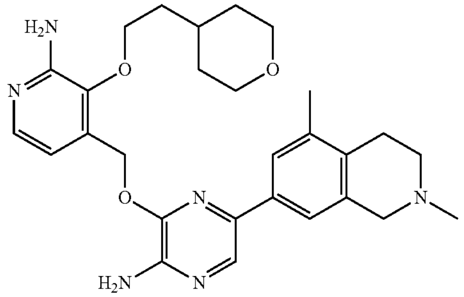
255
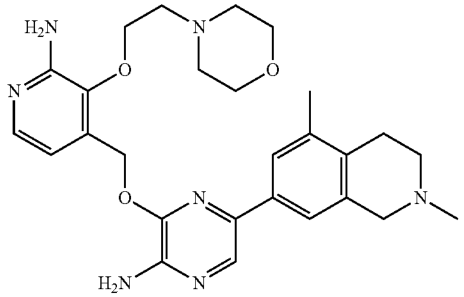
256
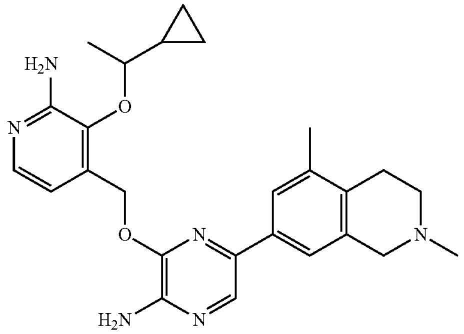
257
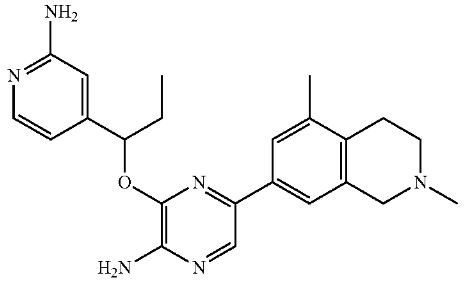
258
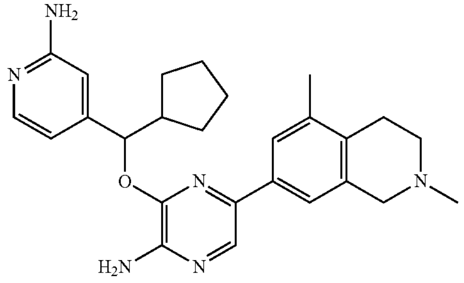

-continued
259
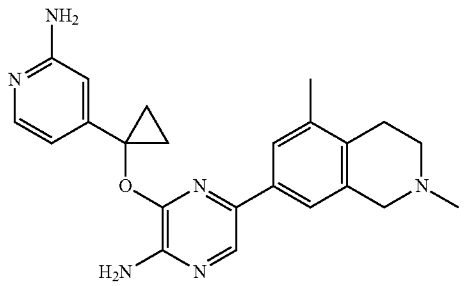
260
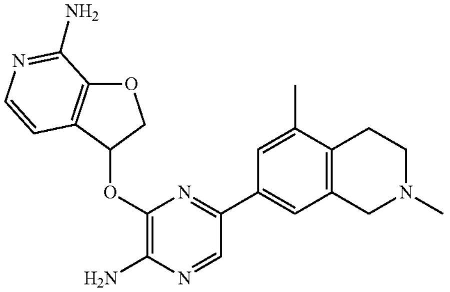
261
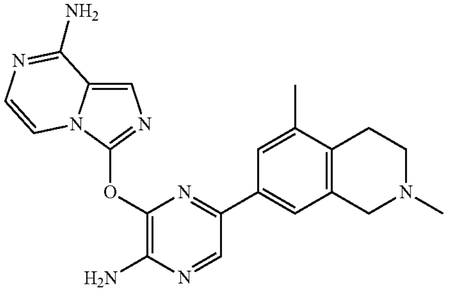
262
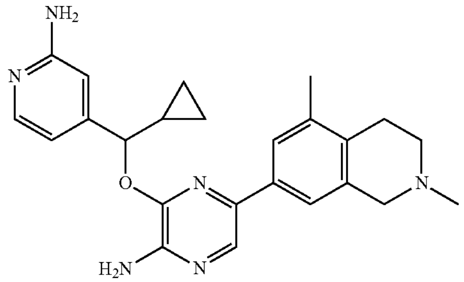
263
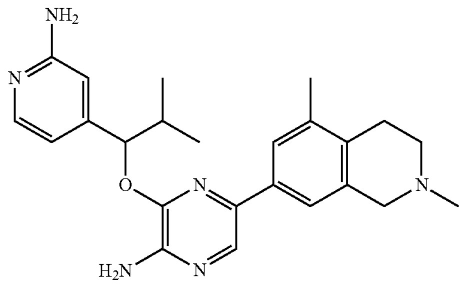
-continued
264
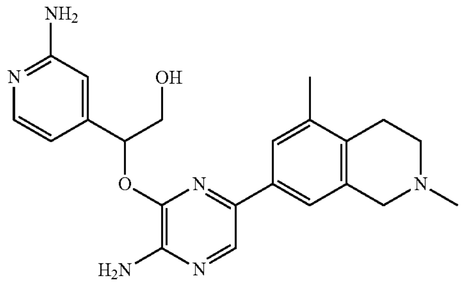
265
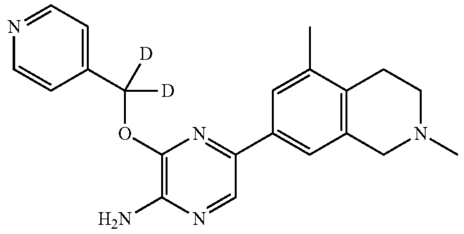
266
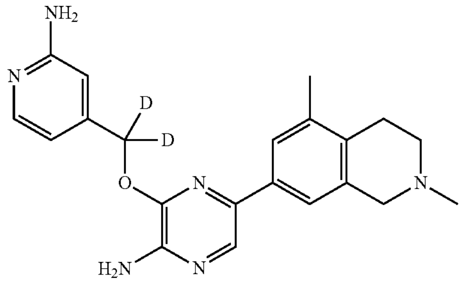
267
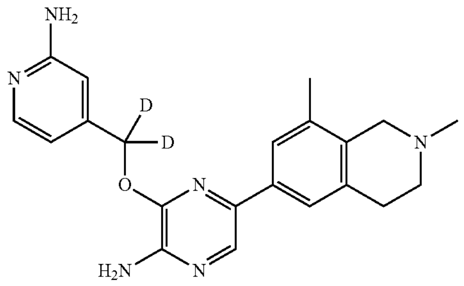
268
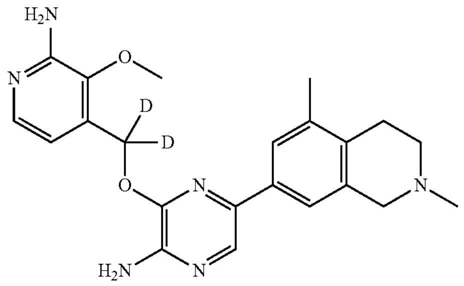

-continued
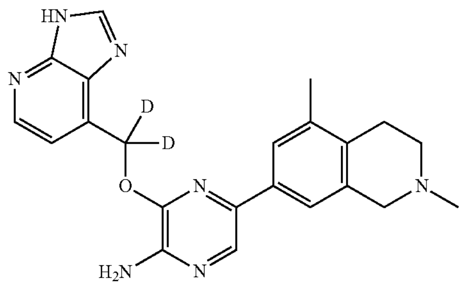
269
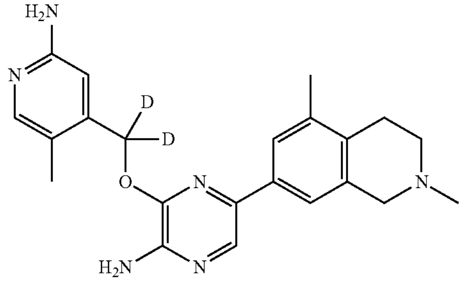
270
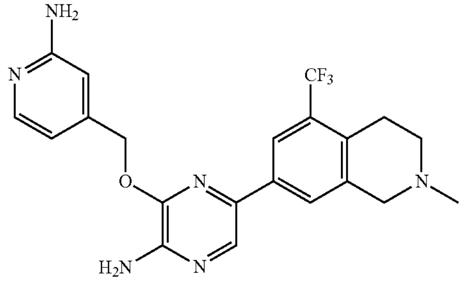
271
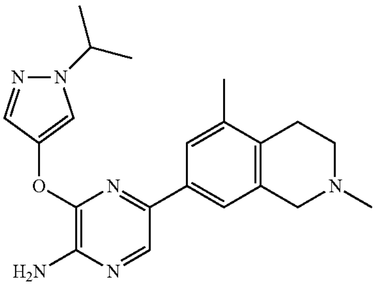
272
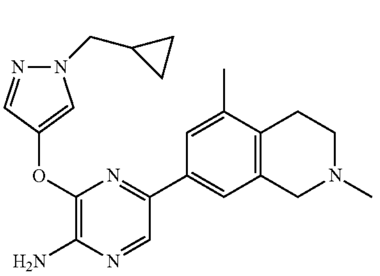
273
-continued
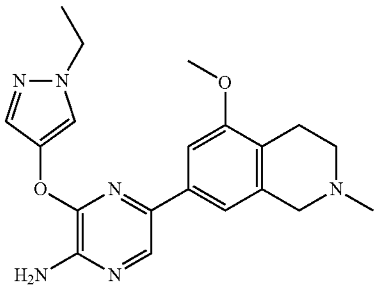
274
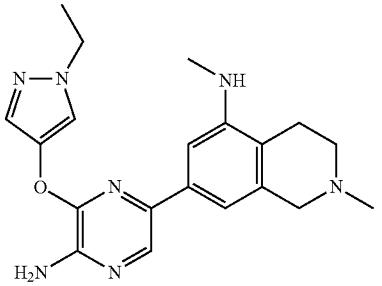
275
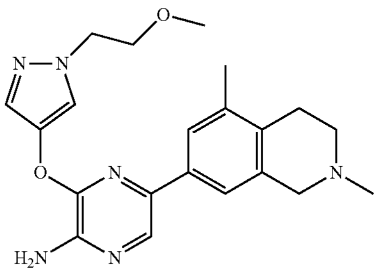
276
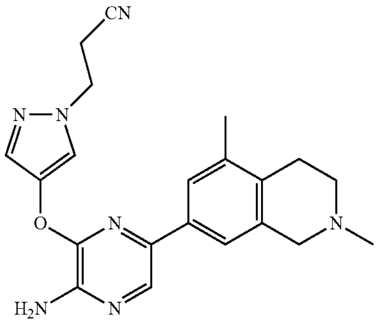
277
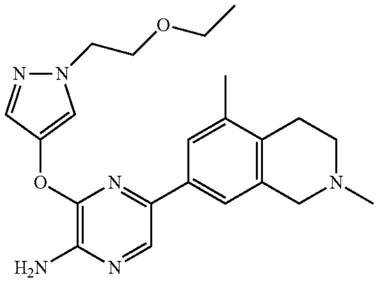
278

-continued
279
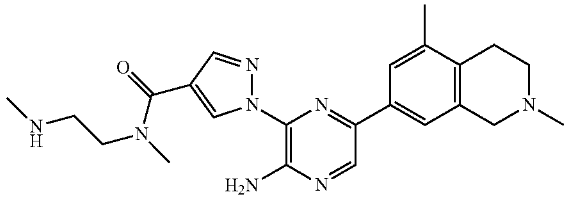
280A
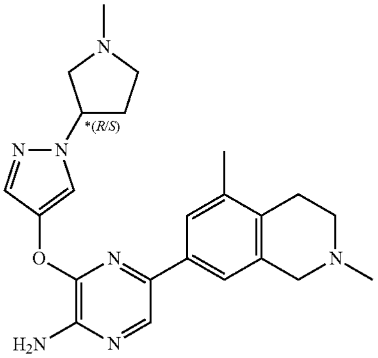
280B
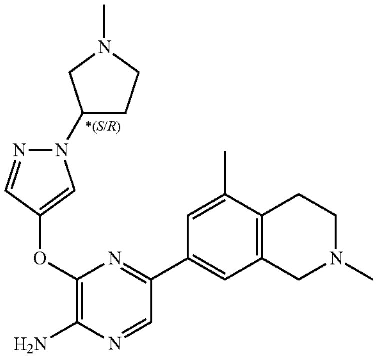
281
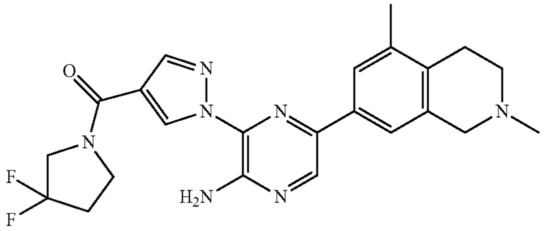
282
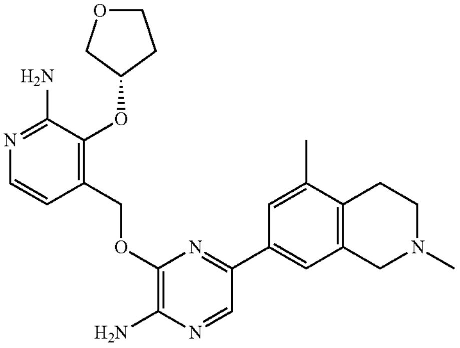
-continued
283
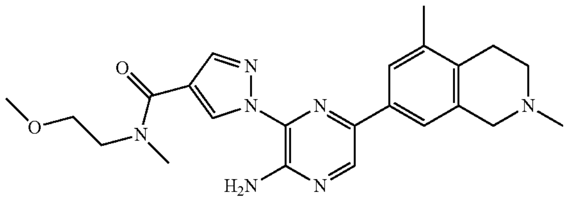
284
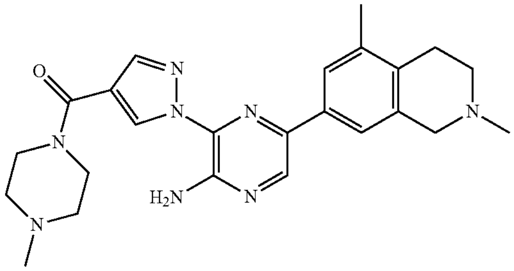
285
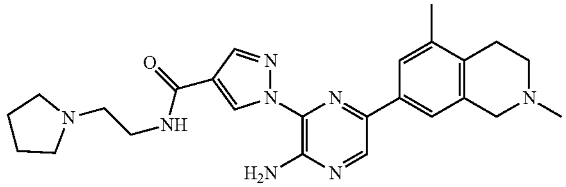
286
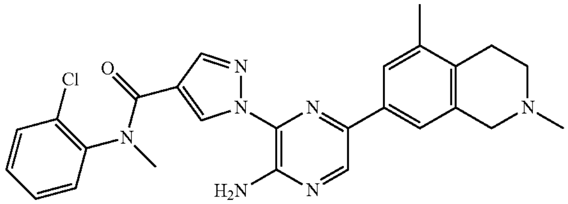
287
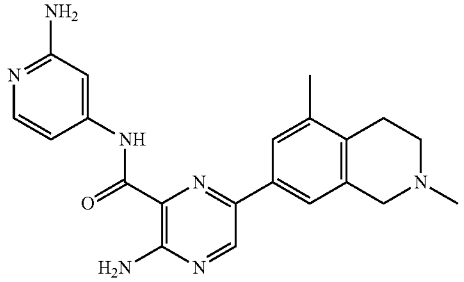
288
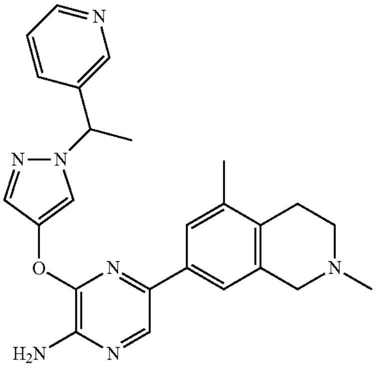

-continued
289
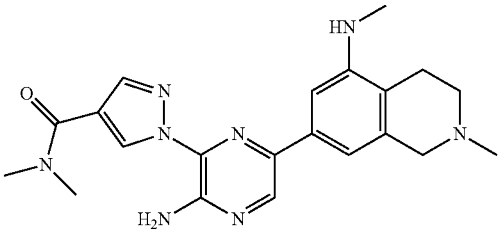
290
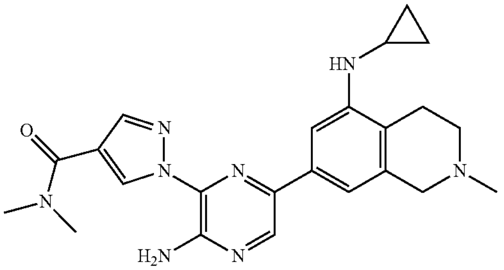
291
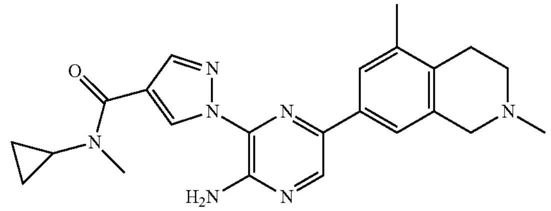
292
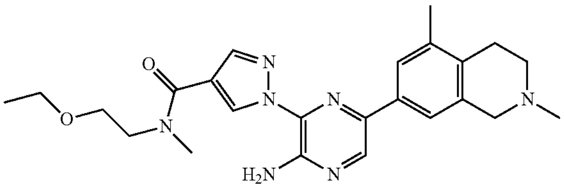
293
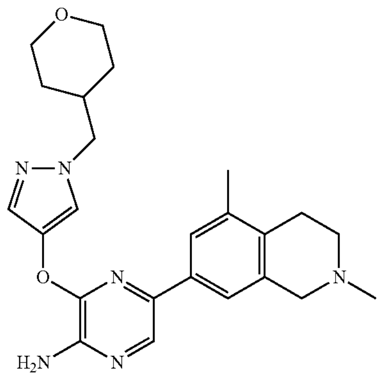
294
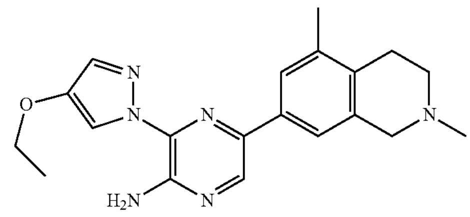
-continued
295
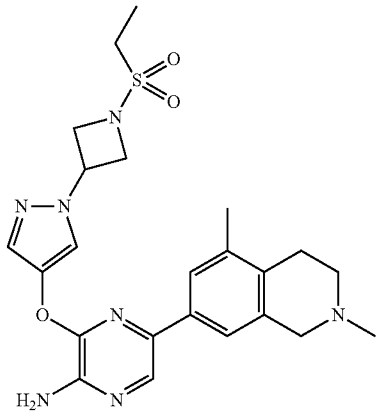
296
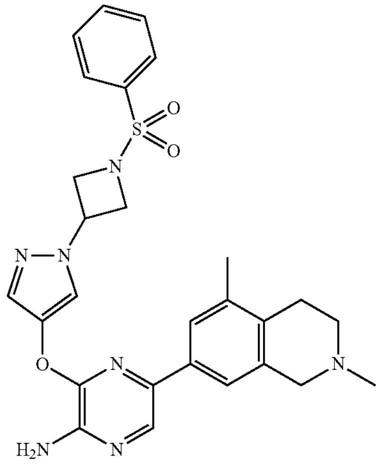
297
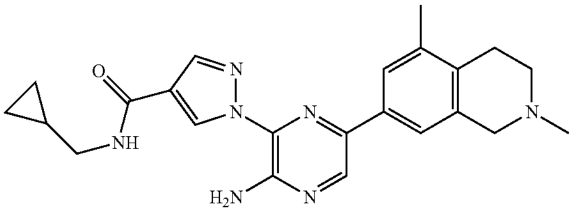
298
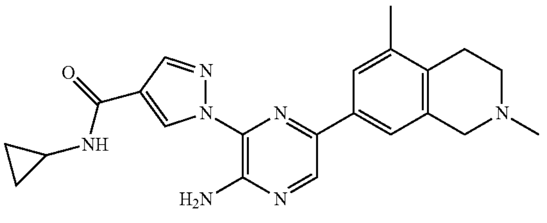
299
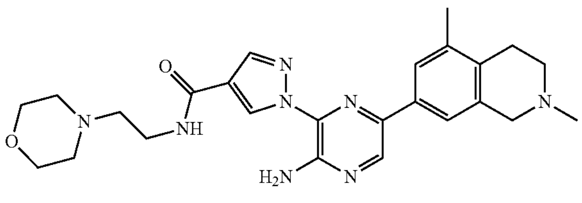

-continued
300
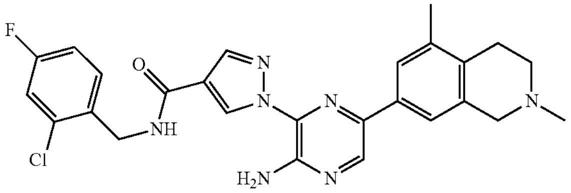
301
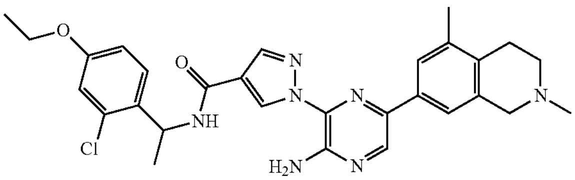
302
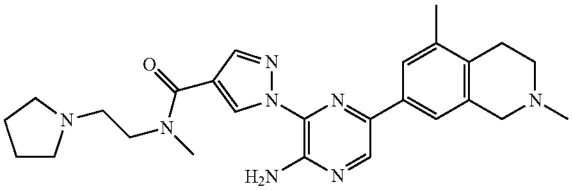
303
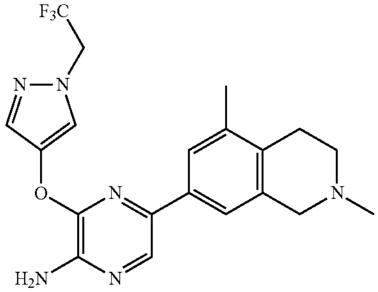
304
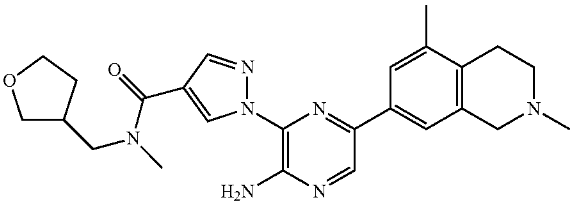
305
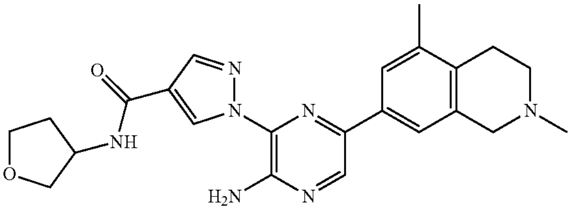
-continued
306
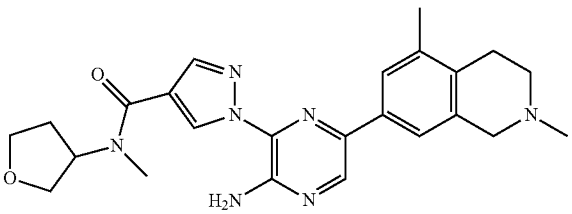
307
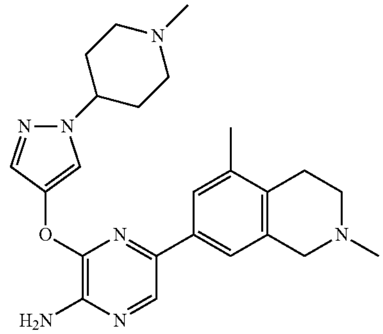
308
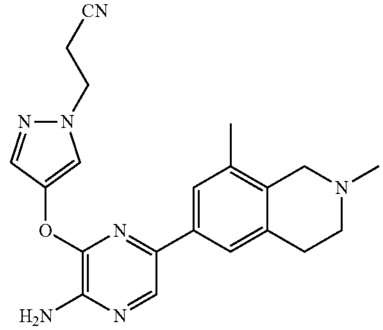
309
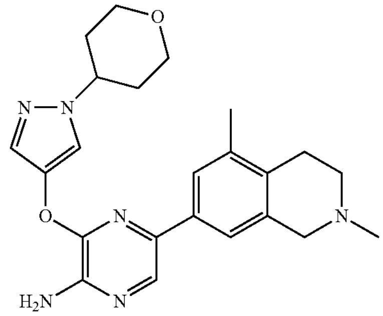
310
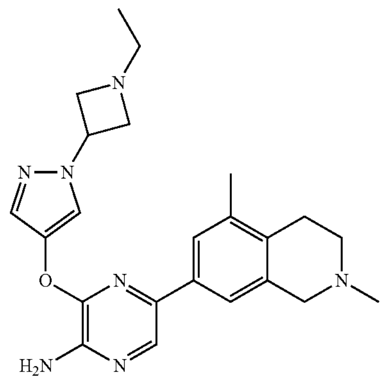

-continued
311
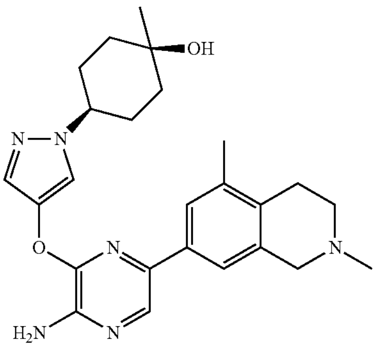
312
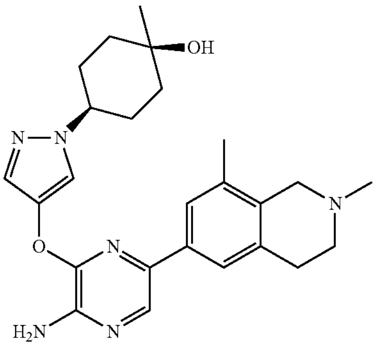
313
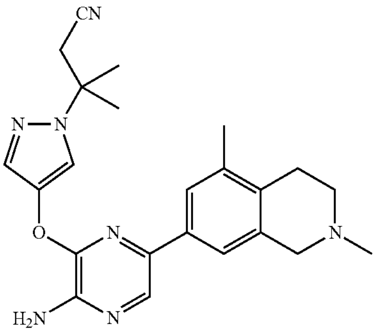
314
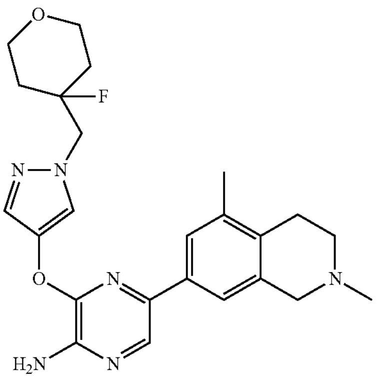
-continued
315
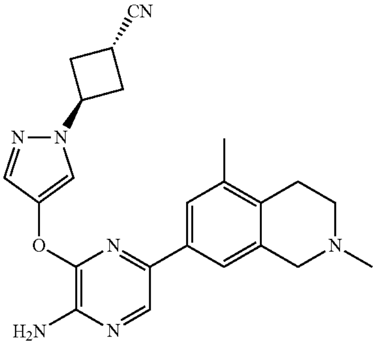
316
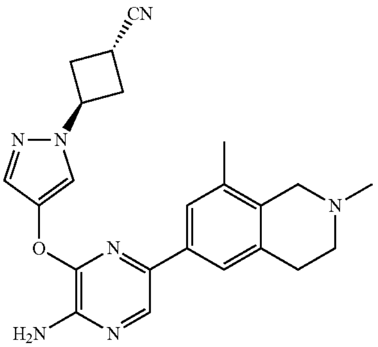
317
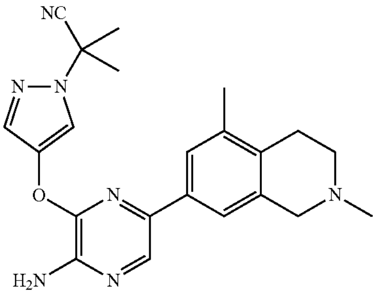
318
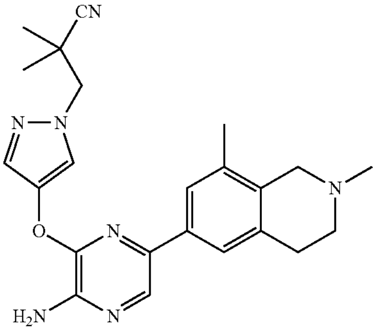
319
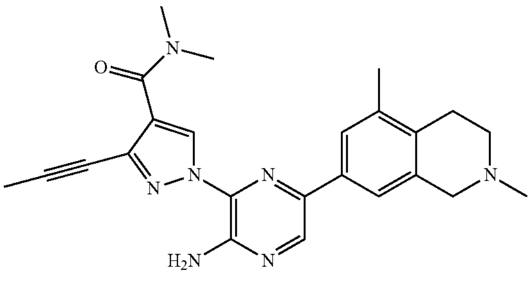

-continued
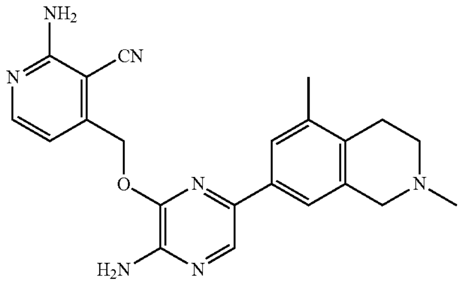
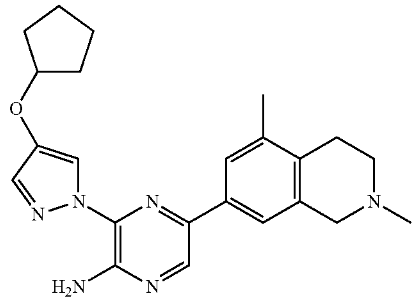
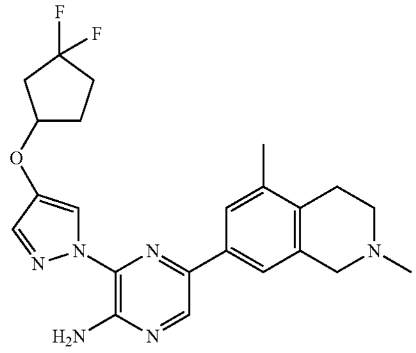
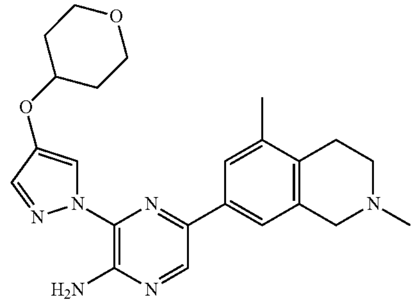
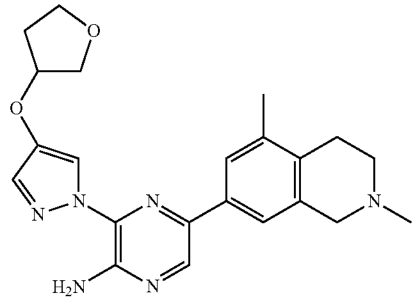
-continued
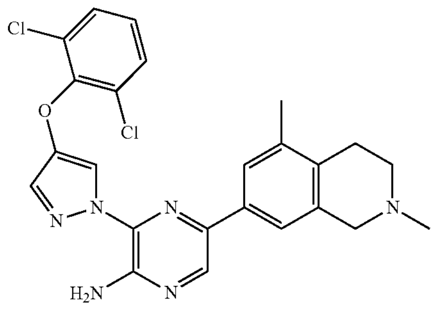
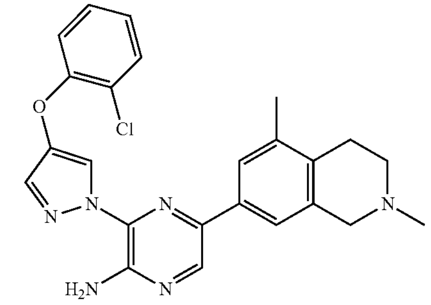
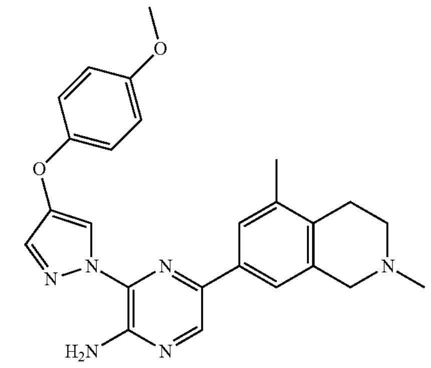
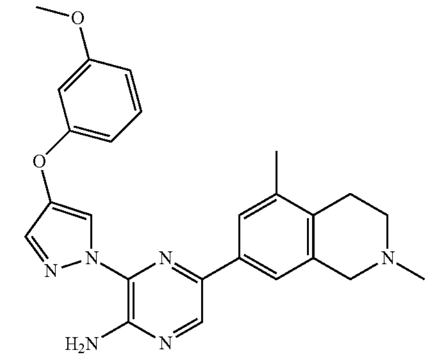
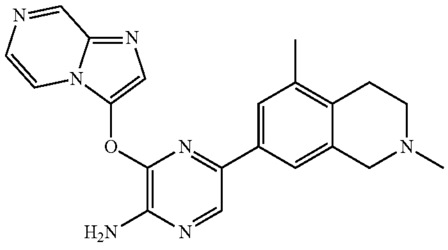

-continued
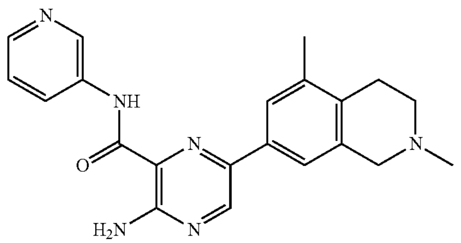
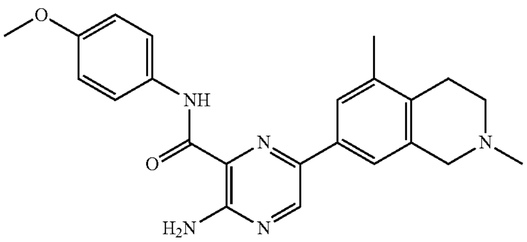
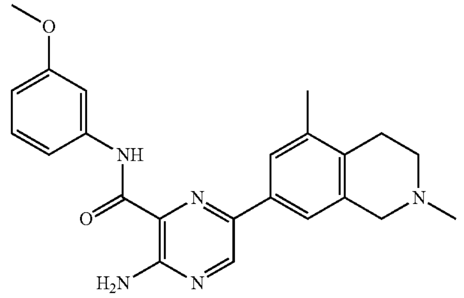
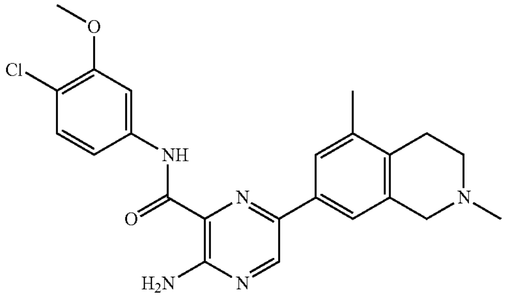
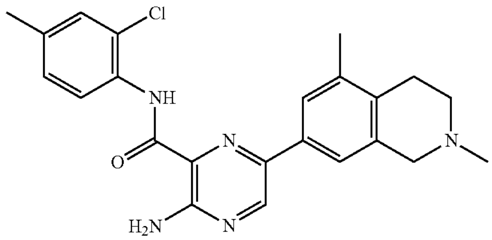
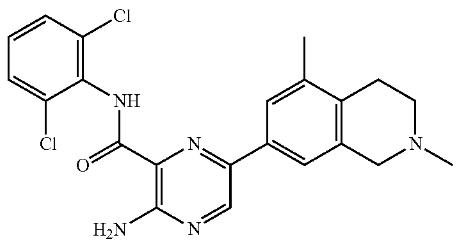
-continued
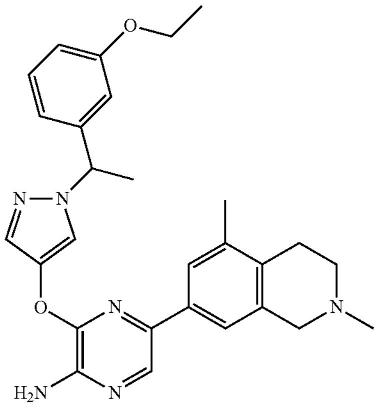
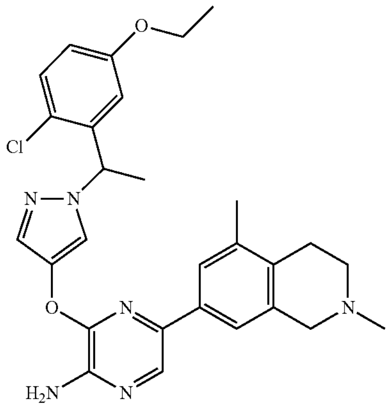
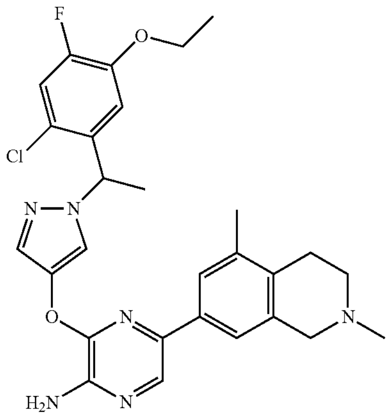
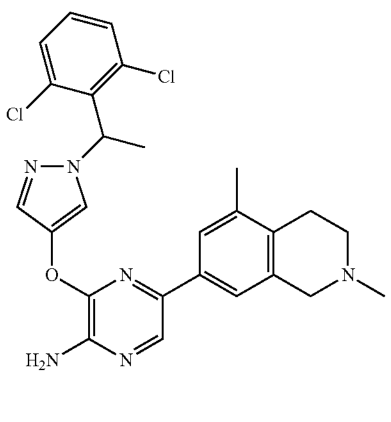

-continued
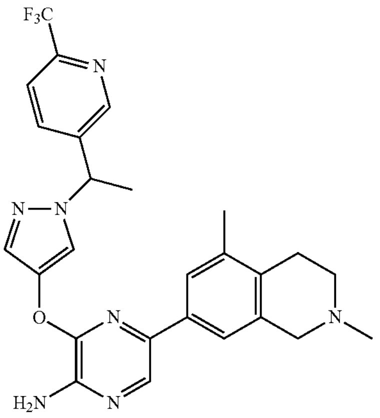
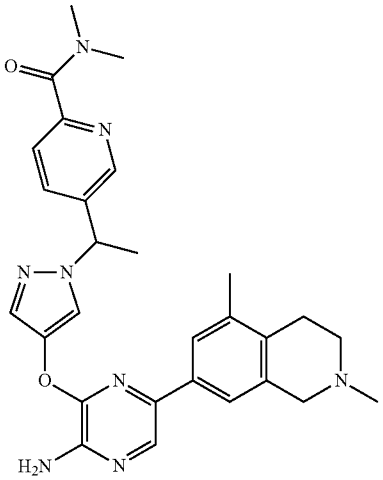
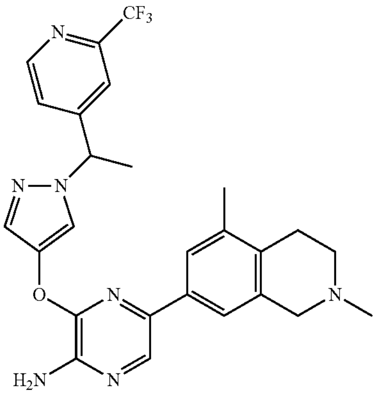
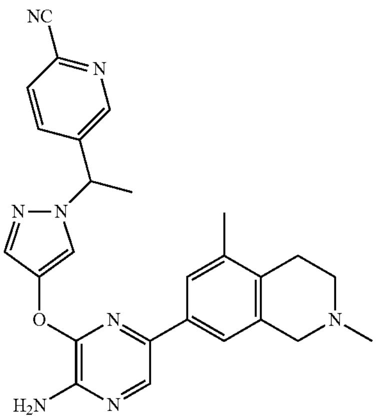
-continued
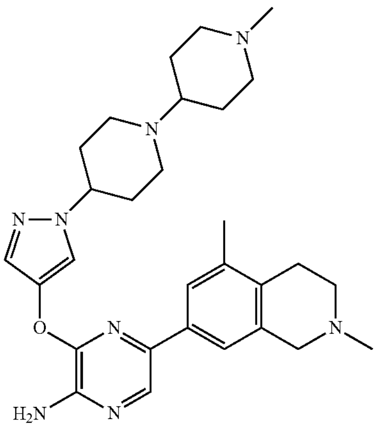
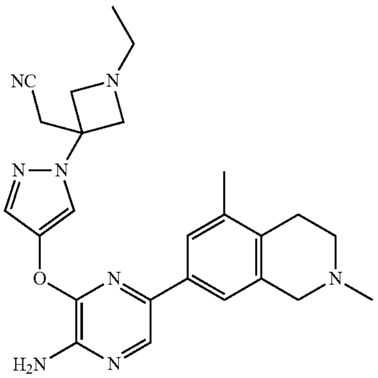
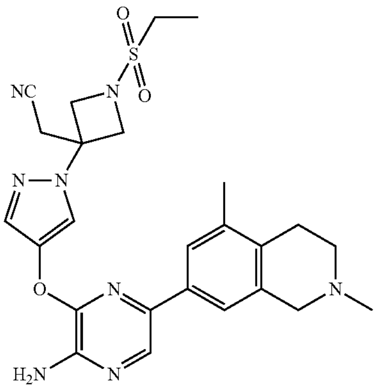
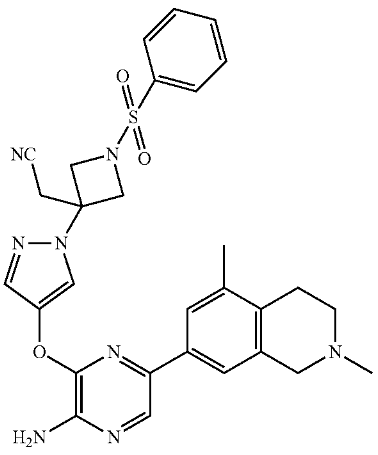

-continued
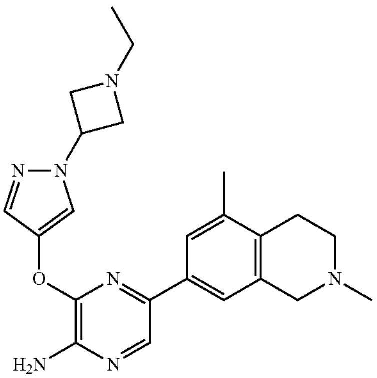
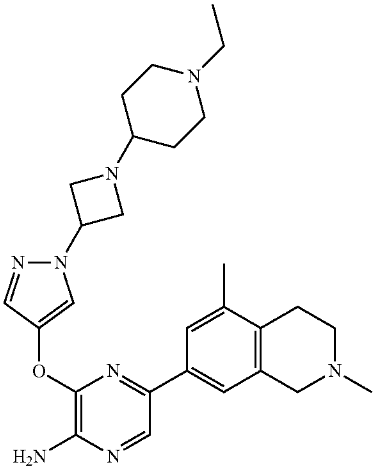
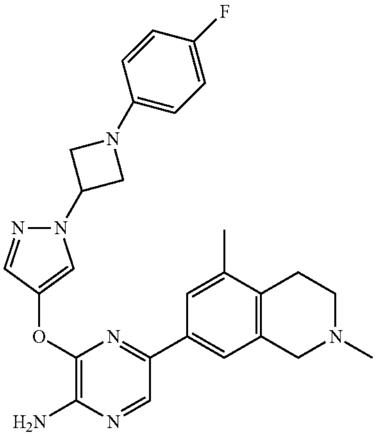
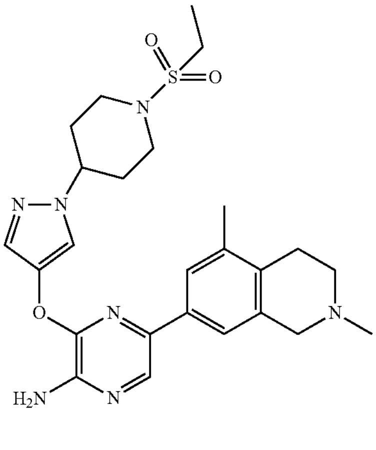
-continued
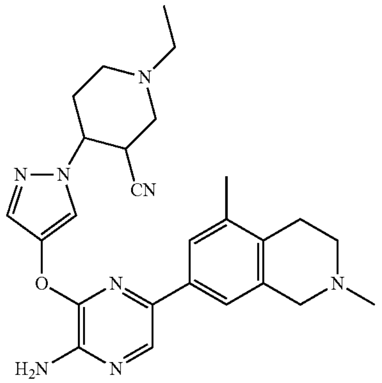
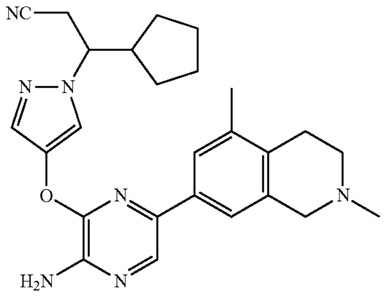
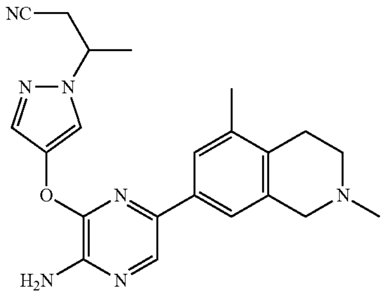
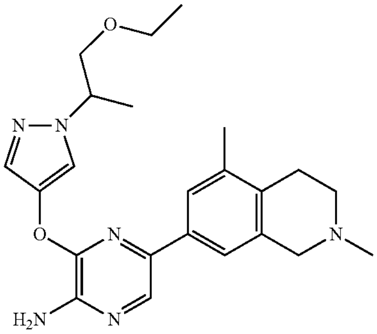
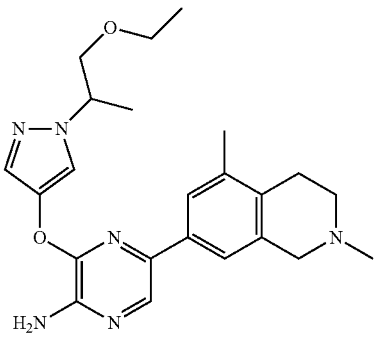

-continued
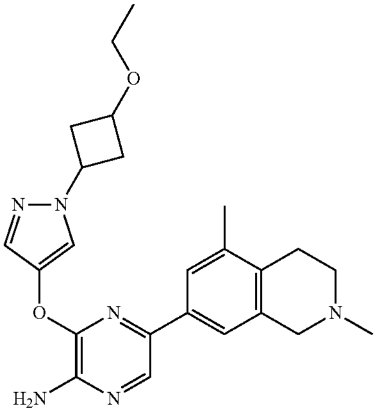
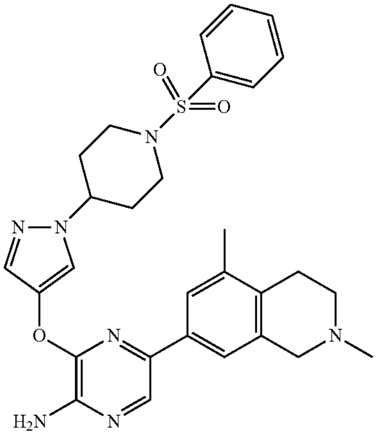
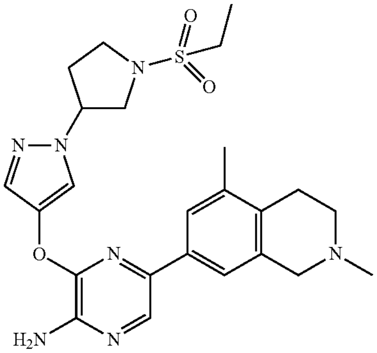
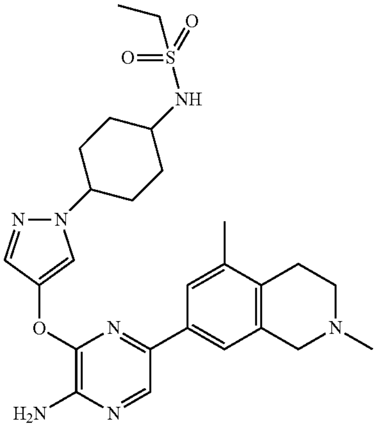
-continued
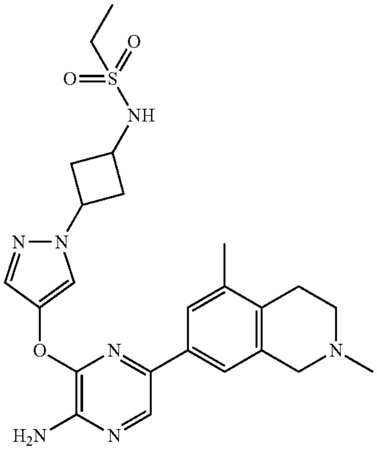
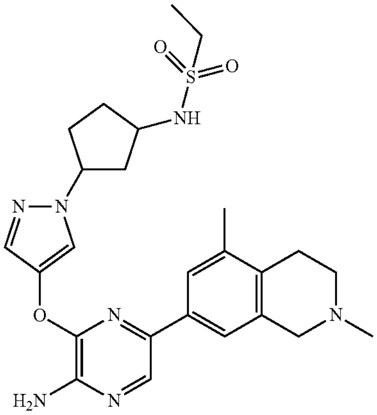
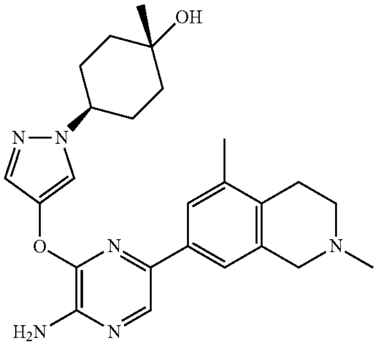
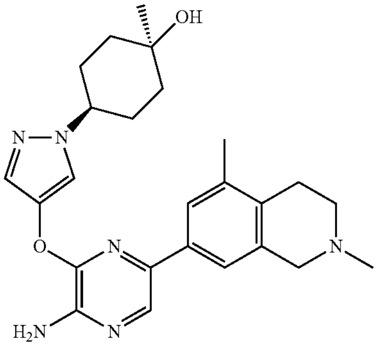

-continued
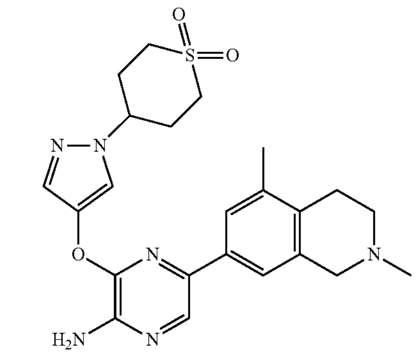
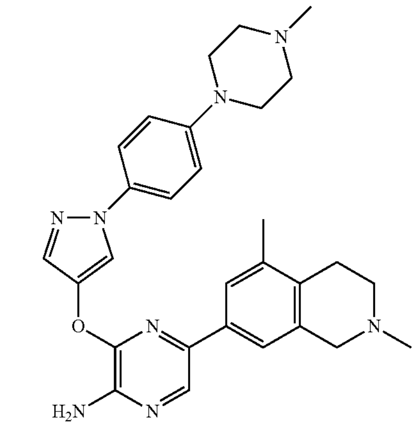
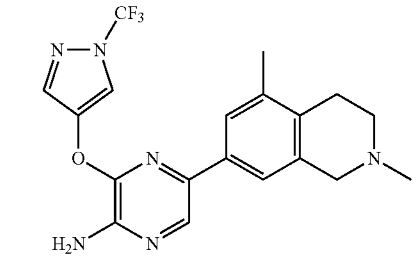
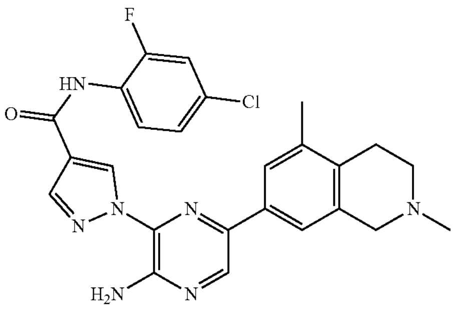
-continued
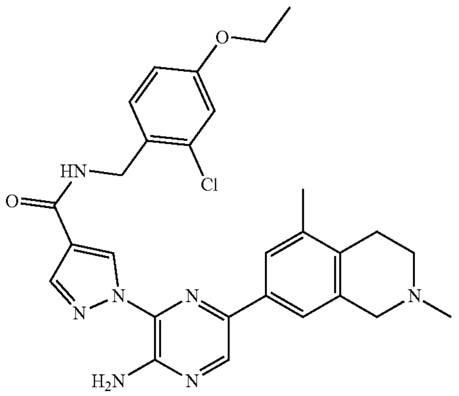
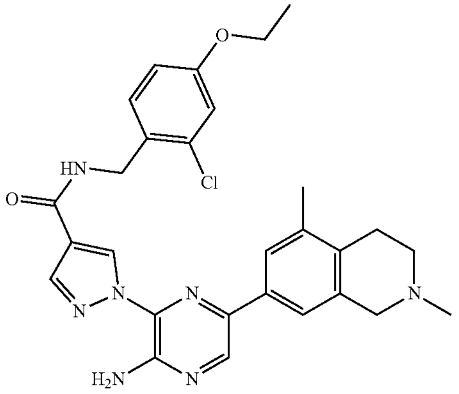
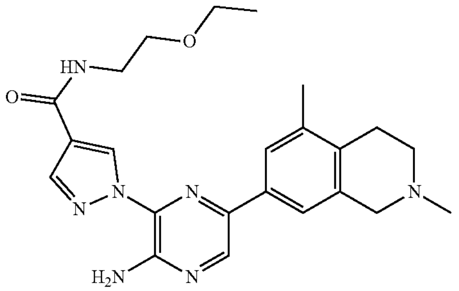
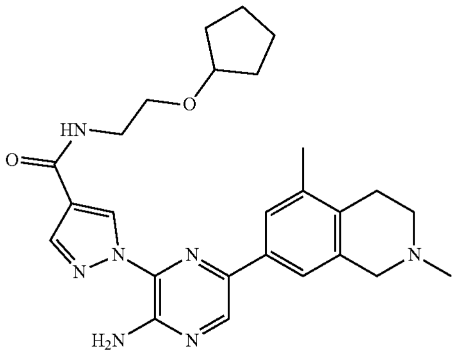

-continued
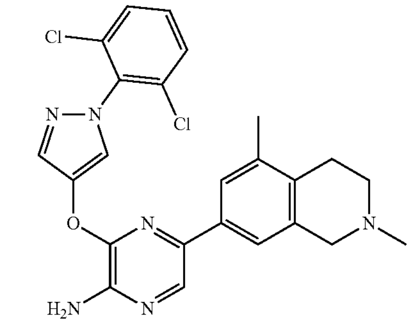
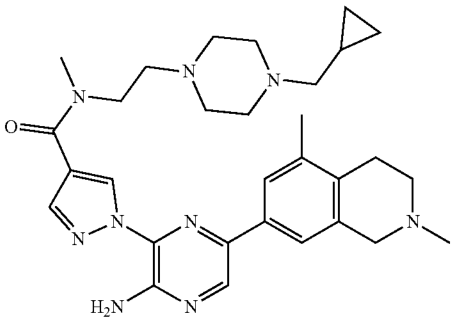
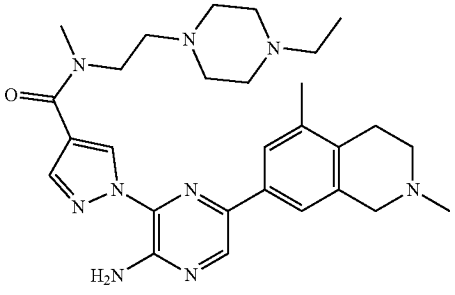
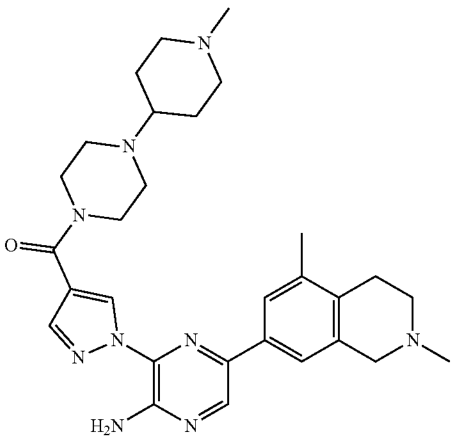
-continued
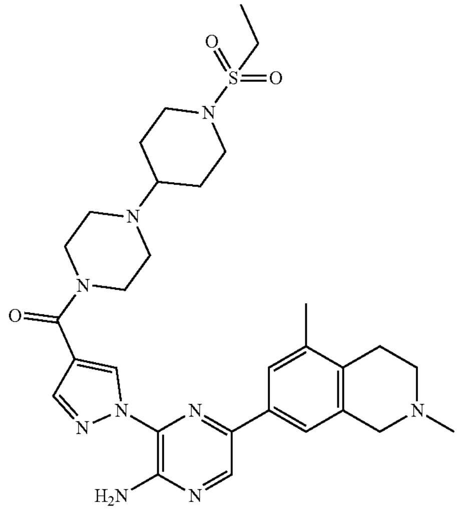
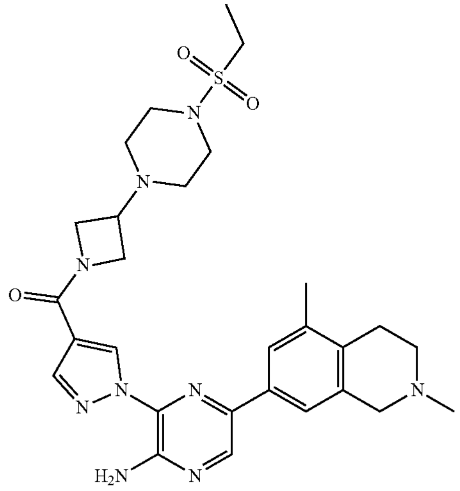
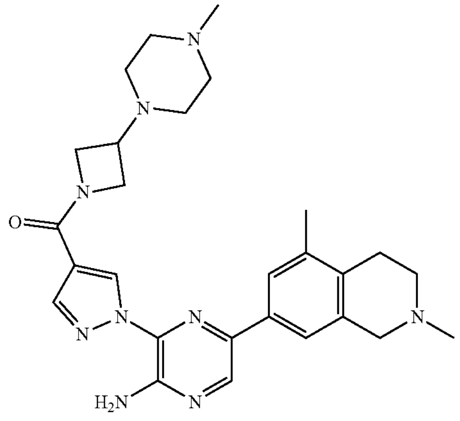
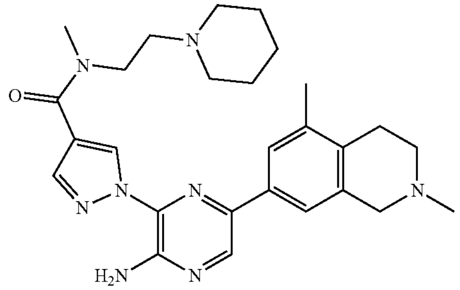

-continued
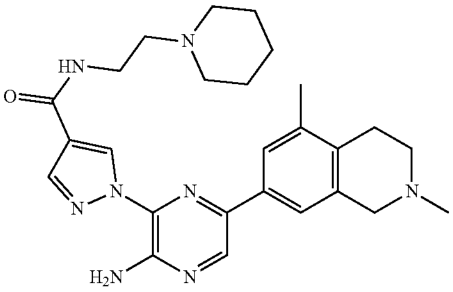
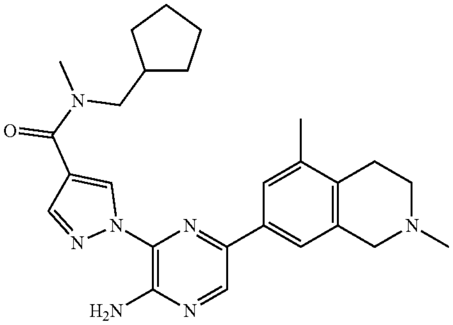
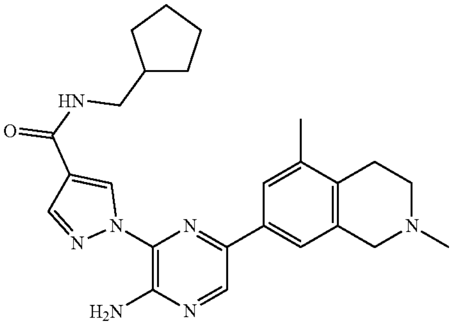
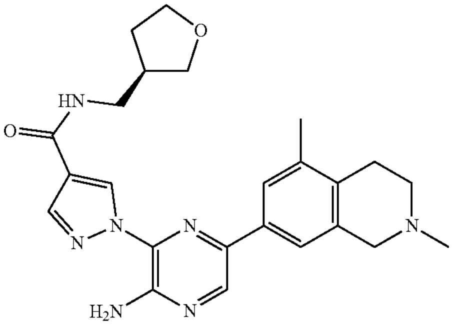
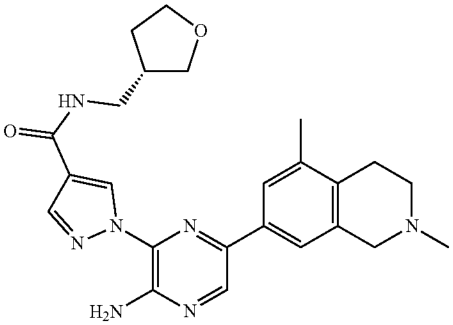
-continued
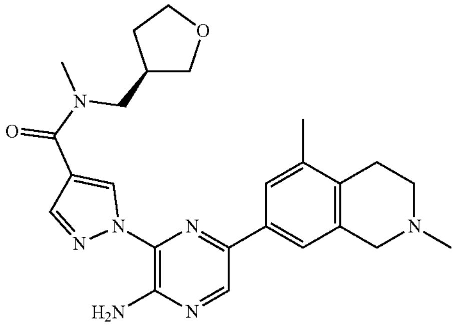
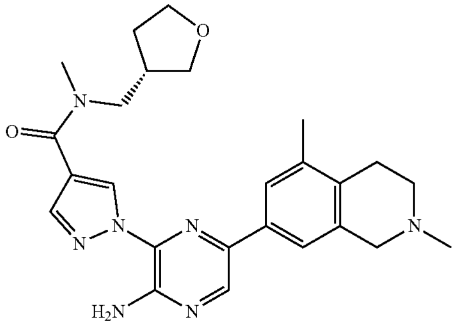
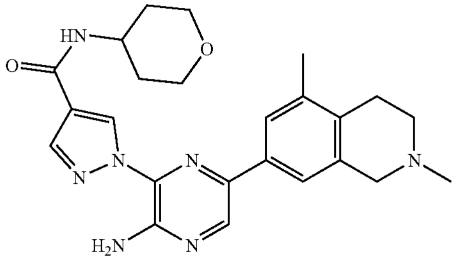
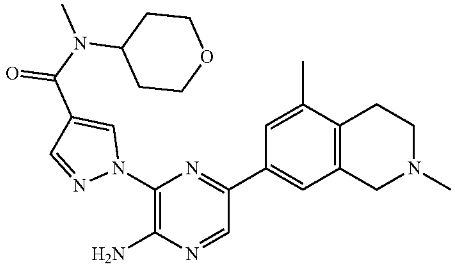
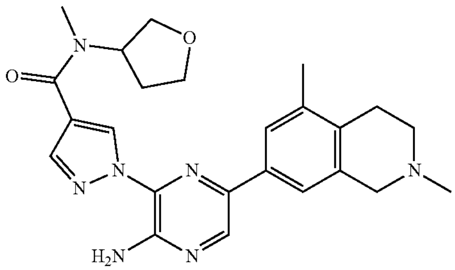
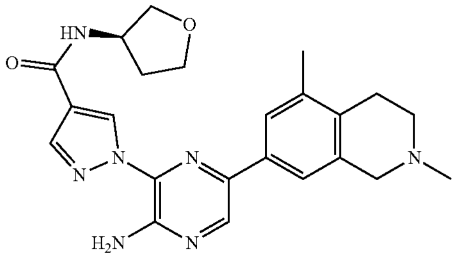

-continued
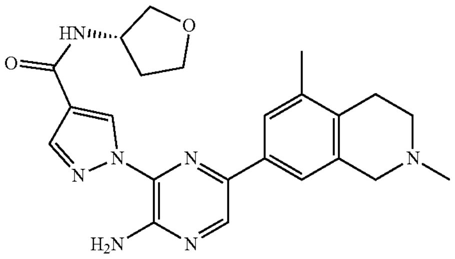
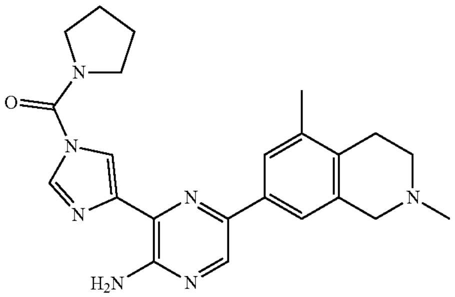
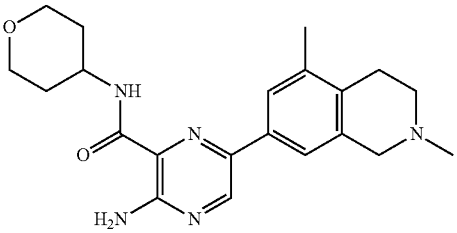
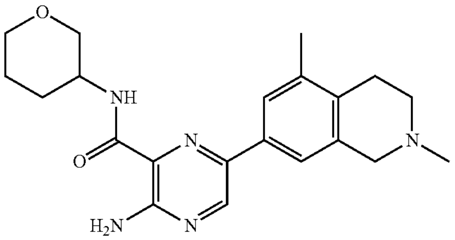
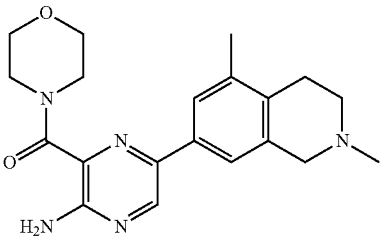
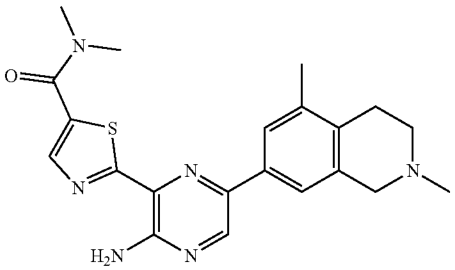
-continued
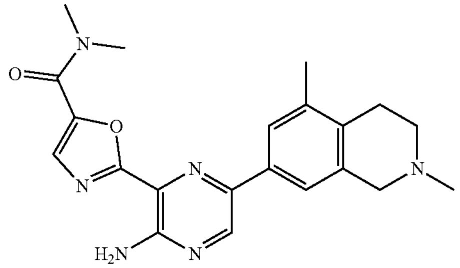
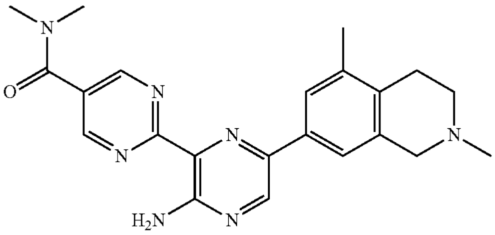
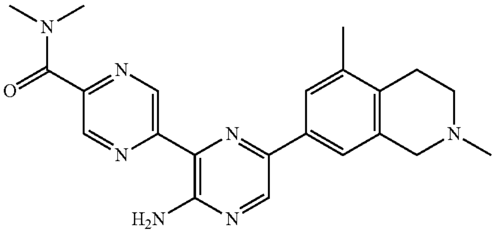
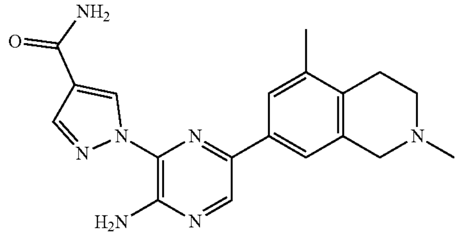
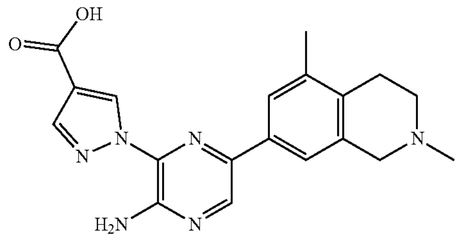
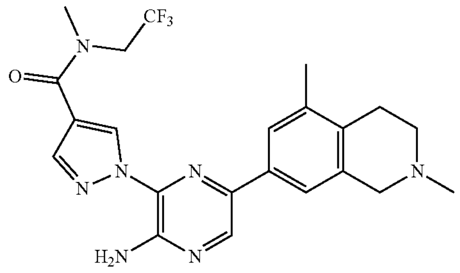

-continued
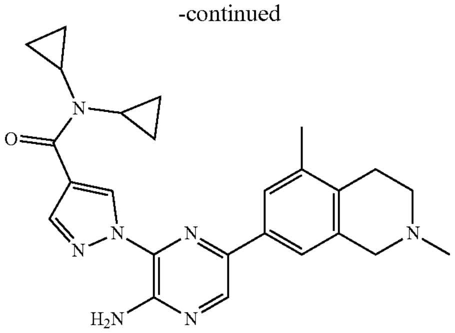
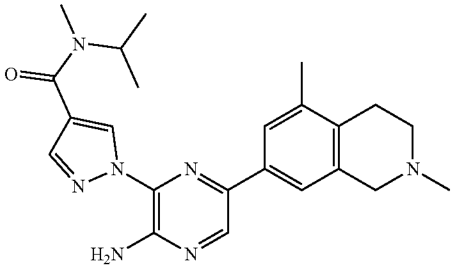
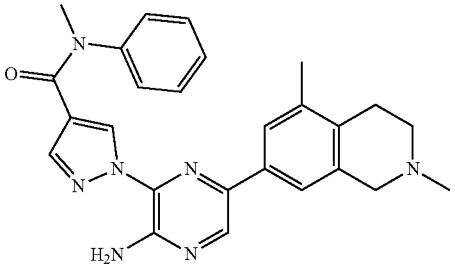
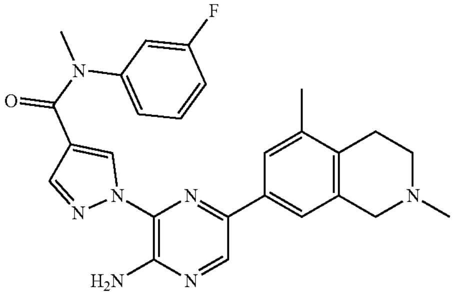
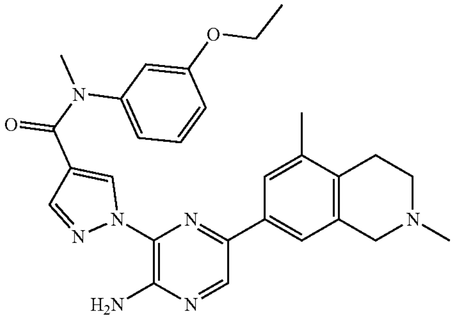
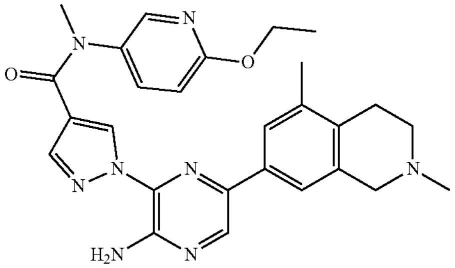
-continued
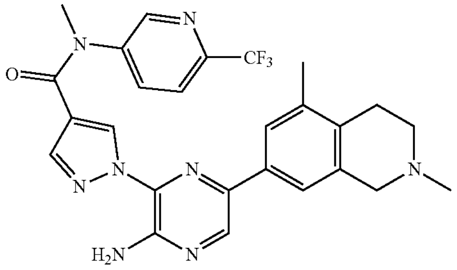
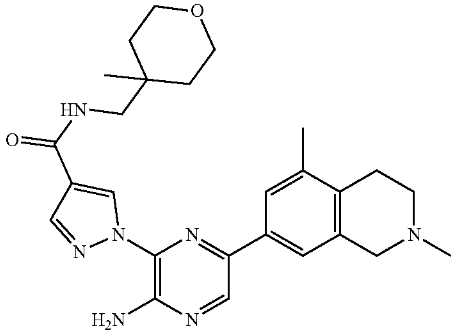
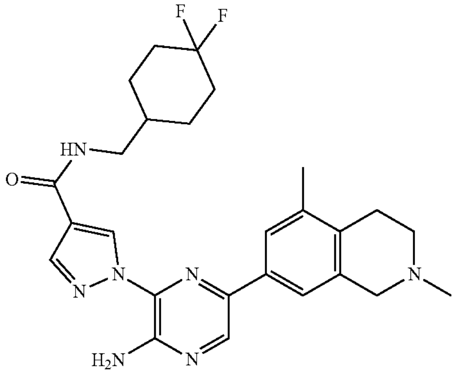
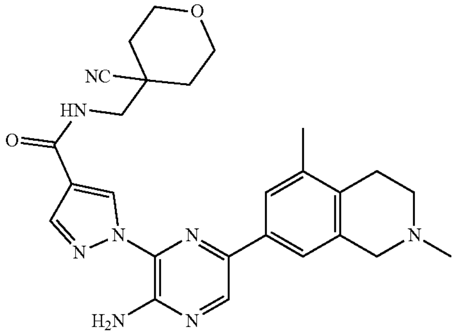
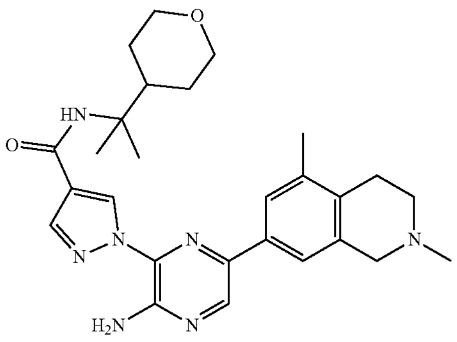

-continued
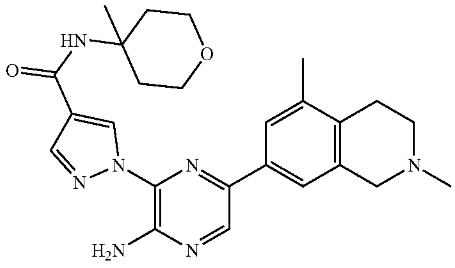
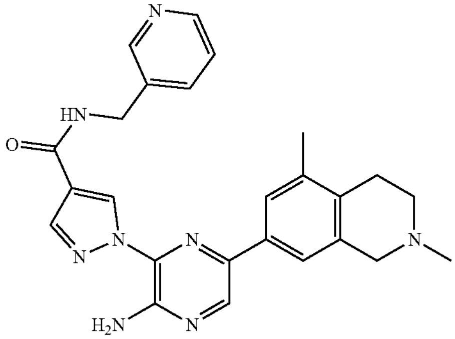
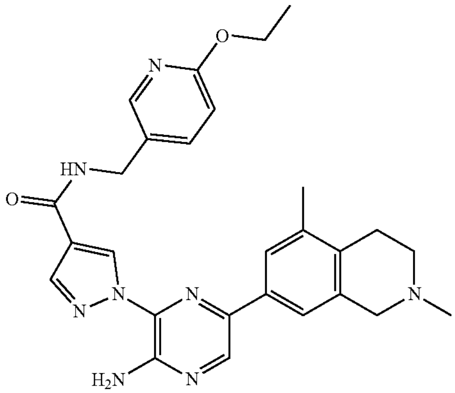
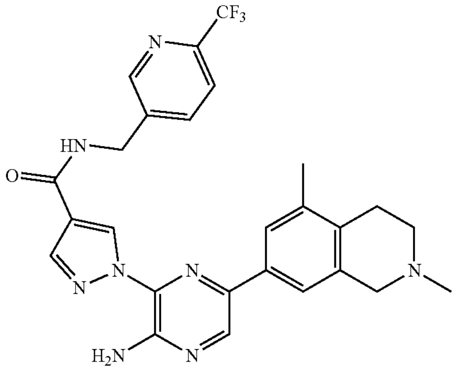
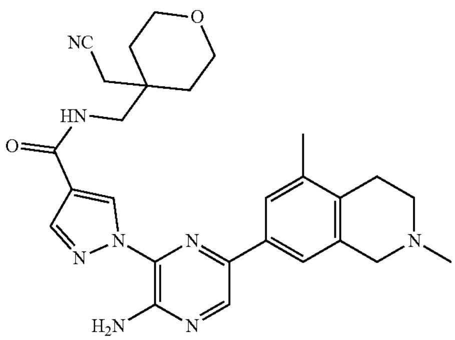
-continued
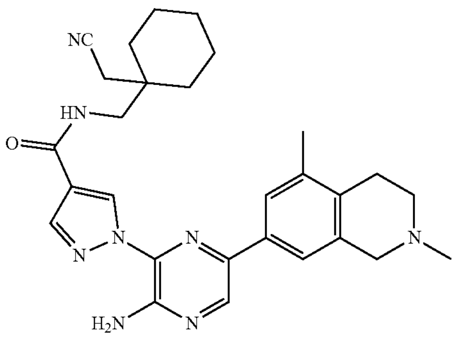
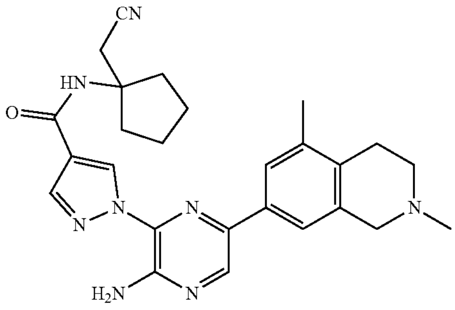
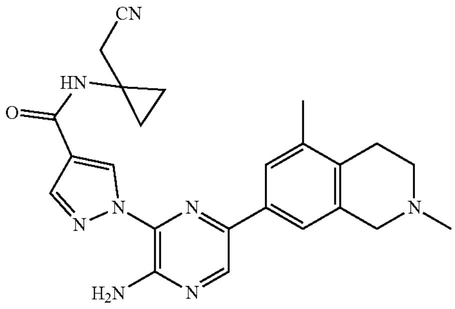
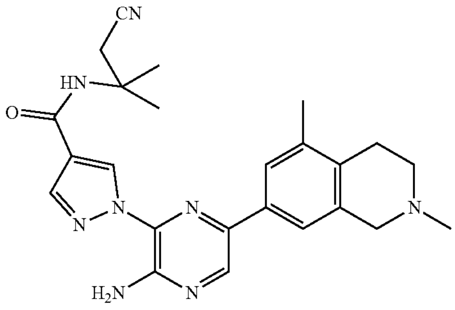
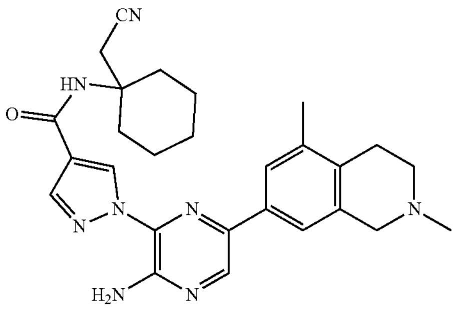

-continued
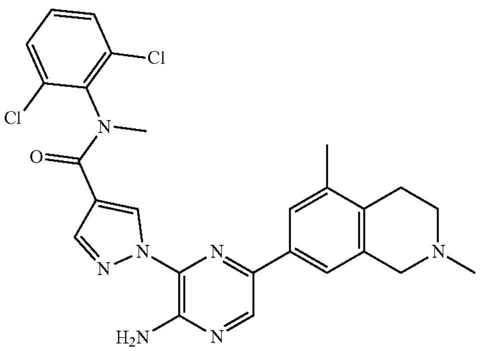
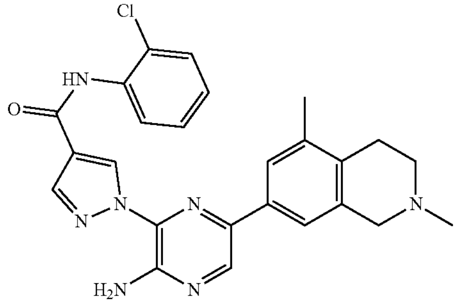
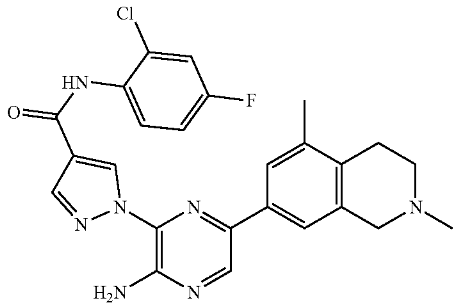
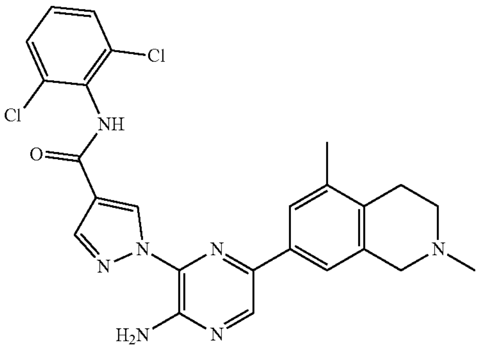
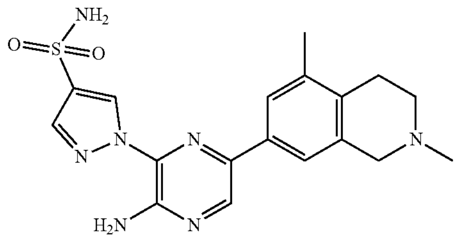
-continued
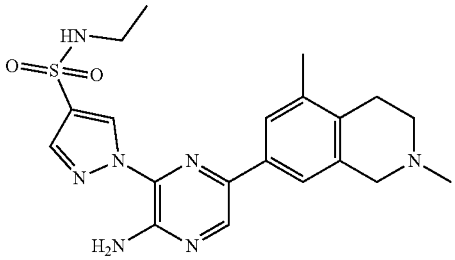
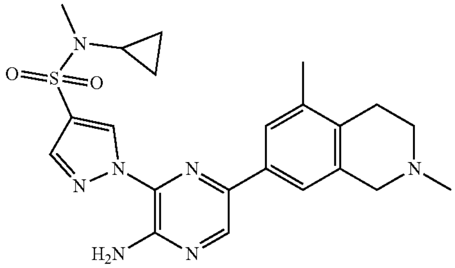
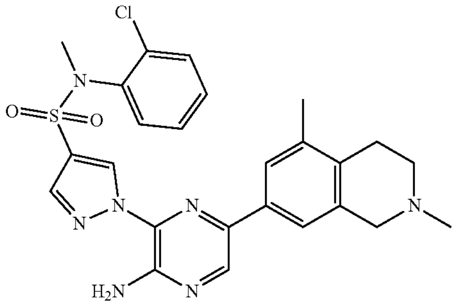
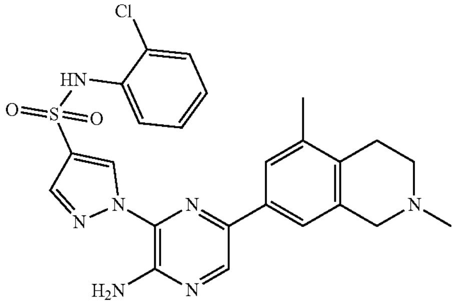
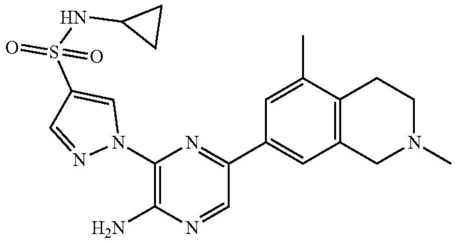
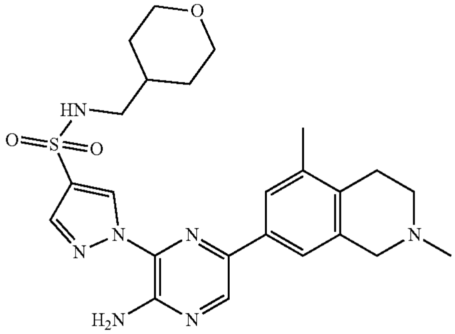

-continued
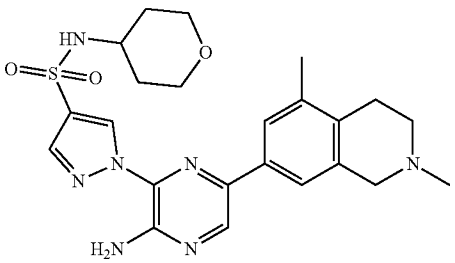
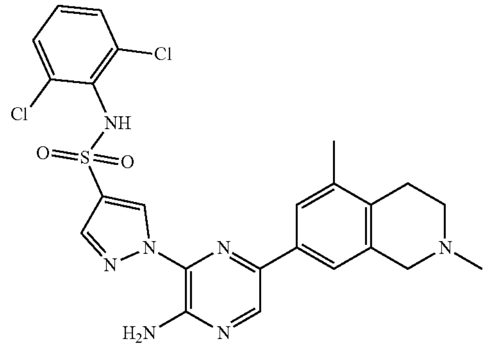
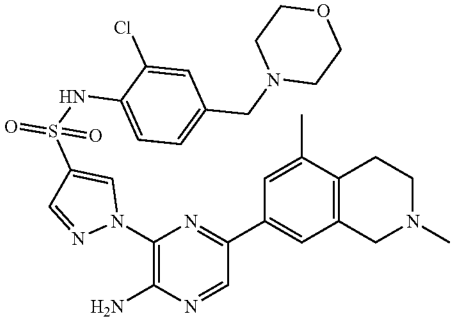
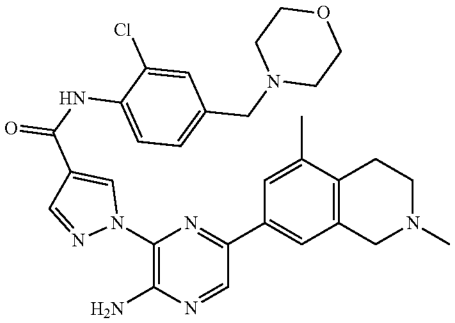
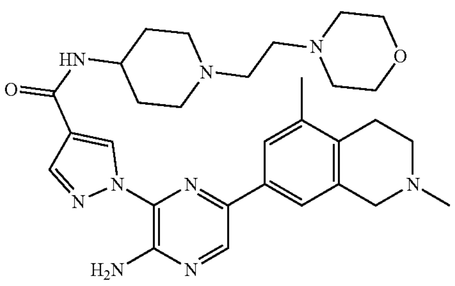
-continued
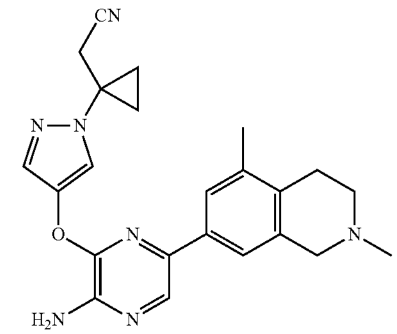
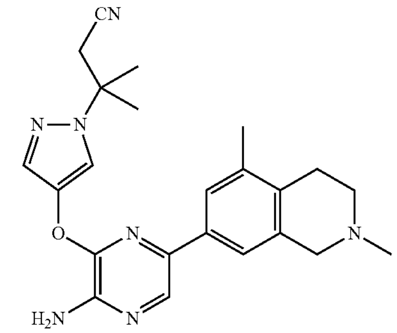
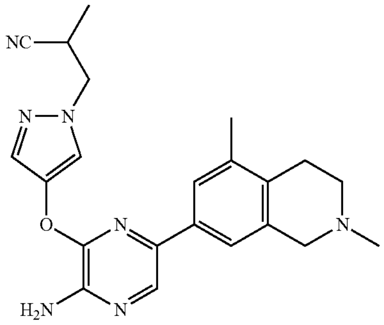
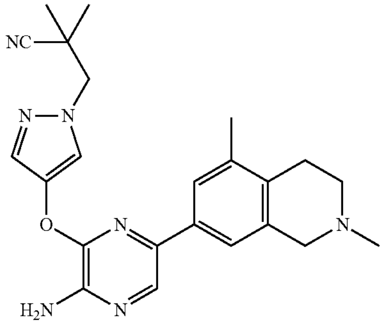
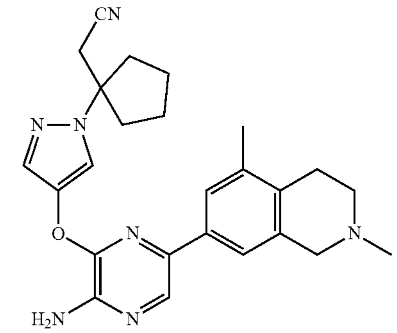

-continued
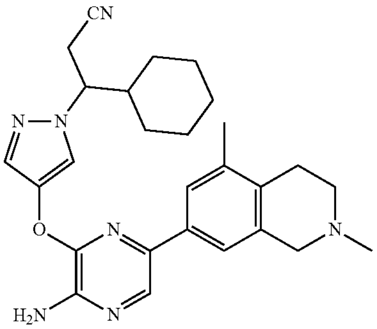
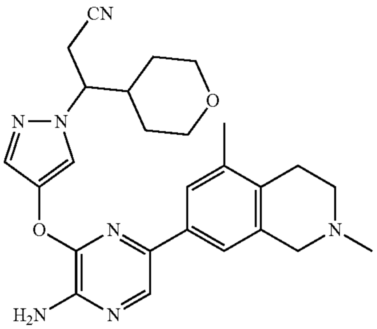
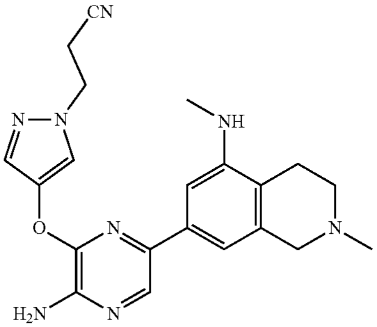
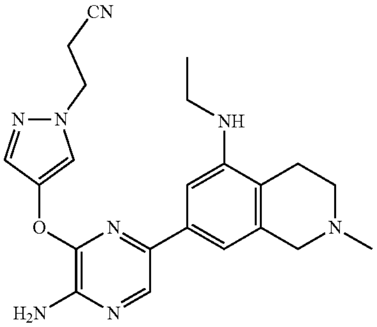
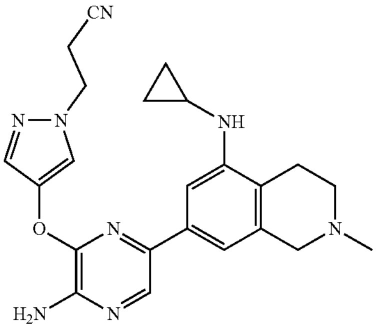
-continued
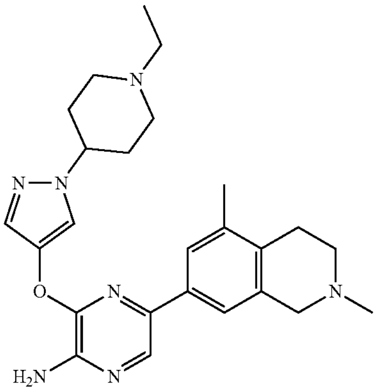
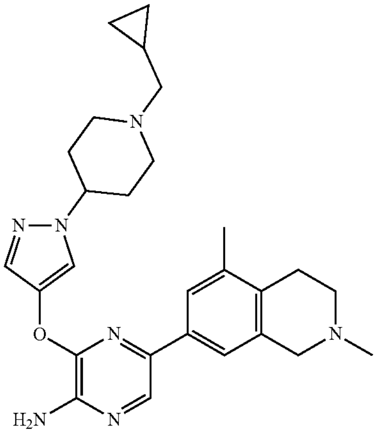
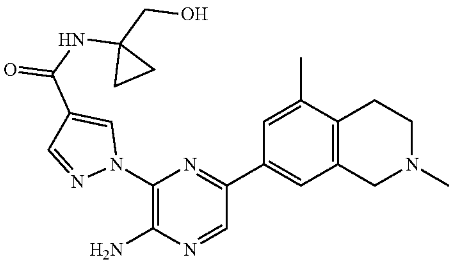
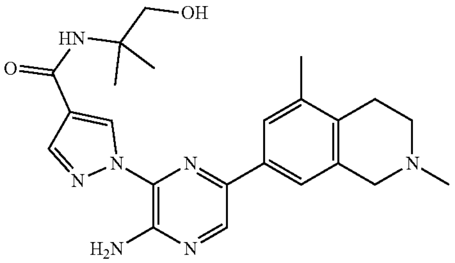
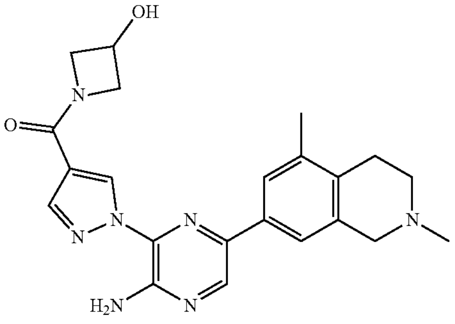

-continued
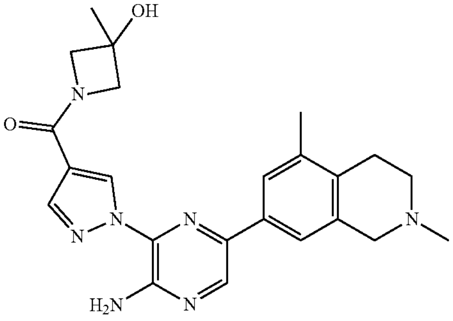
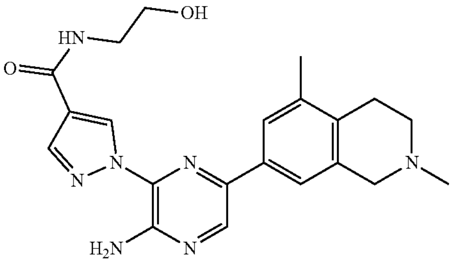
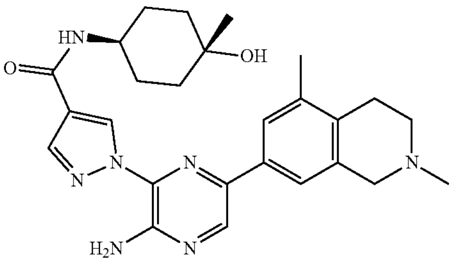
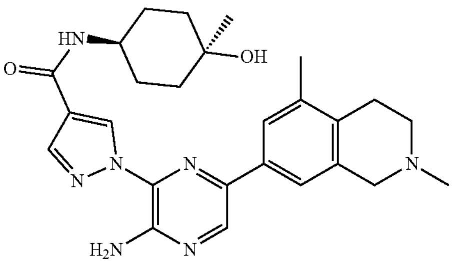
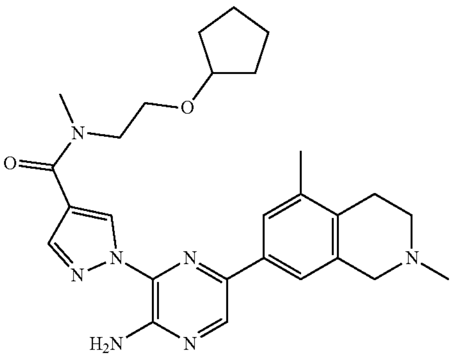
-continued
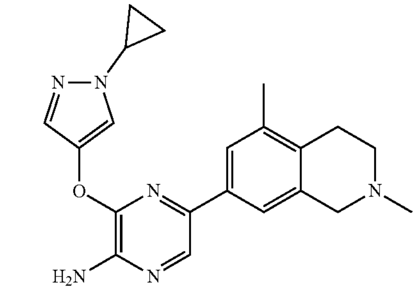
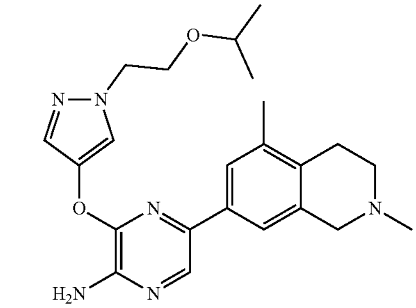
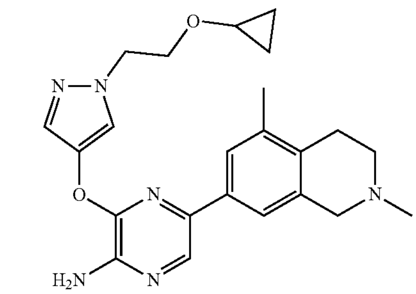
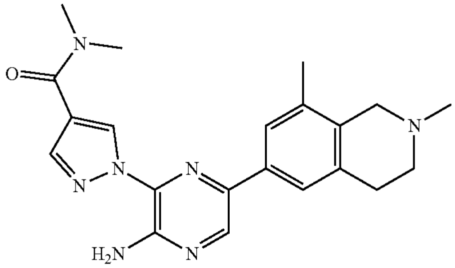
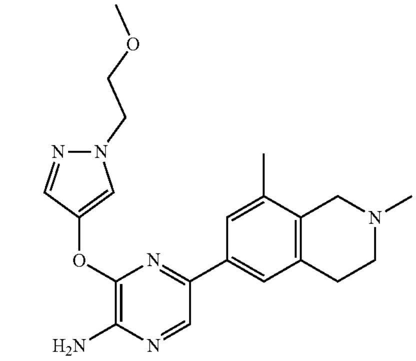

-continued

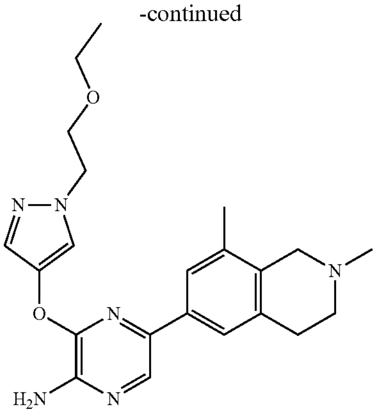

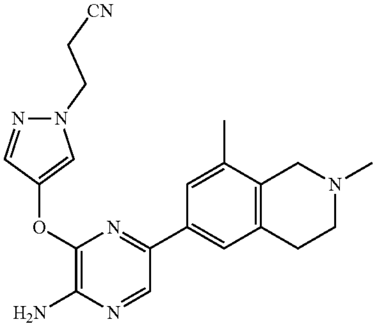

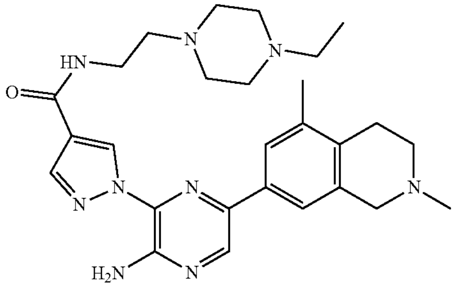

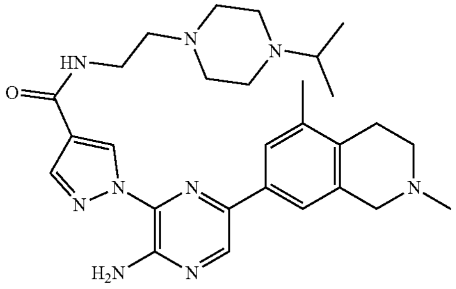

or a pharmaceutically acceptable salt thereof, or a stereoisomer thereof.

In the second aspect, disclosed herein is a pharmaceutical composition comprising the compound disclosed herein, or a pharmaceutically acceptable salt thereof, and at least one pharmaceutically acceptable carrier or excipient.

In the third aspect, disclosed herein is a method of inhibiting HPK1 activity, which comprises administering to an individual the compound disclosed herein, or a pharmaceutically acceptable salt thereof, including the compound of formula (I) or the specific compounds exemplified herein.

In the fourth aspect, disclosed herein is a method of treating a disease or disorder in a patient comprising administering to the patient a therapeutically effective amount of the compound disclosed herein, or a pharmaceutically acceptable salt thereof as an HPK1 kinase inhibitor, wherein the compound disclosed herein includes the compound of formula (I) or the specific compounds exemplified herein. In some embodiments, the disease or disorder is associated with inhibition of HPK1 interaction. Preferably, the disease or disorder is cancer.

DETAILED DESCRIPTION OF THE INVENTION

The following terms have the indicated meaning throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" refers to a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" refers to 1-propyl or n-propyl ("n-Pr"), 2-propyl or isopropyl ("i-Pr").

The term "butyl" refers to 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" refers to 1-pentyl, 2-pentyl, 3-pentyl, 2-methyl-2-butyl, 3-methyl-2-butyl, 3-methyl-1-butyl, 2-methyl-1-butyl.

The term "hexyl" refers to 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "halogen" refers to fluoro (F), chloro (Cl), bromo (Br), and iodo (I).

The term "haloalkyl" refers to an alkyl group in which one or more hydrogen is/are replaced by one or more halogen atoms such as fluoro, chloro, bromo, and iodo. Examples of the haloalkyl include halo$C_{1-8}$alkyl, halo$C_{1-6}$alkyl, or halo $C_{1-4}$alkyl, but not limited to $-CF_3$, $-CH_2Cl$, $-CH_2CF_3$, $-CHCl_2$, $-CF_3$, and the like.

The term "alkenyl" refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "cycloalkyl" refers to a hydrocarbon group selected from saturated cyclic hydrocarbon groups, comprising monocyclic and polycyclic (e.g., bicyclic and tricyclic) groups.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from a monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "fused cycloalkyl" refers to a bicyclic cycloalkyl group as defined herein which is saturated and is formed by two or more rings sharing two adjacent atoms.

The term "bridged cycloalkyl" refers to a cyclic structure which contains carbon atoms and is formed by two rings sharing two atoms which are not adjacent to each other. The term "7 to 10 membered bridged cycloalkyl" refers to a cyclic structure which contains 7 to 12 carbon atoms and is formed by two rings sharing two atoms which are not adjacent to each other.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, cyclohexadienyl, preferably cyclohexenyl.

The term "fused cycloalkenyl" refers to a bicyclic cycloalkyl group as defined herein which contains at least one double bond and is formed by two or more rings sharing two adjacent atoms.

The term "cycloalkynyl" refers to non-aromatic cycloalkyl groups of from 5 to 10 carbon atoms having single or multiple rings and having at least one triple bond.

The term "fused cycloalkynyl" refers to a bicyclic cycloalkyl group as defined herein which contains at least one triple bond and is formed by two or more rings sharing two adjacent atoms.

The term "benzo fused cycloalkyl" is a bicyclic fused cycloalkyl in which a 4- to 8-membered monocyclic cycloalkyl ring fused to a benzene ring. For example, a benzo fused cycloalkyl is or

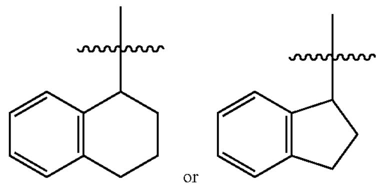 [SMILES: *C1CCCc2ccccc21 ; *C1CCc2ccccc21]

wherein the wavy lines indicate the points of attachment.

The term "benzo fused cycloalkenyl" is a bicyclic fused cycloalkenyl in which a 4- to 8-membered monocyclic cycloalkenyl ring fused to a benzene ring.

The term a "benzo fused cycloalkynyl" is a bicyclic fused cycloalkynyl in which a 4- to 8-membered monocyclic cycloalkynyl ring fused to a benzene ring.

Examples of fused cycloalkyl, fused cycloalkenyl, or fused cycloalkynyl include but are not limited to bicyclo [1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1, 2, 3,4-tetralyl, 1,4-dihydronaphthyl, etc. Preferred embodiments are 8 to 9 membered fused ring, which refers to cyclic structures containing 8 to 9 ring atoms within the above examples.

The term "aryl" used alone or in combination with other terms refers to a group selected from:

a) 5- and 6-membered carbocyclic aromatic rings, e.g., phenyl;
b) bicyclic ring systems such as 7 to 12 membered bicyclic ring systems, wherein at least one ring is carbocyclic and aromatic, e.g., naphthyl and indanyl; and,
c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" refers to a bicyclic aryl ring as defined herein. The typical bicyclic fused aryl is naphthalene.

The term "heteroaryl" refers to a group selected from:

a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" refers to a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

Representative examples of bicyclic fused heteroaryl include, but not limited to, the following groups benzisoxazolyl, benzodiazolyl, benzofuranyl, benzofurazanyl, benzofuryl, benzoimidazolyl, benzoisothiazolyl, benzothiadiazolyl, benzothiazolyl, benzothienyl, benzothiophenyl, benzotriazolyl, benzoxadiazolyl, benzoxazolyl, furopyridinyl, furopyrrolyl, imidazopyridinyl, imidazopyridyl, imidazothiazolyl, indazolyl, indolizinyl, indolyl, isobenzofuryl, isoindolyl, isoquinolinyl (or isoquinolyl), naphthyridinyl, phthalazinyl, pteridinyl, purinyl, pyrazinopyridazinyl, pyrazolopyridinyl, pyrazolopyrimidinyl, pyrazolopyridyl, pyrazolotriazinyl, pyridazolopyridyl, pyrrolopyridinyl, quinazolinyl, quinolinyl (or quinolyl), quinoxalinyl, thiazolopyridyl, thienopyrazinyl, thienopyrazolyl, thienopyridyl, thienopyrrolyl, thienothienyl, or triazolopyridyl.

The term a "benzo fused heteroaryl" is a bicyclic fused heteroaryl in which a 5- to 7-membered (preferably, 5- or 6-membered) monocyclic heteroaryl ring as defined herein fused to a benzene ring.

The terms "aromatic heterocyclic ring" and "heteroaryl" are used interchangeably throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), and indazolyl (such as 1H-indazol-5-yl).

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused ring, i.e., containing monocyclic heterocyclyl, and fused heterocyclic groups.

The term "optionally oxidized sulfur" used herein refers to S, SO or $SO_2$.

The term "monocyclic heterocyclyl" refers to monocyclic groups in which at least one ring member (e.g., 1-3 heteroatoms, 1 or 2 heteroatom(s)) is a heteroatom selected from nitrogen, oxygen or optionally oxidized sulfur. A heterocycle may be saturated or partially saturated.

Exemplary monocyclic 4 to 9-membered heterocyclyl groups include, but not limited to, pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "fused heterocyclyl" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but the fused heterocyclic group does not have a completely conjugated pi-electron system. Preferably, a fused heterocyclyl is 6 to 14-membered, and more preferably 7 to 12-membered, or 7- to 10-membered. According to the number of membered rings, a fused heterocyclyl is divided into bicyclic, tricyclic, tetracyclic, or polycyclic fused heterocyclyl. The group can be attached to the remainder of the molecule through either ring.

Specifically, the term "bicyclic fused heterocyclyl" refers to a 7 to 12-membered, preferably 7- to 10-membered, more preferably 9- or 10-membered fused heterocyclyl as defined herein comprising two fused rings and comprising 1 to 4 heteroatoms selected from nitrogen, oxygen or optionally oxidized sulfur as ring members. Typically, a bicyclic fused heterocyclyl is 5-membered/5-membered, 5-membered/6-membered, 6-membered/6-membered, or 6-membered/7-membered bicyclic fused heterocyclyl. Representative examples of (bicyclic) fused heterocycles include, but not limited to, the following groups octahydrocyclopenta[c]pyrrole, octahydropyrrolo[3,4-c]pyrrolyl, octahydroisoindolyl, isoindolinyl, octahydro-benzo[b][1,4]dioxin, indolinyl, isoindolinyl, benzopyranyl, dihydrothiazolopyrimidinyl, tetrahydroquinolyl, tetrahydroisoquinolyl (or tetrahydroisoquinolinyl), dihydrobenzofuranyl, dihydrobenzoxazinyl, dihydrobenzoimidazolyl, tetrahydrobenzothienyl, tetrahydrobenzofuranyl, benzodioxolyl, benzodioxonyl, chromanyl, chromenyl, octahydrochromenyl, dihydrobenzodioxynyl, dihydrobenzoxezinyl, dihydrobenzodioxepinyl, dihydrothienodioxynyl, dihydrobenzooxazepinyl, tetrahydrobenzooxazepinyl, dihydrobenzoazepinyl, tetrahydrobenzoazepinyl, isochromanyl, chromanyl, or tetrahydropyrazolopyrimidinyl (e.g., 4,5,6,7-tetrahydropyrazolo[1,5-a]pyrimidin-3-yl).

The term "benzo fused heterocyclyl" is a bicyclic fused heterocyclyl in which a monocyclic 4 to 9-membered heterocyclyl as defined herein (preferably 5- or 6-membered) fused to a benzene ring.

The term "bridged heterocyclyl" refers to a 5- to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic, or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

The term "at least one substituent" disclosed herein includes, for example, from 1 to 4, such as from 1 to 3, further as 1 or 2, substituents, provided that the theory of valence is met. For example, "at least one substituent $R^d$" disclosed herein includes from 1 to 4, such as from 1 to 3, further as 1 or 2, substituents selected from the list of $R^d$ as disclosed herein.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

Compounds disclosed herein also comprises deuterated compounds. The term "deuterated compound" refers to a compound wherein one or more carbon-bound hydrogen(s) are replaced by one or more deuterium(s). Similarly, the term "deuterated" is be used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclic ring system, substituents found on such ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review.*" *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined herein, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be solution, water solution, oil suspension concentrate, lyophilized powder or the like. Preferably, the formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical catrers suitable for the desired pharmaceutical formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ratio used.

Scheme I

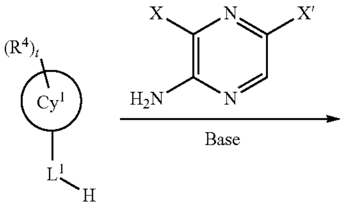

i

-continued

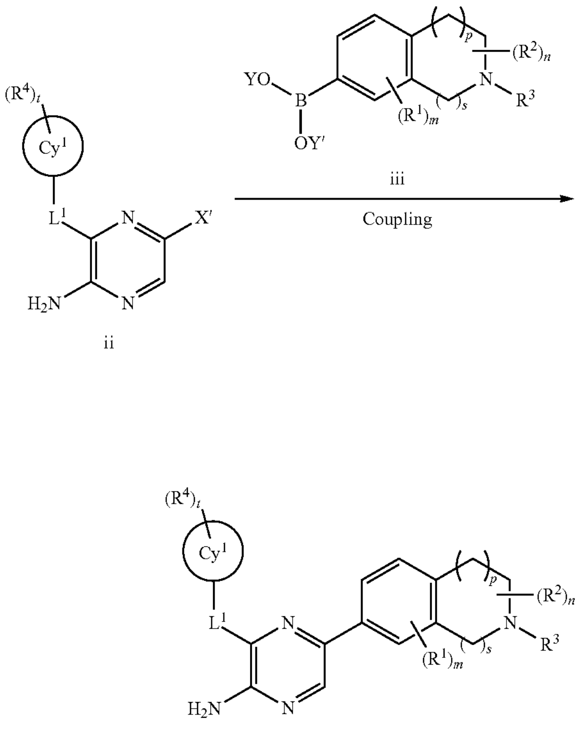

ii iii iv

X, X' = Cl or Br or I Y, Y' = H or alkyl (Y and Y' can be linked through a bond)

For example, compounds of Formula (I) can be formed as shown in Scheme I. Compound (i) can be deprotonated and react with 2-amino-3,5-dihalopyrazine to give compound (ii); compound (ii) can be coupled with compound (iii) using transition metal catalyzed reaction to give compound (iv) [i.e., Formula (I)].

Scheme II

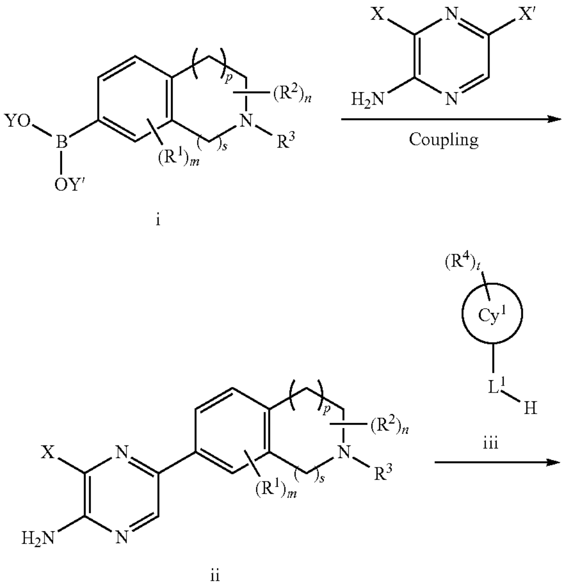

i ii iii

-continued

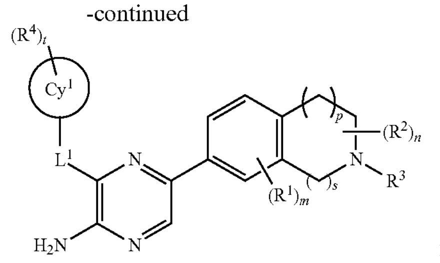

iv

X, X' = Cl or Br or I Y, Y' = H or alkyl (Y and Y' can be linked through a bond)

For example, compounds of Formula (I) can be formed as shown in Scheme II. Compound (vi) can be selectively coupled with 2-amino-3,5-dihalopyrazine to give compound (ii); compound (ii) can be linked with compound (iii) to give compound (iv) [i.e., Formula (I)].

For example, compounds of Formula (Ia) can be formed as shown in Scheme III. Compound (i) can be protected to give compound (ii); compound (ii) can be annulated with formaldehyde to give compound (iii); compound (iii) can be deprotected to give compound (iv); compound (iv) can be alkylated to give compound (v); compound (v) can be borylated to give compound (vi). Compound (vii) can be deprotonated and react with 2-amino-3,5-dihalopyrazine to give compound (viii). Lastly, compound (vi) and compound (viii) can be coupled using transition metal catalyzed reaction to give compound (ix) [i.e., Formula (Ia)].

Scheme IV

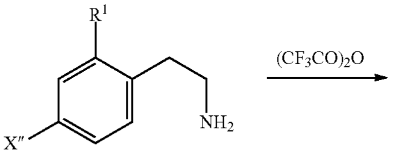

i

Scheme III

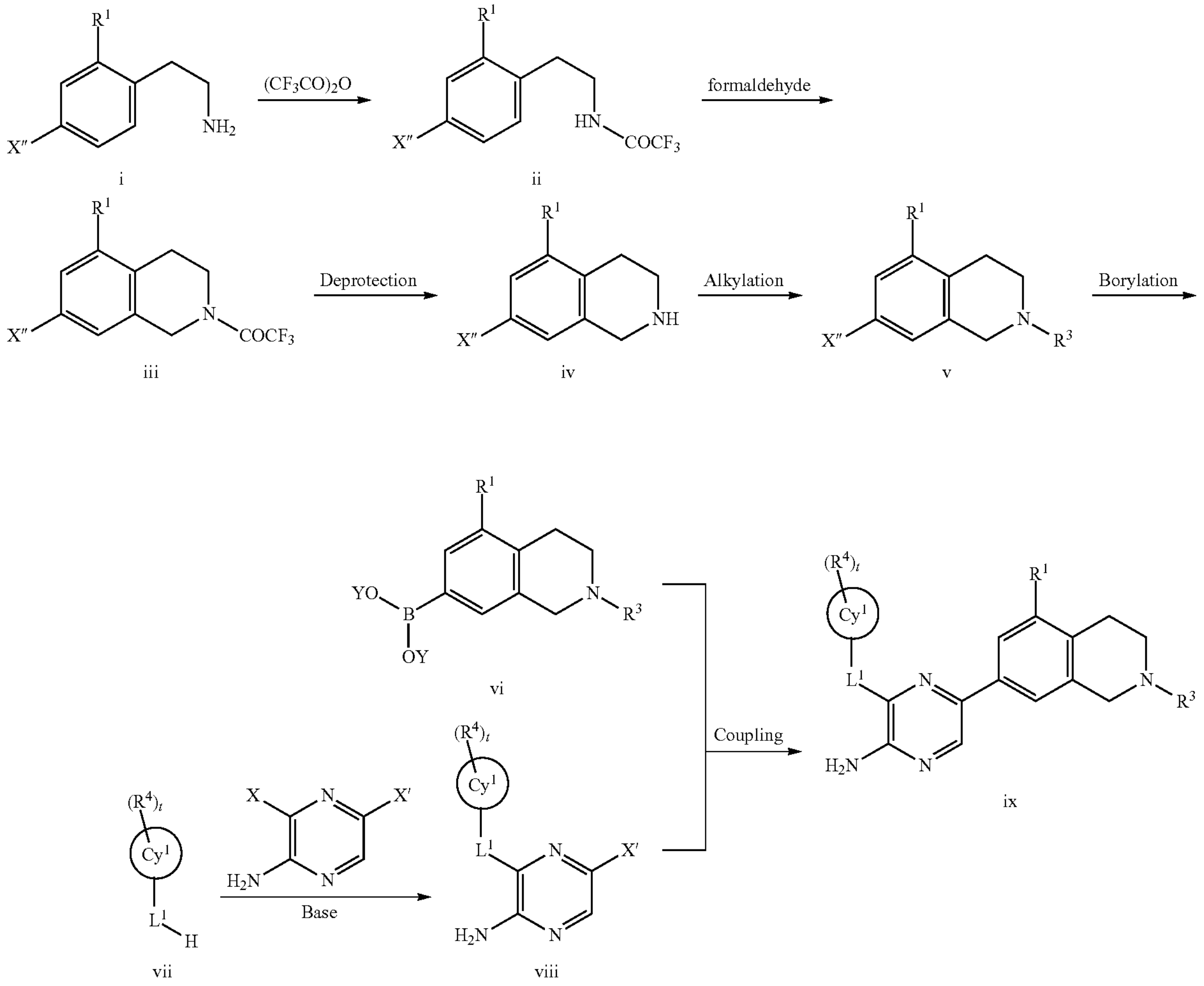

i ii iii iv v vi vii viii ix

X, X', X'' = Cl or Br or I

Y, Y' = H or alkyl (Y and Y' can be linked through a bond)

-continued

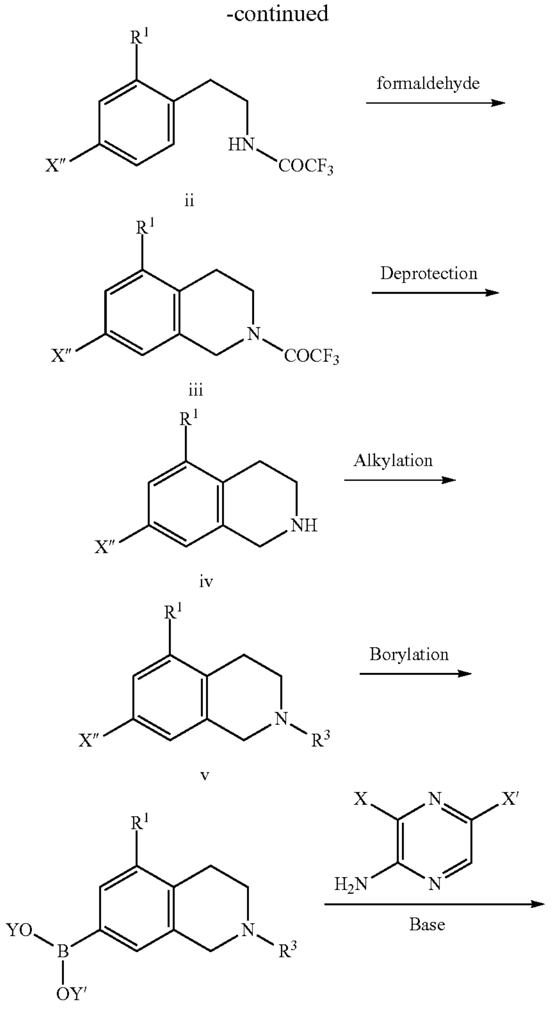

-continued

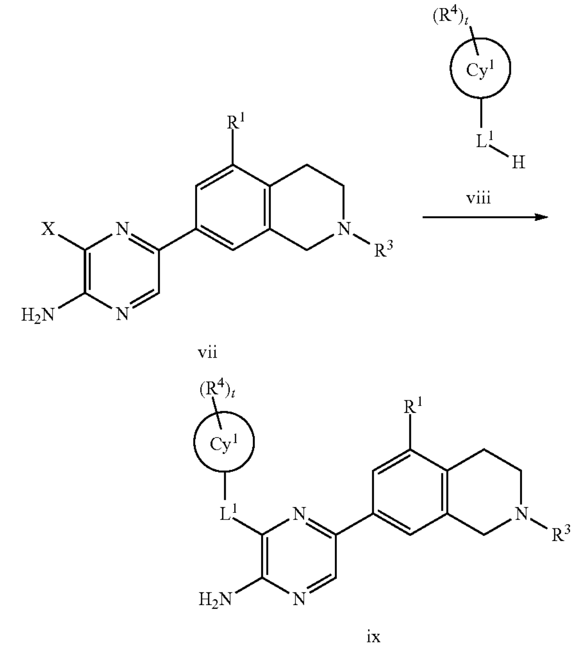

X, X', X'' = Cl or Br or I Y, Y' = H or alkyl (Y and Y' can be linked through a bond)

For example, compounds of Formula (Ia) can be formed as shown in Scheme IV. Compound (i) can be protected to give compound (ii); compound (ii) can be annulated with formaldehyde to give compound (iii); compound (iii) can be deprotected to give compound (iv); compound (iv) can be alkylated to give compound (v); compound (v) can be borylated to compound (vi); compound (vi) can be selectively coupled with 2-amino-3,5-dihalopyrazine to give compound (vii); compound (vii) can be linked with compound (viii) to give compound (ix) [i.e., Formula (Ia)].

Scheme V

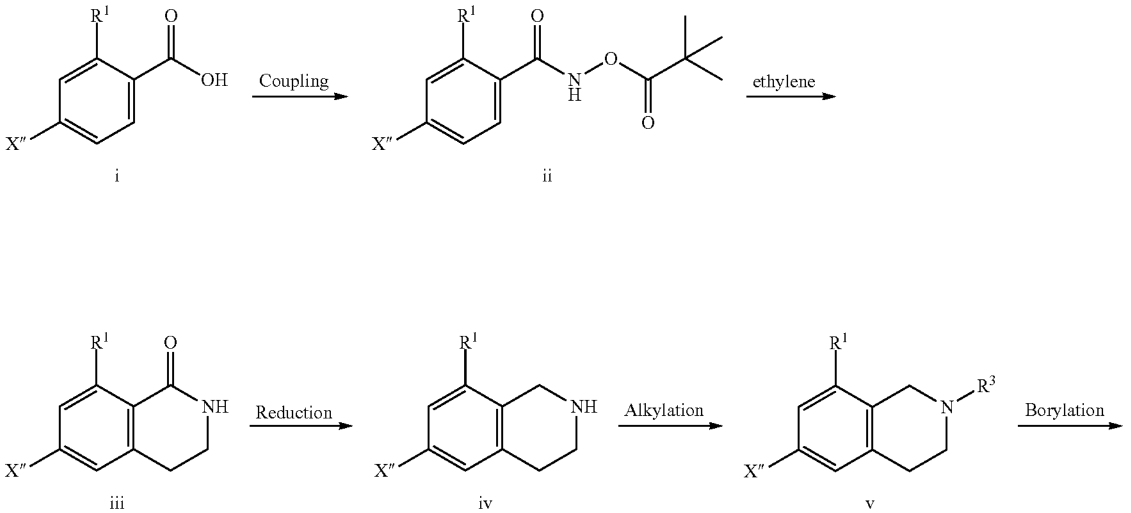

-continued

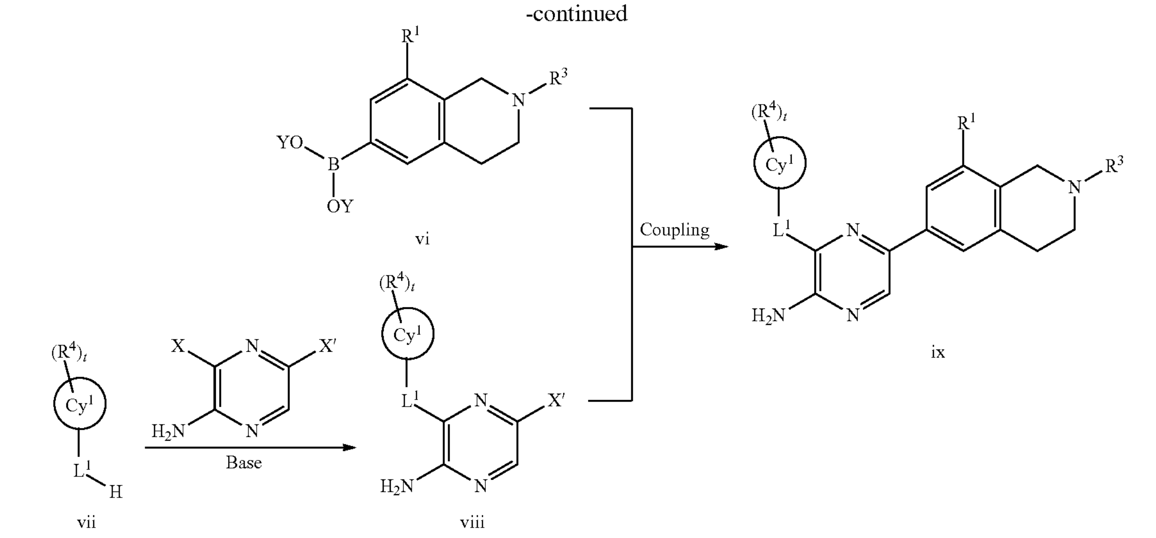

X, X′, X″ = Cl or Br or I
Y, Y′ = H or alkyl (Y and Y′ can be linked through a bond)

For example, compounds of Formula (Ib) can be formed as shown in Scheme V. Compound (i) can be derivatized with O-pivaloylhydroxylamine to give compound (ii); compound (ii) can be annulated with ethylene with transition metal catalyzed reaction to give compound (iii); compound (iii) can be reduced to give compound (iv); compound (iv) can be alkylated to give compound (v); compound (v) can be borylated to give compound (vi). Compound (vii) can be deprotonated and react with 2-amino-3,5-dihalopyrazine to give compound (viii). Lastly, compound (vi) and compound (viii) can be coupled using transition metal catalyzed reaction to give compound (ix) [i.e., Formula (Ib)].

Scheme VI

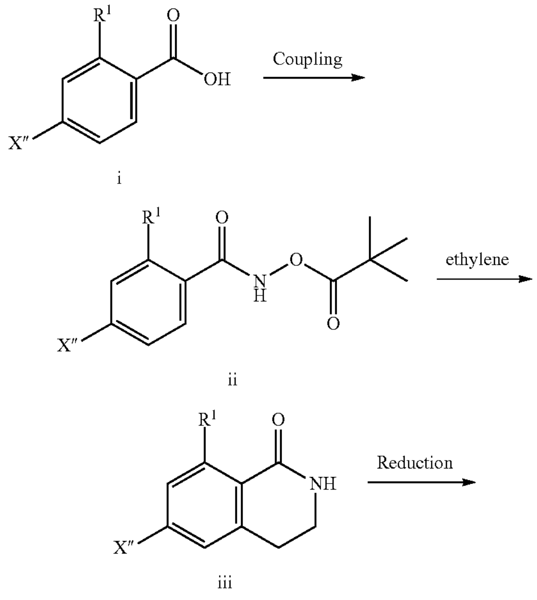

-continued

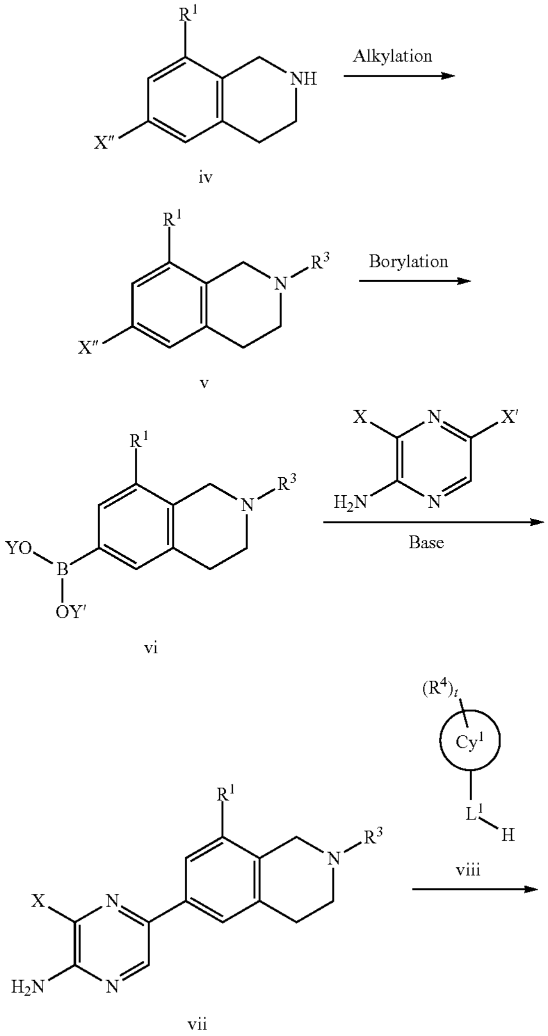

-continued

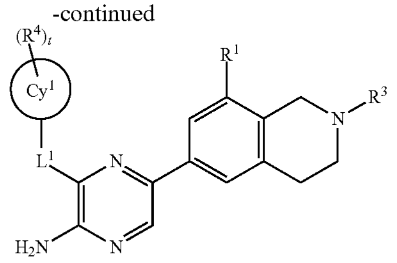

ix

X, X', X'' = Cl or Br or I Y, Y' = H or alkyl (Y and Y' can be linked through a bond)

For example, compounds of Formula (Ib) can be formed as shown in Scheme VI. Compound (i) can be derivatized with O-pivaloylhydroxylamine to give compound (ii); compound (ii) can be annulated with ethylene with transition metal catalyzed reaction to give compound (iii); compound (iii) can be reduced to give compound (iv); compound (iv) can be alkylated to give compound (v); compound (v) can be borylated to compound (vi); compound (vi) can be selectively coupled with 2-amino-3,5-dihalopyrazine to give compound (vii); compound (vii) can be linked with compound (viii) to give compound (ix) [i.e., Formula (Ib)].

Abbreviations

Boc tert-butyloxycarbonyl
Me methyl
TEA triethylamine
TFAA trifluoroacetic anhydride
LC-MS liquid chromatograph mass spectrometer
NMR nuclear magnetic resonance
DCM dichloromethane
Et ethyl
Ac acetyl
BPD bis(pinacolato)diboron
dppf 1,1'-bis(diphenylphosphino)ferrocene
THF tetrahydrofuran
HPLC high performance liquid chromatography
DMSO dimethyl sulfoxide
PE petroleum ether
DMF N,N-dimethylformamide
Bu butyl
Ph phenyl
TLC thin layer chromatography
UV ultraviolet
dba dibenzylideneacetone
Tf trifluorosulfonyl
MTBE methyl tert-butyl ether
DIPEA N,N-diisopropylethylamine
SEM 2-(trimethylsilyl)ethoxymethyl
LDA lithium diisopropylamide
pTSA p-toluenesulfonic acid
HATU 2-(7-azabenzotriazol-1-yl)-N,N,N',N'-tetramethyluronium hexafluorophosphate
DMAP 4-dimethylaminopyridine

EXAMPLES

Example 1: 5-(2,5-dimethyl-1,2,3,4-tetrahydroisoquinolin-7-yl)-3-(pyridin-4-ylmethoxy)pyrazin-2-amine

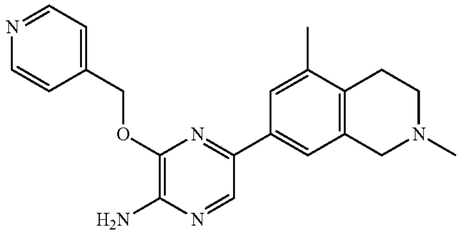 [SMILES: Cc1cc(-c2cnc(N)c(OCc3ccncc3)n2)cc2c1CCN(C)C2]

Step 1: 2-(4-bromo-2-methylphenyl)ethanamine hydrochloride

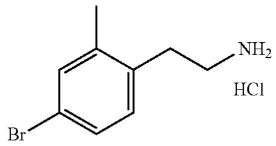

At 0° C., to a solution of 2-(4-bromo-2-methylphenyl) acetonitrile (30.0 g, 0.143 mol) in MeOH (200 mL) was added $NiCl_2·6H_2O$ (3.39 g, 0.0143 mol), $Boc_2O$ (62.3 g, 0.286 mol). Then $NaBH_4$ (64.8 g, 1.71 mol) was added in portions within 15 min. The resulting mixture was stirred for 5 h at room temperature. The reaction mixture was quenched with ice water. The resulting solution was extracted with ethyl acetate (1000 mL×3). The organic phases were combined, washed with brine, dried over $Na_2SO_4$ and concentrated under reduced pressure. To the residue was added HCl in MeOH (7 N, 50 mL, 0.350 mol) at room temperature, and the solution was stirred for 16 h at room temperature. The solvent was concentrated under reduced pressure to give the title compound (35.0 g, crude). LC-MS $(M+H)^+$=214.0.

Step 2: N-[2-(4-bromo-2-methylphenyl)ethyl]-2,2,2-trifluoroacetamide

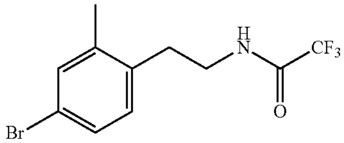 [SMILES: Cc1cc(Br)ccc1CCNC(=O)C(F)(F)F]

At 0° C., to a solution of 2-(4-bromo-2-methylphenyl) ethanamine hydrochloride (350 mg, crude) in DCM (15 mL) was added TEA (345 mg, 3.42 mmol) and TFAA (356 mg, 1.70 mmol) with stirring under nitrogen atmosphere. After 15 h, the reaction was then quenched by the addition of water (20 mL). The resulting solution was extracted with DCM (35 mL×3). The organic phases were combined, washed with brine, dried over $Na_2SO_4$ and concentrated under reduced pressure to give the title compound (271 mg, 61% for 2 steps). LC-MS $(M+H)^+$=310.0.

Step 3: 1-(7-bromo-5-methyl-3,4-dihydro-1H-isoquinolin-2-yl)-2,2,2-trifluoroethanone

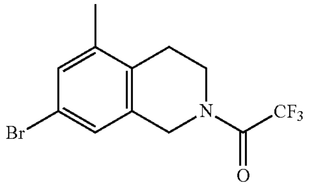 [SMILES: Cc1cc(Br)cc2c1CCN(C(=O)C(F)(F)F)C2]

To a solution of N-[2-(4-bromo-2-methylphenyl)ethyl]-2,2,2-trifluoroacetamide (271 mg, 0.874 mmol) in AcOH (3 mL) was added $H_2SO_4$ (2 mL) and paraformaldehyde (176 mg, 1.95 mmol) with stirring at room temperature. After 16 h, the reaction was then diluted by the addition of water (30 mL). The resulting solution was extracted with ethyl acetate (50 mL×3). The organic phases were combined, washed with brine, dried over $Na_2SO_4$ and concentrated under reduced pressure. The residue was purified by C18 column chromatography, eluted with MeCN in water (40% to 70%) to give the title compound (100 mg, 36%). LC-MS $(M+H)^+$=322.2.

Step 4: 7-bromo-5-methyl-1,2,3,4-tetrahydroisoquinoline

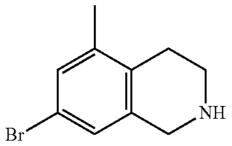

To a solution of 1-(7-bromo-5-methyl-3,4-dihydro-1H-isoquinolin-2-yl)-2,2,2-trifluoroethanone (100 mg, 0.270 mmol) in EtOH (5 mL) and water (1 mL) was added $K_2CO_3$ (147 mg, 1.06 mmol) with stirring at room temperature. The resulting mixture was warmed to 80° C. After 2 h, the reaction was cooled down and diluted with water (10 mL). The resulting mixture was extracted with DCM (30 mL×3). The organic phases were combined, washed with brine, dried over $Na_2SO_4$ and concentrated under reduced pressure to give the title compound (49 mg, 81%). LC-MS $(M+H)^+$=226.1.

Step 5: 7-bromo-2,5-dimethyl-1,2,3,4-tetrahydroisoquinoline

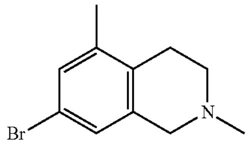

To a stirred solution of 7-bromo-5-methyl-1,2,3,4-tetrahydroisoquinoline (100 mg, 0.398 mmol) and formalin (40%, 45 mg, 0.597 mmol) in MeOH (5 mL) was added $NaBH_3CN$ (39 mg, 0.60 mmol) in portions at room temperature under nitrogen atmosphere. After 3 h, the resulting mixture was concentrated under reduced pressure and the residue was purified by silica gel column chromatography, eluted with DCM/MeOH (10:1) to give the title compound (102 mg, 99%). LC-MS $(M+H)^+$=240.0.

Step 6: 2,5-dimethyl-7-(4,4,5,5-tetramethyl-1,3,2-dioxaborolan-2-yl)-1,2,3,4-tetrahydroisoquinoline

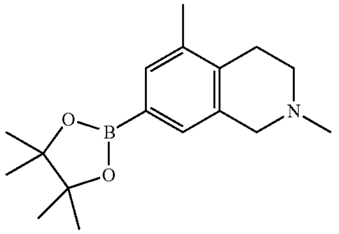

7-bromo-2,5-dimethyl-1,2,3,4-tetrahydroisoquinoline (2.5 g, 10.4 mmol), BPD (3.96 g, 15.6 mmol), $Pd(dppf)Cl_2$ (457 mg, 0.62 mmol) and AcOK (2.0 g, 20.8 mmol) was added to dioxane (50 mL) under nitrogen. The reaction mixture was heated to reflux overnight then cooled to room temperature. EtOAc (50 mL) was added and the mixture was washed with brine (30 mL×2). The aqueous layer was extracted with EtOAc (50 mL). The combined organic layer was dried over $Na_2SO_4$ then concentrated under reduced pressure. The residue was purified by silica gel column chromatography, eluted with MeOH/DCM (1:15) to give the title compound (2.11 g, 71%). LC-MS $(M+H)^+$=288.1.

Step 7: 5-bromo-3-(pyridin-4-ylmethoxy)pyrazin-2-amine

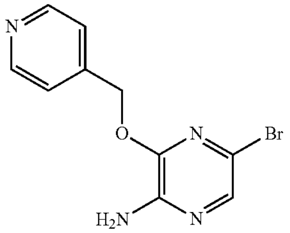

To a solution of 4-pyridinemethanol (246 mg, 2.25 mmol) in THF (15 mL) was added NaH (60%, 90 mg, 2.25 mmol) at room temperature. The resulting mixture was stirred for 3 h at room temperature under nitrogen atmosphere. To the above mixture was added 3,5-dibromopyrazin-2-amine (475 mg, 1.88 mmol) in portions over 10 min at room temperature. The resulting mixture was stirred for additional 2 h at 70° C. under a reflux condenser. The reaction mixture was cooled to room temperature and quenched by addition of ice water (20 mL). The resulting mixture was extracted with ethyl acetate (30 mL×3). The organic phases were combined, washed with brine and dried over $Na_2SO_4$. The solvent was concentrated under reduced pressure and the residue was purified by flash chromatography, eluting with ethyl acetate in DCM (0% to 80% gradient) to give the title compound (76 mg, 56%). LC-MS $(M+H)^+=281.2$.

Step 8: 5-(2,5-dimethyl-1,2,3,4-tetrahydroisoquinolin-7-yl)-3-(pyridin-4-ylmethoxy)pyrazin-2-amine

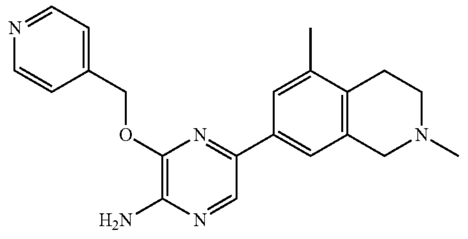

5-bromo-3-(pyridin-4-ylmethoxy)pyrazin-2-amine (50 mg, 0.174 mmol), 2,5-dimethyl-7-(4,4,5,5-tetramethyl-1,3,2-dioxaborolan-2-yl)-3,4-dihydro-1H-isoquinoline (60 mg, 0.209 mmol), $Pd(dppf)Cl_2 \cdot DCM$ (15 mg, 0.017 mmol), $K_2CO_3$ (49 mg, 0.348 mmol) was added to dioxane (4.0 mL) and water (1.0 mL) at room temperature. The resulting mixture was stirred for 2 h at 100° C. under nitrogen. The mixture was cool to room temperature and concentrated under vacuum. The residue was purified by basic $Al_2O_3$ gel column chromatography, eluted with DCM/MeOH (1:1) to yield a preliminarily purified material. The material was purified by prep-HPLC to give Example 1 (37 mg, 58%). $^1H$ NMR (400 MHz, DMSO-d6) δ 8.61-8.55 (m, 2H), 8.08 (s, 1H), 7.60-7.54 (m, 2H), 7.48 (s, 1H), 7.36 (s, 1H), 6.51 (s, 2H), 5.55 (s, 2H), 3.48 (s, 2H), 2.71-2.58 (m, 4H), 2.34 (s, 3H), 2.21 (s, 3H). LC-MS $(M+H)^+=362.2$.

Example 2: 5-(2,5-dimethyl-1,2,3,4-tetrahydroisoquinolin-7-yl)-3-((1-methylpiperidin-4-yl)methoxy)pyrazin-2-amine

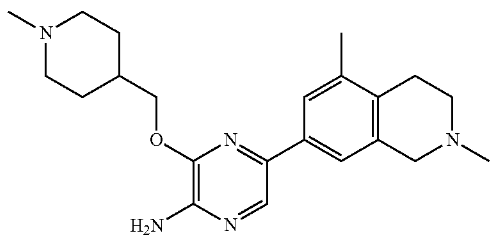

Step 1: 5-bromo-3-((1-methylpiperidin-4-yl)methoxy)pyrazin-2-amine

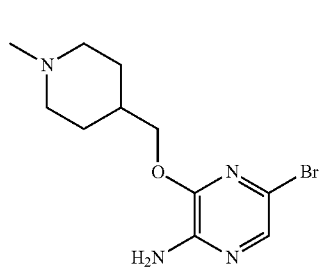 [SMILES: CN1CCC(COc2nc(Br)cnc2N)CC1]

The title compound (149 mg, 57%) was prepare in a manner similar to that in Example 1 step 7 from (1-methylpiperidin-4-yl)methanol and 3,5-dibromopyrazin-2-amine. LC-MS $(M+H)^+=301.1$.

Step 2: 5-(2,5-dimethyl-1,2,3,4-tetrahydroisoquinolin-7-yl)-3-((1-methylpiperidin-4-yl)methoxy)pyrazin-2-amine

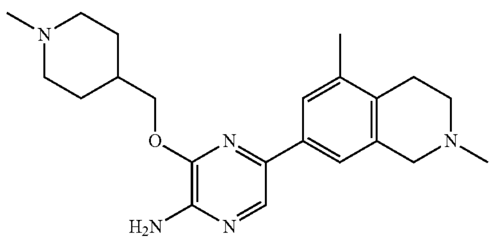

Example 2 (23 mg, 13%) was prepared in a manner similar to that in Example 1 step 8 from 2,5-dimethyl-7-(4,4,5,5-tetramethyl-1,3,2-dioxaborolan-2-yl)-1,2,3,4-tetrahydroisoquinoline and 5-bromo-3-((1-methylpiperidin-4-yl)methoxy)pyrazin-2-amine. $^1H$ NMR (400 MHz, DMSO-d6) δ 8.02 (s, 1H), 7.52 (s, 1H), 7.40 (s, 1H), 6.29 (s, 2H), 4.24 (d, J=6.0 Hz, 2H), 3.50 (s, 2H), 2.82 (d, J=11.2 Hz, 2H), 2.70-2.60 (m, 4H), 2.34 (s, 3H), 2.22 (s, 3H), 2.18 (s, 3H), 1.95-1.76 (m, 5H), 1.42-1.28 (m, 2H). LC-MS $(M+H)^+=382.2$.

Example 3: 5-(2,5-dimethyl-1,2,3,4-tetrahydroisoquinolin-7-yl)-3-(pyrimidin-4-ylmethoxy)pyrazin-2-amine

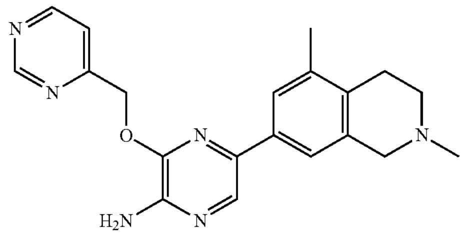

Step 1: 5-bromo-3-(pyrimidin-4-ylmethoxy)pyrazin-2-amine

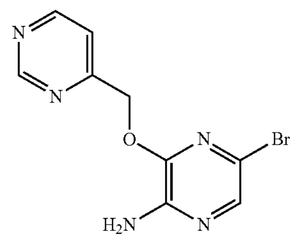 [SMILES: Nc1ncc(Br)nc1OCc1ccncn1]

The title compound (185 mg, 31%) was prepared in a manner similar to that in Example 1 step 7 from 3,5-dibromopyrazin-2-amine and pyrimidin-4-ylmethanol. LC-MS $(M+H)^+=282.0$.

Step 2: 5-(2,5-dimethyl-1,2,3,4-tetrahydroisoquinolin-7-yl)-3-(pyrimidin-4-ylmethoxy)pyrazin-2-amine

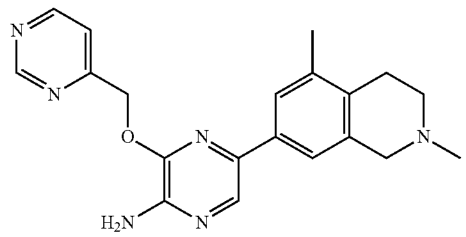

Example 3 (39 mg, 12%) was prepared in a manner similar to that in Example 1 step 8 from 2,5-dimethyl-7-(4,4,5,5-tetramethyl-1,3,2-dioxaborolan-2-yl)-1,2,3,4-tetrahydroisoquinoline and 5-bromo-3-(pyrimidin-4-ylmethoxy)pyrazin-2-amine. $^1$H NMR (400 MHz, DMSO-d6) δ 9.19 (s, 1H), 8.83 (d, J=5.2 Hz, 1H), 8.09 (s, 1H), 7.81 (d, J=5.2, 1H), 7.40 (s, 1H), 7.29 (s, 1H), 6.59 (s, 2H), 5.56 (s, 2H), 3.47 (s, 2H), 2.69-2.59 (m, 4H), 2.35 (s, 3H), 2.19 (s, 3H). LC-MS $(M+H)^+$=363.2

Example 4: (1-(3-amino-6-(2,5-dimethyl-1,2,3,4-tetrahydroisoquinolin-7-yl)pyrazin-2-yl)-1H-indazol-5-yl)methanol

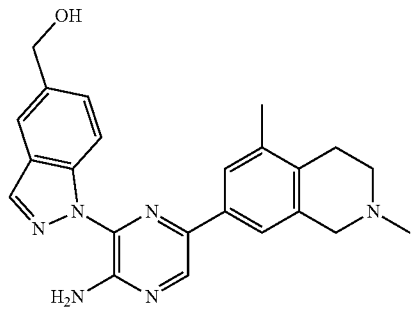 [SMILES: Cc1cc(-c2cnc(N)c(-n3ncc4cc(CO)ccc43)n2)cc2c1CCN(C)C2]

Step 1: (1-(3-amino-6-bromopyrazin-2-yl)-1H-indazol-5-yl)methanol

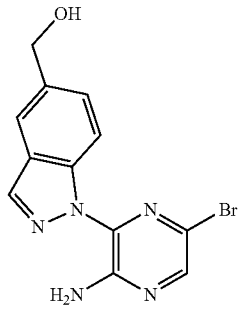 [SMILES: Nc1ncc(Br)nc1-n1ncc2cc(CO)ccc21]

The title compound (357 mg, 35%) was prepared in a manner similar to that in Example 1 step 7 from 3,5-dibromopyrazin-2-amine and (1H-indazol-5-yl)methanol. LC-MS $(M+H)^+$=320.2.

Step 2: (1-(3-amino-6-(2,5-dimethyl-1,2,3,4-tetrahydroisoquinolin-7-yl)pyrazin-2-yl)-1H-indazol-5-yl)methanol

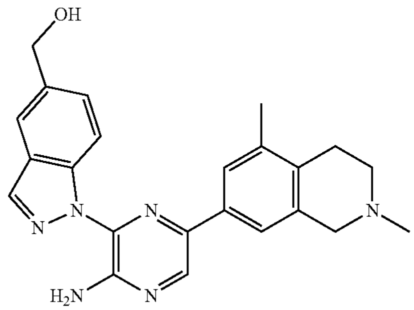 [SMILES: Cc1cc(-c2cnc(N)c(-n3ncc4cc(CO)ccc43)n2)cc2c1CCN(C)C2]

Example 4 (8 mg, 6%) was prepared in a manner similar to that in Example 1 step 8 from 2,5-dimethyl-7-(4,4,5,5-tetramethyl-1,3,2-dioxaborolan-2-yl)-1,2,3,4-tetrahydroisoquinoline and (1-(3-amino-6-bromopyrazin-2-yl)-1H-indazol-5-yl)methanol. $^1$H NMR (400 MHz, DMSO-d6) δ 8.51 (s, 1H), 8.50-8.41 (m, 2H), 7.86 (s, 1H), 7.63 (s, 1H), 7.58 (d, J=8.8 Hz, 1H), 7.50 (s, 1H), 4.65 (s, 2H), 3.54 (s, 2H), 2.72-2.56 (m, 4H), 2.34 (s, 3H), 2.24 (s, 3H). LC-MS $(M+H)^+$=401.2.

Example 5: (2-(3-amino-6-(2,5-dimethyl-1,2,3,4-tetrahydroisoquinolin-7-yl)pyrazin-2-yl)-2H-indazol-5-yl)methanol

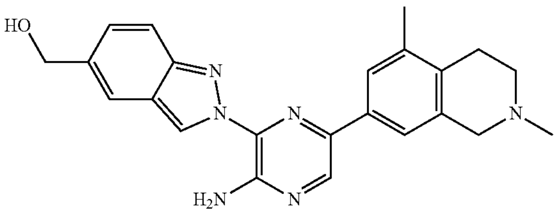 [SMILES: Cc1cc(-c2cnc(N)c(-n3cc4cc(CO)ccc4n3)n2)cc2c1CCN(C)C2]

Step 1: (2-(3-amino-6-bromopyrazin-2-yl)-2H-indazol-5-yl)methanol

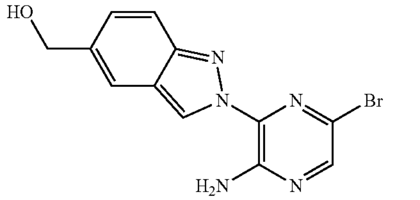 [SMILES: Nc1ncc(Br)nc1-n1cc2cc(CO)ccc2n1]

The title compound (260 mg, 26%) was another product that was isolated from Example 4 step 1. LC-MS $(M+H)^+$=320.2.

Step 2: (2-(3-amino-6-(2,5-dimethyl-1,2,3,4-tetrahydroisoquinolin-7-yl)pyrazin-2-yl)-2H-indazol-5-yl) methanol

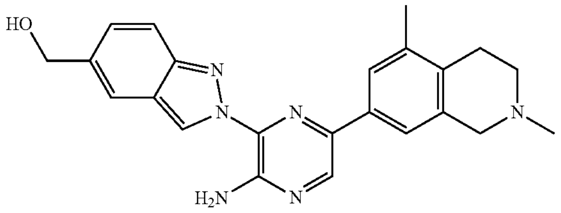 [SMILES: Cc1cc(-c2cnc(N)c(-n3cc4cc(CO)ccc4n3)n2)cc2c1CCN(C)C2]

Example 5 (14 mg, 10%) was prepared in a manner similar to that in Example 1 step 8 from 2,5-dimethyl-7-(4,4,5,5-tetramethyl-1,3,2-dioxaborolan-2-yl)-1,2,3,4-tetrahydroisoquinoline and (2-(3-amino-6-bromopyrazin-2-yl)-2H-indazol-5-yl)methanol. $^{1}$H NMR (400 MHz, DMSO-d6) δ 9.38 (s, 1H), 8.67 (s, 1H), 7.76-7.69 (m, 3H), 7.63 (s, 1H), 7.34 (d, J=8.9, 1.6 Hz, 1H), 4.56 (s, 2H), 3.57 (s, 2H), 2.74-2.63 (m, 4H), 2.36 (s, 3H), 2.26 (s, 3H). LC-MS $(M+H)^+$=401.2.

Example 6: 3-(1H-pyrazol-4-yloxy)-5-(2,5-dimethyl-1,2,3,4-tetrahydroisoquinolin-7-yl)pyrazin-2-amine

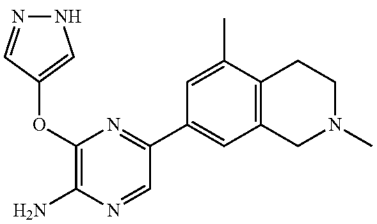 [SMILES: Cc1cc(-c2cnc(N)c(Oc3cn[nH]c3)n2)cc2c1CCN(C)C2]

Step 1: 3-(1H-pyrazol-4-yloxy)-5-bromopyrazin-2-amine

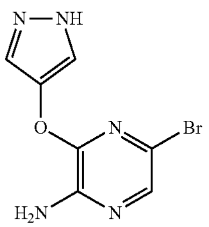 [SMILES: Nc1ncc(Br)nc1Oc1cn[nH]c1]

To a solution of 1H-pyrazol-4-ol (285 mg, 3.39 mmol) in DMSO (5 mL) was added 3,5-dibromopyrazin-2-amine (814 mg, 3.39 mmol), $K_2CO_3$ (946 mg, 6.78 mmol) at room temperature. The resulting mixture was stirred for overnight at 75° C. under nitrogen atmosphere. The mixture was cooled to room temperature and concentrated under reduced pressure. The residue was loaded onto C18 gel column, eluted with MeOH in water (10% to 95% gradient) to give the title compound (87 mg, 10%). LC-MS $(M+H)^+$=256.0.

Step 2: 3-(1H-pyrazol-4-yloxy)-5-(2,5-dimethyl-1,2,3,4-tetrahydroisoquinolin-7-yl)pyrazin-2-amine

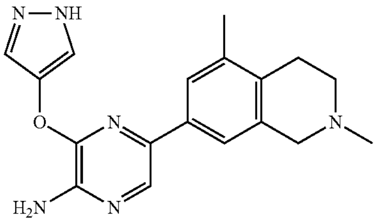 [SMILES: Cc1cc(-c2cnc(N)c(Oc3cn[nH]c3)n2)cc2c1CCN(C)C2]

Example 6 (12 mg, 17%) was prepared in a manner similar to that in Example 1 step 8 from 2,5-dimethyl-7-(4,4,5,5-tetramethyl-1,3,2-dioxaborolan-2-yl)-1,2,3,4-tetrahydroisoquinoline and 3-(1H-pyrazol-4-yloxy)-5-bromopyrazin-2-amine. $^{1}$H NMR (400 MHz, DMSO-d6) δ 12.76 (br s, 1H), 8.16 (s, 1H), 7.83 (br s, 2H), 7.45 (s, 1H), 7.32 (s, 1H), 6.62 (s, 2H), 3.47 (s, 2H), 2.70-2.57 (m, 4H), 2.33 (s, 3H), 2.20 (s, 3H). LC-MS $(M+H)^+$=337.2.

Example 7: 1-(3-amino-6-(2,5-dimethyl-1,2,3,4-tetrahydroisoquinolin-7-yl)pyrazin-2-yl)-1H-pyrazol-4-ol

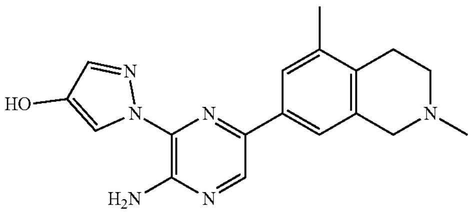 [SMILES: Cc1cc(-c2cnc(N)c(-n3cc(O)cn3)n2)cc2c1CCN(C)C2]

Step 1: 1-(3-amino-6-bromopyrazin-2-yl)-1H-pyrazol-4-ol

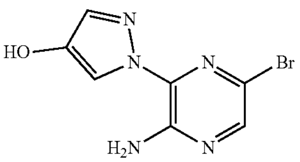 [SMILES: Nc1ncc(Br)nc1-n1cc(O)cn1]

The title compound (70 mg, 21%) was another product that was isolated from Example 6 step 1. LC-MS $(M+H)^+$=256.0.

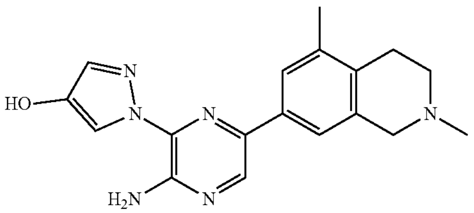 [SMILES: Cc1cc(-c2cnc(N)c(-n3cc(O)cn3)n2)cc2c1CCN(C)C2]

Step 2: 1-(3-amino-6-(2,5-dimethyl-1,2,3,4-tetrahydroisoquinolin-7-yl)pyrazin-2-yl)-1H-pyrazol-4-ol

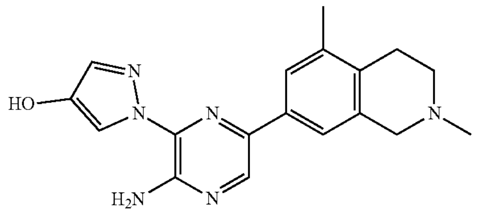 [SMILES: Cc1cc(-c2cnc(N)c(-n3cc(O)cn3)n2)cc2c1CCN(C)C2]

Example 7 (13 mg, 9%) was prepared in a manner similar to that in Example 1 step 8 from 2,5-dimethyl-7-(4,4,5,5-tetramethyl-1,3,2-dioxaborolan-2-yl)-1,2,3,4-tetrahydroisoquinoline and 1-(3-amino-6-bromopyrazin-2-yl)-1H-pyrazol-4-ol. $^1$H NMR (400 MHz, DMSO-d6) δ 9.23 (s, 1H), 8.47 (s, 1H), 8.26 (s, 1H), 7.66 (s, 1H), 7.54 (s, 2H), 7.46 (s, 2H), 3.53 (s, 2H), 2.75-2.59 (m, 4H), 2.35 (s, 3H), 2.25 (s, 3H). LC-MS $(M+H)^+$=337.1.

Example 8: 5-(2,5-dimethyl-1,2,3,4-tetrahydroisoquinolin-7-yl)-3-((3-fluoropyridin-4-yl)methoxy)pyrazin-2-amine

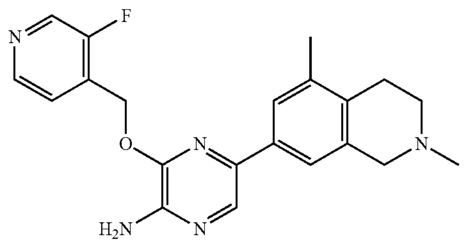 [SMILES: Cc1cc(-c2cnc(N)c(OCc3ccncc3F)n2)cc2c1CCN(C)C2]

Step 1: 5-bromo-3-((3-fluoropyridin-4-yl)methoxy)pyrazin-2-amine

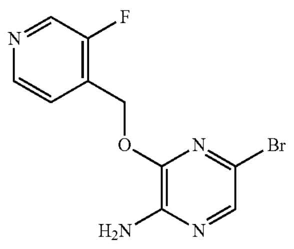 [SMILES: Nc1ncc(Br)nc1OCc1ccncc1F]

The title compound (648 mg, 64%) was prepared in a manner similar to that in Example 1 step 7 from (3-fluoropyridin-4-yl)methanol and 5-bromo-3-chloropyrazin-2-amine. LC-MS $(M+H)^+$=298.9.

Step 2: 5-(2,5-dimethyl-1,2,3,4-tetrahydroisoquinolin-7-yl)-3-((3-fluoropyridin-4-yl)methoxy)pyrazin-2-amine

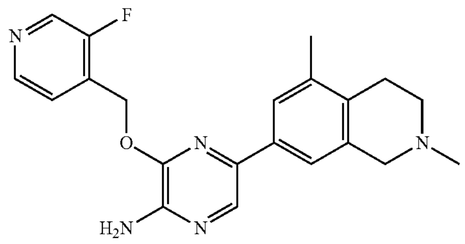 [SMILES: Cc1cc(-c2cnc(N)c(OCc3ccncc3F)n2)cc2c1CCN(C)C2]

Example 8 (42 mg, 11%) was prepared in a manner similar to that in Example 1 step 8 from 5-bromo-3-((3-fluoropyridin-4-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.62 (s, 1H), 8.46 (d, J=4.9 Hz, 1H), 8.10 (s, 1H), 7.78-7.71 (m, 1H), 7.49 (s, 1H), 7.37 (s, 1H), 6.54 (s, 2H), 5.62 (s, 2H), 3.55-3.51 (m, 2H), 2.71-2.67 (m, 4H), 2.38 (s, 3H), 2.22 (s, 3H). LC-MS $(M+H)^+$=380.3.

Example 9: 5-(2,5-dimethyl-1,2,3,4-tetrahydroisoquinolin-7-yl)-3-((3-methylpyridin-4-yl)methoxy)pyrazin-2-amine

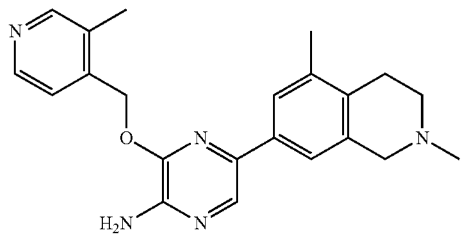

Step 1: 5-bromo-3-((3-methylpyridin-4-yl)methoxy)pyrazin-2-amine

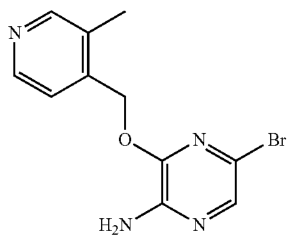 [SMILES: Cc1cnccc1COc1nc(Br)cnc1N]

The title compound (360 mg, 63%) was prepared in a manner similar to that in Example 1 step 7 from (3-methylpyridin-4-yl)methanol and 3,5-dibromopyrazin-2-amine. LC-MS $(M+H)^+$=295.1.

Step 2: 5-(2,5-dimethyl-1,2,3,4-tetrahydroisoquinolin-7-yl)-3-((3-methylpyridin-4-yl)methoxy)pyrazin-2-amine

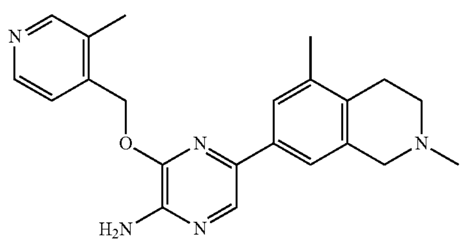 [SMILES: Cc1cnccc1COc1nc(-c2cc(C)c3c(c2)CN(C)CC3)cnc1N]

Example 9 (23 mg, 15%) was prepared in a manner similar to that in Example 1 step 8 from 5-bromo-3-((3-methylpyridin-4-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.44-8.37 (m, 2H), 8.06 (s, 1H), 7.53 (d, J=5.0 Hz, 1H), 7.47 (s, 1H), 7.36 (s, 1H), 6.49 (s, 2H), 5.53 (s, 2H), 3.48 (s, 2H), 2.69-2.58 (m, 4H), 2.39 (s, 3H), 2.34 (s, 3H), 2.20 (s, 3H). LC-MS $(M+H)^+$=376.2.

Example 10: 3-((2-aminopyridin-4-yl)methoxy)-5-(2,5-dimethyl-1,2,3,4-tetrahydroisoquinolin-7-yl)pyrazin-2-amine

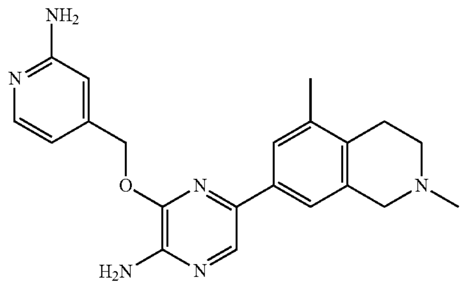

Step 1: 3-((2-aminopyridin-4-yl)methoxy)-5-bromopyrazin-2-amine

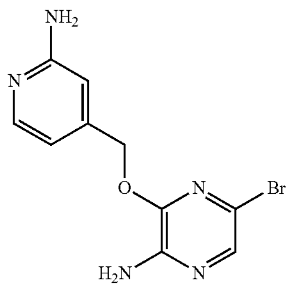

The title compound (721 mg, 66%) was prepared in a manner similar to that in Example 1 step 7 from (2-aminopyridin-4-yl)methanol and 3,5-dibromopyrazin-2-amine. LC-MS $(M+H)^+$=296.1.

Step 2: 3-((2-aminopyridin-4-yl)methoxy)-5-(2,5-dimethyl-1,2,3,4-tetrahydroisoquinolin-7-yl)pyrazin-2-amine

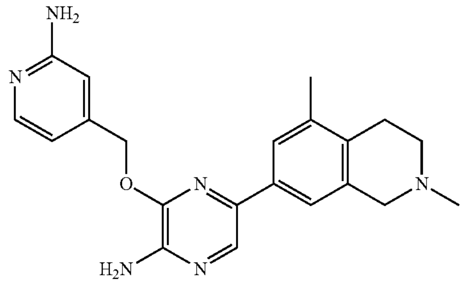

Example 10 (18 mg, 9%) was prepared in a manner similar to that in Example 1 step 8 from 3-((2-aminopyridin-4-yl)methoxy)-5-bromopyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.06 (s, 1H), 7.89 (d, J=5.2 Hz, 1H), 7.49 (s, 1H), 7.36 (s, 1H), 6.63 (d, J=5.3 Hz, 1H), 6.54 (s, 1H), 6.43 (s, 2H), 5.90 (s, 2H), 5.38 (s, 2H), 3.49 (s, 2H), 2.71-2.58 (m, 4H), 2.35 (s, 3H), 2.21 (s, 3H). LC-MS $(M+H)^+$=376.2.

Example 11: 3-((2-(cyclopropylethynyl)pyridin-4-yl)methoxy)-5-(2,5-dimethyl-1,2,3,4-tetrahydroisoquinolin-7-yl)pyrazin-2-amine

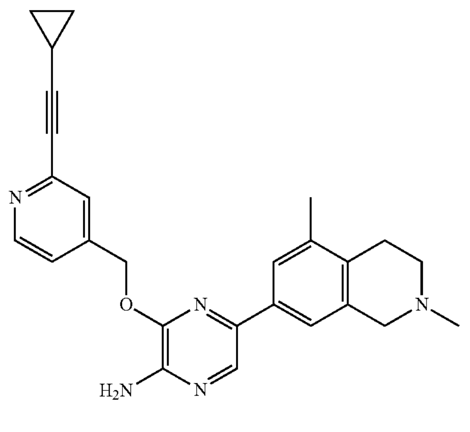 [SMILES: Cc1cc(-c2cnc(N)c(OCc3ccnc(C#CC4CC4)c3)n2)cc2c1CCN(C)C2]

Step 1: (2-(cyclopropylethynyl)pyridin-4-yl)methanol

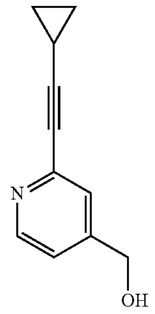 [SMILES: OCc1ccnc(C#CC2CC2)c1]

Into a 8 mL sealed tube was added ethynylcyclopropane (112 mg, 1.60 mmol), (2-bromopyridin-4-yl)methanol (200 mg, 1.04 mmol), CuI (40 mg, 0.198 mmol), Pd(dppf)$Cl_2$ (152 mg, 0.198 mmol), $Et_3N$ (3.80 mL, 27 mmol) and THF (2.0 mL) at room temperature. The resulting mixture was stirred for 20 h at room temperature under nitrogen atmosphere then concentrated under reduced pressure. The residue was purified by silica gel column chromatography, eluted with PE/EtOAc (1:1) to give the title compound (163 mg, 91%). LC-MS $(M+H)^+$=174.1.

Step 2: 5-bromo-3-((2-(cyclopropylethynyl)pyridin-4-yl)methoxy)pyrazin-2-amine

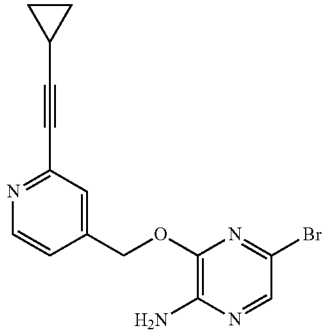 [SMILES: Nc1ncc(Br)nc1OCc1ccnc(C#CC2CC2)c1]

The title compound (48 mg, 12%) was prepared in a manner similar to that in Example 1 step 7 from (2-(cyclopropylethynyl)pyridin-4-yl)methanol and 3,5-dibromopyrazin-2-amine. LC-MS $(M+H)^+$=344.9.

Step 3: 3-((2-(cyclopropylethynyl)pyridin-4-yl)methoxy)-5-(2,5-dimethyl-1,2,3,4-tetrahydroisoquinolin-7-yl)pyrazin-2-amine

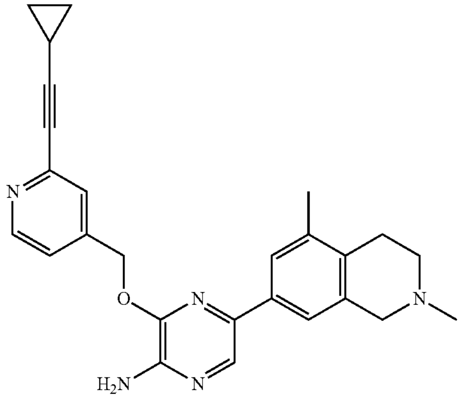 [SMILES: Cc1cc(-c2cnc(N)c(OCc3ccnc(C#CC4CC4)c3)n2)cc2c1CCN(C)C2]

Example 11 (10 mg, 16%) was prepared in a manner similar to that in Example 1 step 8 from 5-bromo-3-((2-(cyclopropylethynyl)pyridin-4-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.48 (d, J=5.1 Hz, 1H), 8.07 (s, 1H), 7.62 (s, 1H), 7.51-7.44 (m, 2H), 7.34 (s, 1H), 6.54 (s, 2H), 5.50 (s, 2H), 3.49 (s, 2H), 2.69-2.59 (m, 4H), 2.35 (s, 3H), 2.21 (s, 3H), 1.64-1.53 (m, 1H), 0.98-0.87 (m, 2H), 0.82-0.74 (m, 2H). LC-MS $(M+H)^+$=426.3.

Example 12: 3-((2-chloro-5-isopropoxypyridin-4-yl)methoxy)-5-(2,5-dimethyl-1,2,3,4-tetrahydroisoquinolin-7-yl)pyrazin-2-amine

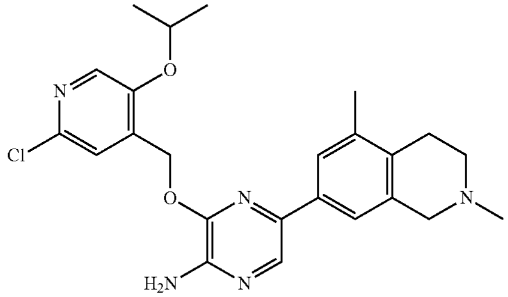 [SMILES: Cc1cc(-c2cnc(N)c(OCc3cc(Cl)ncc3OC(C)C)n2)cc2c1CCN(C)C2]

Step 1: 5-bromo-3-((2-chloro-5-fluoropyridin-4-yl)methoxy)pyrazin-2-amine

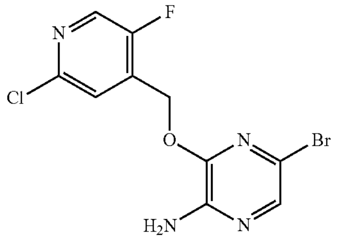 [SMILES: Nc1ncc(Br)nc1OCc1cc(Cl)ncc1F]

The title compound (341 mg, 86%) was prepared in a manner similar to that in Example 1 step 7 from (2-chloro-5-fluoropyridin-4-yl)methanol and 3,5-dibromopyrazin-2-amine. LC-MS $(M+H)^+$=332.8.

Step 2: 3-((2-chloro-5-fluoropyridin-4-yl)methoxy)-5-(2,5-dimethyl-1,2,3,4-tetrahydroisoquinolin-7-yl)pyrazin-2-amine

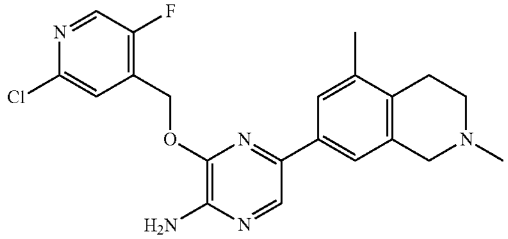 [SMILES: Cc1cc(-c2cnc(N)c(OCc3cc(Cl)ncc3F)n2)cc2c1CCN(C)C2]

The title compound (32 mg, 17%) was prepared in a manner similar to that in Example 1 step 8 from 5-bromo-3-((2-chloro-5-fluoropyridin-4-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.50 (s, 1H), 8.11 (s, 1H), 7.98 (d, J=5.1 Hz, 1H), 7.49 (s, 1H), 7.37 (s, 1H), 6.62 (s, 2H), 5.59 (s, 2H), 3.49 (s, 2H), 2.71-2.58 (m, 4H), 2.34 (s, 3H), 2.21 (s, 3H). LC-MS $(M+H)^+$=414.1.

Step 3: 3-((2-chloro-5-isopropoxypyridin-4-yl)methoxy)-5-(2,5-dimethyl-1,2,3,4-tetrahydroisoquinolin-7-yl)pyrazin-2-amine

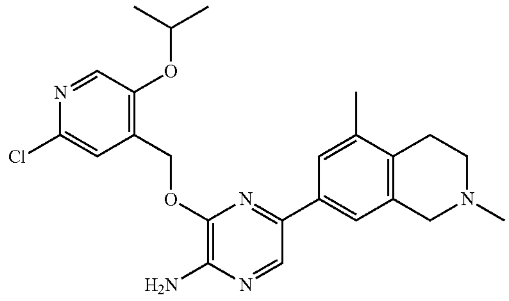 [SMILES: Cc1cc(-c2cnc(N)c(OCc3cc(Cl)ncc3OC(C)C)n2)cc2c1CCN(C)C2]

To a solution of 3-((2-chloro-5-fluoropyridin-4-yl)methoxy)-5-(2,5-dimethyl-1,2,3,4-tetrahydroisoquinolin-7-yl)pyrazin-2-amine (78 mg, 0.188 mmol) in DMF (5 mL) was added $Cs_2CO_3$ (117 mg, 0.377 mmol) and isopropyl alcohol (11 mg, 0.189 mmol) at room temperature. The resulting mixture was stirred for 1.5 h at 100° C. The reaction mixture was cooled to room temperature and the solvent was concentrated under reduced pressure. The residue was purified by prep-HPLC to give Example 12 (24 mg, 27%). $^1$H NMR (400 MHz, DMSO-d6) δ 8.23 (s, 1H), 8.11 (s, 1H), 7.74 (s, 1H), 7.52 (s, 1H), 7.39 (s, 1H), 6.63 (s, 2H), 5.51 (d, J=1.0 Hz, 2H), 4.88-4.77 (m, 1H), 3.56 (s, 2H), 2.73-2.68 (m, 4H), 2.40 (s, 3H), 2.22 (s, 3H), 1.34 (d, J=6.0 Hz, 6H). LC-MS $(M+H)^+$=455.0.

Example 13: 3-(6,7-dihydro-5H-cyclopenta[c]pyridin-5-yloxy)-5-(2,5-dimethyl-1,2,3,4-tetrahydroisoquinolin-7-yl)pyrazin-2-amine

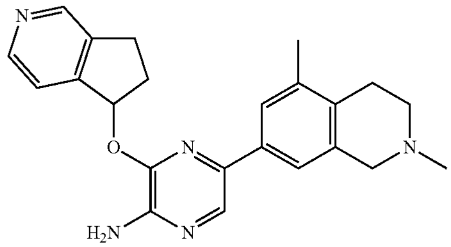 [SMILES: Cc1cc(-c2cnc(N)c(OC3CCc4cnccc43)n2)cc2c1CCN(C)C2]

Step 1: 5-bromo-3-(6,7-dihydro-5H-cyclopenta[c]pyridin-5-yloxy)pyrazin-2-amine

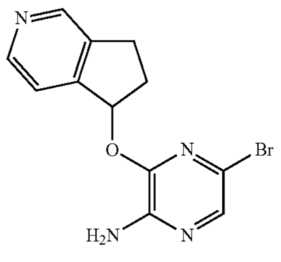 [SMILES: Nc1ncc(Br)nc1OC1CCc2cnccc21]

At 0° C., to a solution of 5H, 6H, 7H-cyclopenta[c]pyridin-5-ol (120 mg, 0.890 mmol) in THF (8 mL) was added NaH (60%, 36 mg, 0.890 mmol). The resulting mixture was stirred for 20 min at 0° C. To the above mixture was added 3,5-dibromopyrazin-2-amine (150 mg, 0.593 mmol). The resulting mixture was stirred for 16 h at 70° C. The reaction mixture was cooled to room temperature and quenched by the addition of water (30 mL). The mixture was extracted with ethyl acetate (50 mL×3). The organic phases were combined, washed with brine and dried over $Na_2SO_4$. The solvent was concentrated under reduced pressure and the residue was purified by flash chromatography, eluting with MeOH in DCM (0% to 10% gradient) to give the title compound (152 mg, 88%). LC-MS $(M+H)^+$=307.0.

Step 2: 3-(6,7-dihydro-5H-cyclopenta[c]pyridin-5-yloxy)-5-(2,5-dimethyl-1,2,3,4-tetrahydroisoquinolin-7-yl)pyrazin-2-amine

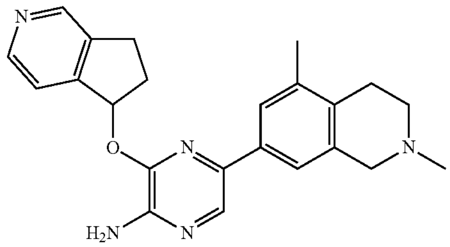

Example 13 (24 mg, 12%) was prepared in a manner similar to that in Example 1 step 8 from 5-bromo-3-(6,7-dihydro-5H-cyclopenta[c]pyridin-5-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.62 (s, 1H), 8.42 (d, J=5.0 Hz, 1H), 8.11 (s, 1H), 7.60 (s, 1H), 7.51-7.44 (m, 2H), 6.67-6.59 (m, 1H), 6.33 (s, 2H), 3.34 (s, 2H), 3.24-3.12 (m, 1H), 3.00 (m, 1H), 2.79-2.66 (m, 3H), 2.66-2.59 (m, 2H), 2.34 (s, 3H), 2.30-2.13 (m, 4H). LC-MS $(M+H)^+$=388.2.

Example 14: 4-(4-(((3-amino-6-(2,5-dimethyl-1,2,3,4-tetrahydroisoquinolin-7-yl)pyrazin-2-yl)oxy)methyl)pyridin-2-yl)-2-methylbut-3-yn-2-ol

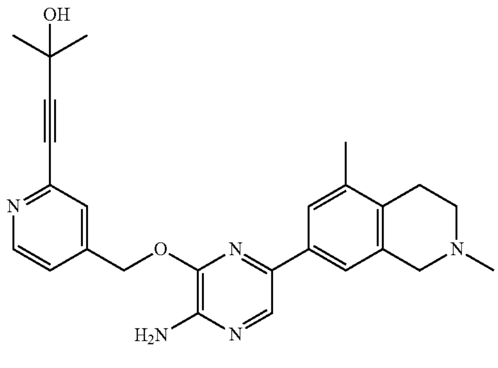 [SMILES: Cc1cc(-c2cnc(N)c(OCc3ccnc(C#CC(C)(C)O)c3)n2)cc2c1CCN(C)C2]

Step 1: (2,5-dimethyl-1,2,3,4-tetrahydroisoquinolin-7-yl)boronic acid

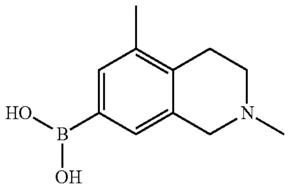

To a solution of 7-bromo-2,5-dimethyl-1,2,3,4-tetrahydroisoquinoline (20.0 g, 83.3 mmol) in THF (200 mL) was added n-BuLi (1.6 M, 78 mL, 125 mmol) at −78° C. dropwise. The mixture was stirred at −78° C. for 30 min after addition. To the mixture was added triisopropyl borate (23.5 g, 125 mmol) dropwise at −78° C. The mixture was stirred at −78° C. for 1 h, and at 0° C. for 30 min. The mixture was quenched with water (200 mL), basified to pH=14 with aqueous NaOH (2 M), and washed with EtOAc (50 mL). The aqueous layer was acidified with aqueous HCl (1 M) to pH=9. The precipitate was collected by filtration and dried under vacuum to give the title compound (15.0 g, 87%). LC-MS $(M+H)^+$=206.0.

Step 2: 4-(4-(hydroxymethyl)pyridin-2-yl)-2-methylbut-3-yn-2-ol

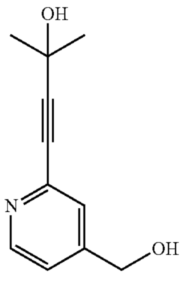

To a solution of (2-bromopyridin-4-yl)methanol (1.0 g, 5.3 mmol) and 2-methylbut-3-yn-2-ol (0.5 g, 5.9 mmol) in THF (20 mL) was added CuI (30 mg, 0.16 mmol), $PPh_3$ (70 mg, 0.27 mmol), $Pd(PPh_3)_2Cl_2$ (75 mg, 0.11 mmol) and $Et_3N$ (6 mL). The mixture was stirred at 70° C. overnight under $N_2$. The mixture was cooled to room temperature and concentrated. The residue was purified by silica gel column chromatography, eluted with PE/EtOAc (1:1) to give the title compound (800 mg, 79%). LC-MS $(M+H)^+$=192.0.

Step 3: 4-(4-(((3-amino-6-bromopyrazin-2-yl)oxy)methyl)pyridin-2-yl)-2-methylbut-3-yn-2-ol

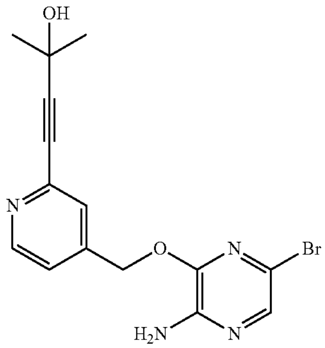 [SMILES: CC(C)(O)C#Cc1cc(COc2nc(Br)cnc2N)ccn1]

To a solution of 4-(4-(hydroxymethyl)pyridin-2-yl)-2-methylbut-3-yn-2-ol (100 mg, 0.52 mmol) in DMF (5 mL) was added NaH (60%, 65 mg, 1.63 mmol) at 0° C. The mixture was stirred for 10 min at 0° C. To the mixture was added 3,5-dibromopyrazin-2-amine (130 mg, 0.52 mmol). The mixture was stirred for 2 h at 0° C. The mixture was diluted with water (20 mL) and extracted with EtOAc (20 mL×3). The combined organic layer was washed with water (30 mL), brine (30 mL), dried over $Na_2SO_4$. The residue was purified by silica gel column chromatography, eluted with PE/EtOAc (1:1) to give the title compound (150 mg, 79%). LC-MS $(M+H)^+$=362.9, 364.9.

Step 4: 4-(4-(((3-amino-6-(2,5-dimethyl-1,2,3,4-tetrahydroisoquinolin-7-yl)pyrazin-2-yl)oxy)methyl)pyridin-2-yl)-2-methylbut-3-yn-2-ol

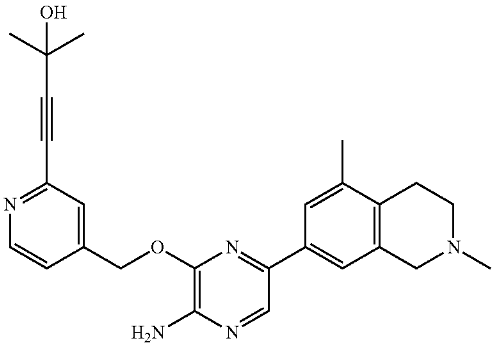 [SMILES: Cc1cc(-c2cnc(N)c(OCc3ccnc(C#CC(C)(C)O)c3)n2)cc2c1CCN(C)C2]

To a mixture of 4-(4-(((3-amino-6-bromopyrazin-2-yl)oxy)methyl)pyridin-2-yl)-2-methylbut-3-yn-2-ol (150 mg, 0.41 mmol) and (2,5-dimethyl-1,2,3,4-tetrahydroisoquinolin-7-yl)boronic acid (90 mg, 0.47 mmol) in 1,4-dioxane (10 mL) and water (5 mL) was added $Pd(dppf)Cl_2$ (20 mg, 0.02 mmol) and $K_2CO_3$ (120 mg, 0.87 mmol). The mixture was stirred at 80° C. for 15 h under $N_2$. The mixture was cooled to room temperature and diluted with water (10 mL), then extracted with EtOAc (10 mL×3). The combined organic phase was washed with brine, dried over $Na_2SO_4$, filtered and concentrated. The residue was purified by prep-TLC (DCM/MeOH=10/1) to give Example 14 (30 mg, 16%). $^1H$ NMR (400 MHz, DMSO-d6) δ 8.53 (d, J=4.7 Hz, 1H), 8.07 (s, 1H), 7.62 (s, 1H), 7.54 (d, J=5.0 Hz, 1H), 7.46 (s, 1H), 7.35 (s, 1H), 6.53 (s, 2H), 5.57 (s, 1H), 5.53 (s, 2H), 3.48 (s, 2H), 2.72-2.57 (m, 4H), 2.35 (s, 3H), 2.21 (s, 3H), 1.47 (s, 6H). LC-MS $(M+H)^+$=444.5.

Example 15: 5-(2,5-dimethyl-1,2,3,4-tetrahydroisoquinolin-7-yl)-3-(pyridin-3-ylmethoxy)pyrazin-2-amine

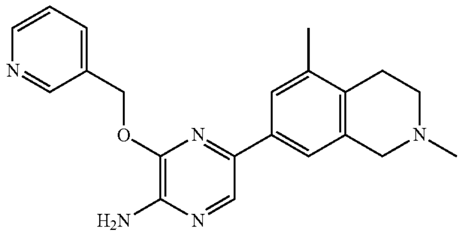

Step 1: 5-bromo-3-(pyridin-3-ylmethoxy)pyrazin-2-amine

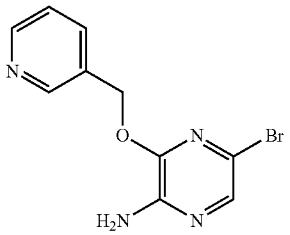 [SMILES: Nc1ncc(Br)nc1OCc1cccnc1]

NaH (60%, 240 mg, 6.0 mmol) was added in portions to a solution of pyridin-3-ylmethanol (654 mg, 6.0 mmol) in THF (20 mL) at 0° C. The mixture was stirred for 30 min, then 3,5-dibromopyrazin-2-amine (1.0 g, 4.0 mmol) was added. The mixture was stirred at 70° C. for 2 h. After being cooled to room temperature, the reaction mixture was concentrated, diluted with water (100 mL) and extracted with EtOAc (100 mL×2). The combined organic layer was dried, filtered and concentrated. The residue was purified by silica gel chromatography to give the title compound (800 mg, 71%). LC-MS $(M+H)^+$=281.0, 283.0.

Step 2: 5-(2,5-dimethyl-1,2,3,4-tetrahydroisoquinolin-7-yl)-3-(pyridin-3-ylmethoxy)pyrazin-2-amine

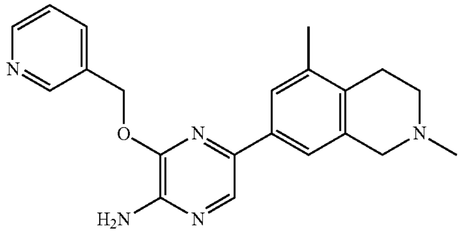

5-bromo-3-(pyridin-3-ylmethoxy)pyrazin-2-amine (300 mg, 1.1 mmol), (2,5-dimethyl-1,2,3,4-tetrahydroisoquinolin-7-yl)boronic acid (328 mg, 1.6 mmol), Pd(dppf)$Cl_2$ (87.3 mg, 0.11 mmol) and $K_2CO_3$ (368 mg, 2.7 mmol) was added to dioxane (10 mL) and $H_2O$ (2.5 mL) under $N_2$. The mixture was warmed to 80° C. and stirred overnight. After being cooled to room temperature, the mixture was diluted with water (20 mL) and extracted with DCM (20 mL×3). The combined organic layer was dried, filtered and concentrated. The residue was purified by prep-HPLC to give Example 15 (24 mg, 6%). $^1H$ NMR (400 MHz, DMSO-d6) δ 8.79 (s, 1H), 8.53 (d, J=4.0 Hz, 1H), 8.07 (s, 1H), 7.98 (d, J=8.0 Hz, 1H), 7.56 (s, 1H), 7.41-7.44 (m, 2H), 6.44 (s, 2H), 5.54 (s, 2H), 3.61 (s, 2H), 2.67 (s, 4H), 2.33 (s, 3H), 1.91 (s, 3H). LC-MS $(M+H)^+$=362.4.

Example 16: 5-(2,5-dimethyl-1,2,3,4-tetrahydroisoquinolin-7-yl)-3-((2-methylpyridin-4-yl)methoxy)pyrazin-2-amine

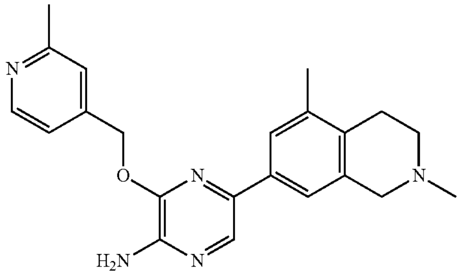 [SMILES: Cc1cc(COc2nc(-c3cc(C)c4c(c3)CN(C)CC4)cnc2N)ccn1]

Step 1: 5-bromo-3-((2-methylpyridin-4-yl)methoxy)pyrazin-2-amine

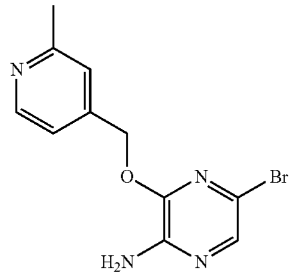 [SMILES: Cc1cc(COc2nc(Br)cnc2N)ccn1]

NaH (60%, 195 mg, 4.9 mmol) was added in portions to a solution of (2-methylpyridin-4-yl)methanol (500 mg, 4.0 mmol) in THF (10 mL) at 0° C. The reaction mixture was stirred for 30 min, then 3,5-dibromopyrazin-2-amine (1.1 g, 4.5 mmol) was added. The mixture was stirred at 70° C. for 2 h. After being cooled to room temperature, the reaction mixture was concentrated, diluted with water (100 mL) and extracted with EtOAc (100 mL×2). The combined organic layers were dried, filtered and concentrated. The residue was purified by silica gel chromatography to give the title compound (1.0 g, 83%). LC-MS $(M+H)^+$=295.0, 297.0.

Step 2:5-(2,5-dimethyl-1,2,3,4-tetrahydroisoquinolin-7-yl)-3-((2-methylpyridin-4-yl)methoxy)pyrazin-2-amine

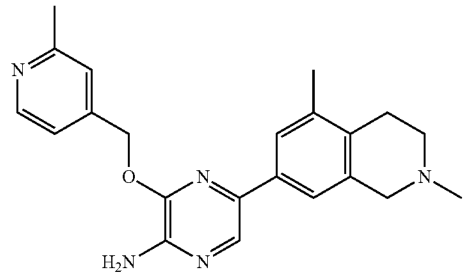 [SMILES: Cc1cc(COc2nc(-c3cc(C)c4c(c3)CN(C)CC4)cnc2N)ccn1]

5-bromo-3-((2-methylpyridin-4-yl)methoxy)pyrazin-2-amine (200 mg, 0.7 mmol), (2,5-dimethyl-1,2,3,4-tetrahydroisoquinolin-7-yl)boronic acid (209 mg, 1.0 mmol), $Pd(dppf)Cl_2$ (44 mg, 0.05 mmol) and $K_2CO_3$ (235 mg, 1.7 mmol) was added to dioxane (7.5 mL) and $H_2O$ (2.5 mL) under $N_2$. The mixture was warmed to 80° C. and stirred overnight. After being cooled to room temperature, the mixture was diluted with water (20 mL) and extracted with DCM (20 mL×3). The combined organic layer was dried, filtered and concentrated. The residue was purified by prep-HPLC to give Example 16 (45 mg, 17%). $^1$H NMR (400 MHz, DMSO-d6) δ 8.43 (d, J=4.0 Hz, 1H), 8.07 (s, 1H), 7.52-7.42 (m, 2H), 7.34-7.37 (m, 2H), 6.50 (s, 2H), 5.50 (s, 2H), 3.49 (s, 2H), 2.70-2.60 (m, 4H), 2.50 (s, 3H), 2.35 (s, 3H), 2.21 (s, 3H). LC-MS $(M+H)^+$=376.4.

Example 17: 3-((2,6-dichlorobenzyl)oxy)-5-(2,5-dimethyl-1,2,3,4-tetrahydroisoquinolin-7-yl)pyrazin-2-amine

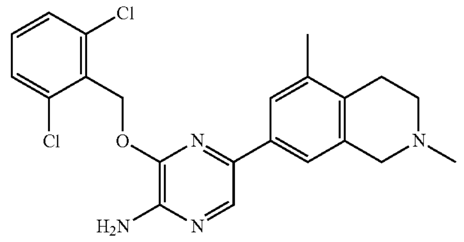 [SMILES: Cc1cc(-c2cnc(N)c(OCc3c(Cl)cccc3Cl)n2)cc2c1CCN(C)C2]

Step 1: 5-bromo-3-((2,6-dichlorobenzyl)oxy)pyrazin-2-amine

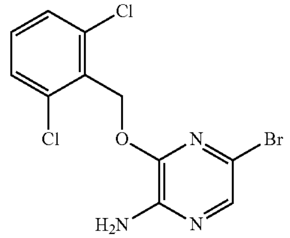 [SMILES: Nc1ncc(Br)nc1OCc1c(Cl)cccc1Cl]

NaH (60%, 40 mg, 1.0 mmol) was added to a solution of 3,5-dibromopyrazin-2-amine (200 mg, 0.80 mmol) and (2,6-dichlorophenyl)methanol (140 mg, 0.80 mmol) in THF (15 mL). The reaction mixture was heated to reflux overnight. The mixture was cooled to room temperature and concentrated in vacuo. The crude was purified by prep-TLC (PE/EtOAc=5:1) to give the title compound (53 mg, 19%). LC-MS $(M+H)^+$=347.9, 349.9.

Step 2: 3-((2,6-dichlorobenzyl)oxy)-5-(2,5-dimethyl-1,2,3,4-tetrahydroisoquinolin-7-yl)pyrazin-2-amine

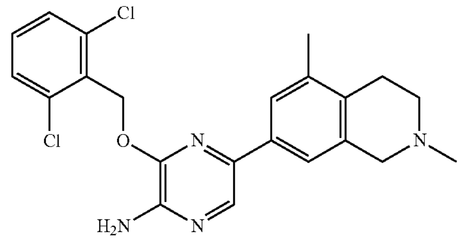 [SMILES: Cc1cc(-c2cnc(N)c(OCc3c(Cl)cccc3Cl)n2)cc2c1CCN(C)C2]

5-bromo-3-((2,6-dichlorobenzyl)oxy)pyrazin-2-amine (53 mg, 0.15 mmol), 2,5-dimethyl-7-(4,4,5,5-tetramethyl-1,3,2-dioxaborolan-2-yl)-1,2,3,4-tetrahydroisoquinoline (52 mg, 0.18 mmol), $Pd(dppf)Cl_2$ (11 mg, 0.02 mmol), $K_2CO_3$ (42 mg, 0.30 mmol) was added to a mixture of dioxane (10 mL) and water (2 mL) under nitrogen. The reaction mixture was heated to reflux overnight. The mixture was cooled to room temperature and diluted with water (20 mL), then extracted with EtOAC (30 mL×2). Combined organic layer was washed with brine (20 mL), dried over $Na_2SO_4$, and concentrated in vacuo. The crude was purified by prep-TLC (DCM/MeOH=10:1) to give Example 17 (3 mg, 5%). $^1$H NMR (400 MHz, DMSO-d6) δ 8.15 (s, 1H), 7.75 (s, 1H), 7.65-7.53 (m, 3H), 7.48 (s, 1H), 6.36 (s, 2H), 5.66 (s, 2H), 4.30 (s, 2H), 3.37 (s, 2H), 2.94 (s, 2H), 2.85 (s, 3H), 2.29 (s, 3H). LC-MS $(M+H)^+$=429.1.

Example 18: 3-(benzyloxy)-5-(2,5-dimethyl-1,2,3,4-tetrahydroisoquinolin-7-yl)pyrazin-2-amine

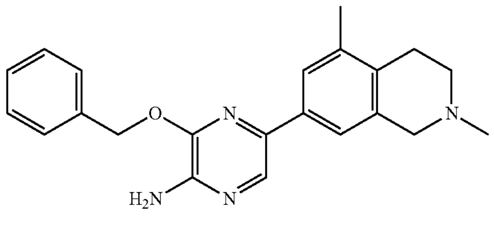 [SMILES: Cc1cc(-c2cnc(N)c(OCc3ccccc3)n2)cc2c1CCN(C)C2]

Step 1: 3-(benzyloxy)-5-bromopyrazin-2-amine

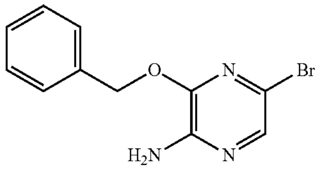 [SMILES: Nc1ncc(Br)nc1OCc1ccccc1]

NaH (60%, 52 mg, 1.3 mmol) was added to a solution of 3,5-dibromopyrazin-2-amine (253 mg, 1.0 mmol), phenylmethanol (108 mg, 1.0 mmol) in THF (10 mL) under nitrogen. The solution was heated to reflux for 4 h, then cooled to room temperature. The reaction mixture was diluted with EtOAc (20 mL), washed with brine (20 mL), dried over $Na_2SO_4$ and concentrated in vacuo. The residue was purified by prep-TLC (PE/EA=5:1) to give the title compound (170 mg, 61%). LC-MS $(M+H)^+$=280.0, 282.0.

Step 2: 3-(benzyloxy)-5-(2,5-dimethyl-1,2,3,4-tetrahydroisoquinolin-7-yl)pyrazin-2-amine

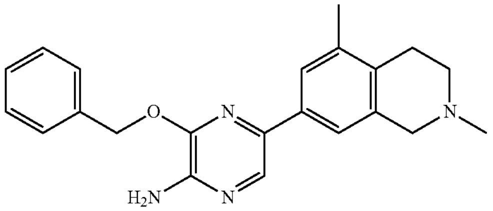

Example 18 (25 mg, 11%) was prepared in a manner similar to that in Example 17 step 2 from (2,5-dimethyl-1,2,3,4-tetrahydroisoquinolin-7-yl)boronic acid and 3-(benzyloxy)-5-bromopyrazin-2-amine. $^1H$ NMR (400 MHz, DMSO-d6) δ 8.05 (s, 1H), 7.59-7.49 (m, 3H), 7.44-7.36 (m, 3H), 7.32 (t, J=7.1 Hz, 1H), 6.37 (s, 2H), 5.51 (s, 2H), 3.51 (s, 2H), 2.70-2.55 (m, 4H), 2.35 (s, 3H), 2.22 (s, 3H). LC-MS $(M+H)^+$=361.2.

Example 19: 5-(2,5-dimethyl-1,2,3,4-tetrahydroisoquinolin-7-yl)-3-((2-(pyridin-3-ylethynyl)pyridin-4-yl)methoxy)pyrazin-2-amine

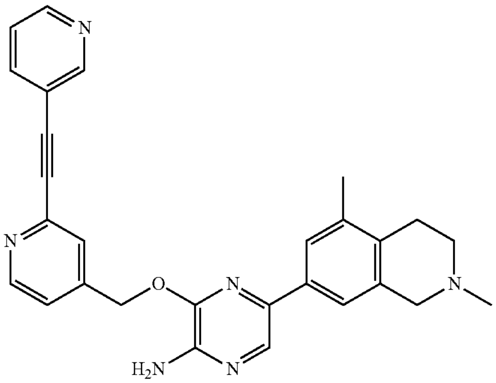 [SMILES: Cc1cc(-c2cnc(N)c(OCc3ccnc(C#Cc4cccnc4)c3)n2)cc2c1CCN(C)C2]

Step 1: (2-(pyridin-3-ylethynyl)pyridin-4-yl)methanol

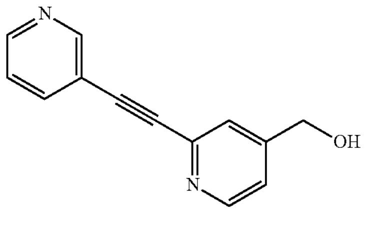 [SMILES: OCc1ccnc(C#Cc2cccnc2)c1]

(2-bromopyridin-4-yl)methanol (548 mg, 2.9 mmol), 3-ethynylpyridine (300 mg, 2.9 mmol), $Pd(PPh_3)Cl_2$ (90 mg, 0.2 mmol), CuI (28 mg, 0.15 mmol) and $Et_3N$ (2.0 mL, 14.6 mmol) was added to THF (20 mL) under nitrogen. The reaction mixture was heated to reflux for overnight. The reaction mixture was cooled to room temperature and diluted with EtOAc (30 mL), washed with brine (20 mL) and dried over $Na_2SO_4$. The crude was purified by prep-TLC (DCM/MeOH=20:1) to give the title compound (380 mg, 62%). LC-MS $(M+H)^+$=211.0.

Step 2: 5-bromo-3-((2-(pyridin-3-ylethynyl)pyridin-4-yl)methoxy)pyrazin-2-amine

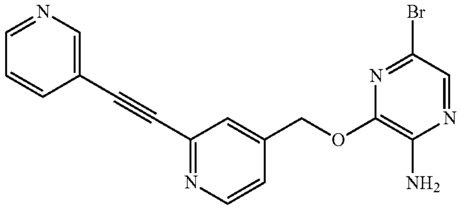 [SMILES: Nc1ncc(Br)nc1OCc1ccnc(C#Cc2cccnc2)c1]

3,5-dibromopyrazin-2-amine (458 mg, 1.8 mmol), (2-(pyridin-3-ylethynyl)pyridin-4-yl)methanol (380 mg, 1.8 mmol) and NaH (60%, 217 mg, 5.4 mmol) was sequentially added to THF (20 mL). The reaction mixture was stirred at room temperature overnight, then diluted with EtOAc (20 mL), washed with brine (20 mL), dried over $Na_2SO_4$, concentrated in vacuo. The crude was purified by prep-TLC (PE/EtOAc=5:1) to give the title compound (200 mg, 29%). LC-MS $(M+H)^+$=382.0.

Step 3: 5-(2,5-dimethyl-1,2,3,4-tetrahydroisoquinolin-7-yl)-3-((2-(pyridin-3-ylethynyl)pyridin-4-yl)methoxy)pyrazin-2-amine

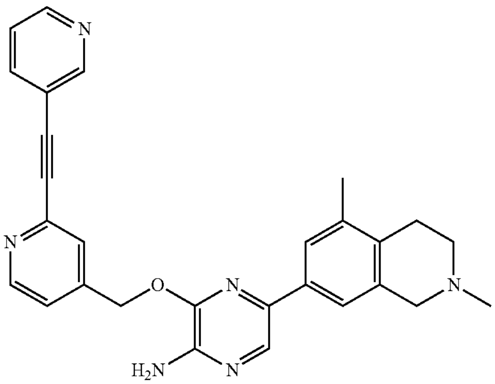 [SMILES: Cc1cc(-c2cnc(N)c(OCc3ccnc(C#Cc4cccnc4)c3)n2)cc2c1CCN(C)C2]

Example 19 (20 mg, 8%) was prepared in a manner similar to that in Example 17 step 2 from (2,5-dimethyl-1,2,3,4-tetrahydroisoquinolin-7-yl)boronic acid and 5-bromo-3-((2-(pyridin-3-ylethynyl)pyridin-4-yl)methoxy)pyrazin-2-amine. $^1H$ NMR (400 MHz, DMSO-d6) δ 8.81 (s, 1H), 8.67-8.61 (m, 2H), 8.09 (s, 1H), 8.05 (d, J=7.9 Hz, 1H), 7.93 (s, 1H), 7.62 (d, J=4.8 Hz, 1H), 7.54-7.46 (m, 2H), 7.35 (s, 1H), 6.57 (s, 2H), 5.57 (s, 2H), 3.50 (s, 2H), 2.64 (d, J=7.6 Hz, 4H), 2.31 (s, 3H), 2.21 (s, 3H). LC-MS $(M+H)^+$=463.2.

Example 20: 5-(2,5-dimethyl-1,2,3,4-tetrahydroisoquinolin-7-yl)-3-((2-((4-fluorophenyl)ethynyl)pyridin-4-yl)methoxy)pyrazin-2-amine

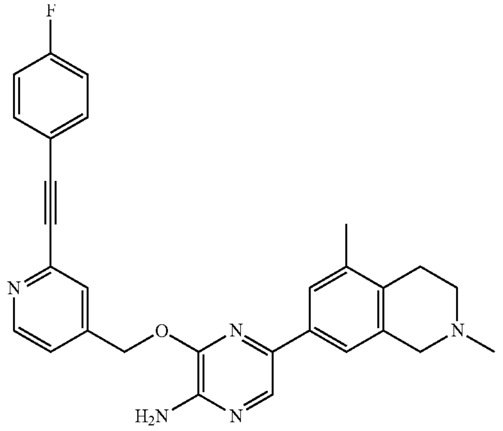 [SMILES: Cc1cc(-c2cnc(N)c(OCc3ccnc(C#Cc4ccc(F)cc4)c3)n2)cc2c1CCN(C)C2]

Step 1: (2-((4-fluorophenyl)ethynyl)pyridin-4-yl)methanol

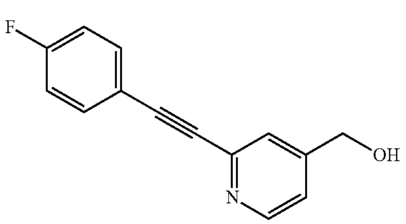 [SMILES: OCc1ccnc(C#Cc2ccc(F)cc2)c1]

The title compound (430 mg, 76%) was prepared in a manner similar to that in Example 19 step 1 from (2-bromopyridin-4-yl)methanol and 1-ethynyl-4-fluorobenzene. LC-MS $(M+H)^+=227.1$.

Step 2: 5-bromo-3-((2-((4-fluorophenyl)ethynyl)pyridin-4-yl)methoxy)pyrazin-2-amine

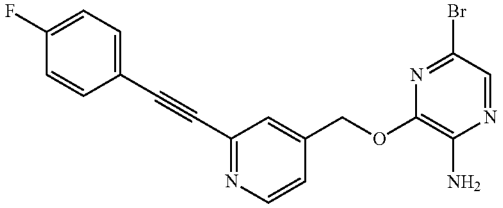 [SMILES: Nc1ncc(Br)nc1OCc1ccnc(C#Cc2ccc(F)cc2)c1]

The title compound (140 mg, 19%) was prepared in a manner similar to that in Example 19 step 2 from 3,5-dibromopyrazin-2-amine and (2-((4-fluorophenyl)ethynyl)pyridin-4-yl)methanol. LC-MS $(M+H)^+=399.0$.

Step 3: 5-(2,5-dimethyl-1,2,3,4-tetrahydroisoquinolin-7-yl)-3-((2-((4-fluorophenyl)ethynyl)pyridin-4-yl)methoxy)pyrazin-2-amine

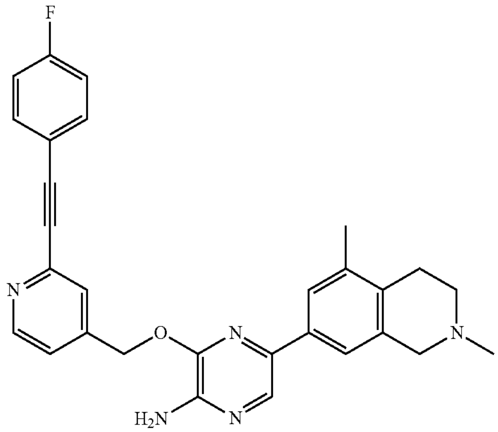 [SMILES: Cc1cc(-c2cnc(N)c(OCc3ccnc(C#Cc4ccc(F)cc4)c3)n2)cc2c1CCN(C)C2]

Example 20 (20 mg, 12%) was prepared in a manner similar to that in Example 17 step 2 from (2,5-dimethyl-1,2,3,4-tetrahydroisoquinolin-7-yl)boronic acid and 5-bromo-3-((2-((4-fluorophenyl)ethynyl)pyridin-4-yl)methoxy)pyrazin-2-amine. $^1H$ NMR (400 MHz, DMSO-d6) δ 8.60 (d, J=4.8 Hz, 1H), 8.08 (s, 1H), 7.88 (s, 1H), 7.72-7.66 (m, 2H), 7.59 (d, J=4.9 Hz, 1H), 7.48 (s, 1H), 7.38-7.28 (m, 3H), 6.56 (s, 2H), 5.56 (s, 2H), 3.49 (s, 2H), 2.65 (d, J=4.5 Hz, 2H), 2.61 (d, J=4.2 Hz, 2H), 2.30 (s, 3H), 2.21 (s, 3H). LC-MS $(M+H)^+=480.2$.

Example 21: 3-((3-chloropyridin-4-yl)methoxy)-5-(2,5-dimethyl-1,2,3,4-tetrahydroisoquinolin-7-yl)pyrazin-2-amine

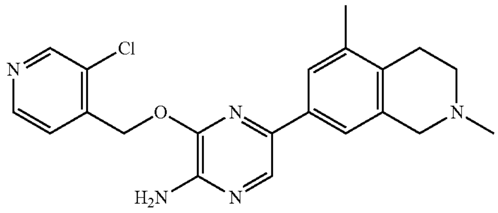 [SMILES: Cc1cc(-c2cnc(N)c(OCc3ccncc3Cl)n2)cc2c1CCN(C)C2]

Step 1: 5-bromo-3-((3-chloropyridin-4-yl)methoxy)pyrazin-2-amine

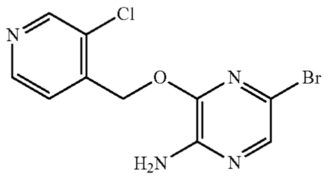 [SMILES: Nc1ncc(Br)nc1OCc1ccncc1Cl]

The title compound (80 mg, 18%) was prepared in a manner similar to that in Example 17 step 1 from 3,5- dibromopyrazin-2-amine and (3-chloropyridin-4-yl)methanol. LC-MS $(M+H)^+$=314.9, 316.9.

Step 2: 3-((3-chloropyridin-4-yl)methoxy)-5-(2,5-dimethyl-1,2,3,4-tetrahydroisoquinolin-7-yl)pyrazin-2-amine

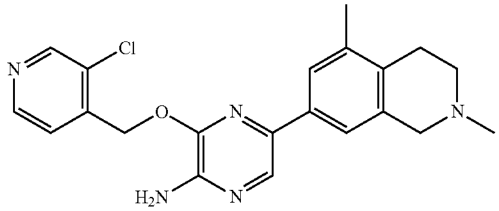

Example 21 (20 mg, 12%) was prepared in a manner similar to that in Example 17 step 2 from (2,5-dimethyl-1,2,3,4-tetrahydroisoquinolin-7-yl)boronic acid and 5-bromo-3-((3-chloropyridin-4-yl)methoxy)pyrazin-2-amine. $^1H$ NMR (400 MHz, DMSO-d6) δ 8.68 (s, 1H), 8.53 (d, J=4.9 Hz, 1H), 8.09 (s, 1H), 7.73 (d, J=4.8 Hz, 1H), 7.45 (s, 1H), 7.33 (s, 1H), 6.57 (s, 2H), 5.61 (s, 2H), 3.47 (s, 2H), 2.72-2.60 (m, 2H), 2.34 (s, 3H), 2.19 (s, 3H). LC-MS $(M+H)^+$=396.1.

Example 22: 5-(2,5-dimethyl-1,2,3,4-tetrahydroisoquinolin-7-yl)-3-(quinolin-4-ylmethoxy)pyrazin-2-amine

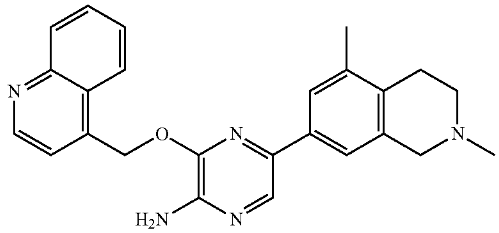 [SMILES: Cc1cc(-c2cnc(N)c(OCc3ccnc4ccccc34)n2)cc2c1CCN(C)C2]

Step 1: quinolin-4-ylmethanol

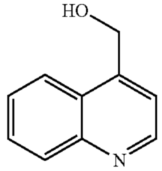 [SMILES: OCc1ccnc2ccccc12]

$NaBH_4$ (582 mg, 15.4 mmol) was added to a solution of quinoline-4-carbaldehyde (2.0 g, 12.8 mmol) in MeOH (25 mL) at 0° C. The reaction mixture was stirred overnight at room temperature then concentrated in vacuo. Water (10 mL) was added and the mixture was extracted with DCM (20 mL×3). The combined organic layer was washed with brine (10 mL) and dried over $Na_2SO_4$. The residue was purified by silica gel chromatography to give the title compound (1.9 g, 94%). LC-MS $(M+H)^+$=160.0.

Step 2: 5-bromo-3-(quinolin-4-ylmethoxy)pyrazin-2-amine

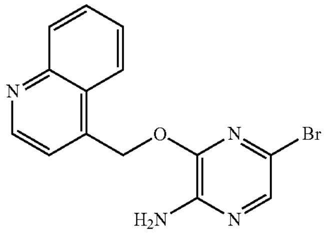 [SMILES: Nc1ncc(Br)nc1OCc1ccnc2ccccc12]

NaH (60%, 119 mg, 2.97 mmol) was added to a solution of quinolin-4-ylmethanol (313 mg, 1.98 mmol) and 3,5-dibromopyrazin-2-amine (500 mg, 1.98 mmol) in anhydrous THF (20 mL) at 0° C. The reaction mixture was heated to at 50° C. and stirred overnight. After cooled to 0° C., water (10 mL) was added and the mixture extracted with ethyl acetate (10 mL×3). The combined organic layer was washed with brine (10 mL) and dried over $Na_2SO_4$. The residue was purified by silica gel chromatography to give the title compound (261 mg, 40%). LC-MS $(M+H)^+$=331.0.

Step 3: 5-(2,5-dimethyl-1,2,3,4-tetrahydroisoquinolin-7-yl)-3-(quinolin-4-ylmethoxy)pyrazin-2-amine

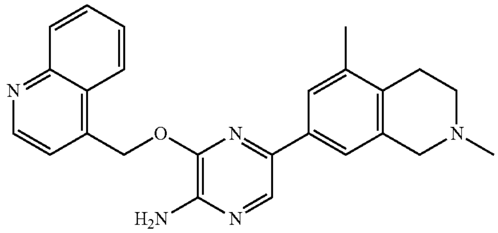 [SMILES: Cc1cc(-c2cnc(N)c(OCc3ccnc4ccccc34)n2)cc2c1CCN(C)C2]

5-bromo-3-(quinolin-4-ylmethoxy)pyrazin-2-amine (261 mg, 0.79 mmol), (2,5-dimethyl-1,2,3,4-tetrahydroisoquinolin-7-yl)boronic acid (242 mg, 1.82 mmol), $K_2CO_3$ (218 mg, 1.58 mmol) and Pd(dppf)$Cl_2$ (29 mg, 0.04 mmol) was dissolved in a mixture of 1,4-dioxane (20 mL) and water (4 mL). The mixture was heated to 90° C. under $N_2$ overnight. After being cooled to room temperature, the solvent was removed in vacuo. Brine (15 mL) was added and the mixture was extracted with ethyl acetate (10 mL×3). The combined organic layer was washed with brine (10 mL) and dried over $Na_2SO_4$. The residue was purified by prep-HPLC to give Example 22 (93 mg, 29%). $^1H$ NMR (400 MHz, DMSO-d6) δ 8.90 (d, J=3.6 Hz, 1H), 8.31 (d, J=8.1 Hz, 1H), 8.09 (d, J=7.1 Hz, 2H), 7.82 (t, J=7.2 Hz, 1H), 7.79-7.63 (m, 2H), 7.45 (s, 1H), 7.29 (s, 1H), 6.56 (s, 2H), 6.04 (s, 2H), 3.56 (s, 2H), 2.69-2.77 (m, 4H), 2.44 (s, 3H), 2.15 (s, 3H). LC-MS $(M+H)^+$=412.0.

Example 23: 5-(2,5-dimethyl-1,2,3,4-tetrahydroisoquinolin-7-yl)-3-((2-(pyridin-4-ylethynyl)pyridin-4-yl)methoxy)pyrazin-2-amine

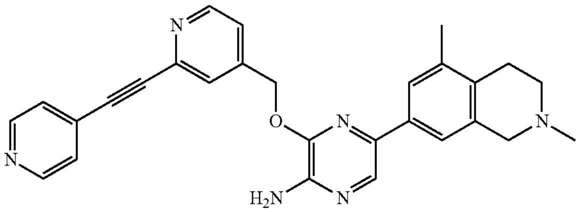 [SMILES: Cc1cc(-c2cnc(N)c(OCc3ccnc(C#Cc4ccncc4)c3)n2)cc2c1CCN(C)C2]

Step 1: (2-(pyridin-4-ylethynyl)pyridin-4-yl)methanol

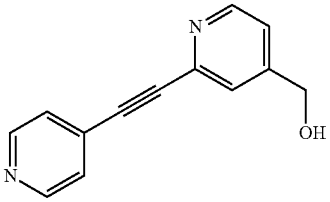 [SMILES: OCc1ccnc(C#Cc2ccncc2)c1]

The title compound (335 mg, 82%) was prepared in a manner similar to that in Example 19 step 1 from 4-ethynylpyridine and (2-bromopyridin-4-yl)methanol. LC-MS $(M+H)^+$=211.0.

Step 2: 5-bromo-3-((2-(pyridin-4-ylethynyl)pyridin-4-yl)methoxy)pyrazin-2-amine

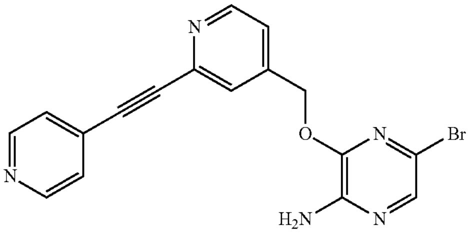 [SMILES: Nc1ncc(Br)nc1OCc1ccnc(C#Cc2ccncc2)c1]

The title compound (330 mg, 54%) was prepared in a manner similar to that in Example 19 step 2 from 3,5-dibromopyrazin-2-amine and (2-(pyridin-4-ylethynyl)pyridin-4-yl)methanol. LC-MS $(M+H)^+$=382.0.

Step 3: 5-(2,5-dimethyl-1,2,3,4-tetrahydroisoquinolin-7-yl)-3-((2-(pyridin-4-ylethynyl)pyridin-4-yl)methoxy)pyrazin-2-amine

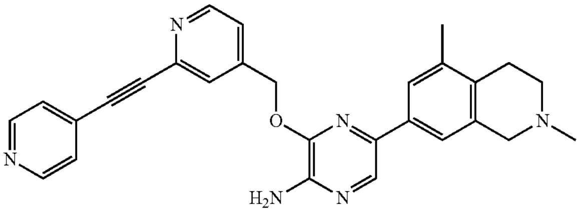 [SMILES: Cc1cc(-c2cnc(N)c(OCc3ccnc(C#Cc4ccncc4)c3)n2)cc2c1CCN(C)C2]

Example 23 (89 mg, 22%) was prepared in a manner similar to that in Example 17 step 2 from (2,5-dimethyl-1,2,3,4-tetrahydroisoquinolin-7-yl)boronic acid and 5-bromo-3-((2-(pyridin-4-ylethynyl)pyridin-4-yl)methoxy)pyrazin-2-amine. $^1$H NMR (400 MHz, DMSO-d6) δ 8.68 (d, J=4.7 Hz, 2H), 8.64 (d, J=5.0 Hz, 1H), 8.09 (s, 1H), 7.96 (s, 1H), 7.65 (d, J=4.7 Hz, 1H), 7.59 (d, J=4.6 Hz, 2H), 7.48 (s, 1H), 7.35 (s, 1H), 6.58 (s, 2H), 5.57 (s, 2H), 3.48 (s, 2H), 2.60-2.65 (m, 4H), 2.29 (s, 3H), 2.20 (s, 3H). LC-MS $(M+H)^+$=463.0.

Example 24: 5-(2,5-dimethyl-1,2,3,4-tetrahydroisoquinolin-7-yl)-3-((2-(3,3-dimethylbut-1-yn-1-yl)pyridin-4-yl)methoxy)pyrazin-2-amine

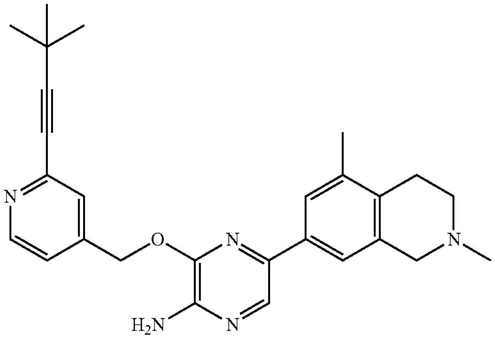 [SMILES: Cc1cc(-c2cnc(N)c(OCc3ccnc(C#CC(C)(C)C)c3)n2)cc2c1CCN(C)C2]

Step 1: (2-(3,3-dimethylbut-1-yn-1-yl)pyridin-4-yl)methanol

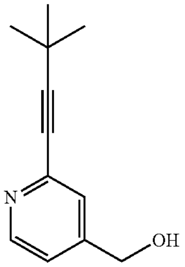

The title compound (240 mg, 79%) was prepared in a manner similar to that in Example 14 step 2 from (2-bromopyridin-4-yl)methanol and 3,3-dimethylbut-1-yne. LC-MS $(M+H)^+$=190.1.

Step 2: 5-bromo-3-((2-(3,3-dimethylbut-1-yn-1-yl)pyridin-4-yl)methoxy)pyrazin-2-amine

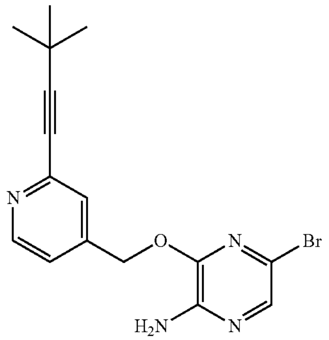 [SMILES: CC(C)(C)C#Cc1cc(COc2nc(Br)cnc2N)ccn1]

The title compound (250 mg, 53%) was prepared in a manner similar to that in Example 14 step 3 from (2-(3,3-dimethylbut-1-yn-1-yl)pyridin-4-yl)methanol and 3,5-dibromopyrazin-2-amine. LC-MS $(M+H)^+$=360.9, 362.9.

Step 3: 5-(2,5-dimethyl-1,2,3,4-tetrahydroisoquinolin-7-yl)-3-((2-(3,3-dimethylbut-1-yn-1-yl)pyridin-4-yl)methoxy)pyrazin-2-amine

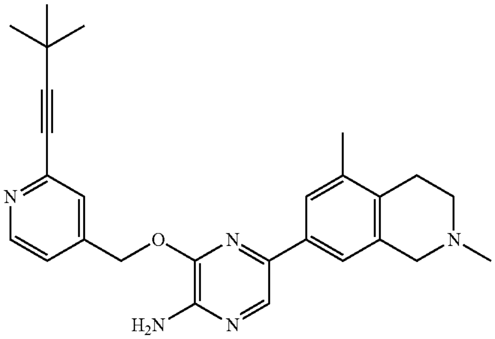 [SMILES: Cc1cc(-c2cnc(N)c(OCc3ccnc(C#CC(C)(C)C)c3)n2)cc2c1CCN(C)C2]

Example 24 (100 mg, 32%) was prepared in a manner similar to that in Example 14 step 4 from 5-bromo-3-((2-(3,3-dimethylbut-1-yn-1-yl)pyridin-4-yl)methoxy)pyrazin-2-amine and (2,5-dimethyl-1,2,3,4-tetrahydroisoquinolin-7-yl)boronic acid. $^1H$ NMR (400 MHz, DMSO-d6) δ 8.50 (d, J=5.0 Hz, 1H), 8.07 (s, 1H), 7.60 (s, 1H), 7.51 (d, J=5.0 Hz, 1H), 7.46 (s, 1H), 7.35 (s, 1H), 6.54 (s, 2H), 5.51 (s, 2H), 3.48 (s, 2H), 2.70-2.64 (m, 2H), 2.64-2.58 (m, 2H), 2.34 (s, 3H), 2.21 (s, 3H), 1.30 (s, 9H). LC-MS $(M+H)^+$=442.5.

Example 25: 5-(2,5-dimethyl-1,2,3,4-tetrahydroisoquinolin-7-yl)-3-((2-(prop-1-ynyl)pyridin-4-yl)methoxy)pyrazin-2-amine

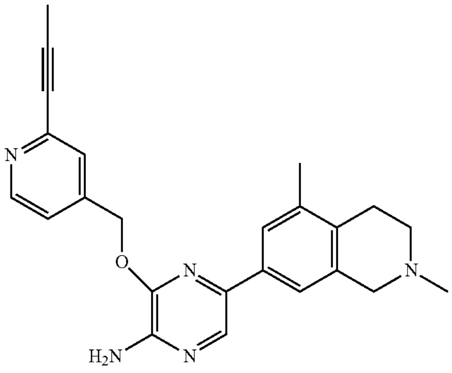 [SMILES: CC#Cc1cc(COc2nc(-c3cc(C)c4c(c3)CN(C)CC4)cnc2N)ccn1]

Step 1: (2-(prop-1-ynyl)pyridin-4-yl)methanol

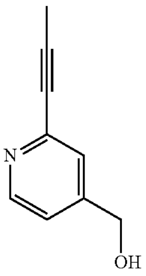

The title compound (270 mg, 90%) was prepared in a manner similar to that in Example 11 step 1 from (2-bromopyridin-4-yl)methanol and prop-1-yne. LC-MS $(M+H)^+$=147.9.

Step 2: 5-bromo-3-((2-(prop-1-ynyl)pyridin-4-yl)methoxy)pyrazin-2-amine

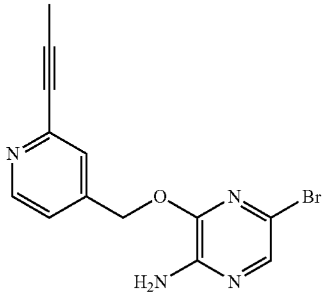 [SMILES: CC#Cc1cc(COc2nc(Br)cnc2N)ccn1]

The title compound (120 mg, 45%) was prepared in a manner similar to Example 1 step 7 from (2-(prop-1-ynyl)pyridin-4-yl)methanol and 3,5-dibromopyrazin-2-amine. LC-MS $(M+H)^+$=319.0.

Step 3: 5-(2,5-dimethyl-1,2,3,4-tetrahydroisoquinolin-7-yl)-3-((2-(prop-1-ynyl)pyridin-4-yl)methoxy)pyrazin-2-amine

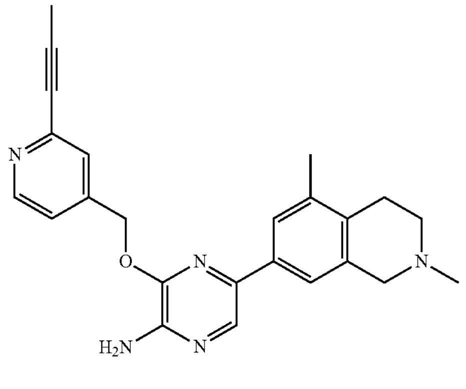 [SMILES: CC#Cc1cc(COc2nc(-c3cc(C)c4c(c3)CN(C)CC4)cnc2N)ccn1]

Example 25 (15 mg, 11%) was prepared in a manner similar to that in Example 1 step 8 from 5-bromo-3-((2-(prop-1-ynyl)pyridin-4-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. $^{1}$H NMR (400 MHz, DMSO-d6) δ 8.51 (d, J=5.1 Hz, 1H), 8.08 (s, 1H), 7.65 (s, 1H), 7.53-7.45 (m, 2H), 7.35 (s, 1H), 6.53 (s, 2H), 5.52 (s, 2H), 3.50 (s, 2H), 2.71-2.59 (m, 4H), 2.36 (s, 3H), 2.22 (s, 3H), 2.08 (s, 3H). LC-MS $(M+H)^+$=400.2.

Example 26: 5-(2,5-dimethyl-1,2,3,4-tetrahydroisoquinolin-7-yl)-3-(5,6,7,8-tetrahydroisoquinolin-5-yloxy)pyrazin-2-amine

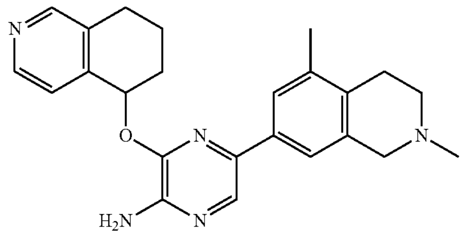 [SMILES: Cc1cc(-c2cnc(N)c(OC3CCCc4cnccc43)n2)cc2c1CCN(C)C2]

Step 1: 3-chloro-5-(2,5-dimethyl-1,2,3,4-tetrahydroisoquinolin-7-yl)pyrazin-2-amine

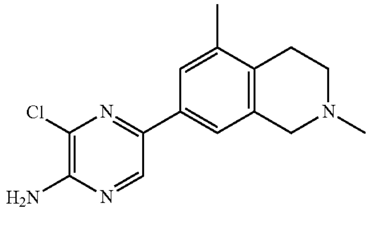 [SMILES: Cc1cc(-c2cnc(N)c(Cl)n2)cc2c1CCN(C)C2]

The title compound (720 mg, 79%) was prepared in a manner similar to that in Example 1 step 8 from 2,5-dimethyl-7-(4,4,5,5-tetramethyl-1,3,2-dioxaborolan-2-yl)-3,4-dihydro-1H-isoquinoline and 5-bromo-3-chloropyrazin-2-amine. LC-MS $(M+H)^+$=289.2.

Step 2: 5-(2,5-dimethyl-1,2,3,4-tetrahydroisoquinolin-7-yl)-3-(5,6,7,8-tetrahydroisoquinolin-5-yloxy)pyrazin-2-amine

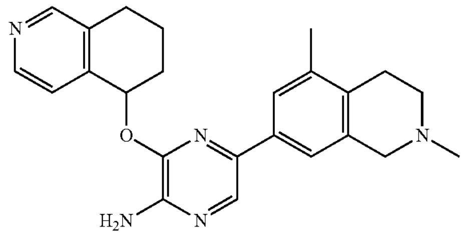 [SMILES: Cc1cc(-c2cnc(N)c(OC3CCCc4cnccc43)n2)cc2c1CCN(C)C2]

Example 26 (26 mg, 210%) was prepared in a manner similar to that in Example 1 step 7 from 5,6,7,8-tetrahydroisoquinolin-5-ol and 3-chloro-5-(2,5-dimethyl-1,2,3,4-tetrahydroisoquinolin-7-yl)pyrazin-2-amine. 1H NMR (400 MHz, DMSO-d6) δ 8.44 (s, 1H), 8.35 (d, J=5.1 Hz, 1H), 8.09 (s, 1H), 7.56 (s, 1H), 7.44 (s, 1H), 7.34 (d, J=5.1 Hz, 1H), 6.43 (t, J=5.5 Hz, 1H), 6.30 (s, 2H), 3.50 (s, 2H), 2.94-2.73 (m, 2H), 2.71-2.59 (m, 4H), 2.34 (s, 3H), 2.23 (s, 3H), 2.23-2.15 (m, 1H), 2.10-1.98 (m, 1H), 1.94-1.86 (m, 1H). LC-MS $(M+H)^+$=402.2.

Example 27: 3-((5-chloropyridin-3-yl)methoxy)-5-(2,5-dimethyl-1,2,3,4-tetrahydroisoquinolin-7-yl)pyrazin-2-amine

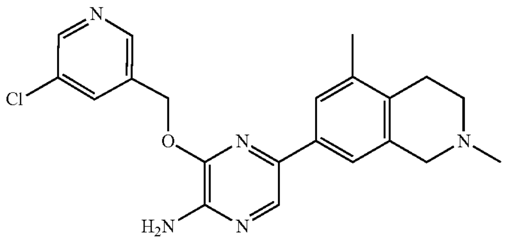 [SMILES: Cc1cc(-c2cnc(N)c(OCc3cncc(Cl)c3)n2)cc2c1CCN(C)C2]

Step 1: 5-bromo-3-((5-chloropyridin-3-yl)methoxy)pyrazin-2-amine

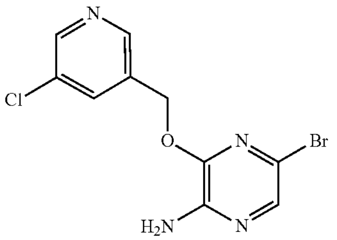 [SMILES: Nc1ncc(Br)nc1OCc1cncc(Cl)c1]

The title compound (387 mg, 90%) was prepared in a manner similar to that in Example 1 step 7 from (5-chloropyridin-3-yl)methanol and 5-bromo-3-chloropyrazin-2-amine. LC-MS $(M+H)^+$=316.9.

Step 2: 3-((5-chloropyridin-3-yl)methoxy)-5-(2,5-dimethyl-1,2,3,4-tetrahydroisoquinolin-7-yl)pyrazin-2-amine

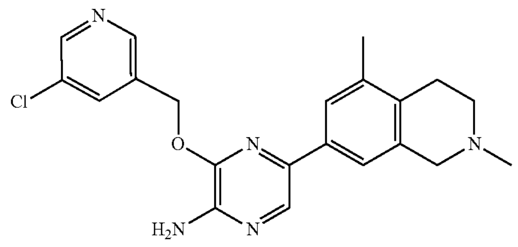 [SMILES: Cc1cc(-c2cnc(N)c(OCc3cncc(Cl)c3)n2)cc2c1CCN(C)C2]

Example 27 (32 mg, 14%) was prepared in a manner similar to that in Example 1 step 8 from 5-bromo-3-((5-chloropyridin-3-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.77 (s, 1H), 8.60 (s, 1H), 8.22 (s, 1H), 8.09 (s, 1H), 7.55 (s, 1H), 7.43 (s, 1H), 6.50 (s, 2H), 5.56 (s, 2H), 3.52 (s, 2H), 2.73-2.61 (m, 4H), 2.36 (s, 3H), 2.24 (s, 3H). LC-MS $(M+H)^+$=396.0.

Example 28: 5-(2,5-dimethyl-1,2,3,4-tetrahydroisoquinolin-7-yl)-3-((3-methoxypyridin-4-yl)methoxy)pyrazin-2-amine

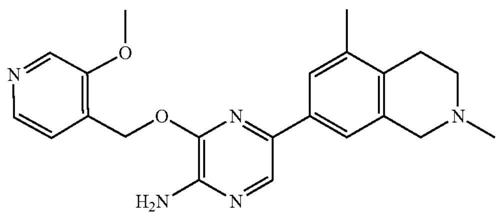 [SMILES: COc1cnccc1COc1nc(-c2cc(C)c3c(c2)CN(C)CC3)cnc1N]

Step 1: (3-methoxypyridin-4-yl)methanol

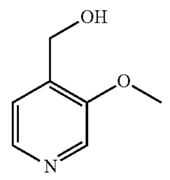

$BH_3$ in THF (1.0 M, 26.2 mL, 26.2 mmol) was added to a solution of 3-methoxyisonicotinic acid (2.0 g, 13.1 mmol) in anhydrous THF (10 mL). The mixture was stirred at room temperature overnight, then cooled to 0° C. followed by addition of MeOH (20 mL). HCl in dioxane (4.0 M, 10 mL) was added and the mixture was stirred at room temperature for 30 minutes. The mixture was concentrated in vacuo. The residue was purified by silica gel column chromatography to give the title compound (492 mg, 26%). LC-MS $(M+H)^+$=140.0.

Step 2: 5-bromo-3-((3-methoxypyridin-4-yl)methoxy)pyrazin-2-amine

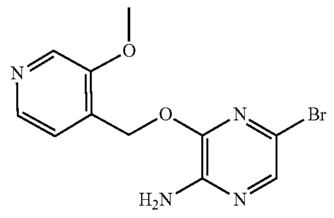 [SMILES: COc1cnccc1COc1nc(Br)cnc1N]

The title compound (335 mg, 55%) was prepared in a manner similar to that in Example 17 step 1 from 3,5-dibromopyrazin-2-amine and (3-methoxypyridin-4-yl)methanol. LC-MS $(M+H)^+$=311.0.

Step 3: 5-(2,5-dimethyl-1,2,3,4-tetrahydroisoquinolin-7-yl)-3-((3-methoxypyridin-4-yl)methoxy)pyrazin-2-amine

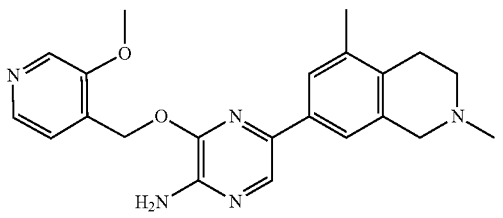 [SMILES: COc1cnccc1COc1nc(-c2cc(C)c3c(c2)CN(C)CC3)cnc1N]

Example 28 (200 mg, 48%) was prepared in a manner similar to that in Example 17 step 2 from (2,5-dimethyl-1,2,3,4-tetrahydroisoquinolin-7-yl)boronic acid and 5-bromo-3-((3-methoxypyridin-4-yl)methoxy)pyrazin-2-amine. $^1$H NMR (400 MHz, DMSO-d6) δ 8.41 (s, 1H), 8.23 (d, J=4.6 Hz, 1H), 8.06 (s, 1H), 7.57 (d, J=4.5 Hz, 1H), 7.45 (s, 1H), 7.33 (s, 1H), 6.51 (s, 2H), 5.51 (s, 2H), 3.99 (s, 3H), 3.47 (s, 2H), 2.61-2.66 (m, 4H), 2.34 (s, 3H), 2.20 (s, 3H). LC-MS $(M+H)^+$=392.0.

Example 29: 3-((2-amino-3-methylpyridin-4-yl)methoxy)-5-(2,5-dimethyl-1,2,3,4-tetrahydroisoquinolin-7-yl)pyrazin-2-amine

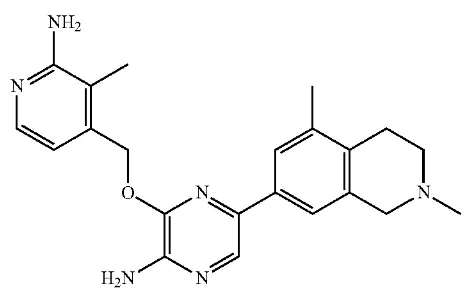

Step 1: methyl 2-amino-3-methylisonicotinate

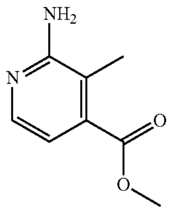

Methyl 2-chloro-3-methylisonicotinate (2.52 g, 13.6 mmol), benzophenonimine (2.76 g, 15.0 mmol), $Pd(dba)_2$ (705 mg, 1.36 mmol), Xantphos (1.62 g, 2.72 mmol) and $Cs_2CO_3$ (6.2 g, 15.5 mmol) in dioxane (30 mL) and toluene (30 mL) was stirred at 100° C. overnight under nitrogen atmosphere. The reaction mixture was cooled to 0° C., then a methanol solution of HCl (1 M, 50 mL) was added to the reaction solution, and the mixture was stirred at room temperature for 3 hours. The solvent was concentrated under reduced pressure. The residue was basified to pH=8-9 with $NaHCO_3$ and extracted with EtOAc (30 mL×3). The combined organic layer was washed with brine (30 mL), dried over $Na_2SO_4$, filtered and concentrated under reduced pressure. The residue was purified by silica gel column chromatography, eluted with PE/EtOAc (5:1 to 2:1) to give the title compound (1.3 g, 57%). LC-MS $(M+H)^+$=167.0.

Step 2: (2-amino-3-methylpyridin-4-yl)methanol

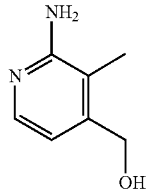

A solution of methyl 2-amino-3-methylisonicotinate (1.3 g, 7.8 mmol) in THF (2 mL) was added to a suspension of $LiAlH_4$ (593 mg, 15.6 mmol) in THF (8 mL) dropwise at 0° C. After stirring for 2 h, the reaction mixture was cooled to 0° C. and water (0.6 mL) was slowly added, followed by addition of 3.0 M NaOH solution (0.6 mL) and another portion of water (1.8 mL). The mixture was stirred at room temperature for 10 minutes, then filtered. The organic phase was dried over $Na_2SO_4$, filtered and concentrated to give the title compound (1.0 g, 93%). LC-MS $(M+H)^+$=139.1.

Step 3: 3-((2-amino-3-methylpyridin-4-yl)methoxy)-5-bromopyrazin-2-amine

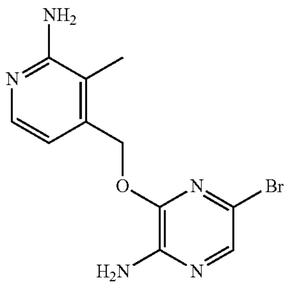 [SMILES: Cc1c(COc2nc(Br)cnc2N)ccnc1N]

NaH (60%, 145 mg, 3.62 mmol) was added to a solution of (2-amino-3-methylpyridin-4-yl)methanol (500 mg, 3.62 mmol) and 3,5-dibromopyrazin-2-amine (700 mg, 2.79 mmol) in THF (20 mL). The reaction mixture was stirred at reflux for 5 h. After being cooled to room temperature, water (20 mL) was added and the mixture was extracted with EtOAc (30 mL×2). The combined organic layer was washed with brine (20 mL), dried over $Na_2SO_4$, filtered and concentrated under reduced pressure. The residue was purified by silica gel column chromatography, eluted with PE/EtOAc (5:1 to 1:1) to give the title compound (600 mg, 54%). LC-MS $(M+H)^+$=309.9, 311.9.

Step 4: 3-((2-amino-3-methylpyridin-4-yl)methoxy)-5-(2,5-dimethyl-1,2,3,4-tetrahydroisoquinolin-7-yl)pyrazin-2-amine

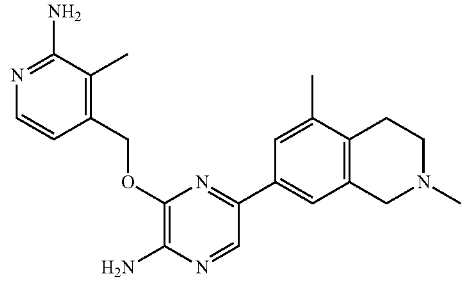

Example 29 (110 mg, 28%) was prepared in a manner similar to that in Example 17 step 2 from 3-((2-amino-3-methylpyridin-4-yl)methoxy)-5-bromopyrazin-2-amine and ((2,5-dimethyl-1,2,3,4-tetrahydroisoquinolin-7-yl)boronic acid. $^1H$ NMR (400 MHz, DMSO-d6) δ 8.04 (s, 1H), 7.77 (d, J=4.6 Hz, 1H), 7.50 (s, 1H), 7.38 (s, 1H), 6.71 (d, J=4.8 Hz, 1H), 6.40 (s, 2H), 5.71 (s, 2H), 5.43 (s, 2H), 3.48 (s, 2H), 2.74-2.59 (m, 4H), 2.34 (s, 3H), 2.21 (s, 3H), 2.10 (s, 3H). LC-MS $(M+H)^+$=391.4.

Example 30: 5-(2,5-dimethyl-1,2,3,4-tetrahydroisoquinolin-7-yl)-3-((3-isopropoxypyridin-4-yl)methoxy)pyrazin-2-amine

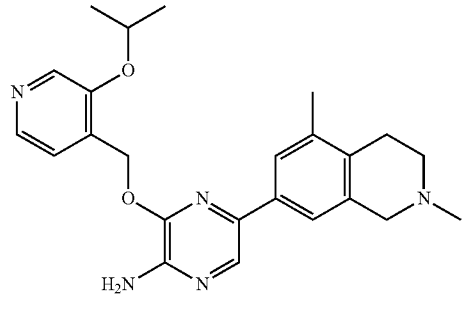 [SMILES: Cc1cc(-c2cnc(N)c(OCc3ccncc3OC(C)C)n2)cc2c1CCN(C)C2]

Step 1: methyl 3-isopropoxyisonicotinate

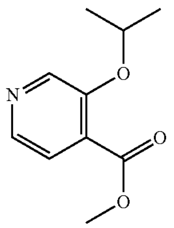

To a solution of methyl 3-hydroxyisonicotinate (500 mg, 3.27 mmol) and 2-iodopropane (558 mg, 3.27 mmol) in anhydrous DMF (10 mL) was added $K_2CO_3$ (677 mg, 4.91 mmol), and the mixture was stirred at 60° C. overnight. The mixture was cooled to room temperature and diluted with EtOAc (30 mL). The mixture was washed with water (20 mL), and the aqueous layer was extracted with EtOAc (20 mL×3), dried over $Na_2SO_4$, filtered and concentrated in vacuo. The residue was purified by silica gel column chromatography, eluted with PE/EtOAc (5:1) to give the title compound (380 mg, 60%). LC-MS $(M+H)^+$=196.2.

Step 2: (3-isopropoxypyridin-4-yl)methanol

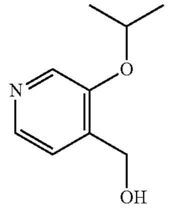

To a 0° C. solution of methyl 3-isopropoxyisonicotinate (380 mg, 1.95 mmol) in anhydrous THF (10 mL) was added $LiAlH_4$ (156 mg, 3.90 mmol). The reaction mixture was stirred at room temperature for 1 h. The reaction mixture was quenched by water (10 mL), and the mixture was extracted with EtOAc (10 mL×3). The combined organic layer was dried over $Na_2SO_4$, filtered and concentrated in vacuo to give the title compound (277 mg, 85%). LC-MS $(M+H)^+$=168.2.

Step 3: 5-bromo-3-((3-isopropoxypyridin-4-yl) methoxy)pyrazin-2-amine

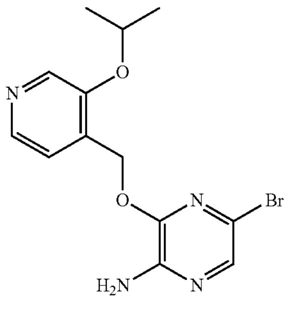 [SMILES: CC(C)Oc1cnccc1COc1nc(Br)cnc1N]

The title compound (300 mg, 53%) was prepared in a manner similar to that in Example 17 step 1 from 3,5-dibromopyrazin-2-amine and (3-isopropoxypyridin-4-yl) methanol. LC-MS $(M+H)^+$=339.1, 341.1.

Step 4: 5-(2,5-dimethyl-1,2,3,4-tetrahydroisoquinolin-7-yl)-3-((3-isopropoxypyridin-4-yl)methoxy) pyrazin-2-amine

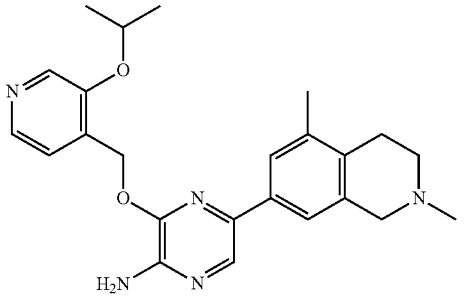 [SMILES: Cc1cc(-c2cnc(N)c(OCc3ccncc3OC(C)C)n2)cc2c1CCN(C)C2]

Example 30 (121 mg, 33%) was prepared in a manner similar to that in Example 17 step 2 from (2,5-dimethyl-1,2,3,4-tetrahydroisoquinolin-7-yl)boronic acid and 5-bromo-3-((3-isopropoxypyridin-4-yl)methoxy)pyrazin-2-amine. $^1H$ NMR (400 MHz, DMSO-d6) δ 8.41 (s, 1H), 8.18 (d, J=4.6 Hz, 1H), 8.07 (s, 1H), 7.54 (d, J=4.4 Hz, 1H), 7.47 (s, 1H), 7.34 (s, 1H), 6.51 (s, 2H), 5.54 (s, 2H), 4.89-4.73 (m, 1H), 3.45 (s, 2H), 2.71-2.55 (m, 4H), 2.33 (s, 3H), 2.19 (s, 3H), 1.33 (d, J=6.0 Hz, 6H). LC-MS $(M+H)^+$=420.5.

Example 31: 3-((2-aminopyridin-4-yl)methoxy)-5-(2,8-dimethyl-1,2,3,4-tetrahydroisoquinolin-6-yl) pyrazin-2-amine

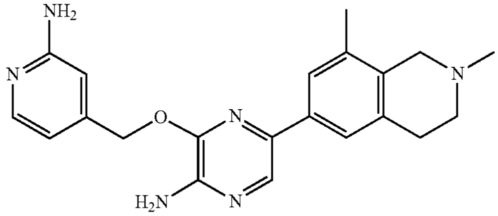 [SMILES: Cc1cc(-c2cnc(N)c(OCc3ccnc(N)c3)n2)cc2c1CN(C)CC2]

Step 1: tert-butyl (pivaloyloxy)carbamate

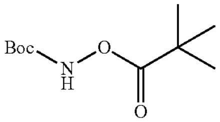

Pivalic anhydride (23.1 g, 123.9 mmol) was added to a solution of tert-butyl hydroxycarbamate (15.0 g, 112.7 mmol) in acetonitrile (300 mL) at 0° C. The mixture was heated to reflux overnight and solvent was removed in vacuo. The crude was dissolved in ethyl acetate (300 mL) and cooled to 0° C. before saturated $NaHCO_3$ (200 mL) was added. The organic layer was separated and washed with saturated $NaHCO_3$ (200 mL×2) and brine (50 mL), then dried over $Na_2SO_4$. The solvent was evaporated under reduced pressure to give the title compound (24.8 g, 100%). H NMR (400 MHz, $CDCl_3$) δ 7.81 (s, 1H), 1.49 (s, 9H), 1.31 (s, 9H).

Step 2: O-pivaloylhydroxylamine trifluoromethanesulfonate Salt

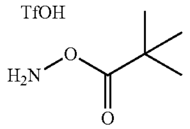

TfOH (18.9 g, 125.7 mmol) was added to a solution of tert-butyl (pivaloyloxy)carbamate (24.8 g, 114.3 mmol) in MTBE (230 mL) at 0° C. and stirred at room temperature for 4 h. The volume of solution was reduced to about 100 mL under reduced pressure and the precipitate was collected by filtration. The solid was dried under vacuum to give the title compound (26.0 g, 85%). LC-MS $(M+H)^+$=118.0.

Step 3: 4-bromo-2-methyl-N-(pivaloyloxy)benzamide

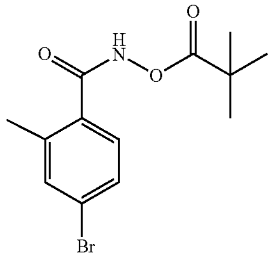 [SMILES: Cc1cc(Br)ccc1C(=O)NOC(=O)C(C)(C)C]

DIPEA (15.7 g, 121.6 mmol) was added to a solution of 4-bromo-2-methylbenzoic acid (8.82 g, 40.52 mmol) in THF (150 mL) at 0° C., followed by T3P (25.8 g, 81.1 mmol) and O— pivaloylhydroxylamine trifluoromethanesulfonate salt (26.0 g, 97.3 mmol). The reaction was stirred at room temperature overnight. Brine (100 mL) was added and the mixture was extracted with ethyl acetate (100 mL×3). The combined organic layer was dried over $Na_2SO_4$, filtered and concentrated under reduced pressure. The residue was purified by silica gel column chromatography to give the title compound (7.5 g, 59%). LC-MS $(M+H)^+$=314.0.

Step 4: 6-bromo-8-methyl-3,4-dihydroisoquinolin-1(2H)-one

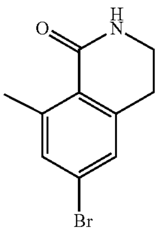

KOAc (5.16 g, 52.5 mmol) and dichloro(pentamethylcyclopentadienyl)rhodium(III) dimer (737.7 mg, 1.19 mmol) was added to a solution of 4-bromo-2-methyl-N-(pivaloyloxy)benzamide (7.5 g, 23.9 mmol) in acetonitrile (150 mL). The solution was stirred under an ethylene atmosphere (3 bar) at room temperature for overnight. The solvent was removed in vacuo and the residue was partitioned between water (20 mL) and ethyl acetate (50 mL). The organic layer was dried over $Na_2SO_4$, filtered and concentrated. The residue was purified by silica gel column chromatography to give the title compound (4.67 g, 82%). LC-MS $(M+H)^+$=240.0.

Step 5: 6-bromo-8-methyl-1,2,3,4-tetrahydroisoquinoline

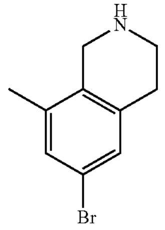

6-bromo-8-methyl-3,4-dihydroisoquinolin-1(2H)-one (4.67 g, 19.5 mmol) was dissolved in $BH_3$ in THF (1.0 M, 77.8 mL, 77.8 mmol) and the reaction mixture was refluxed overnight. The mixture was cooled to 0° C. and MeOH (5 mL) was added followed by HCl (2 M, 25 mL). The solution was heated to 80° C. for 3 h. The mixture was cooled to room temperature and solvent was removed in vacuo. The residue was dissolved in DCM (50 mL) and the solution was successively washed with saturated $NaHCO_3$ (30 mL) and brine (30 mL), dried over $Na_2SO_4$, filtered and concentrated. The residue was purified by silica gel column chromatography to give the title compound (3.79 g, 86%). LC-MS $(M+H)^+$=226.0.

Step 6: 6-bromo-2,8-dimethyl-1,2,3,4-tetrahydroisoquinoline

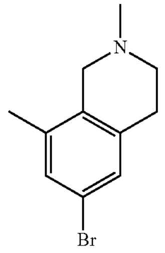

Formalin (37%, 3.48 g, 42.90 mmol) was added to a solution of 6-bromo-8-methyl-1,2,3,4-tetrahydroisoquinoline (1.94 g, 8.58 mmol) in DCM (30 mL). After 5 min, $NaBH(OAc)_3$ (3.64 g, 17.2 mmol) was added and the mixture was stirred at room temperature overnight. Saturated $NaHCO_3$ (20 mL) was added and the mixture was extracted with DCM (30 mL×2). The combined organic layer was dried over $Na_2SO_4$, filtered and concentrated. The residue was purified by silica gel column chromatography to give the title compound (1.85 g, 90%). LC-MS $(M+H)^+$=240.0.

Step 7: 2,8-dimethyl-6-(4,4,5,5-tetramethyl-1,3,2-dioxaborolan-2-yl)-1,2,3,4-tetrahydroisoquinoline

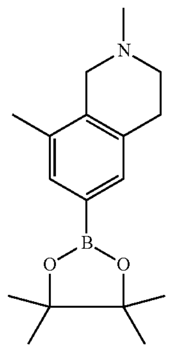

6-bromo-2,8-dimethyl-1,2,3,4-tetrahydroisoquinoline (1.85 g, 7.71 mmol), BPD (3.92 g, 15.4 mmol), $Pd(dppf)Cl_2$ (282 mg, 0.385 mmol) and KOAc (2.27 g, 23.1 mmol) was added to 1,4-dioxane (25 mL) and the mixture was heated to 95° C. under $N_2$ overnight. After cooled to room temperature, the mixture was concentrated in vacuo. The residue was purified by silica gel column chromatography to give the title compound (1.77 g, 80%). LC-MS $(M+H)^+$=288.0.

Step 8: 3-((2-aminopyridin-4-yl)methoxy)-5-(2,8-dimethyl-1,2,3,4-tetrahydroisoquinolin-6-yl)pyrazin-2-amine

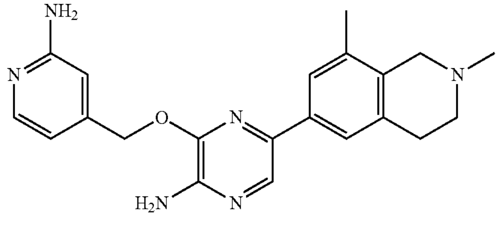

Example 31 (20 mg, 3.1%) was prepared in a manner similar to that in Example 17 step 2 from 3-((2-aminopyridin-4-yl)methoxy)-5-bromopyrazin-2-amine and 2,8-dimethyl-6-(4,4,5,5-tetramethyl-1,3,2-dioxaborolan-2-yl)-1,2,3,4-tetrahydroisoquinoline. $^1H$ NMR (400 MHz, DMSO-d6) δ 8.06 (s, 1H), 7.88 (d, J=5.1 Hz, 1H), 7.45 (s, 1H), 7.42 (s, 1H), 6.62 (d, J=4.8 Hz, 1H), 6.52 (s, 1H), 6.42 (s, 2H), 5.88 (s, 2H), 5.37 (s, 2H), 3.39 (s, 2H), 2.86-2.80 (m, 2H), 2.50-2.58 (m, 2H), 2.38 (s, 3H), 2.18 (s, 3H). LC-MS $(M+H)^+$=377.4

Example 32: 3-((2-amino-5-methylpyridin-4-yl)methoxy)-5-(2,5-dimethyl-1,2,3,4-tetrahydroisoquinolin-7-yl)pyrazin-2-amine

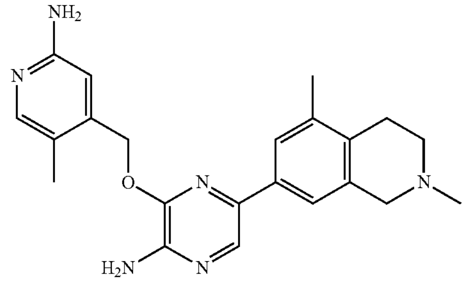

Step 1: methyl 2-amino-5-methylisonicotinate

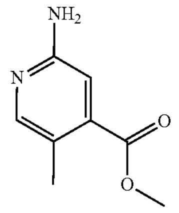

Solid methyl 2-amino-5-bromoisonicotinate (2.31 g, 10 mmol), $Pd(OAc)_2$ (225 mg, 1 mmol), S-Phos (821 mg, 2 mmol) and $K_3PO_4$ (4.24 g, 20 mmol) was placed in a flask and flushed with $N_2$. DMSO (50 ml) was added at room temperature followed by trimethylboroxine in THF (3.5 M, 11 mL, 40 mmol). The mixture was heated to 80° C. overnight. After being cooled to room temperature, the mixture was diluted with EtOAc (250 mL) and washed with $H_2O$ (50 mL×3). The organic phase was dried over $Na_2SO_4$, filtered and concentrated under reduced pressure. The residue was purified by silica gel column chromatography, eluted with PE/EtOAc (5:1 to 2:1) to give the title compound (1.3 g, 78%). LCMS $(M+H)^+$=167.0.

Step 2: (2-amino-5-methylpyridin-4-yl)methanol

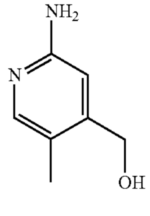

A solution of methyl 2-amino-5-methylisonicotinate (1.3 g, 7.8 mmol) in THF (2 mL) was added dropwise to a suspension of $LiAlH_4$ (593 mg, 15.6 mmol) in THF (8 mL) at 0° C. and the mixture was stirred for 2 h at room temperature. The solution was cooled to 0° C. and $H_2O$ (0.6 mL) was slowly added, followed by addition of 3.0 M NaOH solution (0.6 mL) and another portion of water (1.8 mL). The mixture was stirred at room temperature for 10 minutes, then filtered. The organic phase was dried over $Na_2SO_4$, filtered and concentrated to give the title compound (1.0 g, 93%). LC-MS $(M+H)^+$=139.1.

Step 3: 3-((2-amino-5-methylpyridin-4-yl)methoxy)-5-bromopyrazin-2-amine

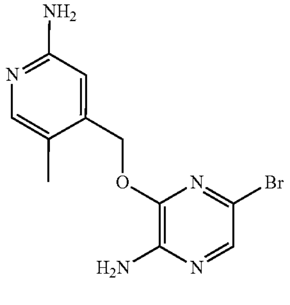 [SMILES: Cc1cnc(N)cc1COc1nc(Br)cnc1N]

NaH (60%, 310 mg, 7.8 mmol) was added to a solution of (2-amino-5-methylpyridin-4-yl)methanol (700 mg, 5.07 mmol), 3,5-dibromopyrazin-2-amine (980 mg, 3.9 mmol) in THF (20 mL) at 0° C. The reaction was stirred at reflux for 5 h. After being cooled to room temperature, water (20 mL) was added and the mixture was extracted with EtOAc (30 mL×2). The combined organic layer was washed with brine (20 mL), dried over $Na_2SO_4$, filtered and concentrated under reduced pressure. The residue was purified by silica gel column chromatography, eluted with PE/EtOAc (5:1 to 1:1) to give the title compound (600 mg, 50%). LC-MS $(M+H)^+$=309.9, 311.9.

Step 4: 3-((2-amino-5-methylpyridin-4-yl)methoxy)-5-(2,5-dimethyl-1,2,3,4-tetrahydroisoquinolin-7-yl)pyrazin-2-amine

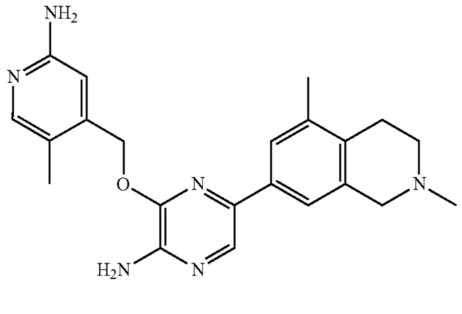 [SMILES: Cc1cnc(N)cc1COc1nc(-c2cc(C)c3c(c2)CN(C)CC3)cnc1N]

Example 32 (158 mg, 41%) was prepared in a manner similar to that in Example 17 step 2 from 3-((2-amino-5-methylpyridin-4-yl)methoxy)-5-bromopyrazin-2-amine and ((2,5-dimethyl-1,2,3,4-tetrahydroisoquinolin-7-yl)boronic acid. $^1H$ NMR (400 MHz, DMSO-d6) δ 8.05 (s, 1H), 7.73 (s, 1H), 7.47 (s, 1H), 7.34 (s, 1H), 6.55 (s, 1H), 6.41 (s, 2H), 5.62 (s, 2H), 5.37 (s, 2H), 3.47 (s, 2H), 2.70-2.57 (m, 4H), 2.33 (s, 3H), 2.20 (s, 3H), 2.17 (s, 3H). LC-MS $(M+H)^+$=391.4.

Example 33: 3-((3-(benzyloxy)pyridin-4-yl)methoxy)-5-(2,5-dimethyl-1,2,3,4-tetrahydroisoquinolin-7-yl)pyrazin-2-amine

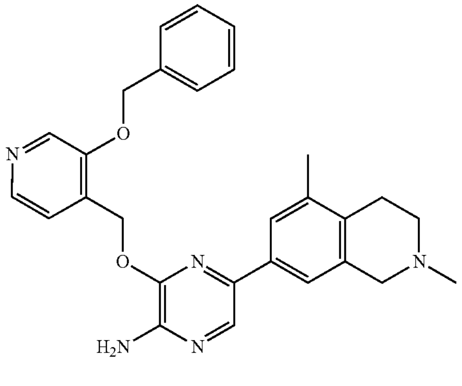 [SMILES: Cc1cc(-c2cnc(N)c(OCc3ccncc3OCc3ccccc3)n2)cc2c1CCN(C)C2]

Step 1: methyl 3-(benzyloxy)isonicotinate

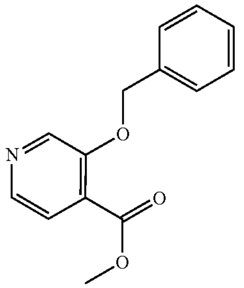 [SMILES: COC(=O)c1ccncc1OCc1ccccc1]

The title compound (200 mg, 25%) was prepared in a manner similar to that in Example 30 step 1 from methyl 3-hydroxyisonicotinate and benzyl bromide. LC-MS $(M+H)^+$=244.2.

Step 2: (3-(benzyloxy)pyridin-4-yl)methanol

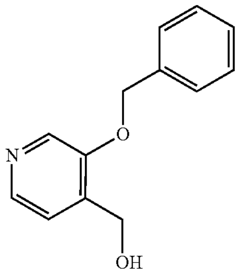 [SMILES: OCc1ccncc1OCc1ccccc1]

The title compound (157 mg, 89%) was prepared in a manner similar to that in Example 30 step 2 from methyl 3-(benzyloxy)isonicotinate. LC-MS $(M+H)^+$=216.2.

Step 3: 3-((3-(benzyloxy)pyridin-4-yl)methoxy)-5-bromopyrazin-2-amine

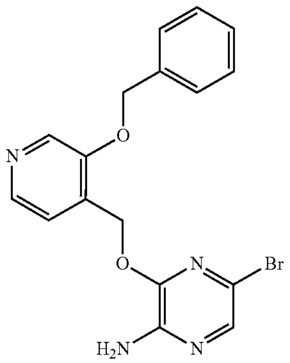 [SMILES: Nc1ncc(Br)nc1OCc1ccncc1OCc1ccccc1]

The title compound (211 mg, 75%) was prepared in a manner similar to that in Example 17 step 1 from 3,5-dibromopyrazin-2-amine and (3-(benzyloxy)pyridin-4-yl) methanol. LC-MS $(M+H)^+$=387.2.

Step 4: 3-((3-(benzyloxy)pyridin-4-yl)methoxy)-5-(2,5-dimethyl-1,2,3,4-tetrahydroisoquinolin-7-yl) pyrazin-2-amine

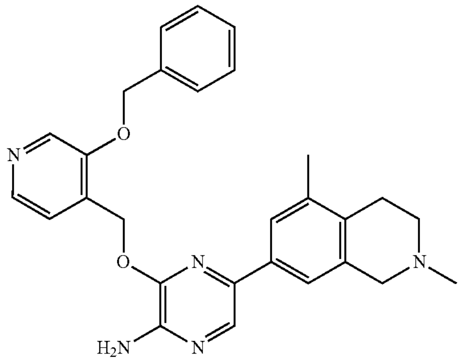 [SMILES: Cc1cc(-c2cnc(N)c(OCc3ccncc3OCc3ccccc3)n2)cc2c1CCN(C)C2]

Example 33 (45 mg, 18%) was prepared in a manner similar to that in Example 17 step 2 from 3-((3-(benzyloxy) pyridin-4-yl)methoxy)-5-bromopyrazin-2-amine and ((2,5-dimethyl-1,2,3,4-tetrahydroisoquinolin-7-yl)boronic acid. $^1$H NMR (400 MHz, DMSO-d6) δ 8.48 (s, 1H), 8.24 (d, J=4.7 Hz, 1H), 8.08 (s, 1H), 7.67 (d, J=4.7 Hz, 1H), 7.57-7.50 (m, 2H), 7.47 (s, 1H), 7.43-7.29 (m, 4H), 6.54 (s, 2H), 5.59 (s, 2H), 5.35 (s, 2H), 3.41 (s, 2H), 2.69-2.55 (m, 4H), 2.32 (s, 3H), 2.17 (s, 3H). LC-MS $(M+H)^+$=468.5.

Example 34: 3-((1H-pyrrolo[2,3-b]pyridin-4-yl) methoxy)-5-(2,5-dimethyl-1,2,3,4-tetrahydroisoquinolin-7-yl)pyrazin-2-amine

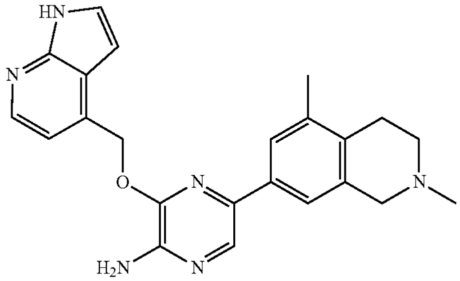 [SMILES: Cc1cc(-c2cnc(N)c(OCc3ccnc4[nH]ccc34)n2)cc2c1CCN(C)C2]

Step 1: 1-((2-(trimethylsilyl)ethoxy)methyl)-1H-pyrrolo[2,3-b]pyridine-4-carbonitrile

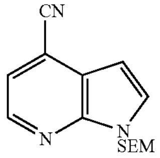 [SMILES: C[Si](C)(C)CCOCn1ccc2c(C#N)ccnc21]

To a solution of 1H-pyrrolo[2,3-b]pyridine-4-carbonitrile (2.0 g, 14.0 mmol) in THF (40 mL) was added NaH (60%, 672 mg, 16.8 mmol) at 0° C. After 15 min, SEMCl (3.02 g, 18.2 mmol) was added. The resulting solution was stirred for 2 h at room temperature. The reaction mixture was poured into water (100 mL) and then extracted with ethyl acetate (100 mL×3). The combined organic layer was washed with brine (100 mL), dried over $Na_2SO_4$, filtered and concentrated under vacuum. The residue was purified by silica gel column chromatography, eluted with PE/EtOAc (10:1) to give the title compound (3.0 g, 78%). LC-MS $(M+H)^+$=274.0.

Step 2: 1-((2-(trimethylsilyl)ethoxy)methyl)-1H-pyrrolo[2,3-b]pyridine-4-carboxylic acid

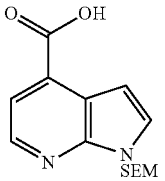 [SMILES: C[Si](C)(C)CCOCn1ccc2c(C(=O)O)ccnc21]

To a solution of 1-((2-(trimethylsilyl)ethoxy)methyl)-1H-pyrrolo[2,3-b]pyridine-4-carbonitrile (3.0 g, 10.9 mmol) in EtOH (40 mL) and $H_2O$ (40 mL) was added NaOH (4.36 g, 109 mmol). The resulting solution was stirred for 16 h at 80° C. After being cooled to room temperature, EtOH was removed under vacuum. The mixture was diluted with water (100 mL) and then washed with EtOAc (100 mL). The aqueous layer was acidified with HCl (1 M) until pH=3. The precipitated was collected by filtration and dried under vacuum to give the title compound (2.0 g, 62%). LC-MS $(M+H)^+$=293.0.

Step 3: (1-((2-(trimethylsilyl)ethoxy)methyl)-1H-pyrrolo[2,3-b]pyridin-4-yl)methanol

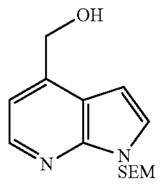 [SMILES: C[Si](C)(C)CCOCn1ccc2c(CO)ccnc21]

To a solution of 1-((2-(trimethylsilyl)ethoxy)methyl)-1H-pyrrolo[2,3-b]pyridine-4-carboxylic acid (2.0 g, 6.85 mmol) in THF (40 mL) was added $LiAlH_4$ (672 mg, 10.3 mmol) at 0° C. The reaction mixture was stirred for 4 h at room temperature, then NaOH solution (2 M, 0.50 mL) was carefully added. And the mixture was concentrated under vacuum. The residue was purified by silica gel column chromatography, eluted with PE/EtOAc (10:1) to give the title compound (550 mg, 29%). LC-MS $(M+H)^+$=279.0.

Step 4: 5-bromo-3-((1-((2-(trimethylsilyl)ethoxy)methyl)-1H-pyrrolo[2,3-b]pyridin-4-yl)methoxy)pyrazin-2-amine

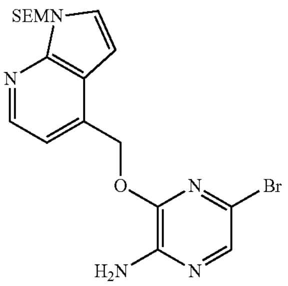 [SMILES: C[Si](C)(C)CCOCn1ccc2c(COc3nc(Br)cnc3N)ccnc21]

To a solution of (1-((2-(trimethylsilyl)ethoxy)methyl)-1H-pyrrolo[2,3-b]pyridin-4-yl)methanol (550 mg, 1.98 mmol) in DMF (15 mL) was added NaH (60%, 103 mg, 2.57 mmol) at 0° C. After 15 min, 3,5-dibromopyrazin-2-amine (495 mg, 1.98 mmol) was added. The resulting solution was stirred for 4 h at room temperature. The reaction mixture was poured into water (100 mL) and then extracted with EtOAc (100 mL×3). The combined organic layer was washed with brine (100 mL), dried over $Na_2SO_4$, filtered and concentrated under vacuum. The residue was purified by silica gel column chromatography, eluted with PE/EtOAc (1:1) to give the title compound (400 mg, 45%). LC-MS $(M+H)^+$=449.9.

Step 5: 5-(2,5-dimethyl-1,2,3,4-tetrahydroisoquinolin-7-yl)-3-((1-((2-(trimethylsilyl)ethoxy)methyl)-1H-pyrrolo[2,3-b]pyridin-4-yl)methoxy)pyrazin-2-amine

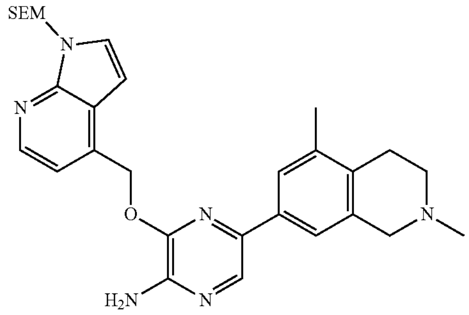 [SMILES: Cc1cc(-c2cnc(N)c(OCc3ccnc4c3ccn4COCC[Si](C)(C)C)n2)cc2c1CCN(C)C2]

To a solution of 5-bromo-3-((1-((2-(trimethylsilyl)ethoxy)methyl)-1H-pyrrolo[2,3-b]pyridin-4-yl)methoxy)pyrazin-2-amine (300 mg, 0.67 mmol) in 1,4-dioxane (20 mL) and water (4 mL) was added (2,5-dimethyl-1,2,3,4-tetrahydroisoquinolin-7-yl)boronic acid (137 mg, 0.67 mmol), $K_2CO_3$ (276 mg, 2.00 mmol) and Pd(dppf)$Cl_2$ (57 mg, 0.07 mmol). The resulting solution was stirred for 16 h at 90° C. under nitrogen. After being cooled to room temperature, the reaction mixture was poured into water (100 mL) and then extracted with EtOAc (100 mL×3). The combined organic layer was washed with brine (100 mL), dried over $Na_2SO_4$, filtered and concentrated under vacuum. The residue was purified by silica gel column chromatography, eluted with DCM/MeOH (20:1) to give the title compound (300 mg, 84%).

LC-MS $(M+H)^+$=531.0.

Step 6: 3-((1H-pyrrolo[2,3-b]pyridin-4-yl)methoxy)-5-(2,5-dimethyl-1,2,3,4-tetrahydroisoquinolin-7-yl)pyrazin-2-amine

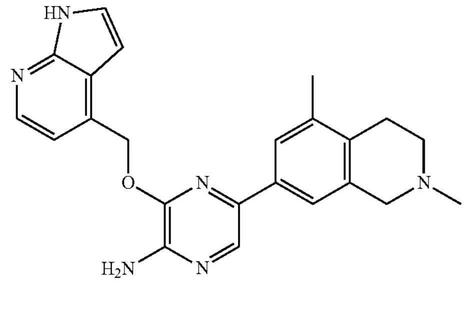 [SMILES: Cc1cc(-c2cnc(N)c(OCc3ccnc4[nH]ccc34)n2)cc2c1CCN(C)C2]

To a solution of 5-(2,5-dimethyl-1,2,3,4-tetrahydroisoquinolin-7-yl)-3-((1-((2-(trimethylsilyl)ethoxy)methyl)-1H-pyrrolo[2,3-b]pyridin-4-yl)methoxy)pyrazin-2-amine (300 mg, 0.57 mmol) in DCM (10 mL) was added TFA (3 mL). The solution was stirred for 3 h at room temperature and concentrated under vacuum, then MeOH (5 mL) and $NH_4OH$ (25%, 5 mL) was added. The mixture was stirred for 3 h at room temperature and concentrated under vacuum. The crude product was purified by prep-HPLC to give Example 34 (20 mg, 9%). $^1H$ NMR (400 MHz, DMSO-$d_6$) δ 11.70 (s, 1H), 8.20 (d, J=4.9 Hz, 1H), 8.02 (s, 1H), 7.51-7.45 (m, 1H), 7.41 (s, 1H), 7.27 (s, 2H), 7.22 (d, J=4.7

Hz, 1H), 6.71 (s, 1H), 6.47 (s, 2H), 5.80 (s, 2H), 3.42 (s, 2H), 2.65-2.56 (m, 4H), 2.34 (s, 3H), 2.17 (s, 3H). LC-MS $(M+H)^+$=401.4.

Example 35: 3-((2-amino-3-methoxypyridin-4-yl)methoxy)-5-(2,5-dimethyl-1,2,3,4-tetrahydroisoquinolin-7-yl)pyrazin-2-amine

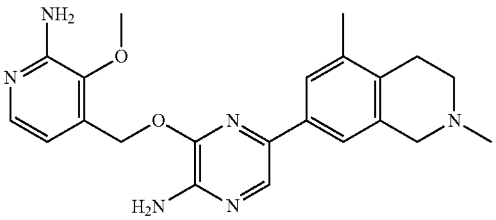 [SMILES: COc1c(COc2nc(-c3cc(C)c4c(c3)CN(C)CC4)cnc2N)ccnc1N]

Step 1: 2-chloro-3-methoxyisonicotinic acid

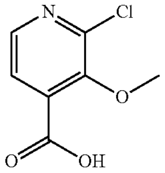

To a solution of 2-chloro-3-methoxypyridine (1.5 g, 10 mmol) in THF (20 mL) was added LDA in THF/hexane (2.0 M, 10 mL, 20 mmol) dropwise at −78° C. and the mixture was stirred at −78° C. for 2 h. Crushed dry ice (10 g) was carefully added to the mixture and the mixture was stirred at −78° C. for 1 h. The mixture was warmed to room temperature and water (50 mL) was carefully added. The mixture was washed with EtOAc (30 mL) and the aqueous layer was collected. The aqueous layer was acidified with HCl (2 M) to pH=4, then extracted with EtOAc (30 mL×3). The combined organic layer was dried over $Na_2SO_4$, filtered and concentrated under reduced pressure to give the title compound (600 mg, 31%). LC-MS $(M+H)^+$=187.9.

Step 2: ethyl 2-chloro-3-methoxyisonicotinate

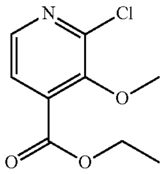

To a solution of 2-chloro-3-methoxyisonicotinic acid (600 mg, 3.2 mmol) in EtOH (20 mL) was added $H_2SO_4$ (0.50 mL). The mixture was stirred at 70° C. overnight. After being cooled to room temperature, most of EtOH was evaporated under vacuum. The residue was neutralized with saturated $NaHCO_3$ (50 mL) and extracted with EtOAc (30 mL×3). The combined organic phase was washed with brine, dried over $Na_2SO_4$, filtered and concentrated. The residue was purified by silica gel column chromatography, eluted with PE/EtOAc (10:1) to give the title compound (500 mg, 71%). LC-MS $(M+H)^+$=215.9.

Step 3: ethyl 2-amino-3-methoxyisonicotinate

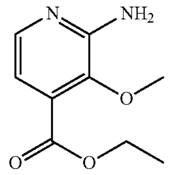

To a mixture of ethyl 2-chloro-3-methoxyisonicotinate (500 mg, 2.3 mmol) and benzophenonimine (500 mg, 2.7 mmol) in dioxane (20 mL) was added $Pd(dba)_2$ (130 mg, 0.20 mmol), Xantphos (260 mg, 0.40 mmol) and $Cs_2CO_3$ (1.5 g, 4.6 mmol). The mixture was stirred at 100° C. overnight under nitrogen atmosphere. The mixture was cooled and filtered. To the filtrate was added HCl (6 M, 2 mL). The mixture was stirred for 1 h. The mixture was neutralized with $NaHCO_3$ solution (50 mL) and extracted with EtOAc (3×30 mL). The combined organic layer was washed with brine, dried over $Na_2SO_4$, filtered and concentrated. The residue was purified by silica gel column chromatography, eluted with PE/EtOAc (2:1) to give the title compound (300 mg, 65%). LC-MS $(M+H)^+$=197.1.

Step 4: (2-amino-3-methoxypyridin-4-yl)methanol

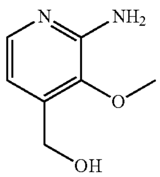

To a solution of ethyl 2-amino-3-methoxyisonicotinate (300 mg, 1.5 mmol) in THF (10 mL) was added $LiAlH_4$ (170 mg, 4.5 mmol) at 0° C. The mixture was stirred at room temperature for 1 h. To the mixture was sequentially added water (170 mg) and NaOH solution (15%, w/w, 400 mg), stirred for 15 min and diluted with EtOAc (30 mL). The mixture was filtered and the filtrated was concentrated under vacuum. The residue was purified by silica gel column chromatography, eluted with PE/EtOAc (3:1 to 1:1) to give the title compound (150 mg, 66%). LC-MS $(M+H)^+$=155.1.

Step 5: 3-((2-amino-3-methoxypyridin-4-yl)methoxy)-5-bromopyrazin-2-amine

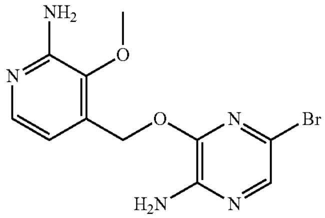 [SMILES: COc1c(COc2nc(Br)cnc2N)ccnc1N]

To a mixture of (2-amino-3-methoxypyridin-4-yl)methanol (150 mg, 1.0 mmol) in THF (10 mL) was added NaH (60%, 120 mg, 3.0 mmol). The mixture was stirred at room temperature for 10 min. To the mixture was added 3,5-dibromopyrazin-2-amine (250 mg, 1.0 mmol). The mixture was stirred at 60° C. for 3 h, cooled to room temperature and diluted with water (30 mL). The mixture was extracted with EtOAc (20 mL×3). The combined organic layers was washed with brine, dried over $Na_2SO_4$, filtered and concentrated. The residue was purified by silica gel column chromatography, eluted with PE/EtOAc (1:1) to give the title compound (100 mg, 30%). LC-MS $(M+H)^+$=326.0.

Step 6: 3-((2-amino-3-methoxypyridin-4-yl)methoxy)-5-(2,5-dimethyl-1,2,3,4-tetrahydroisoquinolin-7-yl)pyrazin-2-amine

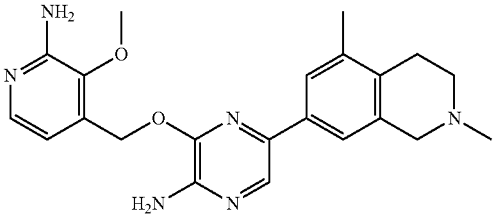 [SMILES: COc1c(COc2nc(-c3cc(C)c4c(c3)CN(C)CC4)cnc2N)ccnc1N]

Example 35 (40 mg, 32%) was prepared in a manner similar to that in Example 17 step 2 from 3-((2-amino-3-methoxypyridin-4-yl)methoxy)-5-bromopyrazin-2-amine and (2,5-dimethyl-1,2,3,4-tetrahydroisoquinolin-7-yl)boronic acid. $^1H$ NMR (400 MHz, DMSO-d6) δ 8.05 (s, 1H), 7.66 (d, J=5.1 Hz, 1H), 7.48 (s, 1H), 7.35 (s, 1H), 6.66 (d, J=5.1 Hz, 1H), 6.43 (s, 2H), 5.90 (s, 2H), 5.49 (s, 2H), 3.75 (s, 3H), 3.47 (s, 2H), 2.70-2.64 (m, 2H), 2.64-2.58 (m, 2H), 2.33 (s, 3H), 2.20 (s, 3H). LC-MS $(M+H)^+$=407.5.

Example 36: 5-(2,5-dimethyl-1,2,3,4-tetrahydroisoquinolin-7-yl)-3-(1H-pyrazol-4-yl)pyrazin-2-amine

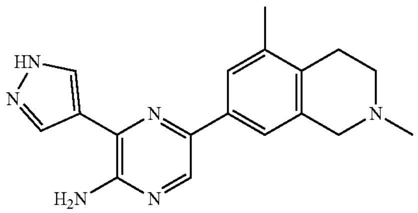 [SMILES: Cc1cc(-c2cnc(N)c(-c3cn[nH]c3)n2)cc2c1CCN(C)C2]

To a solution of 1H-pyrazol-4-ylboronic acid (116 mg, 1.04 mmol) in dioxane (8 mL) was added 3-chloro-5-(2,5-dimethyl-1,2,3,4-tetrahydroisoquinolin-7-yl)pyrazin-2-amine (200 mg, 0.69 mmol), water (2 mL), bis(tricyclohexylphosphine)dichloropalladium (51 mg, 0.069 mmol) and $K_2CO_3$ (191 mg, 1.38 mmol). The mixture was stirred for 2 h at 120° C. under nitrogen atmosphere then cooled to room temperature. The mixture was diluted with water (30 mL) then extracted with EtOAc (30 mL×3). The organic phases were combined, washed with brine, dried over $Na_2SO_4$ and concentrated under reduced pressure. The residue was purified by prep-HPLC to give Example 36 (23 mg, 10%). $^1H$ NMR (400 MHz, DMSO-d6) δ 13.18 (s, 1H), 8.53-8.05 (m, 3H), 7.67 (s, 1H), 7.55 (s, 1H), 6.15 (s, 2H), 3.53 (s, 2H), 2.79-2.59 (m, 4H), 2.35 (s, 3H), 2.25 (s, 3H). LC-MS $(M+H)^+$=321.0.

Example 37: 5-(2,5-dimethyl-1,2,3,4-tetrahydroisoquinolin-7-yl)-3-((3-((tetrahydro-2H-pyran-4-yl)methoxy)pyridin-4-yl)methoxy)pyrazin-2-amine

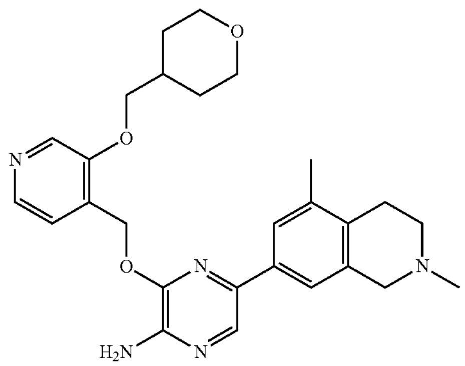

Step 1: methyl 3-((tetrahydro-2H-pyran-4-yl)methoxy)isonicotinate

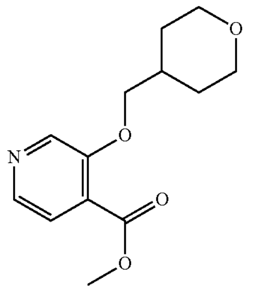 [SMILES: COC(=O)c1ccncc1OCC1CCOCC1]

The title compound (480 mg, 59%) was prepared in a manner similar to that in Example 30 step 1 from methyl 3-hydroxyisonicotinate and 4-(bromomethyl)tetrahydro-2H-pyran. LC-MS $(M+H)^+$=252.3.

Step 2: (3-((tetrahydro-2H-pyran-4-yl)methoxy)pyridin-4-yl)methanol

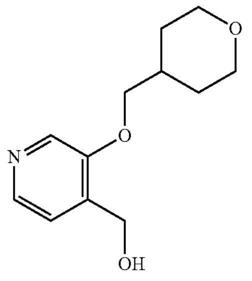 [SMILES: OCc1ccncc1OCC1CCOCC1]

The title compound (355 mg, 83%) was prepared in a manner similar to that in Example 30 step 2 from methyl 3-((tetrahydro-2H-pyran-4-yl)methoxy)isonicotinate. LC-MS $(M+H)^+$=224.3.

Step 3: 5-bromo-3-((3-((tetrahydro-2H-pyran-4-yl) methoxy)pyridin-4-yl)methoxy)pyrazin-2-amine

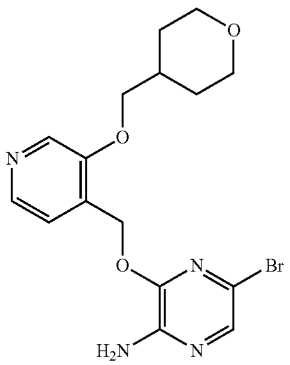 [SMILES: Nc1ncc(Br)nc1OCc1ccncc1OCC1CCOCC1]

The title compound (210 mg, 33%) was prepared in a manner similar to that in Example 17 step 1 from 3,5-dibromopyrazin-2-amine and (3-((tetrahydro-2H-pyran-4-yl)methoxy)pyridin-4-yl)methanol. LC-MS $(M+H)^+$=395.2, 397.2.

Step 4: 5-(2,5-dimethyl-1,2,3,4-tetrahydroisoquinolin-7-yl)-3-((3-((tetrahydro-2H-pyran-4-yl)methoxy) pyridin-4-yl)methoxy)pyrazin-2-amine

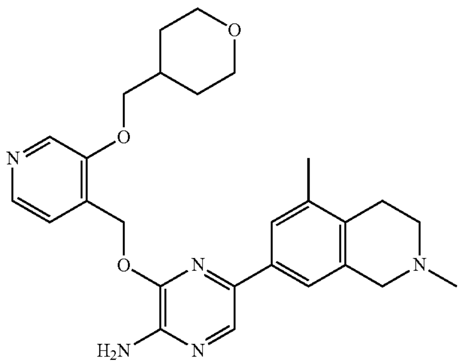 [SMILES: Cc1cc(-c2cnc(N)c(OCc3ccncc3OCC3CCOCC3)n2)cc2c1CCN(C)C2]

Example 37 (75 mg, 30%) was prepared in a manner similar to that in Example 17 step 2 from 5-bromo-3-((3-((tetrahydro-2H-pyran-4-yl)methoxy)pyridin-4-yl) methoxy)pyrazin-2-amine and ((2,5-dimethyl-1,2,3,4-tetrahydroisoquinolin-7-yl)boronic acid. $^1$H NMR (400 MHz, DMSO-d6) δ 8.38 (s, 1H), 8.23 (d, J=4.3 Hz, 1H), 8.09 (s, 1H), 7.64 (d, J=4.3 Hz, 1H), 7.48 (s, 1H), 7.36 (s, 1H), 6.52 (s, 2H), 5.54 (s, 2H), 4.05 (d, J=5.9 Hz, 2H), 3.96-3.80 (m, 2H), 3.47 (s, 2H), 3.39-3.24 (m, 2H), 2.75-2.57 (m, 4H), 2.34 (s, 3H), 2.20 (s, 3H), 2.12-1.98 (m, 1H), 1.76-1.64 (m, 2H), 1.48-1.31 (m, 2H). LC-MS $(M+H)^+$=476.5.

Example 38: 3-((2-((cyclopropylmethyl)amino)pyridin-4-yl)methoxy)-5-(2,5-dimethyl-1,2,3,4-tetrahydroisoquinolin-7-yl)pyrazin-2-amine

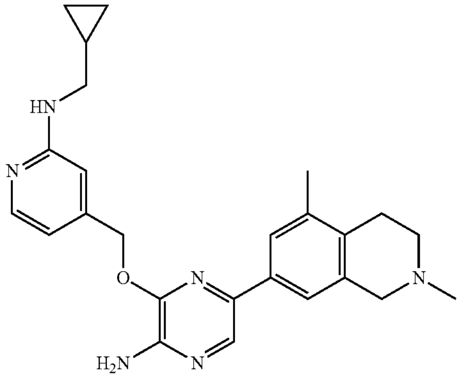 [SMILES: Cc1cc(-c2cnc(N)c(OCc3ccnc(NCC4CC4)c3)n2)cc2c1CCN(C)C2]

Step 1: (2-((cyclopropylmethyl)amino)pyridin-4-yl)methanol

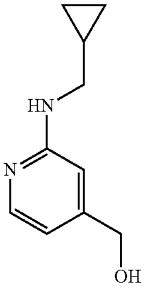 [SMILES: OCc1ccnc(NCC2CC2)c1]

AcOH (483 mg, 8.06 mmol) was added to a solution of (2-aminopyridin-4-yl)methanol (1.0 g, 8.06 mmol) and cyclopropyl carboxaldehyde (672 mg, 9.6 mmol) in THF (30 mL) at 0° C. Sodium triacetoxyborohydride (3.4 g, 16.1 mmol) was added in portions. The reaction mixture was stirred at room temperature for overnight. The mixture was diluted with water (50 mL) and extracted with EtOAc (50 mL×2). The combined organic layer was dried over $Na_2SO_4$, filtered and concentrated. The residue was purified by silica gel column chromatography to give the title compound (800 mg, 60%). LC-MS $(M+H)^+$=179.0.

Step 2: 5-bromo-3-((2-((cyclopropylmethyl)amino) pyridin-4-yl)methoxy)pyrazin-2-amine

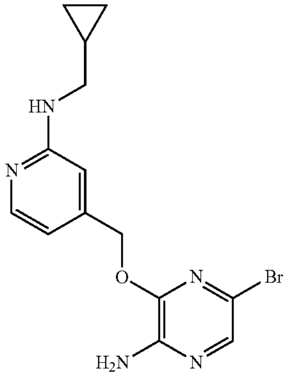 [SMILES: Nc1ncc(Br)nc1OCc1ccnc(NCC2CC2)c1]

NaH (60%, 216 mg, 5.4 mmol) was added to a solution of (2-((cyclopropylmethyl)amino)pyridin-4-yl)methanol (800 mg, 4.5 mmol) in THF (20 mL) at 0° C. The mixture was stirred at 0° C. for 30 min, then 3,5-dibromopyrazin-2-amine (1.35 g, 5.4 mmol) was added in portions. The mixture was warmed to 70° C. and stirred for 2 h under $N_2$ then cooled to room temperature. The mixture was diluted with water (50 mL) and extracted with EtOAc (50 mL×2). The combined organic layer was dried over $Na_2SO_4$, filtered and concentrated. The residue was purified by silica gel column chromatography to give the title compound (900 mg, 60%). LC-MS $(M+H)^+$=350.0, 352.0.

Step 3: 3-((2-((cyclopropylmethyl)amino)pyridin-4-yl)methoxy)-5-(2,5-dimethyl-1,2,3,4-tetrahydroisoquinolin-7-yl)pyrazin-2-amine

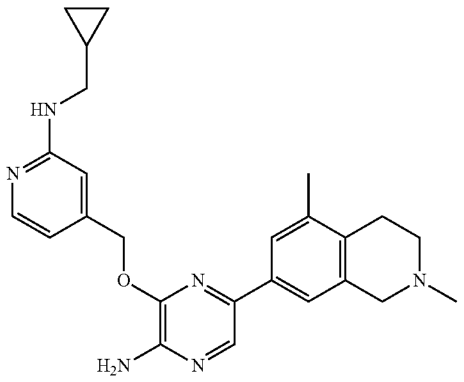 [SMILES: Cc1cc(-c2cnc(N)c(OCc3ccnc(NCC4CC4)c3)n2)cc2c1CCN(C)C2]

Example 38 (75 mg, 20%) was prepared in a manner similar to that in Example 17 step 2 from 5-bromo-3-((2-((cyclopropylmethyl)amino)pyridin-4-yl)methoxy)pyrazin-2-amine and (2,5-dimethyl-1,2,3,4-tetrahydroisoquinolin-7-yl)boronic acid. $^1$H NMR (400 MHz, DMSO-d6) δ 8.05 (s, 1H), 7.92 (d, J=4.0 Hz, 1H), 7.48 (s, 1H), 7.36 (s, 1H), 6.58 (m, 2H), 6.53 (t, J=8.0 Hz, 1H), 6.42 (s, 2H), 5.37 (s, 2H), 3.47 (s, 2H), 3.10 (t, J=8.0 Hz, 2H), 2.61-2.66 (m, 4H), 2.33 (s, 3H), 2.20 (s, 3H), 0.97-1.06 (m, 1H), 0.40 (d, J=8.0 Hz, 2H), 0.17 (d, J=8.0 Hz, 2H). LC-MS $(M+H)^+$=431.5.

Example 39: N-(4-(((3-amino-6-(2,5-dimethyl-1,2,3,4-tetrahydroisoquinolin-7-yl)pyrazin-2-yl)oxy)methyl)pyridin-2-yl)acetamide

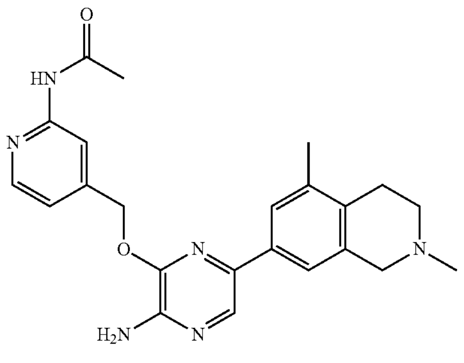 [SMILES: CC(=O)Nc1cc(COc2nc(-c3cc(C)c4c(c3)CN(C)CC4)cnc2N)ccn1]

Step 1: (2-acetamidopyridin-4-yl)methyl acetate

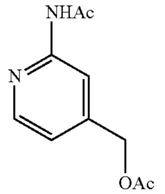 [SMILES: CC(=O)Nc1cc(COC(C)=O)ccn1]

$Ac_2O$ (4.92 g, 48.3 mmol) was added to a solution of (2-aminopyridin-4-yl)methanol (2.0 g, 16.1 mmol) in pyridine (18 mL, 224 mmol) at 0° C. The mixture was stirred for overnight at room temperature. The mixture was diluted with water (100 mL) and extracted with EtOAc (100 mL×2). The combined organic layer was dried over $Na_2SO_4$, filtered and concentrated to give the title compound (3.5 g, crude). The material was used in step 2 without further purifications. LC-MS $(M+H)^+$=209.0.

Step 2: N-(4-(hydroxymethyl)pyridin-2-yl)acetamide

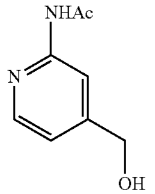 [SMILES: CC(=O)Nc1cc(CO)ccn1]

Ammonium hydroxide solution (28%, 10 mL) was added to a solution of crude (2-acetamidopyridin-4-yl)methyl acetate (3.5 g) in MeOH (30 mL). The mixture was stirred for overnight at room temperature. The mixture was concentrated under reduced pressure and the residue was purified by silica gel column chromatography to give the title compound (2.5 g, 90% over 2 steps). LC-MS $(M+H)^+$=167.0.

Step 3: N-(4-(((3-amino-6-bromopyrazin-2-yl)oxy)methyl)pyridin-2-yl)acetamide

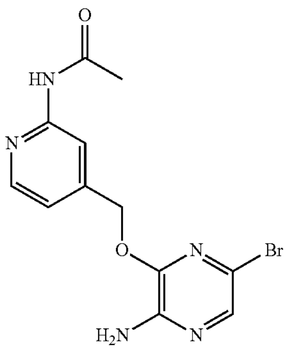 [SMILES: CC(=O)Nc1cc(COc2nc(Br)cnc2N)ccn1]

The title compound (100 mg, 10%) was prepared in a manner similar to that in Example 38 step 2 from N-(4-

(hydroxymethyl)pyridin-2-yl)acetamide and 3,5-dibromopyrazin-2-amine. LC-MS $(M+H)^+$=338.0, 340.0.

Step 4: N-(4-(((3-amino-6-(2,5-dimethyl-1,2,3,4-tetrahydroisoquinolin-7-yl)pyrazin-2-yl)oxy)methyl) pyridin-2-yl)acetamide

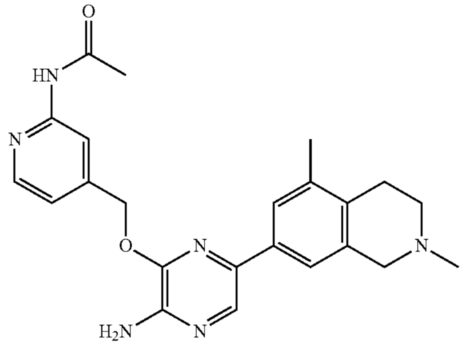 [SMILES: CC(=O)Nc1cc(COc2nc(-c3cc(C)c4c(c3)CN(C)CC4)cnc2N)ccn1]

Example 39 (20 mg, 16%) was prepared in a manner similar to that in Example 17 step 2 from N-(4-(((3-amino-6-bromopyrazin-2-yl)oxy)methyl)pyridin-2-yl)acetamide and (2,5-dimethyl-1,2,3,4-tetrahydroisoquinolin-7-yl)boronic acid. $^1$H NMR (400 MHz, DMSO-d6) δ 10.51 (s, 1H), 8.28 (s, 1H), 8.21 (s, 1H), 8.05 (s, 1H), 7.44 (s, 1H), 7.30 (s, 1H), 7.23 (s, 1H), 6.45 (s, 2H), 5.51 (s, 2H), 3.45 (s, 2H), 2.61-2.66 (m, 4H), 2.30 (s, 3H), 2.19 (s, 3H), 2.09 (s, 3H). LC-MS $(M+H)^+$=419.5.

Example 40: 5-(2,5-dimethyl-1,2,3,4-tetrahydroisoquinolin-7-yl)-3-((2-(ethylamino)pyridin-4-yl) methoxy)pyrazin-2-amine

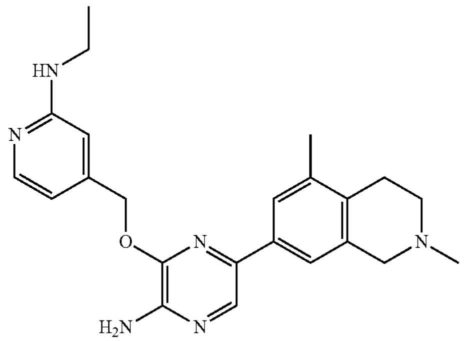 [SMILES: CCNc1cc(COc2nc(-c3cc(C)c4c(c3)CN(C)CC4)cnc2N)ccn1]

Step 1: (2-(ethylamino)pyridin-4-yl)methanol

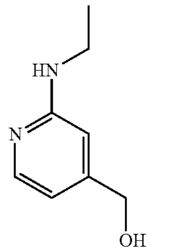

$LiAlH_4$ (228 mg, 6.0 mmol) was added in portions to N-(4-(hydroxymethyl)pyridin-2-yl)acetamide (500 mg, 3.0 mmol) in THF (10 mL) at 0° C. The mixture was warmed to 60° C. and stirred for 4 h. After being cooled to room temperature, water (0.3 mL) was added and the mixture was filtered. The filtrate was concentrated to give the title compound (150 mg) as a crude. The material was used in step 2 without further purifications. LC-MS $(M+H)^+$=153.0.

Step 2: 5-bromo-3-((2-(ethylamino)pyridin-4-yl) methoxy)pyrazin-2-amine

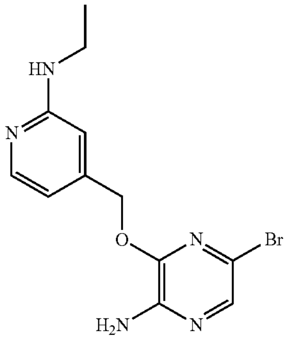 [SMILES: CCNc1cc(COc2nc(Br)cnc2N)ccn1]

This compound (75 mg, 8% over 2 steps) was prepared in a manner similar to that in Example 38 step 2 from (2-(ethylamino)pyridin-4-yl)methanol and 3,5-dibromopyrazin-2-amine. LC-MS $(M+H)_+$=324.0, 326.0.

Step 3: 5-(2,5-dimethyl-1,2,3,4-tetrahydroisoquinolin-7-yl)-3-((2-(ethylamino)pyridin-4-yl)methoxy) pyrazin-2-amine

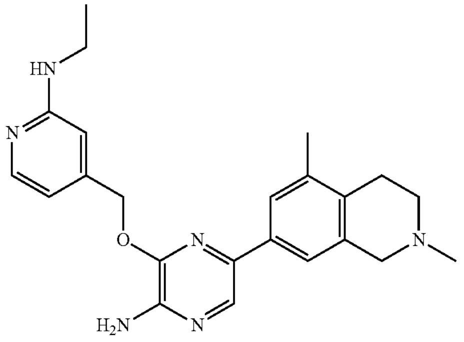 [SMILES: CCNc1cc(COc2nc(-c3cc(C)c4c(c3)CN(C)CC4)cnc2N)ccn1]

Example 40 (33 mg, 35%) was prepared in a similar manner to that in Example 38 step 3 from 5-bromo-3-((2-(ethylamino)pyridin-4-yl)methoxy)pyrazin-2-amine and (2,5-dimethyl-1,2,3,4-tetrahydroisoquinolin-7-yl)boronic acid. $^1$H NMR (400 MHz, DMSO-d6) δ 8.05 (1H), 7.93 (d, J=4.0 Hz, 1H), 7.48 (s, 1H), 7.35 (s, 1H), 6.59 (d, J=4.0 Hz, 1H), 6.53 (s, 1H), 6.42 (s, 3H), 5.37 (s, 2H), 3.47 (s, 2H), 3.19-3.26 (m, 2H), 2.61-2.66 (m, 4H), 2.34 (s, 3H), 2.20 (s, 3H), 1.10 (t, J=8.0 Hz, 3H). LC-MS $(M+H)^+$=405.5.

Example 41: 3-((2-amino-3-ethoxypyridin-4-yl)methoxy)-5-(2,5-dimethyl-1,2,3,4-tetrahydroisoquinolin-7-yl)pyrazin-2-amine

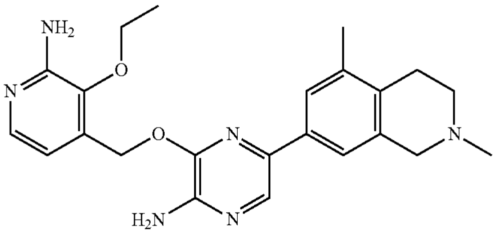 [SMILES: CCOc1c(COc2nc(-c3cc(C)c4c(c3)CN(C)CC4)cnc2N)ccnc1N]

Step 1: 2-chloro-3-ethoxypyridine

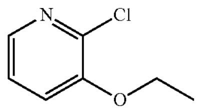

To a solution of 2-chloropyridin-3-ol (2.6 g, 20 mmol) in DMSO (30 mL) was added KOH (1.1 g, 20 mmol). The mixture was stirred at room temperature for 1 h. To the mixture was added EtI (3.1 g, 20 mmol). The mixture was stirred at room temperature for 3 h, diluted with water (30 mL) and extracted with EtOAc (30 mL×3). The combined organic layer was successively washed with water (50 mL), brine (50 mL), dried over $Na_2SO_4$, filtered and concentrated. The residue was purified by silica gel column chromatography, eluted with PE/EtOAc (5:1) to give title compound (2.7 g, 85%). LC-MS $(M+H)^+$=158.0.

Step 2: 2-chloro-3-ethoxyisonicotinic acid

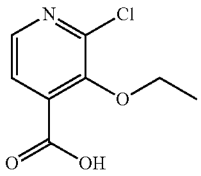

The title compound (250 mg, 12%) was prepared in a manner similar to that in Example 35 step 1 from 2-chloro-3-ethoxypyridine. LC-MS $(M+H)^+$=202.0.

Step 3: ethyl 2-chloro-3-ethoxyisonicotinate

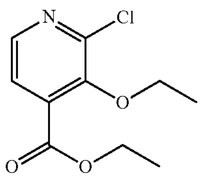

The title compound (200 mg, 72%) was prepared in a manner similar to that in Example 35 step 2 from 2-chloro-3-ethoxyisonicotinic acid and ethanol. LC-MS $(M+H)^+$=230.1.

Step 4: ethyl 2-amino-3-ethoxyisonicotinate

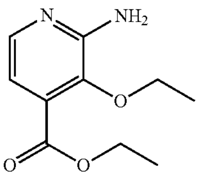

The title compound (100 mg, 77%) was prepared in a manner similar to that in Example 35 step 3 from ethyl 2-chloro-3-ethoxyisonicotinate and diphenylmethanimine. LC-MS $(M+H)^+$=211.1.

Step 5: (2-amino-3-ethoxypyridin-4-yl)methanol

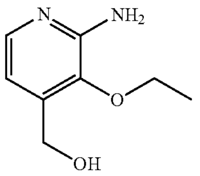

The title compound (60 mg, 80%) was prepared in a manner similar to that in Example 35 step 4 from ethyl 2-amino-3-ethoxyisonicotinate. LC-MS $(M+H)^+$=168.1.

Step 6: 3-((2-amino-3-ethoxypyridin-4-yl)methoxy)-5-bromopyrazin-2-amine

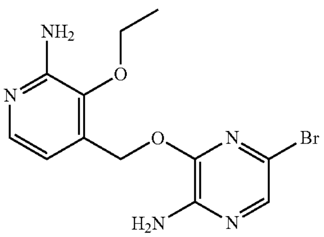 [SMILES: CCOc1c(COc2nc(Br)cnc2N)ccnc1N]

The title compound (60 mg, 50%) was prepared in a manner similar to that in Example 35 step 5 from (2-amino-3-ethoxypyridin-4-yl)methanol and 3,5-dibromopyrazin-2-amine. LC-MS $(M+H)^+$=340.0.

Step 7: 3-((2-amino-3-ethoxypyridin-4-yl)methoxy)-5-(2,5-dimethyl-1,2,3,4-tetrahydroisoquinolin-7-yl) pyrazin-2-amine

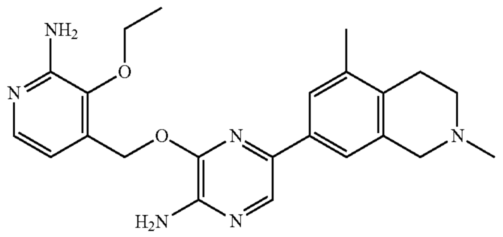 [SMILES: CCOc1c(COc2nc(-c3cc(C)c4c(c3)CN(C)CC4)cnc2N)ccnc1N]

Example 41 (20 mg, 23%) was prepared in a manner similar to that in Example 17 step 2 from 3-((2-amino-3-ethoxypyridin-4-yl)methoxy)-5-bromopyrazin-2-amine and (2,5-dimethyl-1,2,3,4-tetrahydroisoquinolin-7-yl)boronic acid. $^1$H NMR (400 MHz, DMSO-d6) δ 8.06 (s, 1H), 7.66 (d, J=5.1 Hz, 1H), 7.50 (s, 1H), 7.38 (s, 1H), 6.71 (d, J=5.0 Hz, 1H), 6.44 (s, 2H), 5.81 (s, 2H), 5.51 (s, 2H), 3.94 (q, J=7.0 Hz, 2H), 3.47 (s, 2H), 2.70-2.64 (m, 2H), 2.64-2.58 (m, 2H), 2.33 (s, 3H), 2.20 (s, 3H), 1.37 (t, J=7.0 Hz, 3H). LC-MS $(M+H)^+$=421.5.

Example 42: 5-(2,5-dimethyl-1,2,3,4-tetrahydroisoquinolin-7-yl)-3-((3-phenoxypyridin-4-yl)methoxy) pyrazin-2-amine

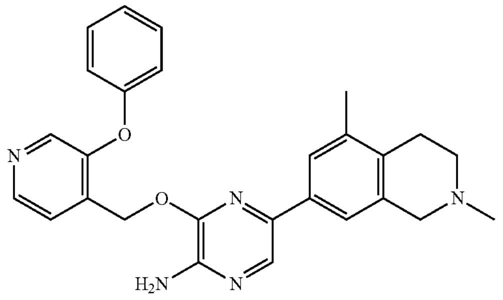 [SMILES: Cc1cc(-c2cnc(N)c(OCc3ccncc3Oc3ccccc3)n2)cc2c1CCN(C)C2]

Step 1: methyl 3-phenoxyisonicotinate

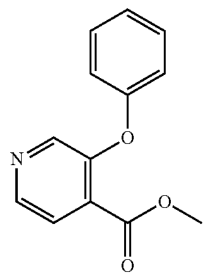 [SMILES: COC(=O)c1ccncc1Oc1ccccc1]

Diphenyliodonium trifluoromethanesulfonate (2.0 g, 4.6 mmol), methyl 3-hydroxyisonicotinate (700 mg, 4.6 mmol) and t-BuOK (564 mg, 5.0 mmol) was added to THF (30 mL) at room temperature and the mixture was stirred for overnight. Water (30 mL) was added and the mixture was extracted with EtOAc (30 mL). The organic layer was washed with brine (30 mL), dried over $Na_2SO_4$, filtered and concentrated under reduced pressure. The residue was purified by prep-TLC with PE/EA (4:1) to give the title compound (650 mg, 62%). LC-MS $(M+H)^+$=230.0.

Step 2: (3-phenoxypyridin-4-yl)methanol

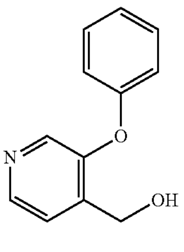 [SMILES: OCc1ccncc1Oc1ccccc1]

The title compound (355 mg, 83%) was prepared in a manner similar to that in Example 30 step 2 from methyl 3-phenoxyisonicotinate. LC-MS $(M+H)^+$=202.0.

Step 3: 5-bromo-3-((3-phenoxypyridin-4-yl) methoxy)pyrazin-2-amine

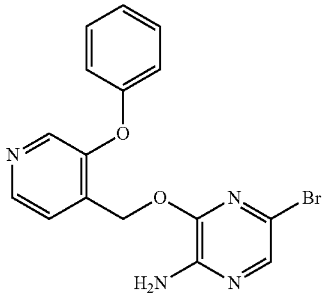 [SMILES: Nc1ncc(Br)nc1OCc1ccncc1Oc1ccccc1]

The title compound (90 mg, 44%) was prepared in a manner similar to that in Example 17 step 1 from 3,5-dibromopyrazin-2-amine and (3-phenoxypyridin-4-yl) methanol. LC-MS $(M+H)^+$=373.0 375.0.

Step 4: 5-(2,5-dimethyl-1,2,3,4-tetrahydroisoquinolin-7-yl)-3-((3-phenoxypyridin-4-yl)methoxy) pyrazin-2-amine

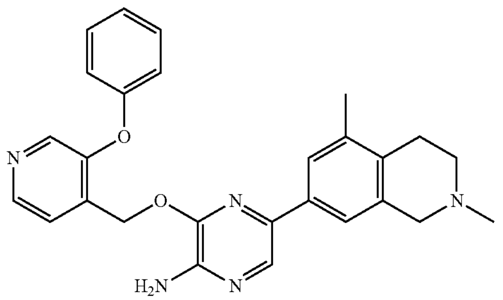 [SMILES: Cc1cc(-c2cnc(N)c(OCc3ccncc3Oc3ccccc3)n2)cc2c1CCN(C)C2]

Example 42 (40 mg, 37%) was prepared in a manner similar to that in Example 17 step 2 from 5-bromo-3-((3- phenoxypyridin-4-yl)methoxy)pyrazin-2-amine and ((2,5-dimethyl-1,2,3,4-tetrahydroisoquinolin-7-yl)boronic acid. $^1$H NMR (400 MHz, DMSO) δ 8.44 (d, J=4.8 Hz, 1H), 8.26 (s, 1H), 8.06 (s, 1H), 7.77 (d, J=4.6 Hz, 1H), 7.44-7.34 (m, 3H), 7.28 (s, 1H), 7.16 (t, J=7.3 Hz, 1H), 7.06 (d, J=7.8 Hz, 2H), 6.49 (s, 2H), 5.54 (s, 2H), 3.42 (s, 2H), 2.65 (d, J=4.4 Hz, 2H), 2.61 (d, J=4.7 Hz, 2H), 2.33 (s, 3H), 2.17 (s, 3H). LC-MS $(M+H)^+$=454.2.

Example 43: 3-((1H-pyrazol-3-yl)methoxy)-5-(2,5-dimethyl-1,2,3,4-tetrahydroisoquinolin-7-yl)pyrazin-2-amine

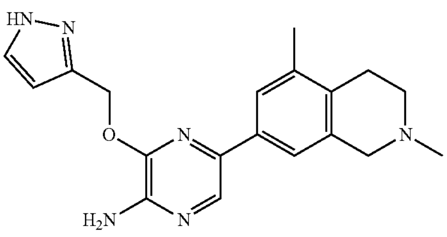 [SMILES: Cc1cc(-c2cnc(N)c(OCc3cc[nH]n3)n2)cc2c1CCN(C)C2]

Step 1: (1-((2-(trimethylsilyl)ethoxy)methyl)-1H-pyrazol-3-yl)methanol

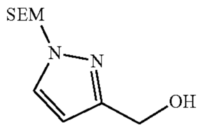 [SMILES: C[Si](C)(C)CCOCn1ccc(CO)n1]

To a solution of 1H-pyrazol-3-ylmethanol (475 mg, 4.84 mmol) in DMF (10 mL) was added NaH (60%, 291 mg, 7.26 mmol) at 0° C. The mixture was stirred for 10 min at 0° C. followed by addition of SEMCl (847 mg, 5.08 mmol) dropwise over 10 min. The mixture was stirred for additional 3 h at room temperature under nitrogen atmosphere. The reaction was then quenched by addition of iced water (30 mL). The mixture was extracted with ethyl acetate (50 mL×3). The combined organic phase was washed with brine, dried over $Na_2SO_4$ and concentrated under reduced pressure. The residue was purified by silica gel column chromatography, eluted with DCM/MeOH (1:0 to 4:1) to give the title compound (250 mg, 22%). LC-MS $(M+H)^+$=229.0.

Step 2: 5-bromo-3-((1-((2-(trimethylsilyl)ethoxy)methyl)-1H-pyrazol-3-yl)methoxy)pyrazin-2-amine

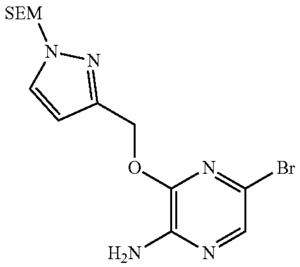 [SMILES: C[Si](C)(C)CCOCn1ccc(COc2nc(Br)cnc2N)n1]

The title compound (311 mg, 97%) was prepared in a manner similar to that in Example 1 step 7 from (1-((2-(trimethylsilyl)ethoxy)methyl)-1H-pyrazol-3-yl)methanol and 5-bromo-3-chloropyrazin-2-amine. LC-MS $(M+H)^+$=402.0.

Step 3: 5-(2,5-dimethyl-1,2,3,4-tetrahydroisoquinolin-7-yl)-3-((1-((2-(trimethylsilyl)ethoxy)methyl)-1H-pyrazol-3-yl)methoxy)pyrazin-2-amine

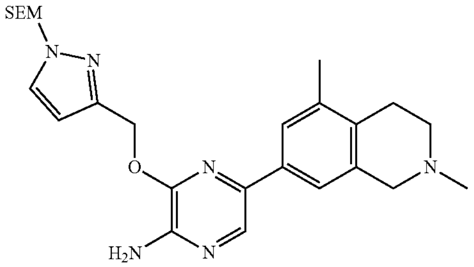 [SMILES: Cc1cc(-c2cnc(N)c(OCc3ccn(COCC[Si](C)(C)C)n3)n2)cc2c1CCN(C)C2]

The title compound (150 mg, 40%) was prepared in a manner similar to that in Example 1 step 8 from 5-bromo-3-((1-((2-(trimethylsilyl)ethoxy)methyl)-1H-pyrazol-3-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. LC-MS $(M+H)^+$=481.0.

Step 4: 3-((1H-pyrazol-3-yl)methoxy)-5-(2,5-dimethyl-1,2,3,4-tetrahydroisoquinolin-7-yl)pyrazin-2-amine

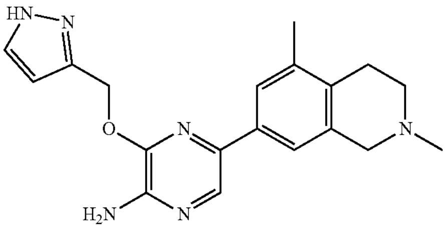 [SMILES: Cc1cc(-c2cnc(N)c(OCc3cc[nH]n3)n2)cc2c1CCN(C)C2]

At 0° C., to a solution of 5-(2,5-dimethyl-1,2,3,4-tetrahydroisoquinolin-7-yl)-3-((1-((2-(trimethylsilyl)ethoxy)methyl)-1H-pyrazol-3-yl)methoxy)pyrazin-2-amine (146 mg, 0.304 mmol) in DCM (6 mL) was added TFA (346 mg, 3.04 mmol). The mixture was stirred for 16 h at room temperature under nitrogen atmosphere. The solvent was evaporated under reduced pressure and the residue was purified by prep-HPLC to give Example 43 (23 mg, 21%). $^1$H NMR (400 MHz, DMSO-d6) δ 12.81 (s, 1H), 8.07 (s, 1H), 7.72-7.55 (m, 2H), 7.47 (s, 1H), 6.44-6.39 (m, 1H), 6.31 (s, 2H), 5.49 (s, 2H), 3.52 (s, 2H), 2.73-2.60 (m, 4H), 2.35 (s, 3H), 2.24 (s, 3H). LC-MS $(M+H)^+$=351.0.

Example 44: 3-((3H-imidazo[4,5-b]pyridin-7-yl)methoxy)-5-(2,5-dimethyl-1,2,3,4-tetrahydroisoquinolin-7-yl)pyrazin-2-amine and 3-((1H-imidazo[4,5-b]pyridin-7-yl)methoxy)-5-(2,5-dimethyl-1,2,3,4-tetrahydroisoquinolin-7-yl)pyrazin-2-amine

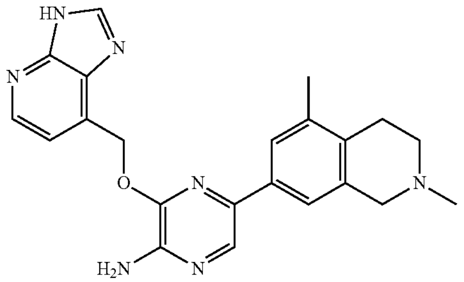

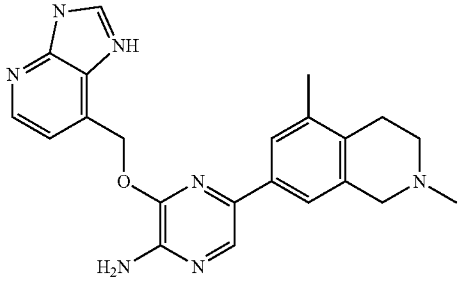

Step 1: 7-methyl-3H-imidazo[4,5-b]pyridine

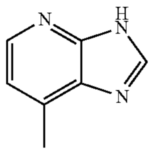

To a solution of 4-methylpyridine-2,3-diamine (2.0 g, 16.3 mmol) in $CH(OMe)_3$ (30 mL) was added pTSA (279 mg, 1.63 mmol). The mixture was stirred for 16 h at 100° C., cooled to room temperature and concentrated under vacuum. The residue was purified by silica gel column chromatography, eluted with DCM:MeOH (20:1) to give the title compound (1.7 g, 78%). LC-MS $(M+H)^+$=134.0.

Step 2: 3H-imidazo[4,5-b]pyridine-7-carboxylic acid

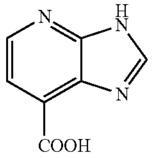 [SMILES: O=C(O)c1ccnc2[nH]cnc12]

To a mixture of 7-methyl-3H-imidazo[4,5-b]pyridine (1.7 g, 12.8 mmol) and $Na_2CO_3$ in water (60 mL) was added $KMnO_4$ (5.05 g, 31.9 mmol) at 100° C. The mixture was stirred for 1 h at 100° C. and cooled to 60° C. $MnO_2$ is filtered off, and the solid was washed with warm water (60° C., 20 mL×2). The filtrate was concentrated in vacuum to a volume of 50 mL, then acidified with 10% HCl solution until pH=3. The solid was collected by filtration, washed with water (10 mL×2) then dried under vacuum to give the title compound (750 mg, 36%). LC-MS $(M+H)^+$=164.0.

Step 3: methyl 3H-imidazo[4,5-b]pyridine-7-carboxylate

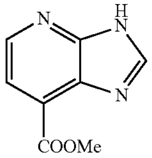 [SMILES: COC(=O)c1ccnc2[nH]cnc12]

To a solution of 3H-imidazo[4,5-b]pyridine-7-carboxylic acid (750 mg, 4.6 mmol) in MeOH (20 mL) was added $H_2SO_4$ (2 mL). The reaction mixture was stirred for 16 h at 60° C., cooled to room temperature then concentrated under vacuum until the volume was about 10 mL. The solution was cooled to 0° C. then neutralized with aqueous ammonia until pH=9. The solid was collected by filtration, washed with water (10 mL×2) then dried under vacuum to give the title compound (510 mg, 63%). LC-MS $(M+H)^+$=178.0.

Step 4: methyl 3-((2-(trimethylsilyl)ethoxy)methyl)-3H-imidazo[4,5-b]pyridine-7-carboxylate

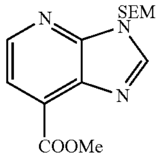

To a solution of methyl 3H-imidazo[4,5-b]pyridine-7-carboxylate (510 mg, 2.88 mmol) in DMF (20 mL) was added NaH (60%, 138 mg, 3.46 mmol) at 0° C. and the mixture was stirred for 15 min, followed by addition of SEMCl (622 mg, 3.74 mmol). The resulting solution was stirred for 3 h at room temperature. The reaction mixture was poured into water (100 mL) and extracted with EtOAc (100 mL). The organic layer was washed with brine (100 mL), dried over $Na_2SO_4$, filtered and concentrated under vacuum. The residue was purified by silica gel column chromatography, eluted with PE:EA (1:1) to give the title compound (376 mg, 43%). LC-MS $(M+H)^+$=308.0.

Step 5: (3-((2-(trimethylsilyl)ethoxy)methyl)-3H-imidazo[4,5-b]pyridin-7-yl)methanol

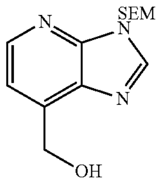

To a solution of methyl 3-((2-(trimethylsilyl)ethoxy) methyl)-3H-imidazo[4,5-b]pyridine-7-carboxylate (376 mg, 1.22 mmol) in THF (15 mL) was added $LiAlH_4$ (70 mg, 1.84 mmol) at 0° C. The mixture was stirred for 4 h at room temperature. The reaction mixture was poured into NaOH (2 M, 0.5 mL) and concentrated under vacuum. The residue was purified by silica gel column chromatography, eluted with DCM:MeOH (20:1) to give the title compound (76 mg, 22%). LC-MS $(M+H)^+$=280.0.

Step 6: 5-bromo-3-((3-((2-(trimethylsilyl)ethoxy) methyl)-3H-imidazo[4,5-b]pyridin-7-yl)methoxy) pyrazin-2-amine

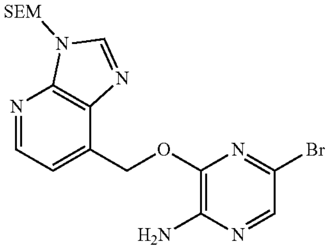 [SMILES: C[Si](C)(C)CCOCn1cnc2c(COc3nc(Br)cnc3N)ccnc21]

To a solution of (3-((2-(trimethylsilyl)ethoxy)methyl)-3H-imidazo[4,5-b]pyridin-7-yl)methanol (76 mg, 0.27 mmol) in THF (8 mL) was added NaH (60%, 22 mg, 0.54 mmol) at 0° C. and stirred for 15 min, followed by addition of 3,5-dibromopyrazin-2-amine (103 mg, 0.41 mmol). The mixture was stirred for 4 h at 50° C. The reaction mixture was poured into water (50 mL) and extracted with EtOAc (50 mL×3). The combined organic layer was washed with brine (50 mL), dried over $Na_2SO_4$, filtered and concentrated under vacuum. The residue was purified by silica gel column chromatography, eluted with DCM:MeOH (20:1) to give the title compound (85 mg, 70%). LC-MS $(M+H)^+$=450.9.

Step 7: 5-(2,5-dimethyl-1,2,3,4-tetrahydroisoquinolin-7-yl)-3-((3-((2-(trimethylsilyl)ethoxy)methyl)-3H-imidazo[4,5-b]pyridin-7-yl)methoxy)pyrazin-2-amine

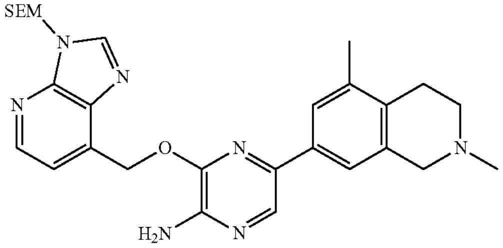 [SMILES: Cc1cc(-c2cnc(N)c(OCc3ccnc4c3ncn4COCC[Si](C)(C)C)n2)cc2c1CCN(C)C2]

To a solution of 5-bromo-3-((3-((2-(trimethylsilyl) ethoxy)methyl)-3H-imidazo[4,5-b]pyridin-7-yl)methoxy) pyrazin-2-amine (85 mg, 0.19 mmol) in 1,4-dioxane (10 mL) and water (2 mL) was added (2,5-dimethyl-1,2,3,4-tetrahydroisoquinolin-7-yl)boronic acid (39 mg, 0.19 mmol), $K_2CO_3$ (78 mg, 0.57 mmol) and Pd(dppf)$Cl_2$ (15 mg, 0.02 mmol). The resulting solution was stirred for 16 h at 90° C. under nitrogen. The reaction mixture was poured into water (50 mL) and extracted with EtOAc (50 mL×3). The combined organic layer was washed with brine (50 mL), dried over $Na_2SO_4$, filtered and concentrated under vacuum. The residue was purified by silica gel column chromatography, eluted with DCM:MeOH (10:1) to give the title compound (80 mg, 80%). LC-MS $(M+H)^+$=532.1.

Step 8: 3-((3H-imidazo[4,5-b]pyridin-7-yl) methoxy)-5-(2,5-dimethyl-1,2,3,4-tetrahydroisoquinolin-7-yl)pyrazin-2-amine and 3-((1H-imidazo[4,5-b]pyridin-7-yl)methoxy)-5-(2,5-dimethyl-1,2,3,4-tetrahydroisoquinolin-7-yl)pyrazin-2-amine

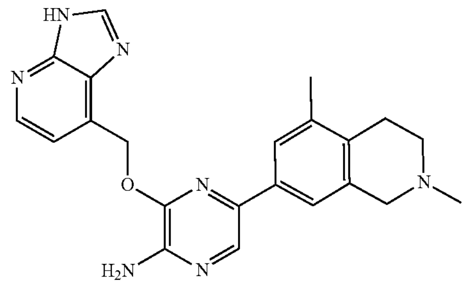

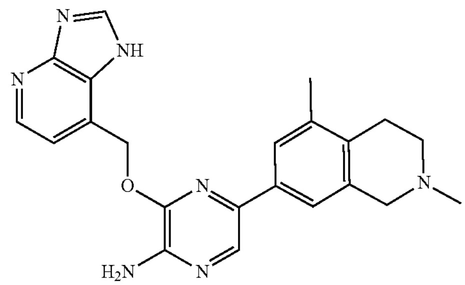

To a solution of 5-(2,5-dimethyl-1,2,3,4-tetrahydroisoquinolin-7-yl)-3-((3-((2-(trimethylsilyl)ethoxy)methyl)-3H-imidazo[4,5-b]pyridin-7-yl)methoxy)pyrazin-2-amine (80 mg, 0.15 mmol) in DCM (5 mL) was added TFA (2 mL). The resulting solution was stirred for 3 h at room temperature and concentrated under vacuum, then MeOH (3 mL) and ammonium hydroxide (25%, 3 mL) was added. The mixture was stirred for 3 h at room temperature and concentrated under vacuum. The residue was purified by prep-HPLC to give Example 44, as a mixture of two tautomers (4.3 mg, 7%). $^1H$ NMR (400 MHz, DMSO-d6) δ 13.33-12.92 (m, 1H), 8.64-8.43 (m, 1H), 8.43-8.26 (m, 1H), 8.13-7.98 (m, 1H), 7.50-7.38 (m, 2H), 7.38-7.20 (m, 1H), 6.59-6.41 (m, 2H), 6.03-5.72 (m, 2H), 3.53-3.38 (m, 2H), 2.72-2.61 (m, 4H), 2.38-2.31 (m, 3H), 2.22-2.12 (m, 3H). LC-MS $(M+H)^+$=402.4.

Example 45: 5-(2,5-dimethyl-1,2,3,4-tetrahydroisoquinolin-7-yl)-3-(1-ethyl-1H-pyrazol-4-yloxy)pyrazin-2-amine

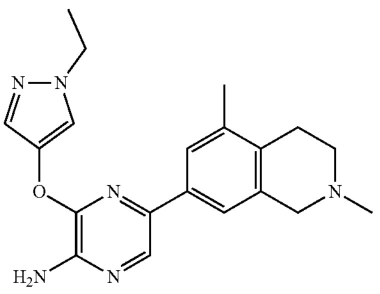 [SMILES: CCn1cc(Oc2nc(-c3cc(C)c4c(c3)CN(C)CC4)cnc2N)cn1]

Step 1: 5-bromo-3-(1-ethyl-1H-pyrazol-4-yloxy)pyrazin-2-amine

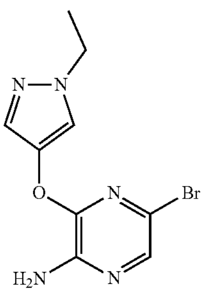 [SMILES: CCn1cc(Oc2nc(Br)cnc2N)cn1]

The title compound (190 mg, 31%) was prepared in a manner similar to that in Example 1 step 7 from 1-ethyl-1H-pyrazol-4-ol and 3,5-dibromopyrazin-2-amine. LC-MS $(M+H)^+$=284.0.

Step 2: 5-(2,5-dimethyl-1,2,3,4-tetrahydroisoquinolin-7-yl)-3-(1-ethyl-1H-pyrazol-4-yloxy)pyrazin-2-amine

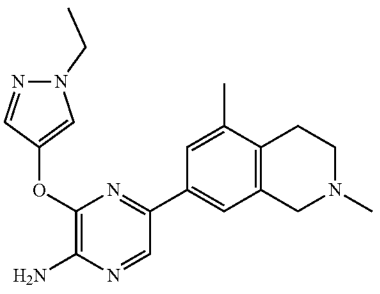 [SMILES: CCn1cc(Oc2nc(-c3cc(C)c4c(c3)CN(C)CC4)cnc2N)cn1]

Example 45 (28 mg, 14%) was prepared in a manner similar to that in Example 1 step 8 from 5-bromo-3-(1-ethyl-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.19 (s, 1H), 8.05 (s, 1H), 7.59 (s, 1H), 7.48 (s, 1H), 7.35 (s, 1H), 6.62 (s, 2H), 4.22-4.12 (m, 2H), 3.49 (s, 2H), 2.70-2.61 (m, 4H), 2.35 (s, 3H), 2.21 (s, 3H), 1.42 (t, J=7.3 Hz, 3H). LC-MS $(M+H)^+$=365.2.

Example 46: 1-(3-amino-6-(2,5-dimethyl-1,2,3,4-tetrahydroisoquinolin-7-yl)pyrazin-2-yl)-N,N-dimethyl-1H-pyrazole-4-carboxamide

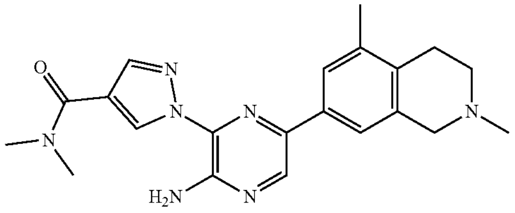

Step 1: ethyl 1-(3-amino-6-(2,5-dimethyl-1,2,3,4-tetrahydroisoquinolin-7-yl)pyrazin-2-yl)-1H-pyrazole-4-carboxylate

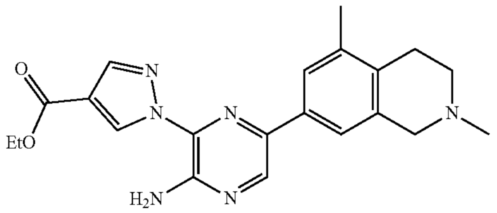 [SMILES: CCOC(=O)c1cnn(-c2nc(-c3cc(C)c4c(c3)CN(C)CC4)cnc2N)c1]

The title compound (176 mg, 52%) was prepared in a manner similar to that in Example 6 step 1 from 3-chloro-5-(2,5-dimethyl-1,2,3,4-tetrahydroisoquinolin-7-yl)pyrazin-2-amine and ethyl 1H-pyrazole-4-carboxylate. LC-MS $(M+H)^+$=393.0.

Step 2: 1-(3-amino-6-(2,5-dimethyl-1,2,3,4-tetrahydroisoquinolin-7-yl)pyrazin-2-yl)-1H-pyrazole-4-carboxylic acid

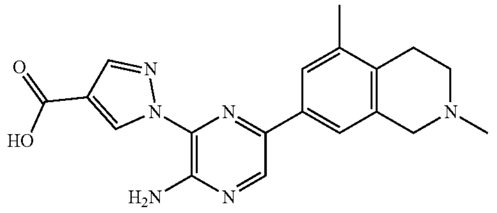 [SMILES: Cc1cc(-c2cnc(N)c(-n3cc(C(=O)O)cn3)n2)cc2c1CCN(C)C2]

To a solution of ethyl 1-(3-amino-6-(2,5-dimethyl-1,2,3,4-tetrahydroisoquinolin-7-yl)pyrazin-2-yl)-1H-pyrazole-4-carboxylate (200 mg, 0.510 mmol) in THF (10 mL) was added LiOH in $H_2O$ (1 M, 5 mL, 5.0 mmol) at room temperature. The mixture was stirred for 2 h at room temperature. The mixture was diluted with water (20 mL) and extracted with EtOAc (30 mL×3). The combined organic layer was washed with brine, dried over $Na_2SO_4$ and concentrated under reduced pressure. The residue was purified by silica gel column chromatography, eluted with hexane/EtOAc (1:0 to 3:2) to give the title compound (96 mg, 51%). LC-MS $(M+H)^+$=365.1.

Step 3: 1-(3-amino-6-(2,5-dimethyl-1,2,3,4-tetrahydroisoquinolin-7-yl)pyrazin-2-yl)-N,N-dimethyl-1H-pyrazole-4-carboxamide

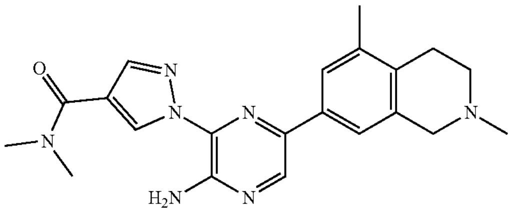

HATU (157 mg, 0.41 mmol) was added to a solution of 1-(3-amino-6-(2,5-dimethyl-1,2,3,4-tetrahydroisoquinolin-7-yl)pyrazin-2-yl)-1H-pyrazole-4-carboxylic acid (96 mg, 0.26 mmol) and DIPEA (102 mg, 0.79 mmol) in DMF (3 mL) 0° C. under $N_2$. To the above mixture was added dimethylamine hydrochloride (27 mg, 0.33 mmol) and the mixture was stirred for additional 16 h at room temperature. The mixture was diluted with water (20 mL) and extracted with EtOAc (30 mL×3). The combined organic layer was washed with brine, dried over $Na_2SO_4$ and concentrated under reduced pressure. The residue was purified by prep-HPLC to give Example 46 (9 mg, 9%). $^1$H NMR (400 MHz, DMSO-d6) δ 9.01 (s, 1H), 8.64 (s, 1H), 8.14 (s, 1H), 7.71 (s, 1H), 7.60 (s, 1H), 7.49-7.37 (m, 2H), 3.54 (s, 2H), 3.21 (s, 3H), 3.01 (s, 3H), 2.75-2.58 (m, 4H), 2.35 (s, 3H), 2.26 (s, 3H). LC-MS $(M+H)^+$=392.3.

Example 47A/47B: (R)-3-(1-(3-amino-6-(2,5-dimethyl-1,2,3,4-tetrahydroisoquinolin-7-yl)pyrazin-2-yloxy)ethyl)-2,4-dichloro-N-cyclopropylbenzamide & (S)-3-(1-(3-amino-6-(2,5-dimethyl-1,2,3,4-tetrahydroisoquinolin-7-yl)pyrazin-2-yloxy)ethyl)-2,4-dichloro-N-cyclopropylbenzamide

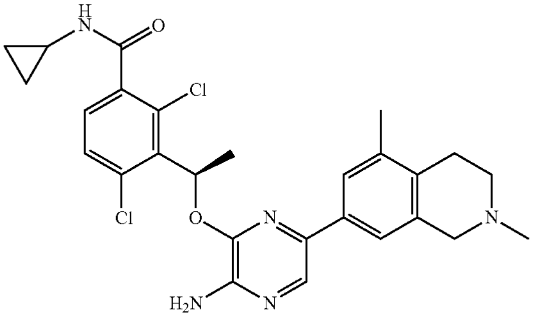

-continued

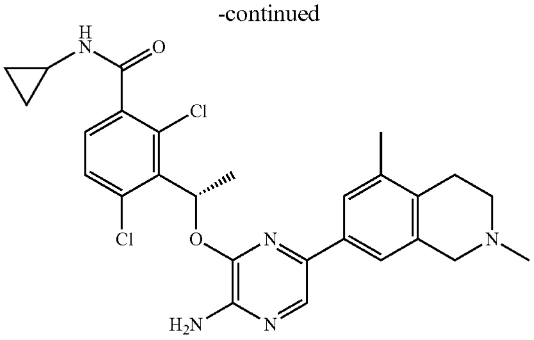

Step 1: tert-butyl 2,4-dichlorobenzoate

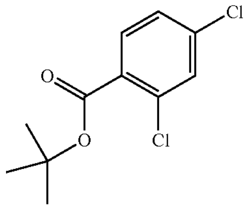

To a solution of 2,4-dichlorobenzoic acid (10.00 g, 52.35 mmol) in THF (100 mL) was added $Boc_2O$ (12.34 g, 56.54 mmol) and DMAP (640 mg, 5.235 mmol) at room temperature. The mixture was stirred for 12 h at 40° C. under nitrogen atmosphere then cooled to room temperature. Water (200 mL) was added and the mixture was extracted with EtOAc (300 mL×3). The combined organic layer was washed with brine, dried over $Na_2SO_4$ and concentrated under reduced pressure. The residue was purified by silica gel column chromatography, eluted with hexane/EtOAc (1:0 to 9:1) to give the title compound (10.0 g, 77%). LC-MS $(M+H)^+$=247.0.

Step 2: tert-butyl 2,4-dichloro-3-formylbenzoate

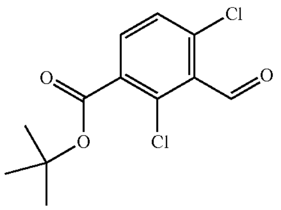 [SMILES: CC(C)(C)OC(=O)c1ccc(Cl)c(C=O)c1Cl]

At −78° C., to a solution of tert-butyl 2,4-dichlorobenzoate (10.00 g, 40.5 mmol) in THF (100 mL) was added LDA in THF (1.6 M, 30 mL, 48 mmol). The mixture was stirred for 90 min at −78° C. under nitrogen atmosphere followed by addition of DMF (8.87 g, 121 mmol). The mixture was stirred for 110 min at −78° C. under nitrogen atmosphere. The reaction mixture was poured into HCl (6 M, 50 mL) and extracted with EtOAc (100 mL×2). The combined organic layer was dried over $MgSO_4$, filtered and concentrated under reduced pressure. The residue was purified by silica gel column chromatography, eluted with hexane/EtOAc (1:0 to 9:1) to give the title compound (10.0 g, 89%). $^1$H NMR (300

MHz, DMSO-d6) δ 10.34 (s, 1H), 7.86 (d, J=8.4 Hz, 1H), 7.69 (d, J=8.4 Hz, 1H), 1.56 (s, 9H).

Step 3: tert-butyl 2,4-dichloro-3-(1-hydroxyethyl)benzoate

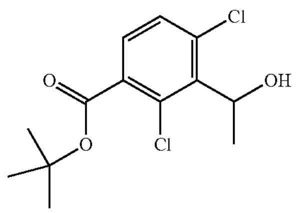 [SMILES: CC(O)c1c(Cl)ccc(C(=O)OC(C)(C)C)c1Cl]

At −78° C., to a solution of tert-butyl 2,4-dichloro-3-formylbenzoate (10.0 g, 36.3 mmol) in THF (150 mL) was added MeMgBr in THF (1 M, 43 mL, 43.0 mmol) under nitrogen atmosphere. The mixture was stirred for 1 h at room temperature. Then aqueous HCl (1 M, 200 mL) was carefully added. The mixture was extracted with EtOAc (300 mL×3). The combined organic layer was washed with brine dried over $Na_2SO_4$ and concentrated under reduced pressure. The residue was purified by silica gel column chromatography, eluted with hexane/EtOAc (1:0 to 4:1) to give the title compound (9.30 g, 88%). LC-MS $(M+H)^+$=291.0.

Step 4: tert-butyl 3-(1-(3-amino-6-bromopyrazin-2-yloxy)ethyl)-2,4-dichlorobenzoate

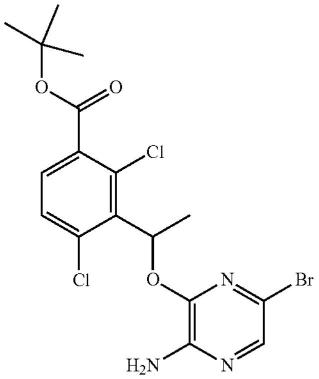 [SMILES: CC(Oc1nc(Br)cnc1N)c1c(Cl)ccc(C(=O)OC(C)(C)C)c1Cl]

The title compound (1.42 g, 18%) was prepared in a manner similar to that in Example 1 step 7 from tert-butyl 2,4-dichloro-3-(1-hydroxyethyl)benzoate and 5-bromo-3-chloropyrazin-2-amine. LC-MS $(M+H)^+$=462.0.

Step 5: tert-butyl 3-(1-(3-amino-6-(2,5-dimethyl-1,2,3,4-tetrahydroisoquinolin-7-yl)pyrazin-2-yloxy)ethyl)-2,4-dichlorobenzoate

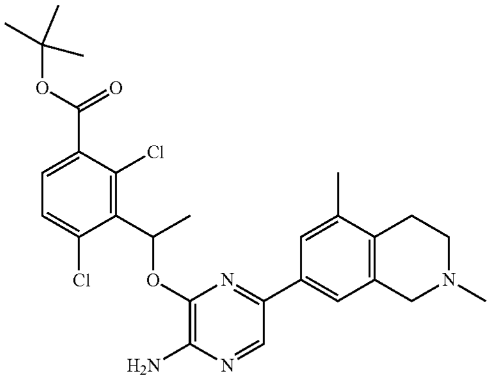 [SMILES: Cc1cc(-c2cnc(N)c(OC(C)c3c(Cl)ccc(C(=O)OC(C)(C)C)c3Cl)n2)cc2c1CCN(C)C2]

The title compound (1.30 g, 74%) was prepared in a manner similar to that in Example 1 step 8 from tert-butyl 3-(1-(3-amino-6-bromopyrazin-2-yloxy)ethyl)-2,4-dichlorobenzoate and 2,5-dimethyl-7-(4,4,5,5-tetramethyl-1,3,2-dioxaborolan-2-yl)-1,2,3,4-tetrahydroisoquinoline. LC-MS $(M+H)^+$=543.2.

Step 6: 3-(1-(3-amino-6-(2,5-dimethyl-1,2,3,4-tetrahydroisoquinolin-7-yl)pyrazin-2-yloxy)ethyl)-2,4-dichlorobenzoic acid

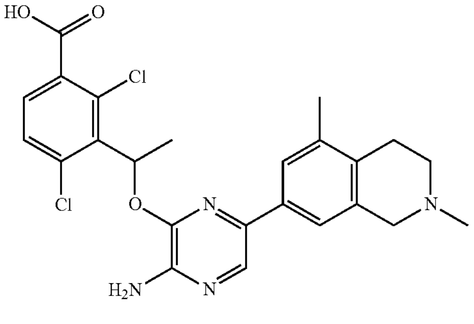 [SMILES: Cc1cc(-c2cnc(N)c(OC(C)c3c(Cl)ccc(C(=O)O)c3Cl)n2)cc2c1CCN(C)C2]

The title compound (990 mg, 92%) was prepared in a manner similar to that in Example 43 step 4 from tert-butyl 3-(1-(3-amino-6-(2,5-dimethyl-1,2,3,4-tetrahydroisoquinolin-7-yl)pyrazin-2-yloxy)ethyl)-2,4-dichlorobenzoate. LC-MS $(M+H)^+$=487.1.

Step 7: (R)-3-(1-(3-amino-6-(2,5-dimethyl-1,2,3,4-tetrahydroisoquinolin-7-yl)pyrazin-2-yloxy)ethyl)-2,4-dichloro-N-cyclopropylbenzamide & (S)-3-(1-(3-amino-6-(2,5-dimethyl-1,2,3,4-tetrahydroisoquinolin-7-yl)pyrazin-2-yloxy)ethyl)-2,4-dichloro-N-cyclopropylbenzamide

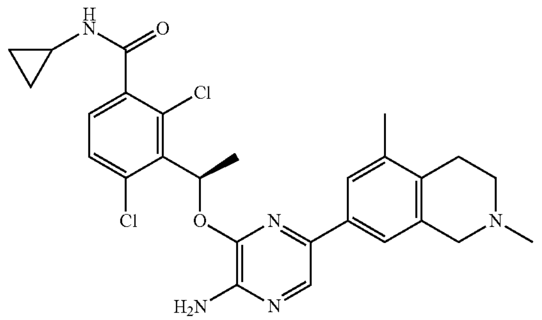

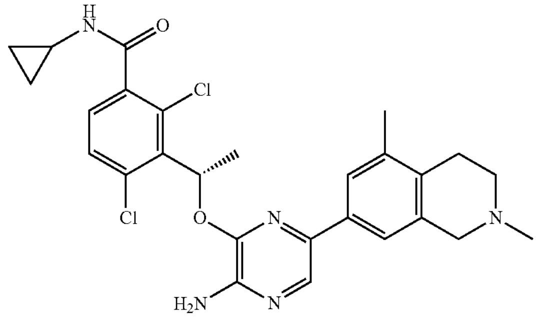

Example 47A/47B was prepared in a manner similar to that in Example 46 step 3 from 3-(1-(3-amino-6-(2,5-dimethyl-1,2,3,4-tetrahydroisoquinolin-7-yl)pyrazin-2-yloxy)ethyl)-2,4-dichlorobenzoic acid and cyclopropylamine. The enantiomers were separated on chiral-HPLC to give (R)-3-(1-(3-amino-6-(2,5-dimethyl-1,2,3,4-tetrahydroisoquinolin-7-yl)pyrazin-2-yloxy)ethyl)-2,4-dichloro-N-cyclopropylbenzamide (Example 47A) and (S)-3-(1-(3-amino-6-(2,5-dimethyl-1,2,3,4-tetrahydroisoquinolin-7-yl)pyrazin-2-yloxy)ethyl)-2,4-dichloro-N-cyclopropylbenzamide (Example 47B).

Analytical chiral HPLC condition: CHIRALPAK IG-3, 0.46×5 cm, 3.0 m. Mobile phase: 0.2% isopropylamine in (Hexane:DCM=3:1):EtOH, 1 mL/min in 6 min.

Example 47A: (36 mg, 36%) $^1$H NMR (400 MHz, DMSO-d6) δ 8.50 (d, J=4.4 Hz, 1H), 8.01 (s, 1H), 7.55-7.42 (m, 2H), 7.31 (s, 1H), 7.26 (d, J=8.2 Hz, 1H), 6.72-6.66 (m, 1H), 6.32 (s, 2H), 3.49 (s, 2H), 2.83-2.74 (m, 1H), 2.69-2.61 (m, 4H), 2.37 (s, 3H), 2.19 (s, 3H), 1.78 (d, J=6.9 Hz, 3H), 0.72-0.63 (m, 2H), 0.54-0.45 (m, 2H). LC-MS $(M+H)^+$=526.2. Chiral HPLC: tR=3.99 min.

Example 47B: (23 mg, 23%)$^1$H NMR (400 MHz, DMSO-d6) δ 8.50 (d, J=4.4 Hz, 1H), 8.01 (s, 1H), 7.55-7.42 (m, 2H), 7.31 (s, 1H), 7.26 (d, J=8.2 Hz, 1H), 6.72-6.66 (m, 1H), 6.32 (s, 2H), 3.49 (s, 2H), 2.83-2.74 (m, 1H), 2.69-2.61 (m, 4H), 2.37 (s, 3H), 2.19 (s, 3H), 1.78 (d, J=6.9 Hz, 3H), 0.72-0.63 (m, 2H), 0.54-0.45 (m, 2H). LC-MS $(M+H)^+$=526.2. Chiral HPLC: tR=4.86 min.

Example 116: 5-(2,5-dimethyl-1,2,3,4-tetrahydroisoquinolin-7-yl)-3-((1-methyl-1H-pyrazol-4-yl)oxy)pyrazin-2-amine

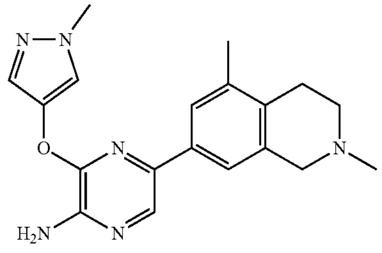 [SMILES: Cc1cc(-c2cnc(N)c(Oc3cnn(C)c3)n2)cc2c1CCN(C)C2]

Step 1: 1-methyl-4-(4,4,5,5-tetramethyl-1,3,2-dioxaborolan-2-yl)-1H-pyrazole

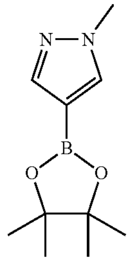

To a solution of 4-(4,4,5,5-tetramethyl-1,3,2-dioxaborolan-2-yl)-1H-pyrazole (1.0 g, 5.15 mmol) and MeI (1.1 g, 7.73 mmol) in THF (50 mL) was added NaH (60%, 412 mg, 10.3 mmol) at 0° C. The mixture was stirred at 60° C. under $N_2$ for 8 h. The mixture was cooled to room temperature, quenched with water (100 mL) and extracted with EtOAc (100 mL×3). The combined organic layer was dried over $Na_2SO_4$, filtered and concentrated to give the title compound (680 mg, 63%). LC-MS $(M+H)^+$=209.2.

Step 2: 1-methyl-1H-pyrazol-4-ol

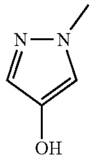

To a solution of 1-methyl-4-(4,4,5,5-tetramethyl-1,3,2-dioxaborolan-2-yl)-1H-pyrazole (680 mg, 3.27 mmol) and aqueous NaOH (3 M, 2.2 mL, 6.54 mmol) in THF (20 mL) was added $H_2O_2$ (741 mg, 6.54 mmol). The mixture was stirred at room temperature for 3 hours. pH of the mixture was adjusted 7 with aqueous HCl (3 M), and the mixture was extracted with EtOAc (50 mL×3). The combined organic layer was dried over $Na_2SO_4$, filtered and concentrated to give the title compound (330 mg, 99%).

Step 3: 5-bromo-3-((1-methyl-1H-pyrazol-4-yl)oxy)pyrazin-2-amine

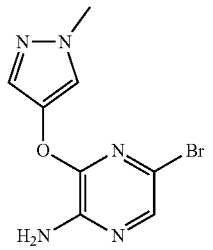

To a solution of 1-methyl-1H-pyrazol-4-ol (330 mg, 3.27 mmol) and 3,5-dibromopyrazin-2-amine (852 mg, 3.37 mmol) in DMSO (20 mL) was added $K_2CO_3$ (1.4 g, 10.1 mmol). The mixture was stirred at 75° C. under $N_2$ for 6 h then cooled to room temperature. Water (40 mL) was added and the mixture was extracted with EtOAc (50 mL×3). The combined organic layer was dried over $Na_2SO_4$, filtered and concentrated under reduced pressure. The residue was purified by silica gel chromatography, eluted with MeOH/DCM (1:100) to give the title compound (420 mg, 48%). LC-MS $(M+H)^+$=270.1, 272.1.

Step 4: 5-(2,5-dimethyl-1,2,3,4-tetrahydroisoquinolin-7-yl)-3-((1-methyl-1H-pyrazol-4-yl)oxy)pyrazin-2-amine

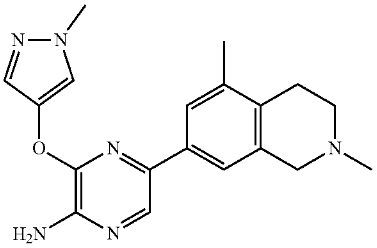 [SMILES: Cc1cc(-c2cnc(N)c(Oc3cnn(C)c3)n2)cc2c1CCN(C)C2]

To a solution of 5-bromo-3-((1-methyl-1H-pyrazol-4-yl)oxy)pyrazin-2-amine (420 mg, 1.56 mmol), (2,5-dimethyl-1,2,3,4-tetrahydroisoquinolin-7-yl)boronic acid (336 mg, 1.64 mmol) and Pd(dppf)$Cl_2$·DCM (64 mg, 0.078 mmol) in 1,4-dioxane (15 mL) and water (15 mL) was added $K_2CO_3$ (646 mg, 4.68 mmol). The mixture was stirred at 90° C. under $N_2$ for 12 h then cooled to room temperature. Water (20 mL) was added and the mixture was successively extracted with EtOAc (50 mL×3). The combined organic layer was dried over $Na_2SO_4$, filtered and concentrated under reduced pressure. The residue was purified by silica gel chromatography, eluted with MeOH/DCM (1:20) then prep-TLC, developed with MeOH/DCM (1:10) to give Example 116 (246 mg, 45%). $^1$H NMR (400 MHz, DMSO-d6) δ 8.17 (s, 1H), 7.98 (s, 1H), 7.59 (s, 1H), 7.47 (s, 1H), 7.33 (s, 1H), 6.65 (s, 2H), 3.87 (s, 3H), 3.48 (s, 2H), 2.71-2.57 (m, 4H), 2.34 (s, 3H), 2.21 (s, 3H). LC-MS $(M+H)^+$=351.2.

Example 141: 5-(2,5-dimethyl-1,2,3,4-tetrahydroisoquinolin-7-yl)-3-(thieno[2,3-c]pyridin-3-yloxy)pyrazin-2-amine

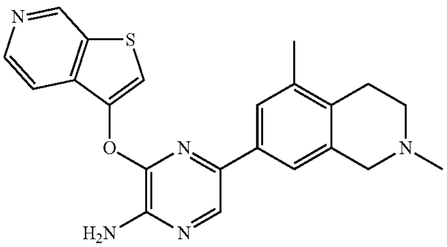 [SMILES: Cc1cc(-c2cnc(N)c(Oc3csc4cnccc34)n2)cc2c1CCN(C)C2]

Step 1: 3-(4,4,5,5-tetramethyl-1,3,2-dioxaborolan-2-yl)thieno[2,3-c]pyridine

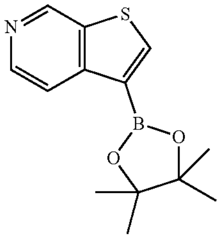 [SMILES: CC1(C)OB(c2csc3cnccc23)OC1(C)C]

The title compound (300 mg, 52%) was prepared in a manner similar to that in Example 1 step 6 from 3-bromothieno[2,3-c]pyridine. LC-MS (M-pin)$^+$=180.1.

Step 2: thieno[2,3-c]pyridin-3-ol

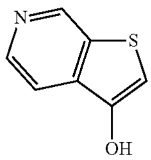

The title compound (230 mg, 89%) was prepared in a manner similar to that in Example 116 step 2 from 3-(4,4,5,5-tetramethyl-1,3,2-dioxaborolan-2-yl)thieno[2,3-c]pyridine. LC-MS $(M+H)^+$=152.1.

Step 3: 5-bromo-3-(thieno[2,3-c]pyridin-3-yloxy)pyrazin-2-amine

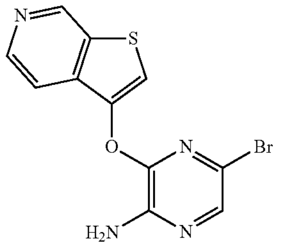 [SMILES: Nc1ncc(Br)nc1Oc1csc2cnccc12]

The title compound (250 mg, 58%) was prepared in a manner similar to that in Example 116 step 3 from thieno [2,3-c]pyridin-3-ol and 3,5-dibromopyrazin-2-amine. LC-MS $(M+H)^+$=323.0.

Step 4: 5-(2,5-dimethyl-1,2,3,4-tetrahydroisoquinolin-7-yl)-3-(thieno[2,3-c]pyridin-3-yloxy)pyrazin-2-amine Example 141 (45 mg, 36%) was prepared in a manner similar to that in Example 1 step 8 from 5-bromo-3-(thieno [2,3-c]pyridin-3-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 9.30 (s, 1H), 8.51 (d, J=5.5 Hz, 1H), 8.28 (s, 1H), 8.21 (s, 1H), 7.91 (d, J=5.5 Hz, 1H), 7.32 (s, 1H), 7.21 (s, 1H), 6.87 (s, 2H), 3.41 (s, 2H), 2.66-2.55 (m, 4H), 2.32 (s, 3H), 2.13 (s, 3H). LC-MS $(M+H)^+$=404.3.

Example 149: 3-((3-cyclopropoxypyridin-4-yl)methoxy)-5-(2,5-dimethyl-1,2,3,4-tetrahydroisoquinolin-7-yl)pyrazin-2-amine

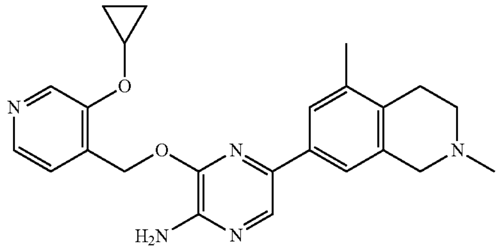 [SMILES: Cc1cc(-c2cnc(N)c(OCc3ccncc3OC3CC3)n2)cc2c1CCN(C)C2]

Step 1: methyl 3-cyclopropoxyisonicotinate

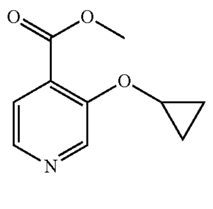

NaH (60%, 503 mg, 12.6 mmol) was added to a solution of methyl 3-fluoroisonicotinate (1.0 g, 6.45 mmol) and cyclopropanol (749 mg, 12.9 mmol) in dry THF (30 mL) at 0° C. and the mixture was stirred at room temperature overnight. Brine (20 mL) was added and the mixture was extracted with ethyl acetate (20 mL). The organic layer was separated, dried over $Na_2SO_4$, filtered and concentrated. The residue was purified by silica gel column chromatography to give the title compound (850 mg, 68%). LC-MS $(M+H)^+$=194.0.

Step 2: (3-cyclopropoxypyridin-4-yl)methanol

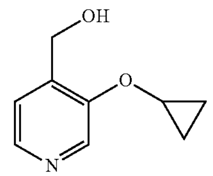 [SMILES: OCc1ccncc1OC1CC1]

The title compound (850 mg, 86%) was prepared in a manner similar to that in Example 30 step 2 from methyl 3-cyclopropoxyisonicotinate. LC-MS $(M+H)^+$=166.0.

Step 3: 5-bromo-3-((3-cyclopropoxypyridin-4-yl)methoxy)pyrazin-2-amine

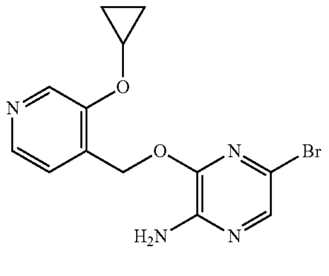 [SMILES: Nc1ncc(Br)nc1OCc1ccncc1OC1CC1]

The title compound (560 mg, 70%) was prepared in a manner similar to that in Example 17 step 1 from 3,5-dibromopyrazin-2-amine and (3-cyclopropoxypyridin-4-yl)methanol. LC-MS $(M+H)^+$=337.0.

Step 4: 3-((3-cyclopropoxypyridin-4-yl)methoxy)-5-(2,5-dimethyl-1,2,3,4-tetrahydroisoquinolin-7-yl)pyrazin-2-amine

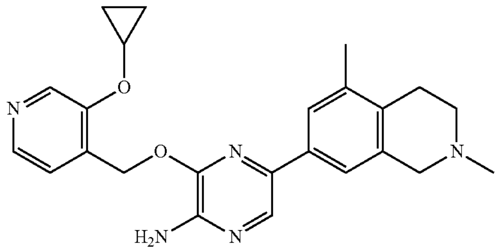 [SMILES: Cc1cc(-c2cnc(N)c(OCc3ccncc3OC3CC3)n2)cc2c1CCN(C)C2]

Example 149 (135 mg, 20%) was prepared in a manner similar to that in Example 17 step 2 from (2,5-dimethyl-1,2,3,4-tetrahydroisoquinolin-7-yl)boronic acid and 5-bromo-3-((3-cyclopropoxypyridin-4-yl)methoxy)pyrazin-2-amine. $^1$H NMR (400 MHz, DMSO-d6) δ 8.65 (s, 1H), 8.24 (d, J=4.6 Hz, 1H), 8.06 (s, 1H), 7.54 (d, J=4.3 Hz, 1H), 7.44 (s, 1H), 7.32 (s, 1H), 6.51 (s, 2H), 5.46 (s, 2H), 4.16-4.08 (s, 1H), 3.47 (s, 2H), 2.70-2.57 (m, 4H), 2.33 (s, 3H), 2.20 (s, 3H), 0.90-0.72 (m, 4H). LC-MS $(M+H)^+$=418.0.

Example 150: 5-(2,5-dimethyl-1,2,3,4-tetrahydroiso-quinolin-7-yl)-3-((3-((tetrahydro-2H-pyran-4-yl)oxy)pyridin-4-yl)methoxy)pyrazin-2-amine

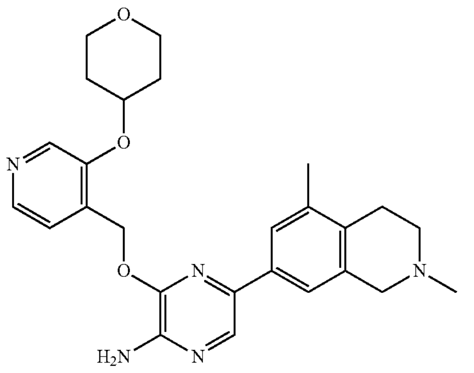 [SMILES: Cc1cc(-c2cnc(N)c(OCc3ccncc3OC3CCOCC3)n2)cc2c1CCN(C)C2]

Step 1: methyl 3-((tetrahydro-2H-pyran-4-yl)oxy)isonicotinate

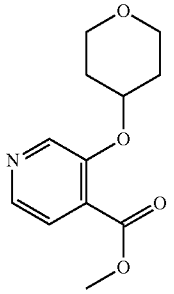 [SMILES: COC(=O)c1ccncc1OC1CCOCC1]

The title compound (192 mg, 24%) was prepared in a manner similar to that in Example 30 step 1 from methyl 3-hydroxyisonicotinate and 4-bromotetrahydro-2H-pyran. LC-MS $(M+H)^+$=238.2.

Step 2: (3-((tetrahydro-2H-pyran-4-yl)oxy)pyridin-4-yl)methanol

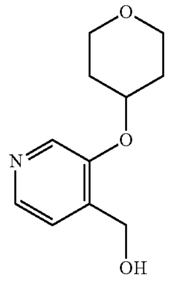 [SMILES: OCc1ccncc1OC1CCOCC1]

The title compound (178 mg, quantitative) was prepared in a manner similar to that in Example 30 step 2 from methyl 3-((tetrahydro-2H-pyran-4-yl)oxy)isonicotinate. LC-MS $(M+H)^+$=210.1.

Step 3: 5-bromo-3-((3-((tetrahydro-2H-pyran-4-yl)oxy)pyridin-4-yl)methoxy)pyrazin-2-amine

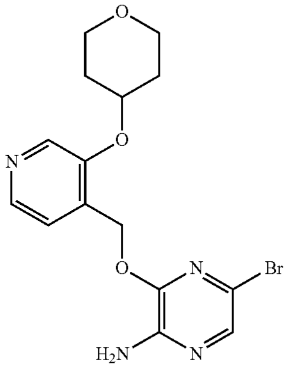 [SMILES: Nc1ncc(Br)nc1OCc1ccncc1OC1CCOCC1]

The title compound (114 mg, 35%) was prepared in a manner similar to that in Example 17 step 1 from 3,5-dibromopyrazin-2-amine and (3-((tetrahydro-2H-pyran-4-yl)oxy)pyridin-4-yl)methanol. LC-MS $(M+H)^+$=381.1, 383.1.

Step 4: 5-(2,5-dimethyl-1,2,3,4-tetrahydroisoquinolin-7-yl)-3-((3-((tetrahydro-2H-pyran-4-yl)oxy)pyridin-4-yl)methoxy)pyrazin-2-amine

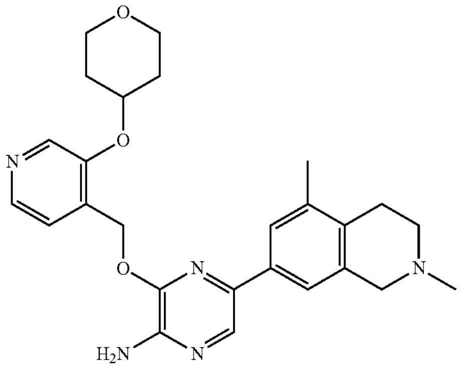 [SMILES: Cc1cc(-c2cnc(N)c(OCc3ccncc3OC3CCOCC3)n2)cc2c1CCN(C)C2]

Example 150 (18 mg, 13%) was prepared in a manner similar to that in Example 17 step 2 from 5-bromo-3-((3-((tetrahydro-2H-pyran-4-yl)oxy)pyridin-4-yl)methoxy)pyrazin-2-amine and ((2,5-dimethyl-1,2,3,4-tetrahydroisoquinolin-7-yl)boronic acid. $^1H$ NMR (400 MHz, DMSO-d6) δ 8.47 (s, 1H), 8.21 (d, J=4.6 Hz, 1H), 8.09 (s, 1H), 7.62 (d, J=4.4 Hz, 1H), 7.48 (s, 1H), 7.36 (s, 1H), 6.54 (s, 2H), 5.58 (s, 2H), 4.91-4.78 (m, 1H), 3.91-3.78 (m, 2H), 3.60-3.49 (m, 2H), 3.46 (s, 2H), 2.72-2.56 (m, 4H), 2.33 (s, 3H), 2.19 (s, 3H), 2.08-1.97 (m, 2H), 1.76-1.62 (m, 2H). LC-MS $(M+H)^+$=462.5.

Example 152: 3-((2-amino-3-chloropyridin-4-yl)methoxy)-5-(2,5-dimethyl-1,2,3,4-tetrahydroisoquinolin-7-yl)pyrazin-2-amine

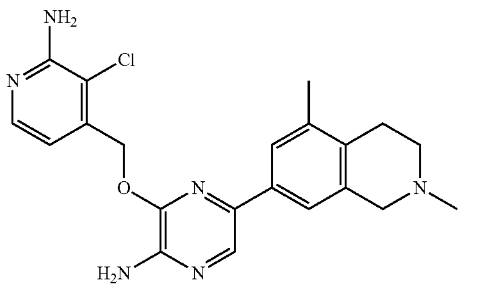 [SMILES: Cc1cc(-c2cnc(N)c(OCc3ccnc(N)c3Cl)n2)cc2c1CCN(C)C2]

Step 1: ethyl 2,3-dichloroisonicotinate

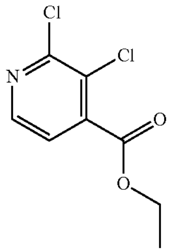

2,3-dichloroisonicotinic acid (2.0 g, 10.4 mmol) and $H_2SO_4$ (1.0 mL) was carefully added to EtOH (20 mL) and the mixture was stirred at 78° C. overnight. The solvent was concentrated under reduced pressure. The residue was basified to pH=8-9 with $NaHCO_3$ and extracted with EtOAc (30 mL×3). The combined organic layer was washed with brine (30 mL), dried over $Na_2SO_4$, filtered and concentrated under reduced pressure to give the title compound (2.2 g, 96%). LC-MS $(M+H)^+$=220.0.

Step 2: ethyl 2-amino-3-chloroisonicotinate

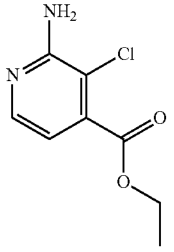

The title compound (0.80 g, 40%) was prepared in a manner similar to that in Example 29 step 1 from ethyl 2,3-dichloroisonicotinate. LC-MS $(M+H)^+$=201.0.

Step 3: (2-amino-3-chloropyridin-4-yl)methanol

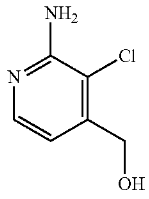

The title compound (590 mg, 93%) was prepared in a manner similar to that in Example 29 step 2 from ethyl 2-amino-3-chloroisonicotinate. LC-MS $(M+H)^+$=159.0.

Step 4: 3-((2-amino-3-chloropyridin-4-yl)methoxy)-5-bromopyrazin-2-amine

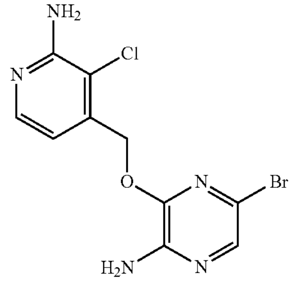 [SMILES: Nc1ncc(Br)nc1OCc1ccnc(N)c1Cl]

The title compound (400 mg, 63%) was prepared in a manner similar to that in Example 29 step 3 from (2-amino-3-chloropyridin-4-yl)methanol and 3,5-dibromopyrazin-2-amine. LC-MS $(M+H)^+$=330.0, 332.0.

Step 5: 3-((2-amino-3-chloropyridin-4-yl)methoxy)-5-(2,5-dimethyl-1,2,3,4-tetrahydroisoquinolin-7-yl)pyrazin-2-amine

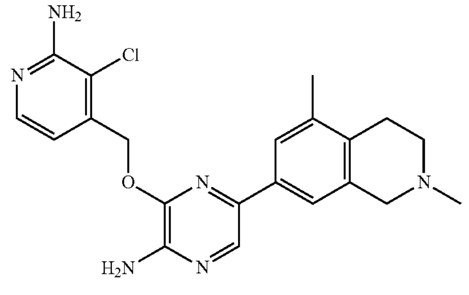

Example 152 (80 mg, 40%) was prepared in a manner similar to that in Example 17 step 2 from 3-((2-amino-3-chloropyridin-4-yl)methoxy)-5-bromopyrazin-2-amine and ((2,5-dimethyl-1,2,3,4-tetrahydroisoquinolin-7-yl)boronic acid. $^1H$ NMR (400 MHz, DMSO-d6) δ 8.07 (s, 1H), 7.87 (d, J=5.0 Hz, 1H), 7.46 (s, 1H), 7.34 (s, 1H), 6.79 (d, J=5.0 Hz, 1H), 6.50 (s, 2H), 6.33 (s, 2H), 5.51 (s, 2H), 3.47 (s, 2H), 2.70-2.58 (m, 4H), 2.34 (s, 3H), 2.20 (s, 3H). LC-MS $(M+H)^+$=411.4.

Example 161: 3-((2-amino-5-cyclopropoxypyridin-4-yl)methoxy)-5-(2,5-dimethyl-1,2,3,4-tetrahydroisoquinolin-7-yl)pyrazin-2-amine

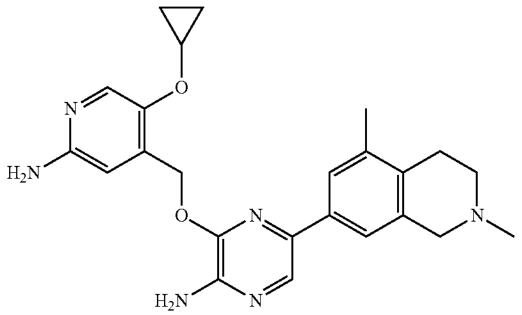 [SMILES: Cc1cc(-c2cnc(N)c(OCc3cc(N)ncc3OC3CC3)n2)cc2c1CCN(C)C2]

Step 1: 2-bromo-5-cyclopropoxyisonicotinic acid

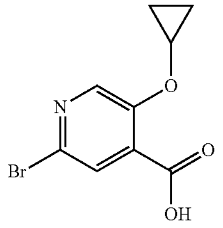 [SMILES: O=C(O)c1cc(Br)ncc1OC1CC1]

The title compound (963 mg, 41%) was prepared in a manner similar to that in Example 149 step 1 from 2-bromo-5-fluoroisonicotinic acid and cyclopropanol. LC-MS $(M+H)^+$=258.0.

Step 2: methyl 2-bromo-5-cyclopropoxyisonicotinate

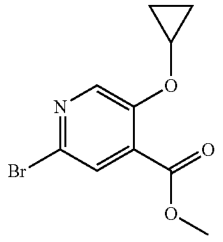

The title compound (816 mg, 77%) was prepared in a manner similar to that in Example 44 step 3 from 2-bromo-5-cyclopropoxyisonicotinic acid. LC-MS $(M+H)^+$=272.0.

Step 3: methyl 2-(tert-butoxycarbonylamino)-5-cyclopropoxyisonicotinate

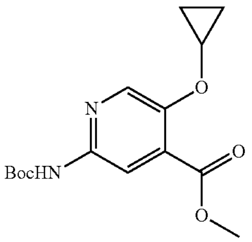 [SMILES: COC(=O)c1cc(NC(=O)OC(C)(C)C)ncc1OC1CC1]

To a stirred solution of methyl 2-bromo-5-cyclopropoxy-pyridine-4-carboxylate (800 mg, 2.94 mmol) and $BocNH_2$ (413 mg, 3.53 mmol) in dioxane (20 mL) was added X-Phos (280 mg, 0.59 mmol), $Cs_2CO_3$ (1.92 g, 5.88 mmol) and $Pd_2(dba)_3$ (269 mg, 0.294 mmol). The mixture was stirred for 2 h at 100° C. under nitrogen. The mixture was cooled to room temperature then diluted with water (30 mL). The mixture was successively extracted with EtOAc (10 mL×3). The combined organic layer was washed with water (30 mL) and dried over anhydrous $Na_2SO_4$. After filtration, the filtrate was concentrated under reduced pressure. The residue was purified by silica gel column chromatography, eluted with EtOAc/PE (1:3) to give the title compound (369 mg, 41%). LC-MS $(M+H)^+$=309.2.

Step 4: tert-butyl 5-cyclopropoxy-4-(hydroxymethyl)pyridin-2-ylcarbamate

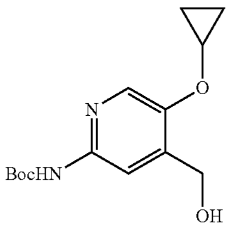 [SMILES: CC(C)(C)OC(=O)Nc1cc(CO)c(OC2CC2)cn1]

At 0° C., to a solution of methyl 2-(tert-butoxycarbonylamino)-5-cyclopropoxyisonicotinate (350 mg, 1.14 mmol) in THF (10 mL) was added $LiBH_4$ (124 mg, 5.68 mmol) and MeOH (2 mL). The mixture was stirred for 2 h at 70° C. under nitrogen. The mixture was cooled to room temperature then quenched with water (30 mL). The mixture was extracted with ethyl acetate (30 mL×3). The combined organic layer was washed with brine (10 mL), dried over $Na_2SO_4$ and filtered. The filtrate was concentrated under reduced pressure and the residue was purified by silica gel flash chromatography, eluted with EtOAc/PE (0% to 35% gradient) to give the title compound (287 mg, 90%). LC-MS $(M+H)^+$=281.2.

Step 5: tert-butyl 4-((3-amino-6-bromopyrazin-2-yloxy)methyl)-5-cyclopropoxypyridin-2-ylcarbamate

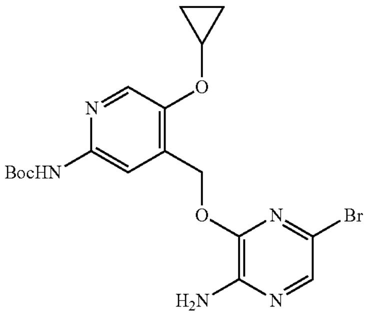 [SMILES: CC(C)(C)OC(=O)Nc1cc(COc2nc(Br)cnc2N)c(OC2CC2)cn1]

The title compound (254 mg, 63%) was prepared in a manner similar to that in Example 1 step 7 from tert-butyl 5-cyclopropoxy-4-(hydroxymethyl)pyridin-2-ylcarbamate and 3,5-dibromopyrazin-2-amine. LC-MS $(M+H)^+$=452.1.

Step 6: tert-butyl 4-((3-amino-6-(2,5-dimethyl-1,2,3,4-tetrahydroisoquinolin-7-yl)pyrazin-2-yloxy)methyl)-5-cyclopropoxypyridin-2-ylcarbamate

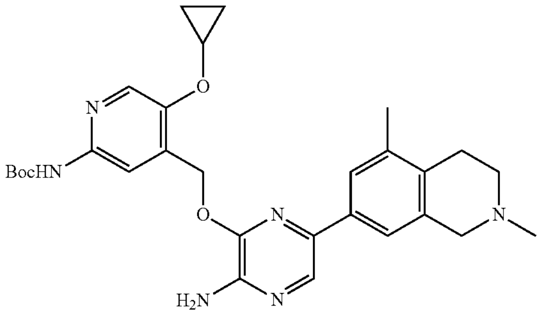 [SMILES: Cc1cc(-c2cnc(N)c(OCc3cc(NC(=O)OC(C)(C)C)ncc3OC3CC3)n2)cc2c1CCN(C)C2]

The title compound (222 mg, 75%) was prepared in a manner similar to that in Example 1 step 8 from tert-butyl 4-((3-amino-6-bromopyrazin-2-yloxy)methyl)-5-cyclopropoxypyridin-2-ylcarbamate and 2,5-dimethyl-7-(4,4,5,5-tetramethyl-1,3,2-dioxaborolan-2-yl)-1,2,3,4-tetrahydroisoquinoline. LC-MS $(M-H)^+$=533.4.

Step 7: 3-((2-amino-5-cyclopropoxypyridin-4-yl)methoxy)-5-(2,5-dimethyl-1,2,3,4-tetrahydroisoquinolin-7-yl)pyrazin-2-amine Example 161 (36 mg, 22%) was prepared in a manner similar to that in Example 34 step 6 from tert-butyl 4-((3-amino-6-(2,5-dimethyl-1,2,3,4-tetrahydroisoquinolin-7-yl)pyrazin-2-yloxy)methyl)-5-cyclopropoxypyridin-2-ylcarbamate. $^1$H NMR (400 MHz, DMSO-d6) δ 8.06 (s, 1H), 7.92 (s, 1H), 7.44 (s, 1H), 7.32 (s, 1H), 6.54 (s, 1H), 6.40 (s, 2H), 5.46 (s, 2H), 5.36 (s, 2H), 3.94-3.85 (m, 1H), 3.48 (s, 2H), 2.71-2.58 (m, 4H), 2.34 (s, 3H), 2.20 (s, 3H), 0.79-0.64 (m, 4H). LC-MS $(M+H)^+$=433.2.

Example 179: 3-((2-aminopyridin-4-yl)methoxy)-5-(5-methoxy-2-methyl-1,2,3,4-tetrahydroisoquinolin-7-yl)pyrazin-2-amine

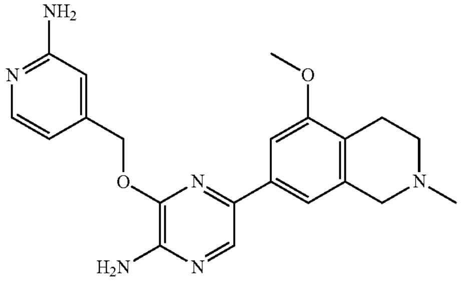 [SMILES: COc1cc(-c2cnc(N)c(OCc3ccnc(N)c3)n2)cc2c1CCN(C)C2]

Step 1: N-(3-bromo-5-methoxybenzyl)-2,2-dimethoxyethanamine

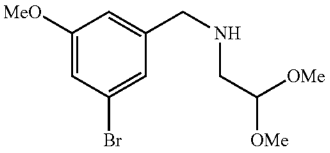 [SMILES: COc1cc(Br)cc(CNCC(OC)OC)c1]

To a solution of 2,2-dimethoxyethanamine (1.09 g, 10.4 mmol) in toluene (15 mL) was added 3-bromo-5-methoxybenzaldehyde (2.04 g, 9.50 mmol) at room temperature. The resulting mixture was stirred for 15 h at 120° C. under nitrogen atmosphere then cooled down to room temperature. The reaction mixture was concentrated under reduced pressure then re-dissolved in MeOH (15 mL). The mixture was cooled in ice bath and to which was added $NaBH_4$ (4.18 mg, 110 mmol) in portions within 10 min. The resulting mixture was warmed to room temperature. After 5 h, the reaction was quenched with ice water (20 mL). The resulting mixture was extracted with ethyl acetate (50 mL×3). The organic phases were combined, washed with brine and dried over $Na_2SO_4$. The solvent was concentrated under reduced pressure to give the title compound (2.80 g, crude). LCMS $(M+H)^+$=304.4.

Step 2: 7-bromo-5-methoxy-1,2,3,4-tetrahydroisoquinolin-4-ol

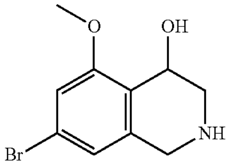

A mixture of N-(3-bromo-5-methoxybenzyl)-2,2-dimethoxyethanamine (2.80 g, from step 4) in HCl (6 M, 6.0 mL) was stirred for 16 h at 40° C. The mixture cooled down to room temperature and concentrated under reduced pressure. The residue was purified by prep-HPLC to give the title compound (108 mg, 5% over 2 steps). LCMS $(M+H)^+$=258.1.

Step 3: 7-bromo-5-methoxy-1,2,3,4-tetrahydroisoquinoline

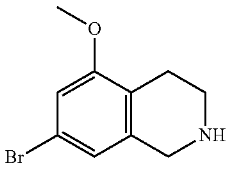

To a stirred mixture of 7-bromo-5-methoxy-1,2,3,4-tetrahydroisoquinolin-4-ol (100 mg, 0.38 mmol) and triethylsilane (1.00 mL, 8.6 mmol) in DCM (5 mL) was added TFA (0.50 mL, 4.4 mmol) dropwise at room temperature under nitrogen atmosphere. The resulting mixture was stirred for 48 h at 40° C. The reaction mixture was cooled down to room temperature and concentrated under reduced pressure. The crude was partitioned between EtOAc (30 mL) and saturated $NaHCO_3$ (30 mL). The combined organic layer was separated, dried over $Na_2SO_4$ and filtered. The filtrate was concentrated under reduced pressure. The residue was purified by C18 chromatography, eluted with MeCN in 0.05% aqueous $NH_4HCO_3$ solution (45% to 70%) to give the title compound (75 mg, 81%). $^1$H NMR (400 MHz, DMSO-d6) δ 6.92 (d, J=1.9 Hz, 1H), 6.84 (d, J=1.9 Hz, 1H), 3.82-3.74 (m, 5H), 2.90 (t, J=6.0 Hz, 2H), 2.77 (s, 1H), 2.43 (t, J=6.0 Hz, 2H). LCMS $(M+H)^+$=242.1.

Step 4: 7-bromo-5-methoxy-2-methyl-1,2,3,4-tetrahydroisoquinoline

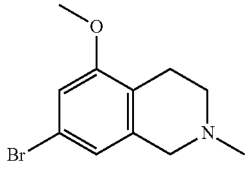

The title compound (600 mg, 99%) was prepared in a manner similar to that in Example 1 step 5 from 7-bromo-5-methoxy-1,2,3,4-tetrahydroisoquinoline. LC-MS $(M+H)^+$=256.0.

Step 5: 5-methoxy-2-methyl-7-(4,4,5,5-tetramethyl-1,3,2-dioxaborolan-2-yl)-1,2,3,4-tetrahydroisoquinoline

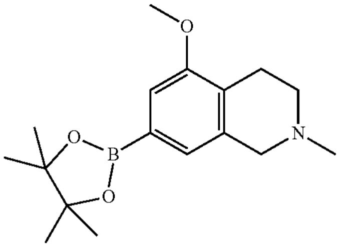

The title compound (705 mg, 99%) was prepared in a manner similar to that in Example 1 step 6 from 7-bromo-5-methoxy-2-methyl-1,2,3,4-tetrahydroisoquinoline. LC-MS $(M+H)^+$=304.2.

Step 6: 3-((2-aminopyridin-4-yl)methoxy)-5-(5-methoxy-2-methyl-1,2,3,4-tetrahydroisoquinolin-7-yl)pyrazin-2-amine

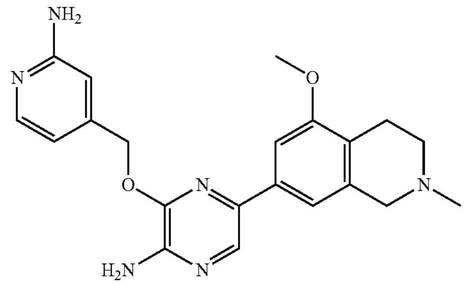 [SMILES: COc1cc(-c2cnc(N)c(OCc3ccnc(N)c3)n2)cc2c1CCN(C)C2]

Example 179 (23 mg, 14%) was prepared in a manner similar to that in Example 17 step 2 from 3-((2-aminopyridin-4-yl)methoxy)-5-bromopyrazin-2-amine and 5-methoxy-2-methyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.11 (s, 1H), 7.87 (d, J=5.2 Hz, 1H), 7.22-7.14 (m, 2H), 6.65-6.59 (m, 1H), 6.56-6.45 (m, 3H), 5.89 (s, 2H), 5.38 (s, 2H), 3.81 (s, 3H), 3.47 (s, 2H), 2.70-2.55 (m, 2H), 2.34 (s, 3H). LC-MS $(M+H)^+$=393.3.

Example 180: 5-(5-methoxy-2-methyl-1,2,3,4-tetrahydroisoquinolin-7-yl)-3-((3-methoxypyridin-4-yl)methoxy)pyrazin-2-amine

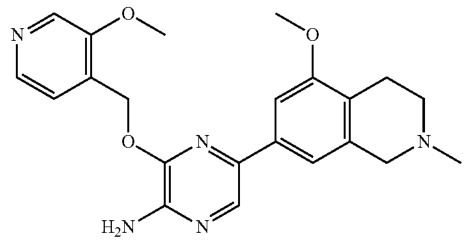 [SMILES: COc1cnccc1COc1nc(-c2cc3c(c(OC)c2)CCN(C)C3)cnc1N]

Example 180 (11 mg, 7%) was prepared in a manner similar to that in Example 17 step 2 from 5-bromo-3-((3-methoxypyridin-4-yl)methoxy)pyrazin-2-amine and 5-methoxy-2-methyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.40 (s, 1H), 8.23 (d, J=4.8 Hz, 1H), 8.13 (s, 1H), 7.54 (d, J=4.8 Hz, 1H), 7.21-7.12 (m, 2H), 6.55 (s, 2H), 5.53 (s, 2H), 3.98 (s, 3H), 3.79 (s, 3H), 3.46 (s, 2H), 2.67-2.55 (m, 2H), 2.33 (s, 3H). LC-MS $(M+H)^+$=408.2.

Example 188: 5-(2,5-dimethyl-1,2,3,4-tetrahydroisoquinolin-7-yl)-3-((5-methoxy-1H-pyrrolo[2,3-b]pyridin-4-yl)methoxy)pyrazin-2-amine

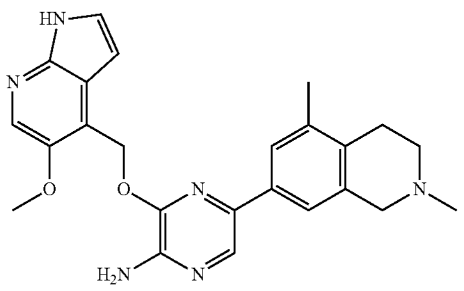 [SMILES: COc1cnc2[nH]ccc2c1COc1nc(-c2cc(C)c3c(c2)CN(C)CC3)cnc1N]

Step 1: 4-iodo-5-methoxy-1H-pyrrolo[2,3-b]pyridine

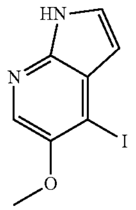

To a solution of 4-chloro-5-methoxy-1H-pyrrolo[2,3-b]pyridine (950 mg, 5.20 mmol) in MeCN (35 mL) was added NaI (3.90 g, 26.0 mmol) and acetyl chloride (782 mg, 9.96 mmol) dropwise at room temperature. The mixture was stirred for 2 h at 80° C. The mixture was cooled to room temperature and concentrated under vacuum. Aqueous $K_2CO_3$ (10%, 80 mL) and $NaHSO_4$ (10%, 80 mL) was added and the mixture was extracted with EtOAc (200 mL×2). The combined organic layer was washed with brine (50 mL), dried over $Na_2SO_4$, filtered and concentrated under reduced pressure. The residue was dissolved in THF (30 mL) and aqueous NaOH (1 M, 30 mL) and the mixture was stirred for 1 h at room temperature. The reaction was quenched with sat. $NH_4Cl$ (100 mL). The mixture was extracted with EtOAc (100 mL×2). The combined organic layer was washed with brine (50 mL), dried over $Na_2SO_4$, filtered and concentrated under reduced pressure to give the title compound (1.07 g, 74%). LC-MS $(M+H)^+$=275.0.

Step 2: 4-iodo-5-methoxy-1-((2-(trimethylsilyl)ethoxy)methyl)-1H-pyrrolo[2,3-b]pyridine

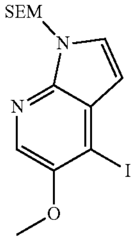 [SMILES: COc1cnc2c(ccn2COCC[Si](C)(C)C)c1I]

The title compound (502 mg, 74%) was prepared in a manner similar to that in Example 34 step 1 from 4-iodo-5-methoxy-1H-pyrrolo[2,3-b]pyridine. LC-MS $(M+H)^+$=405.1.

Step 3: (5-methoxy-1-((2-(trimethylsilyl)ethoxy)methyl)-1H-pyrrolo[2,3-b]pyridin-4-yl)methanol

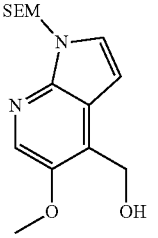 [SMILES: COc1cnc2c(ccn2COCC[Si](C)(C)C)c1CO]

The title compound (211 mg, 60%) was prepared in a manner similar to that in Example 222 step 2 from 4-iodo-5-methoxy-1-((2-(trimethylsilyl)ethoxy)methyl)-1H-pyrrolo[2,3-b]pyridine and (tributylstannyl)methanol. LC-MS $(M+H)^+$=309.1.

Step 4: 5-bromo-3-((5-methoxy-1-((2-(trimethylsilyl)ethoxy)methyl)-1H-pyrrolo[2,3-b]pyridin-4-yl)methoxy)pyrazin-2-amine

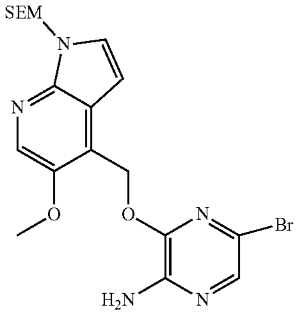 [SMILES: COc1cnc2c(ccn2COCC[Si](C)(C)C)c1COc1nc(Br)cnc1N]

The title compound (55 mg, 20%) was prepared in a manner similar to that in Example 34 step 4 from (5-methoxy-1-((2-(trimethylsilyl)ethoxy)methyl)-1H-pyrrolo[2,3-b]pyridin-4-yl)methanol and 3,5-dibromopyrazin-2-amine. LC-MS $(M+H)^+$=480.2.

Step 5: 5-(2,5-dimethyl-1,2,3,4-tetrahydroisoquinolin-7-yl)-3-((5-methoxy-1-((2-(trimethylsilyl)ethoxy)methyl)-1H-pyrrolo[2,3-b]pyridin-4-yl)methoxy)pyrazin-2-amine

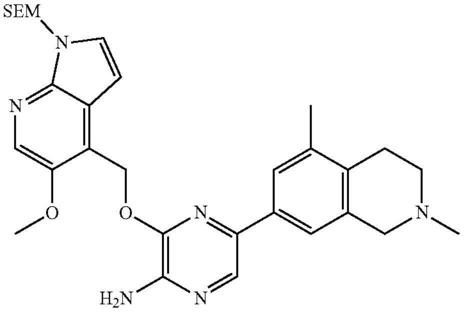 [SMILES: COc1cnc2c(ccn2COCC[Si](C)(C)C)c1COc1nc(-c2cc(C)c3c(c2)CN(C)CC3)cnc1N]

The title compound (52 mg, 82%) was prepared in a manner similar to that in Example 34 step 5 from 5-bromo-3-((5-methoxy-1-((2-(trimethylsilyl)ethoxy)methyl)-1H-pyrrolo[2,3-b]pyridin-4-yl)methoxy)pyrazin-2-amine and 2,5-dimethyl-7-(4,4,5,5-tetramethyl-1,3,2-dioxaborolan-2-yl)-1,2,3,4-tetrahydroisoquinoline. LC-MS $(M+H)^+=561.5$.

Step 6: 5-(2,5-dimethyl-1,2,3,4-tetrahydroisoquinolin-7-yl)-3-((5-methoxy-1H-pyrrolo[2,3-b]pyridin-4-yl)methoxy)pyrazin-2-amine Example 188 (5 mg, 11%) was prepared in a manner similar to that in Example 34 step 6 from 5-(2,5-dimethyl-1,2,3,4-tetrahydroisoquinolin-7-yl)-3-((5-methoxy-1-((2-(trimethylsilyl)ethoxy)methyl)-1H-pyrrolo[2,3-b]pyridin-4-yl)methoxy)pyrazin-2-amine. $^1H$ NMR (400 MHz, DMSO-d6) δ 11.46 (s, 1H), 8.15 (s, 1H), 8.01 (s, 1H), 7.48 (s, 1H), 7.44-7.34 (m, 2H), 6.63-6.57 (m, 1H), 6.39 (s, 2H), 5.81 (s, 2H), 3.97 (s, 3H), 3.66 (s, 2H), 2.85-2.68 (m, 4H), 2.46 (s, 3H), 2.21 (s, 3H). LC-MS $(M+H)^+=431.2$.

Example 193: 3-((2-amino-3-((tetrahydro-2H-pyran-4-yl)methoxy)pyridin-4-yl)methoxy)-5-(2,5-dimethyl-1,2,3,4-tetrahydroisoquinolin-7-yl)pyrazin-2-amine

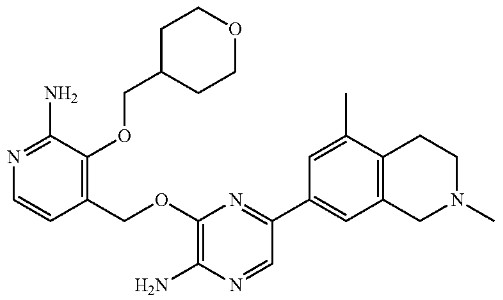 [SMILES: Cc1cc(-c2cnc(N)c(OCc3ccnc(N)c3OCC3CCOCC3)n2)cc2c1CCN(C)C2]

Step 1: tert-butyl (2-chloropyridin-3-yl) carbonate

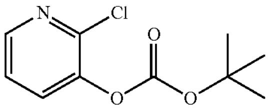

To a solution of 2-chloropyridin-3-ol (19.5 g, 150 mmol) in dichloromethane (300 mL) was added $(Boc)_2O$ (36.5 g, 167 mmol) and DMAP (500 mg, 4.1 mmol). The mixture was stirred at room temperature for 2 hours then concentrated under reduced pressure to give the title compound (37.7 g, crude). The material was used in step 2 without further purifications. LC-MS $(M+H)^+=230.1$.

Step 2: tert-butyl 2-chloro-3-hydroxyisonicotinate

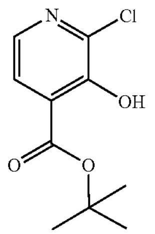

To a solution of tert-butyl (2-chloropyridin-3-yl) carbonate (37.7 g, crude) in THF (300 mL) was added LDA (2.0 M, 150 mL, 300 mmol) at −78° C. The mixture was stirred for 3 h at −78° C. then quenched with water (200 mL). The pH of the mixture was neutralized with HCl (6 M) to 6. The mixture was extracted with EtOAc (300 mL×2). The combined organic layer was washed with brine, dried over $Na_2SO_4$, filtered and concentrated under reduced pressure. The residue was purified by silica gel column chromatography, eluted with EtOAc/PE (1:10) to give the title compound (10.0 g, 29% over 2 steps). LC-MS $(M+H)^+=230.1$.

Step 3: tert-butyl 2-chloro-3-((tetrahydro-2H-pyran-4-yl)methoxy)isonicotinate

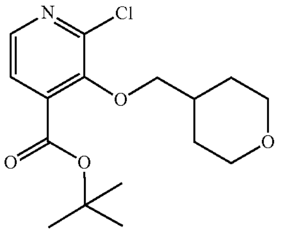 [SMILES: CC(C)(C)OC(=O)c1ccnc(Cl)c1OCC1CCOCC1]

To a solution of tert-butyl 2-chloro-3-hydroxyisonicotinate (1.0 g, 4.4 mmol) in DMSO (10 mL) was added KOH (250 mg, 4.4 mmol). After 1 h, 4-(bromomethyl)tetrahydro-2H-pyran (790 mg, 4.4 mmol) was added. The mixture was stirred at room temperature for 15 h, then at 70° C. for 6 h. The mixture was cooled and diluted with water (30 mL), extracted with EtOAc (30 mL×3). The combined organic layer was washed with brine (50 mL), dried over $Na_2SO_4$, filtered and concentrated. The residue was purified by silica gel column chromatography, eluted with EtOAc/PE (1:10) to give the title compound (600 mg, 42%). LC-MS $(M+H)^+=328.1$.

Step 4: tert-butyl 2-amino-3-((tetrahydro-2H-pyran-4-yl)methoxy)isonicotinate

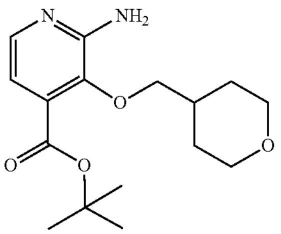 [SMILES: CC(C)(C)OC(=O)c1ccnc(N)c1OCC1CCOCC1]

The title compound (300 mg, 54%) was prepared in a manner similar to that in Example 35 step 3 from tert-butyl 2-chloro-3-((tetrahydro-2H-pyran-4-yl)methoxy)isonicotinate. LC-MS $(M+H)^+$=309.2.

Step 5: (2-amino-3-((tetrahydro-2H-pyran-4-yl) methoxy)pyridin-4-yl)methanol

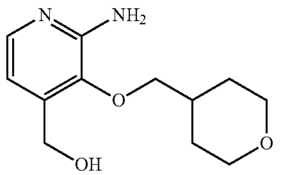 [SMILES: Nc1nccc(CO)c1OCC1CCOCC1]

The title compound (180 mg, 75%) was prepared in a manner similar to that in Example 35 step 4 from tert-butyl 2-amino-3-((tetrahydro-2H-pyran-4-yl)methoxy)isonicotinate. LC-MS $(M+H)^+$=239.1.

Step 6: 3-((2-amino-3-((tetrahydro-2H-pyran-4-yl) methoxy)pyridin-4-yl)methoxy)-5-bromopyrazin-2-amine

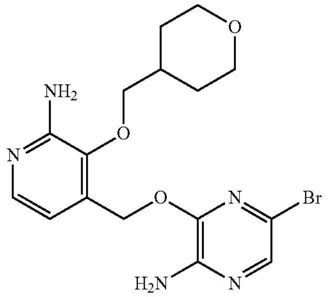 [SMILES: Nc1ncc(Br)nc1OCc1ccnc(N)c1OCC1CCOCC1]

The title compound (120 mg, 39%) was prepared in a manner similar to that in Example 35 step 5 from (2-amino-3-((tetrahydro-2H-pyran-4-yl)methoxy)pyridin-4-yl)methanol and 3,5-dibromopyrazin-2-amine. LC-MS $(M+H)^+$=410.1.

Step 7: 3-((2-amino-3-((tetrahydro-2H-pyran-4-yl) methoxy)pyridin-4-yl)methoxy)-5-(2,5-dimethyl-1,2,3,4-tetrahydroisoquinolin-7-yl)pyrazin-2-amine Example 193 (25 mg, 34%) was prepared in a manner similar to that in Example 17 step 2 from 3-((2-amino-3-((tetrahydro-2H-pyran-4-yl)methoxy)pyridin-4-yl) methoxy)-5-bromopyrazin-2-amine and (2,5-dimethyl-1,2,3,4-tetrahydroisoquinolin-7-yl)boronic acid. $^1$H NMR (400 MHz, DMSO-d6) δ 8.07 (s, 1H), 7.69 (d, J=5.1 Hz, 1H), 7.51 (s, 1H), 7.40 (s, 1H), 6.79 (d, J=5.0 Hz, 1H), 6.45 (s, 2H), 5.74 (s, 2H), 5.49 (s, 2H), 3.87-3.78 (m, 2H), 3.71 (d, J=6.2 Hz, 2H), 3.48 (s, 2H), 3.32-3.24 (m, 2H), 2.70-2.65 (s, 2H), 2.64-2.58 (m, 2H), 2.34 (s, 3H), 2.21 (s, 3H), 2.10 (brs, 1H), 1.77-1.68 (m, 2H), 1.41-1.28 (m, 2H). LC-MS $(M+H)^+$=491.5.

Example 204: 7-(5-amino-6-((2-aminopyridin-4-yl) methoxy)pyrazin-2-yl)-N,2-dimethyl-1,2,3,4-tetrahydroisoquinolin-5-amine

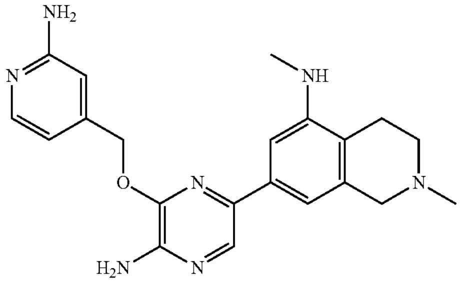

Step 1: 5-nitro-1,2,3,4-tetrahydroisoquinoline

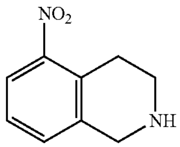 [SMILES: O=[N+]([O-])c1cccc2c1CCNC2]

To a stirred mixture of 5-nitroisoquinoline (10.0 g, 54.6 mmol) in AcOH (272 mL) was added $NaBH_4$ (7.60 g, 191 mmol) in portions at 0° C. under $N_2$. The mixture was stirred for 1 h at room temperature then concentrated under reduced pressure. Water (100 mL) was carefully added and the pH of the mixture was adjusted to 9 with NaOH solution. The resulting mixture was extracted with EtOAc (3×20 mL), dried over anhydrous $Na_2SO_4$, filtered and concentrated under reduced pressure. The residue was purified by silica gel column chromatography, eluted with MeOH/DCM (10:1) to give the title compound (7.0 g, 71%). LC-MS $(M+H)^+$=179.1.

Step 2: 7-bromo-5-nitro-1,2,3,4-tetrahydroisoquinoline

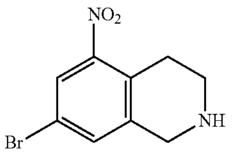

To a solution of 5-nitro-1,2,3,4-tetrahydroisoquinoline (5.0 g, 28.0 mmol) in $H_2SO_4$ (50 mL) was carefully added potassium bromate (4.58 g, 28.0 mmol) in portions over 30 min at room temperature. The resulting mixture was stirred for overnight at room temperature. The reaction was then quenched by carefully adding to ice water (100 mL). The pH of the mixture was adjusted to 9 by NaOH solution. The mixture was successively extracted with DCM (300 mL×3). The combined organic phase was washed with brine (100 mL) and dried over $Na_2SO_4$. The filtrate was concentrated under reduced pressure and the residue was purified by flash chromatography, eluted with MeOH/DCM (0:1 to 1:9) to give the title compound (1.43 g, 20%). LC-MS $(M+H)^+$=257.0.

Step 3: 7-bromo-2-methyl-5-nitro-1,2,3,4-tetrahydroisoquinoline

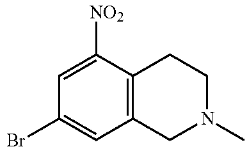

The title compound (1.46 g, 63%) was prepared in a manner similar to that in Example 1 step 5 from 7-bromo-5-nitro-1,2,3,4-tetrahydroisoquinoline and formalin. LC-MS $(M+H)^+$=271.0.

Step 4: 7-bromo-2-methyl-1,2,3,4-tetrahydroisoquinolin-5-amine

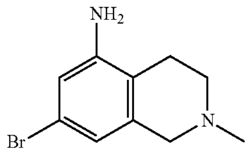

A mixture of 7-bromo-2-methyl-5-nitro-3,4-dihydro-1H-isoquinoline (1.28 g, 4.70 mmol), iron powder (1.38 g, 23.5 mmol) and $NH_4Cl$ (1.06 g, 18.8 mmol) in ethanol (100 mL) and water (10 mL) was stirred for 6 h at 70° C. under $N_2$. The mixture was cooled to room temperature and concentrated under reduced pressure. The residue was directly purified by silica gel column chromatography, eluted with MeOH/DCM (1:5) to give the title compound (1.1 g, 89%). LC-MS $(M+H)^+$=241.1.

Step 5: 7-bromo-N,2-dimethyl-1,2,3,4-tetrahydroisoquinolin-5-amine

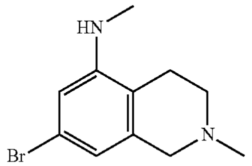

To a solution of 7-bromo-2-methyl-3,4-dihydro-1H-isoquinolin-5-amine (285 mg, 1.18 mmol) in MeOH (12 mL) was added paraformaldehyde (71 mg, 2.36 mmol), and NaOMe (1.32 mL, 30 w %) dropwise at room temperature under nitrogen atmosphere. The resulting mixture was stirred for additional 16 h at 60° C. The mixture was cooled to room temperature. To the above mixture was added $NaBH_4$ (112 mg, 2.96 mmol) in portions. The resulting mixture was stirred for additional overnight at room temperature. The reaction was then quenched by addition of water (20 mL). The resulting solution was extracted with DCM (60 mL×3). The organic phases were combined, washed with brine (50 mL), dried over $Na_2SO_4$ and filtered. The solvent was concentrated under reduced pressure and the residue was purified by flash chromatography, eluted with MeOH/DCM (0:1 to 1:9) to give the title compound (177 mg, 59%). LC-MS $(M+H)^+$=255.0.

Step 6: N,2-dimethyl-7-(4,4,5,5-tetramethyl-1,3,2-dioxaborolan-2-yl)-1,2,3,4-tetrahydroisoquinolin-5-amine

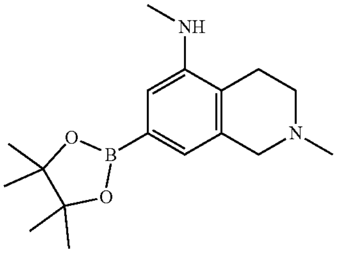

The title compound (207 mg, 90%) was prepared in a manner similar to that in Example 1 step 6 from methyl 7-bromo-N,2-dimethyl-1,2,3,4-tetrahydroisoquinolin-5-amine and BPD. LC-MS $(M+H)^+$=303.3.

Step 7: tert-butyl 4-((3-amino-6-(2-methyl-5-(methylamino)-1,2,3,4-tetrahydroisoquinolin-7-yl)pyrazin-2-yloxy)methyl)pyridin-2-ylcarbamate

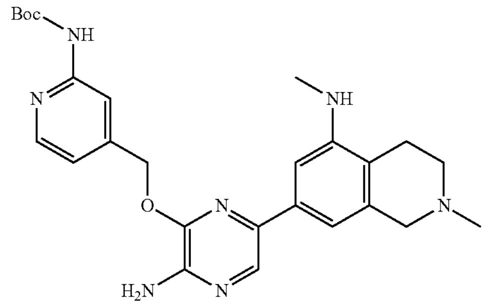 [SMILES: CNc1cc(-c2cnc(N)c(OCc3ccnc(NC(=O)OC(C)(C)C)c3)n2)cc2c1CCN(C)C2]

The title compound (54 mg, 19%) was prepared in a manner similar to that in Example 1 step 8 from N,2-dimethyl-7-(4,4,5,5-tetramethyl-1,3,2-dioxaborolan-2-yl)-1,2,3,4-tetrahydroisoquinolin-5-amine and tert-butyl 4-((3-amino-6-bromopyrazin-2-yloxy)methyl)pyridin-2-ylcarbamate. LC-MS $(M+H)^+$=492.4.

Step 8: 7-(5-amino-6-((2-aminopyridin-4-yl)methoxy)pyrazin-2-yl)-N,2-dimethyl-1,2,3,4-tetrahydroisoquinolin-5-amine Example 204 (6 mg, 16%) was prepared in a manner similar to that in Example 34 step 6 from tert-butyl 4-((3-amino-6-(2-methyl-5-(methylamino)-1,2,3,4-tetrahydroisoquinolin-7-yl)pyrazin-2-yloxy)methyl)pyridin-2-ylcarbamate. $^1H$ NMR (400 MHz, DMSO-d6) δ 8.03 (s, 1H), 7.87 (d, J=5.2 Hz, 1H), 6.83-6.75 (m, 2H), 6.61 (d, J=5.3 Hz, 1H), 6.51 (s, 1H), 6.37 (s, 2H), 5.87 (s, 2H), 5.37 (s, 2H), 5.01-4.96 (m, 1H), 3.42 (s, 2H), 2.79-2.83 (m, 3H), 2.64-2.57 (m, 2H), 2.49-2.42 (m, 2H), 2.32 (s, 3H). LC-MS $(M+H)^+$=392.2.

Example 205: 7-(5-amino-6-((3-methoxypyridin-4-yl)methoxy)pyrazin-2-yl)-N,2-dimethyl-1,2,3,4-tetrahydroisoquinolin-5-amine

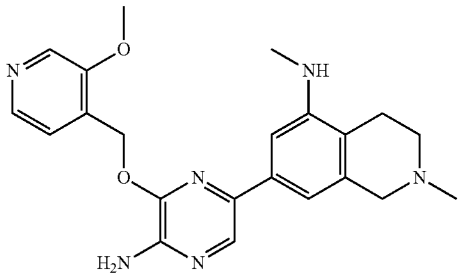 [SMILES: CNc1cc(-c2cnc(N)c(OCc3ccncc3OC)n2)cc2c1CCN(C)C2]

Example 205 (4.6 mg, 2%) was prepared in a manner similar to that in Example 1 step 8 from 5-bromo-3-((3-methoxypyridin-4-yl)methoxy)pyrazin-2-amine and N,2-dimethyl-7-(4,4,5,5-tetramethyl-1,3,2-dioxaborolan-2-yl)-1,2,3,4-tetrahydroisoquinolin-5-amine. $^1$H NMR (400 MHz, DMSO-d6) δ 8.40 (s, 1H), 8.22 (d, J=4.7 Hz, 1H), 8.04 (s, 1H), 7.52 (d, J=4.7 Hz, 1H), 6.79 (s, 1H), 6.74 (s, 1H), 6.46 (s, 2H), 5.53 (s, 2H), 5.03-4.97 (m, 1H), 3.98 (s, 3H), 3.40 (s, 2H), 2.72 (d, J=5.0 Hz, 3H), 2.63-2.56 (m, 2H), 2.49-2.41 (m, 2H), 2.32 (s, 3H). LC-MS $(M+H)^+$=407.2.

Example 222: 4-((3-amino-6-(2,5-dimethyl-1,2,3,4-tetrahydroisoquinolin-7-yl)pyrazin-2-yloxy)methyl)pyridine-2,6-diamine

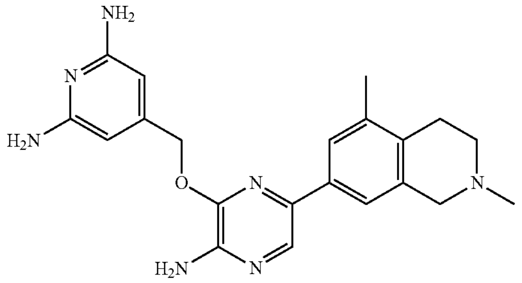 [SMILES: Cc1cc(-c2cnc(N)c(OCc3cc(N)nc(N)c3)n2)cc2c1CCN(C)C2]

Step 1: di-tert-butyl (4-bromopyridine-2,6-diyl)bis((tert-butoxycarbonyl)carbamate)

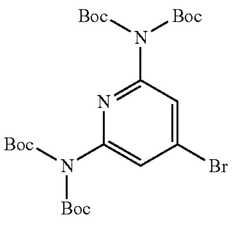 [SMILES: CC(C)(C)OC(=O)N(C(=O)OC(C)(C)C)c1cc(Br)cc(N(C(=O)OC(C)(C)C)C(=O)OC(C)(C)C)n1]

To a stirred solution of 4-bromopyridine-2,6-diamine (500 mg, 2.53 mmol) and $Boc_2O$ (1.70 g, 7.40 mmol) in THF (15 mL) was added $Et_3N$ (806 mg, 7.81 mmol). The mixture was stirred for overnight at 70° C. under nitrogen. The mixture was cooled to room temperature and concentrated under reduced pressure. The residue was purified by silica gel column chromatography, eluted with DCM/PE (1:1) to give the title compound (640 mg, 43%). LC-MS $(M+H)^+$=588.1.

Step 2: di-tert-butyl (4-(hydroxymethyl)pyridine-2,6-diyl)bis((tert-butoxycarbonyl)carbamate)

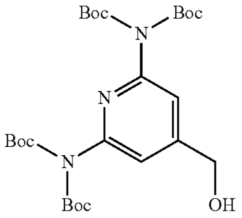 [SMILES: CC(C)(C)OC(=O)N(C(=O)OC(C)(C)C)c1cc(CO)cc(N(C(=O)OC(C)(C)C)C(=O)OC(C)(C)C)n1]

A solution of di-tert-butyl (4-bromopyridine-2,6-diyl)bis((tert-butoxycarbonyl)carbamate) (630 mg, 1.07 mmol), (tributylstannyl)methanol (693 mg, 2.12 mmol) and $Pd(PPh_3)_4$ (124 mg, 0.10 mmol) in toluene (15 mL) was stirred for overnight at 100° C. under nitrogen. The mixture was cooled to room temperature and concentrated under reduced pressure. The residue was purified by silica gel column chromatography to give the title compound (221 mg, 40%). LC-MS $(M+H)^+$=540.3.

Step 3: di-tert-butyl (4-(((3-amino-6-bromopyrazin-2-yl)oxy)methyl)pyridine-2,6-diyl)bis((tert-butoxycarbonyl)carbamate)

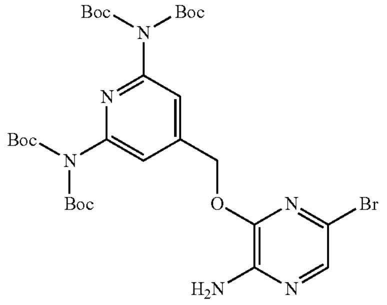 [SMILES: CC(C)(C)OC(=O)N(C(=O)OC(C)(C)C)c1cc(COc2nc(Br)cnc2N)cc(N(C(=O)OC(C)(C)C)C(=O)OC(C)(C)C)n1]

The title compound (106 mg, 43%) was prepared in a manner similar to that in Example 1 step 7 from di-tert-butyl (4-(hydroxymethyl)pyridine-2,6-diyl)bis((tert-butoxycarbonyl)carbamate) and 3,5-dibromopyrazin-2-amine. LC-MS $(M+H)^+$=711.5.

Step 4: 4-((3-amino-6-bromopyrazin-2-yloxy)methyl)pyridine-2,6-diamine

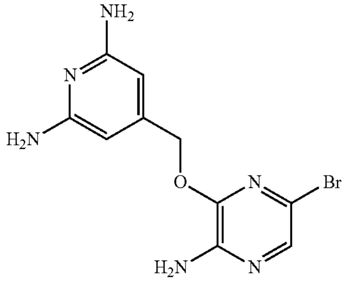 [SMILES: Nc1cc(COc2nc(Br)cnc2N)cc(N)n1]

The title compound (45 mg, 97%) was prepared in a manner similar to that in Example 34 step 6 from di-tert-butyl (4-(((3-amino-6-bromopyrazin-2-yl)oxy)methyl)pyridine-2,6-diyl)bis((tert-butoxycarbonyl)carbamate). LC-MS $(M+H)^+$=310.9.

Step 5: 4-((3-amino-6-(2,5-dimethyl-1,2,3,4-tetrahydroisoquinolin-7-yl)pyrazin-2-yloxy)methyl)pyridine-2,6-diamine

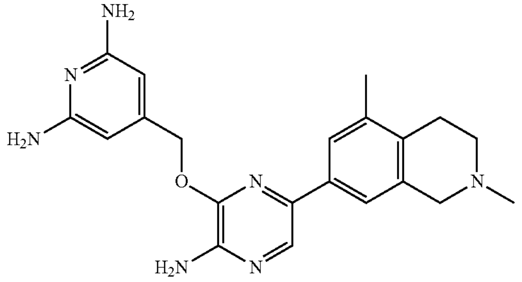 [SMILES: Cc1cc(-c2cnc(N)c(OCc3cc(N)nc(N)c3)n2)cc2c1CCN(C)C2]

Example 222 (11 mg, 19%) was prepared in a manner similar to that in Example 1 step 8 from 4-((3-amino-6-bromopyrazin-2-yloxy)methyl)pyridine-2,6-diamine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.04 (s, 1H), 7.50 (s, 1H), 7.38 (s, 1H), 6.34 (s, 2H), 5.74 (s, 2H), 5.36 (s, 4H), 5.23 (s, 2H), 3.51 (s, 2H), 2.71-2.61 (m, 4H), 2.35 (s, 3H), 2.22 (s, 3H). LC-MS $(M+H)^+$=392.2.

Example 242: 5-(2,8-dimethyl-1,2,3,4-tetrahydroisoquinolin-6-yl)-3-(1-isopropyl-1H-pyrazol-4-yloxy)pyrazin-2-amine

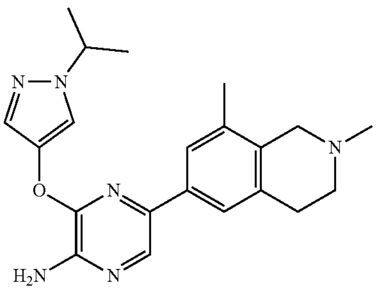 [SMILES: Cc1cc(-c2cnc(N)c(Oc3cnn(C(C)C)c3)n2)cc2c1CN(C)CC2]

Step 1: 1-isopropyl-4-(4,4,5,5-tetramethyl-1,3,2-dioxaborolan-2-yl)-1H-pyrazole

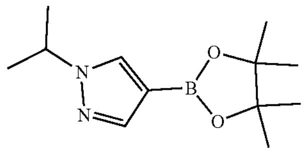 [SMILES: CC(C)n1cc(B2OC(C)(C)C(C)(C)O2)cn1]

The title compound (1.10 g, 45%) was prepared in a manner similar to that in Example 116 step 1 from 4-(4,4,5,5-tetramethyl-1,3,2-dioxaborolan-2-yl)-1H-pyrazole and 2-bromopropane. LC-MS $(M+H)^+$=237.2.

Step 2: 1-isopropyl-1H-pyrazol-4-ol

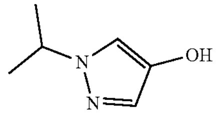

The title compound (488 mg, 83%) was prepared in a manner similar to that in Example 116 step 2 from 1-isopropyl-4-(4,4,5,5-tetramethyl-1,3,2-dioxaborolan-2-yl)-1H-pyrazole. LC-MS $(M+H)^+$=127.1.

Step 3: 5-bromo-3-(1-isopropyl-1H-pyrazol-4-yloxy)pyrazin-2-amine

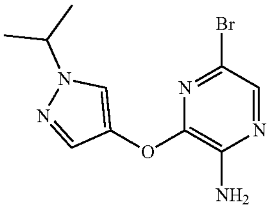 [SMILES: CC(C)n1cc(Oc2nc(Br)cnc2N)cn1]

The title compound (300 mg, 25%) was prepared in a manner similar to that in Example 116 step 3 from 1-isopropyl-1H-pyrazol-4-ol and 3,5-dibromopyrazin-2-amine. LC-MS $(M+H)^+$=298.1.

Step 4: 5-(2,8-dimethyl-1,2,3,4-tetrahydroisoquinolin-6-yl)-3-(1-isopropyl-1H-pyrazol-4-yloxy)pyrazin-2-amine Example 242 (35 mg, 27%) was prepared in a manner similar to that in Example 1 step 8 from 5-bromo-3-(1-isopropyl-1H-pyrazol-4-yloxy)pyrazin-2-amine and 2,8-dimethyl-6-(4,4,5,5-tetramethyl-1,3,2-dioxaborolan-2-yl)-1,2,3,4-tetrahydroisoquinoline. $^1$H NMR (400 MHz, DMSO-d6) δ 8.20 (s, 1H), 8.10 (s, 1H), 7.56 (s, 1H), 7.48-7.40 (m, 2H), 6.63 (s, 1H), 4.57-4.46 (m, 1H), 3.40 (s, 2H), 2.872.79 (m, 2H), 2.61-2.54 (m, 2H), 2.38 (s, 3H), 2.18 (s, 3H), 1.50-1.44 (m, 6H). LC-MS $(M+H)^+$=379.2.

Example 249: 3-((2-amino-3-((tetrahydro-2H-pyran-4-yl)oxy)pyridin-4-yl)methoxy)-5-(2,5-dimethyl-1,2,3,4-tetrahydroisoquinolin-7-yl)pyrazin-2-amine

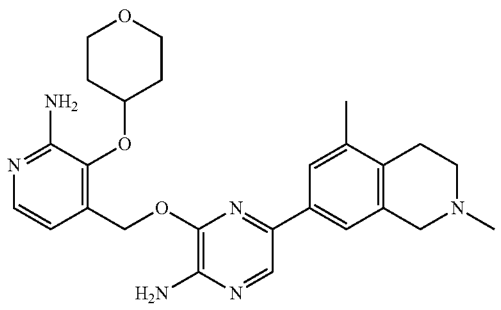 [SMILES: Cc1cc(-c2cnc(N)c(OCc3ccnc(N)c3OC3CCOCC3)n2)cc2c1CCN(C)C2]

Step 1: 3-hydroxy-2-nitroisonicotinic acid

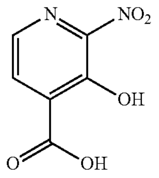 [SMILES: O=C(O)c1ccnc([N+](=O)[O-])c1O]

3-hydroxyisonicotinic acid (25.0 g, 180 mmol) was dissolved in concentrated $H_2SO_4$ (200 mL). To the mixture was carefully added concentrated $HNO_3$ (40 mL) dropwise. The mixture was stirred at room temperature overnight. The mixture was poured in ice-water (500 mL). The precipitate was collected by filtration, then triturated with EtOH (50 mL). The precipitate was collected by filtration then dried under vacuum to give the title compound (12.0 g, 36%). LC-MS $(M+H)^+$=185.0.

Step 2: methyl 3-hydroxy-2-nitroisonicotinate

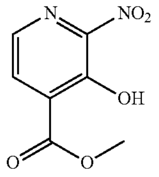

To a mixture of 3-hydroxy-2-nitroisonicotinic acid (200 mg, 1.1 mmol) in MeOH (20 mL) was added concentrated $H_2SO_4$ (0.5 mL). The mixture was stirred overnight at 70° C. The mixture was cooled to room temperature and neutralized with $NaHCO_3$ solution (30 mL) The mixture was extracted with dichloromethane (30 mL×3). The combined organic layer was washed with brine (30 mL), dried over $Na_2SO_4$, filtered and concentrated to give the title compound (200 mg, 90%). LC-MS $(M+H)^+$=213.0.

Step 3: methyl 2-nitro-3-((tetrahydro-2H-pyran-4-yl)oxy)isonicotinate

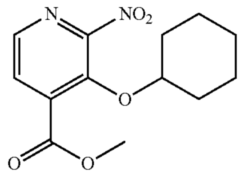 [SMILES: COC(=O)c1ccnc([N+](=O)[O-])c1OC1CCCCC1]

To a solution of methyl 3-hydroxy-2-nitroisonicotinate (200 mg, 1.0 mmol) and 4-bromotetrahydro-2H-pyran (500 mg, 3.0 mmol) in DMF (10 mL) was added $K_2CO_3$ (420 mg, 3.0 mmol). The mixture was stirred at 100° C. overnight. The mixture was cooled, diluted with water (30 mL) then extracted with EtOAc (30 mL×3). The combined organic layer was successively washed with water (50 mL) and brine (50 mL), dried over $Na_2SO_4$, filtered and concentrated. The residue was purified by silica gel column chromatography, eluted with EtOAc:PE (1:3) to give the title compound (200 mg, 70%). LC-MS $(M+H)^+$=283.1.

Step 4: methyl 2-amino-3-((tetrahydro-2H-pyran-4-yl)oxy)isonicotinate

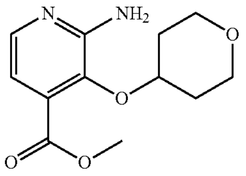 [SMILES: COC(=O)c1ccnc(N)c1OC1CCOCC1]

To a mixture of methyl 2-nitro-3-((tetrahydro-2H-pyran-4-yl)oxy)isonicotinate (200 mg, 0.7 mmol) in MeOH (20 mL) was added Pd/C (10%, 20 mg). The mixture was stirred for 2 h under $H_2$ (1 atm). The mixture was filtered and the filtrate was concentrated under reduced pressure to give title compound (180 mg, 99%). LC-MS $(M+H)^+$=253.1.

Step 5: (2-amino-3-((tetrahydro-2H-pyran-4-yl)oxy)pyridin-4-yl)methanol

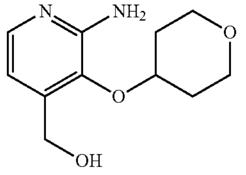 [SMILES: Nc1nccc(CO)c1OC1CCOCC1]

The title compound (160 mg, 99%) was prepared in a manner similar to that in Example 35 step 4 from methyl 2-amino-3-((tetrahydro-2H-pyran-4-yl)oxy)isonicotinate. LC-MS $(M+H)^+$=225.1.

Step 6: 3-((2-amino-3-((tetrahydro-2H-pyran-4-yl)oxy)pyridin-4-yl)methoxy)-5-bromopyrazin-2-amine

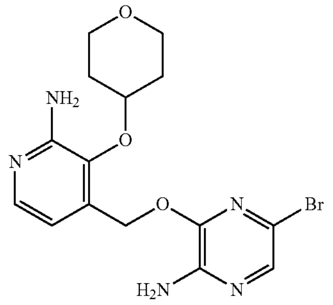 [SMILES: Nc1ncc(Br)nc1OCc1ccnc(N)c1OC1CCOCC1]

The title compound (100 mg, 36%) was prepared in a manner similar to that in Example 35 step 5 from (2-amino-3-((tetrahydro-2H-pyran-4-yl)oxy)pyridin-4-yl)methanol and 3,5-dibromopyrazin-2-amine. LC-MS $(M+H)^+=396.1$.

Step 7: 3-((2-amino-3-((tetrahydro-2H-pyran-4-yl)oxy)pyridin-4-yl)methoxy)-5-(2,5-dimethyl-1,2,3,4-tetrahydroisoquinolin-7-yl)pyrazin-2-amine Example 249 (15 mg, 24%) was prepared in a manner similar to that in Example 17 step 3 from 3-((2-amino-3-((tetrahydro-2H-pyran-4-yl)oxy)pyridin-4-yl)methoxy)-5-bromopyrazin-2-amine and (2,5-dimethyl-1,2,3,4-tetrahydroisoquinolin-7-yl)boronic acid. $^1$H NMR (400 MHz, DMSO-d6) δ 8.07 (s, 1H), 7.69 (d, J=5.1 Hz, 1H), 7.52 (s, 1H), 7.40 (s, 1H), 6.80 (d, J=5.1 Hz, 1H), 6.45 (s, 2H), 5.73 (s, 2H), 5.51 (s, 2H), 4.20-4.11 (m, 1H), 3.91-3.84 (m, 2H), 3.48 (s, 2H), 3.30-3.26 (m, 2H), 2.71-2.65 (m, 2H), 2.65-2.59 (m, 2H), 2.34 (s, 3H), 2.21 (s, 3H), 1.99-1.91 (m, 2H), 1.82-1.70 (m, 2H). LC-MS $(M+H)^+=477.5$.

Example 266: 3-((2-aminopyridin-4-yl)methoxy-d2)-5-(2,5-dimethyl-1,2,3,4-tetrahydroisoquinolin-7-yl)pyrazin-2-amine

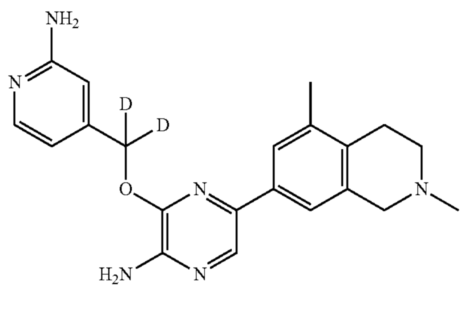 [SMILES: [2H]C([2H])(Oc1nc(-c2cc(C)c3c(c2)CN(C)CC3)cnc1N)c1ccnc(N)c1]

Step 1: (2-aminopyridin-4-yl)methan-d2-ol

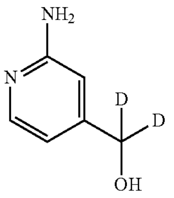 [SMILES: [2H]C([2H])(O)c1ccnc(N)c1]

The title compound (410 mg, 100%) was prepared in a manner similar to that in Example 29 step 2 from methyl 2-aminoisonicotinate and LiAlD4. LC-MS $(M+H)^+=127.0$.

Step 2: 3-((2-aminopyridin-4-yl)methoxy-d2)-5-bromopyrazin-2-amine

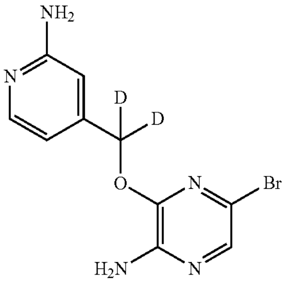 [SMILES: [2H]C([2H])(Oc1nc(Br)cnc1N)c1ccnc(N)c1]

The title compound (700 mg, 710%) was prepared in a manner similar to that in compound 29 step 3 from (2-aminopyridin-4-yl)methan-d2-ol and 3,5-dibromopyrazin-2-amine. LC-MS $(M+H)^+=298.0$, 300.0.

Step 3: 3-((2-aminopyridin-4-yl)methoxy-d2)-5-(2,5-dimethyl-1,2,3,4-tetrahydroisoquinolin-7-yl)pyrazin-2-amine Example 266 (238 mg, 47%) was prepared in a manner similar to that in Example 17 step 2 from 3-((2-aminopyridin-4-yl)methoxy-d2)-5-bromopyrazin-2-amine and ((2,5-dimethyl-1,2,3,4-tetrahydroisoquinolin-7-yl)boronic acid. $^1$H NMR (400 MHz, DMSO-d6) δ 8.06 (s, 1H), 7.88 (d, J=5.2 Hz, 1H), 7.50 (s, 1H), 7.37 (s, 1H), 6.62 (d, J=4.6 Hz, 1H), 6.53 (s, 1H), 6.45 (s, 2H), 5.91 (s, 2H), 3.56 (s, 2H), 2.74-2.64 (m, 4H), 2.39 (s, 3H), 2.21 (s, 3H). LC-MS $(M+H)^+=379.4$.

Example 271: 3-((2-aminopyridin-4-yl)methoxy)-5-(2-methyl-5-(trifluoromethyl)-1,2,3,4-tetrahydroisoquinolin-7-yl)pyrazin-2-amine

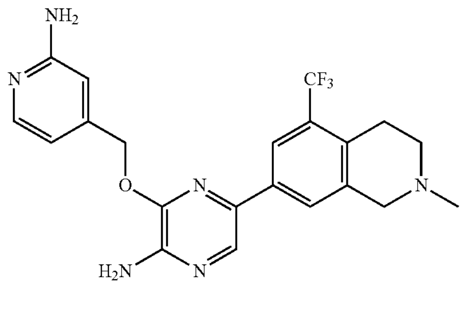

Step 1: 2-(4-bromo-2-(trifluoromethyl)phenyl)ethan-1-amine

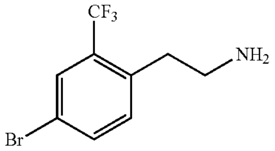 [SMILES: NCCc1ccc(Br)cc1C(F)(F)F]

The title compound (5.0 g, 99%) was prepared in a manner similar to that in Example 1 step 1 from 2-(4-bromo-2-(trifluoromethyl)phenyl)acetonitrile. LC-MS $(M+H)^+$=268.0, 270.0.

Step 2: N-(4-bromo-2-(trifluoromethyl)phenethyl)-2,2,2-trifluoroacetamide

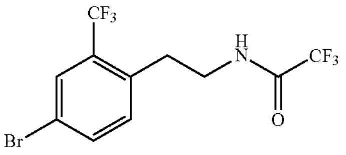 [SMILES: O=C(NCCc1ccc(Br)cc1C(F)(F)F)C(F)(F)F]

The title compound (6.0 g, 88%) was prepared in a manner similar to that in Example 1 step 2 from 2-(4-bromo-2-(trifluoromethyl)phenyl)ethan-1-amine. LC-MS $(M+H)^+$=364.0, 366.0.

Step 3: 1-(7-bromo-5-(trifluoromethyl)-3,4-dihydroisoquinolin-2(1H)-yl)-2,2,2-trifluoroethan-1-one

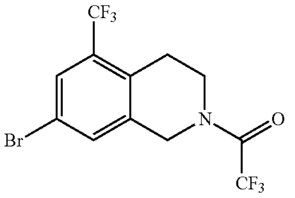

The title compound (5.0 g, 80%) was prepared in a manner similar to that in Example 1 step 3 from N-(4-bromo-2-(trifluoromethyl)phenethyl)-2,2,2-trifluoroacetamide. LC-MS $(M+H)^+$=376.0, 378.0.

Step 4: 7-bromo-5-(trifluoromethyl)-1,2,3,4-tetrahydroisoquinoline

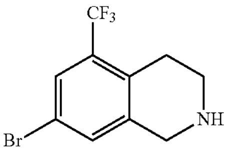 [SMILES: FC(F)(F)c1cc(Br)cc2c1CCNC2]

The title compound (3.5 g, 94%) was prepared in a manner similar to that in Example 1 step 4 from 1-(7-bromo-5-(trifluoromethyl)-3,4-dihydroisoquinolin-2(1H)-yl)-2,2,2-trifluoroethan-1-one. LC-MS $(M+H)^+$=280.0, 282.0.

Step 5: 7-bromo-2-methyl-5-(trifluoromethyl)-1,2,3,4-tetrahydroisoquinoline

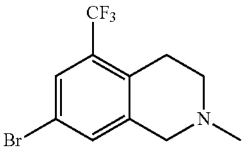 [SMILES: CN1CCc2c(cc(Br)cc2C(F)(F)F)C1]

The title compound (3.6 g, 98%) was prepared in a manner similar to that in Example 1 step 5 from 7-bromo-5-(trifluoromethyl)-1,2,3,4-tetrahydroisoquinoline. LC-MS $(M+H)^+$=294.0, 296.0.

Step 6: (2-methyl-5-(trifluoromethyl)-1,2,3,4-tetrahydroisoquinolin-7-yl)boronic acid

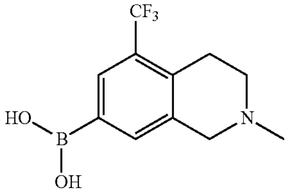 [SMILES: CN1CCc2c(cc(B(O)O)cc2C(F)(F)F)C1]

The title compound (1.8 g, 62%) was prepared in a manner similar to that in Example 14 step 1 from 7-bromo-2-methyl-5-(trifluoromethyl)-1,2,3,4-tetrahydroisoquinoline. LC-MS $(M+H)^+$=260.0.

Step 7: 3-((2-aminopyridin-4-yl)methoxy)-5-(2-methyl-5-(trifluoromethyl)-1,2,3,4-tetrahydroisoquinolin-7-yl)pyrazin-2-amine Example 271 (95 mg, 33%) was prepared in a manner similar to that in Example 17 step 2 from 3-((2-aminopyridin-4-yl)methoxy)-5-bromopyrazin-2-amine and (2-methyl-5-(trifluoromethyl)-1,2,3,4-tetrahydroisoquinolin-7-yl)boronic acid. $^1$H NMR (400 MHz, DMSO-d6) δ 8.20 (s, 1H), 7.96 (s, 1H), 7.87 (d, J=4.9 Hz, 1H), 7.84 (s, 1H), 6.66 (s, 2H), 6.62 (d, J=5.1 Hz, 1H), 6.50 (s, 1H), 5.89 (s, 2H), 5.37 (s, 2H), 3.59 (s, 2H), 2.96-2.88 (m, 2H), 2.66-2.60 (m, 2H), 2.36 (s, 3H). LCMS $(M+H)^+$=431.4.

Example 272: 5-(2,5-dimethyl-1,2,3,4-tetrahydroisoquinolin-7-yl)-3-(1-isopropyl-1H-pyrazol-4-yloxy)pyrazin-2-amine

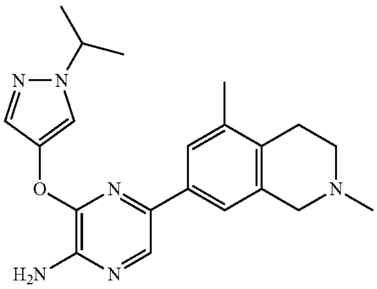 [SMILES: Cc1cc(-c2cnc(N)c(Oc3cnn(C(C)C)c3)n2)cc2c1CCN(C)C2]

Example 272 (31 mg, 25%) was prepared in a manner similar to that in Example 1 step 8 from 5-bromo-3-(1-isopropyl-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.19 (s, 1H), 8.09 (s, 1H), 7.57 (s, 1H), 7.48 (s, 1H), 7.36 (s, 1H), 6.63 (s, 2H), 4.58-4.46 (m, 1H), 3.47 (s, 2H), 2.72-2.59 (m, 4H), 2.34 (s, 3H), 2.20 (s, 3H), 1.52-1.42 (m, 6H). LC-MS $(M+H)^+$=379.2.

Example 273: 3-((1-(cyclopropylmethyl)-1H-pyrazol-4-yl)oxy)-5-(2,5-dimethyl-1,2,3,4-tetrahydroisoquinolin-7-yl)pyrazin-2-amine

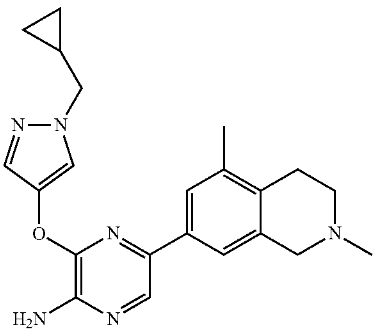 [SMILES: Cc1cc(-c2cnc(N)c(Oc3cnn(CC4CC4)c3)n2)cc2c1CCN(C)C2]

Step 1: 1-(cyclopropylmethyl)-4-(4,4,5,5-tetramethyl-1,3,2-dioxaborolan-2-yl)-1H-pyrazole

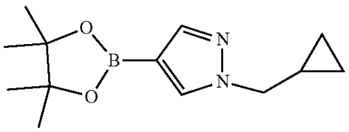 [SMILES: CC1(C)OB(c2cnn(CC3CC3)c2)OC1(C)C]

NaH (60%, 463 mg, 11.6 mmol) was added to a solution of 4-(4,4,5,5-tetramethyl-1,3,2-dioxaborolan-2-yl)-1H-pyrazole (1.5 g, 7.73 mmol) in anhydrous DMF (20 mL) at 0° C. After 5 min, (bromomethyl)cyclopropane (1.25 g, 9.28 mmol) was added at 0° C. and the mixture was stirred for overnight. Water (20 mL) was added at 0° C. and the mixture was extracted with ethyl acetate (30 mL×2). The combined organic layer was washed with brine (30 mL), dried over $Na_2SO_4$ and filtered. The residue was purified by silica gel chromatography to give the title compound (1.42 g, 74%). LC-MS $(M+H)^+$=249.0.

Step 2: 1-(cyclopropylmethyl)-1H-pyrazol-4-ol

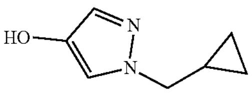

NaOH solution (2.0 M, 5.8 mL, 11.6 mmol) and $H_2O_2$ (30%, 11.6 mmol) was added to a solution of 1-(cyclopropylmethyl)-4-(4,4,5,5-tetramethyl-1,3,2-dioxaborolan-2-yl)-1H-pyrazole (1.42 g, 5.72 mmol) in THF (20 mL) at 0° C. The mixture was stirred at room temperature for 1 h. Water (20 mL) was added and the mixture was extracted with ethyl acetate (30 mL×2). The combined organic layer was washed with saturated $Na_2S_2O_3$ (20 mL), brine (20 mL), dried over $Na_2SO_4$, filtered and concentrated under reduced pressure. The residue was purified by silica gel chromatography to give the title compound (790 mg, 99%). LC-MS $(M+H)^+$=139.0.

Step 3: 5-bromo-3-((1-(cyclopropylmethyl)-1H-pyrazol-4-yl)oxy)pyrazin-2-amine

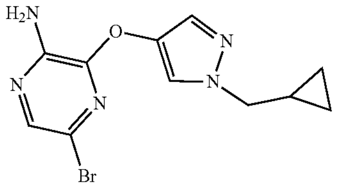 [SMILES: Nc1ncc(Br)nc1Oc1cnn(CC2CC2)c1]

$K_2CO_3$ (1.18 g, 8.58 mmol) was added to a solution of 1-(cyclopropylmethyl)-1H-pyrazol-4-ol (780 mg, 5.72 mmol) and 3,5-dibromopyrazin-2-amine (1.74 g, 6.86 mmol) in DMSO (10 mL) and the mixture was heated to 80° C. and stirred for 3 h. The mixture was cooled to room temperature and water (30 mL) was added. The mixture was extracted with ethyl acetate (30 mL×2). The combined organic layer was washed with brine, dried over $Na_2SO_4$ and filtered. The residue was purified by silica gel chromatograph to give the title compound (1.40 g, 80%). LC-MS $(M+H)^+$=310.0.

Step 4: 3-((1-(cyclopropylmethyl)-1H-pyrazol-4-yl)oxy)-5-(2,5-dimethyl-1,2,3,4-tetrahydroisoquinolin-7-yl)pyrazin-2-amine 5-bromo-3-((1-(cyclopropylmethyl)-1H-pyrazol-4-yl)oxy)pyrazin-2-amine (700 mg, 2.26 mmol), (2,5-dimethyl-1,2,3,4-tetrahydroisoquinolin-7-yl)boronic acid (694 mg, 3.39 mmol), Pd(dppf)$Cl_2$ (83 mg, 0.113 mmol) and $K_2CO_3$ (624 mg, 4.52 mmol) was added to 1,4-dioxane (20 mL) and water (4 mL) and the mixture was heated to 90° C. under $N_2$ for 3 h. The mixture was cooled to room temperature then concentrated under reduced pressure. Water (20 mL) was added and the mixture was extracted with ethyl acetate (30 mL×2). The combined organic layer was washed with brine (20 mL), dried over $Na_2SO_4$ and filtered. The residue was purified by silica gel chromatography to give Example 273 (380 mg, 43%). $^1$H NMR (400 MHz, DMSO-d6) δ 8.18 (s, 1H), 8.10 (s, 1H), 7.58 (s, 1H), 7.48 (s, 1H), 7.35 (s, 1H), 6.66 (s, 2H), 4.00 (d, J=7.0 Hz, 2H), 3.46 (s, 2H), 2.61-2.67 (m, 4H), 2.33 (s, 3H), 2.20 (s, 3H), 1.28 (s, 1H), 0.55 (d, J=7.0 Hz, 2H), 0.41 (d, J=3.7 Hz, 2H). LC-MS $(M+H)^+$=391.0.

Example 274: 3-(1-ethyl-1H-pyrazol-4-yloxy)-5-(5-methoxy-2-methyl-1,2,3,4-tetrahydroisoquinolin-7-yl)pyrazin-2-amine

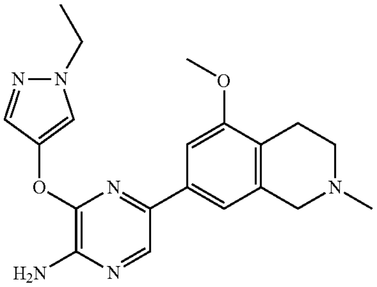 [SMILES: CCn1cc(Oc2nc(-c3cc4c(c(OC)c3)CCN(C)C4)cnc2N)cn1]

Example 274 (9 mg, 27%) was prepared in a manner similar to that in Example 1 step 8 from 5-bromo-3-(1-ethyl-1H-pyrazol-4-yloxy)pyrazin-2-amine and 5-methoxy-2-methyl-7-(4,4,5,5-tetramethyl-1,3,2-dioxaborolan-2-yl)-1,2,3,4-tetrahydroisoquinoline. $^{1}$H NMR (400 MHz, DMSO-d6) δ 8.22 (s, 1H), 8.05 (s, 1H), 7.57 (s, 1H), 7.21 (s, 1H), 7.13 (s, 1H), 6.66 (s, 2H), 4.19-4.06 (m, 2H), 3.80 (s, 3H), 3.45 (s, 2H), 2.66-2.53 (m, 4H), 2.32 (s, 3H), 1.37 (t, J=7.3 Hz, 3H). LC-MS $(M+H)^+$=381.2.

Example 275: 7-(5-amino-6-(1-ethyl-1H-pyrazol-4-yloxy)pyrazin-2-yl)-N,2-dimethyl-1,2,3,4-tetrahydroisoquinolin-5-amine

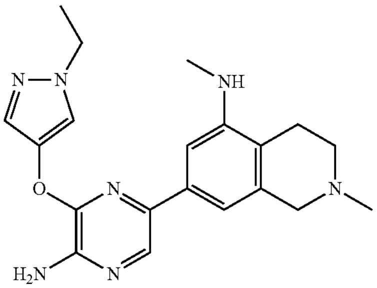 [SMILES: CCn1cc(Oc2nc(-c3cc4c(c(NC)c3)CCN(C)C4)cnc2N)cn1]

Example 275 (32 mg, 34%) was prepared in a manner similar to that in Example 1 step 8 from 5-bromo-3-(1-ethyl-1H-pyrazol-4-yloxy)pyrazin-2-amine and N,2-dimethyl-7-(4,4,5,5-tetramethyl-1,3,2-dioxaborolan-2-yl)-1,2,3,4-tetrahydroisoquinolin-5-amine. $^{1}$H NMR (400 MHz, DMSO-d6) δ 8.14 (s, 1H), 8.03 (s, 1H), 7.58 (s, 1H), 6.80 (s, 2H), 6.56 (s, 2H), 5.08-4.97 (m, 1H), 4.18-4.05 (m, 2H), 3.42 (s, 2H), 2.75 (d, J=4.7 Hz, 3H), 2.67-2.57 (m, 2H), 2.48-2.40 (m, 2H), 2.32 (s, 3H), 1.37 (t, J=7.2 Hz, 3H). LC-MS $(M+H)^+$=380.2.

Example 276: 5-(2,5-dimethyl-1,2,3,4-tetrahydroisoquinolin-7-yl)-3-((1-(2-methoxyethyl)-1H-pyrazol-4-yl)oxy)pyrazin-2-amine

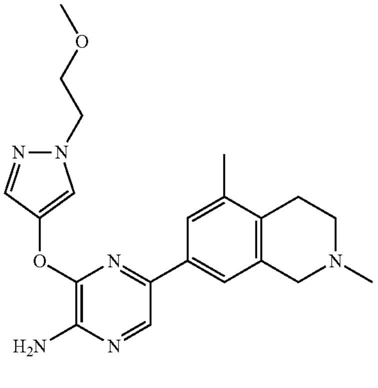 [SMILES: COCCn1cc(Oc2nc(-c3cc(C)c4c(c3)CN(C)CC4)cnc2N)cn1]

Step 1: 1-(2-methoxyethyl)-4-(4,4,5,5-tetramethyl-1,3,2-dioxaborolan-2-yl)-1H-pyrazole

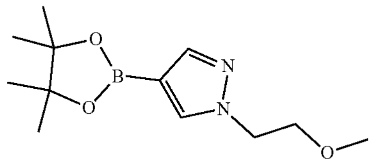

The title compound (700 mg, 54%) was prepared in a manner similar to that in Example 116 step 1 from 4-(4,4,5,5-tetramethyl-1,3,2-dioxaborolan-2-yl)-1H-pyrazole and 1-bromo-2-methoxyethane. LC-MS $(M+H)^+$=253.2.

Step 2: 1-(2-methoxyethyl)-1H-pyrazol-4-ol

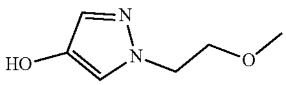

The title compound (330 mg, 84%) was prepared in a manner similar to that in Example 116 step 2 from 1-(2-methoxyethyl)-4-(4,4,5,5-tetramethyl-1,3,2-dioxaborolan-2-yl)-1H-pyrazole. LC-MS $(M+H)^+$=143.2.

Step 3: 5-bromo-3-((1-(2-methoxyethyl)-1H-pyrazol-4-yl)oxy)pyrazin-2-amine

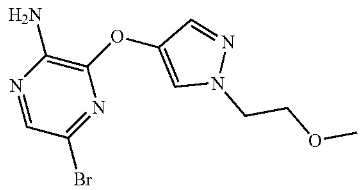 [SMILES: COCCn1cc(Oc2nc(Br)cnc2N)cn1]

The title compound (250 mg, 34%) was prepared in a manner similar to that in Example 116 step 3 from 1-(2-methoxyethyl)-1H-pyrazol-4-ol and 3,5-dibromopyrazin-2-amine. LC-MS $(M+H)^+$=314.1, 316.1.

Step 4: 5-(2,5-dimethyl-1,2,3,4-tetrahydroisoquinolin-7-yl)-3-((1-(2-methoxyethyl)-1H-pyrazol-4-yl)oxy)pyrazin-2-amine Example 276 (79 mg, 25%) was prepared in a manner similar to that in Example 116 step 4 from 5-bromo-3-((1-(2-methoxyethyl)-1H-pyrazol-4-yl)oxy)pyrazin-2-amine and (2,5-dimethyl-1,2,3,4-tetrahydroisoquinolin-7-yl)boronic acid. $^1H$ NMR (400 MHz, DMSO-d6) δ 8.18 (s, 1H), 8.03 (s, 1H), 7.61 (s, 1H), 7.48 (s, 1H), 7.34 (s, 1H), 6.66 (s, 2H), 4.31-4.23 (m, 2H), 3.76-3.68 (m, 2H), 3.49 (s, 2H), 3.25 (s, 3H), 2.71-2.58 (m, 4H), 2.35 (s, 3H), 2.21 (s, 3H). LC-MS $(M+H)^+$=395.4.

Example 277: 3-(4-((3-amino-6-(2,5-dimethyl-1,2,3,4-tetrahydroisoquinolin-7-yl)pyrazin-2-yl)oxy)-1H-pyrazol-1-yl)propanenitrile

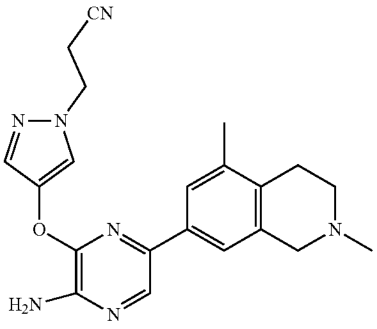 [SMILES: Cc1cc(-c2cnc(N)c(Oc3cnn(CCC#N)c3)n2)cc2c1CCN(C)C2]

Step 1: 3-(4-(4,4,5,5-tetramethyl-1,3,2-dioxaborolan-2-yl)-1H-pyrazol-1-yl)propanenitrile

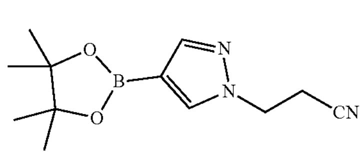 [SMILES: CC1(C)OB(c2cnn(CCC#N)c2)OC1(C)C]

The title compound (500 mg, 39%) was prepared in a manner similar to that in Example 273 step 1 from 4-(4,4,5,5-tetramethyl-1,3,2-dioxaborolan-2-yl)-1H-pyrazole and 3-bromopropanenitrile. LC-MS $(M+H)^+$=248.0.

Step 2: 3-(4-hydroxy-1H-pyrazol-1-yl)propanenitrile

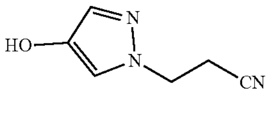

The title compound (270 mg, 97%) was prepared in a manner similar to that in Example 273 step 2 from 3-(4-(4,4,5,5-tetramethyl-1,3,2-dioxaborolan-2-yl)-1H-pyrazol-1-yl)propanenitrile. LC-MS $(M+H)^+$=138.0.

Step 3: 3-(4-((3-amino-6-bromopyrazin-2-yl)oxy)-1H-pyrazol-1-yl)propanenitrile

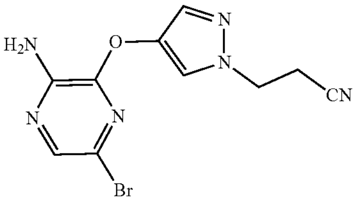 [SMILES: N#CCCn1cc(Oc2nc(Br)cnc2N)cn1]

The title compound (200 mg, 33%) was prepared in a manner similar to that in Example 273 step 3 from 3-(4-hydroxy-1H-pyrazol-1-yl)propanenitrile and 3,5-dibromopyrazin-2-amine. LC-MS $(M+H)^+$=309.0.

Step 4: 3-(4-((3-amino-6-(2,5-dimethyl-1,2,3,4-tetrahydroisoquinolin-7-yl)pyrazin-2-yl)oxy)-1H-pyrazol-1-yl)propanenitrile Example 277 (35 mg, 29%) was prepared in a manner similar to that in Example 273 step 4 from 3-(4-((3-amino-6-bromopyrazin-2-yl)oxy)-1H-pyrazol-1-yl)propanenitrile and ((2,5-dimethyl-1,2,3,4-tetrahydroisoquinolin-7-yl)boronic acid. $^1H$ NMR (400 MHz, DMSO-d6) δ 8.21 (s, 1H), 8.13 (s, 1H), 7.70 (s, 1H), 7.52 (s, 1H), 7.38 (s, 1H), 6.71 (s, 2H), 4.42 (t, J=6.3 Hz, 2H), 3.70 (br s, 2H), 3.11 (t, J=6.3 Hz, 2H), 2.91-2.79 (m, 2H), 2.78-2.70 (m, 2H), 2.46 (s, 3H), 2.22 (s, 3H). LC-MS $(M+H)^+$=390.3.

Example 278: 5-(2,5-dimethyl-1,2,3,4-tetrahydroisoquinolin-7-yl)-3-((1-(2-ethoxyethyl)-1H-pyrazol-4-yl)oxy)pyrazin-2-amine

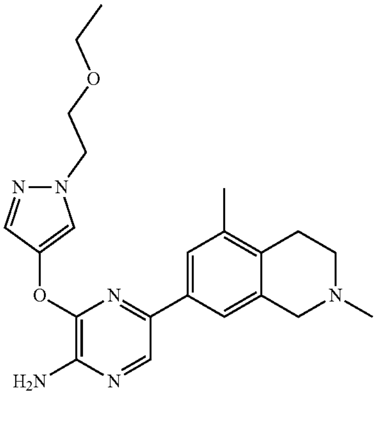 [SMILES: CCOCCn1cc(Oc2nc(-c3cc(C)c4c(c3)CN(C)CC4)cnc2N)cn1]

Step 1: 1-(2-ethoxyethyl)-4-(4,4,5,5-tetramethyl-1,3,2-dioxaborolan-2-yl)-1H-pyrazole

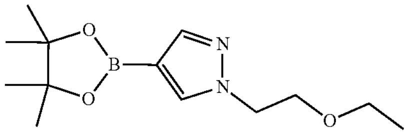 [SMILES: CCOCCn1cc(B2OC(C)(C)C(C)(C)O2)cn1]

To a solution of 4-(4,4,5,5-tetramethyl-1,3,2-dioxaborolan-2-yl)-1H-pyrazole (1.0 g, 5.15 mmol) in THF (20 mL) was added NaH (60%, 412 mg, 10.3 mmol) at 0° C. and the mixture was stirred for 30 min. 1-bromo-2-ethoxyethane (1.18 g, 7.72 mmol) was added. The resulting solution was stirred for 6 h at 65° C. and cooled to room temperature. The reaction mixture was poured into water (100 mL) and then extracted with EtOAc (100 mL×3). The combined organic layer was washed with brine (100 mL), dried over $Na_2SO_4$, filtered and concentrated under vacuum. The residue was purified by silica gel column chromatography, eluted with EtOAc/PE (1:1) to give the title compound (450 mg, 33%). LC-MS $(M+H)^+$=267.2.

Step 2: 1-(2-ethoxyethyl)-1H-pyrazol-4-ol

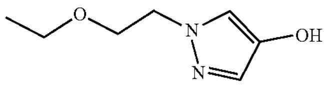

To a solution of 1-(2-ethoxyethyl)-4-(4,4,5,5-tetramethyl-1,3,2-dioxaborolan-2-yl)-1H-pyrazole (450 mg, 1.69 mmol) in THF (10 mL) was added aqueous NaOH (2 M, 1.7 mL, 3.4 mmol) and aqueous $H_2O_2$ (0.39 mL, 3.38 mmol). The mixture was stirred for 2 h at room temperature. The pH of the mixture was acidified with HCl (1 M) to 7 and then extracted with EtOAc (50 mL×3). The combined organic layer was dried over $Na_2SO_4$, filtered and concentrated under vacuum to give the title compound (450 mg, crude). The material was used in step 3 without further purifications. LC-MS $(M+H)^+$=157.2.

Step 3: 5-bromo-3-((1-(2-ethoxyethyl)-1H-pyrazol-4-yl)oxy)pyrazin-2-amine

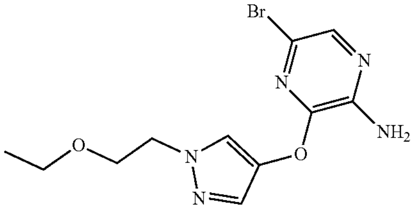 [SMILES: CCOCCn1cc(Oc2nc(Br)cnc2N)cn1]

To a solution of 1-(2-ethoxyethyl)-1H-pyrazol-4-ol (450 mg, crude) in DMSO (8 mL) was added $K_2CO_3$ (1.20 g, 8.60 mmol) and 3,5-dibromopyrazin-2-amine (1.09 g, 4.29 mmol). The mixture was stirred for 3 h at 70° C. and cooled to room temperature. The mixture was poured into water (80 mL) and then extracted with EtOAc (80 mL×3). The combined organic layer was washed with brine (80 mL×2), dried over $Na_2SO_4$, filtered and concentrated under vacuum. The residue was purified by silica gel column chromatography, eluted with EtOAc/PE (1:1) to give the title compound (170 mg, 31% over 2 steps). LC-MS $(M+H)^+$=328.

Step 4: 5-(2,5-dimethyl-1,2,3,4-tetrahydroisoquinolin-7-yl)-3-((1-(2-ethoxyethyl)-1H-pyrazol-4-yl)oxy)pyrazin-2-amine To a solution of 5-bromo-3-((1-(2-ethoxyethyl)-1H-pyrazol-4-yl)oxy)pyrazin-2-amine (170 mg, 0.52 mmol) in 1,4-dioxane (10 mL) and water (2 mL) was added (2,5-dimethyl-1,2,3,4-tetrahydroisoquinolin-7-yl)boronic acid (117 mg, 0.57 mmol), $K_2CO_3$ (215 mg, 1.56 mmol) and Pd(dppf)$Cl_2$ (42 mg, 0.05 mmol). The mixture was stirred for 16 h at 90° C. under nitrogen. The reaction mixture was cooled to room temperature and poured into water (50 mL). The mixture was extracted with EtOAc (50 mL×3). The combined organic layer was washed with brine (50 mL), dried over $Na_2SO_4$, filtered and concentrated under vacuum. The residue was purified by prep-HPLC to give Example 278 (85 mg, 40%). $^1$H NMR (400 MHz, DMSO-$d_6$) δ 8.18 (s, 1H), 8.03 (s, 1H), 7.62 (s, 1H), 7.48 (s, 1H), 7.34 (s, 1H), 6.65 (s, 2H), 4.27 (t, J=5.3 Hz, 2H), 3.75 (t, J=5.3 Hz, 2H), 3.47 (s, 2H), 3.43 (q, J=7.0 Hz, 1H), 2.74-2.57 (m, 4H), 2.33 (s, 3H), 2.21 (s, 3H), 1.05 (t, J=7.0 Hz, 3H). LC-MS $(M+H)^+$=409.3.

Example 279: 1-(3-amino-6-(2,5-dimethyl-1,2,3,4-tetrahydroisoquinolin-7-yl)pyrazin-2-yl)-N-methyl-N-(2-(methylamino)ethyl)-1H-pyrazole-4-carboxamide

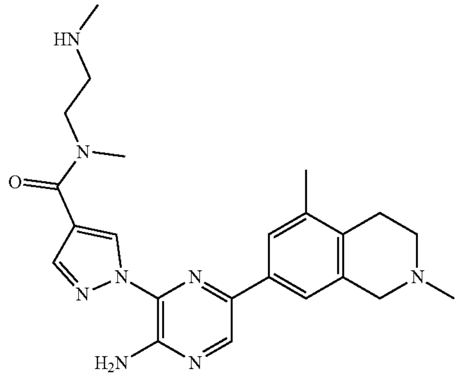 [SMILES: CNCCN(C)C(=O)c1cnn(-c2nc(-c3cc(C)c4c(c3)CN(C)CC4)cnc2N)c1]

Step 1: 3-chloro-5-(2,5-dimethyl-1,2,3,4-tetrahydroisoquinolin-7-yl)pyrazin-2-amine

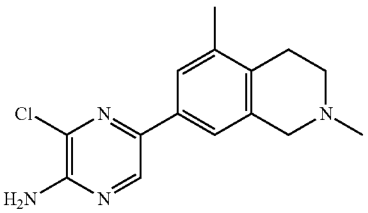 [SMILES: Cc1cc(-c2cnc(N)c(Cl)n2)cc2c1CCN(C)C2]

To a solution of 5-bromo-3-chloropyrazin-2-amine (4.17 g, 20.0 mmol) and (2,5-dimethyl-1,2,3,4-tetrahydroisoquinolin-7-yl)boronic acid (4.1 g, 20.0 mmol) in dioxane (100 mL) and water (20 mL) was added Pd(dppf)$Cl_2$ (732 mg, 1.0 mmol) and $K_2CO_3$ (5.52 g, 40.0 mmol). The mixture was stirred at 60° C. for 5 h under nitrogen. The mixture was cooled to room temperature and diluted with EtOAc (200 mL), washed with brine (100 mL), dried over $Na_2SO_4$, filtered and concentrated under reduced pressure. The residue was purified by silica gel column chromatography, eluted with MeOH/DCM (1:40) to give the title compound (2.50 g, 43%). LC-MS $(M+H)^+$=289.0.

Step 2: methyl 1-(3-amino-6-(2,5-dimethyl-1,2,3,4-tetrahydroisoquinolin-7-yl)pyrazin-2-yl)-1H-pyrazole-4-carboxylate

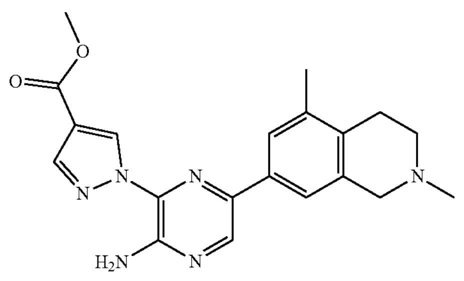 [SMILES: COC(=O)c1cnn(-c2nc(-c3cc(C)c4c(c3)CN(C)CC4)cnc2N)c1]

To a solution of methyl 1H-pyrazole-4-carboxylate (984 mg, 7.81 mmol) in DMF (20 mL) was added NaH (60%, 312 mg, 7.81 mmol) at 0° C. The mixture was stirred at room temperature for 0.5 h, then 3-chloro-5-(2,5-dimethyl-1,2,3,4-tetrahydroisoquinolin-7-yl)pyrazin-2-amine (1.5 g, 5.21 mmol) was added. After 5 h, the mixture was quenched with water (50 mL) at 0° C. and extracted with EtOAc (100 mL). The organic layer was separated, washed with brine (50 mL), dried over $Na_2SO_4$ and concentrated under reduced pressure. The residue was purified by silica gel column chromatography, eluted with MeOH/DCM (1:30) to give the title compound (480 mg, 24%). LC-MS $(M+H)^+$=378.9.

Step 3: 1-(3-amino-6-(2,5-dimethyl-1,2,3,4-tetrahydroisoquinolin-7-yl)pyrazin-2-yl)-1H-pyrazole-4-carboxylic acid

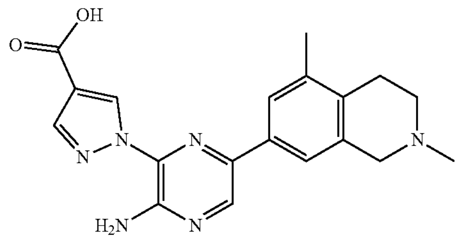 [SMILES: Cc1cc(-c2cnc(N)c(-n3cc(C(=O)O)cn3)n2)cc2c1CCN(C)C2]

To a solution of methyl 1-(3-amino-6-(2,5-dimethyl-1,2,3,4-tetrahydroisoquinolin-7-yl)pyrazin-2-yl)-1H-pyrazole-4-carboxylate (480 mg, 1.27 mmol) in a mixture of MeOH (10 mL) and water (10 mL) was added LiOH (91 mg, 3.81 mmol). The reaction mixture was stirred at room temperature overnight then methanol was evaporated under reduced pressure. The remaining solution was acidified with HCl (1.0 M) to pH=5-6, and the precipitate was collected by filtration then dried under vacuum to give the title compound (300 mg, 65%). LC-MS $(M+H)^+$=365.2.

Step 4: 1-(3-amino-6-(2,5-dimethyl-1,2,3,4-tetrahydroisoquinolin-7-yl)pyrazin-2-yl)-N-methyl-N-(2-(methylamino)ethyl)-1H-pyrazole-4-carboxamide To a solution of 1-(3-amino-6-(2,5-dimethyl-1,2,3,4-tetrahydroisoquinolin-7-yl)pyrazin-2-yl)-1H-pyrazole-4-carboxylic acid (150 mg, 0.41 mmol) in DMF (5 mL) was added HATU (235 mg, 0.62 mmol) and DIPEA (213 mg, 1.65 mmol). The mixture was stirred for 30 min at 25° C., then N,N-dimethylethane-1,2-diamine (180 mg, 2.05 mmol) was added. The mixture was stirred for 3 h at room temperature. The reaction mixture was poured into water (50 mL) and then extracted with EtOAc (50 mL×2). The combined organic layer was washed with brine (50 mL×2), dried over $Na_2SO_4$, filtered and concentrated under vacuum. The residue was purified by prep-HPLC to give Example 279 (60 mg, 34%). $^1H$ NMR (400 MHz, DMSO-$d_6$) δ 9.05 (s, 1H), 8.66 (s, 1H), 8.18 (s, 1H), 7.72 (s, 1H), 7.61 (s, 1H), 7.44 (s, 2H), 3.80-3.70 (m, 2H), 3.69-3.52 (m, 2H), 3.26-3.20 (m, 2H), 3.17-3.11 (m, 2H), 2.81-2.65 (m, 4H), 2.63-2.54 (m, 3H), 2.44-2.36 (m, 4H), 2.34-2.22 (m, 4H). LC-MS $(M+H)^+$=435.4.

Example 280A/280B: (R)-5-(2,5-dimethyl-1,2,3,4-tetrahydroisoquinolin-7-yl)-3-(1-(1-methylpyrrolidin-3-yl)-1H-pyrazol-4-yloxy)pyrazin-2-amine & (S)-5-(2,5-dimethyl-1,2,3,4-tetrahydroisoquinolin-7-yl)-3-(1-(1-methylpyrrolidin-3-yl)-1H-pyrazol-4-yloxy)pyrazin-2-amine

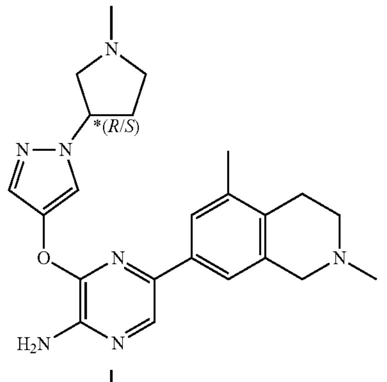

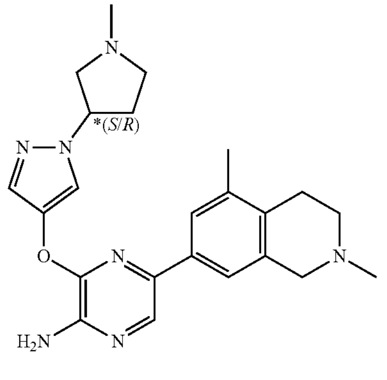

Step 1: 1-methylpyrrolidin-3-yl 4-methylbenzenesulfonate

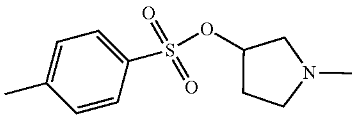

To a solution of 1-methylpyrrolidin-3-ol (0.95 g, 9.392 mmol) in DCM (15 mL) was added DMAP (327 mg, 2.82 mmol), TEA (1.92 g, 18.8 mmol), and p-toluenesulfonyl chloride (2.24 g, 11.7 mmol) at room temperature. The mixture was stirred for 16 h at room temperature under nitrogen then concentrated under reduced pressure. The residue was purified by silica gel chromatography, eluted with MeOH/DCM (0% to 15% gradient) to give the title compound (750 mg, 31%).

Step 2: 5-bromo-3-(1-(1-methylpyrrolidin-3-yl)-1H-pyrazol-4-yloxy)pyrazin-2-amine

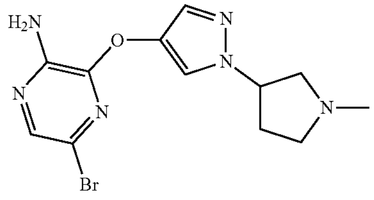 [SMILES: CN1CCC(n2cc(Oc3nc(Br)cnc3N)cn2)C1]

The title compound (105 mg, 36%) was prepared in a manner similar to that in Example 116 step 1 from 1-methylpyrrolidin-3-yl 4-methylbenzenesulfonate and 3-(1H-pyrazol-4-yloxy)-5-bromopyrazin-2-amine. LC-MS $(M+H)^+$=338.9.

Step 3: (R)-5-(2,5-dimethyl-1,2,3,4-tetrahydroisoquinolin-7-yl)-3-(1-(1-methylpyrrolidin-3-yl)-1H-pyrazol-4-yloxy)pyrazin-2-amine & (S)-5-(2,5-dimethyl-1,2,3,4-tetrahydroisoquinolin-7-yl)-3-(1-(1-methylpyrrolidin-3-yl)-1H-pyrazol-4-yloxy)pyrazin-2-amine

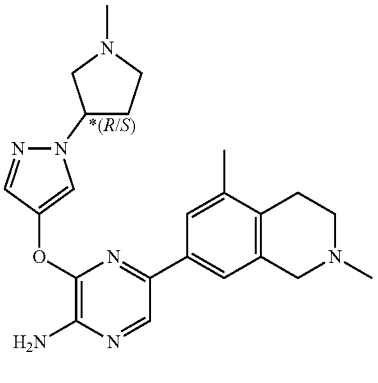

-continued

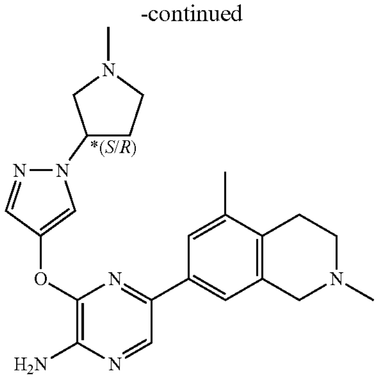

To a solution of 5-bromo-3-(1-(1-methylpyrrolidin-3-yl)-1H-pyrazol-4-yloxy)pyrazin-2-amine (90 mg, 0.265 mmol) in isopropanol (8 mL) was added 2,5-dimethyl-7-(4,4,5,5-tetramethyl-1,3,2-dioxaborolan-2-yl)-3,4-dihydro-1H-isoquinoline (152 mg, 0.531 mmol), $Pd(Amphos)Cl_2$ (29 mg, 0.040 mmol), $K_3PO_4$ (57 mg, 0.265 mmol), and $H_2O$ (2 mL) at room temperature. The mixture was irradiated with microwave for 1 h at 80° C. The mixture was cooled to room temperature and then diluted with water (30 mL). The mixture was extracted with ethyl acetate (50 mL×3). The combined organic layer was washed with brine (50 mL) and dried over $Na_2SO_4$ filtered and concentrated under reduced pressure. The residue was purified by prep-HPLC then chiral prep-HPLC to give Example 280A and Example 280B.

Analytical chiral HPLC condition: CHIRALPAK IG-3, 0.46×5 cm, 3.0 μm. Mobile phase: Hexane (10 mM $NH_3$) in (EtOH:DCM=1:1), 7:3 isocratic, 1 mL/min.

Example 280A: (10 mg, 17%) $^1H$ NMR (400 MHz, $CDCl_3$) δ 8.15 (s, 1H), 8.02 (s, 1H), 7.69 (s, 1H), 7.50 (s, 1H), 7.37 (s, 1H), 4.93 (br s, 3H), 4.98-4.87 (m, 1H), 3.63 (s, 2H), 3.01-2.89 (m, 3H), 2.88-2.71 (m, 4H), 2.62-2.52 (m, 2H), 2.49 (s, 3H), 2.43 (s, 3H), 2.32-2.20 (m, 4H). LC-MS $(M+H)^+$=420.3. Chiral HPLC: tR=4.45 min.

Example 280B: (15 mg, 26%) $^1H$ NMR (400 MHz, $CDCl_3$) δ 8.15 (s, 1H), 8.01 (s, 1H), 7.69 (s, 1H), 7.50 (s, 1H), 7.37 (s, 1H), 5.00-4.89 (m, 3H), 4.98-4.87 (m, 1H), 3.66 (s, 2H), 3.00-2.89 (m, 3H), 2.88-2.71 (m, 4H), 2.62-2.52 (m, 2H), 2.49 (s, 3H), 2.43 (s, 3H), 2.33-2.20 (m, 4H). LC-MS $(M+H)^+$=420.3. Chiral HPLC: tR=4.96 min.

Example 281: (1-(3-amino-6-(2,5-dimethyl-1,2,3,4-tetrahydroisoquinolin-7-yl)pyrazin-2-yl)-1H pyrazol-4-yl)(3,3-difluoropyrrolidin-1-yl)methanone

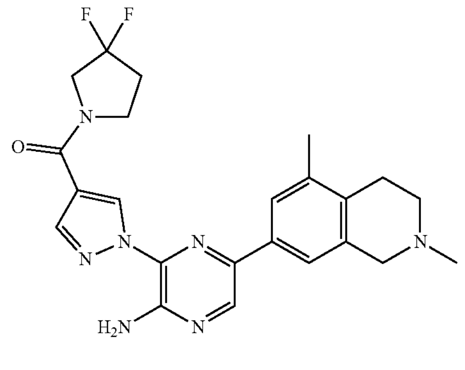 [SMILES: Cc1cc(-c2cnc(N)c(-n3cc(C(=O)N4CCC(F)(F)C4)cn3)n2)cc2c1CCN(C)C2]

Example 281 (26 mg, 21%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and 3,3-difluoropyrrolidine. $^1$H NMR (400 MHz, DMSO-d6) δ 9.08 (s, 1H), 8.66 (s, 1H), 8.26 (s, 1H), 7.71 (s, 1H), 7.60 (s, 1H), 7.38 (s, 2H), 4.34-4.23 (m, 1H), 4.10-4.02 (m, 1H), 3.98-3.87 (m, 1H), 3.78-3.70 (m, 1H), 3.55 (s, 2H), 2.75-2.61 (m, 4H), 2.61-2.52 (m, 1H), 2.49-2.41 (m, 1H), 2.36 (s, 3H), 2.27 (s, 3H). LC-MS $(M+H)^+$=454.3.

Example 282: (S)-3-((2-amino-3-((tetrahydrofuran-3-yl)oxy)pyridin-4-yl)methoxy)-5-(2,5-dimethyl-1,2,3,4-tetrahydroisoquinolin-7-yl)pyrazin-2-amine

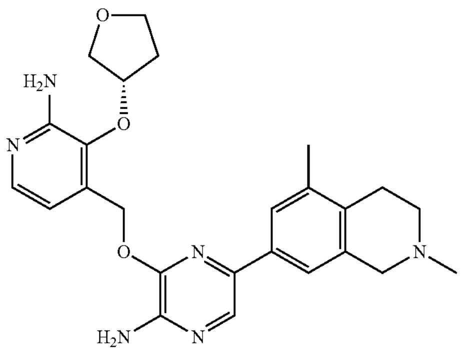 [SMILES: Cc1cc(-c2cnc(N)c(OCc3ccnc(N)c3O[C@H]3CCOC3)n2)cc2c1CCN(C)C2]

Step 1: methyl (S)-2-chloro-3-((tetrahydrofuran-3-yl)oxy)isonicotinate

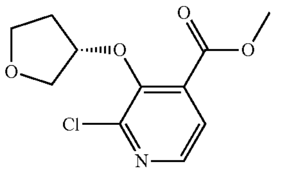 [SMILES: COC(=O)c1ccnc(Cl)c1O[C@H]1CCOC1]

NaH (60%, 858 mg, 21.4 mmol) was added to a solution of 2-chloro-3-fluoroisonicotinic acid (1.5 g, 8.6 mmol) and (S)-tetrahydrofuran-3-ol (754 mg, 8.6 mmol) in DMF (20 mL) and the mixture was stirred at room temperature overnight. Water (60 mL) was added and the mixture was extracted with EtOAc (50 mL). The organic layer was washed with brine (30 mL), dried over $Na_2SO_4$, filtered and concentrated in vacuo. The residue was dissolved in methanol (100 mL) and concentrated $H_2SO_4$ (3.0 mL) was carefully added. The reaction mixture was heated to reflux for overnight. Solvent was removed in vacuo and the residue was carefully diluted with ice-water (70 mL), then extracted with EtOAc (30 mL). The organic layer was separated and washed with brine (30 mL), dried over $Na_2SO_4$, filtered and concentrated. The residue was purified by prep-TLC, developed with PE/EtOAc (2:1) to give the title compound (1.1 g, 50%). LC-MS $(M+H)^+$=258.0.

Step 2: methyl (S)-2-amino-3-((tetrahydrofuran-3-yl)oxy)isonicotinate

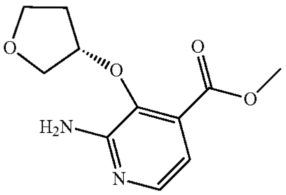 [SMILES: COC(=O)c1ccnc(N)c1O[C@H]1CCOC1]

methyl (S)-2-chloro-3-((tetrahydrofuran-3-yl)oxy)isonicotinate (1.1 g, 4.3 mmol), diphenylmethanimine (852 mg, 4.7 mmol), $Pd_2(dba)_3$ (123 mg, 0.21 mmol), Xantphos (247 mg, 0.43 mmol) and $Cs_2CO_3$ (2.8 g, 8.6 mmol) was added to toluene (30 mL) and dioxane (30 mL) under nitrogen. The mixture was heated to reflux overnight then cooled to RT, filtered and the solid was washed with DCM (20 mL). The filtrate was concentrated in vacuo. The residue was re-dissolved in methanol (10 mL) and HCl (3.0 M, 10 mL) was added. The mixture was stirred for 30 min followed by addition of water (20 mL). The mixture was extracted with EtOAc (30 mL) and the organic layer was concentrated in vacuo. The residue was purified by prep-TLC, developed with PE/EtOAc (2:1) to give the title compound (490 mg, 50%). LC-MS $(M+H)^+$=239.1.

Step 3: (S)-(2-amino-3-((tetrahydrofuran-3-yl)oxy)pyridin-4-yl)methanol

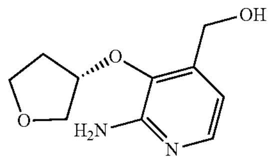 [SMILES: Nc1nccc(CO)c1O[C@H]1CCOC1]

The title compound (400 mg, 93%) was prepared in a manner similar to that in Example 29 step 2 from methyl (S)-2-amino-3-((tetrahydrofuran-3-yl)oxy)isonicotinate. LC-MS $(M+H)^+$=211.1.

Step 4: (S)-3-((2-amino-3-((tetrahydrofuran-3-yl)oxy)pyridin-4-yl)methoxy)-5-bromopyrazin-2-amine

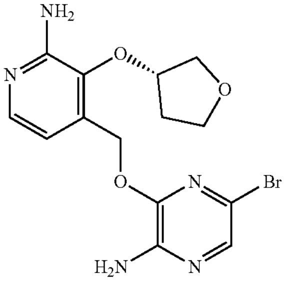 [SMILES: Nc1ncc(Br)nc1OCc1ccnc(N)c1O[C@H]1CCOC1]

The title compound (43 mg, 19%) was prepared in a manner similar to that in Example 29 step 3 from (S)-(2-amino-3-((tetrahydrofuran-3-yl)oxy)pyridin-4-yl)methanol. LC-MS $(M+H)^+$=382.0.

Step 5: (S)-3-((2-amino-3-((tetrahydrofuran-3-yl)oxy)pyridin-4-yl)methoxy)-5-(2,5-dimethyl-1,2,3,4-tetrahydroisoquinolin-7-yl)pyrazin-2-amine Example 282 (401 mg, 16%) was prepared in a manner similar to that in Example 17 step 2 from (S)-3-((2-amino-3-((tetrahydrofuran-3-yl)oxy)pyridin-4-yl)methoxy)-5-bromopyrazin-2-amine and (2,5-dimethyl-1,2,3,4-tetrahydroisoquinolin-7-yl)boronic acid. $^1$H NMR (400 MHz, DMSO-d6) δ 8.07 (s, 1H), 7.71 (d, J=5.0 Hz, 1H), 7.52 (s, 1H), 7.40 (s, 1H), 6.78 (d, J=4.9 Hz, 1H), 6.47 (s, 2H), 5.81 (s, 2H), 5.54-5.44 (m, 2H), 4.92 (s, 1H), 4.04 (t, J=7.9 Hz, 1H), 3.90 (d, J=10.5 Hz, 1H), 3.84-3.75 (m, 1H), 3.62 (d, J=10.3 Hz, 1H), 3.48 (s, 2H), 2.70-2.58 (m, 4H), 2.34 (s, 3H), 2.21 (s, 3H), 2.16-2.07 (m, 2H). LC-MS $(M+H)^+$=463.4.

Example 283: 1-(3-amino-6-(2,5-dimethyl-1,2,3,4-tetrahydroisoquinolin-7-yl)pyrazin-2-yl)-N-(2-methoxyethyl)-N-methyl-1H-pyrazole-4-carboxamide

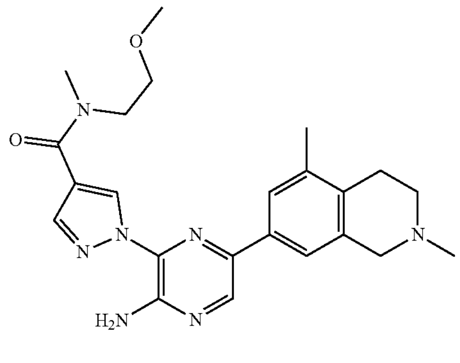 [SMILES: COCCN(C)C(=O)c1cnn(-c2nc(-c3cc(C)c4c(c3)CN(C)CC4)cnc2N)c1]

Step 1: 1-(3-amino-6-(2,5-dimethyl-1,2,3,4-tetrahydroisoquinolin-7-yl)pyrazin-2-yl)-N-(2-methoxyethyl)-N-methyl-1H-pyrazole-4-carboxamide To a solution of 1-(3-amino-6-(2,5-dimethyl-1,2,3,4-tetrahydroisoquinolin-7-yl)pyrazin-2-yl)-1H-pyrazole-4-carboxylic acid (100 mg, 0.275 mmol) in DMF (10 mL) was added 2-methoxy-N-methylethan-1-amine (73 mg, 0.824 mmol), HATU (157 mg, 0.412 mmol) and DIPEA (177 mg, 1.37 mmol) under nitrogen. The reaction mixture was stirred at room temperature overnight. The mixture was diluted with water (30 mL), extracted with EtOAc (20 mL×2). The combined organic layer was washed with brine (30 mL), dried over sodium sulfate, filtered and concentrated under reduced pressure. The residue was purified by prep-HPLC to give Example 283 (5 mg, 4%). $^1$H NMR (400 MHz, DMSO-d6) δ 9.08-9.03 (m, 1H), 8.64 (s, 1H), 8.18-8.10 (m, 1H), 7.71 (s, 1H), 7.60 (s, 1H), 7.45 (s, 2H), 3.72-3.52 (m, 6H), 3.31-2.98 (m, 6H), 2.75-2.50 (m, 4H), 2.38 (s, 3H), 2.26 (s, 3H). LC-MS $(M+H)^+$=436.4.

Example 284: (1-(3-amino-6-(2,5-dimethyl-1,2,3,4-tetrahydroisoquinolin-7-yl)pyrazin-2-yl)-1H-pyrazol-4-yl)(4-methylpiperazin-1-yl)methanone

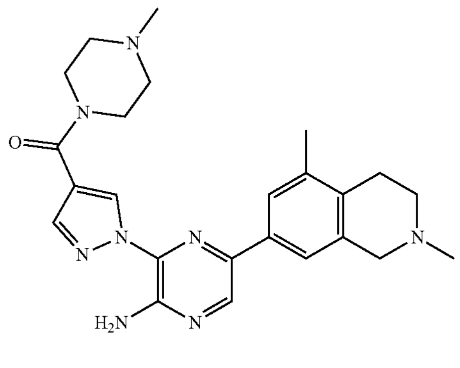 [SMILES: Cc1cc(-c2cnc(N)c(-n3cc(C(=O)N4CCN(C)CC4)cn3)n2)cc2c1CCN(C)C2]

Example 284 (10 mg, 8%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and 1-methylpiperazine. $^1$H NMR (400 MHz, DMSO-d6) δ 9.00 (s, 1H), 8.64 (s, 1H), 8.10 (s, 1H), 7.71 (s, 1H), 7.61 (s, 1H), 7.41 (s, 2H), 3.64 (s, 4H), 3.54 (s, 2H), 2.70 (d, J=4.9 Hz, 2H), 2.64 (d, J=5.0 Hz, 2H), 2.35 (app s, 7H), 2.26 (s, 3H), 2.21 (s, 3H). LC-MS $(M+H)^+$=447.4.

Example 285: 1-(3-amino-6-(2,5-dimethyl-1,2,3,4-tetrahydroisoquinolin-7-yl)pyrazin-2-yl)-N-(2-(pyrrolidin-1-yl)ethyl)-1H-pyrazole-4-carboxamide

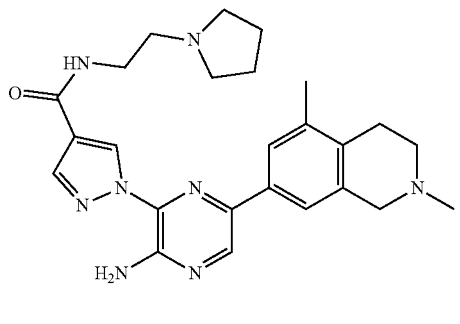

Example 285 (12 mg, 7%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and 2-(pyrrolidin-1-yl)ethanamine. $^1$H NMR (400 MHz, DMSO-d6) δ 9.23 (s, 1H), 8.64 (s, 1H), 8.48-8.41 (m, 1H), 8.24 (s, 1H), 7.70 (s, 1H), 7.58 (s, 1H), 7.47-7.41 (m, 2H), 3.55 (s, 2H), 3.43-3.34 (m, 2H), 2.75-2.56 (m, 6H), 2.53-2.51 (m, 2H), 2.50-2.46 (m, 2H), 2.36 (s, 3H), 2.28 (s, 3H), 1.75-1.63 (m, 4H). LC-MS $(M+H)^+$=461.3.

Example 286: 1-(3-amino-6-(2,5-dimethyl-1,2,3,4-tetrahydroisoquinolin-7-yl)pyrazin-2-yl)-N-(2-chlorophenyl)-N-methyl-1H-pyrazole-4-carboxamide

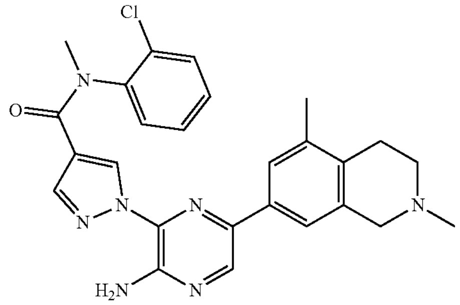 [SMILES: Cc1cc(-c2cnc(N)c(-n3cc(C(=O)N(C)c4ccccc4Cl)cn3)n2)cc2c1CCN(C)C2]

Example 286 (29 mg, 21%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and 2-chloro-N-methylbenzenamine. $^1$H NMR (400 MHz, DMSO-d6) δ 8.58 (s, 1H), 7.81-7.64 (m, 4H), 7.62-7.49 (m, 3H), 7.42-7.32 (m, 3H), 3.63 (s, 2H), 3.30 (s, 3H), 2.77-2.66 (m, 4H), 2.42 (s, 3H), 2.32 (s, 3H). LC-MS $(M+H)^+$=488.1.

Example 287: 3-amino-6-(2,5-dimethyl-1,2,3,4-tetrahydroisoquinolin-7-yl)-N-(pyridin-4-yl)pyrazine-2-carboxamide

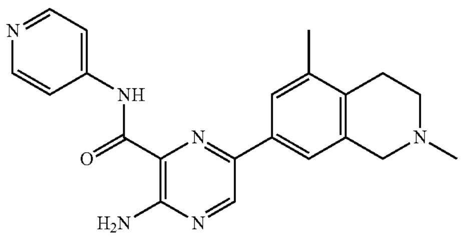 [SMILES: Cc1cc(-c2cnc(N)c(C(=O)Nc3ccncc3)n2)cc2c1CCN(C)C2]

Step 1: 3-amino-6-bromo-N-(pyridin-4-yl)pyrazine-2-carboxamide

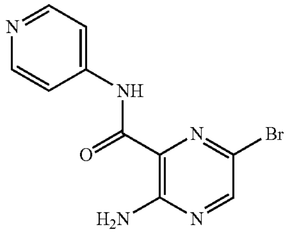 [SMILES: Nc1ncc(Br)nc1C(=O)Nc1ccncc1]

The title compound (69 mg, 11%) was prepared in a manner similar to that in Example 279 step 4 from 3-amino-6-bromopyrazine-2-carboxylic acid and pyridin-4-amine. LC-MS $(M+H)^+$=294.0.

Step 2: 3-amino-6-(2,5-dimethyl-1,2,3,4-tetrahydroisoquinolin-7-yl)-N-(pyridin-4-yl)pyrazine-2-carboxamide Example 287 (12 mg, 5%) was prepared in a manner similar to that in Example 1 step 8 from 3-amino-6-bromo-N-(4-chloro-3-methoxyphenyl)pyrazine-2-carboxamide and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 10.62 (s, 1H), 8.91 (s, 1H), 8.55-8.49 (m, 2H), 7.93-7.87 (m, 2H), 7.85 (s, 1H), 7.76 (s, 1H), 7.64 (s, 2H), 3.57 (s, 2H), 2.77-2.61 (m, 4H), 2.37 (s, 3H), 2.29 (s, 3H). LC-MS $(M+H)^+$=375.1.

Example 288: 5-(2,5-dimethyl-1,2,3,4-tetrahydroisoquinolin-7-yl)-3-(1-(1-(pyridin-3-yl)ethyl)-1H-pyrazol-4-yloxy)pyrazin-2-amine

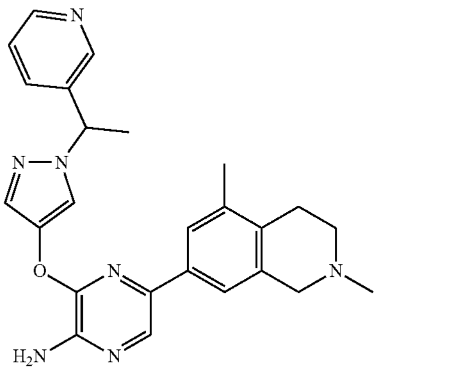 [SMILES: Cc1cc(-c2cnc(N)c(Oc3cnn(C(C)c4cccnc4)c3)n2)cc2c1CCN(C)C2]

Step 1: 3-(1-(4-(4,4,5,5-tetramethyl-1,3,2-dioxaborolan-2-yl)-1H-pyrazol-1-yl)ethyl)pyridine

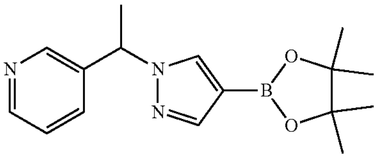 [SMILES: CC(c1cccnc1)n1cc(B2OC(C)(C)C(C)(C)O2)cn1]

The title compound (350 mg, 48%) was prepared in a manner similar to that in Example 116 step 1 from 4-(4,4,5,5-tetramethyl-1,3,2-dioxaborolan-2-yl)-1H-pyrazole and 3-(1-chloroethyl)pyridine. LC-MS $(M+H)^+$=300.1.

Step 2: 1-(1-(pyridin-3-yl)ethyl)-1H-pyrazol-4-ol

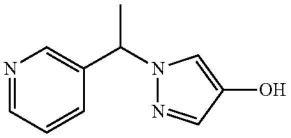

The title compound (140 mg, 79%) was prepared in a manner similar to that in Example 116 step 2 from 3-(1-(4-(4,4,5,5-tetramethyl-1,3,2-dioxaborolan-2-yl)-1H-pyrazol-1-yl)ethyl)pyridine.

LC-MS $(M+H)^+$=190.1.

Step 3: 5-bromo-3-(1-(1-(pyridin-3-yl)ethyl)-1H-pyrazol-4-yloxy)pyrazin-2-amine

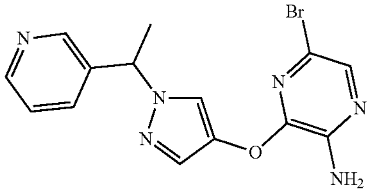 [SMILES: CC(c1cccnc1)n1cc(Oc2nc(Br)cnc2N)cn1]

The title compound (90 mg, 60%) was prepared in a manner similar to that in Example 116 step 3 from 1-(1-(pyridin-3-yl)ethyl)-1H-pyrazol-4-ol and 3,5-dibromopyrazin-2-amine. LC-MS $(M+H)^+$=361.0.

Step 4: 5-(2,5-dimethyl-1,2,3,4-tetrahydroisoquinolin-7-yl)-3-(1-(1-(pyridin-3-yl)ethyl)-1H-pyrazol-4-yloxy)pyrazin-2-amine Example 288 (17 mg, 18%) was prepared in a manner similar to that in Example 116 step 4 from 5-bromo-3-(1-(1-(pyridin-3-yl)ethyl)-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.54-8.47 (m, 2H), 8.24 (s, 1H), 8.19 (s, 1H), 7.72-7.63 (m, 2H), 7.45 (s, 1H), 7.40-7.32 (m, 1H), 7.32-7.27 (m, 1H), 6.66-6.61 (m, 2H), 5.74 (t, J=7.1 Hz, 1H), 3.42 (s, 2H), 2.70-2.57 (m, 4H), 2.34 (s, 3H), 2.17 (s, 3H), 1.88 (d, J=7.1 Hz, 3H). LC-MS $(M+H)^+$=442.2.

Example 289: 1-(3-amino-6-(2-methyl-5-(methylamino)-1,2,3,4-tetrahydroisoquinolin-7-yl)pyrazin-2-yl)-N,N-dimethyl-1H-pyrazole-4-carboxamide

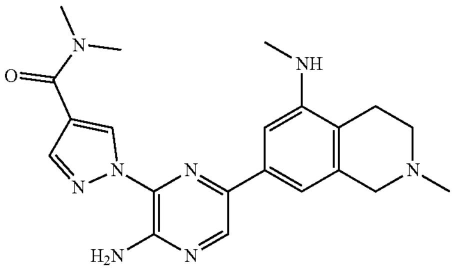

Step 1: ethyl 1-(3-amino-6-bromopyrazin-2-yl)-1H-pyrazole-4-carboxylate

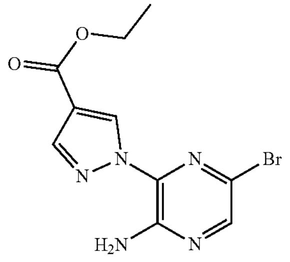 [SMILES: CCOC(=O)c1cnn(-c2nc(Br)cnc2N)c1]

To a stirred solution of ethyl 1H-pyrazole-4-carboxylate (5.0 g, 33.9 mmol) in DMF (100 mL) was added NaH (60%, 2.03 g, 50.8 mmol) at 0° C. under nitrogen. The mixture was stirred for 30 min at 0° C. then 3,5-dibromopyrazin-2-amine (9.0 g, 33.9 mmol) was added. The mixture was stirred for 16 h at 70° C. The mixture was cooled to room temperature then poured to iced water (50 mL). The mixture was extracted with EtOAc (60 mL×2). The combined organic layer was dried over anhydrous $Na_2SO_4$, filtered and concentrated under reduced pressure. The residue was purified by silica gel column chromatography, eluted with MeOH/DCM (1:9) to give the title compound (3.9 g, 35%). LC-MS $(M+H)^+$=312.0.

Step 2: 1-(3-amino-6-bromopyrazin-2-yl)-1H-pyrazole-4-carboxylic acid

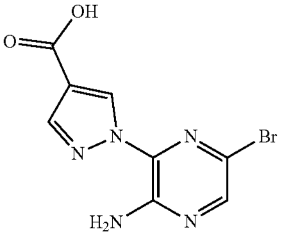 [SMILES: Nc1ncc(Br)nc1-n1cc(C(=O)O)cn1]

A mixture of ethyl 1-(3-amino-6-bromopyrazin-2-yl)pyrazole-4-carboxylate (1.0 g, 3.08 mmol) and NaOH (519 mg, 12.3 mmol) in EtOH (40 mL) and water (24 mL) was stirred for 1 h at 80° C. under nitrogen then cooled to room temperature. The pH of the mixture was adjusted to 6 with aqueous HCl (1 M). The precipitate was collected by filtration and washed with water (10 mL×2) then dried under vacuum to give the title compound (610 mg, 69%). LC-MS $(M+H)^+$=283.9.

Step 3: 1-(3-amino-6-bromopyrazin-2-yl)-N,N-dimethyl-1H-pyrazole-4-carboxamide

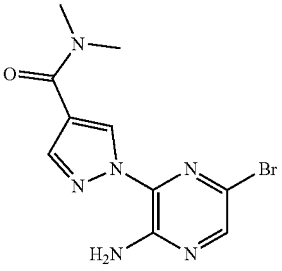 [SMILES: CN(C)C(=O)c1cnn(-c2nc(Br)cnc2N)c1]

The title compound (565 mg, 90%) was prepared in a manner similar to that in Example 279 step 4 from 1-(3-amino-6-bromopyrazin-2-yl)-1H-pyrazole-4-carboxylic acid and dimethylamine. LC-MS $(M+H)^+$=313.0.

Step 4: 1-(3-amino-6-(2-methyl-5-(methylamino)-1,2,3,4-tetrahydroisoquinolin-7-yl)pyrazin-2-yl)-N,N-dimethyl-1H-pyrazole-4-carboxamide Example 289 (26 mg, 21%) was prepared in a manner similar to that in Example 1 step 8 from 1-(3-amino-6- bromopyrazin-2-yl)-N,N-dimethyl-1H-pyrazole-4-carboxamide and N,2-dimethyl-7-(4,4,5,5-tetramethyl-1,3,2-dioxaborolan-2-yl)-1,2,3,4-tetrahydroisoquinolin-5-amine. $^1$H NMR (400 MHz, DMSO-d6) δ 8.95 (s, 1H), 8.62 (s, 1H), 8.15 (s, 1H), 7.39-7.33 (m, 2H), 7.03 (s, 1H), 6.95 (s, 1H), 5.13-5.07 (m, 1H), 3.48 (s, 2H), 3.22 (s, 3H), 3.04-2.99 (m, 2H), 2.85-2.79 (m, 3H), 2.67-2.59 (m, 2H), 2.34 (s, 3H), 2.08 (s, 3H). LC-MS $(M+H)^+$=407.3.

Example 290: 1-(3-amino-6-(5-(cyclopropylamino)-2-methyl-1,2,3,4-tetrahydroisoquinolin-7-yl)pyrazin-2-yl)-N,N-dimethyl-1H-pyrazole-4-carboxamide

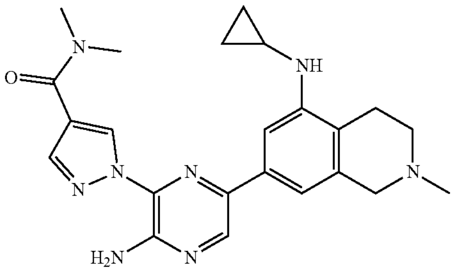 [SMILES: CN1CCc2c(cc(-c3cnc(N)c(-n4cc(C(=O)N(C)C)cn4)n3)cc2NC2CC2)C1]

Step 1: 1-(3-amino-6-(4,4,5,5-tetramethyl-1,3,2-dioxaborolan-2-yl)pyrazin-2-yl)-N,N-dimethyl-1H-pyrazole-4-carboxamide

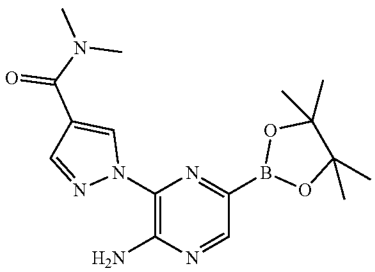 [SMILES: CN(C)C(=O)c1cnn(-c2nc(B3OC(C)(C)C(C)(C)O3)cnc2N)c1]

The title compound (191 mg, 59%) was prepared in a manner similar to that in Example 1 step 6 from 1-(3-amino-6-bromopyrazin-2-yl)-N,N-dimethyl-1H-pyrazole-4-carboxamide. LC-MS $(M\text{-pin})^+$=277.0.

Step 2: 7-bromo-N-(1-methoxycyclopropyl)-2-methyl-1,2,3,4-tetrahydroisoquinolin-5-amine

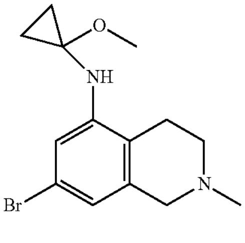 [SMILES: COC1(Nc2cc(Br)cc3c2CCN(C)C3)CC1]

At 0° C., to a solution of 7-bromo-2-methyl-3,4-dihydro-1H-isoquinolin-5-amine (185 mg, 0.77 mmol) in AcOH (4 mL) and MeOH (1 mL) was added (1-ethoxycyclopropoxy) trimethylsilane (206 mg, 1.18 mmol) dropwise. The mixture was stirred for 1 h at 80° C. under nitrogen then cooled to room temperature. The mixture was concentrated under reduced pressure to give the title compound (233 mg, 98%). LC-MS $(M+H)^+$=311.0.

Step 3: 7-bromo-N-cyclopropyl-2-methyl-1,2,3,4-tetrahydroisoquinolin-5-amine

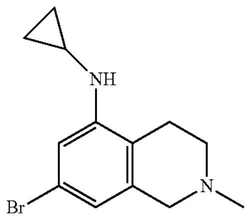 [SMILES: CN1CCc2c(cc(Br)cc2NC2CC2)C1]

At 0° C., to a suspension of $NaBH_4$ (81 mg, 2.13 mmol) in THF (5 mL) was added $BF_3{\cdot}Et_2O$ (303 mg, 2.14 mmol). The mixture was stirred for 1 h, and then 7-bromo-N-(1-methoxycyclopropyl)-2-methyl-1,2,3,4-tetrahydroisoquinolin-5-amine (233 mg, 0.75 mmol) was added. The mixture was warmed to room temperature and stirred for 4 h. The mixture was poured into iced water (20 mL). The mixture was successively extracted with ethyl acetate (20 mL×3). The combined organic layer was washed with brine (20 mL) and dried over $Na_2SO_4$, filtered and concentrated under reduced pressure to give the title compound (183 mg, 87%). LC-MS $(M+H)^+$=281.1.

Step 4: 1-(3-amino-6-(5-(cyclopropylamino)-2-methyl-1,2,3,4-tetrahydroisoquinolin-7-yl)pyrazin-2-yl)-N,N-dimethyl-1H-pyrazole-4-carboxamide

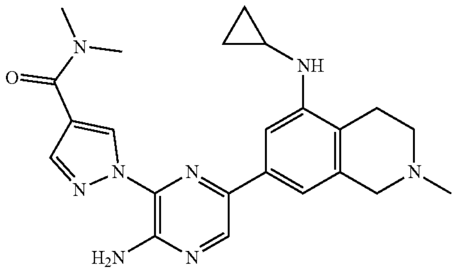 [SMILES: CN1CCc2c(cc(-c3cnc(N)c(-n4cc(C(=O)N(C)C)cn4)n3)cc2NC2CC2)C1]

Example 290 (19 mg, 19%) was prepared in a manner similar to that in Example 1 step 8 from 1-(3-amino-6-(4,4,5,5-tetramethyl-1,3,2-dioxaborolan-2-yl)pyrazin-2-yl)-N,N-dimethyl-1H-pyrazole-4-carboxamide and 7-bromo-N-cyclopropyl-2-methyl-1,2,3,4-tetrahydroisoquinolin-5-amine. $^1$H NMR (400 MHz, DMSO-d6) δ 8.93 (s, 1H), 8.58 (s, 1H), 8.16 (s, 1H), 7.44-7.34 (m, 3H), 7.07 (s, 1H), 5.41 (s, 1H), 3.48 (s, 2H), 3.23 (s, 3H), 3.04-2.99 (m, 4H), 2.65-2.57 (m, 2H), 2.50-2.44 (m, 2H), 2.34 (s, 3H), 0.81-0.72 (m, 2H), 0.53-0.45 (m, 2H). LC-MS $(M+H)^+$=433.3.

Example 291: 1-(3-amino-6-(2,5-dimethyl-1,2,3,4-tetrahydroisoquinolin-7-yl)pyrazin-2-yl)-N-cyclopropyl-N-methyl-1H-pyrazole-4-carboxamide

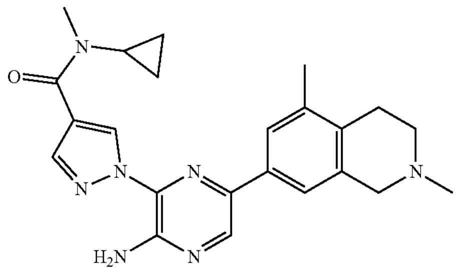 [SMILES: Cc1cc(-c2cnc(N)c(-n3cc(C(=O)N(C)C4CC4)cn3)n2)cc2c1CCN(C)C2]

Example 291 (30 mg, 37%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and N-methylcyclopropanamine. $^1H$ NMR (400 MHz, DMSO-d6) δ 9.07 (s, 1H), 8.63 (s, 1H), 8.25 (s, 1H), 7.68 (s, 1H), 7.57 (s, 1H), 7.41 (d, J=5.0 Hz, 2H), 3.53 (s, 2H), 3.24-3.15 (m, 1H), 3.02 (s, 3H), 2.77-2.59 (m, 4H), 2.35 (s, 3H), 2.25 (s, 3H), 0.89-0.79 (m, 2H), 0.71-0.62 (m, 2H). LC-MS $(M+H)^+$=418.4.

Example 292: 1-(3-amino-6-(2,5-dimethyl-1,2,3,4-tetrahydroisoquinolin-7-yl)pyrazin-2-yl)-N-(2-ethoxyethyl)-N-methyl-1H-pyrazole-4-carboxamide

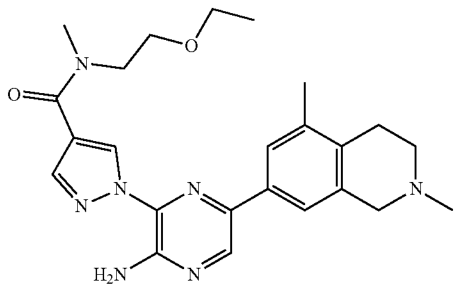 [SMILES: CCOCCN(C)C(=O)c1cnn(-c2nc(-c3cc(C)c4c(c3)CN(C)CC4)cnc2N)c1]

Example 292 (210 mg, 34%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and N-(2-ethoxyethyl)-N-methylamine hydrochloride. $^1H$ NMR (400 MHz, DMSO-d6) δ 9.11-8.98 (m, 1H), 8.63 (s, 1H), 8.20-8.09 (m, 1H), 7.69 (s, 1H), 7.58 (s, 1H), 7.46-7.35 (m, 2H), 3.66-3.44 (m, 8H), 3.30-2.97 (m, 3H), 2.75-2.60 (m, 4H), 2.36 (s, 3H), 2.25 (s, 3H), 1.12 (t, J=6.8 Hz, 3H). LC-MS $(M+H)^+$=450.6.

Example 293: 5-(2,5-dimethyl-1,2,3,4-tetrahydroisoquinolin-7-yl)-3-(1-((tetrahydro-2H-pyran-4-yl)methyl)-1H-pyrazol-4-yloxy)pyrazin-2-amine

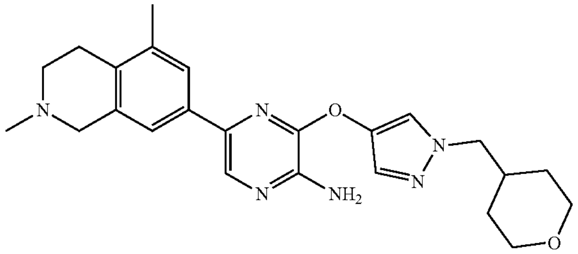 [SMILES: Cc1cc(-c2cnc(N)c(Oc3cnn(CC4CCOCC4)c3)n2)cc2c1CCN(C)C2]

Step 1: 1-((tetrahydro-2H-pyran-4-yl)methyl)-4-(4,4,5,5-tetramethyl-1,3,2-dioxaborolan-2-yl)-1H-pyrazole

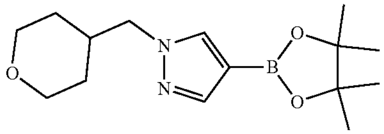 [SMILES: CC1(C)OB(c2cnn(CC3CCOCC3)c2)OC1(C)C]

The title compound (458 mg, 60%) was prepared in a manner similar to that in Example 116 step 1 from 4-(4,4,5,5-tetramethyl-1,3,2-dioxaborolan-2-yl)-1H-pyrazole and 4-(bromomethyl)-tetrahydro-2H-pyran. LC-MS $(M-H)^+$=293.1.

Step 2: 1-((tetrahydro-2H-pyran-4-yl)methyl)-1H-pyrazol-4-ol

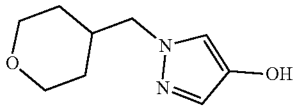 [SMILES: Oc1cnn(CC2CCOCC2)c1]

The title compound (270 mg, 92%) was prepared in a manner similar to that in Example 116 step 2 from 1-((tetrahydro-2H-pyran-4-yl)methyl)-4-(4,4,5,5-tetramethyl-1,3,2-dioxaborolan-2-yl)-1H-pyrazole. LC-MS $(M-H)^+$=183.1.

Step 3: 5-bromo-3-(1-((tetrahydro-2H-pyran-4-yl)methyl)-1H-pyrazol-4-yloxy)pyrazin-2-amine

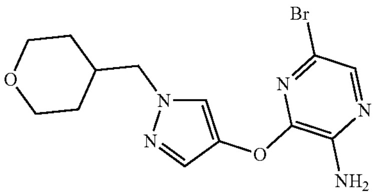 [SMILES: Nc1ncc(Br)nc1Oc1cnn(CC2CCOCC2)c1]

The title compound (242 mg, 80%) was prepared in a manner similar to that in Example 116 step 3 from 1-((tetrahydro-2H-pyran-4-yl)methyl)-1H-pyrazol-4-ol and 5-bromo-3-chloropyrazin-2-amine. LC-MS $(M-H)^+$=354.0.

Step 4: 5-(2,5-dimethyl-1,2,3,4-tetrahydroisoquinolin-7-yl)-3-(1-((tetrahydro-2H-pyran-4-yl)methyl)-1H-pyrazol-4-yloxy)pyrazin-2-amine Example 293 (19 mg, 9%) was prepared in a manner similar to that in Example 1 step 8 from 5-bromo-3-(1-((tetrahydro-2H-pyran-4-yl)methyl)-1H-pyrazol-4-yloxy) pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.18 (s, 1H), 8.02 (d, J=0.8 Hz, 1H), 7.57 (s, 1H), 7.46 (s, 1H), 7.32 (s, 1H), 6.66 (s, 2H), 4.03 (d, J=7.1 Hz, 2H), 3.88-3.79 (m, 2H), 3.47 (s, 2H), 3.32-3.22 (m, 2H), 2.69-2.59 (m, 4H), 2.34 (s, 3H), 2.20 (s, 3H), 2.15-2.02 (m, 1H), 1.49-1.40 (m, 2H), 1.35-1.21 (m, 2H). LC-MS $(M+H)^+$=435.3.

Example 294: 5-(2,5-dimethyl-1,2,3,4-tetrahydroisoquinolin-7-yl)-3-(4-ethoxy-1H-pyrazol-1-yl)pyrazin-2-amine

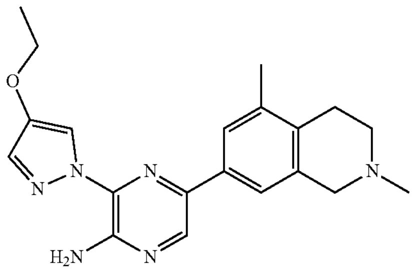 [SMILES: CCOc1cnn(-c2nc(-c3cc(C)c4c(c3)CN(C)CC4)cnc2N)c1]

Step 1: 4-ethoxy-1H-pyrazole

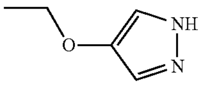

To a stirred mixture of 1H-pyrazol-4-ol (800 mg, 9.04 mmol) and iodoethane (2.23 g, 13.6 mmol) in DMF (10 mL) was added $Cs_2CO_3$ (6.20 g, 18.1 mmol) at room temperature under nitrogen. The mixture was stirred for overnight at room temperature then concentrated under reduced pressure. The residue was purified by silica gel column chromatography, eluted with MeOH/DCM (8:92) to give the title compound (0.778 g, 77%). LC-MS $(M+H)^+$=113.1.

Step 2: 5-bromo-3-(4-ethoxy-1H-pyrazol-1-yl) pyrazin-2-amine

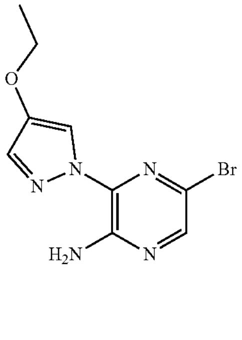 [SMILES: CCOc1cnn(-c2nc(Br)cnc2N)c1]

The title compound (320 mg, 99%) was prepared in a manner similar to that in Example 279 step 2 from 4-ethoxy-1H-pyrazole and 3,5-dibromopyrazin-2-amine. LC-MS $(M+H)^+$=284.0.

Step 3: 5-(2,5-dimethyl-1,2,3,4-tetrahydroisoquinolin-7-yl)-3-(4-ethoxy-1H-pyrazol-1-yl)pyrazin-2-amine Example 294 (26 mg, 13%) was prepared in a manner similar to that in Example 1 step 8 from 5-bromo-3-(4-ethoxy-1H-pyrazol-1-yl)pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.55-8.48 (m, 2H), 7.77-7.68 (m, 2H), 7.59 (s, 1H), 7.45 (s, 2H), 4.16-4.06 (m, 2H), 3.55 (s, 2H), 2.75-2.61 (m, 4H), 2.36 (s, 3H), 2.27 (s, 3H), 1.36 (t, J=7.0 Hz, 3H). LC-MS $(M+H)^+$=365.2.

Example 295: 5-(2,5-dimethyl-1,2,3,4-tetrahydroisoquinolin-7-yl)-3-(1-(1-(ethylsulfonyl)azetidin-3-yl)-1H-pyrazol-4-yloxy)pyrazin-2-amine

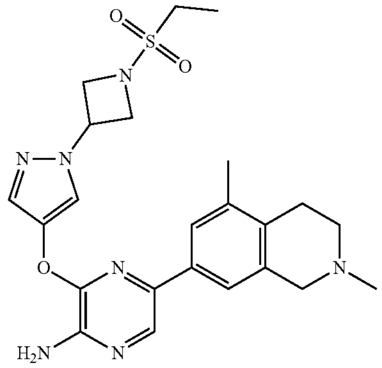 [SMILES: CCS(=O)(=O)N1CC(n2cc(Oc3nc(-c4cc(C)c5c(c4)CN(C)CC5)cnc3N)cn2)C1]

Step 1: tert-butyl 3-(4-(4,4,5,5-tetramethyl-1,3,2-dioxaborolan-2-yl)-1H-pyrazol-1-yl)azetidine-1-carboxylate

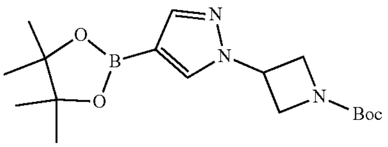 [SMILES: CC(C)(C)OC(=O)N1CC(n2cc(B3OC(C)(C)C(C)(C)O3)cn2)C1]

The title compound (6.59 g, 73%) was prepared in a manner similar to that in Example 116 step 1 from 4-(4,4,5,5-tetramethyl-1,3,2-dioxaborolan-2-yl)-1H-pyrazole and tert-butyl 3-bromoazetidine-1-carboxylate. LC-MS $(M+H)^+$=350.2.

Step 2: 1-(azetidin-3-yl)-4-(4,4,5,5-tetramethyl-1,3,2-dioxaborolan-2-yl)-1H-pyrazole

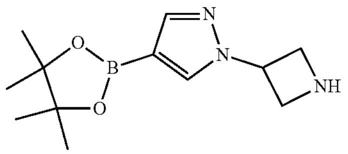 [SMILES: CC1(C)OB(c2cnn(C3CNC3)c2)OC1(C)C]

The title compound (4.0 g, 71%) was prepared in a manner similar to that in Example 34 step 6 from tert-butyl 3-(4-(4,4,5,5-tetramethyl-1,3,2-dioxaborolan-2-yl)-1H-pyrazol-1-yl)azetidine-1-carboxylate. LC-MS $(M+H)^+$=250.2.

Step 3: 1-(1-(ethylsulfonyl)azetidin-3-yl)-4-(4,4,5,5-tetramethyl-1,3,2-dioxaborolan-2-yl)-1H-pyrazole

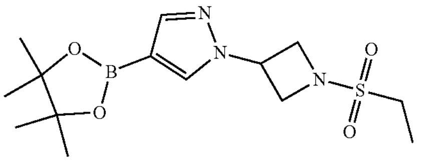 [SMILES: CCS(=O)(=O)N1CC(n2cc(B3OC(C)(C)C(C)(C)O3)cn2)C1]

The title compound (578 mg, 42%) was prepared in a manner similar to that in Example 280A/280B step 1 from 1-(azetidin-3-yl)-4-(4,4,5,5-tetramethyl-1,3,2-dioxaborolan-2-yl)-1H-pyrazole and ethanesulfonyl chloride. LC-MS $(M+H)^+$=342.2.

Step 4: 1-(1-(ethylsulfonyl)azetidin-3-yl)-1H-pyrazol-4-ol

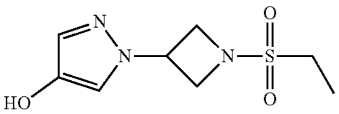

The title compound (277 mg, 74%) was prepared in a manner similar to that in Example 116 step 2 from 1-(1-(ethylsulfonyl)azetidin-3-yl)-4-(4,4,5,5-tetramethyl-1,3,2-dioxaborolan-2-yl)-1H-pyrazole. LC-MS $(M+H)^+$=232.2.

Step 5: 5-bromo-3-(1-(1-(ethylsulfonyl)azetidin-3-yl)-1H-pyrazol-4-yloxy)pyrazin-2-amine

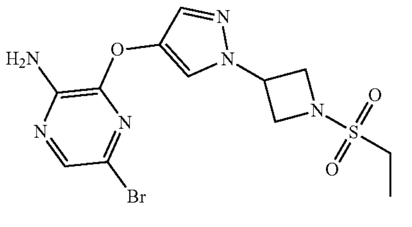 [SMILES: CCS(=O)(=O)N1CC(n2cc(Oc3nc(Br)cnc3N)cn2)C1]

The title compound (145 mg, 33%) was prepared in a manner similar to that in Example 116 step 3 from 1-(1-(ethylsulfonyl)azetidin-3-yl)-1H-pyrazol-4-ol and 3,5-dibromopyrazin-2-amine. LC-MS $(M+H)^+$=403.0.

Step 6: 5-(2,5-dimethyl-1,2,3,4-tetrahydroisoquinolin-7-yl)-3-(1-(1-(ethylsulfonyl)azetidin-3-yl)-1H-pyrazol-4-yloxy)pyrazin-2-amine Example 295 (16 mg, 13%) was prepared in a manner similar to that in Example 1 step 8 from 5-bromo-3-(1-(1-(ethylsulfonyl)azetidin-3-yl)-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.20 (s, 2H), 7.79 (s, 1H), 7.47 (s, 1H), 7.34 (s, 1H), 6.66 (s, 2H), 5.39-5.28 (m, 1H), 4.37-4.25 (m, 4H), 3.50 (s, 2H), 3.28-3.18 (m, 2H), 2.72-2.59 (m, 4H), 2.35 (s, 3H), 2.22 (s, 3H), 1.27 (t, J=7.4 Hz, 3H). LC-MS $(M+H)^+$=484.2.

Example 296: 5-(2,5-dimethyl-1,2,3,4-tetrahydroisoquinolin-7-yl)-3-(1-(1-(phenylsulfonyl)azetidin-3-yl)-1H-pyrazol-4-yloxy)pyrazin-2-amine

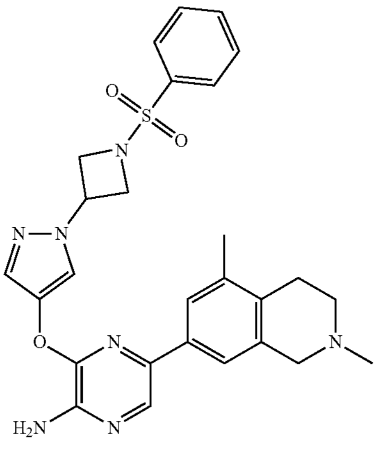 [SMILES: Cc1cc(-c2cnc(N)c(Oc3cnn(C4CN(S(=O)(=O)c5ccccc5)C4)c3)n2)cc2c1CCN(C)C2]

Step 1: 1-(1-(phenylsulfonyl)azetidin-3-yl)-4-(4,4,5,5-tetramethyl-1,3,2-dioxaborolan-2-yl)-1H-pyrazole

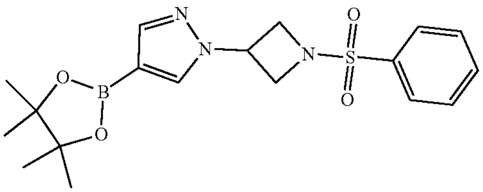 [SMILES: CC1(C)OB(c2cnn(C3CN(S(=O)(=O)c4ccccc4)C3)c2)OC1(C)C]

The title compound (564 mg, 36%) was prepared in a manner similar to that in 280A/280B step 1 from 1-(azetidin-3-yl)-4-(4,4,5,5-tetramethyl-1,3,2-dioxaborolan-2-yl)-1H-pyrazole and benzenesulfonyl chloride. LC-MS $(M+H)^+$=390.1.

Step 2: 1-(1-(phenylsulfonyl)azetidin-3-yl)-1H-pyrazol-4-ol

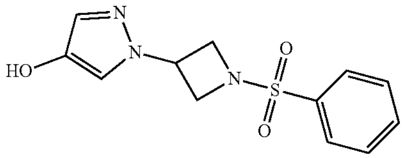 [SMILES: O=S(=O)(c1ccccc1)N1CC(n2cc(O)cn2)C1]

The title compound (327 mg, 61%) was prepared in a manner similar to that in Example 117 step 2 from 1-(1-(phenylsulfonyl)azetidin-3-yl)-4-(4,4,5,5-tetramethyl-1,3,2-dioxaborolan-2-yl)-1H-pyrazole. LC-MS $(M+H)^+$=280.1.

Step 3: 5-bromo-3-(1-(1-(phenylsulfonyl)azetidin-3-yl)-1H-pyrazol-4-yloxy)pyrazin-2-amine

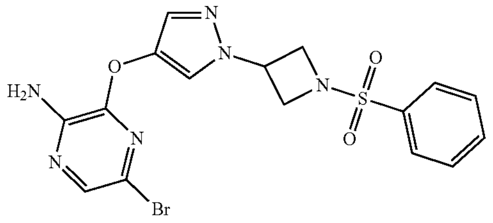 [SMILES: Nc1ncc(Br)nc1Oc1cnn(C2CN(S(=O)(=O)c3ccccc3)C2)c1]

The title compound (290 mg, 60%) was prepared in a manner similar to that in Example 116 step 3 from 1-(1-(phenylsulfonyl)azetidin-3-yl)-1H-pyrazol-4-ol and 3,5-dibromopyrazin-2-amine. LC-MS $(M+H)^+$=451.0.

Step 4: 5-(2,5-dimethyl-1,2,3,4-tetrahydroisoquinolin-7-yl)-3-(1-(1-(phenylsulfonyl)azetidin-3-yl)-1H-pyrazol-4-yloxy)pyrazin-2-amine Example 296 (29 mg, 12%) was prepared in a manner similar to that in Example 1 step 8 from 5-bromo-3-(1-(1-(phenylsulfonyl)azetidin-3-yl)-1H-pyrazol-4-yloxy) pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.19 (s, 1H), 7.94-7.84 (m, 3H), 7.82-7.73 (m, 1H), 7.72-7.64 (m, 2H), 7.61 (s, 1H), 7.44 (s, 1H), 7.31 (s, 1H), 6.62 (s, 2H), 5.22-5.10 (m, 1H), 4.27-4.18 (m, 2H), 4.13-4.05 (m, 2H), 3.50 (s, 2H), 2.71-2.61 (m, 4H), 2.37 (s, 3H), 2.22 (s, 3H). LC-MS $(M+H)^+$=532.3.

Example 297: 1-(3-amino-6-(2,5-dimethyl-1,2,3,4-tetrahydroisoquinolin-7-yl)pyrazin-2-yl)-N-(cyclopropylmethyl)-1H-pyrazole-4-carboxamide

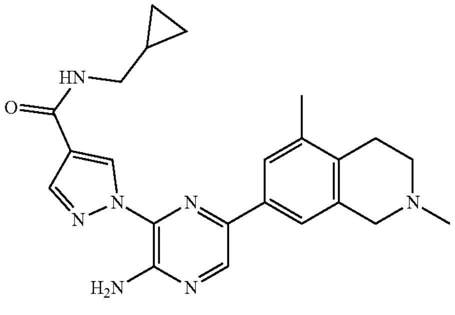 [SMILES: Cc1cc(-c2cnc(N)c(-n3cc(C(=O)NCC4CC4)cn3)n2)cc2c1CCN(C)C2]

Example 297 (26 mg, 28%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and cyclopropylmethanamine. $^1H$ NMR (400 MHz, DMSO-d6) δ 9.24 (s, 1H), 8.64 (s, 1H), 8.54 (t, J=5.7 Hz, 1H), 8.25 (s, 1H), 7.71 (s, 1H), 7.59 (s, 1H), 7.45 (s, 2H), 3.56 (s, 2H), 3.21-3.14 (m, 2H), 2.75-2.61 (m, 4H), 2.36 (s, 3H), 2.28 (s, 3H), 1.08-0.98 (m, 1H), 0.51-0.42 (m, 2H), 0.29-0.21 (m, 2H). LC-MS $(M+H)^+$=418.3.

Example 298: 1-(3-amino-6-(2,5-dimethyl-1,2,3,4-tetrahydroisoquinolin-7-yl)pyrazin-2-yl)-N-cyclopropyl-1H-pyrazole-4-carboxamide

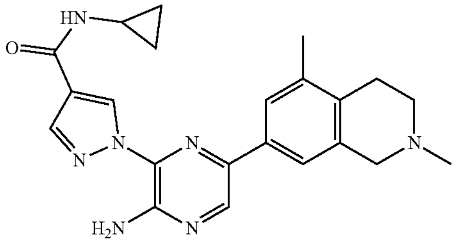 [SMILES: Cc1cc(-c2cnc(N)c(-n3cc(C(=O)NC4CC4)cn3)n2)cc2c1CCN(C)C2]

Example 298 (27 mg, 35%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and cyclopropanamine. $^1H$ NMR (400 MHz, DMSO-d6) δ 9.20 (s, 1H), 8.63 (s, 1H), 8.44 (s, 1H), 8.22 (s, 1H), 7.70 (s, 1H), 7.58 (s, 1H), 7.44 (s, 2H), 3.55 (s, 2H), 2.87-2.76 (m, 1H), 2.76-2.60 (m, 4H), 2.36 (s, 3H), 2.27 (s, 3H), 0.77-0.66 (m, 2H), 0.61-0.53 (m, 2H). LC-MS $(M+H)^+$=404.2.

Example 299: 1-(3-amino-6-(2,5-dimethyl-1,2,3,4-tetrahydroisoquinolin-7-yl)pyrazin-2-yl)-N-(2-morpholinoethyl)-1H-pyrazole-4-carboxamide

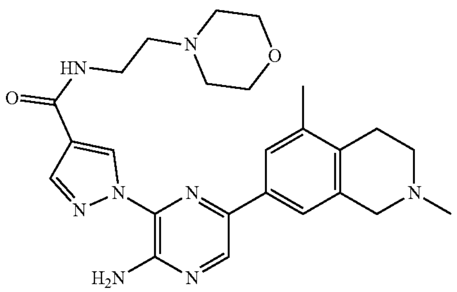 [SMILES: Cc1cc(-c2cnc(N)c(-n3cc(C(=O)NCCN4CCOCC4)cn3)n2)cc2c1CCN(C)C2]

Example 299 (23 mg, 22%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and 2-morpholinoethanamine. $^1H$ NMR (400 MHz, DMSO-d6) δ 9.23 (s, 1H), 8.64 (s, 1H), 8.42 (t, J=5.7 Hz, 1H), 8.23 (s, 1H), 7.71 (s, 1H), 7.59 (s, 1H), 7.45 (s, 2H), 3.62-3.53 (m, 6H), 3.45-3.35 (m, 2H), 2.74-2.68 (m, 2H), 2.73-2.63 (m, 2H), 2.51-2.40 (m, 6H), 2.36 (s, 3H), 2.28 (s, 3H). LC-MS $(M+H)^+$=477.3.

Example 300: 1-(3-amino-6-(2,5-dimethyl-1,2,3,4-tetrahydroisoquinolin-7-yl)pyrazin-2-yl)-N-(2-chloro-4-fluorobenzyl)-1H-pyrazole-4-carboxamide

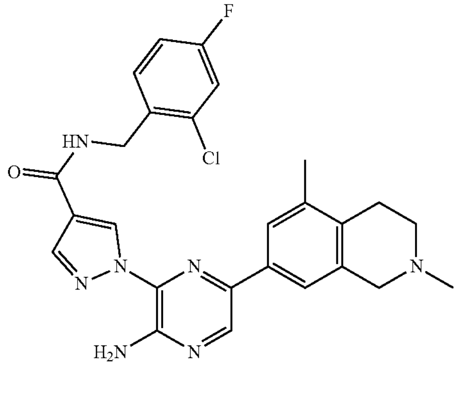 [SMILES: Cc1cc(-c2cnc(N)c(-n3cc(C(=O)NCc4ccc(F)cc4Cl)cn3)n2)cc2c1CCN(C)C2]

Example 300 (26 mg, 27%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and (2-chloro-4-fluorophenyl)methanamine. $^1$H NMR (400 MHz, DMSO-d6) δ 9.30 (s, 1H), 9.01 (t, J=5.8 Hz, 1H), 8.64 (s, 1H), 8.30 (s, 1H), 7.70 (s, 1H), 7.58 (s, 1H), 7.54-7.41 (m, 4H), 7.28-7.19 (m, 1H), 4.56-4.50 (m, 2H), 3.54 (s, 2H), 2.74-2.61 (m, 4H), 2.35 (s, 3H), 2.27 (s, 3H). LC-MS $(M+H)^+$=506.2.

Example 301: 1-(3-amino-6-(2,5-dimethyl-1,2,3,4-tetrahydroisoquinolin-7-yl)pyrazin-2-yl)-N-(1-(2-chloro-4-ethoxyphenyl)ethyl)-1H-pyrazole-4-carboxamide

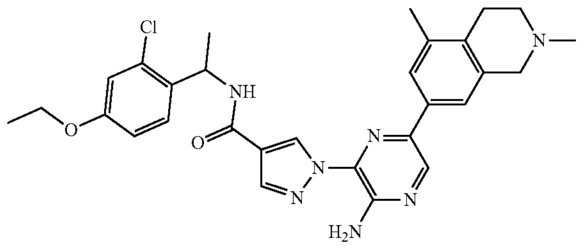 [SMILES: CCOc1ccc(C(C)NC(=O)c2cnn(-c3nc(-c4cc(C)c5c(c4)CN(C)CC5)cnc3N)c2)c(Cl)c1]

Step 1: 1-(2-chloro-4-ethoxyphenyl)ethan-1-one

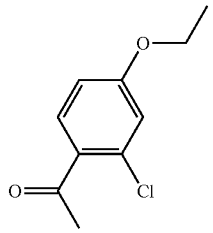

The title compound (1.99 g, 90%) was prepared in a manner similar to that in Example 294 step 1 from 1-(2-chloro-4-hydroxyphenyl)ethanone and iodoethane. LC-MS $(M+H)^+$=199.0.

Step 2: N-(1-(2-chloro-4-ethoxyphenyl)ethyl)-2-methylpropane-2-sulfinamide

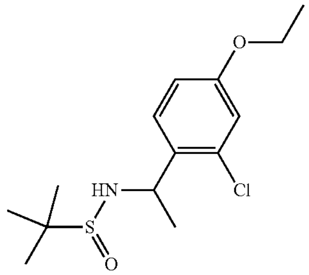 [SMILES: CCOc1ccc(C(C)NS(=O)C(C)(C)C)c(Cl)c1]

To a solution of 1-(2-chloro-4-ethoxyphenyl)ethan-1-one (1.99 g, 10.0 mmol) in THF (50 mL) was added tert-butanesulfinamide (1.82 g, 15.0 mmol) and $Ti(OEt)_4$ (3.43 g, 15.0 mmol) in portions at room temperature. The mixture was stirred for 20 h at 70° C. The reaction mixture is cooled to 0° C., and $NaBH_4$ (1.33 g, 35.1 mmol) was added. The mixture and stirred at 0° C. for 1 h, then quenched with sat. $NaHCO_3$ (50 mL) with vigorous stirring. The mixture was filtered through Celite and the filtrate was extracted with ethyl acetate (100 mL×3). The combined organic layer was washed with brine (100 mL), dried over $Na_2SO_4$, filtered and concentrated under reduced pressure give the title compound (2.50 g, crude). The material was used in step 3 without further purifications. LC-MS $(M+H)^+$=304.1.

Step 3: 1-(2-chloro-4-ethoxyphenyl)ethanamine

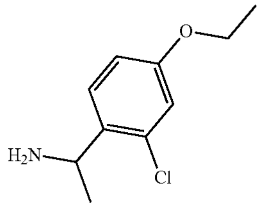

To a solution of N-(1-(2-chloro-4-ethoxyphenyl)ethyl)-2-methylpropane-2-sulfinamide (2.50 g, crude) in MeOH (30 mL) was added aqueous HCl (6 M, 5.0 mL, 30 mmol) dropwise at 0° C. The mixture was stirred for 2 h at room temperature, then solvent was evaporated under reduced pressure. The residue was partitioned between EtOAc (50 mL) and saturated $NaHCO_3$ (50 mL). The organic layer was separated and concentrated under reduced pressure. The residue was purified by silica gel flash chromatography, eluted with MeOH/DCM (0% to 15% gradient) to give the title compound (396 mg, 20% over 2 steps). LC-MS $(M-NH_2)$=183.1.

Step 4: 1-(3-amino-6-(2,5-dimethyl-1,2,3,4-tetrahydroisoquinolin-7-yl)pyrazin-2-yl)-N-(1-(2-chloro-4-ethoxyphenyl)ethyl)-1H-pyrazole-4-carboxamide Example 301 (30 mg, 33%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and 1-(2-chloro-4-ethoxyphenyl)ethanamine. $^1$H NMR (400 MHz, DMSO-d6)

9.26 (s, 1H), 8.80 (d, J=7.5 Hz, 1H), 8.64 (s, 1H), 8.28 (s, 1H), 7.70 (s, 1H), 7.57 (s, 1H), 7.48-7.41 (m, 3H), 7.02-6.97 (m, 1 H), 6.97-6.90 (m, 1H), 5.44-5.33 (m, 1H), 4.08-3.98 (m, 2H), 3.55 (s, 2H), 2.75-2.62 (m, 4H), 2.36 (s, 3H), 2.28 (s, 3H), 1.45 (d, J=7.0 Hz, 3H), 1.31 (t, J=7.0 Hz, 3H). LC-MS $(M+H)^+$=546.3.

Example 302: 1-(3-amino-6-(2,5-dimethyl-1,2,3,4-tetrahydroisoquinolin-7-yl)pyrazin-2-yl)-N-methyl-N-(2-(pyrrolidin-1-yl)ethyl)-1H-pyrazole-4-carboxamide

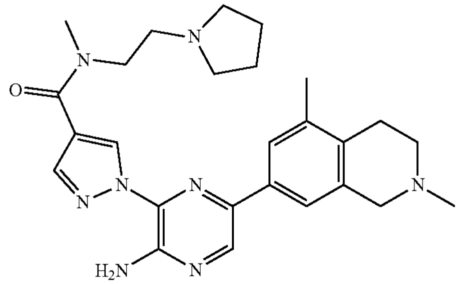 [SMILES: Cc1cc(-c2cnc(N)c(-n3cc(C(=O)N(C)CCN4CCCC4)cn3)n2)cc2c1CCN(C)C2]

Example 302 (28 mg, 27%) was prepared in a manner similar to that in Example 12 final step from 1-(3-amino-6-(2,5-dimethyl-1,2,3,4-tetrahydroisoquinolin-7-yl)pyrazin-2-yl)-1H-pyrazole-4-carboxylic acid and N-methyl-2-(pyrrolidin-1-yl)ethanamine. $^1$H NMR (400 MHz, DMSO-d6) δ 9.03 (s, 1H), 8.63 (s, 1H), 8.14 (s, 1H), 7.70 (s, 1H), 7.59 (s, 1H), 7.42 (s, 2H), 3.61-3.56 (m, 2H), 3.53 (s, 2H), 3.29-2.96 (m, 3H), 2.75-2.60 (m, 6H), 2.45-2.41 (m, 4H), 2.35 (s, 3H), 2.26 (s, 3H), 1.75-1.52 (m, 4H). LC-MS $(M+H)^+$=475.3.

Example 303: 5-(2,5-dimethyl-1,2,3,4-tetrahydroisoquinolin-7-yl)-3-((1-(2,2,2-trifluoroethyl)-1H-pyrazol-4-yl)oxy)pyrazin-2-amine

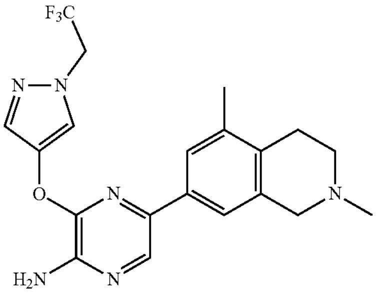 [SMILES: Cc1cc(-c2cnc(N)c(Oc3cnn(CC(F)(F)F)c3)n2)cc2c1CCN(C)C2]

Step 1: 4-(4,4,5,5-tetramethyl-1,3,2-dioxaborolan-2-yl)-1-(2,2,2-trifluoroethyl)-1H-pyrazole

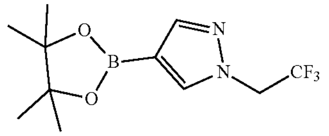 [SMILES: CC1(C)OB(c2cnn(CC(F)(F)F)c2)OC1(C)C]

$Cs_2CO_3$ (1.84 g, 5.7 mmol) was added to a solution of 4-(4,4,5,5-tetramethyl-1,3,2-dioxaborolan-2-yl)-1H-pyrazole (1.0 g, 5.1 mmol) and 1,1,1-trifluoro-2-iodoethane (1.14 g, 5.4 mmol) in DMF (20 mL) and the mixture was heated to 80° C. for overnight. Water (60 mL) was added and the mixture was extracted with EtOAc (30 mL). The organic layer was washed with brine (20 mL), dried over $Na_2SO_4$, filtered and concentrated under reduced pressure. The residue was purified by prep-TLC, developed with EtOAc/PE (1:1) to give the title compound (290 mg, 21%). LC-MS $(M+H)^+$=277.1.

Step 2: 1-(2,2,2-trifluoroethyl)-1H-pyrazol-4-ol

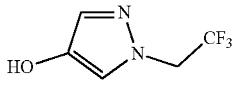 [SMILES: Oc1cnn(CC(F)(F)F)c1]

To a solution of 4-(4,4,5,5-tetramethyl-1,3,2-dioxaborolan-2-yl)-1-(2,2,2-trifluoroethyl)-1H-pyrazole (500 mg, 1.8 mmol) in THF (15 mL) was added aqueous NaOH (3 M, 1.2 mL, 3.6 mmol) and $H_2O_2$ (410 mg, 3.6 mmol) at 0° C. The mixture was stirred at room temperature for 3 h, then water (30 mL) was added and the pH of the mixture was adjusted to 6 with HCl (1 M). The mixture was extracted with EtOAc (30 mL). The organic layer was washed with brine (20 mL), dried over $Na_2SO_4$, filtered and concentrated under reduced pressure. The residue was purified by prep-TLC, developed with EtOAc/PE (1:2) to give the title compound (210 mg, 70%). LC-MS $(M+H)^+$=167.1.

Step 3: 5-bromo-3-((1-(2,2,2-trifluoroethyl)-1H-pyrazol-4-yl)oxy)pyrazin-2-amine

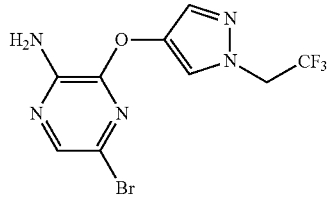 [SMILES: Nc1ncc(Br)nc1Oc1cnn(CC(F)(F)F)c1]

The title compound (140 mg, 31%) was prepared in a manner similar to that in Example 273 step 3 from 3,5-dibromopyrazin-2-amine and 1-(2,2,2-trifluoroethyl)-1H-pyrazol-4-ol. LC-MS $(M+H)^+$=338.0.

Step 4: Compound 11: 5-(2,5-dimethyl-1,2,3,4-tetrahydroisoquinolin-7-yl)-3-((1-(2,2,2-trifluoroethyl)-1H-pyrazol-4-yl)oxy)pyrazin-2-amine Example 303 (15 mg, 9%) was prepared in a manner similar to that in Example 273 step 4 from (2,5-dimethyl-1,2,3,4-tetrahydroisoquinolin-7-yl)boronic acid and 5-bromo-3-(1-(2,2,2-trifluoroethyl)-1H-pyrazol-4-yl)pyrazin-2-amine. $^1$H NMR (400 MHz, DMSO-d6) δ 8.20 (d, J=8.1 Hz, 2H), 7.73 (s, 1H), 7.46 (s, 1H), 7.34 (s, 1H), 6.69 (s, 2H), 5.18 (q, J=9.2 Hz, 2H), 3.46 (s, 2H), 2.66 (d, J=4.5 Hz, 2H), 2.62 (d, J=5.3 Hz, 2H), 2.33 (s, 3H), 2.19 (s, 3H). LC-MS $(M+H)^+$=419.1.

Example 304: 1-(3-amino-6-(2,5-dimethyl-1,2,3,4-tetrahydroisoquinolin-7-yl)pyrazin-2-yl)-N-methyl-N-((tetrahydrofuran-3-yl)methyl)-1H-pyrazole-4-carboxamide

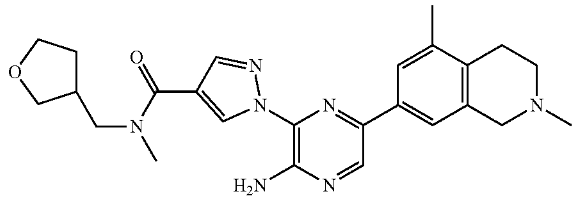 [SMILES: Cc1cc(-c2cnc(N)c(-n3cc(C(=O)N(C)CC4CCOC4)cn3)n2)cc2c1CCN(C)C2]

Example 304 (30 mg, 12%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and N-methyl-1-(tetrahydrofuran-3-yl)methanamine. $^1$H NMR (400 MHz, DMSO-d6) δ 9.02 (s, 1H), 8.63 (s, 1H), 8.23-8.06 (m, 1H), 7.71 (s, 1H), 7.60 (s, 1H), 7.42 (s, 2H), 3.85-3.60 (m, 3H), 3.53 (s, 3H), 3.50-3.40 (m, 2H), 3.28-3.15 (m, 2H), 3.08-2.92 (m, 1H), 2.75-2.55 (m, 5H), 2.35 (s, 3H), 2.26 (s, 3H), 2.08-1.90 (m, 1H), 1.68-1.45 (m, 1H). LC-MS $(M+H)^+$=462.2.

Example 305: 1-(3-amino-6-(2,5-dimethyl-1,2,3,4-tetrahydroisoquinolin-7-yl)pyrazin-2-yl)-N-(tetrahydrofuran-3-yl)-1H-pyrazole-4-carboxamide

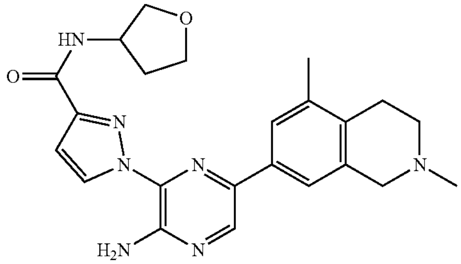 [SMILES: Cc1cc(-c2cnc(N)c(-n3ccc(C(=O)N(C)C4CCOC4)n3)n2)cc2c1CCN(C)C2]

Example 305 (40 mg, 17%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and tetrahydrofuran-3-amine. $^1$H NMR (400 MHz, DMSO-d6) δ 9.26 (s, 1H), 8.63 (s, 1H), 8.53 (d, J=6.6 Hz, 1H), 8.26 (s, 1H), 7.70 (s, 1H), 7.57 (s, 1H), 7.44 (s, 2H), 4.46 (s, 1H), 3.91-3.83 (m, 2H), 3.75-3.69 (m, 1H), 3.63-3.60 (m, 1H), 3.55 (s, 2H), 2.75-2.58 (m, 4H), 2.36 (s, 3H), 2.27 (s, 3H), 2.24-2.12 (m, 1H), 1.97-1.86 (m, 1H). LC-MS $(M+H)^+$=434.2.

Example 306: 1-(3-amino-6-(2,5-dimethyl-1,2,3,4-tetrahydroisoquinolin-7-yl)pyrazin-2-yl)-N-methyl-N-(tetrahydrofuran-3-yl)-1H-pyrazole-4-carboxamide

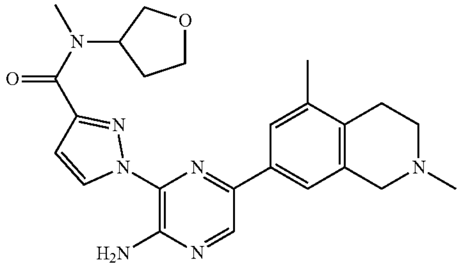

Example 306 (15 mg, 6%) was prepared in a manner similar to that in Example 279 step 4 from 1-(3-amino-6-(2,5-dimethyl-1,2,3,4-tetrahydroisoquinolin-7-yl)pyrazin-2-yl)-1H-pyrazole-4-carboxylic acid and N-methyltetrahydrofuran-3-amine. $^1$H NMR (400 MHz, DMSO-d6) δ 9.00 (s, 1H), 8.64 (s, 1H), 8.13 (s, 1H), 7.71 (s, 1H), 7.60 (s, 1H), 3.99-3.97 (m, 1H), 3.75-3.71 (m, 2H), 3.61-3.59 (m, 1H), 3.53 (s, 2H), 3.06 (s, 4H), 2.70 (s, 2H), 2.63 (s, 2H), 2.35 (s, 3H), 2.26 (s, 3H), 2.24-2.16 (m, 1H), 1.96 (s, 1H). LC-MS $(M+H)^+$=448.3.

Example 307: 5-(2,5-dimethyl-1,2,3,4-tetrahydroisoquinolin-7-yl)-3-(1-(1-methylpiperidin-4-yl)-1H-pyrazol-4-yloxy)pyrazin-2-amine

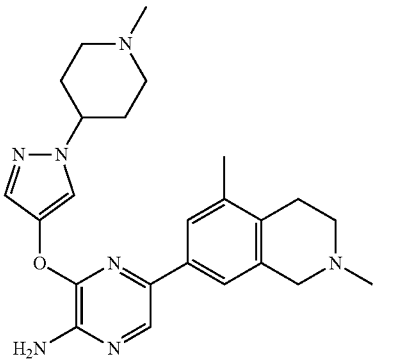 [SMILES: Cc1cc(-c2cnc(N)c(Oc3cnn(C4CCN(C)CC4)c3)n2)cc2c1CCN(C)C2]

Step 1: tert-butyl 4-(4-(4,4,5,5-tetramethyl-1,3,2-dioxaborolan-2-yl)-1H-pyrazol-1-yl)piperidine-1-carboxylate

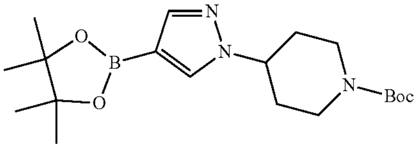 [SMILES: CC(C)(C)OC(=O)N1CCC(n2cc(B3OC(C)(C)C(C)(C)O3)cn2)CC1]

The title compound (528 mg, 29%) was prepared in a manner similar to that in Example 116 step 1 from 4-(4,4, 5,5-tetramethyl-1,3,2-dioxaborolan-2-yl)-1H-pyrazole and tert-butyl 4-(methylsulfonyloxy)piperidine-1-carboxylate. LC-MS $(M+H)^+$=378.2.

Step 2: tert-butyl 4-(4-hydroxy-1H-pyrazol-1-yl) piperidine-1-carboxylate

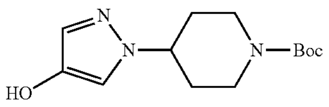 [SMILES: CC(C)(C)OC(=O)N1CCC(n2cc(O)cn2)CC1]

The title compound (282 mg, 75%) was prepared in a manner similar to that in Example 116 step 2 from tert-butyl 4-(4-(4,4,5,5-tetramethyl-1,3,2-dioxaborolan-2-yl)-1H-pyrazol-1-yl)piperidine-1-carboxylate. LC-MS $(M+H)^+$=268.2.

Step 3: 1-(1-methylpiperidin-4-yl)-1H-pyrazol-4-ol

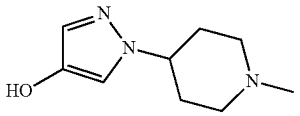

At 0° C., to a solution of tert-butyl 4-(4-hydroxy-1H-pyrazol-1-yl)piperidine-1-carboxylate (235 mg, 0.88 mmol) in THF (3 mL) was added $LiAlH_4$ in THF (1.0 M, 1.3 mL, 1.30 mmol) dropwise under nitrogen. The resulting mixture was stirred for 1 h at 80° C. under nitrogen then cooled to room temperature. The mixture was quenched by the addition of water (0.06 mL) and 20% NaOH (0.06 mL), and then water (10 mL). The mixture was extracted with ethyl acetate (10 mL×3). The combined organic layer was washed with brine (10 mL), dried over $Na_2SO_4$ and filtered. The filtrate was concentrated under reduced pressure to give the title compound (155 mg, 97%). LC-MS $(M+H)^+$=182.1.

Step 4: 5-bromo-3-(1-(1-methylpiperidin-4-yl)-1H-pyrazol-4-yloxy)pyrazin-2-amine

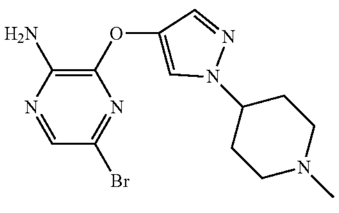 [SMILES: CN1CCC(n2cc(Oc3nc(Br)cnc3N)cn2)CC1]

The title compound (205 mg, 99%) was prepared in a manner similar to that in Example 116 step 3 from 1-(1-methylpiperidin-4-yl)-1H-pyrazol-4-ol and 3,5-dibromopyrazin-2-amine. LC-MS $(M+H)^+$=353.0.

Step 5: 5-(2,5-dimethyl-1,2,3,4-tetrahydroisoquinolin-7-yl)-3-(1-(1-methylpiperidin-4-yl)-1H-pyrazol-4-yloxy)pyrazin-2-amine Example 307 (20 mg, 12%) was prepared in a manner similar to that in Example 1 step 8 from 5-bromo-3-(1-(1-methylpiperidin-4-yl)-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.20 (s, 1H), 8.14 (s, 1H), 7.58 (s, 1H), 7.48 (s, 1H), 7.36 (s, 1H), 6.64 (s, 2H), 4.20-4.08 (m, 1H), 3.47 (s, 2H), 2.92-2.83 (m, 2H), 2.70-2.58 (m, 4H), 2.34 (s, 3H), 2.24-2.18 (m, 6H), 2.14-1.92 (m, 6H). LC-MS $(M+H)^+$=434.2.

Example 308: 3-(4-((3-amino-6-(2,8-dimethyl-1,2,3,4-tetrahydroisoquinolin-6-yl)pyrazin-2-yl)oxy)-1H-pyrazol-1-yl)propanenitrile

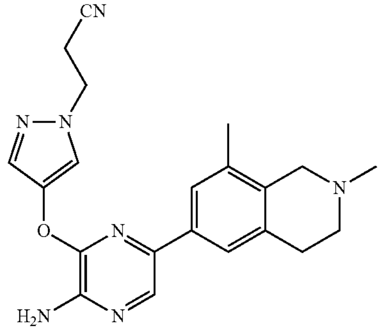 [SMILES: Cc1cc(-c2cnc(N)c(Oc3cnn(CCC#N)c3)n2)cc2c1CN(C)CC2]

Example 308 (176 mg, 56%) was prepared in a manner similar to that in Example 273 step 4 from (2,8-dimethyl-1,2,3,4-tetrahydroisoquinolin-6-yl)boronic acid and 3-(4-((3-amino-6-bromopyrazin-2-yl)oxy)-1H-pyrazol-1-yl)propanenitrile. $^1H$ NMR (400 MHz, DMSO-$d_6$) δ 8.21 (s, 1H), 8.13 (s, 1H), 7.69 (s, 1H), 7.44 (m, 2H), 6.68 (s, 2H), 4.44-4.39 (s, 2H), 3.46-3.36 (m, 2H), 3.22-3.01 (m, 2H), 2.97-2.73 (m, 2H), 2.62-2.53 (m, 2H), 2.38 (s, 3H), 2.18 (s, 3H). LCMS $(M+H)^+$=390.4.

Example 309: 5-(2,5-dimethyl-1,2,3,4-tetrahydroisoquinolin-7-yl)-3-(1-(tetrahydro-2H-pyran-4-yl)-1H-pyrazol-4-yloxy)pyrazin-2-amine

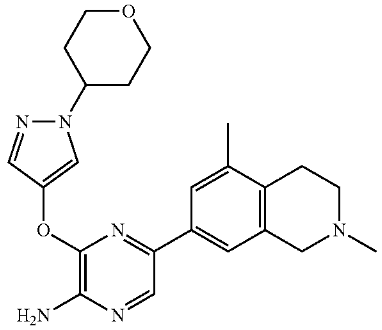 [SMILES: Cc1cc(-c2cnc(N)c(Oc3cnn(C4CCOCC4)c3)n2)cc2c1CCN(C)C2]

Step 1: 1-(tetrahydro-2H-pyran-4-yl)-4-(4,4,5,5-tetramethyl-1,3,2-dioxaborolan-2-yl)-1H-pyrazole

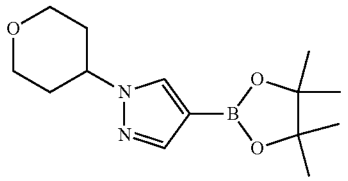 [SMILES: CC1(C)OB(c2cnn(C3CCOCC3)c2)OC1(C)C]

The title compound (618 mg, 22%) was prepared in a manner similar to that in Example 116 step 1 from 4-(4,4,5,5-tetramethyl-1,3,2-dioxaborolan-2-yl)-1H-pyrazole and 4-bromo-tetrahydro-2H-pyran. LC-MS $(M+H)^+$=279.2.

Step 2: 1-(tetrahydro-2H-pyran-4-yl)-1H-pyrazol-4-ol

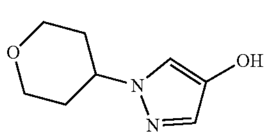 [SMILES: Oc1cnn(C2CCOCC2)c1]

The title compound (297 mg, 82%) was prepared in a manner similar to that in Example 116 step 2 from 1-(tetrahydro-2H-pyran-4-yl)-4-(4,4,5,5-tetramethyl-1,3,2-dioxaborolan-2-yl)-1H-pyrazole. LC-MS $(M+H)^+$=169.1.

Step 3: 5-bromo-3-(1-(tetrahydro-2H-pyran-4-yl)-1H-pyrazol-4-yloxy)pyrazin-2-amine

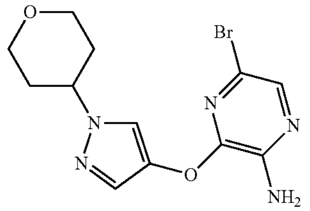 [SMILES: Nc1ncc(Br)nc1Oc1cnn(C2CCOCC2)c1]

The title compound (105 mg, 21%) was prepared in a manner similar to that in Example 116 step 3 from 1-(tetrahydro-2H-pyran-4-yl)-1H-pyrazol-4-ol and 3,5-dibromopyrazin-2-amine. LC-MS $(M+H)^+$=340.0.

Step 4: 5-(2,5-dimethyl-1,2,3,4-tetrahydroisoquinolin-7-yl)-3-(1-(tetrahydro-2H-pyran-4-yl)-1H-pyrazol-4-yloxy)pyrazin-2-amine Example 309 (7 mg, 5%) was prepared in a manner similar to that in Example 1 step 8 from 5-bromo-3-(1-(tetrahydro-2H-pyran-4-yl)-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.22-8.13 (m, 2H), 7.61 (s, 1H), 7.49 (s, 1H), 7.36 (s, 1H), 6.64 (s, 2H), 4.50-4.38 (m, 1H), 4.03-3.93 (m, 2H), 3.56-3.45 (m, 4H), 2.70-2.61 (m, 4H), 2.35 (s, 3H), 2.21 (s, 3H), 2.10-1.89 (m, 4H). LC-MS $(M+H)^+$=421.2.

Example 310: 5-(2,5-dimethyl-1,2,3,4-tetrahydroisoquinolin-7-yl)-3-(1-(1-ethylazetidin-3-yl)-1H-pyrazol-4-yloxy)pyrazin-2-amine

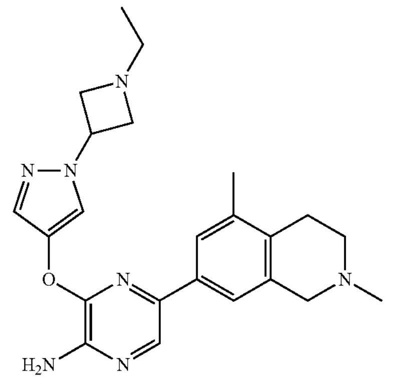 [SMILES: CCN1CC(n2cc(Oc3nc(-c4cc(C)c5c(c4)CN(C)CC5)cnc3N)cn2)C1]

Step 1: 1-(1-ethylazetidin-3-yl)-4-(4,4,5,5-tetramethyl-1,3,2-dioxaborolan-2-yl)-1H-pyrazole

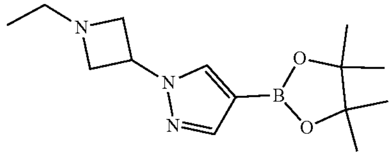 [SMILES: CCN1CC(n2cc(B3OC(C)(C)C(C)(C)O3)cn2)C1]

The title compound (574 mg, 79%) was prepared in a manner similar to that in Example 38 step 1 from 1-(azetidin-3-yl)-4-(4,4,5,5-tetramethyl-1,3,2-dioxaborolan-2-yl)-1H-pyrazole and acetaldehyde. LC-MS $(M+H)^+$=278.1.

Step 2: 1-(1-ethylazetidin-3-yl)-1H-pyrazol-4-ol

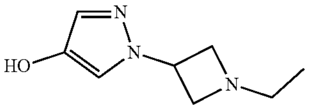

The title compound (300 mg, 83%) was prepared in a manner similar to that in Example 116 step 2 from 1-(1-ethylazetidin-3-yl)-4-(4,4,5,5-tetramethyl-1,3,2-dioxaborolan-2-yl)-1H-pyrazole. LC-MS $(M+H)^+$=168.1.

Step 3: 5-bromo-3-(1-(1-ethylazetidin-3-yl)-1H-pyrazol-4-yloxy)pyrazin-2-amine

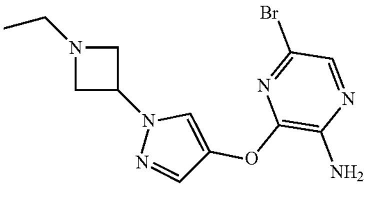 [SMILES: CCN1CC(n2cc(Oc3nc(Br)cnc3N)cn2)C1]

The title compound (291 mg, 48%) was prepared in a manner similar to that in Example 116 step 3 from 1-(1-ethylazetidin-3-yl)-1H-pyrazol-4-ol and 3,5-dibromopyrazin-2-amine. LC-MS $(M+H)^+$=339.0.

Step 4: 5-(2,5-dimethyl-1,2,3,4-tetrahydroisoquinolin-7-yl)-3-(1-(1-ethylazetidin-3-yl)-1H-pyrazol-4-yloxy)pyrazin-2-amine Example 310 (37 mg, 12%) was prepared in a manner similar to that in Example 1 step 8 from 5-bromo-3-(1-(1-ethylazetidin-3-yl)-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.27 (s, 1H), 8.21 (s, 1H), 7.67 (s, 1H), 7.51 (s, 1H), 7.37 (s, 1H), 6.69 (s, 2H), 5.07-4.96 (m, 1H), 3.81-3.73 (m, 2H), 3.57 (s, 2H), 3.45-3.37 (m, 2H), 2.72-2.68 (m, 4H), 2.62-2.52 (m, 2H), 2.39 (s, 3H), 2.22 (s, 3H), 0.94 (t, =7.2 Hz, 3H). LC-MS $(M+H)^+$=420.2.

Example 311: (1s,4s)-4-(4-(3-amino-6-(2,5-dimethyl-1,2,3,4-tetrahydroisoquinolin-7-yl)pyrazin-2-yloxy)-1H-pyrazol-1-yl)-1-methylcyclohexanol

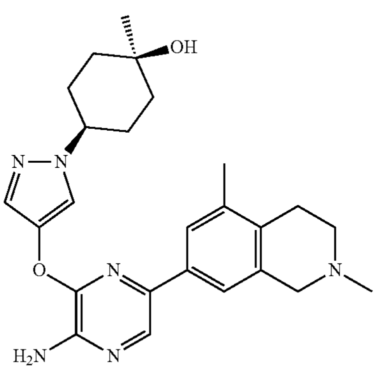 [SMILES: Cc1cc(-c2cnc(N)c(Oc3cnn([C@H]4CC[C@@](C)(O)CC4)c3)n2)cc2c1CCN(C)C2]

Step 1: 1,4-dioxaspiro[4.5]decan-8-yl 4-methylbenzenesulfonate

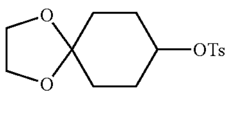 [SMILES: Cc1ccc(S(=O)(=O)OC2CCC3(CC2)OCCO3)cc1]

To a stirred mixture of 1,4-dioxaspiro[4.5]decan-8-ol (10.0 g, 60.0 mmol) and $Et_3N$ (19.2 g, 180 mmol) in DCM (150 mL) was added TsCl (13.9 g, 69.1 mmol) 0° C. The mixture was warmed to room temperature and stirred for 12 h. The mixture was filtered, and the filter cake was rinsed with DCM (10 mL). The combined filtrate was concentrated under reduced pressure. The residue was purified by silica gel column chromatography, eluted with DCM/PE (8:1) to give the title compound (11.0 g, 53%). $^1$H NMR (400 MHz, DMSO-d6) δ 7.83-7.78 (m, 2H), 7.47 (d, J=8.1 Hz, 2H), 4.66-4.58 (m, 1H), 3.88-3.76 (m, 4H), 2.42 (s, 3H), 1.75-1.56 (m, 6H), 1.55-1.47 (m, 2H).

Step 2: 4-iodo-1-(1,4-dioxaspiro[4.5]decan-8-yl)-1H-pyrazole

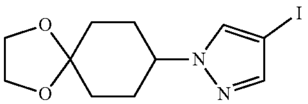 [SMILES: Ic1cnn(C2CCC3(CC2)OCCO3)c1]

To a mixture of 1,4-dioxaspiro[4.5]decan-8-yl 4-methylbenzenesulfonate (9.35 g, 26.9 mmol) and $Cs_2CO_3$ (16.8 g, 49.0 mmol) in DMF (35 mL) was added 4-iodopyrazole (5.00 g, 24.5 mmol). The mixture was warmed to 100° C. and stirred for 12 h. The mixture was cooled to room temperature, diluted with water (300 mL) and extracted with EtOAc (3×300 mL). The combined organic layer was washed with brine (300 mL), dried over anhydrous $Na_2SO_4$ and filtered. The filtrate was concentrated under reduced pressure to give the title compound (7.5 g, 74%). LC-MS $(M+H)^+$=335.1.

Step 3: 4-(4-iodo-1H-pyrazol-1-yl)cyclohexanone

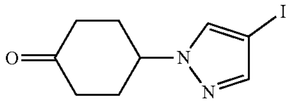 [SMILES: O=C1CCC(n2cc(I)cn2)CC1]

To a solution of 4-iodo-1-(1,4-dioxaspiro[4.5]decan-8-yl)-1H-pyrazole (6.09 g, 18.2 mmol) in MeCN (50 mL) and $H_2O$ (50 mL) was added pyridinium p-toluenesulfonate (9.16 g, 36.4 mmol) at room temperature.

The mixture was stirred for 15 h at 60° C. The solution was cooled to room temperature and extracted with ethyl acetate (200 mL×3). The combined organic layer was washed with brine, dried over $Na_2SO_4$ and filtered. The filtrate was concentrated under reduced pressure to give the title compound (3.90 g, 74%). LC-MS $(M+H)^+$=291.0.

Step 4: (1s,4s)-4-(4-iodo-1H-pyrazol-1-yl)-1-methylcyclohexanol

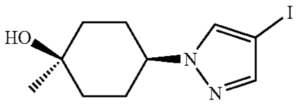

At 0° C., to a stirred solution of 4-(4-iodopyrazol-1-yl)cyclohexan-1-one (2.43 g, 8.39 mmol) in DCM (100 mL) was added $AlMe_3$ (26 mL, 2.0 M, 52 mmol). The mixture was stirred for 2 h at room temperature, then quenched with saturated $NH_4Cl$ (100 mL). The resulting mixture was extracted with DCM (150 mL×3). The combined organic layer was washed with brine, dried over $Na_2SO_4$ and filtered. The filtrate was concentrated under reduced pressure and the residue was purified by flash chromatography, eluting with EtOAc in PE (0% to 15% gradient) to give the title compound (790 mg, 31%). LC-MS $(M+H)^+$=307.0.

Step 5: (1s,4s)-1-methyl-4-(4-(4,4,5,5-tetramethyl-1,3,2-dioxaborolan-2-yl)-1H-pyrazol-1-yl)cyclohexanol

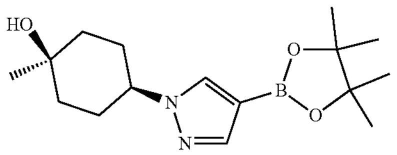

At 0° C., to a solution of (1s,4s)-4-(4-iodopyrazol-1-yl)-1-methylcyclohexan-1-ol (677 mg, 2.21 mmol) in THF (80 mL) was added i-PrMgCl in THF (3.9 mL, 2.0 M, 7.80 mmol) under nitrogen atmosphere. After 1.5 h, 2-methoxy-4,4,5,5-tetramethyl-1,3,2-dioxaborolane (1.75 g, 11.1 mmol) was added dropwise at 0° C. under nitrogen atmosphere. The mixture was warmed to room temperature and stirred for 4 h. The reaction was quenched by saturated $NH_4Cl$ (100 mL). The resulting solution was extracted with ethyl acetate (100 mL×3). The organic phases were combined, washed with brine and dried over $Na_2SO_4$. The solvent was concentrated under reduced pressure to yield the title compound (400 mg, 59%). LC-MS $(M+H)^+$=307.1.

Step 6: 1-((1s,4s)-4-hydroxy-4-methylcyclohexyl)-1H-pyrazol-4-ol

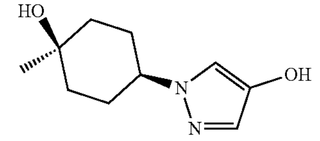

The title compound (140 mg, 61%) was prepared in a manner similar to that in Example 116 step 2 from (1s,4s)-1-methyl-4-(4-(4,4,5,5-tetramethyl-1,3,2-dioxaborolan-2-yl)-1H-pyrazol-1-yl)cyclohexanol. LC-MS $(M+H)^+$=197.2.

Step 7: (1s,4s)-4-(4-(3-amino-6-bromopyrazin-2-yloxy)-1H-pyrazol-1-yl)-1-methylcyclohexanol

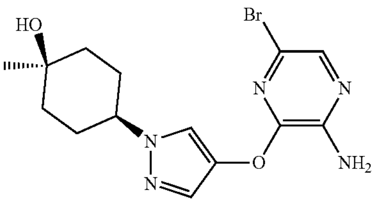 [SMILES: C[C@]1(O)CC[C@@H](n2cc(Oc3nc(Br)cnc3N)cn2)CC1]

The title compound (39 mg, 20%) was prepared in a manner similar to that in Example 116 step 3 from 1-((1s,4s)-4-hydroxy-4-methylcyclohexyl)-1H-pyrazol-4-ol and 3,5-dibromopyrazin-2-amine. LC-MS $(M+H)^+$=367.9.

Step 8: (1s,4s)-4-(4-(3-amino-6-(2,5-dimethyl-1,2,3,4-tetrahydroisoquinolin-7-yl)pyrazin-2-yloxy)-1H-pyrazol-1-yl)-1-methylcyclohexanol Example 311 (12 mg, 25%) was prepared in a manner similar to that in Example 1 step 8 from (1s,4s)-4-(4-(3-amino-6-bromopyrazin-2-yloxy)-1H-pyrazol-1-yl)-1-methylcyclohexanol and 2,5-dimethyl-7-(4,4,5,5-tetramethyl-1,3,2-dioxaborolan-2-yl)-1,2,3,4-tetrahydroisoquinoline. $^1H$ NMR (400 MHz, DMSO-d6) δ 8.21 (s, 1H), 8.12 (s, 1H), 7.56 (s, 1H), 7.50 (d, J=1.8 Hz, 1H), 7.38 (d, J=1.9 Hz, 1H), 6.65 (s, 2H), 4.24 (s, 1H), 4.21-4.04 (m, 1H), 3.49 (s, 2H), 2.71-2.58 (m, 4H), 2.36 (s, 3H), 2.21 (s, 3H), 2.19-2.04 (m, 2H), 1.93-1.81 (m, 2H), 1.74-1.64 (m, 2H), 1.60-1.44 (m, 2H), 1.17 (s, 3H). LC-MS $(M+H)^+$=449.3.

Example 312: (1s,4s)-4-(4-(3-amino-6-(2,8-dimethyl-1,2,3,4-tetrahydroisoquinolin-6-yl)pyrazin-2-yloxy)-1H-pyrazol-1-yl)-1-methylcyclohexanol

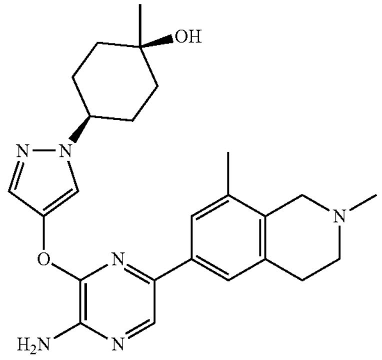 [SMILES: Cc1cc(-c2cnc(N)c(Oc3cnn([C@H]4CC[C@@](C)(O)CC4)c3)n2)cc2c1CN(C)CC2]

Example 312 (22 mg, 23%) was prepared in a manner similar to that in Example 1 step 8 from (1s,4s)-4-(4-(3-amino-6-bromopyrazin-2-yloxy)-1H-pyrazol-1-yl)-1-methylcyclohexanol and 2,8-dimethyl-6-(4,4,5,5-tetramethyl-1,3,2-dioxaborolan-2-yl)-1,2,3,4-tetrahydroisoquinoline. $^1H$ NMR (400 MHz, DMSO-d6) δ 8.20 (s, 1H), 8.09 (s, 1H), 7.55 (s, 1H), 7.49-7.40 (m, 2H), 6.63 (s, 2H), 4.20 (s, 1H), 4.17-4.05 (m, 1H), 3.40 (s, 2H), 2.83 (t, J=5.7 Hz, 2H), 2.58 (t, J=5.8 Hz, 2H), 2.39 (s, 3H), 2.18 (s, 3H), 2.16-2.05 (m, 2H), 1.90-1.81 (m, 2H), 1.72-1.63 (m, 2H), 1.57-1.44 (m, 2H), 1.16 (s, 3H). LC-MS $(M+H)^+$=449.3.

Example 313: 3-(4-(3-amino-6-(2,5-dimethyl-1,2,3,4-tetrahydroisoquinolin-7-yl)pyrazin-2-yloxy)-1H-pyrazol-1-yl)-3-methylbutanenitrile

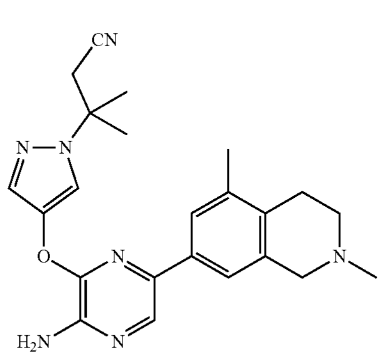 [SMILES: Cc1cc(-c2cnc(N)c(Oc3cnn(C(C)(C)CC#N)c3)n2)cc2c1CCN(C)C2]

Step 1:3-methyl-3-(4-(4,4,5,5-tetramethyl-1,3,2-dioxaborolan-2-yl)-1H-pyrazol-1-yl)butanenitrile

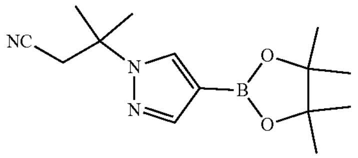 [SMILES: CC(C)(CC#N)n1cc(B2OC(C)(C)C(C)(C)O2)cn1]

The title compound (817 mg, 39%) was prepared in a manner similar to that in Example 273 step 1 from 4-(4,4,5,5-tetramethyl-1,3,2-dioxaborolan-2-yl)-1H-pyrazole and 3-methylbut-2-enenitrile. LC-MS (M+1)=276.3.

Step 2: 3-(4-hydroxy-1H-pyrazol-1-yl)-3-methylbutanenitrile

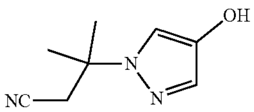

The title compound (200 mg, 73%) was prepared in a manner similar to that in Example 116 step 2 from 3-methyl-3-(4-(4,4,5,5-tetramethyl-1,3,2-dioxaborolan-2-yl)-1H-pyrazol-1-yl)butanenitrile. LC-MS $(M+H)^+$=166.1.

Step 3: 3-(4-(3-amino-6-bromopyrazin-2-yloxy)-1H-pyrazol-1-yl)-3-methylbutanenitrile

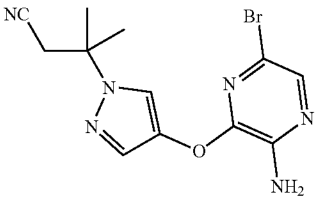 [SMILES: CC(C)(CC#N)n1cc(Oc2nc(Br)cnc2N)cn1]

The title compound (202 mg, 49%) was prepared in a manner similar to that in Example 116 step 3 from 3-(4-hydroxy-1H-pyrazol-1-yl)-3-methylbutanenitrile and 3,5-dibromopyrazin-2-amine. LC-MS $(M+H)^+$=337.2.

Step 4: 3-(4-(3-amino-6-(2,5-dimethyl-1,2,3,4-tetrahydroisoquinolin-7-yl)pyrazin-2-yloxy)-1H-pyrazol-1-yl)-3-methylbutanenitrile Example 313 (29 mg, 30%) was prepared in a manner similar to that in Example 1 step 8 from 3-(4-(3-amino-6-bromopyrazin-2-yloxy)-1H-pyrazol-1-yl)-3-methylbutanenitrile and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.30 (s, 1H), 8.21 (s, 1H), 7.69 (s, 1H), 7.50 (s, 1H), 7.37 (s, 1H), 6.65 (s, 2H), 3.48 (s, 2H), 3.27 (s, 2H), 2.71-2.60 (m, 4H), 2.34 (s, 3H), 2.20 (s, 3H), 1.69 (s, 6H). LC-MS $(M+H)^+$=418.2.

Example 314:5-(2,5-dimethyl-1,2,3,4-tetrahydroisoquinolin-7-yl)-3-(1-((4-fluoro-tetrahydro-2H-pyran-4-yl)methyl)-1H-pyrazol-4-yloxy)pyrazin-2-amine

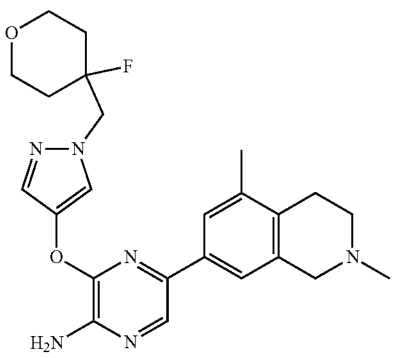 [SMILES: Cc1cc(-c2cnc(N)c(Oc3cnn(CC4(F)CCOCC4)c3)n2)cc2c1CCN(C)C2]

Step 1: (4-fluoro-tetrahydro-2H-pyran-4-yl)methyl 4-methylbenzenesulfonate

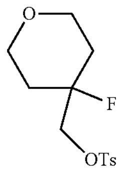 [SMILES: Cc1ccc(S(=O)(=O)OCC2(F)CCOCC2)cc1]

The title compound (300 mg, 46%) was prepared in a manner similar to that in Example 311 step 1 from (4-fluorotetrahydro-2H-pyran-4-yl)methanol. LC-MS $(M+H)^+$=289.0.

Step 2: 1-((4-fluoro-tetrahydro-2H-pyran-4-yl)methyl)-4-(4,4,5,5-tetramethyl-1,3,2-dioxaborolan-2-yl)-1H-pyrazole

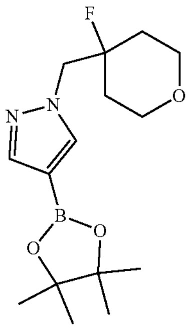 [SMILES: CC1(C)OB(c2cnn(CC3(F)CCOCC3)c2)OC1(C)C]

The title compound (167 mg, 52%) was prepared in a manner similar to that in Example 311 step 5 from (4-fluoro-tetrahydro-2H-pyran-4-yl)methyl 4-methylbenzenesulfonate and 4-(4,4,5,5-tetramethyl-1,3,2-dioxaborolan-2-yl)-1H-pyrazole. LC-MS $(M+H)^+$=311.2.

Step 3: 1-((4-fluoro-tetrahydro-2H-pyran-4-yl)methyl)-1H-pyrazol-4-ol

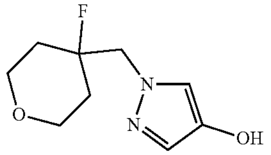 [SMILES: Oc1cnn(CC2(F)CCOCC2)c1]

The title compound (71 mg, 66%) was prepared in a manner similar to that in Example 116 step 2 from 1-((4-fluoro-tetrahydro-2H-pyran-4-yl)methyl)-4-(4,4,5,5-tetramethyl-1,3,2-dioxaborolan-2-yl)-1H-pyrazole. LC-MS $(M+H)^+$=201.1.

Step 4: 5-bromo-3-(1-((4-fluoro-tetrahydro-2H-pyran-4-yl)methyl)-1H-pyrazol-4-yloxy)pyrazin-2-amine

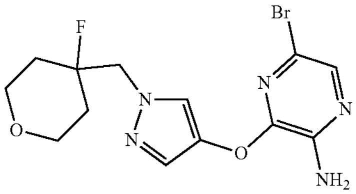 [SMILES: Nc1ncc(Br)nc1Oc1cnn(CC2(F)CCOCC2)c1]

The title compound (78 mg, 59%) was prepared in a manner similar to that in Example 116 step 3 from 1-((4-fluoro-tetrahydro-2H-pyran-4-yl)methyl)-1H-pyrazol-4-ol and 3,5-dibromopyrazin-2-amine. LC-MS $(M+H)^+$=372.1.

Step 5: 5-(2,5-dimethyl-1,2,3,4-tetrahydroisoquinolin-7-yl)-3-(1-((4-fluoro-tetrahydro-2H-pyran-4-yl)methyl)-1H-pyrazol-4-yloxy)pyrazin-2-amine Example 314 (28 mg, 29%) was prepared in a manner similar to that in Example 1 step 8 from 5-bromo-3-(1-((4-fluoro-tetrahydro-2H-pyran-4-yl)methyl)-1H-pyrazol-4-yloxy)pyrazin-2-amine and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.14-8.05 (m, 2H), 7.72-7.60 (m, 2H), 7.48 (s, 1H), 4.54-4.33 (m, 2H), 4.24 (s, 2H), 3.88-3.77 (m, 2H), 3.76-3.63 (m, 2H), 3.47-3.37 (m, 2H), 3.08-2.98 (m, 2H), 2.91 (s, 3H), 2.32 (s, 3H), 2.04-1.73 (m, 2H), 1.72-1.58 (m, 2H). LC-MS $(M+H)^+$=453.2.

Example 315: (1r,3r)-3-(4-((3-amino-6-(2,5-dimethyl-1,2,3,4-tetrahydroisoquinolin-7-yl)pyrazin-2-yl)oxy)-1H-pyrazol-1-yl)cyclobutane-1-carbonitrile

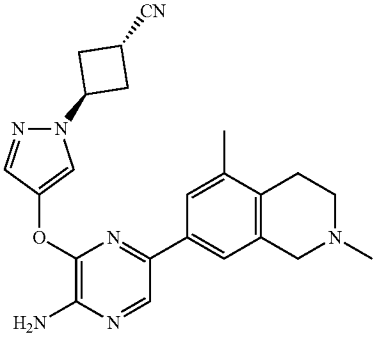 [SMILES: Cc1cc(-c2cnc(N)c(Oc3cnn([C@H]4C[C@H](C#N)C4)c3)n2)cc2c1CCN(C)C2]

Step 1: 3-hydroxycyclobutanecarbonitrile

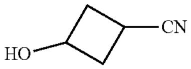

The title compound (428 mg, 55%) was prepared in a manner similar to that in Example 22 step 1 from 3-oxocyclobutanecarbonitrile.

Step 2: 3-cyanocyclobutyl 4-methylbenzenesulfonate

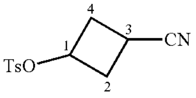

3-cyanocyclobutyl 4-methylbenzenesulfonate

The title compound (1097 mg, 99%) was prepared in a manner similar to that in Example 311 step 1 from 3-hydroxycyclobutanecarbonitrile.

Step 3: 3-(4-(4,4,5,5-tetramethyl-1,3,2-dioxaborolan-2-yl)-1H-pyrazol-1-yl)cyclobutanecarbonitrile

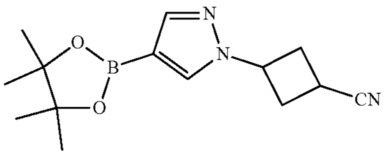 [SMILES: CC1(C)OB(c2cnn(C3CC(C#N)C3)c2)OC1(C)C]

The title compound (728 mg, 61%) was prepared in a manner similar to that in Example 311 step 5 from 3-cyanocyclobutyl 4-methylbenzenesulfonate and 4-(4,4,5,5-tetramethyl-1,3,2-dioxaborolan-2-yl)-1H-pyrazole. LC-MS $(M+H)^+$=274.0.

Step 4: 3-(4-hydroxy-1H-pyrazol-1-yl)cyclobutanecarbonitrile

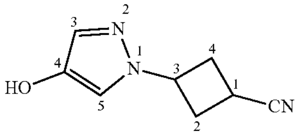

3-(4-hydroxy-1H-pyrazol-1-yl)cyclobutane-1-carbonitrile

The title compound (240 mg, 58%) was prepared in a manner similar to that in Example 116 step 2 from 3-(4-(4,4,5,5-tetramethyl-1,3,2-dioxaborolan-2-yl)-1H-pyrazol-1-yl)cyclobutanecarbonitrile. LC-MS $(M+H)^+$=164.2.

Step 5: 3-(4-(3-amino-6-bromopyrazin-2-yloxy)-1H-pyrazol-1-yl)cyclobutanecarbonitrile

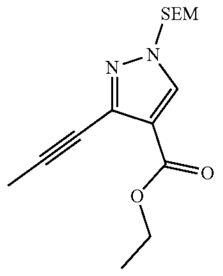 [SMILES: CC#Cc1nn(COCC[Si](C)(C)C)cc1C(=O)OCC]

The title compound (364 mg, 89%) was prepared in a manner similar to that in Example 116 step 3 from 3-(4-hydroxy-1H-pyrazol-1-yl)cyclobutanecarbonitrile and 3,5-dibromopyrazin-2-amine. LC-MS $(M+H)^+$=335.1.

Step 6: (1r,3r)-3-(4-((3-amino-6-(2,5-dimethyl-1,2,3,4-tetrahydroisoquinolin-7-yl)pyrazin-2-yl)oxy)-1H-pyrazol-1-yl)cyclobutane-1-carbonitrile Example 315 (26 mg, 26%) was prepared in a manner similar to that in Example 1 step 8 from 3-(4-(3-amino-6-bromopyrazin-2-yloxy)-1H-pyrazol-1-yl)cyclobutanecarbonitrile and 2,5-dimethyl-7-(4,4,5,5-tetramethyl-1,3,2-dioxaborolan-2-yl)-1,2,3,4-tetrahydroisoquinoline. $^1$H NMR (300 MHz, DMSO-d6) δ 8.20-8.10 (m, 2H), 7.69 (s, 1H), 7.44 (s, 1H), 7.31 (s, 1H), 6.61 (s, 1H), 5.27-5.10 (m, 1H), 3.55-3.42 (m, 3H), 3.01-2.73 (m, 4H), 2.68-2.55 (m, 4H), 2.32 (s, 3H), 2.19 (s, 3H). LC-MS $(M+H)^+$=416.3.

Example 316: (1r,3r)-3-(4-((3-amino-6-(2,8-dimethyl-1,2,3,4-tetrahydroisoquinolin-6-yl)pyrazin-2-yl)oxy)-1H-pyrazol-1-yl)cyclobutane-1-carbonitrile

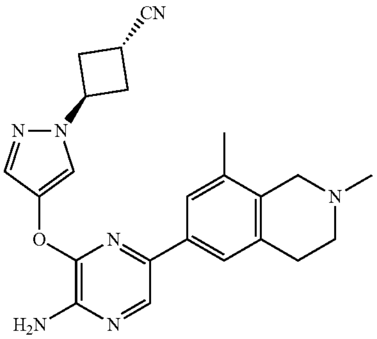 [SMILES: Cc1cc(-c2cnc(N)c(Oc3cnn([C@H]4C[C@H](C#N)C4)c3)n2)cc2c1CN(C)CC2]

Example 316 (23 mg, 46%) was prepared in a manner similar to that in Example 1 step 8 from 3-(4-(3-amino-6-bromopyrazin-2-yloxy)-1H-pyrazol-1-yl)cyclobutanecarbonitrile and 2,8-dimethyl-6-(4,4,5,5-tetramethyl-1,3,2-dioxaborolan-2-yl)-1,2,3,4-tetrahydroisoquinoline. $^1$H NMR (300 MHz, DMSO-d6) δ 8.22-8.11 (m, 2H), 7.68 (s, 1H), 7.45-7.35 (m, 2H), 6.61 (s, 1H), 5.26-5.09 (m, 1H), 3.55-3.41 (m, 1H), 3.38 (s, 2H), 2.98-2.71 (m, 6H), 2.61-2.51 (m, 3H), 2.37 (s, 3H), 2.16 (s, 3H). LC-MS $(M+H)^+$=416.3.

Example 317: 2-(4-(3-amino-6-(2,5-dimethyl-1,2,3,4-tetrahydroisoquinolin-7-yl)pyrazin-2-yloxy)-1H-pyrazol-1-yl)-2-methylpropanenitrile

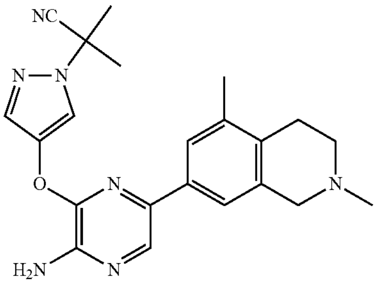 [SMILES: Cc1cc(-c2cnc(N)c(Oc3cnn(C(C)(C)C#N)c3)n2)cc2c1CCN(C)C2]

Step 1: 2-(4-(4,4,5,5-tetramethyl-1,3,2-dioxaborolan-2-yl)-1H-pyrazol-1-yl)acetonitrile

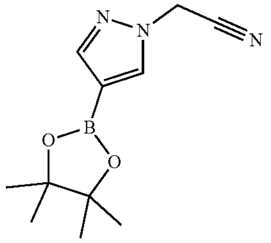 [SMILES: CC1(C)OB(c2cnn(CC#N)c2)OC1(C)C]

The title compound (2467 mg, 43%) was prepared in a manner similar to that in Example 116 step 1 from 4-(4,4,5,5-tetramethyl-1,3,2-dioxaborolan-2-yl)-1H-pyrazole and 2-bromoacetonitrile. LC-MS $(M+H)^+$=233.9.

Step 2: 2-methyl-2-(4-(4,4,5,5-tetramethyl-1,3,2-dioxaborolan-2-yl)-1H-pyrazol-1-yl)propanenitrile

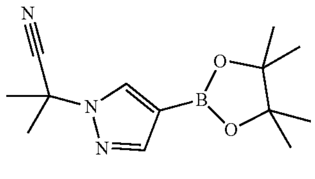 [SMILES: CC(C)(C#N)n1cc(B2OC(C)(C)C(C)(C)O2)cn1]

At 0° C., to a solution of 2-(4-(4,4,5,5-tetramethyl-1,3,2-dioxaborolan-2-yl)-1H-pyrazol-1-yl)acetonitrile (1542 mg, 6.6 mmol) in THF (50 mL) was added methyl iodide (2822 mg, 19.9 mmol), and then the NaHMDS (13.2 mL, 1.0 M in THF, 13.2 mmol) was added dropwise. The mixture was stirred for 1 h at room temperature then quenched with saturated $NH_4Cl$ (100 mL). The mixture was extracted with ethyl acetate (100 mL). The organic phase was washed with brine (50 mL), dried over $Na_2SO_4$ and filtered. The filtrate was concentrated under reduced pressure to give the title compound (848 mg, 49%). LC-MS $(M+H)^+$=261.9.

Step 3: 2-(4-hydroxy-1H-pyrazol-1-yl)-2-methylpropanenitrile

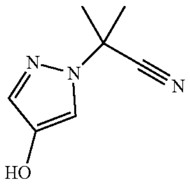

The title compound (380 mg, 77%) was prepared in a manner similar to that in Example 116 step 2 from 2-methyl-2-(4-(4,4,5,5-tetramethyl-1,3,2-dioxaborolan-2-yl)-1H-pyrazol-1-yl)propanenitrile. LC-MS $(M+H)^+$=152.1.

Step 4: 2-(4-(3-amino-6-bromopyrazin-2-yloxy)-1H-pyrazol-1-yl)-2-methylpropanenitrile

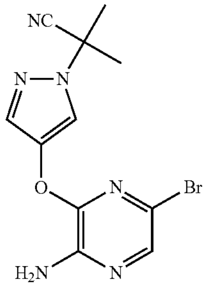 [SMILES: CC(C)(C#N)n1cc(Oc2nc(Br)cnc2N)cn1]

The title compound (350 mg, 59%) was prepared in a manner similar to that in Example 116 step 3 from 2-(4-hydroxy-1H-pyrazol-1-yl)-2-methylpropanenitrile and 5-bromo-3-chloropyrazin-2-amine. LC-MS $(M+H)^+$=323.0.

Step 5: 2-(4-(3-amino-6-(2,5-dimethyl-1,2,3,4-tetrahydroisoquinolin-7-yl)pyrazin-2-yloxy)-1H-pyrazol-1-yl)-2-methylpropanenitrile Example 317 (50 mg, 21%) was prepared in a manner similar to that in Example 1 step 8 from 2-(4-(3-amino-6-bromopyrazin-2-yloxy)-1H-pyrazol-1-yl)-2-methylpropanenitrile and 2,5-dimethyl-7-(4,4,5,5-tetramethyl-1,3,2-dioxaborolan-2-yl)-1,2,3,4-tetrahydroisoquinoline. $^1$H NMR (400 MHz, DMSO-d6) δ 8.40 (s, 1H), 8.20 (s, 1H), 7.78 (s, 1H), 7.47 (s, 1H), 7.34 (s, 1H), 6.66 (s, 2H), 3.46 (s, 2H), 2.69-2.58 (m, 4H), 2.32 (s, 3H), 2.18 (s, 3H), 2.01 (s, 6H). LC-MS $(M+H)^+$=404.2.

Example 318: 3-(4-(3-amino-6-(2,8-dimethyl-1,2,3,4-tetrahydroisoquinolin-6-yl)pyrazin-2-yloxy)-1H-pyrazol-1-yl)-2,2-dimethylpropanenitrile

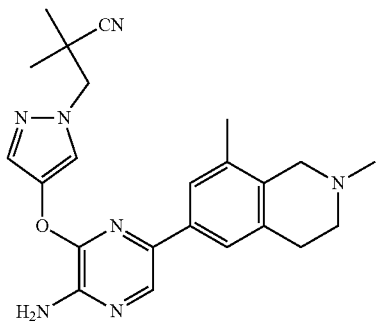 [SMILES: Cc1cc(-c2cnc(N)c(Oc3cnn(CC(C)(C)C#N)c3)n2)cc2c1CN(C)CC2]

Step 1: 2,2-dimethyl-3-(4-(4,4,5,5-tetramethyl-1,3,2-dioxaborolan-2-yl)-1H-pyrazol-1-yl)propanenitrile

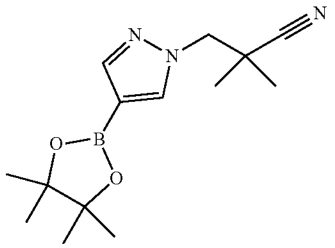 [SMILES: CC(C)(C#N)Cn1cc(B2OC(C)(C)C(C)(C)O2)cn1]

The title compound (973 mg, 52%) was prepared in a manner similar to that in Example 317 step 2 from 3-(4-(4,4,5,5-tetramethyl-1,3,2-dioxaborolan-2-yl)-1H-pyrazol-1-yl)propanenitrile and Mel. LC-MS $(M+H)^+$=276.2.

Step 2: 3-(4-hydroxy-1H-pyrazol-1-yl)-2,2-dimethylpropanenitrile

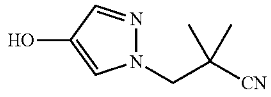

The title compound (584 mg, 75%) was prepared in a manner similar to that in Example 116 step 2 from 2,2-dimethyl-3-(4-(4,4,5,5-tetramethyl-1,3,2-dioxaborolan-2-yl)-1H-pyrazol-1-yl)propanenitrile. LC-MS $(M+H)^+$=166.2.

Step 3: 3-(4-((3-amino-6-bromopyrazin-2-yl)oxy)-1H-pyrazol-1-yl)-2,2-dimethylpropanenitrile

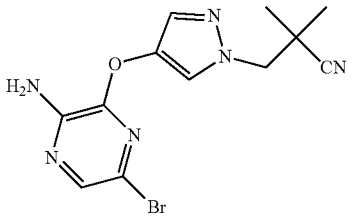 [SMILES: CC(C)(C#N)Cn1cc(Oc2nc(Br)cnc2N)cn1]

The title compound (477 mg, 36%) was prepared in a manner similar to that in Example 116 step 3 from 3-(4-hydroxy-1H-pyrazol-1-yl)-2,2-dimethylpropanenitrile and 3,5-dibromopyrazin-2-amine. LC-MS $(M+H)^+$=337.2.

Step 4: 3-(4-(3-amino-6-(2,8-dimethyl-1,2,3,4-tetrahydroisoquinolin-6-yl)pyrazin-2-yloxy)-1H-pyrazol-1-yl)-2,2-dimethylpropanenitrile Example 318 (26 mg, 12%) was prepared in a manner similar to that in Example 1 step 8 from 3-(4-(3-amino-6-bromopyrazin-2-yloxy)-1H-pyrazol-1-yl)-2,2-dimethylpropanenitrile and 2,8-dimethyl-6-(4,4,5,5-tetramethyl-1,3,2-dioxaborolan-2-yl)-1,2,3,4-tetrahydroisoquinoline. $^1$H NMR (400 MHz, DMSO-d6) δ 8.19 (s, 1H), 8.08 (s, 1H), 7.67 (s, 1H), 7.45-7.36 (m, 2H), 6.65 (s, 2H), 4.36 (s, 2H), 3.38 (s, 2H), 2.86-2.78 (m, 2H), 2.60-2.53 (m, 2H), 2.38 (s, 3H), 2.17 (s, 3H), 1.36 (s, 6H). LC-MS $(M+H)^+$=418.2.

Example 319: 1-(3-amino-6-(2,5-dimethyl-1,2,3,4-tetrahydroisoquinolin-7-yl)pyrazin-2-yl)-N,N-dimethyl-3-(prop-1-ynyl)-1H-pyrazole-4-carboxamide

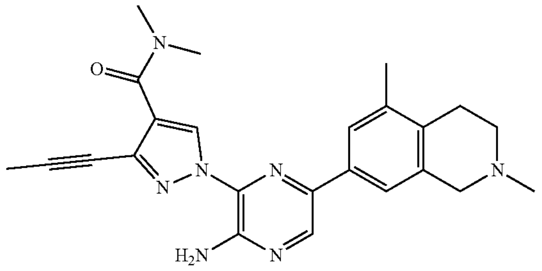 [SMILES: CC#Cc1nn(-c2nc(-c3cc(C)c4c(c3)CN(C)CC4)cnc2N)cc1C(=O)N(C)C]

Step 1: ethyl 3-iodo-1-((2-(trimethylsilyl)ethoxy)methyl)-1H-pyrazole-4-carboxylate

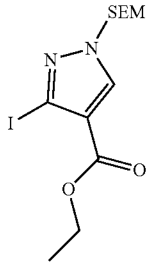 [SMILES: CCOC(=O)c1cn(COCC[Si](C)(C)C)nc1I]

The title compound (5236 mg, 69%) was prepared in a manner similar to that in Example 34 step 1 from ethyl 3-iodo-1H-pyrazole-4-carboxylate and SEM-Cl. LC-MS $(M+H)^+$=397.2.

Step 2: ethyl 3-(prop-1-ynyl)-1-((2-(trimethylsilyl)ethoxy)methyl)-1H-pyrazole-4-carboxylate

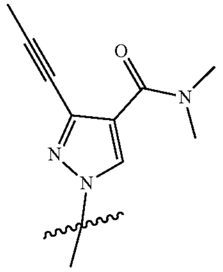

-continued

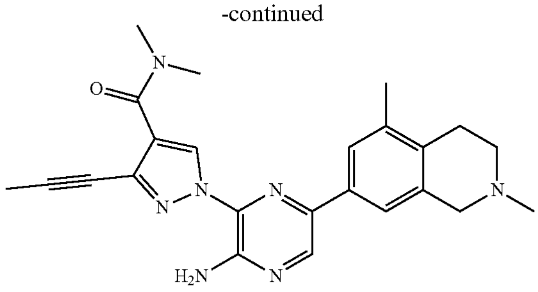

The title compound (2691 mg, 67%) was prepared in a manner similar to that in Example 14 step 2 from ethyl 3-iodo-1-((2-(trimethylsilyl)ethoxy)methyl)-1H-pyrazole-4-carboxylate and propyne. LC-MS $(M+H)^+$=309.3.

Step 3: ethyl 3-(prop-1-ynyl)-1H-pyrazole-4-carboxylate

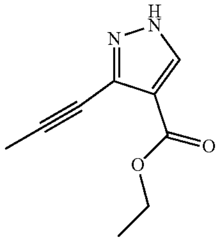

The title compound (469 mg, 58%) was prepared in a manner similar to that in Example 34 step 6 from ethyl 3-(prop-1-ynyl)-1-((2-(trimethylsilyl)ethoxy)methyl)-1H-pyrazole-4-carboxylate. LC-MS $(M+H)^+$=178.9.

Step 4: ethyl 1-(3-amino-6-bromopyrazin-2-yl)-3-(prop-1-ynyl)-1H-pyrazole-4-carboxylate

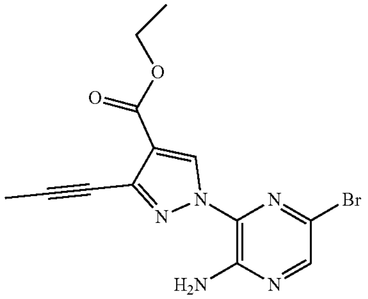 [SMILES: CC#Cc1nn(-c2nc(Br)cnc2N)cc1C(=O)OCC]

The title compound (211 mg, 36%) was prepared in a manner similar to that in Example 289 step 1 from ethyl 3-(prop-1-ynyl)-1H-pyrazole-4-carboxylate and 3,5-dibromopyrazin-2-amine. LC-MS $(M+H)^+$=351.9.

Step 5: ethyl 1-(3-amino-6-(2,5-dimethyl-1,2,3,4-tetrahydroisoquinolin-7-yl)pyrazin-2-yl)-3-(prop-1-ynyl)-1H-pyrazole-4-carboxylate

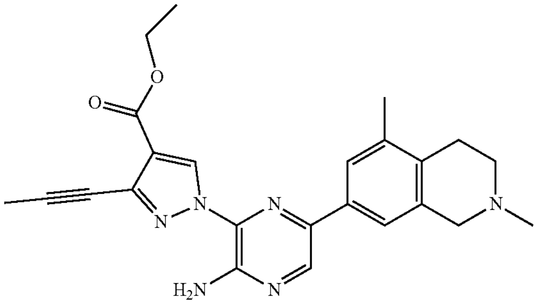 [SMILES: CC#Cc1nn(-c2nc(-c3cc(C)c4c(c3)CN(C)CC4)cnc2N)cc1C(=O)OCC]

The title compound (180 mg, 69%) was prepared in a manner similar to that in Example 1 step 8 from ethyl 1-(3-amino-6-bromopyrazin-2-yl)-3-(prop-1-ynyl)-1H-pyrazole-4-carboxylate and 2,5-dimethyl-7-(4,4,5,5-tetramethyl-1,3,2-dioxaborolan-2-yl)-1,2,3,4-tetrahydroisoquinoline. LC-MS $(M+H)^+=431.1$.

Step 6: 1-(3-amino-6-(2,5-dimethyl-1,2,3,4-tetrahydroisoquinolin-7-yl)pyrazin-2-yl)-3-(prop-1-ynyl)-1H-pyrazole-4-carboxylic acid

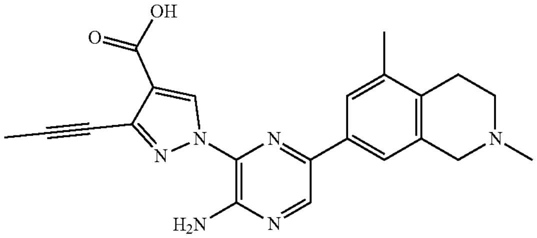 [SMILES: CC#Cc1nn(-c2nc(-c3cc(C)c4c(c3)CN(C)CC4)cnc2N)cc1C(=O)O]

The title compound (108 mg, 64%) was prepared in a manner similar to that in Example 46 step 2 from ethyl 1-(3-amino-6-(2,5-dimethyl-1,2,3,4-tetrahydroisoquinolin-7-yl)pyrazin-2-yl)-3-(prop-1-ynyl)-1H-pyrazole-4-carboxylate. LC-MS $(M+H)^+=403.1$.

Step 7: 1-(3-amino-6-(2,5-dimethyl-1,2,3,4-tetrahydroisoquinolin-7-yl)pyrazin-2-yl)-N,N-dimethyl-3-(prop-1-ynyl)-1H-pyrazole-4-carboxamide Example 319 (48 mg, 41%) was prepared in a manner similar to that in Example 46 step 3 from 1-(3-amino-6-(2,5-dimethyl-1,2,3,4-tetrahydroisoquinolin-7-yl)pyrazin-2-yl)-3-(prop-1-ynyl)-1H-pyrazole-4-carboxylic acid and dimethylamine hydrochloride. 1H NMR (400 MHz, DMSO-d6) δ 9.01 (s, 1H), 8.65 (s, 1H), 7.72 (s, 1H), 7.62 (s, 1H), 7.38 (s, 2H), 3.53 (s, 2H), 3.07-2.99 (m, 6H), 2.72-2.61 (m, 4H), 2.35 (s, 3H), 2.25 (s, 3H), 2.11 (s, 3H). LC-MS $(M+H)^+=430.2$.

Biological Activity

HPK Kinase Activity Assay at 1 mM ATP

Compounds disclosed herein were tested for inhibition of HPK1 kinase (aa1-346, Life Technologies) activity in assays based on the time-resolved fluorescence-resonance energy transfer (TR-FRET) methodology. The assays were carried out in 384-well low volume black plates in a reaction mixture containing HPK1 kinase (40 nM), 1 mM ATP, 0.5 μM STK1 substrate and 0-10 μM compound in buffer containing 50 mM HEPES, 0.01% BSA, 0.1 mM Orthovanadate, 10 mM $MgCl_2$, 1 mM DTT, pH=7.0, 0.005% Tween-20. The kinase was incubated with the compounds disclosed herein or DMSO for 60 minutes at room temperature and the reaction was initiated by the addition of ATP and STK1 substrate. After reaction at room temperature for 120 minutes, an equal volume of stop/detection solution was added according to the manufacture's instruction (CisBio). The stop/detection solution contained STK Antibody-Cryptate and XL665-conjugated streptavidin in Detection Buffer. The TR-FRET signals (ratio of fluorescence emission at 665 nm over emission at 620 nm with excitation at 337 nm wavelength) were recorded on a PHERAstar FS plate reader (BMG Labtech). Phosphorylation of STK1 substrate led to the binding of STK Antibody-Cryptate to the biotinylated STK1 substrate, which places fluorescent donor ($Eu^{3+}$ crypate) in close proximity to the accepter (Streptavidin-XL665), thus resulting in a high degree of fluorescence resonance energy transfer. The inhibition of HPK1 in presence of increasing concentrations of compounds was calculated based on the ratio of fluorescence at 665 nm to that at 620 nm. The $IC_{50}$ for each compound was derived from fitting the data to the four-parameter logistic equation by Graphpad Prism software. The compounds disclosed herein showed the enzymatic activity values as in Table 1.

TABLE 1

Enzymatic activity $IC_{50}$(nM) for the compounds disclosed herein

| Comp No. | Enzymatic activity $IC_{50}$(nM) | Comp No. | Enzymatic activity $IC_{50}$(nM) |
|---|---|---|---|
| 1 | 29 | 2 | 3270 |
| 3 | 364 | 4 | 75 |
| 5 | 172 | 6 | 20 |
| 7 | 15 | 8 | 46 |
| 9 | 17 | 10 | 5.2 |
| 11 | 50 | 12 | 27 |
| 13 | 62 | 14 | 9.4 |
| 15 | 157 | 16 | 49 |
| 17 | 231 | 18 | 73 |
| 19 | 98 | 20 | 151 |
| 21 | 35 | 22 | 38 |
| 23 | 137 | 24 | 61 |
| 25 | 13 | 26 | 113 |
| 27 | 132 | 28 | 10 |
| 29 | 16 | 30 | 7.6 |
| 31 | 25 | 32 | 5.1 |
| 33 | 8.2 | 34 | 12 |
| 35 | 16 | 36 | 93 |
| 37 | 9.3 | 38 | 57 |
| 39 | 85 | 40 | 29 |
| 41 | 8.9 | 42 | 94 |
| 43 | 56 | 44 | 19 |
| 45 | 15 | 46 | 21 |
| 47A | 47 | 47B | 2680 |
| 116 | 42 | 141 | 19 |
| 149 | 16 | 150 | 6.9 |
| 152 | 21 | 161 | 2.8 |
| 179 | 7.2 | 180 | 21 |
| 188 | 8.1 | 193 | 13 |
| 204 | 7.0 | 205 | 12 |
| 222 | 4.0 | 242 | 54 |
| 249 | 8.0 | 266 | 5.1 |
| 271 | 11 | 272 | 8.4 |
| 273 | 12 | 274 | 24 |
| 275 | 14 | 276 | 24 |
| 277 | 6.5 | 278 | 15 |
| 279 | 19 | 280A | 12 |
| 280B | 51 | 281 | 56 |
| 282 | 6.6 | 283 | 6.3 |

TABLE 1-continued

| Enzymatic activity $IC_{50}$(nM) for the compounds disclosed herein | | | |
|---|---|---|---|
| Comp No. | Enzymatic activity $IC_{50}$(nM) | Comp No. | Enzymatic activity $IC_{50}$(nM) |
| 284 | 38 | 285 | 14 |
| 286 | 3.6 | 287 | 25 |
| 288 | 17 | 289 | 9.7 |
| 290 | 16 | 291 | 5.9 |
| 292 | 5.3 | 293 | 37 |
| 294 | 18 | 295 | 36 |
| 296 | 67 | 297 | 6.6 |
| 298 | 4.2 | 299 | 8.9 |
| 300 | 7.5 | 301 | 41 |
| 302 | 54 | 303 | 16 |
| 304 | 10 | 305 | 8.9 |
| 306 | 89 | 307 | 5.9 |
| 308 | 48 | 309 | 22 |
| 310 | 20 | 311 | 7.7 |
| 312 | 63 | 313 | 8.3 |
| 314 | 4.5 | 315 | 33 |
| 316 | 85 | 317 | 20 |
| 318 | 60 | 319 | 18 |

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound of Formula (I):

(I)

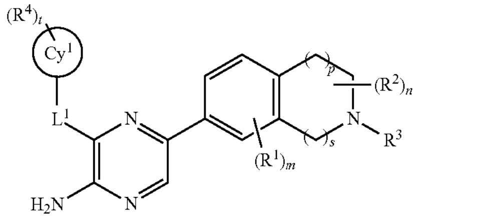

or a pharmaceutically acceptable salt thereof, or a stereoisomer thereof, wherein:

$Cy^1$ is cycloalkyl, aryl, monocyclic heterocyclyl, monocyclic heteroaryl, bicyclic fused heteroaryl, or bicyclic fused heterocyclyl;

$L^1$ is selected from a single bond, alkylene, —O—, —$NR^a$—, —S—, —S(O)—, —$S(O)_2$—, -cycloalkylene, $*^1$-O-alkylene-$**^1$, $*^1$-alkylene-O—$**^1$, $*^1$—$NR^c$-alkylene-$**^1$, $*^1$-alkylene-$NR^c$—$**^1$, alkenylene, or alkynylene; wherein $*^1$ refers to the position attached to the $Cy^1$ moiety, and $**^1$ refers to the position attached to the aminopyrazine moiety;

$R^1$, $R^2$, and $R^4$ at each occurrence are independently hydrogen, halogen, —$C_{1-8}$alkyl, —$C^{2-8}$alkenyl, —$C_{2-8}$alkynyl, cycloalkyl, heterocyclyl, aryl, heteroaryl, oxo, —CN, —$NO_2$, —$OR^a$, —$SO_2R^a$, —$COR^a$, —$CO_2R^a$, —$CONR^aR^b$, —C(═$NR^a$)$NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one $R^d$, $R^3$ is hydrogen, halogen, —$C_{1-8}$alkyl, —$C_{2-8}$alkenyl, —$C_{2-8}$alkynyl, cycloalkyl, heterocyclyl, aryl, or heteroaryl, each of said —$C_{1-8}$alkyl, —$C_{2-8}$alkenyl, —$C_{2-8}$alkynyl, cycloalkyl, heterocyclyl, aryl, or heteroaryl is optionally substituted with at least one $R^d$;

$R^a$, $R^b$, and $R^c$ are each independently hydrogen, deuterium, halogen, —$C_{1-8}$alkyl, —$C_{2-8}$alkenyl, —$C_{2-8}$alkynyl, cycloalkyl, heterocyclyl, aryl, or heteroaryl; each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent $R^e$; or ($R^a$ and $R^b$), ($R^b$ and $R^c$), or ($R^c$ and $R^a$), together with the atom(s) to which they are attached, form a 3- to 12-membered ring, said ring comprising 0, 1 or 2 additional heteroatom(s) independently selected from nitrogen, oxygen or optionally oxidized sulfur as ring member(s), said ring is optionally substituted with at least one substituent $R^e$;

$R^d$ and $R^e$ are each independently halogen, —$C_{1-8}$alkyl, —$C_{2-8}$alkenyl, —$C_{2-8}$alkynyl, cycloalkyl, heterocyclyl, aryl, heteroaryl, oxo, —CN, —$NO_2$, —$OR^f$, —$SO_2R^f$, —$SO_2NR^fR^g$, —$COR^f$, —$CO_2R^f$, —$CONR^fR^g$, —C(═$NR^f$)$NR^gR^h$, —$NR^fR^g$, —$NR^fCOR^g$, —$NR^fCONR^gR^h$, —$NR^fCO_2R^f$, —$NR^f$-$SONR^fR^g$, —$NR^fSO_2NR^gR^h$, or —$NR^fSO_2R^g$, each of said —$C_{1-8}$alkyl, —$C_{2-8}$alkenyl, —$C_{2-8}$alkynyl, cycloalkyl, heterocyclyl, aryl, or heteroaryl is optionally substituted with at least one substituent selected from halogen, —$C_{1-8}$alkyl, —$OR^i$, —$NR^iR^j$, —CO—$NR^iR^j$, cycloalkyl, heterocyclyl, aryl, or heteroaryl;

$R^f$, $R^g$, $R^h$, $R^i$, and $R^j$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, or heteroaryl;

m, n and t are each independently 0, 1, 2, 3 or 4; and p and s are each independently 0, 1, 2, 3, or 4.

2. The compound according to claim 1, wherein $L^1$ is a single bond, —$CR^aR^b$—, —O—, —$NR^a$, $*^1$—$CR^aR^b$—$NR^c**^1$, $*^1$—O—$CR^aR^b$—$**^1$, or —S—; and a) $R^a$, $R^b$, and $R^c$ are each independently hydrogen, deuterium, halogen, —$C_{1-8}$alkyl, or $C_{3-8}$cycloalkyl, each of said —$C_{1-8}$alkyl or $C_{3-8}$cycloalkyl is optionally substituted with $OR^f$; $R^f$ is each independently hydrogen or —$C_{1-8}$alkyl; or $R^a$ and $R^b$ together with the carbon atom to which they are attached, form a 3- to 5-membered ring; or b) $R^a$, $R^b$ and $R^c$ are each independently hydrogen, F, Cl, Br, I, methyl, ethyl, propyl, isopropyl, 2-methylpropyl, butyl, pentyl, or hexyl; each of said methyl, ethyl, propyl, isopropyl, 2-methylpropyl, butyl, pentyl, or hexyl is optionally substituted with OH.

3. The compound according to claim 2, wherein:

$L^1$ is selected from a single bond, —O—, $*^1$—$CH_2$—O—$**^1$, $*^1$—$CHCH_3$—O—$**^1$, $*^1$—$CH_2$—NH—$**^1$, $*^1$—$CH_2$—N($CH_3$)—$**^1$, $*^1$—C$(CH_3)_2$—O—$**^1$, or $*^1$—$CF_2$—O—$**^1$;

m is 1;

$R^1$ is selected from hydrogen, —$C_{1-8}$alkyl, $OR^a$, —$NR^aR^b$, or halogen, said —$C_{1-8}$alkyl is optionally substituted with at least one halogen;

$R^a$ and $R^b$ are each independently hydrogen or $—C_{1-8}$alkyl;

p is 1 and s is 1, or p is 0 and s is 2;

n is 0;

$R^3$ is selected from $—C_{1-8}$alkyl or $C_{4-8}$heterocyclyl, said $—C_{1-8}$alkyl and $C_{4-8}$heterocyclyl are optionally substituted with $R^d$;

$R^d$ is selected from $—C_{1-8}$alkyl, $—NR^fR^g$ or $—CONR^fR^g$; and $R^f$ and $R^g$ are each independently hydrogen or $—C_{1-8}$alkyl.

4. The compound according to claim 3, wherein $R^3$ is selected from methyl, ethyl, propyl, 2-methylpropyl, butyl, pentyl, hexyl, or piperidinyl, said methyl, ethyl, propyl, 2-methylpropyl, butyl, pentyl, hexyl, or piperidinyl is optionally substituted with $R^d$; $R^d$ is selected from methyl, $—NR^fR^g$ or $—CONR^fR^g$; and $R^f$ and $R^g$ are each independently hydrogen, methyl, or butyl.

5. The compound according to claim 1, wherein the compound has a structure of Formula (Ia) or Formula (Ib):

(Ia)

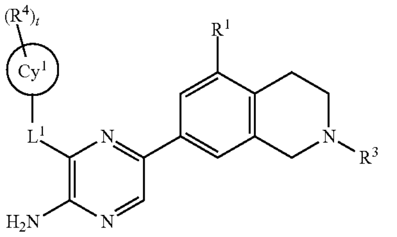

or (Ib)

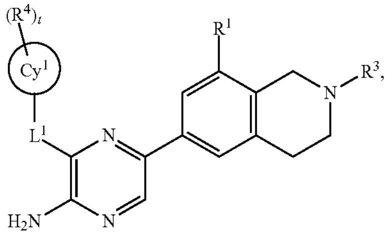

or a pharmaceutically acceptable salt thereof, or a stereoisomer thereof.

6. The compound according to claim 5, wherein $R^1$ and $R^3$ are each independently selected from hydrogen, $—CH_3$, $OCH_3$, halogen, $—NHCH_3$, $—NHCH_2CH_3$,

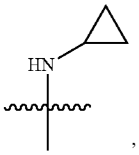

,

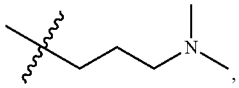

,

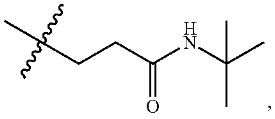

, $CHF_2$, $—CF_3$ or

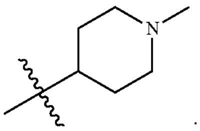 [SMILES: *C1CCN(C)CC1]

.

7. The compound according to claim 5, wherein the compound has a structure selected from Formula (Ic), Formula (Id), Formula (Ie), Formula (If), Formula (Ig), Formula (Ih), Formula (Ii), Formula (Ii), Formula (Ik), Formula (Il), Formula (Im), or Formula (In):

(Ic)

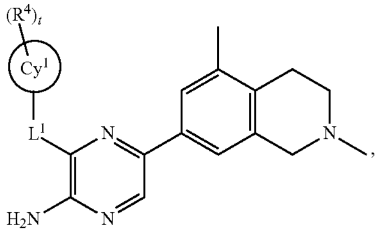

(Id)

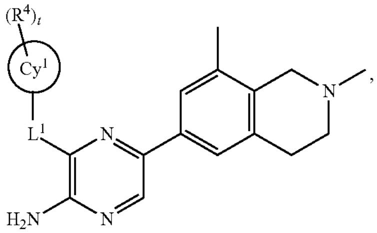

(Ie)

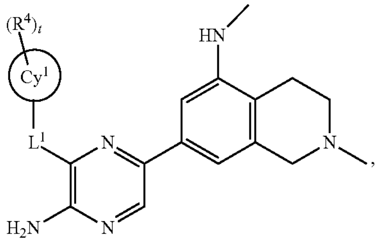

(If)

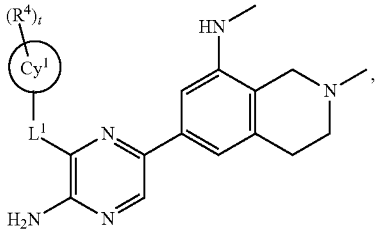

(Ig)

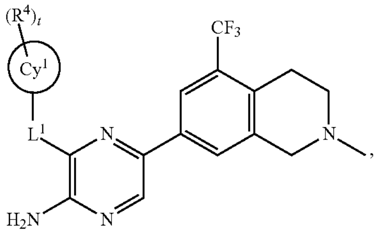

-continued (Ih)

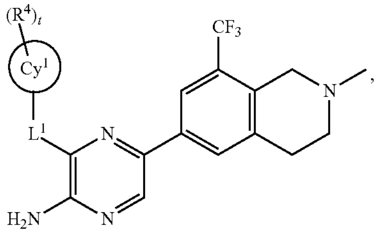

(Ii)

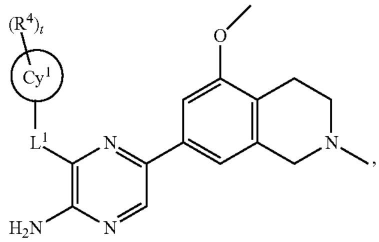

(Ij)

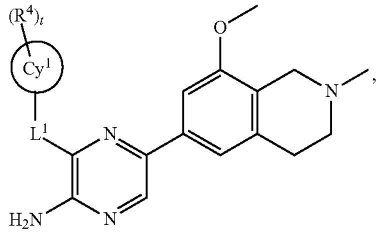

(Ik)

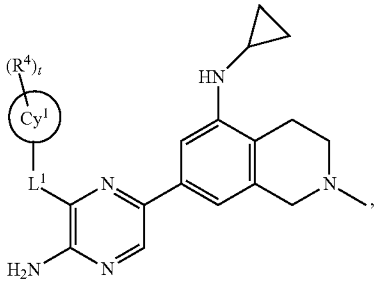

(Il)

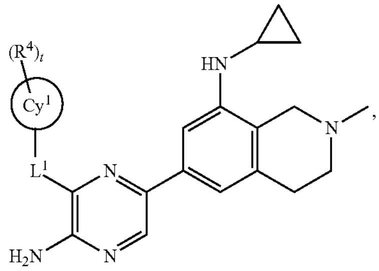

(Im)

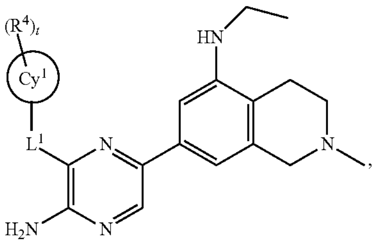

or

-continued (In)

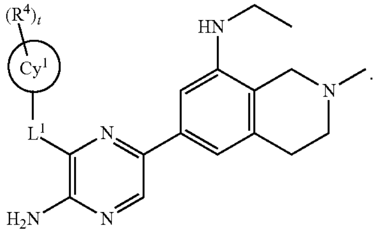

or a pharmaceutically acceptable salt thereof, or a stereoisomer thereof.

8. The compound according to claim 7, wherein the compound has a structure selected from Formula (Ic1), Formula (Ic2), Formula (Ic3), Formula (Ic4), Formula (Ic5), Formula (Ic6), Formula (Ic7), Formula (Ic8), Formula (Ic9), Formula (Ic10), Formula (Ic11), Formula (Ic12), Formula (Ic13), Formula (Ic14), Formula (Ic15), Formula (Id1), Formula (Ie1), Formula (Ih1), Formula (Ii1), Formula (Ie2), or Formula (Ik1):

(Ic1)

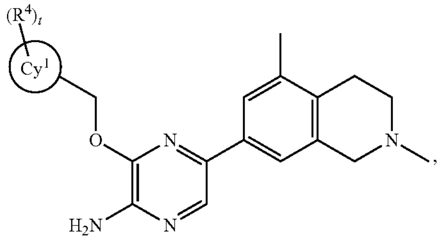

(Ic2)

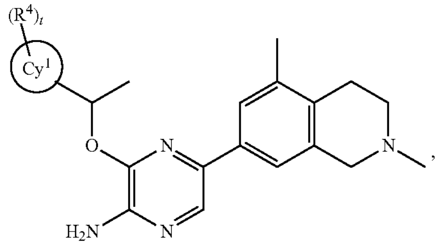

(Ic3)

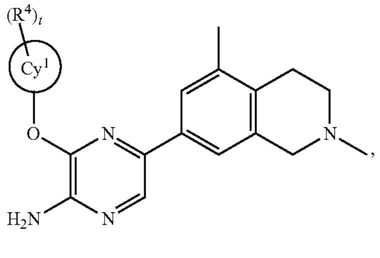

(Ic4)

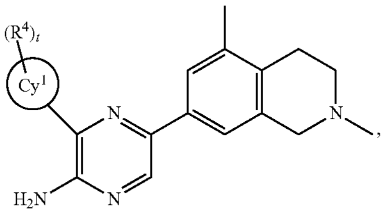

-continued
(Ic5)
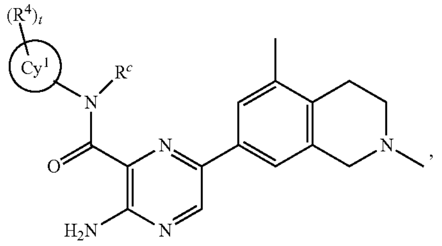
(Ic6)
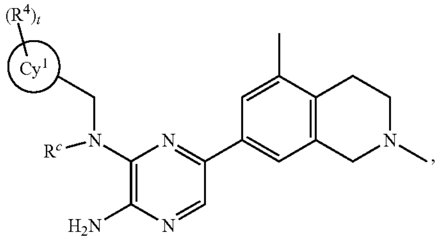
(Ic7)
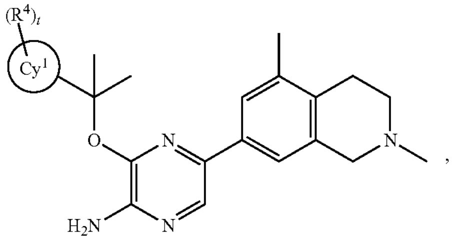
(Ic8)
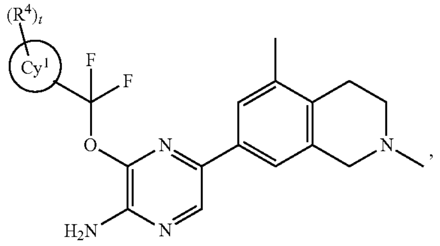
(Ic9)
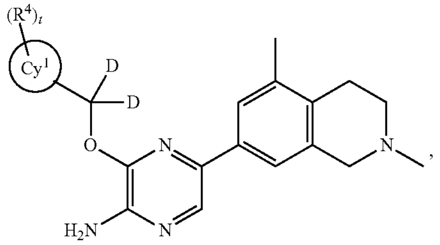
(Ic10)
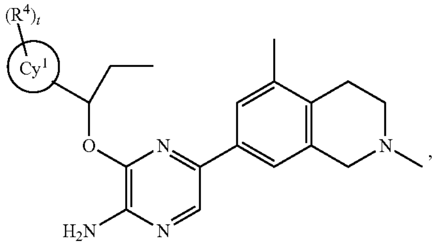
-continued
(Ic11)
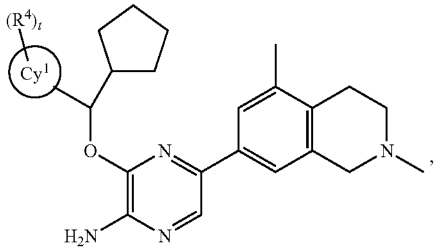
(Ic12)
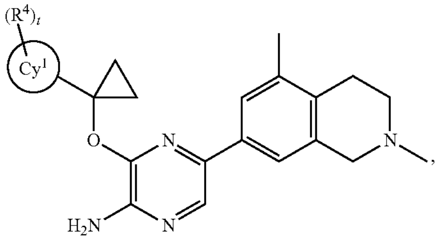
(Ic13)
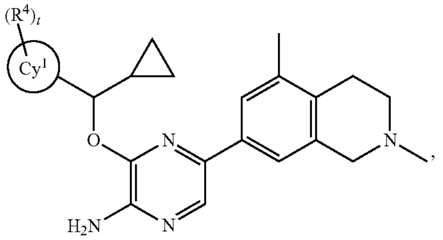
(Ic14)
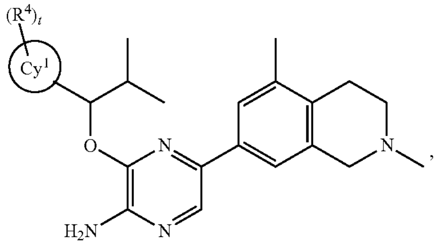
(Ic15)
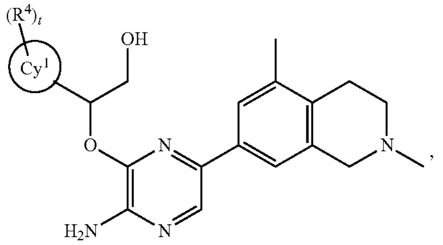
(Ie1)
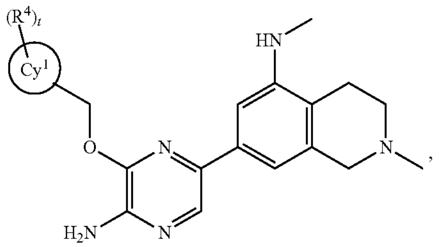

-continued (Id1)

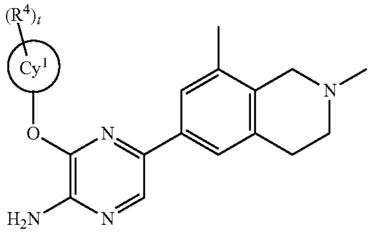

, (Ih1)

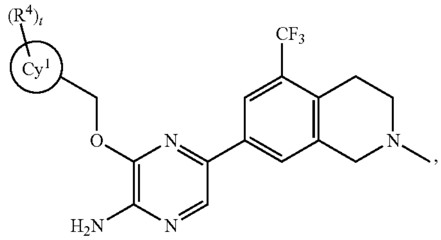

, (Ii1)

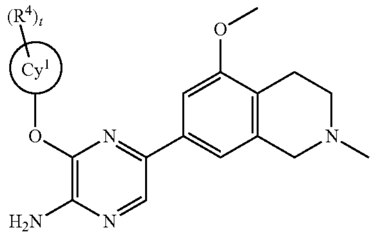

, (Ie2)

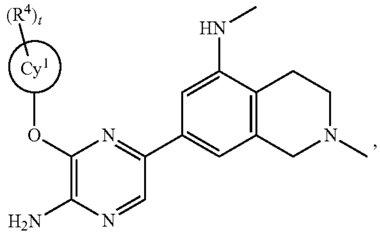

, or (Ik1)

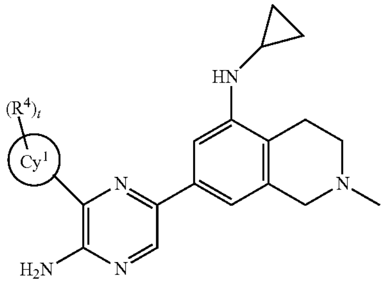

.

or a pharmaceutically acceptable salt thereof, or a stereoisomer thereof;

wherein $R^e$ is hydrogen or —$C_{1-8}$alkyl.

9. The compound according to claim 8, wherein:

a) $Cy^1$ is selected from 3- to 8-membered monocyclic heterocyclyl comprising one or two heteroatoms independently selected from nitrogen, oxygen, or optionally oxidized sulfur as ring member(s), wherein $Cy^1$ is optionally substituted with —$(R^4)$;

b) $Cy^1$ is selected from oxiranyl, aziridinyl, thiiranyl, azetidinyl, oxetanyl, thietanyl, pyrrolidinyl, imidazolidinyl, pyrazolidinyl, piperidinyl, tetrahydropyranyl, morpholinyl, thiomorpholinyl, thioxanyl, piperazinyl, azocanyl, azetidinyl, dihydropyridinyl, tetrahydropyridinyl, pyranyl, homopiperidinyl, homopiperazinyl, azepanyl, oxepanyl, thiepanyl, oxathianyl, 1,4-oxathianyl, 1,4-dioxepanyl, 1,4-oxathiepanyl, 1,4-oxaazepanyl, 1,4-dithiepanyl, 1,4-thiazepanyl, 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl, wherein $Cy^1$ is optionally substituted with —$(R^4)$;

c) $Cy^1$ is monocyclic or bicyclic aryl group optionally substituted with —$(R^4)$;

d) $Cy^1$ is 5- or 6-membered heteroaryl optionally substituted with —$(R^4)$;

e) $Cy^1$ is selected from pyridyl, cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furanyl, benzofuryl, benzoimidazolyl, indolyl, isoindolyl, oxadiazolyl, phthalazinyl, pyrazolyl, pyrazinyl, pyridazinyl, pyrrolyl, or triazoly, wherein $Cy^1$ is optionally substituted with —$(R_4)_t$; or f) $Cy^1$ is selected from 7 to 12-membered bicyclic fused heteroaryl or heterocyclyl comprising one or two or three heteroatoms independently selected from nitrogen, oxygen, or optionally oxidized sulfur as ring member(s), wherein $Cy^1$ is optionally substituted with —$(R^4)_t$.

10. The compound according to claim 9, wherein:

a) $Cy^1$ is selected from piperidinyl, dihydropyridinyl, or pyrrolidinyl, wherein $Cy^1$ is optionally substituted with —$(R_4)_t$; t=0 or 1; and each $R^4$ is selected from hydrogen, oxo, or —$C_{1-8}$alkyl; or b) 2-pyridyl, 3-pyridyl, 4-pyridyl, cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, 1,2,3-thiadiazolyl, 1,2,4-thiadiazolyl, 1,3,4-thiadiazolyl, tetrazolyl, thien-2-yl, thien-3-yl, triazinyl, benzothienyl, furanyl, benzofuryl, benzoimidazolyl, indolyl, isoindolyl, 1,2,3-oxadiazolyl, 1,2,4-oxadiazolyl, 1,3,4-oxadiazolyl, phthalazinyl, pyrazolyl, pyrazinyl, pyridazinyl, pyrrolyl, 1,2,3-triazolyl, 1,2,4-triazolyl, or 1,3,4-triazolyl, wherein $Cy^1$ is optionally substituted with —$(R^4)_t$; or c) $Cy^1$ is naphthyl or phenyl, wherein $Cy^1$ is optionally substituted with —$(R_4)_t$; t=0, 1, 2 or 3; each $R^4$ is independently selected from hydrogen, halogen, —CN, —$COOR^a$, —$OR^a$, —$CONR^aR^b$, —$NR^aR^b$, or —$C_{1-8}$alkyl optionally substituted with halogen or —$OR^f$; and $R^a$, $R^b$ and $R^f$ are each independently hydrogen, —$C_{1-8}$alkyl, —$C_{3-6}$cycloalkyl, or —$C_{3-6}$heterocyclyl; or $R^a$ and $R^b$, together with the nitrogen atom to which they are attached, form a 3- to 12-membered ring, said ring comprising 0, 1 or 2 additional heteroatom(s) independently selected from nitrogen, oxygen or optionally oxidized sulfur as ring member(s); or d) $Cy^1$ is selected from indazole, benzoimidazole, quinoline, pyridooxazine, pyrrolopyridine, isoquinoline, benzoxazine, quinoxaline, isochromene, pyranopyrazole, pyranopyridine, benzodioxole, quinazoline, benzoxazole, indole, pyrrolopyrazine, pyrrolopyrimidine, imidazopyrimidine, or thienopyridine, wherein one or two carbon-carbon double bond or carbon-nitrogen double bond is optionally hydrogenated and $Cy^1$ is optionally substituted with $—(R^4)_t$; t is 0, 1 or 2; each $R^4$ is halogen, $—C_{1-8}$alkyl, oxo, or $—OR^a$, said $—C_{1-8}$alkyl is optionally substituted with halogen, hydroxy or alkoxy; and $R^a$ is hydrogen or $—C_{1-8}$alkyl.
11. The compound according to claim 9, wherein
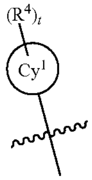
is selected from:
a)
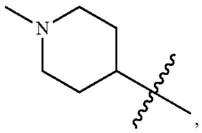, 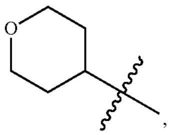, 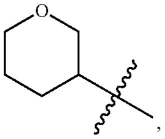, 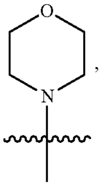, 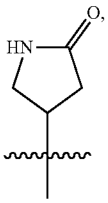, 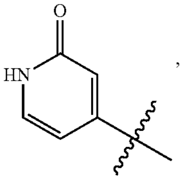, or 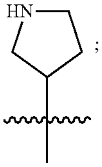;
b)
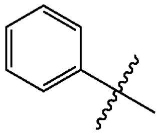, 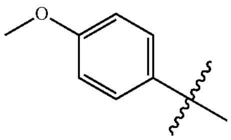, 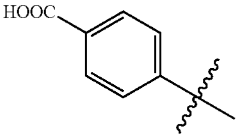, 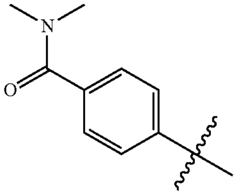, 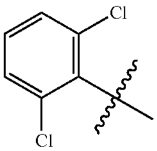, 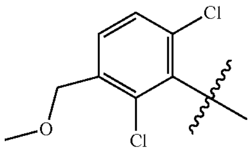,
-continued
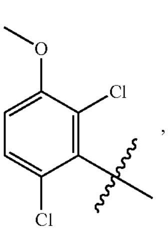, 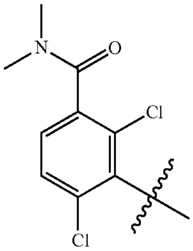, 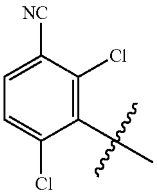, 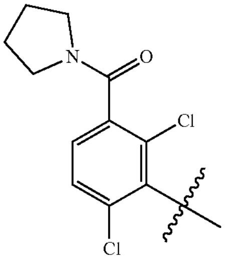, 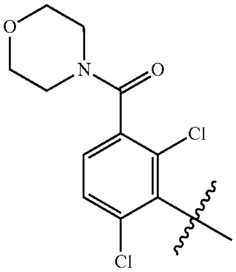, 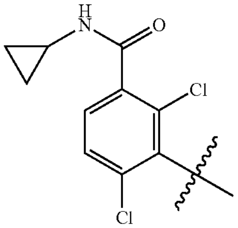, or 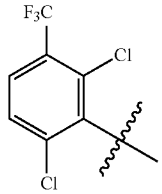;
c)
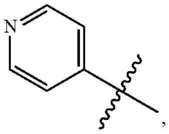, 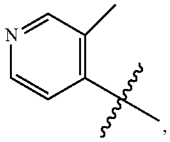, 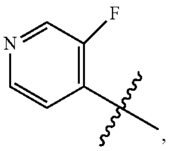, 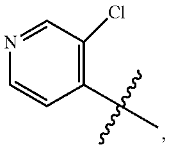, 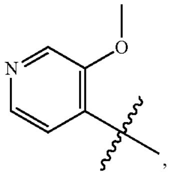, 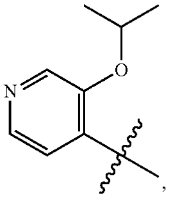, 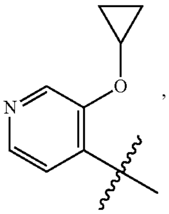, 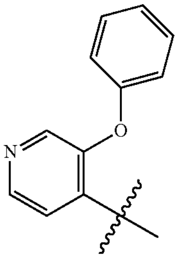, 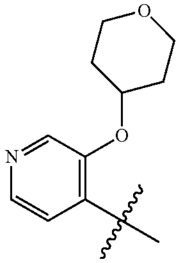, -continued
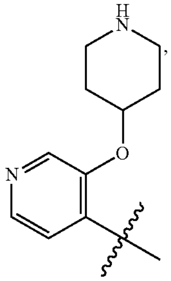,
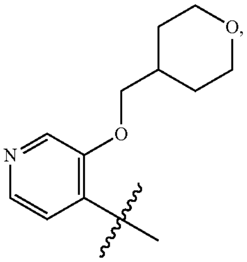,
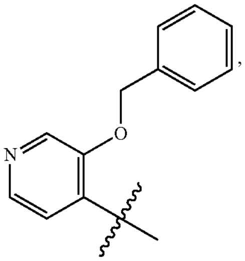,
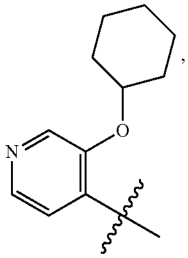,
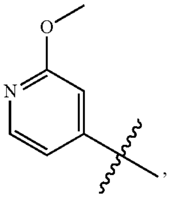,
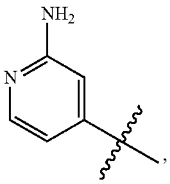,
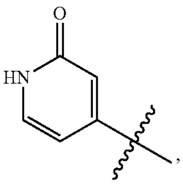,
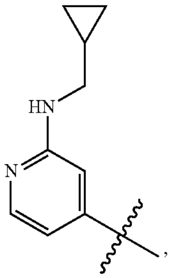,
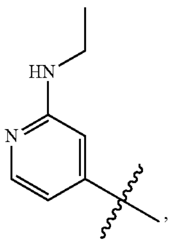,
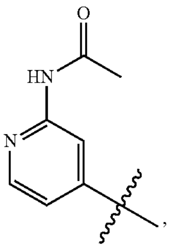,
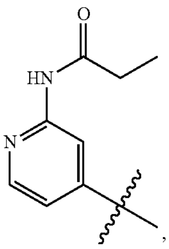,
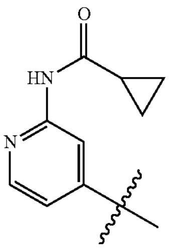,
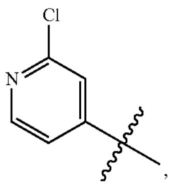,
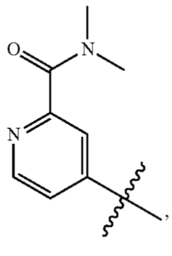,
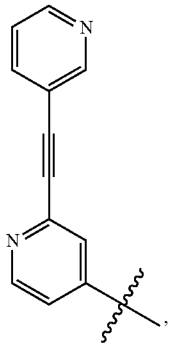,
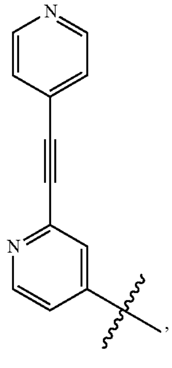,
-continued
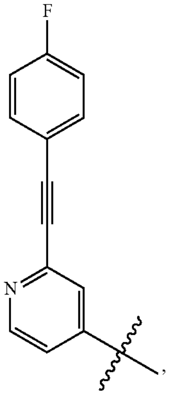,
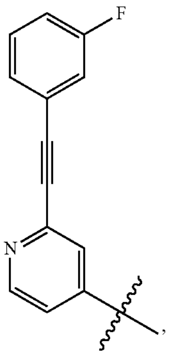,
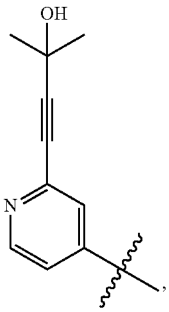,
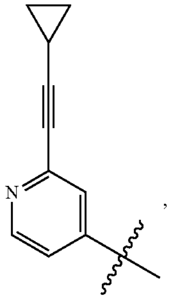,
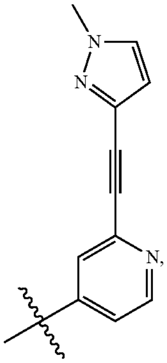,
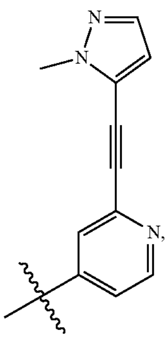,
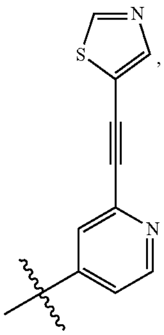,
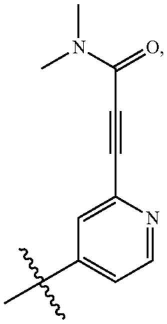,
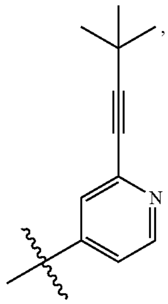,
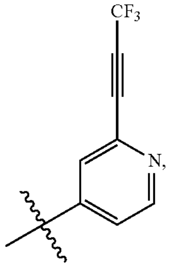,
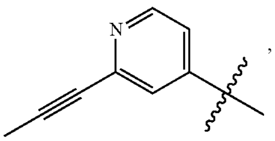,
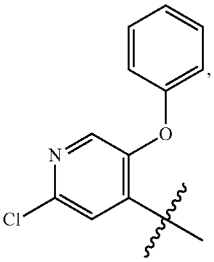,
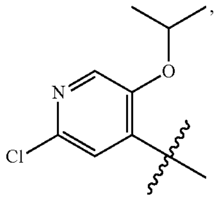, -continued
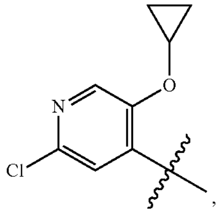,
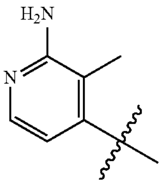,
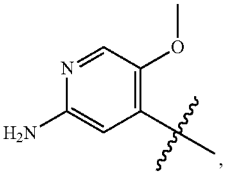,
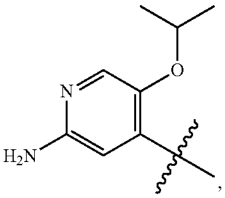,
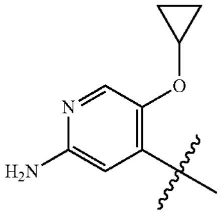,
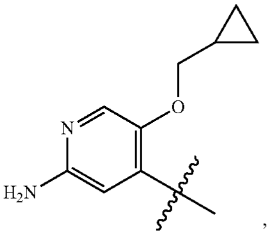,
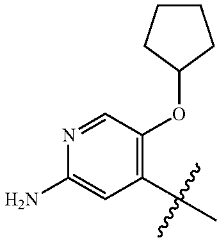,
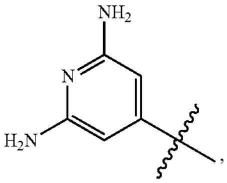,
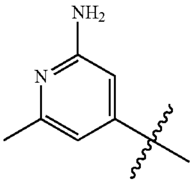,
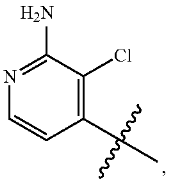,
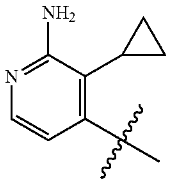,
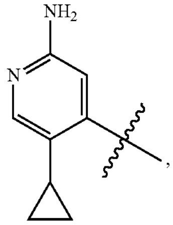,
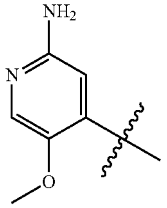,
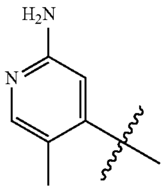,
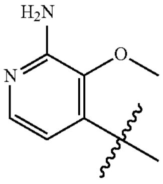,
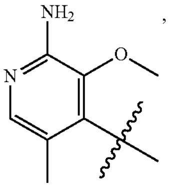,
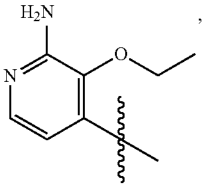,
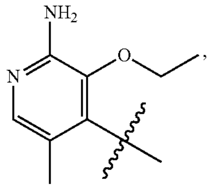,
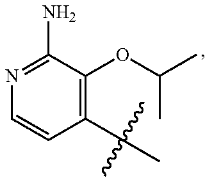,
-continued
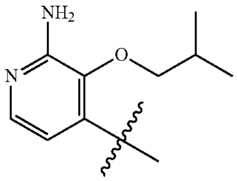,
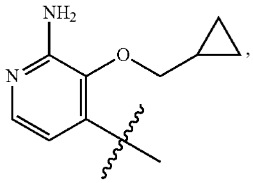,
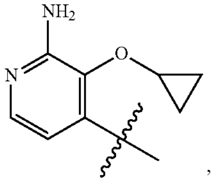,
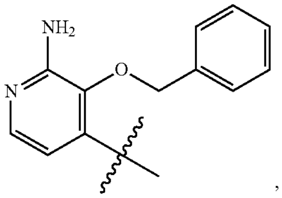,
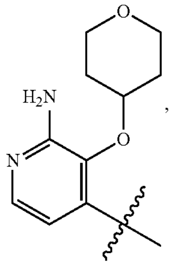,
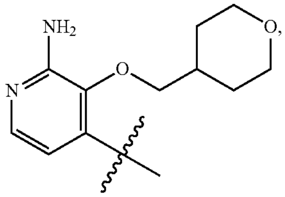,
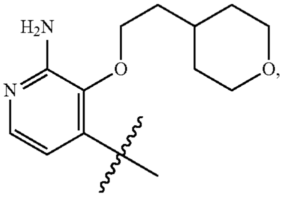,
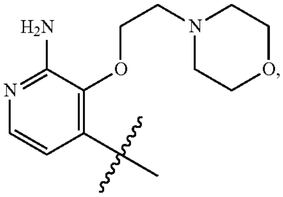,
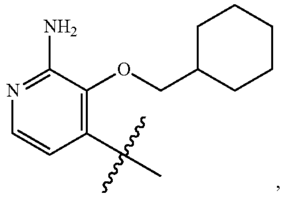,
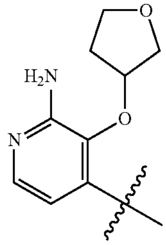,
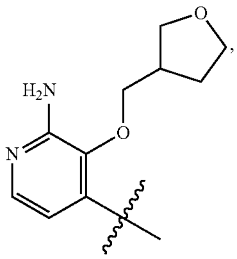,
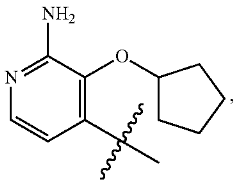,
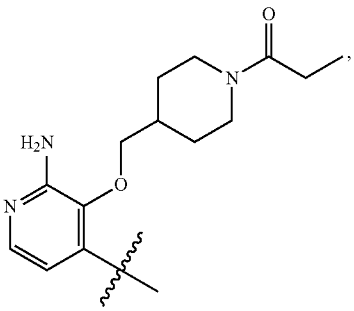,
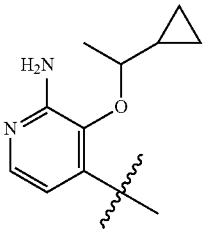, -continued
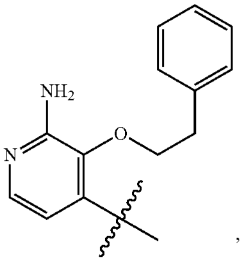
,
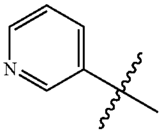
,
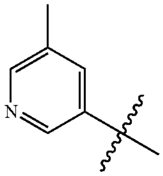
,
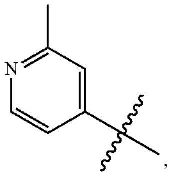
,
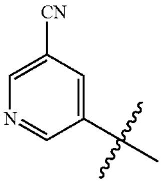
,
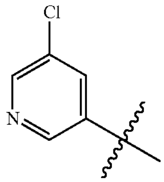
,
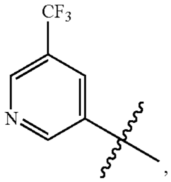
,
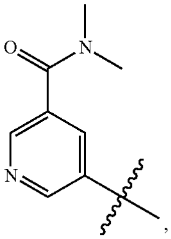
,
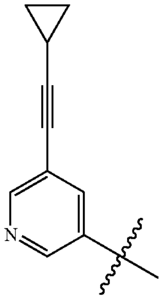
,
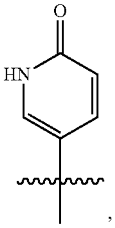
,
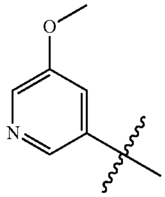
,
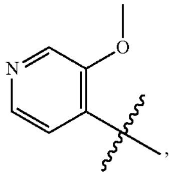
,
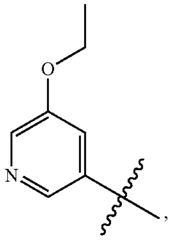
,
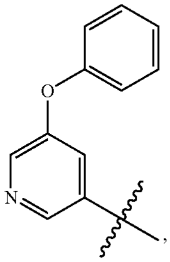
,
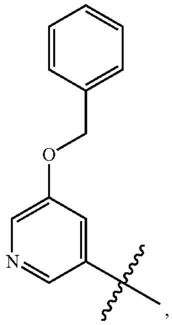
,
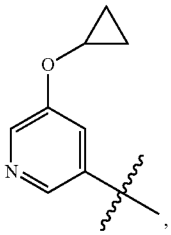
,
-continued
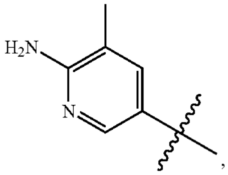
,
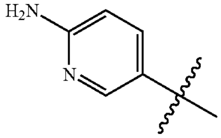
,
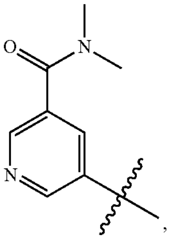
,
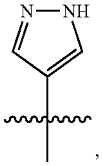
,
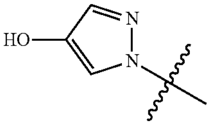
,
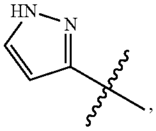
,
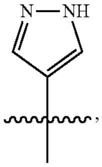
,
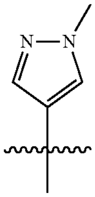
,
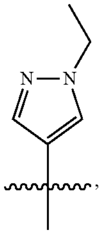
,
,
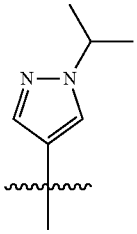
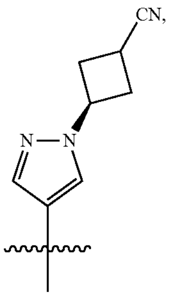
,
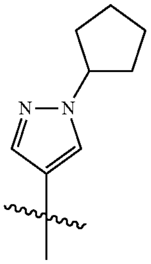
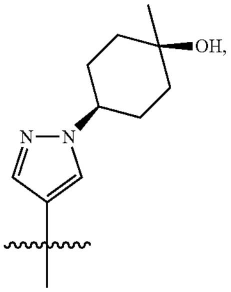
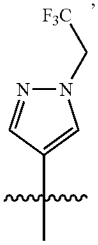
,
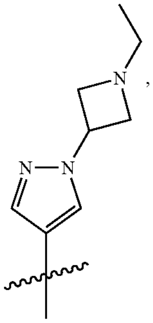
,
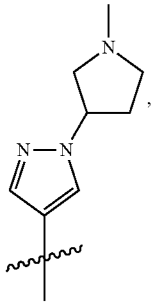
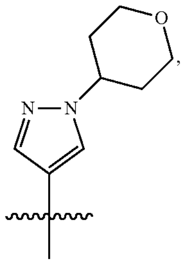
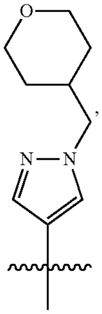
, -continued
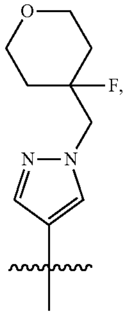
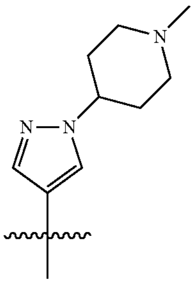
,
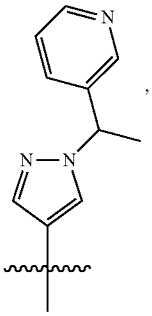
,
,
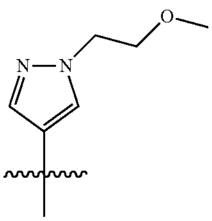
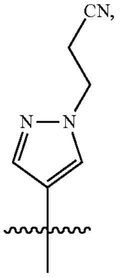
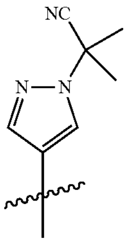
,
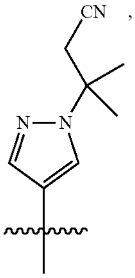
,
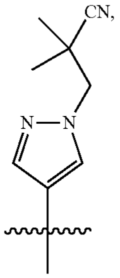
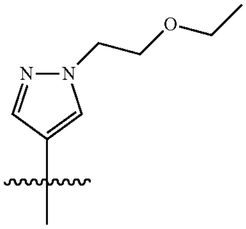
,
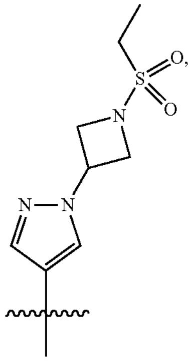
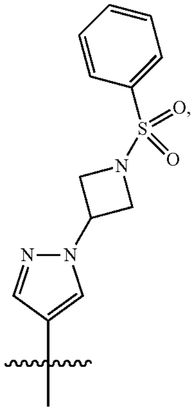
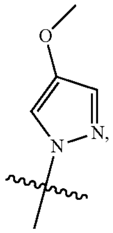
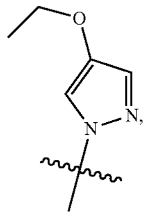
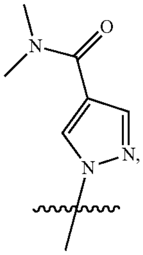
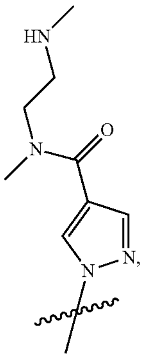
-continued
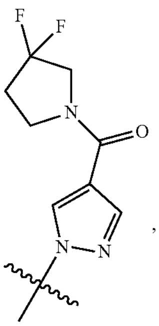
,
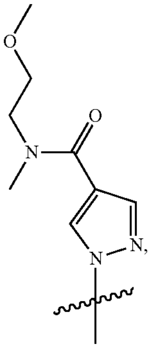
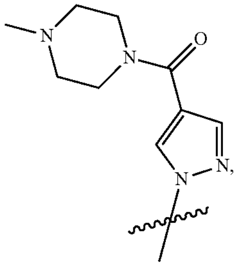
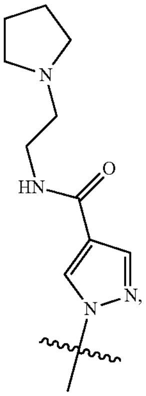
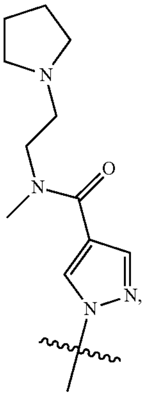
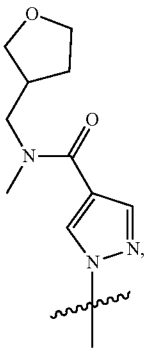
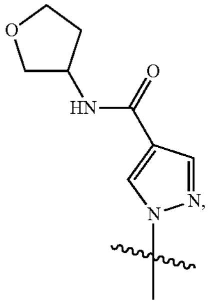
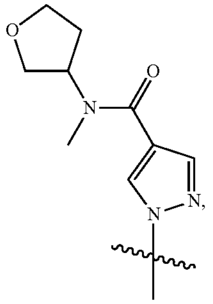
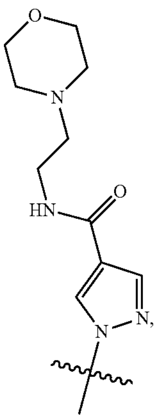
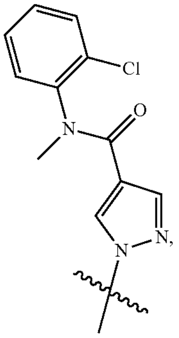
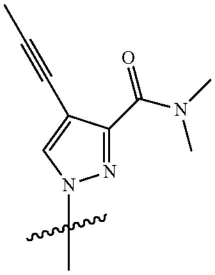
, -continued
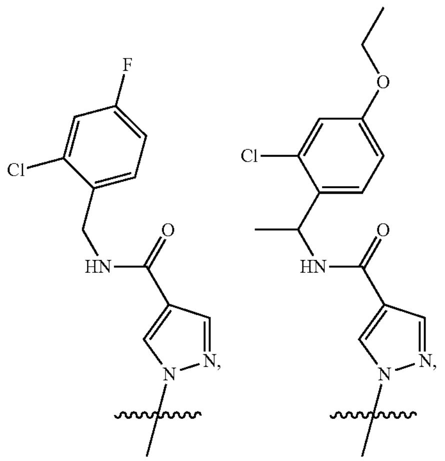
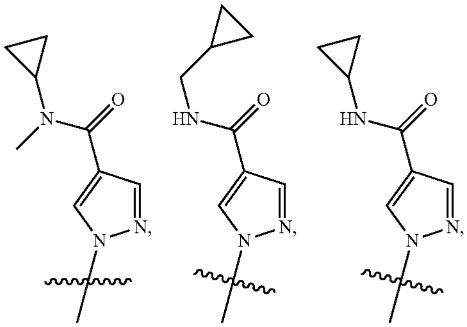
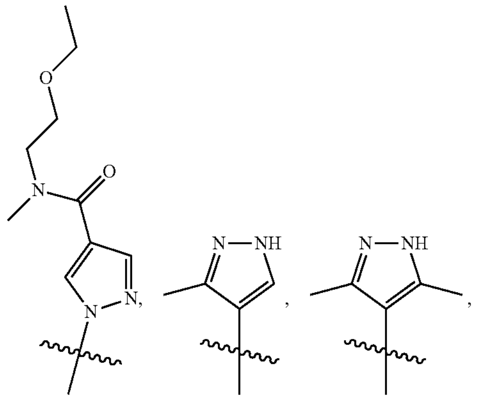
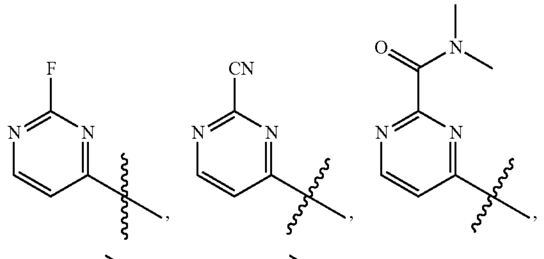
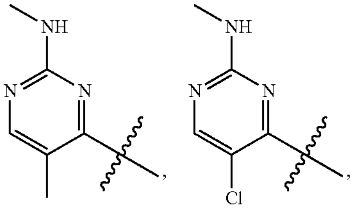
-continued
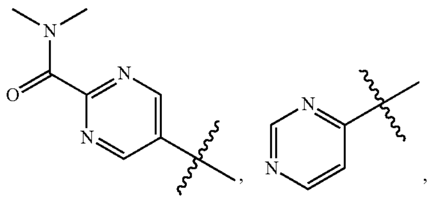
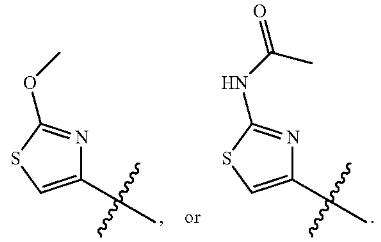
or
d)
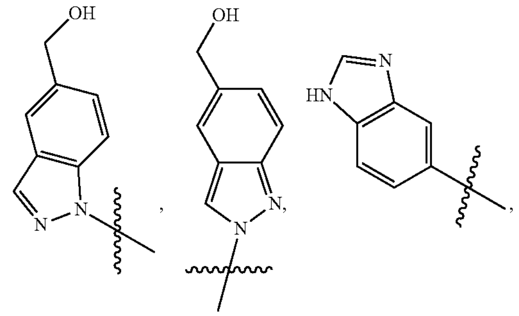
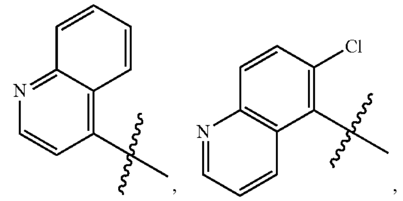
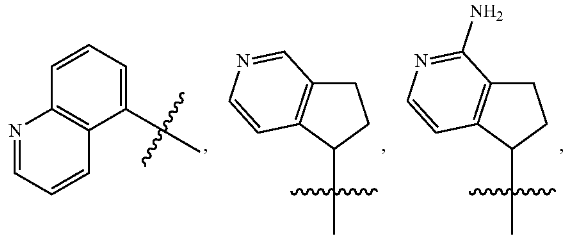
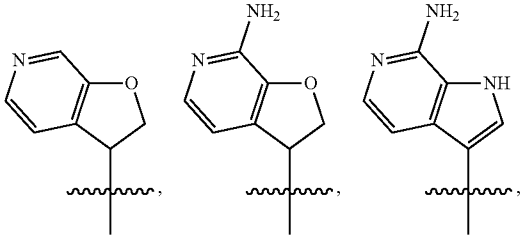

-continued
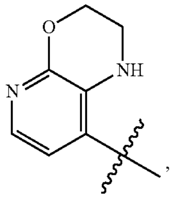, 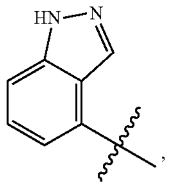, 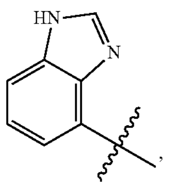,
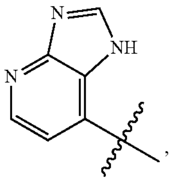, 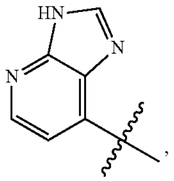, 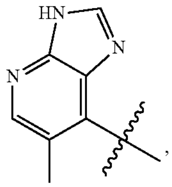,
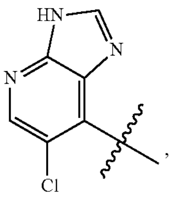, 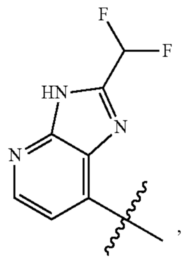, 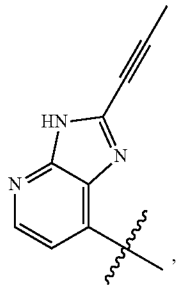,
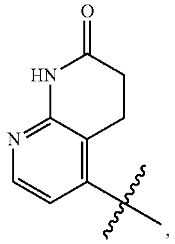, 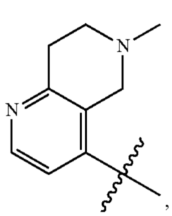, 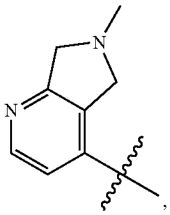,
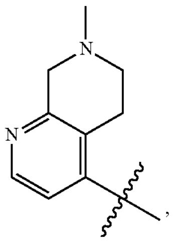, 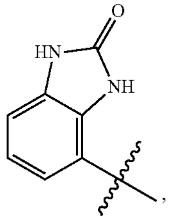, 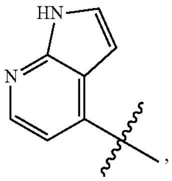,
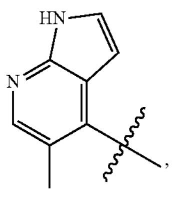, 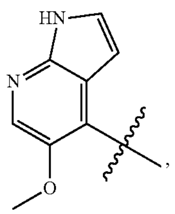, 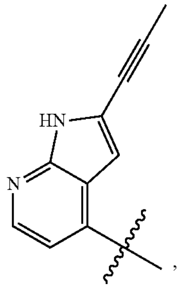,
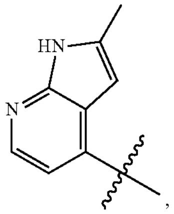, 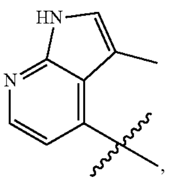, 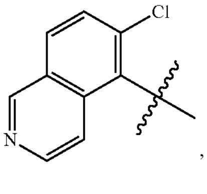,
-continued
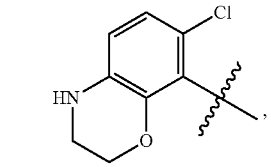, 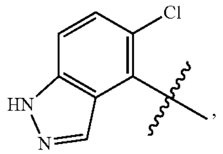,
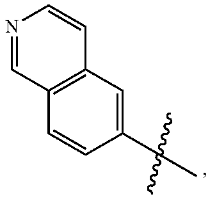, 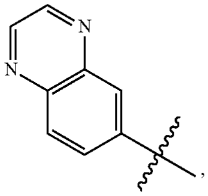,
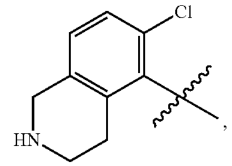, 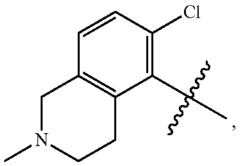,
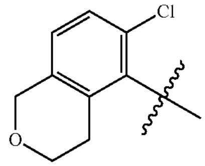, 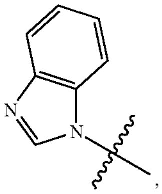, 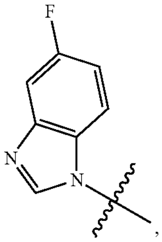,
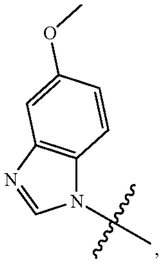, 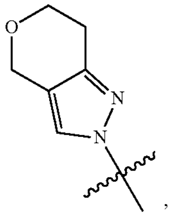,
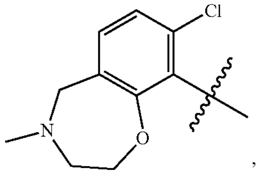, 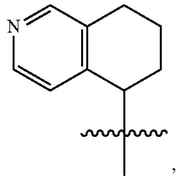,
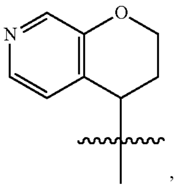, 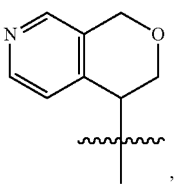, 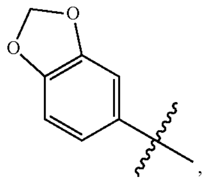,
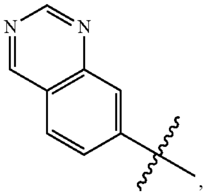, 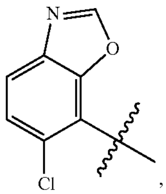, 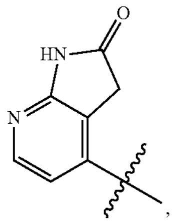, -continued
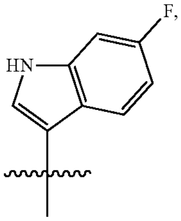 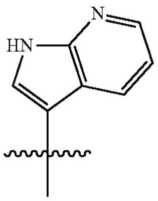, 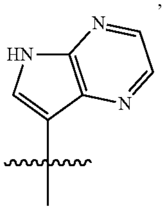,
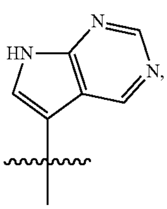 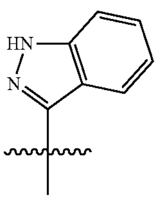, 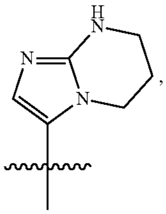,
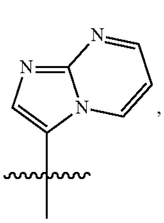, 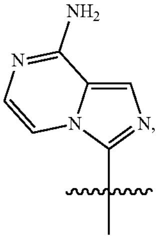 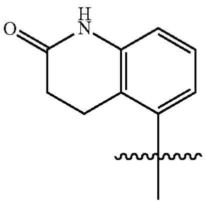,
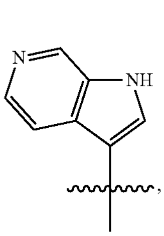 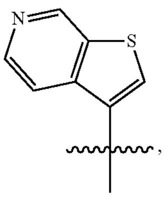 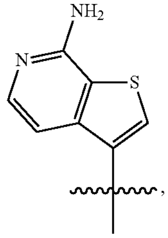
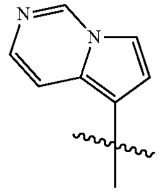 or 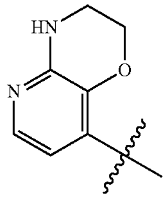.
12. The compound according to claim 9, wherein $Cy^1$ is selected from
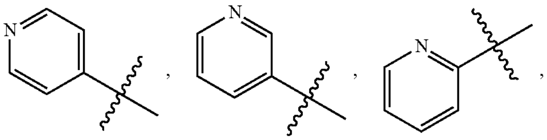
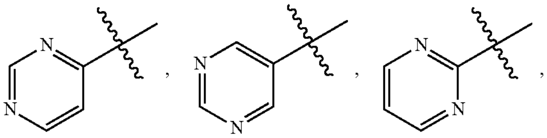
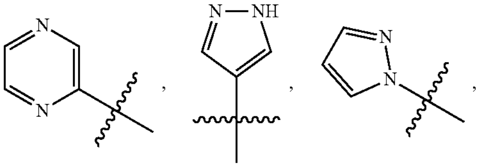
-continued
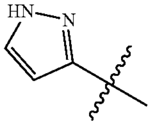, 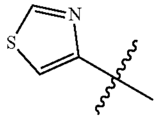, 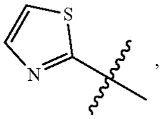,
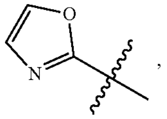,
wherein $Cy^1$ is optionally substituted with —$(R^4)$, t is 0, 1, 2 or 3, provided that chemical valency rules are met.
13. The compound according to claim 9, wherein $Cy^1$ is selected from
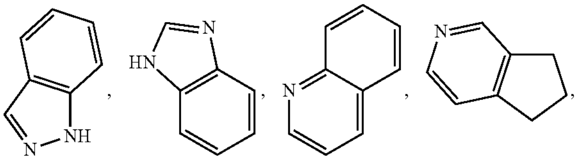
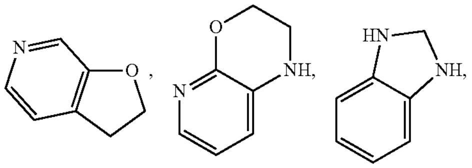
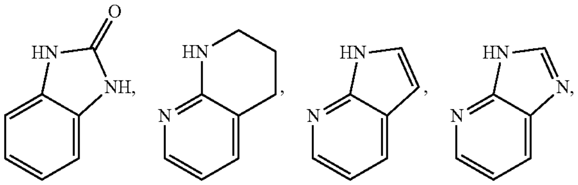
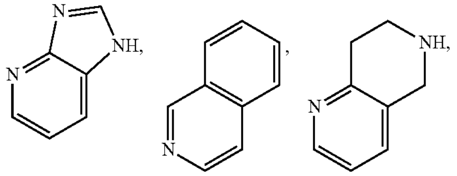
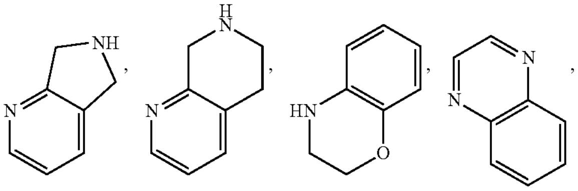
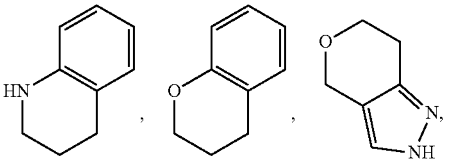
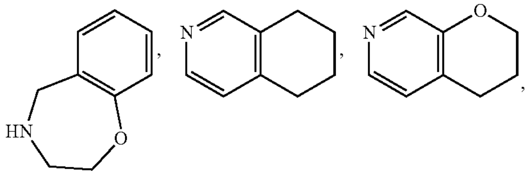

-continued
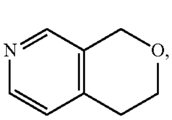, 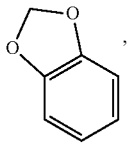, 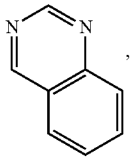,
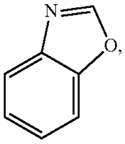, 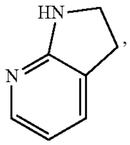, 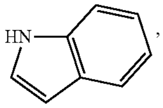,
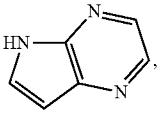, 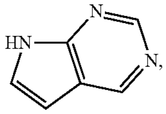, 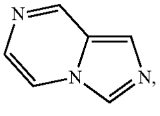,
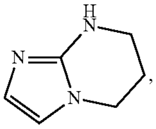, 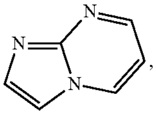, 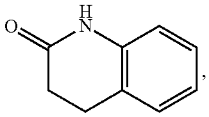,
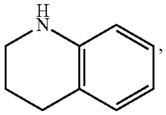, 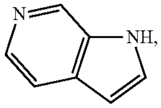, 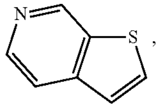,
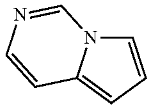, or 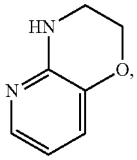,
wherein $Cy^1$ is optionally substituted with —($R^4$).
14. The compound according to claim 1, which is selected from;
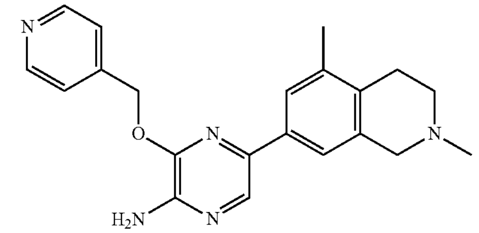
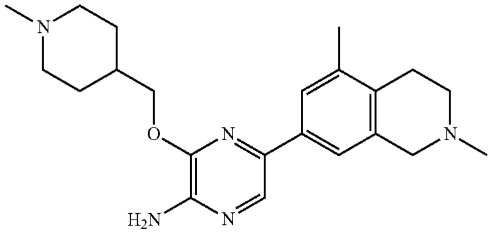
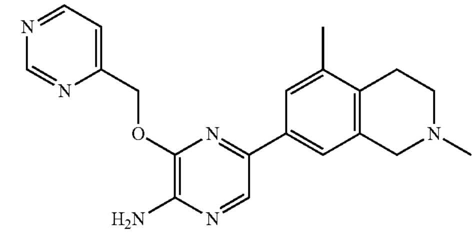
-continued
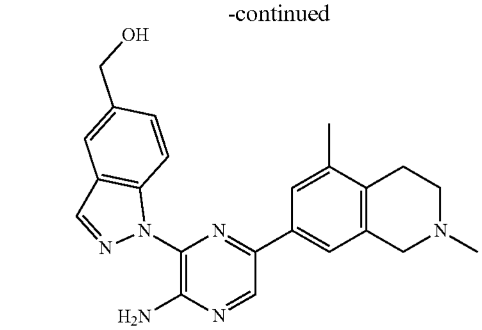
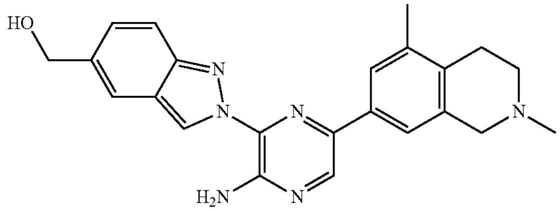
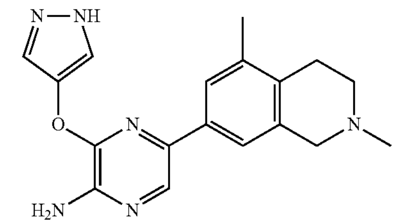
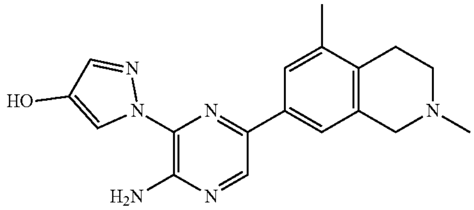
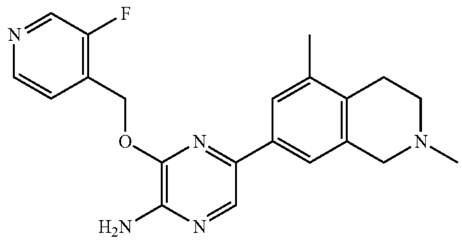
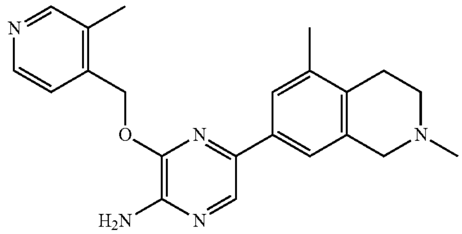
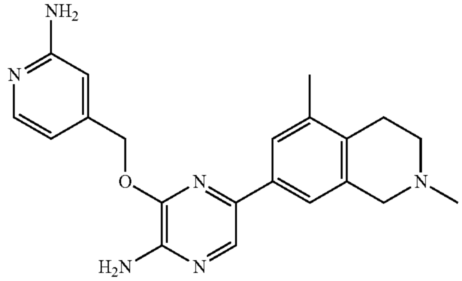

-continued
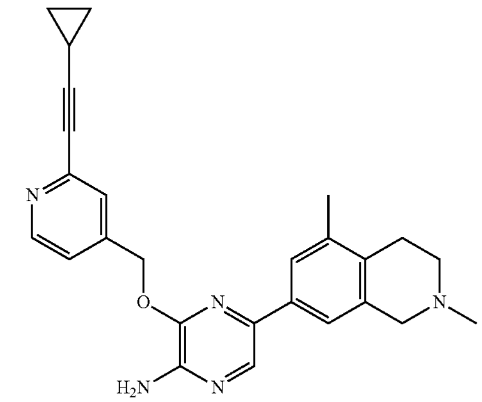
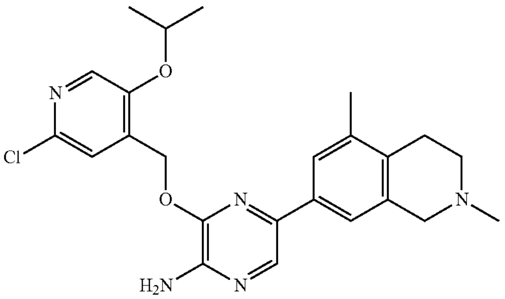
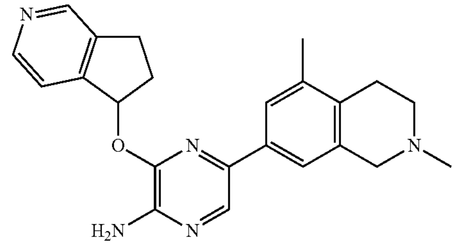
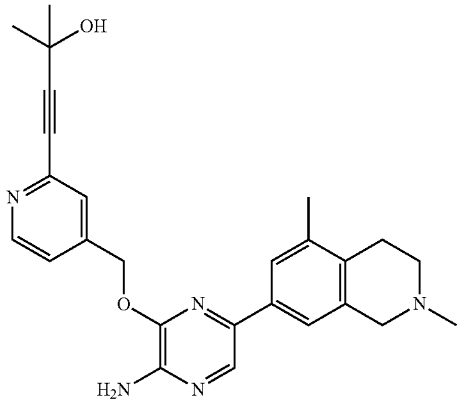
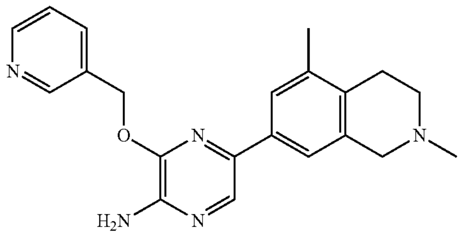
-continued
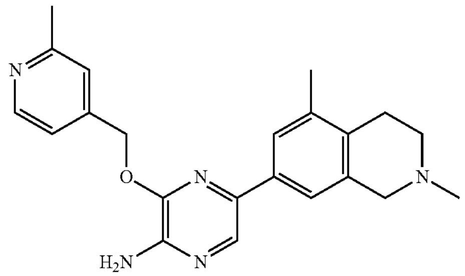
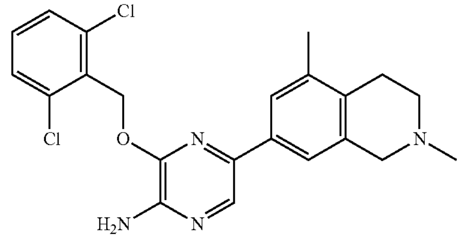
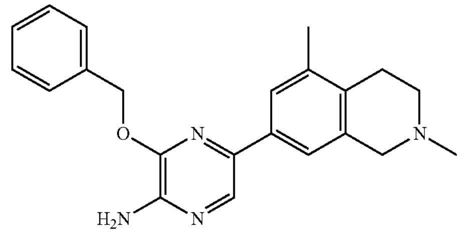
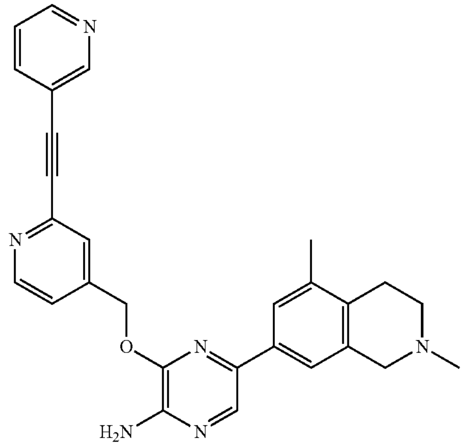
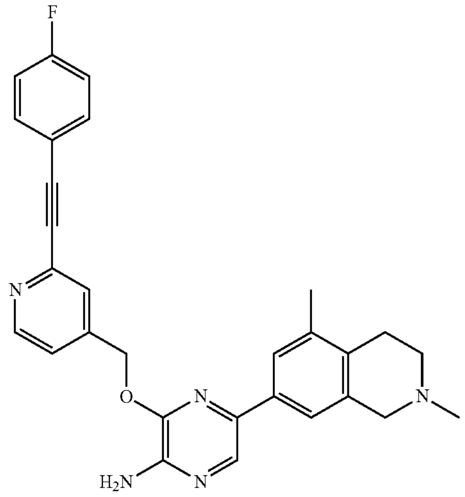

-continued
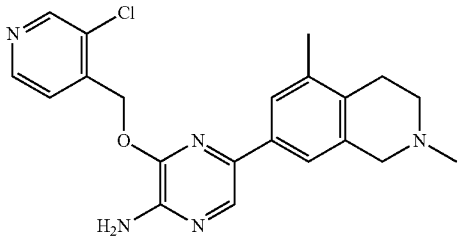
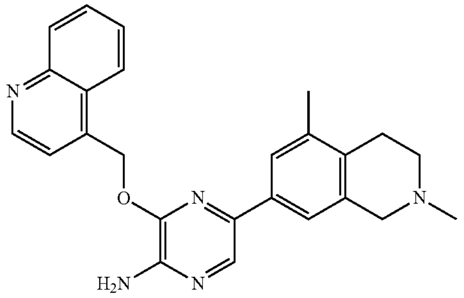
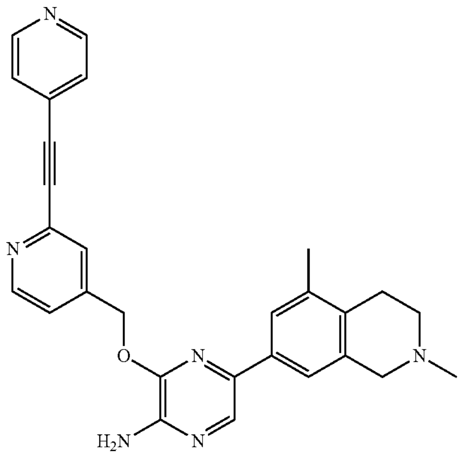
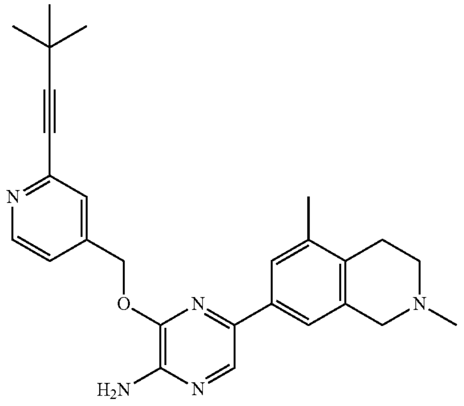
-continued
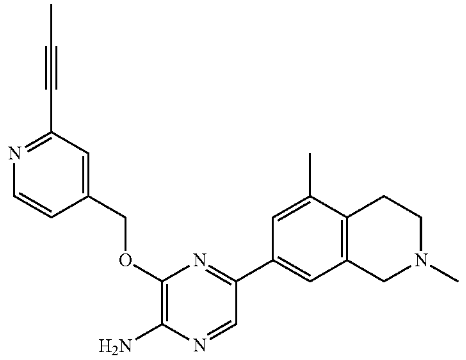
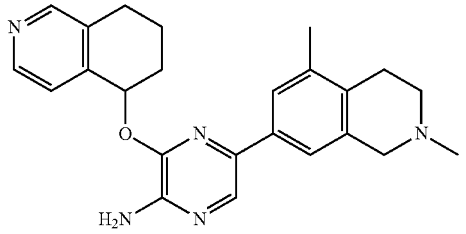
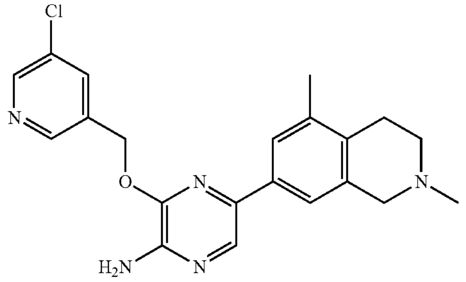
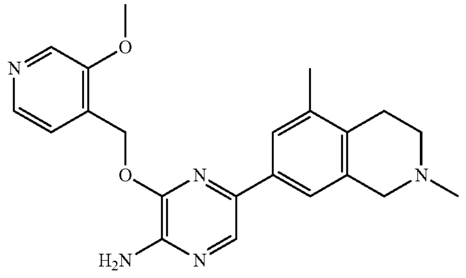
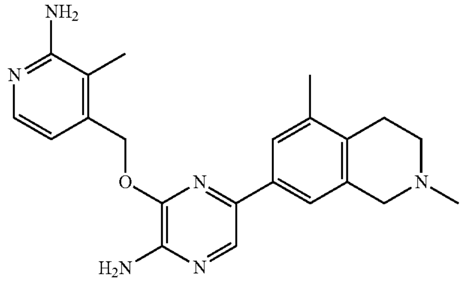

-continued
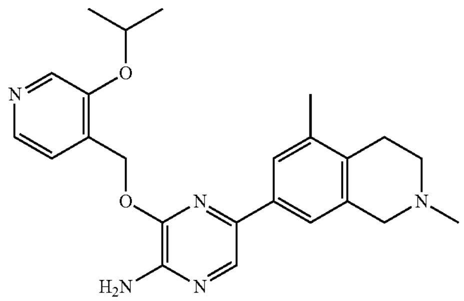
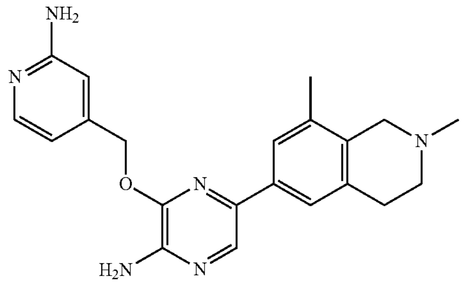
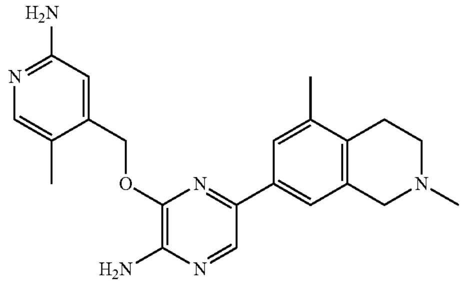
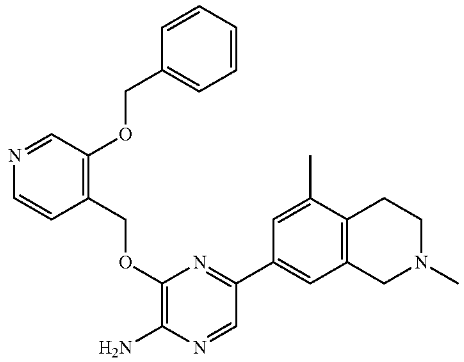
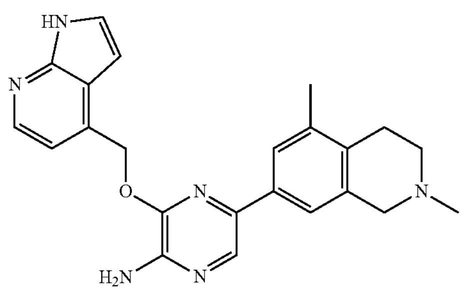
-continued
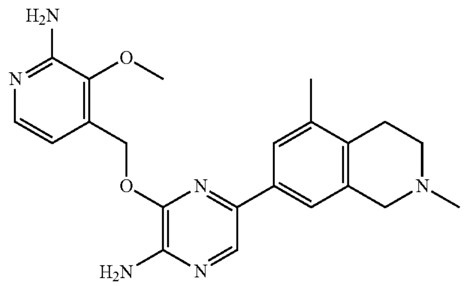
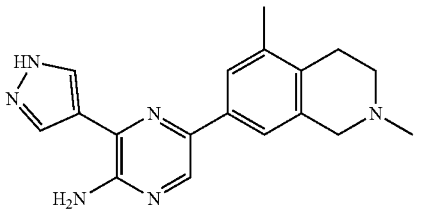
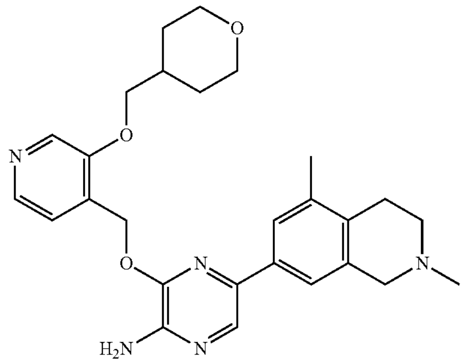
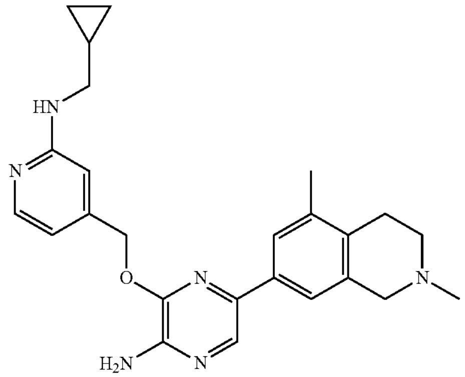
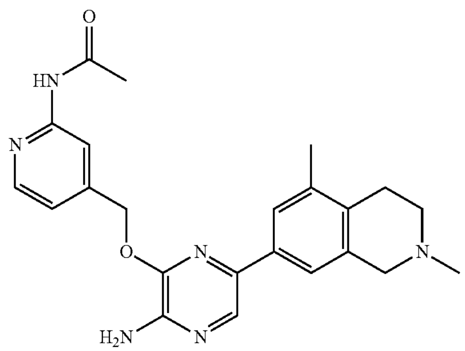

-continued
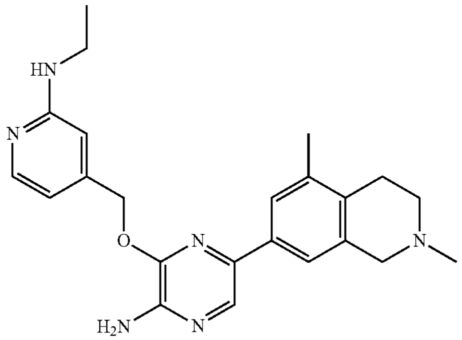
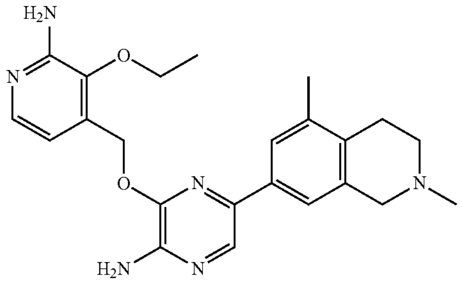
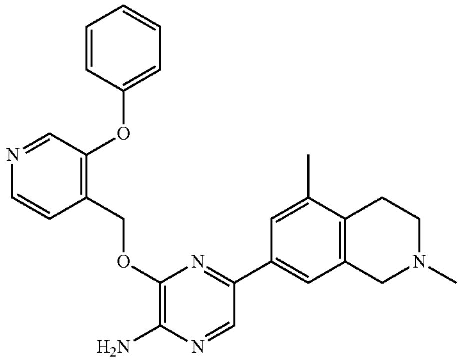
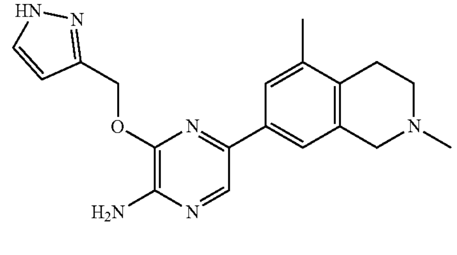
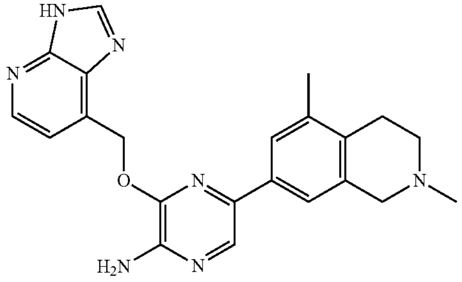
-continued
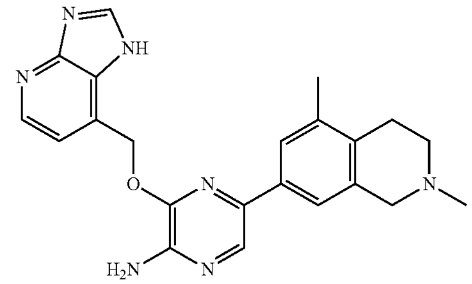
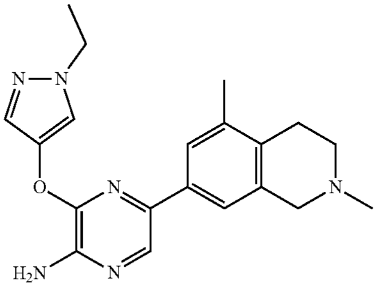
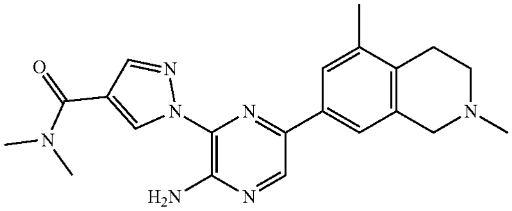
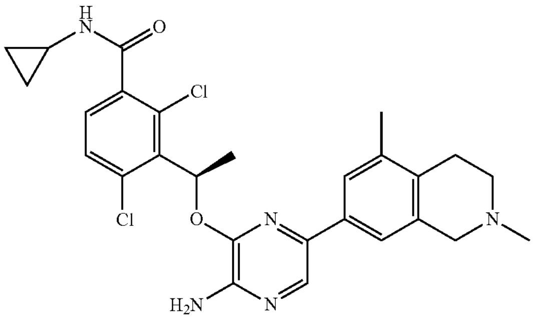
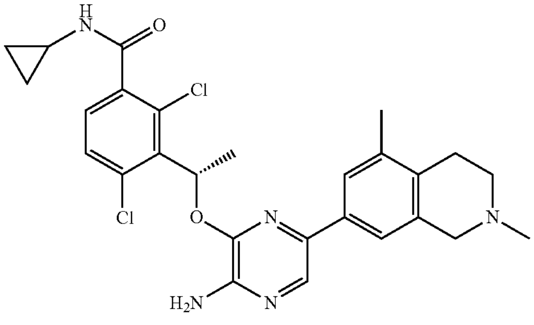
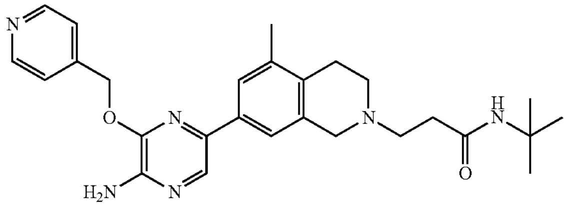

-continued
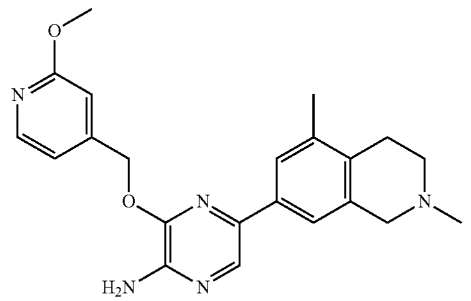
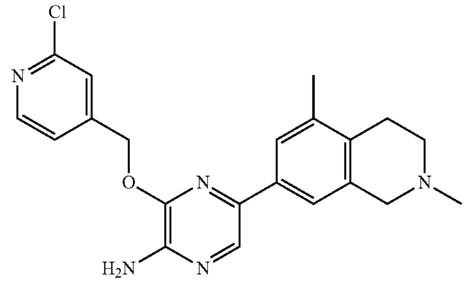
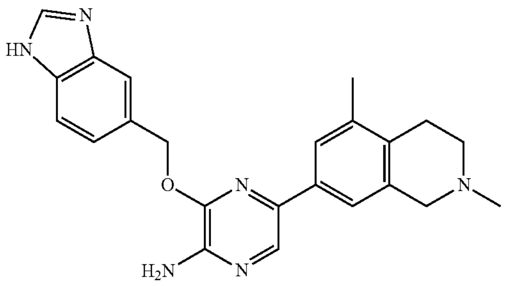
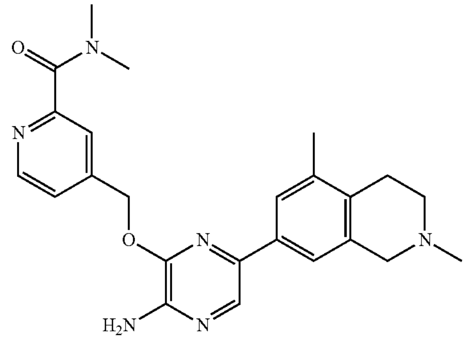
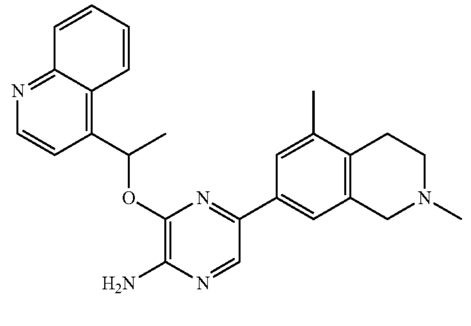
-continued
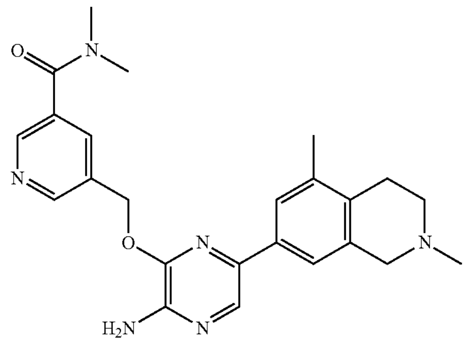
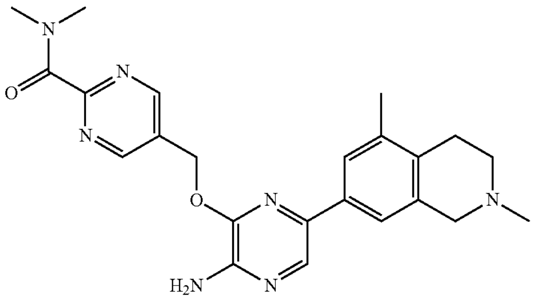
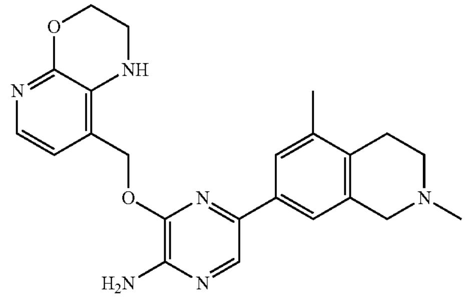
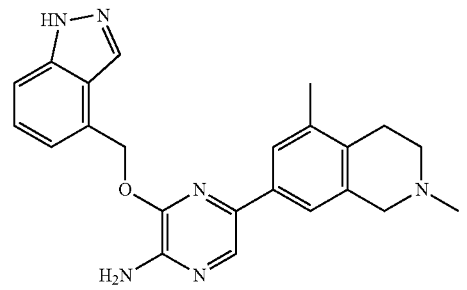
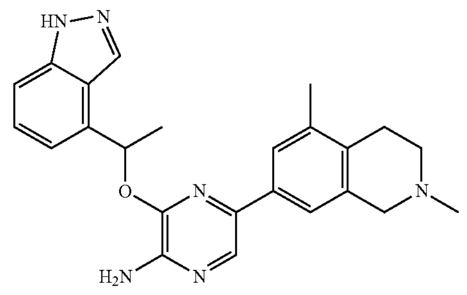

-continued
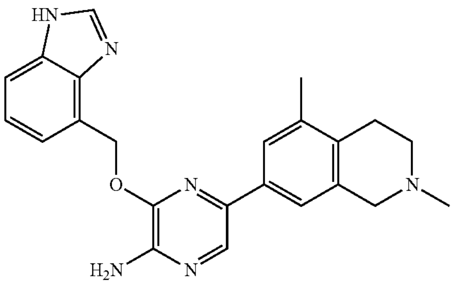
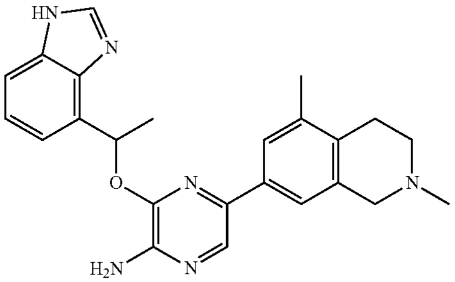
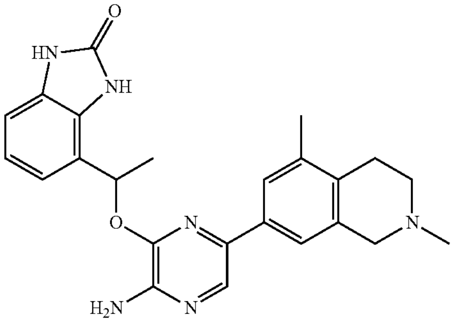
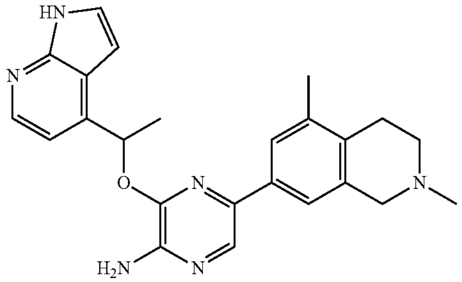
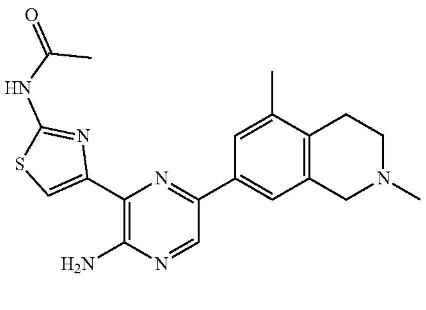
-continued
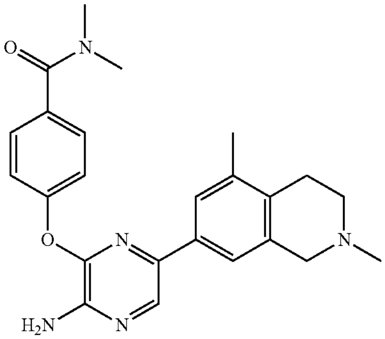
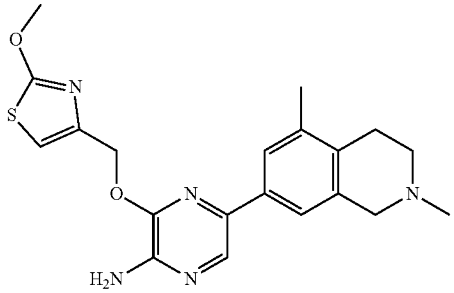
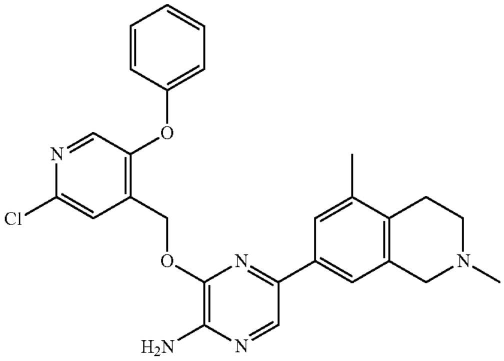
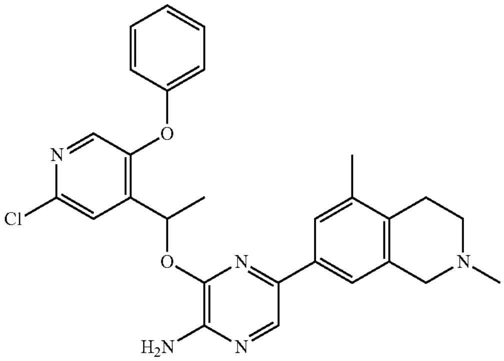
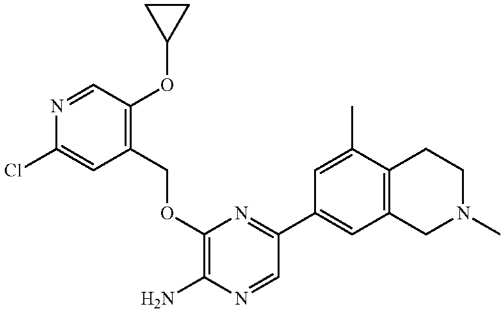

-continued
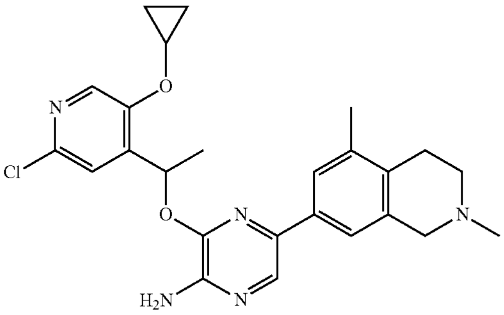
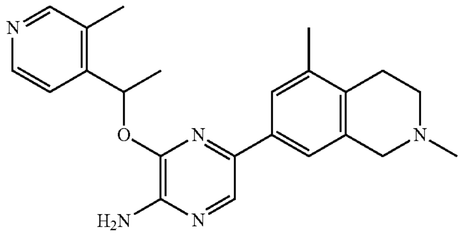
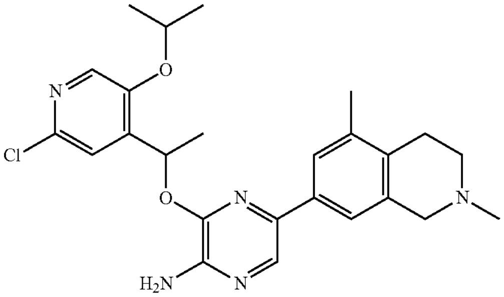
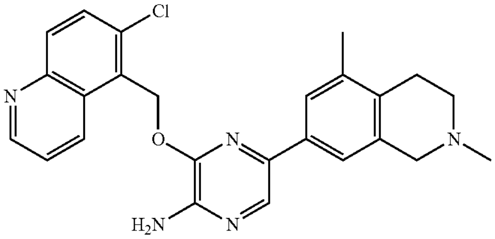
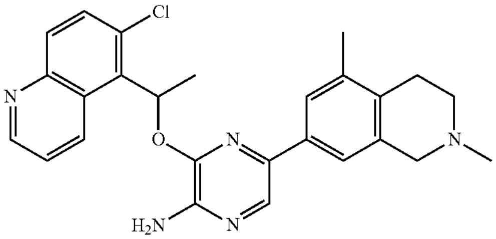
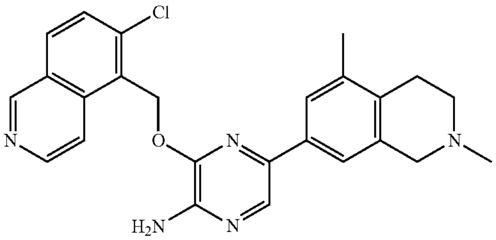
-continued
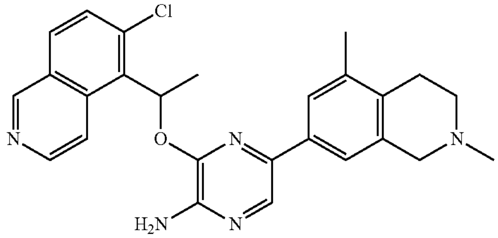
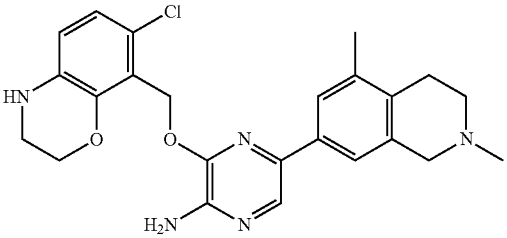
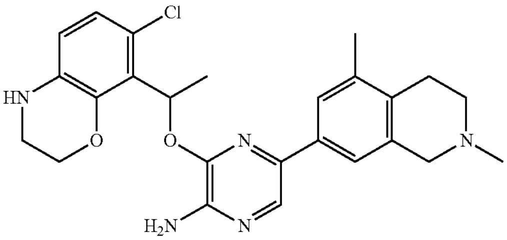
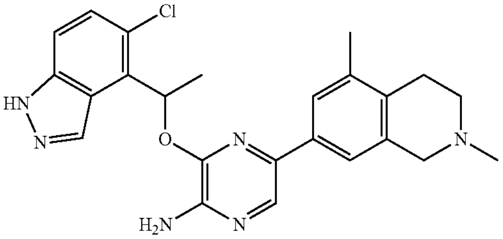
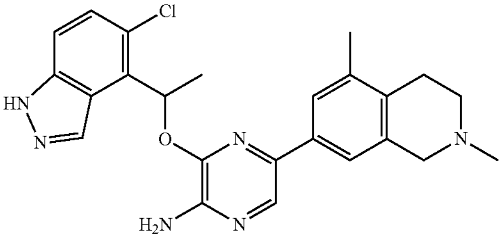
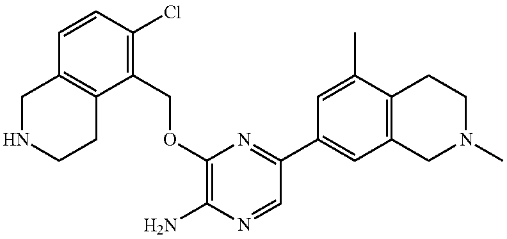
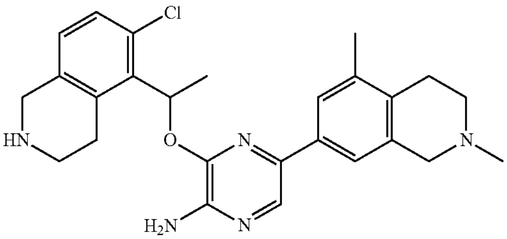

-continued
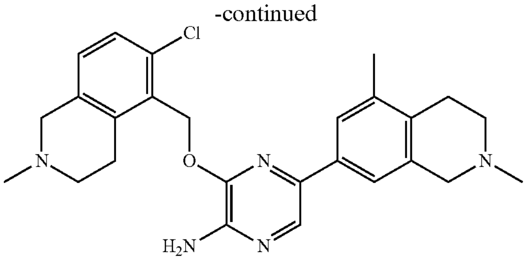
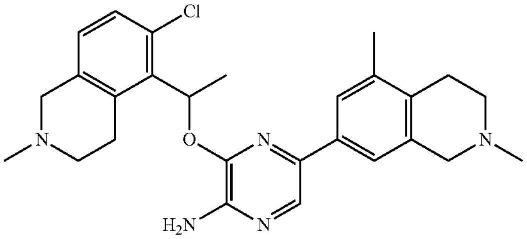
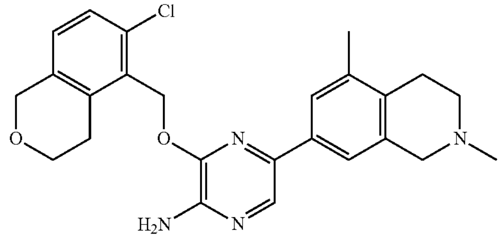
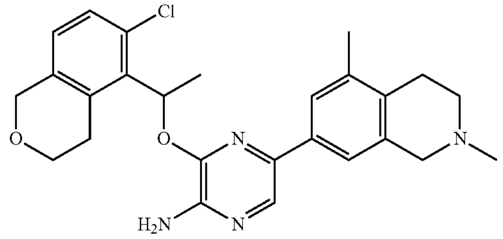
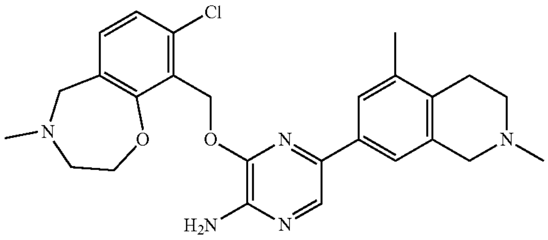
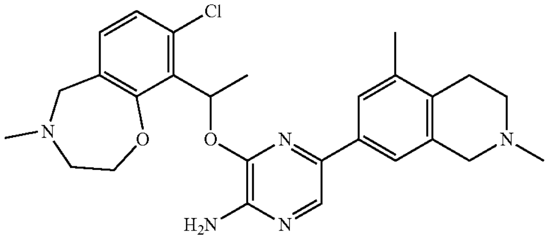
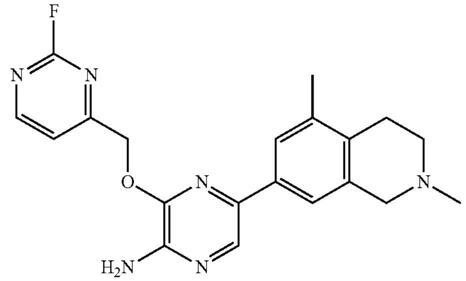
-continued
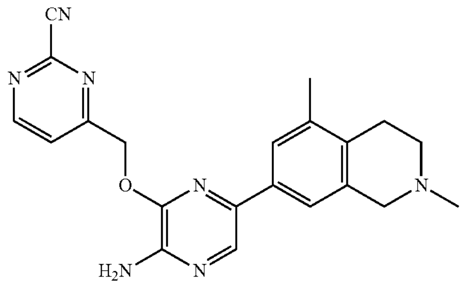
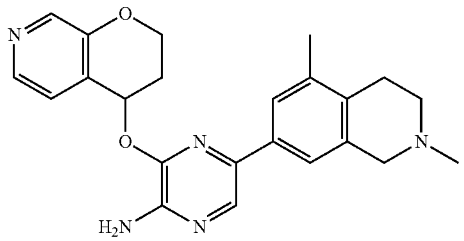
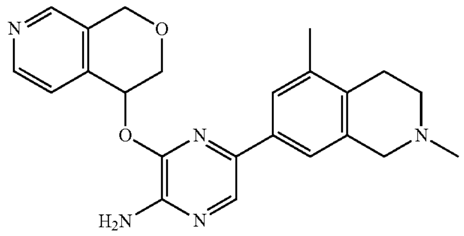
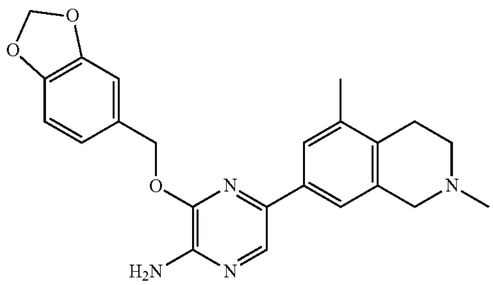
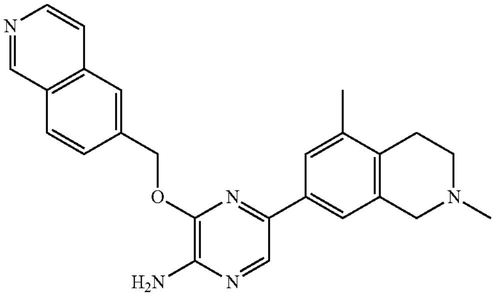
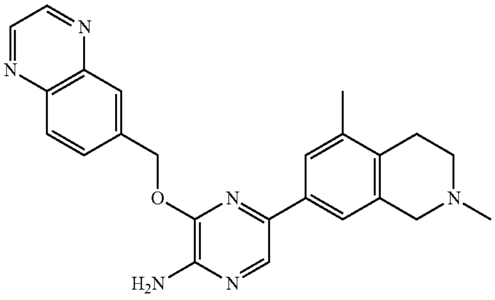

-continued
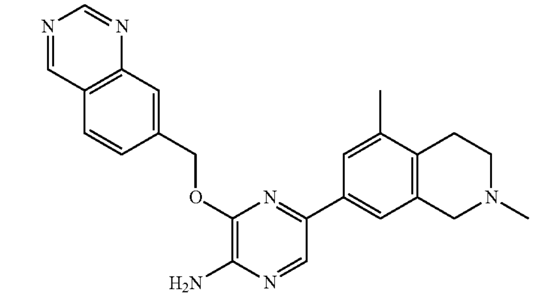
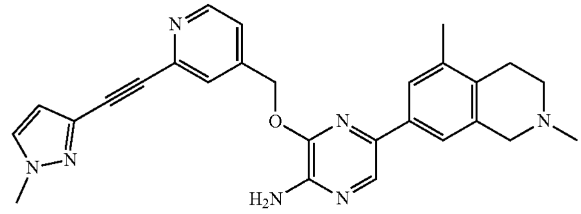
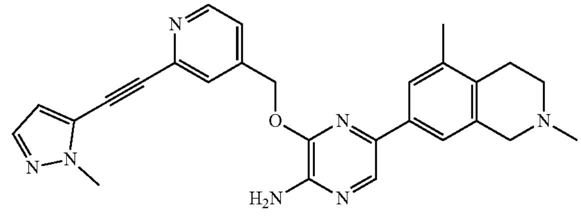
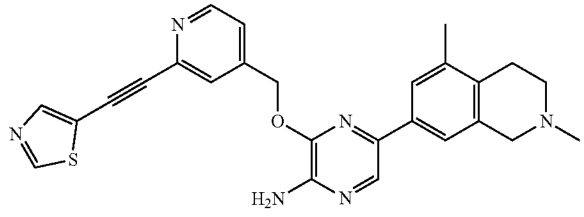
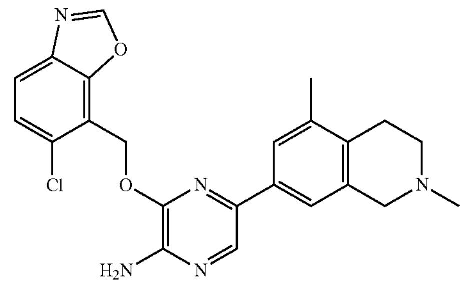
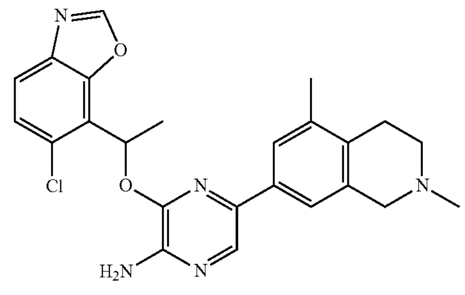
-continued
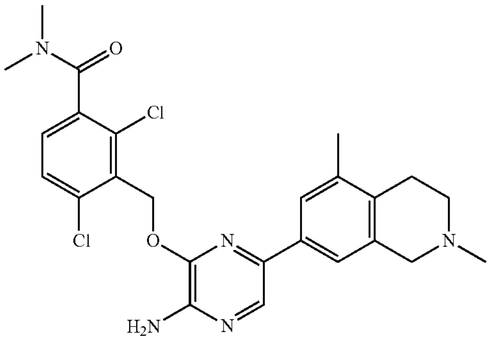
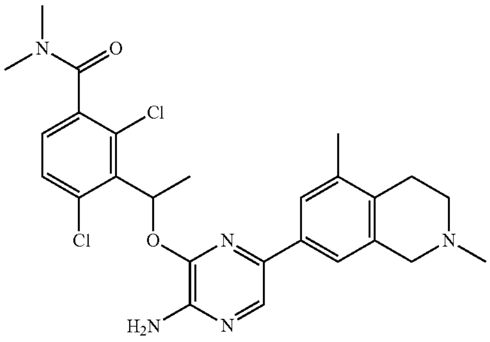
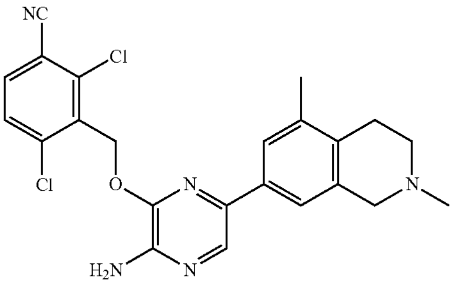
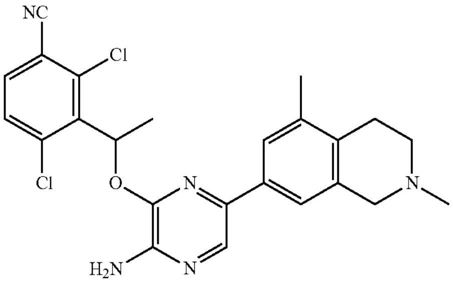
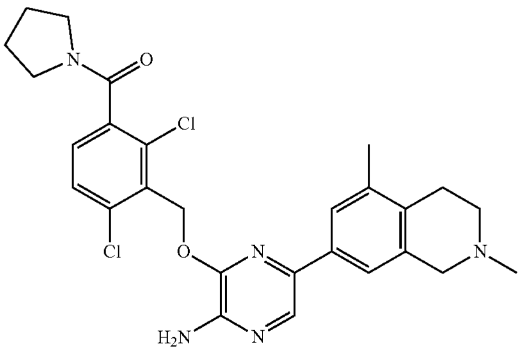

-continued
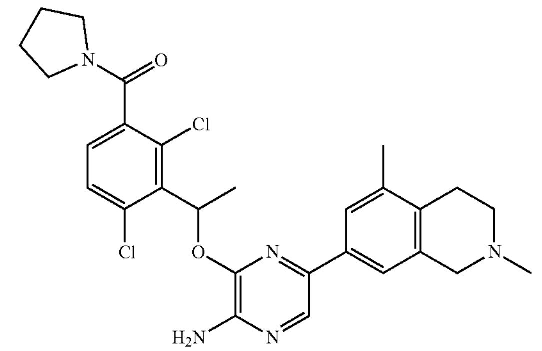
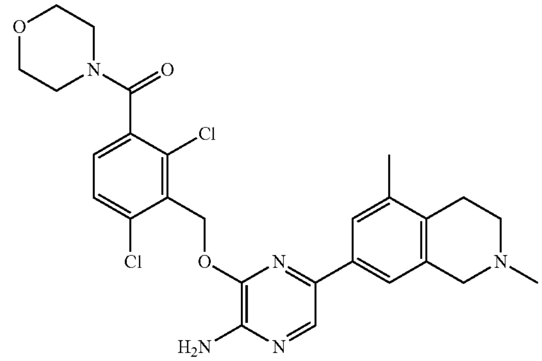
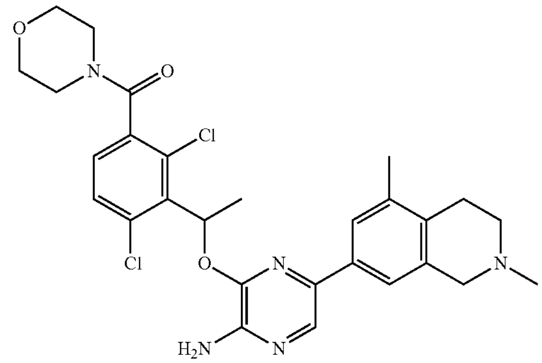
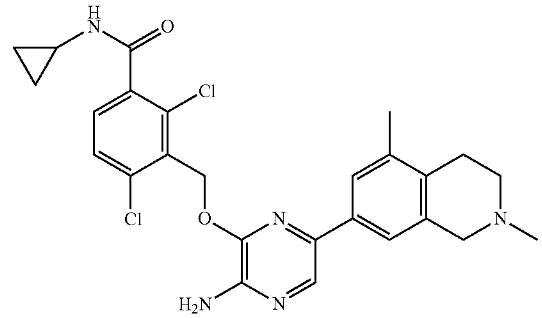
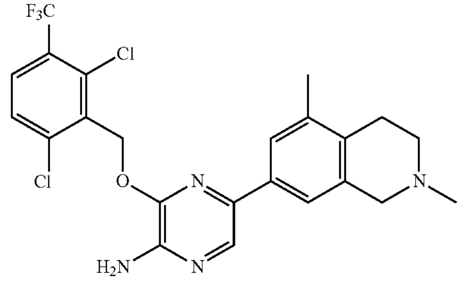
-continued
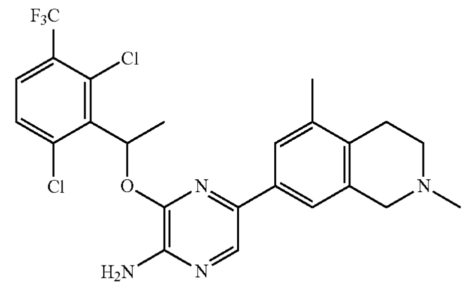
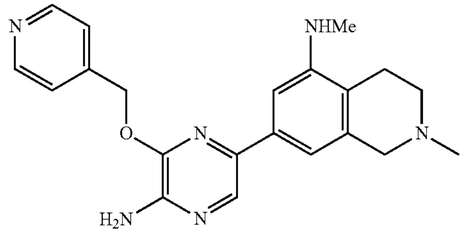
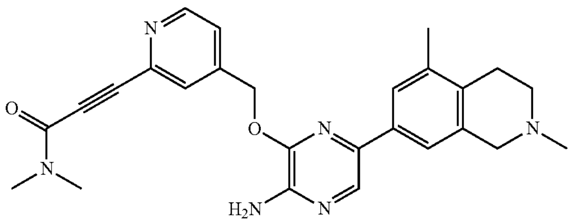
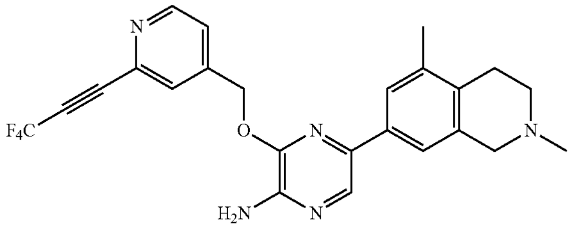
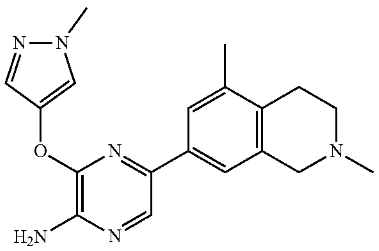
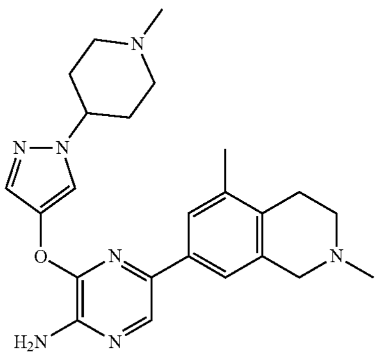

-continued
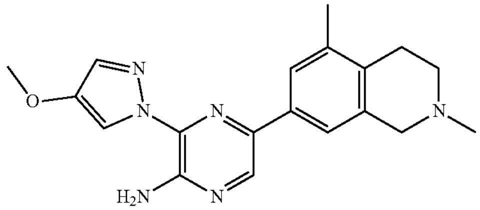
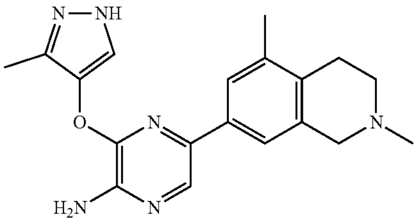
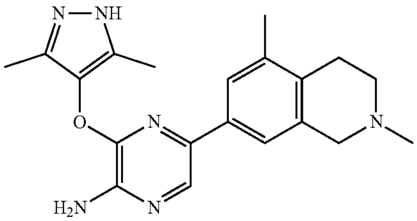
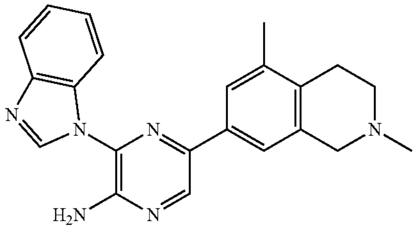
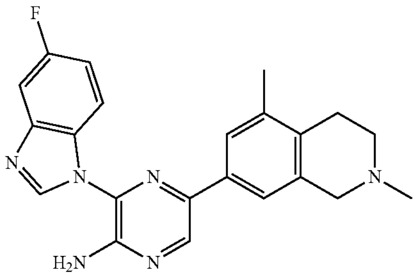
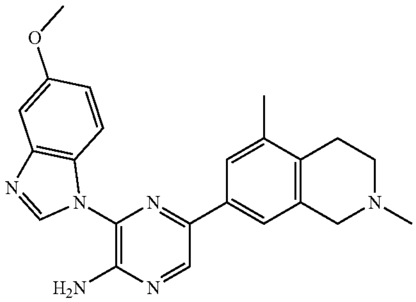
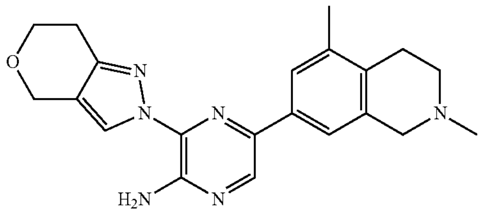
-continued
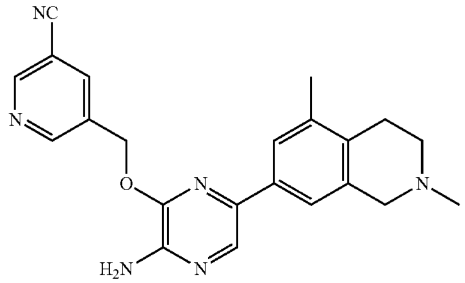
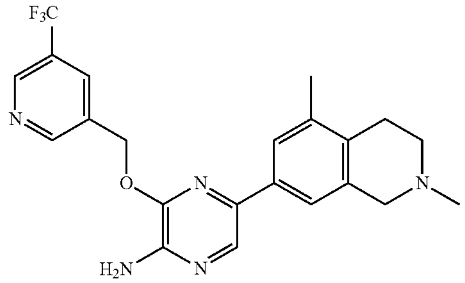
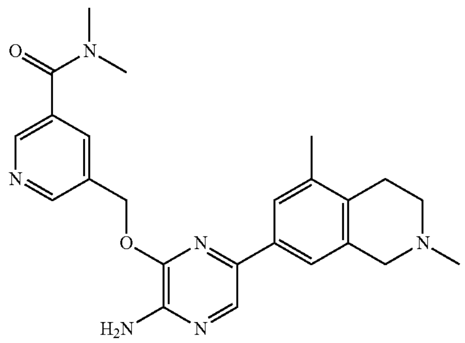
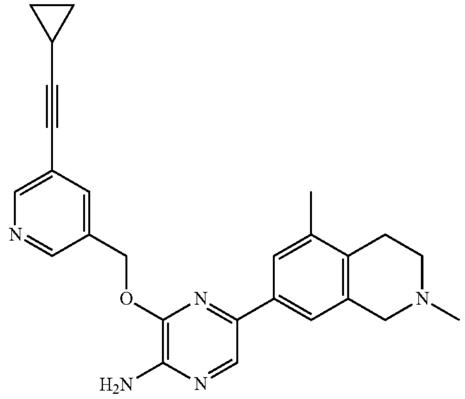
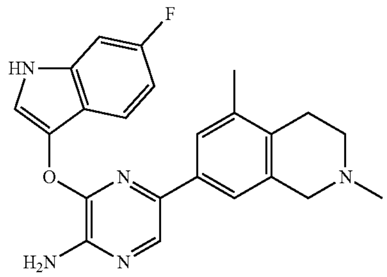

-continued
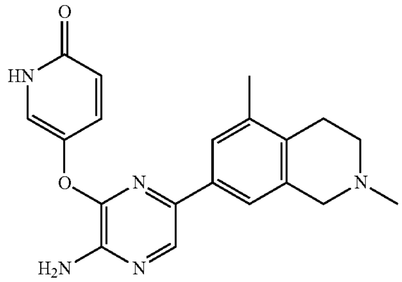
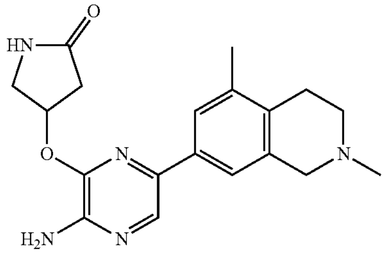
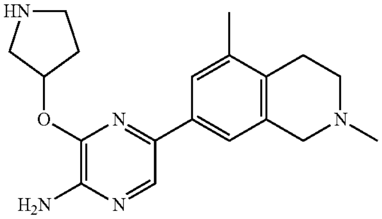
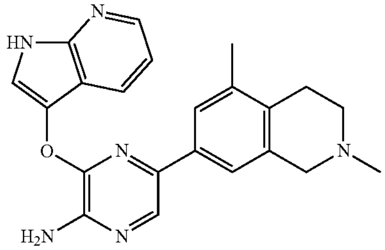
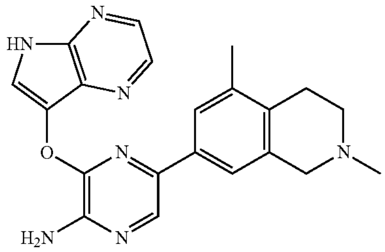
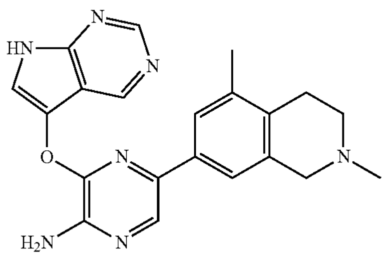
-continued
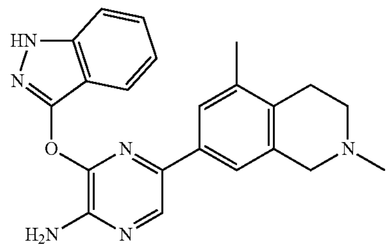
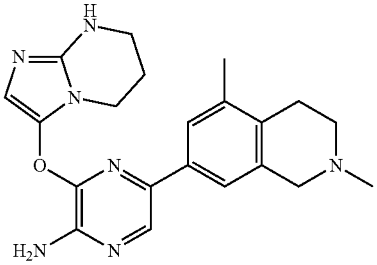
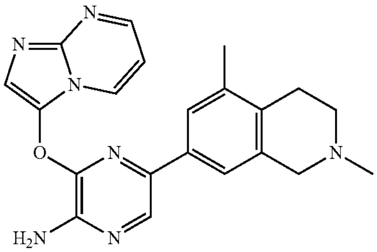
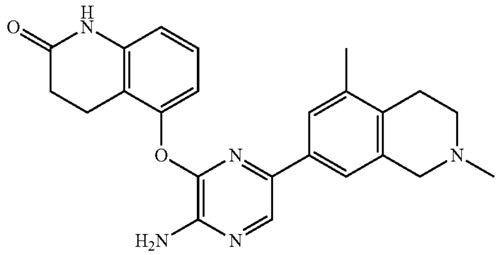
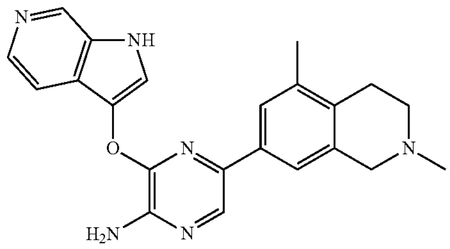
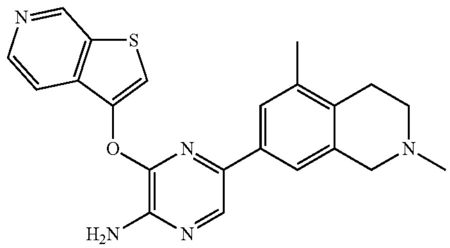

-continued
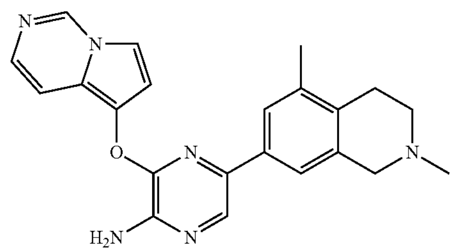
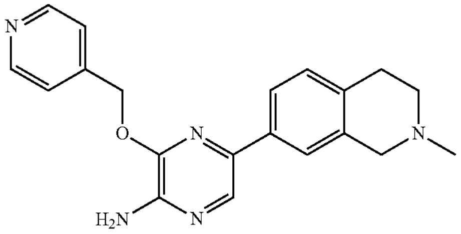
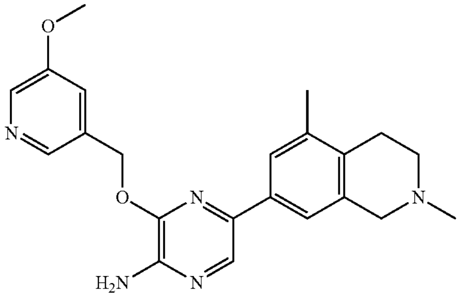
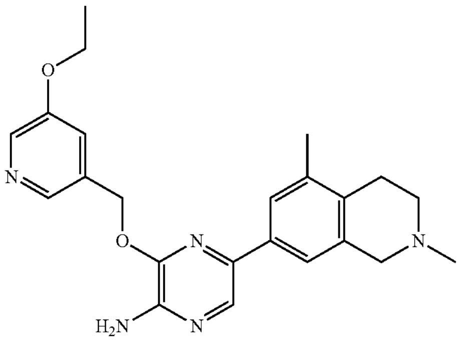
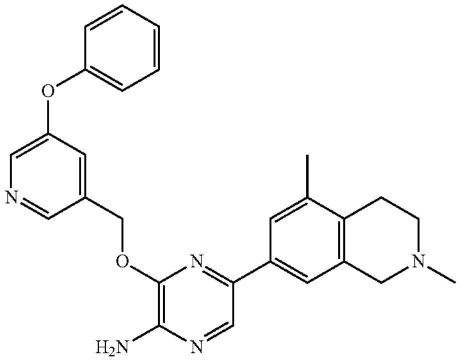
-continued
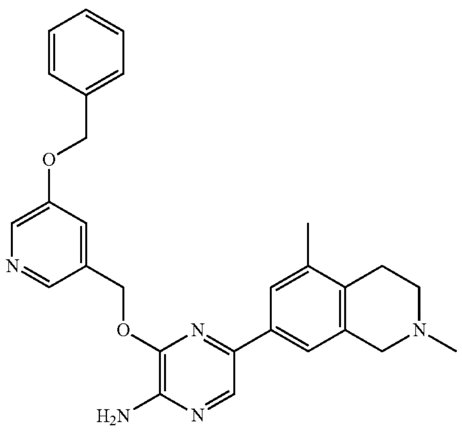
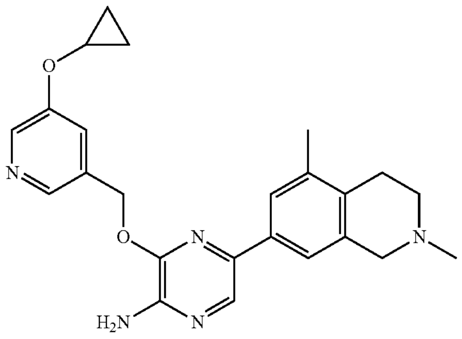
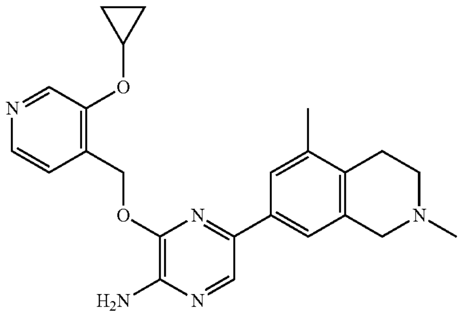
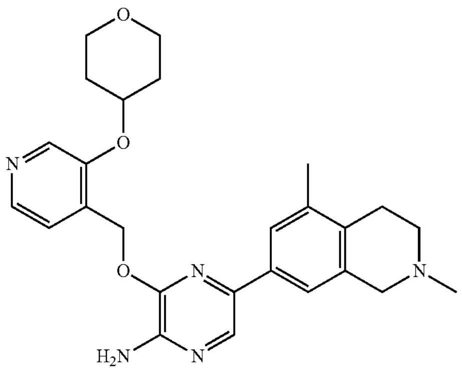

-continued
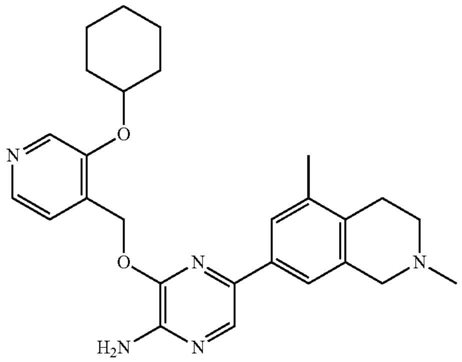
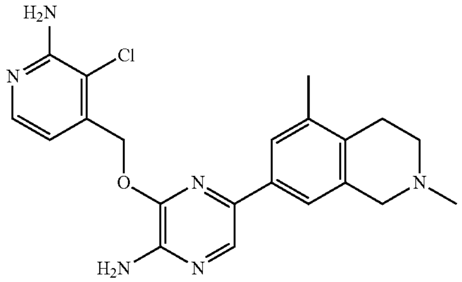
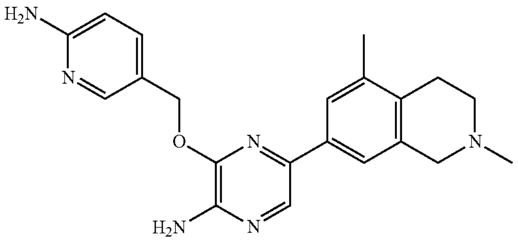
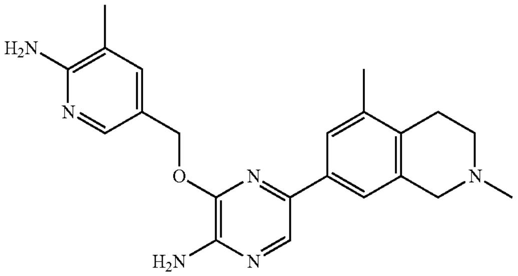
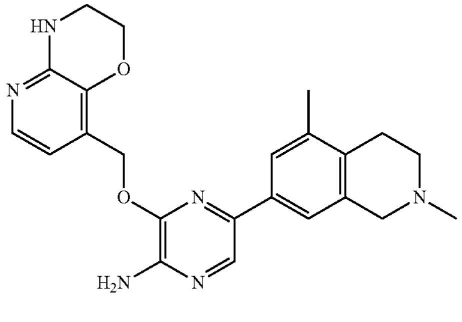
-continued
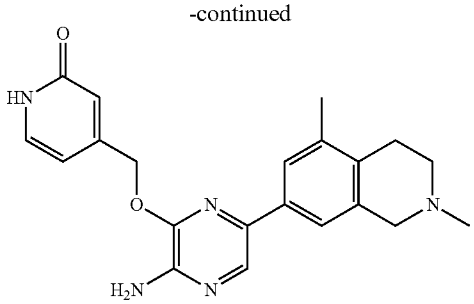
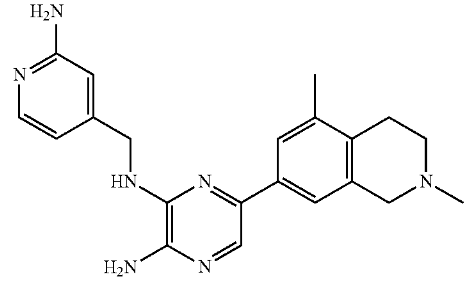
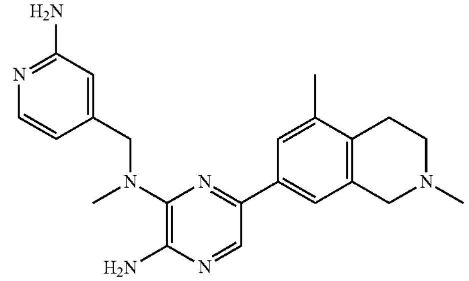
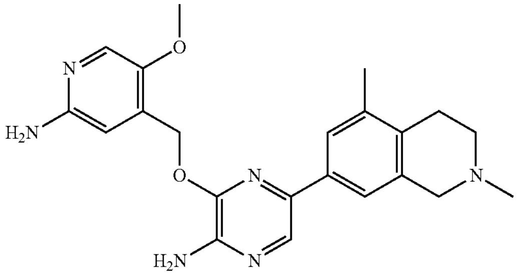
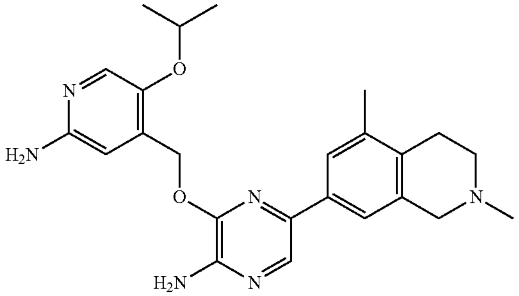
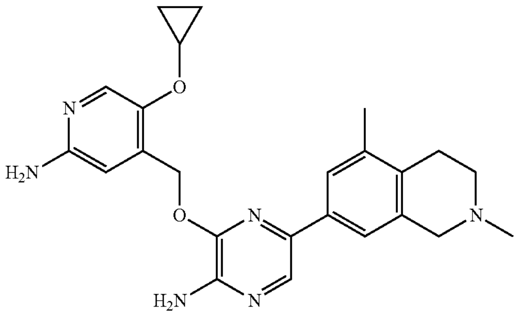

-continued
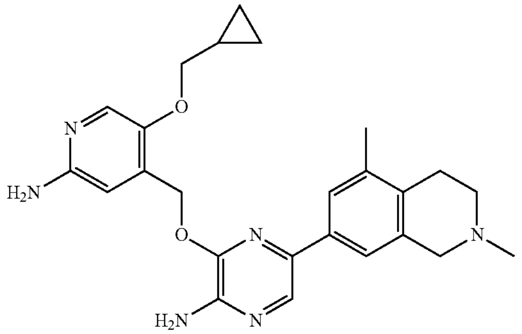
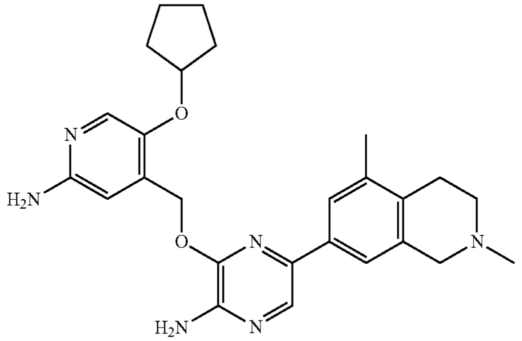
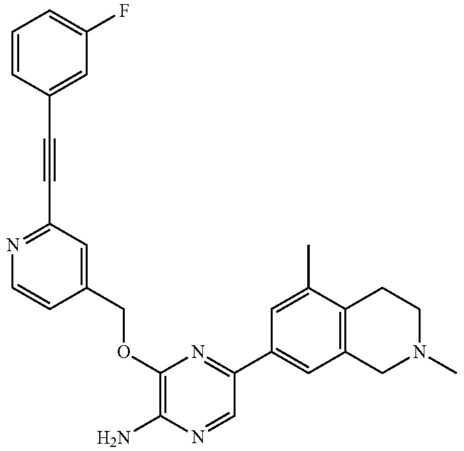
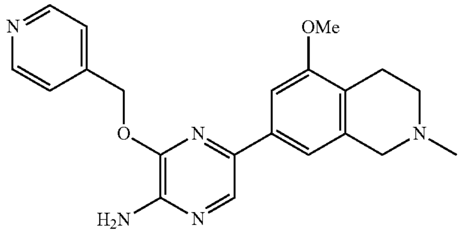
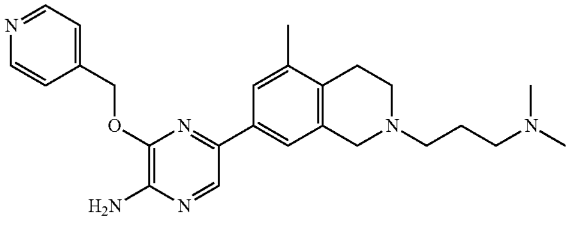
-continued
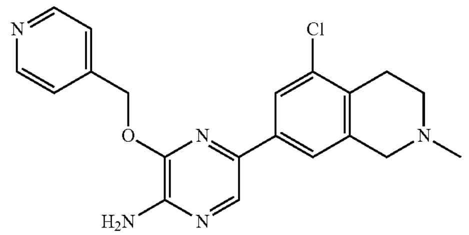
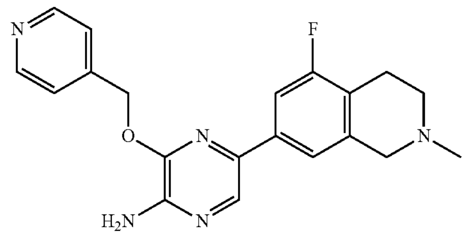
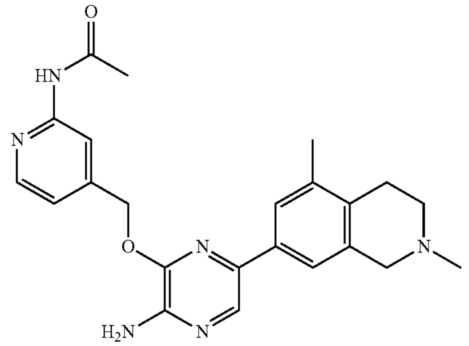
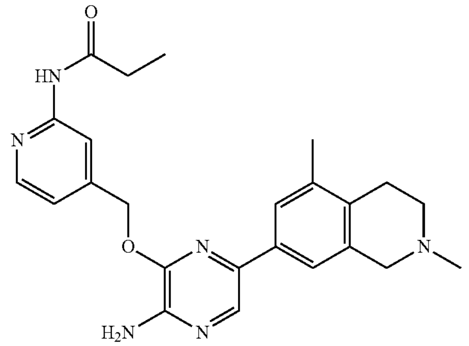
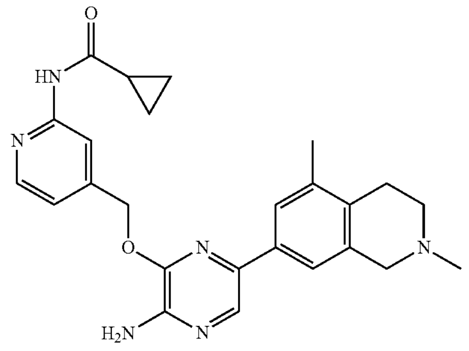

-continued
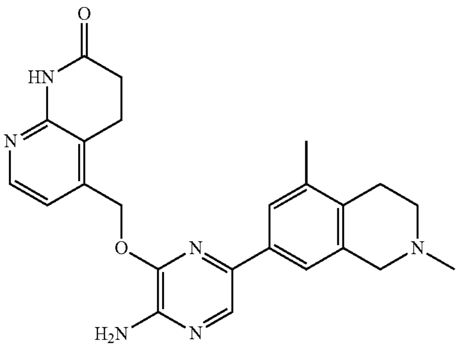
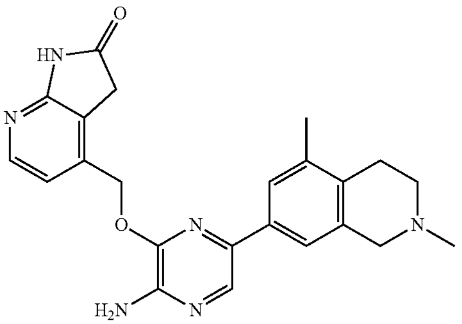
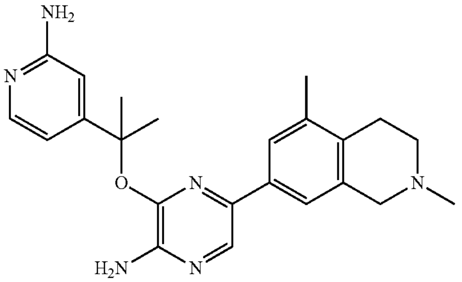
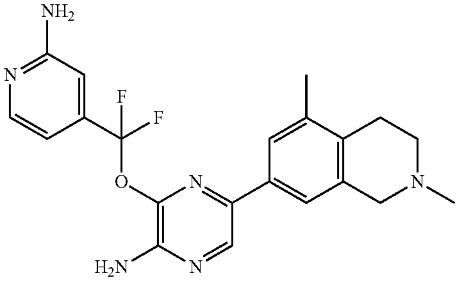
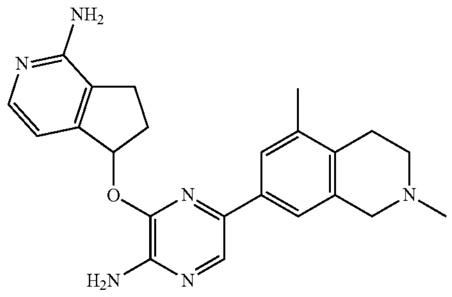
-continued
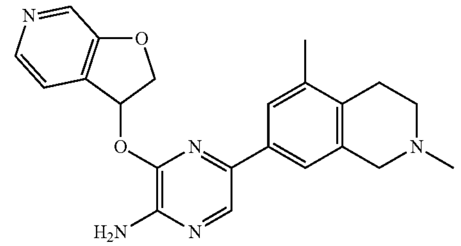
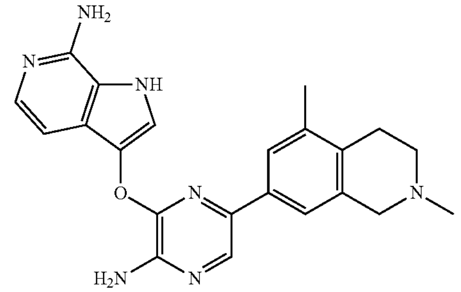
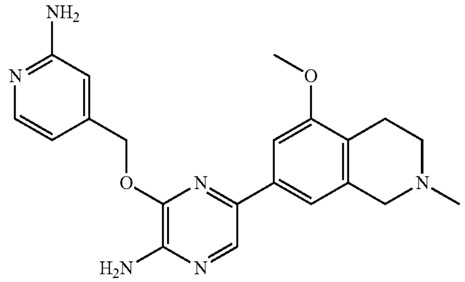
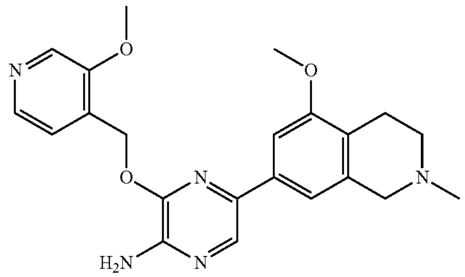
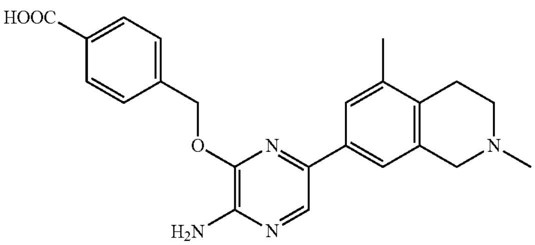
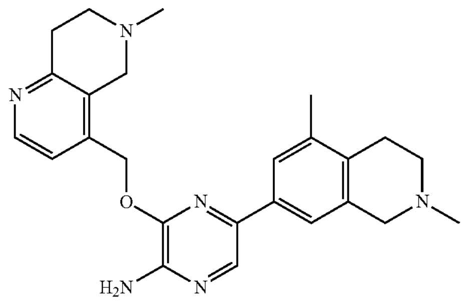

-continued
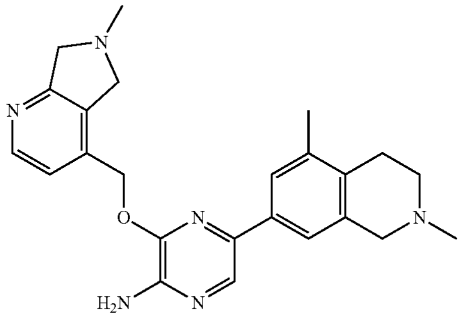
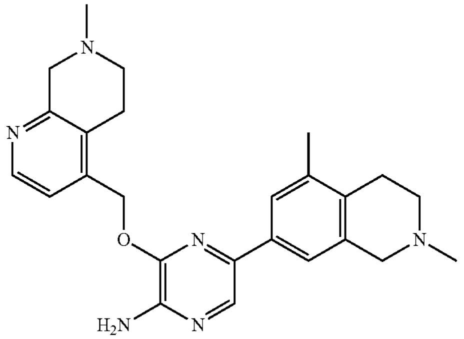
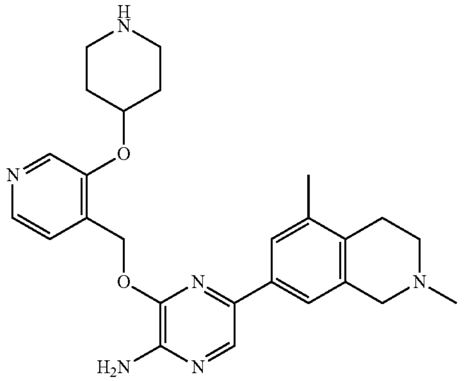
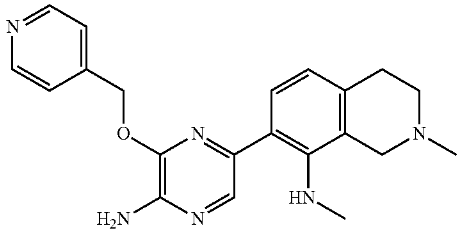
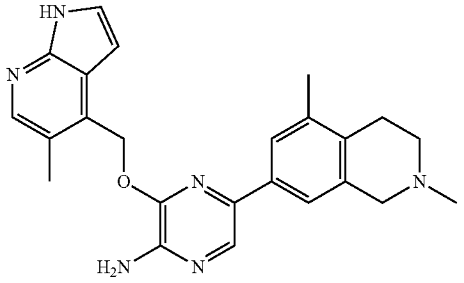
-continued
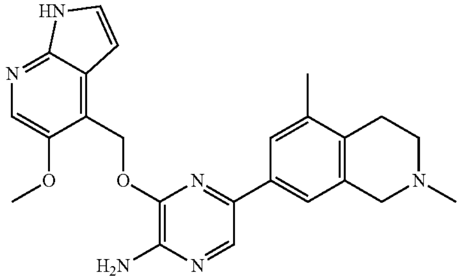
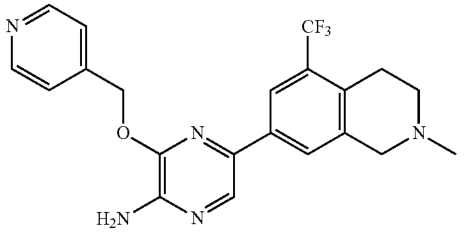
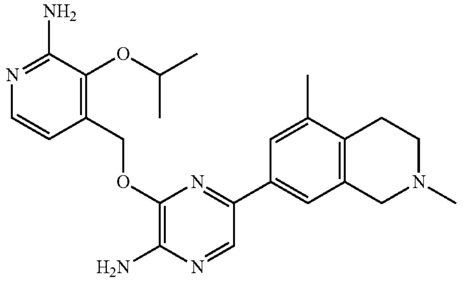
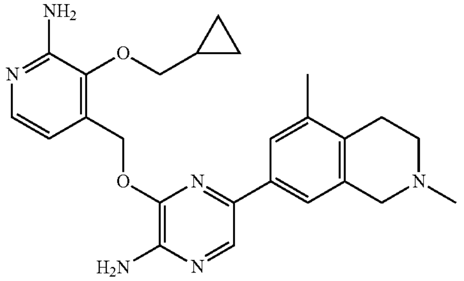
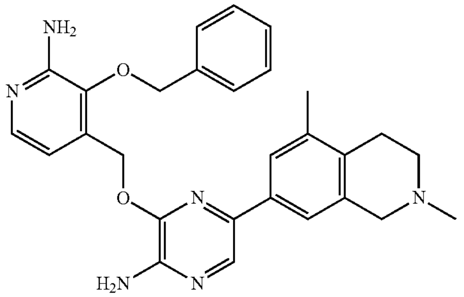
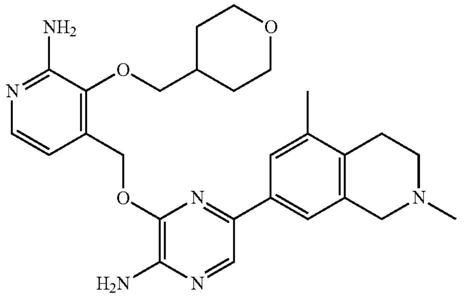

-continued
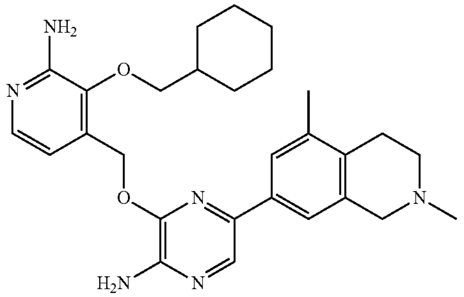
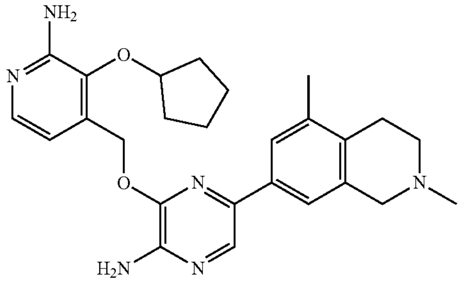
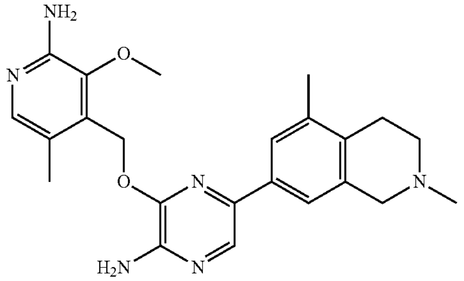
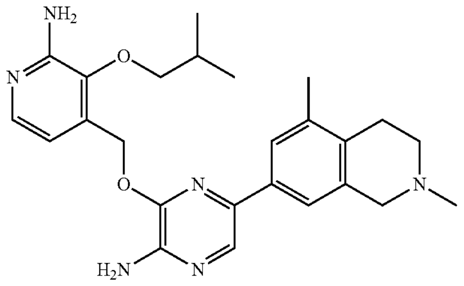
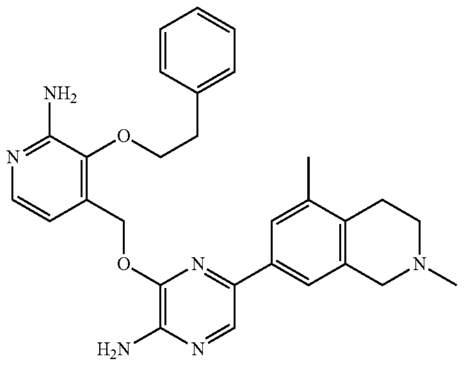
-continued
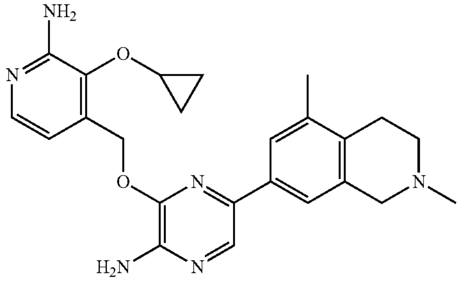
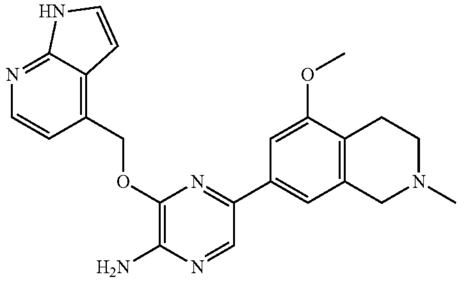
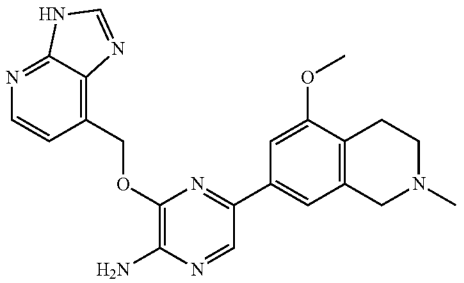
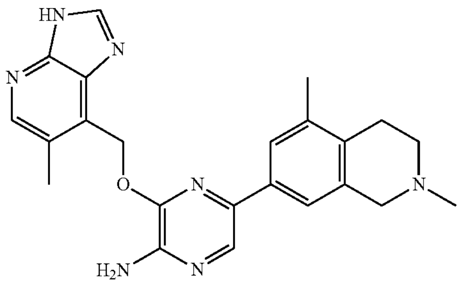
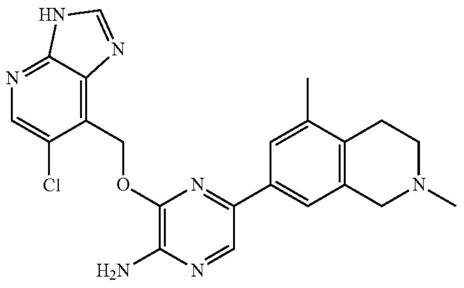
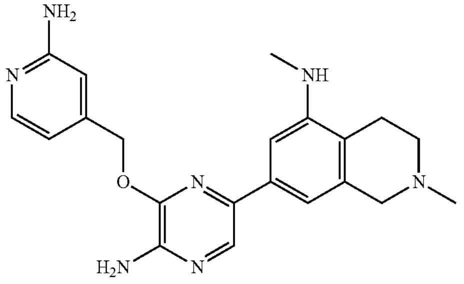

-continued
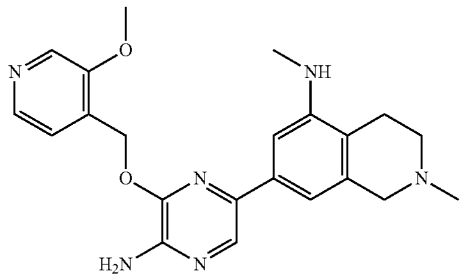
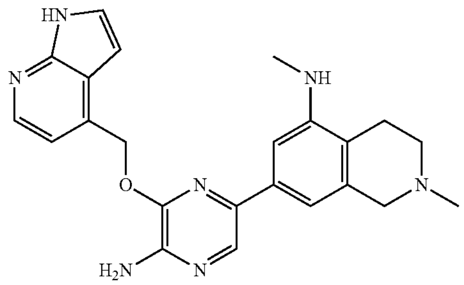
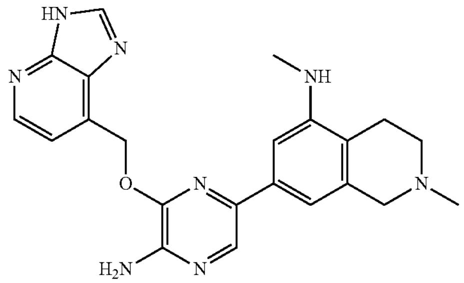
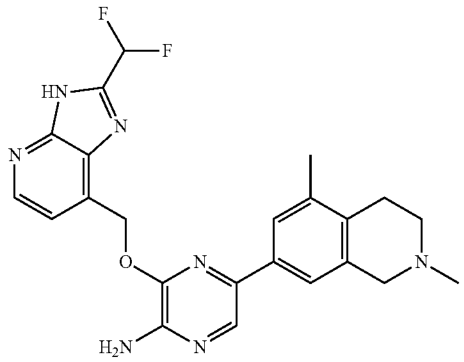
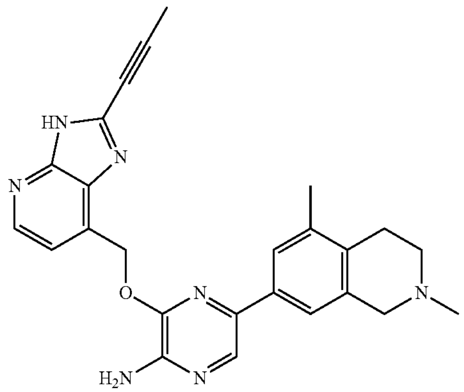
-continued
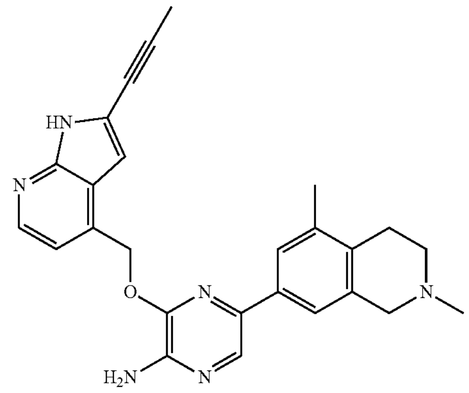
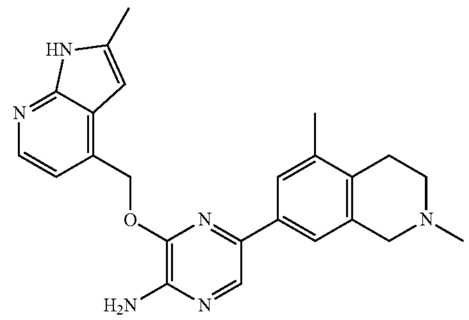
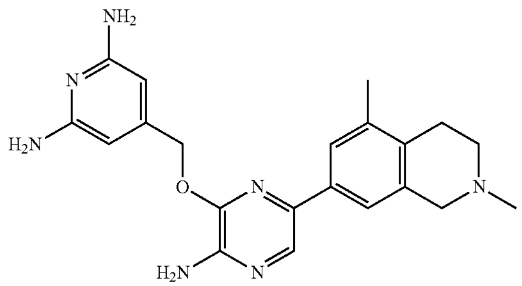
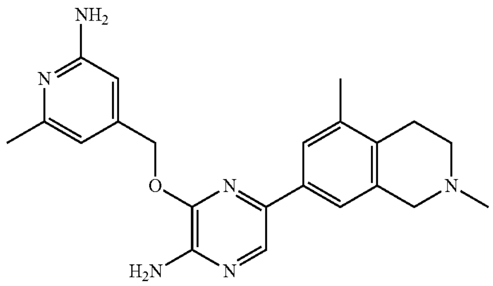
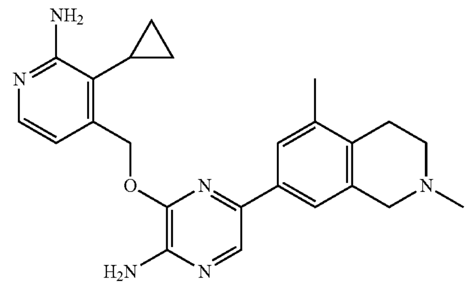

-continued
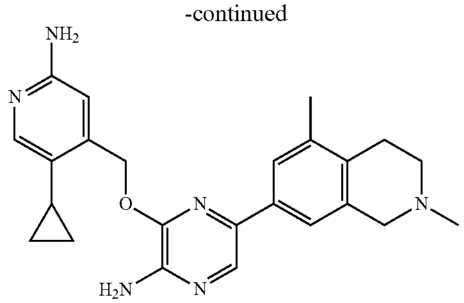
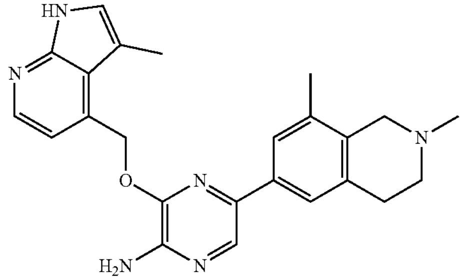
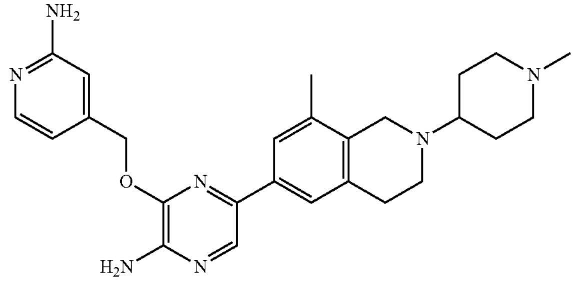
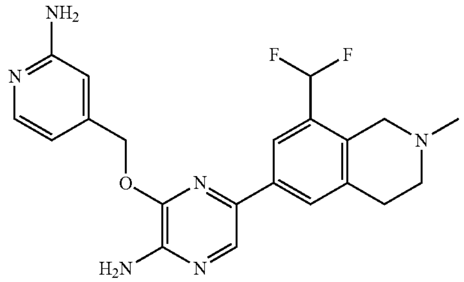
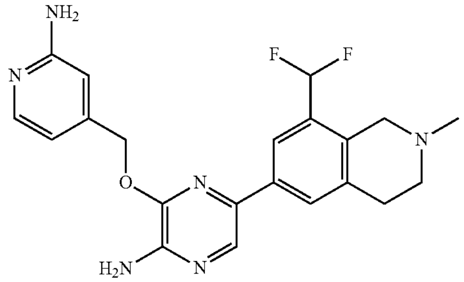
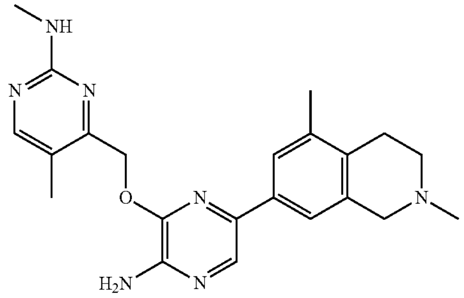
-continued
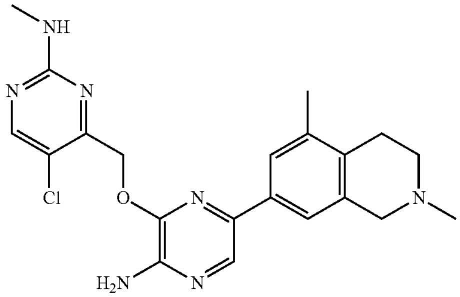
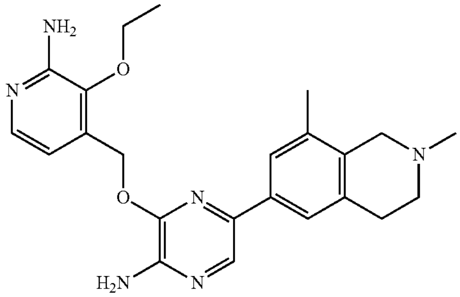
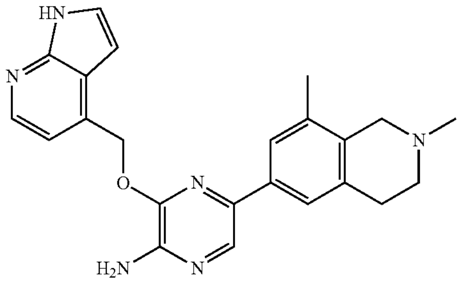
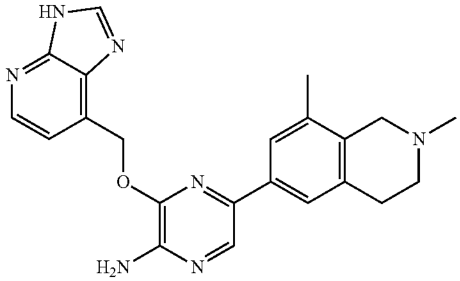
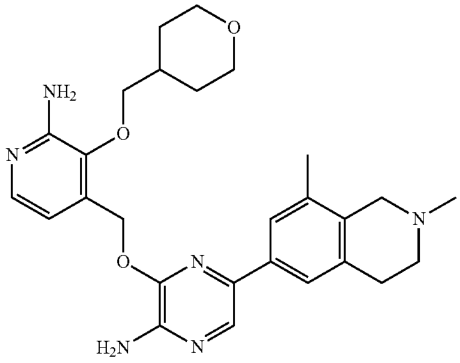

-continued
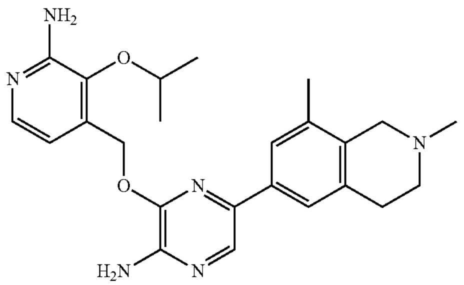
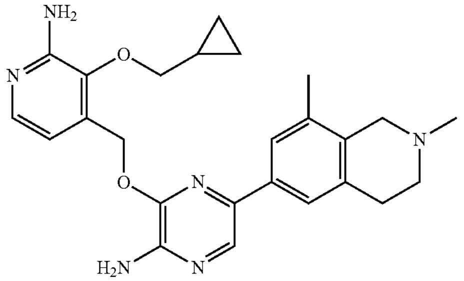
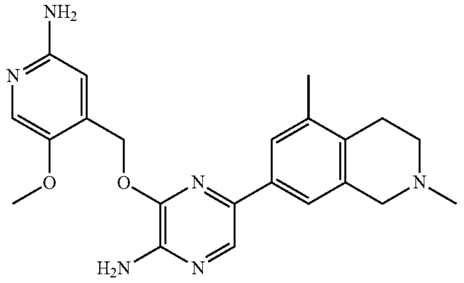
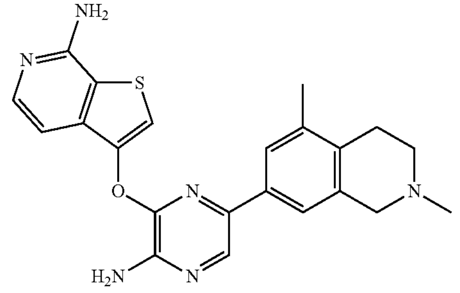
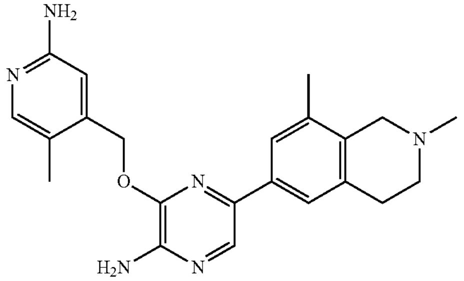
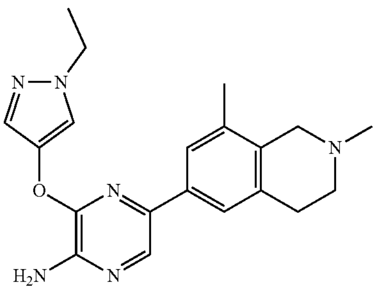
-continued
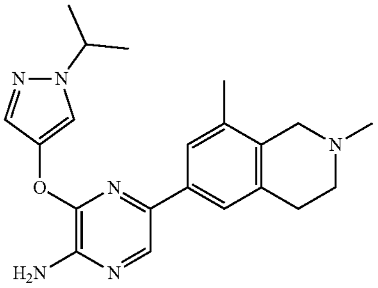
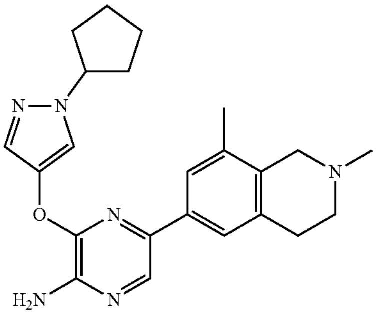
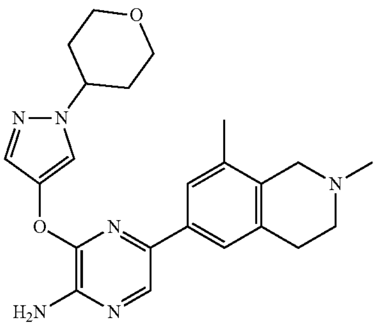
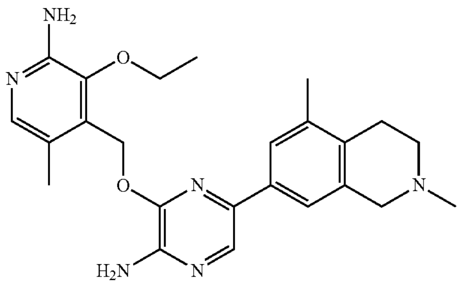
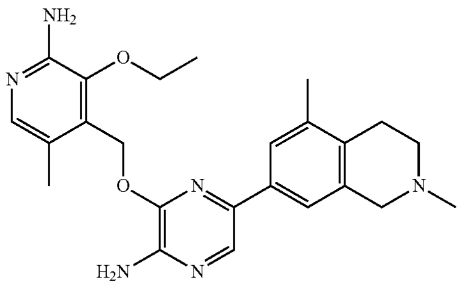

-continued
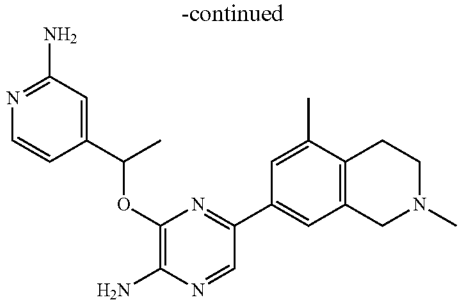
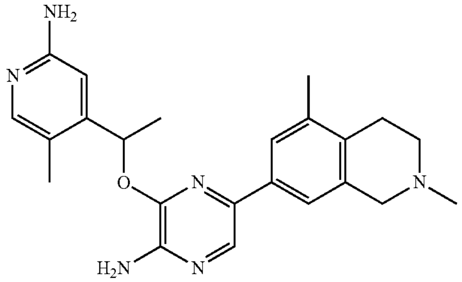
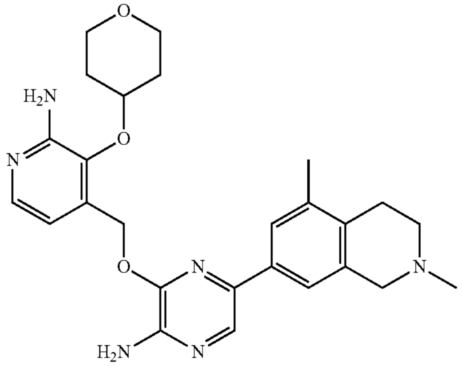
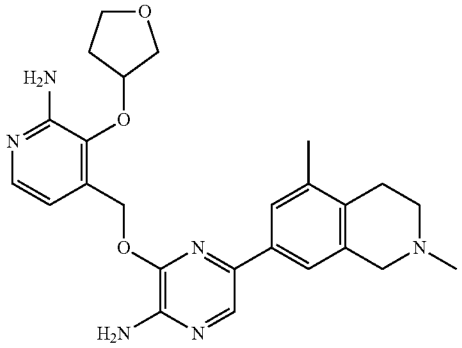
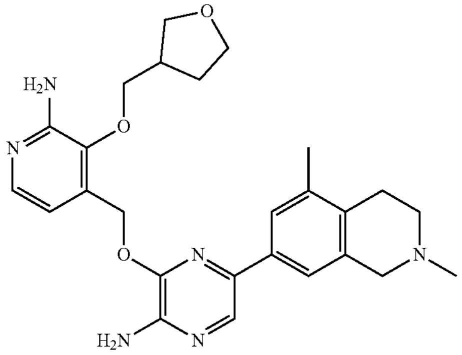
-continued
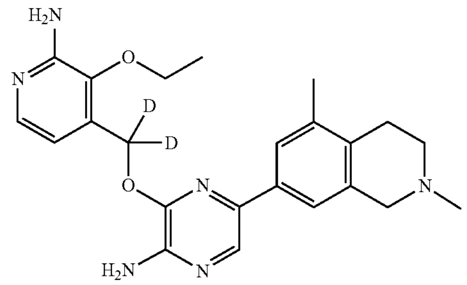
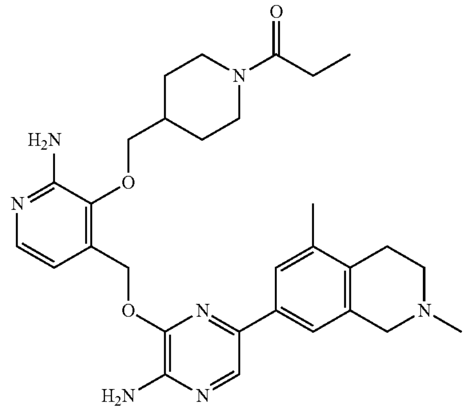
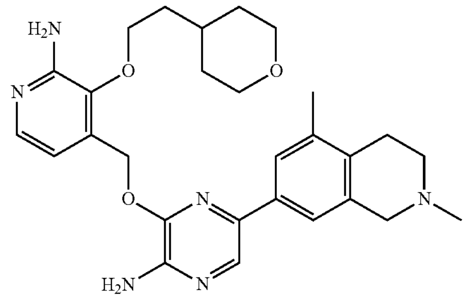
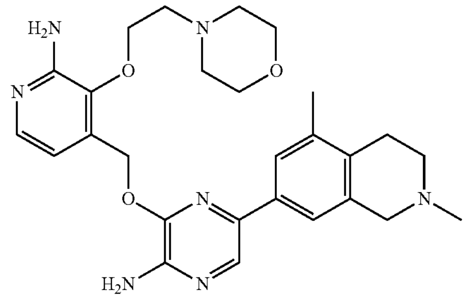
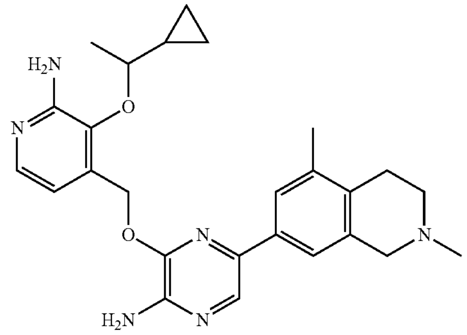

-continued
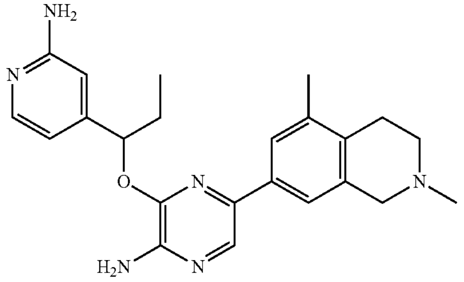
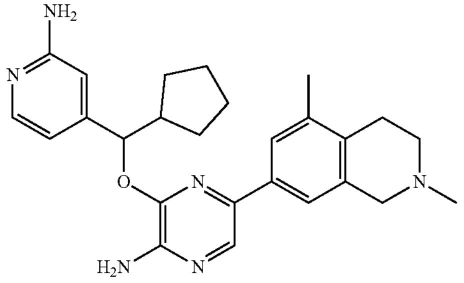
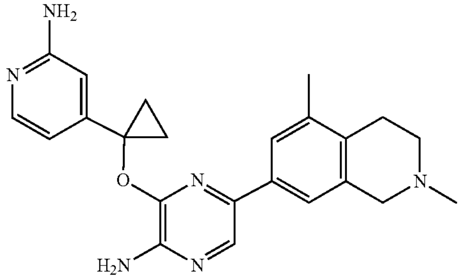
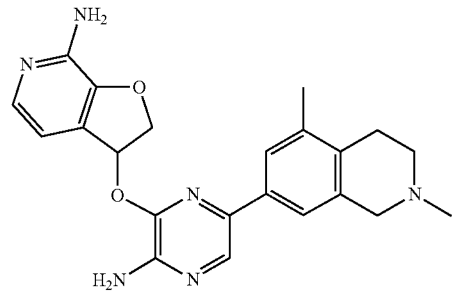
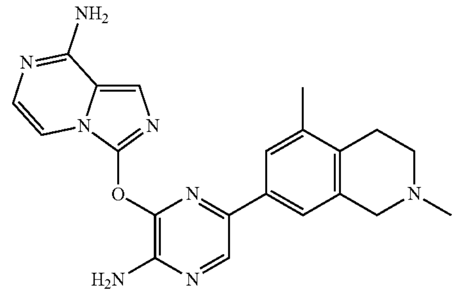
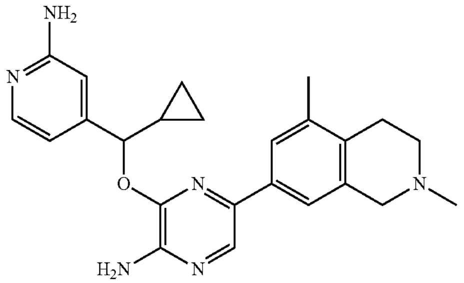
-continued
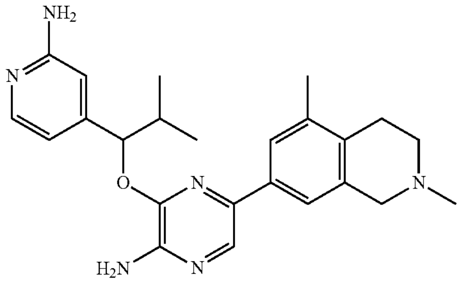
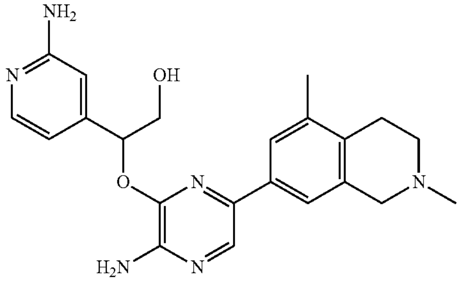
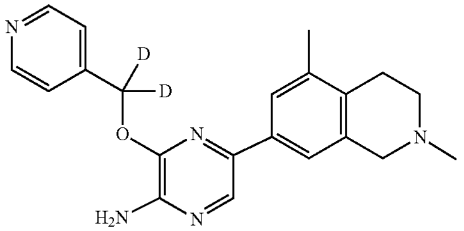
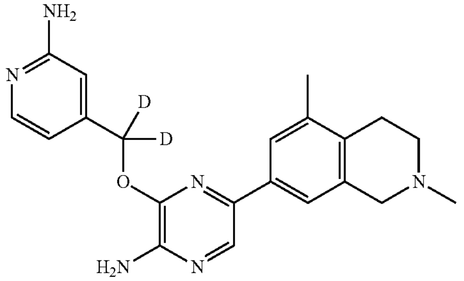
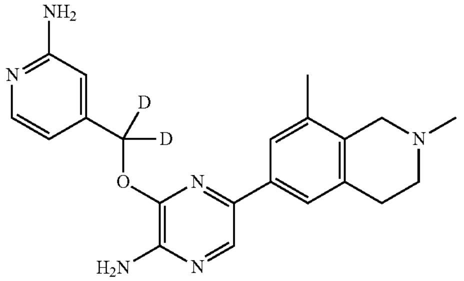
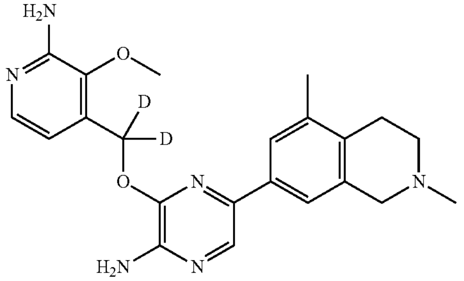

-continued
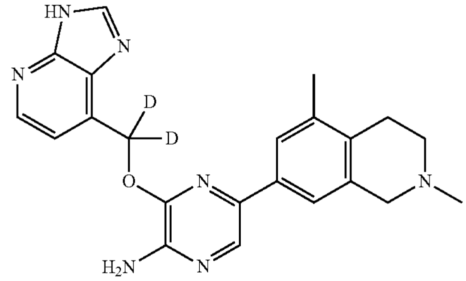
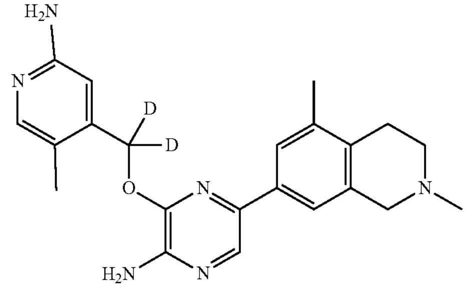
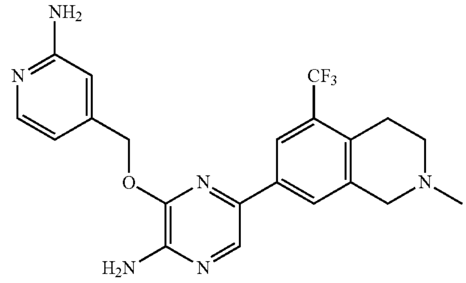
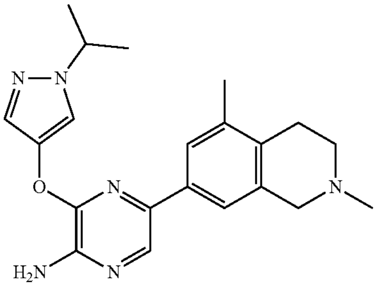
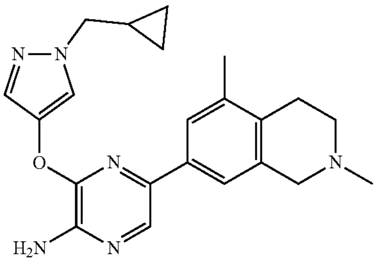
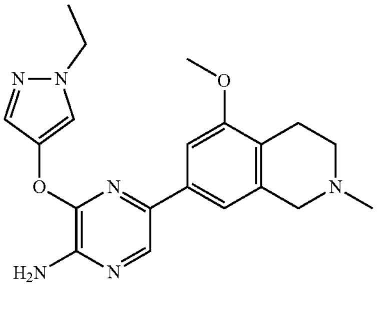
-continued
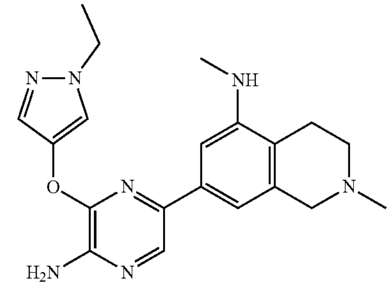
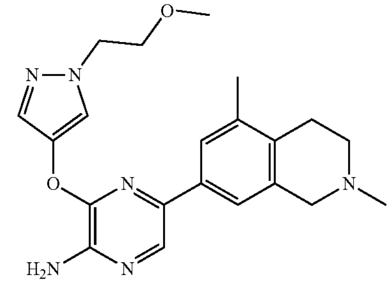
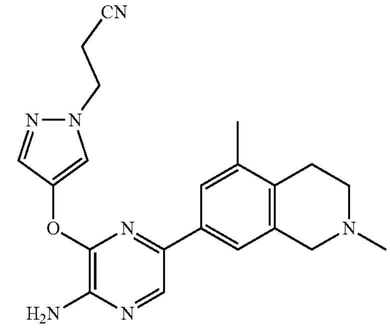
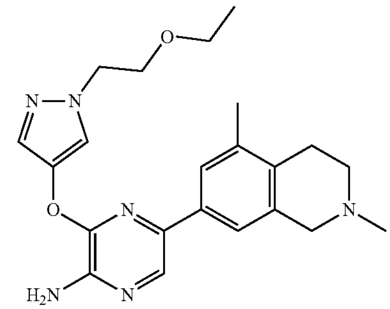
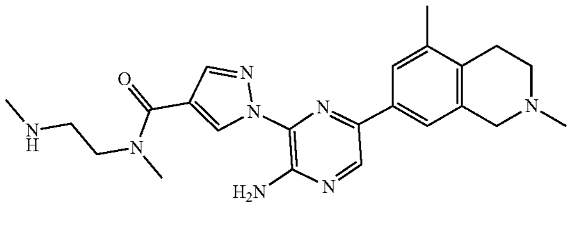

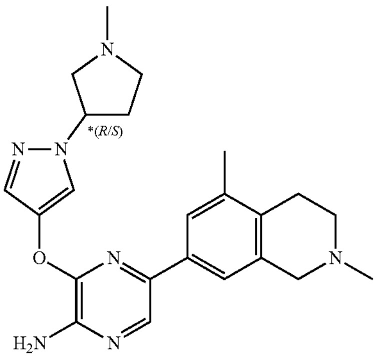
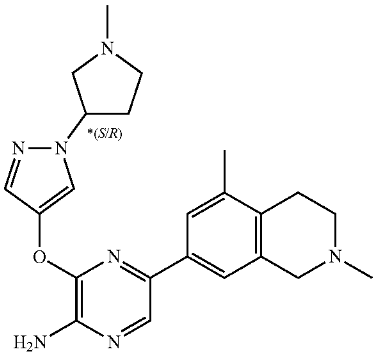
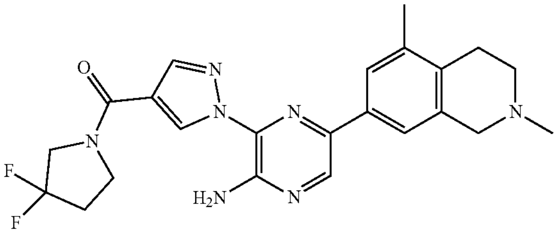
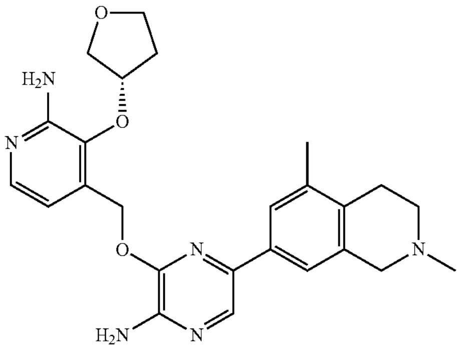
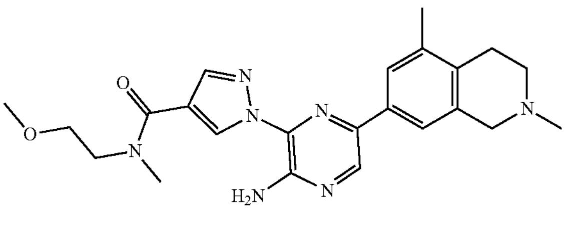
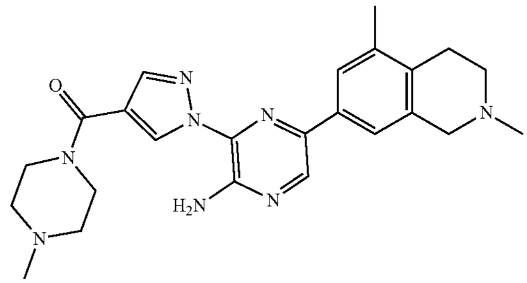
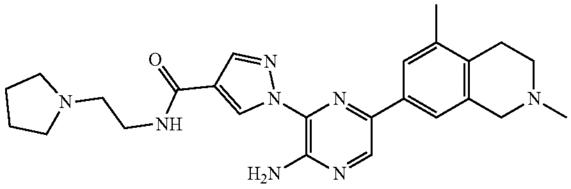
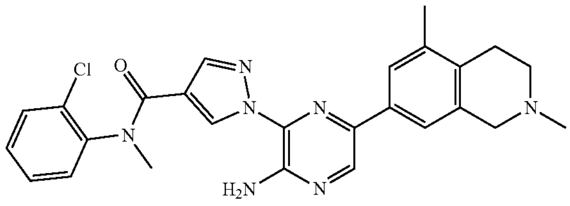
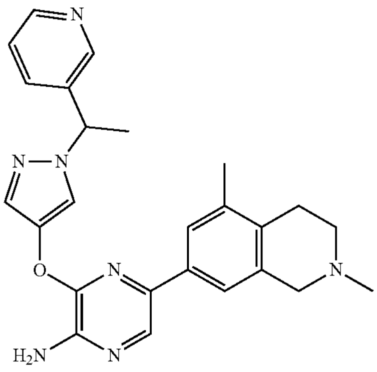
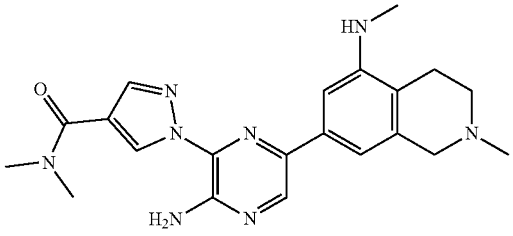
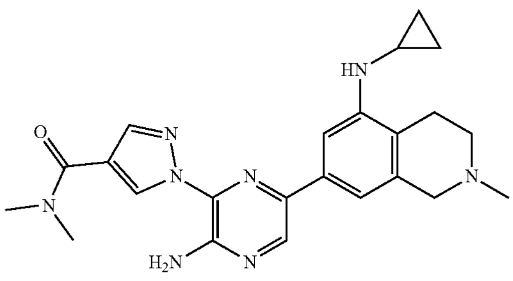

-continued
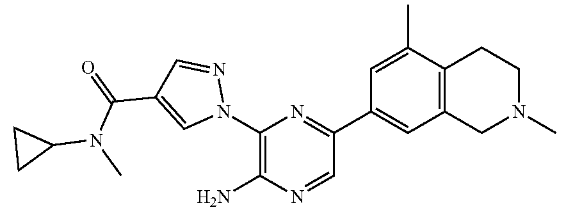
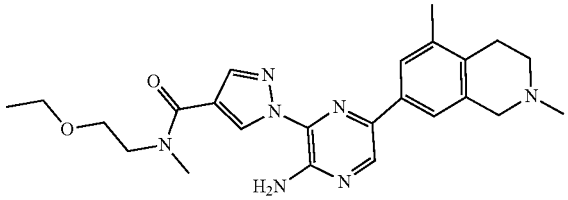
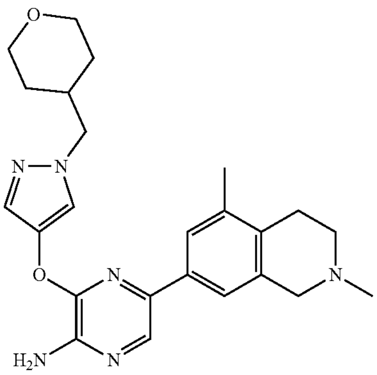
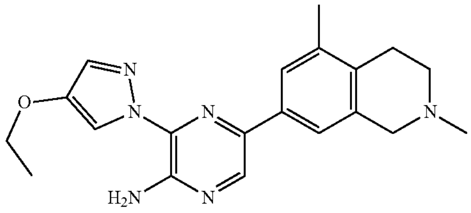
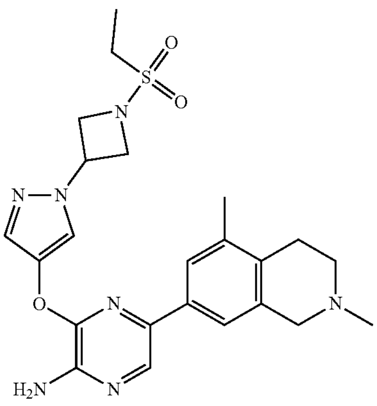
-continued
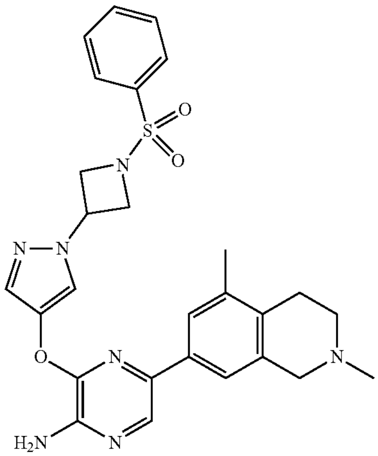
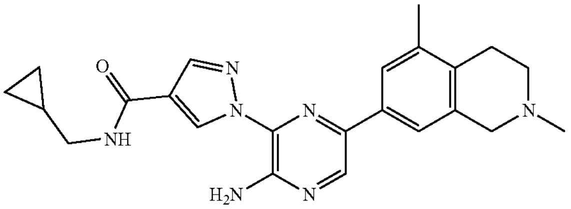
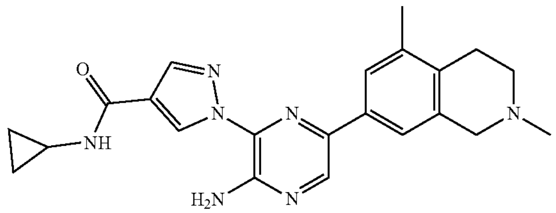
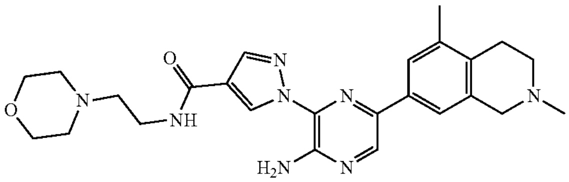
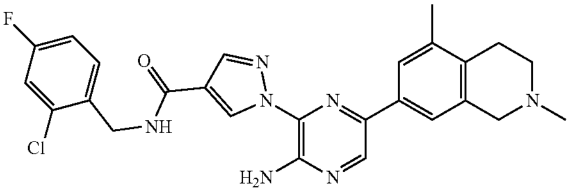
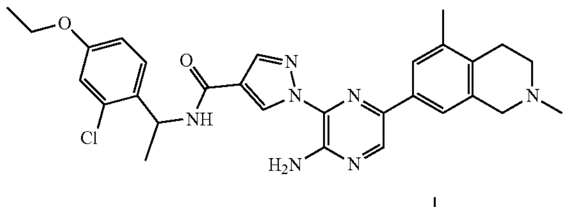
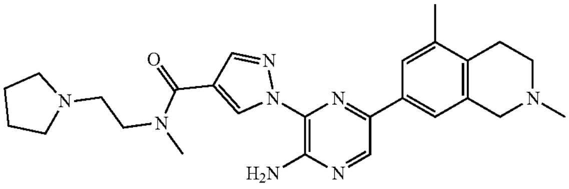

-continued
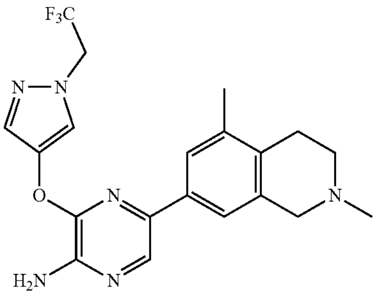
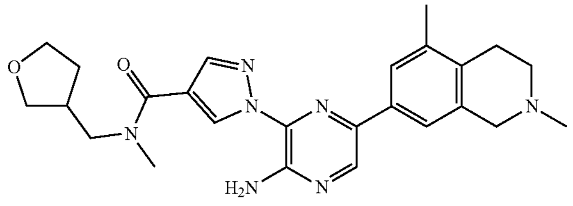
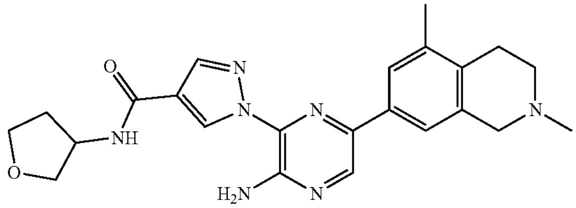
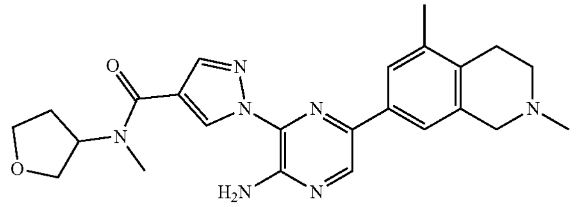
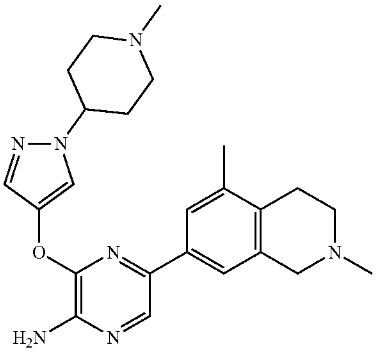
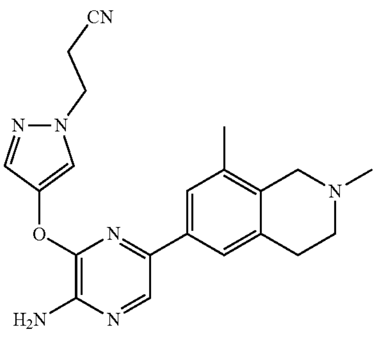
-continued
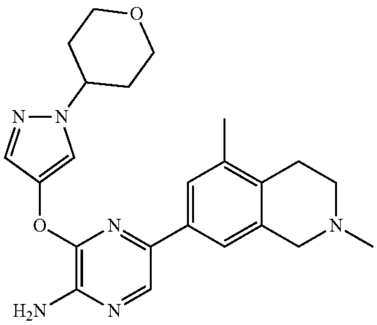
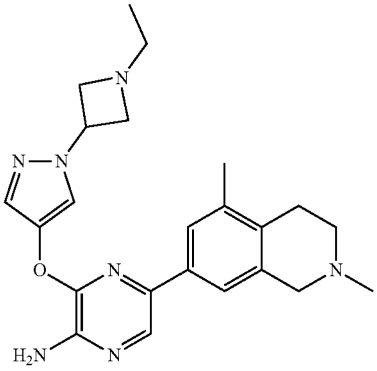
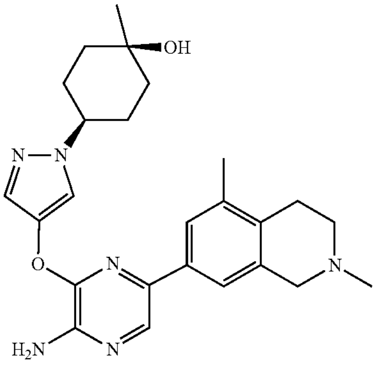
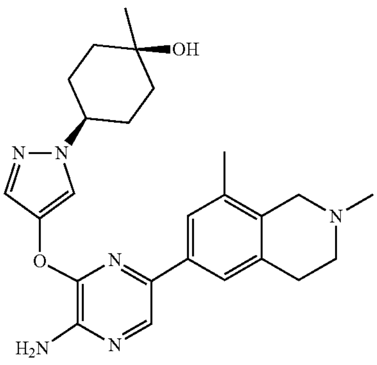

-continued
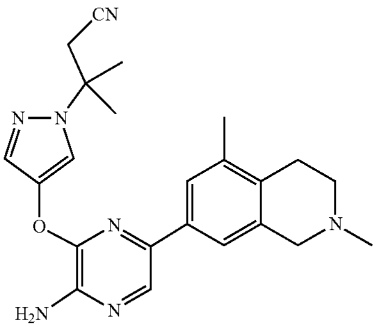
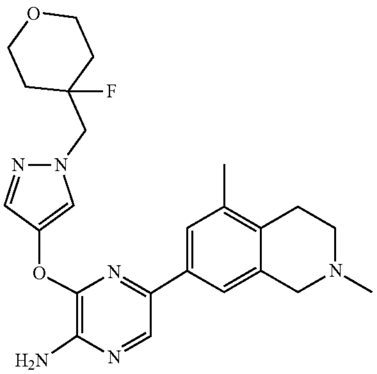
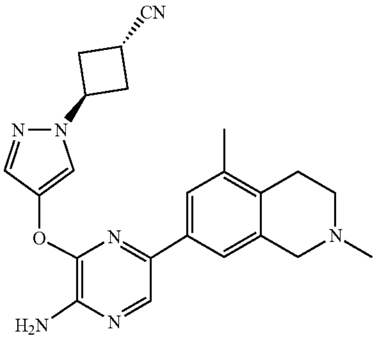
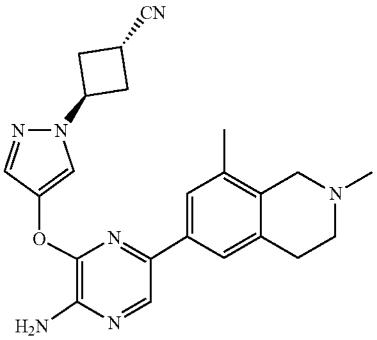
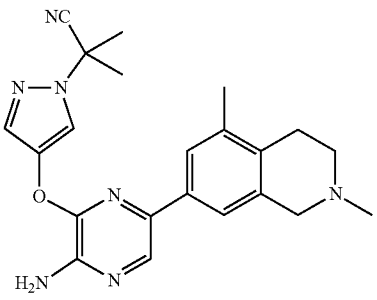
-continued
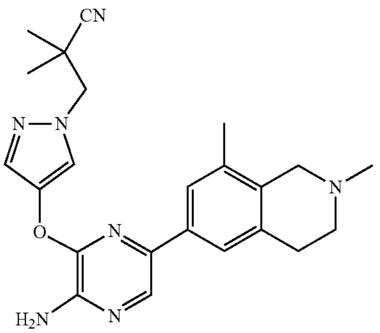
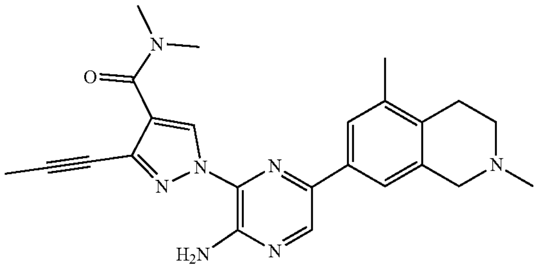
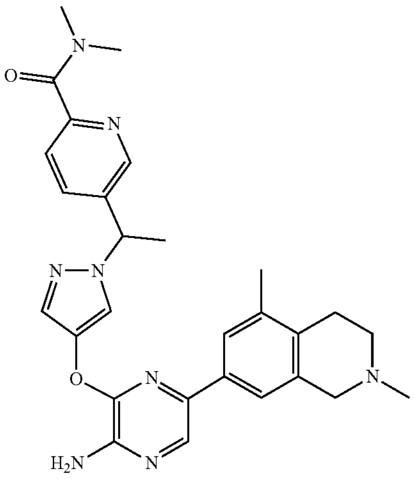
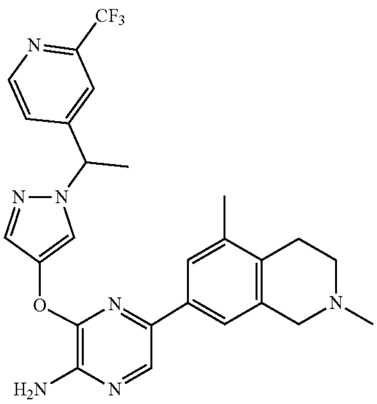

-continued
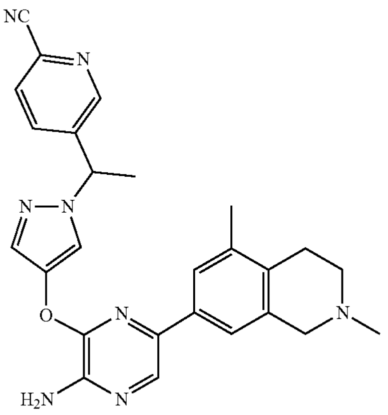
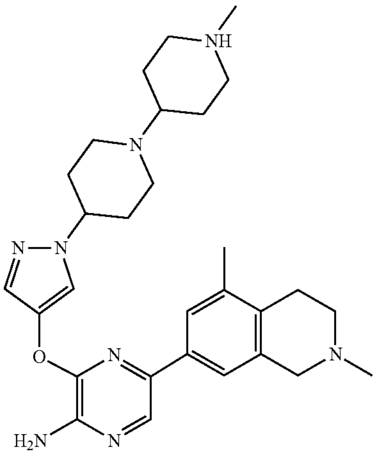
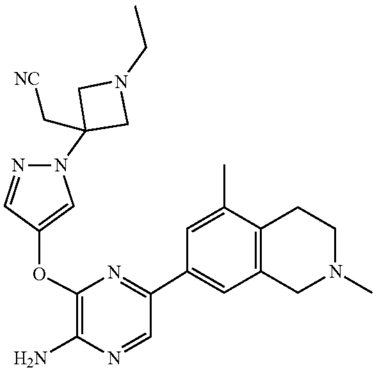
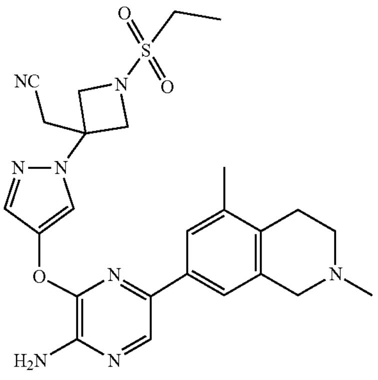
-continued
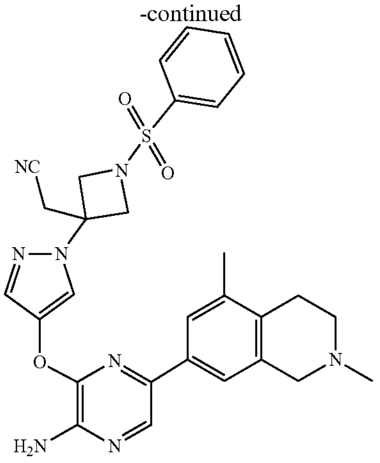
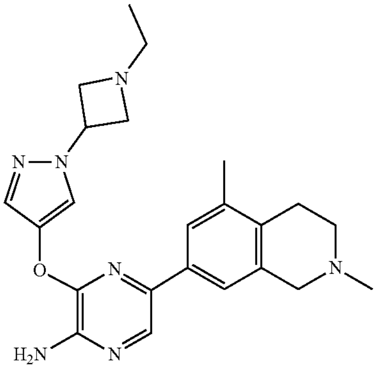
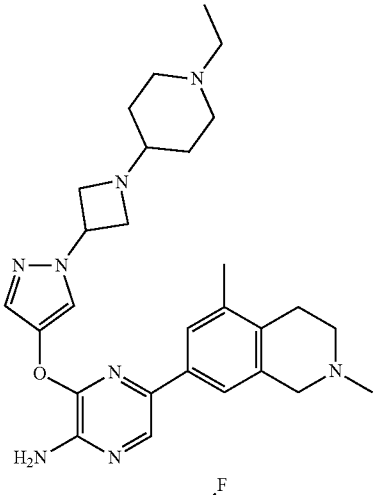
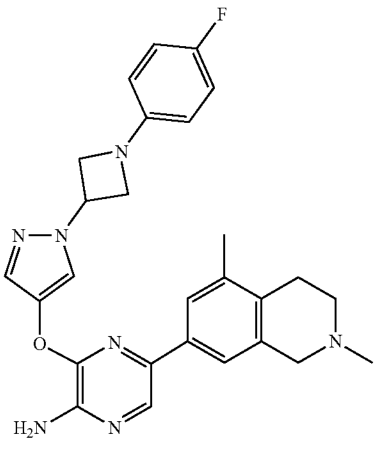

-continued
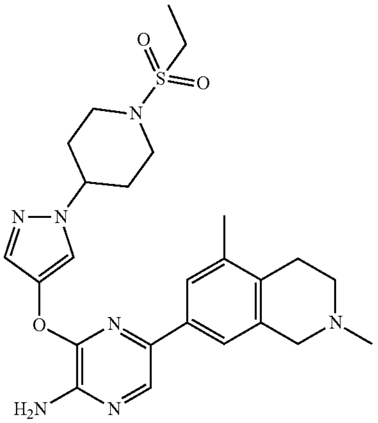
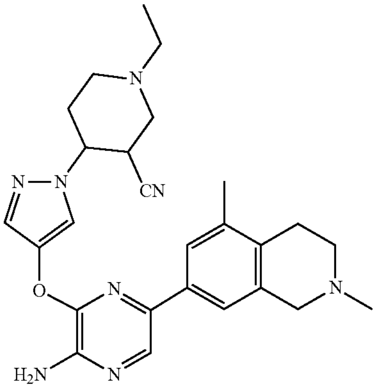
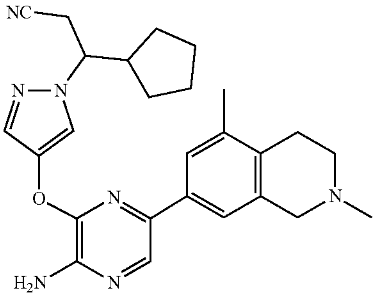
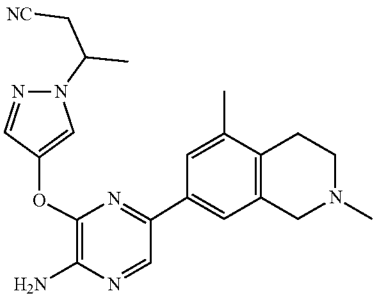
-continued
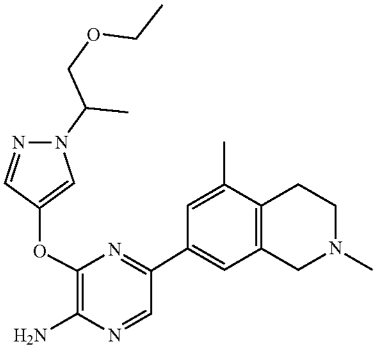
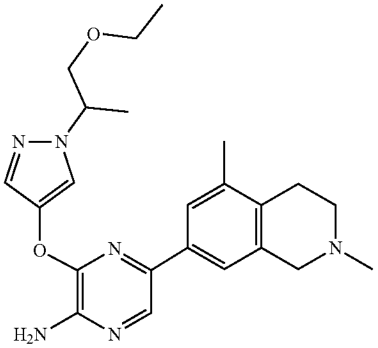
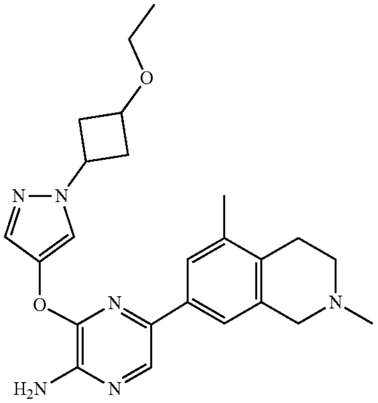
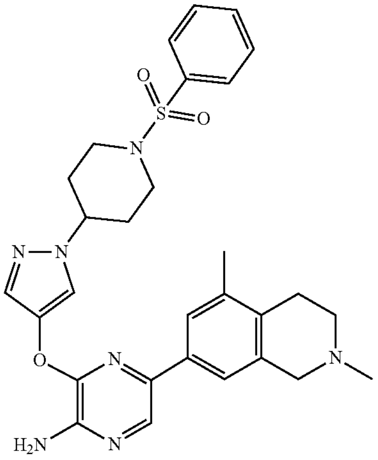

-continued
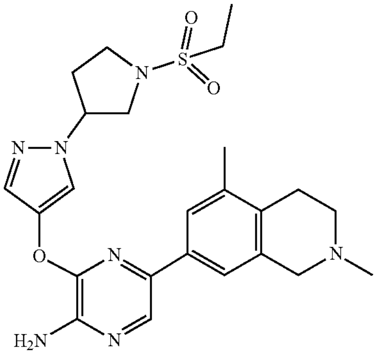
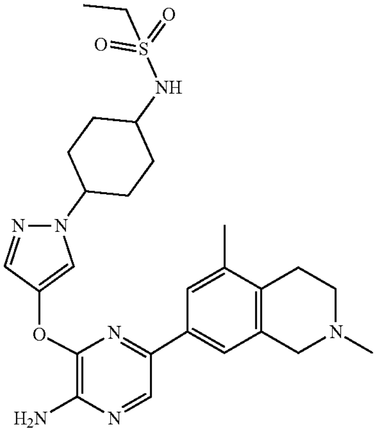
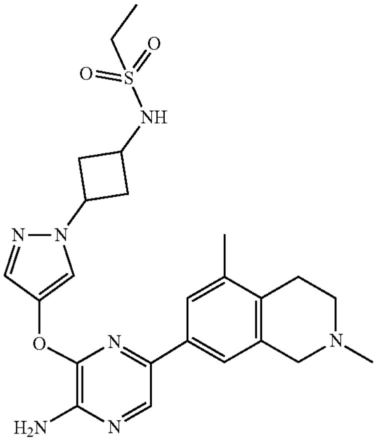
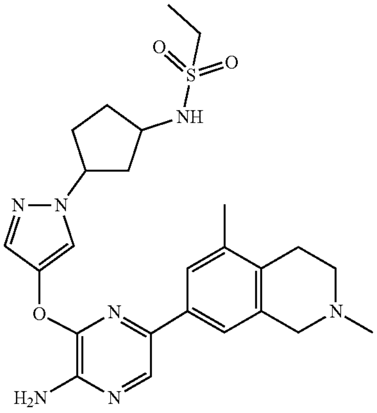
-continued
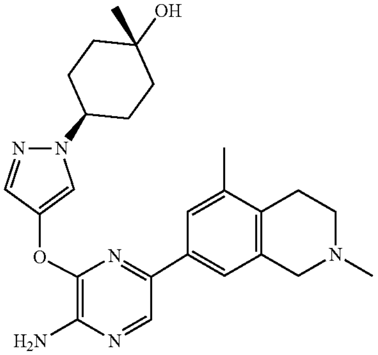
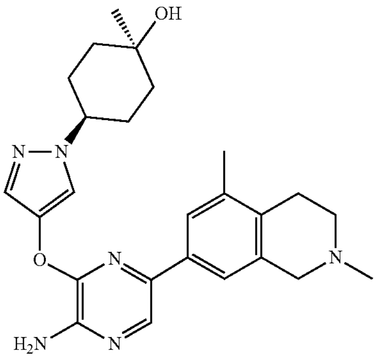
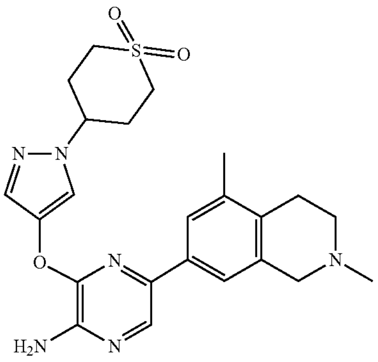
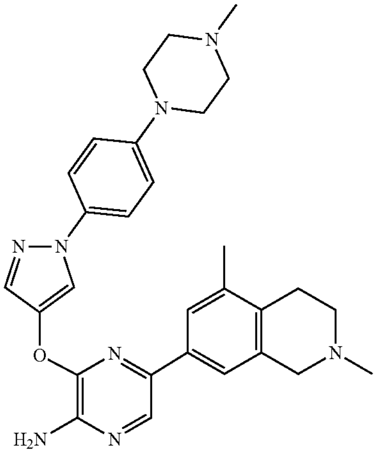

-continued
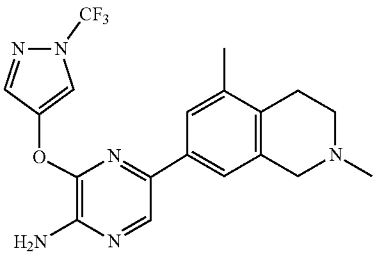
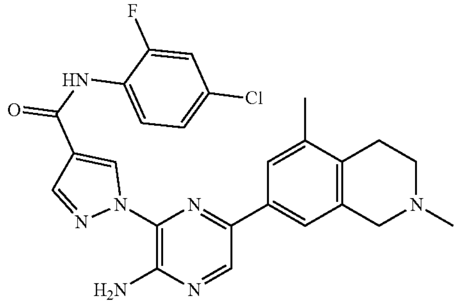
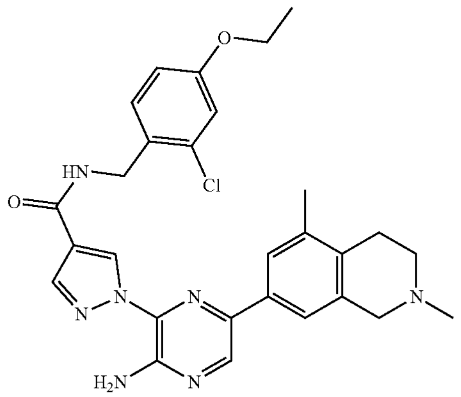
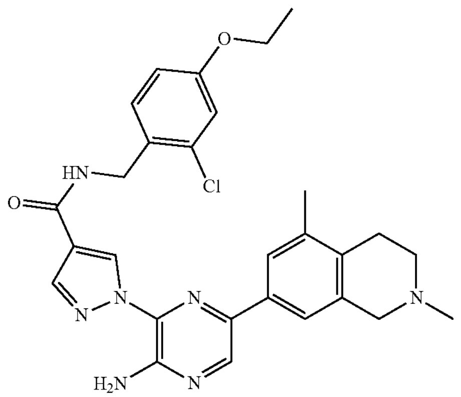
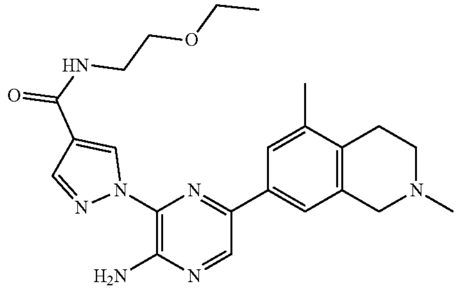
-continued
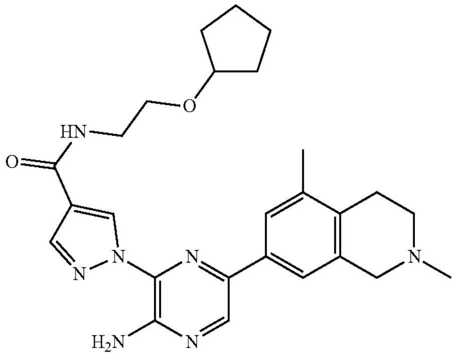
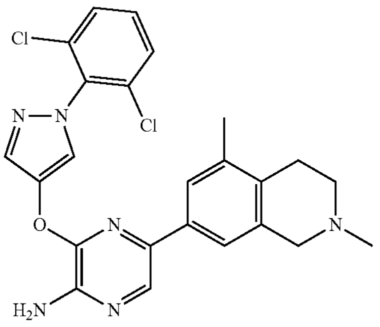
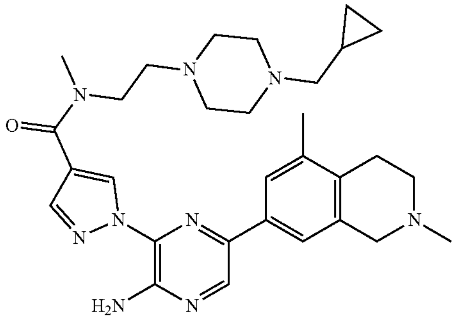
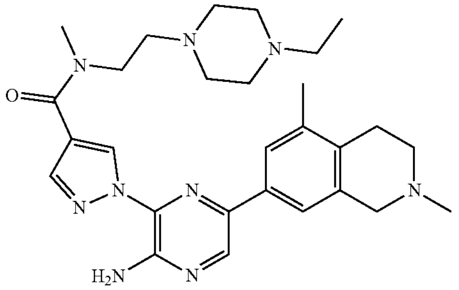
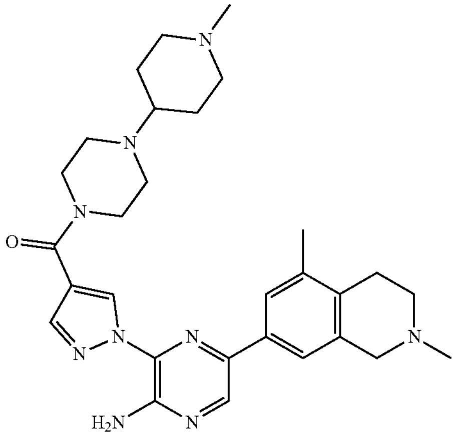

-continued
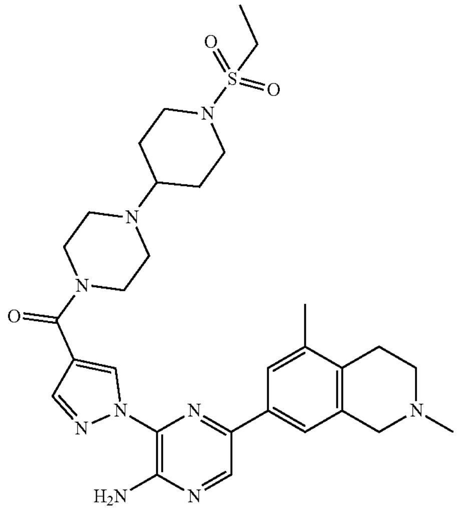
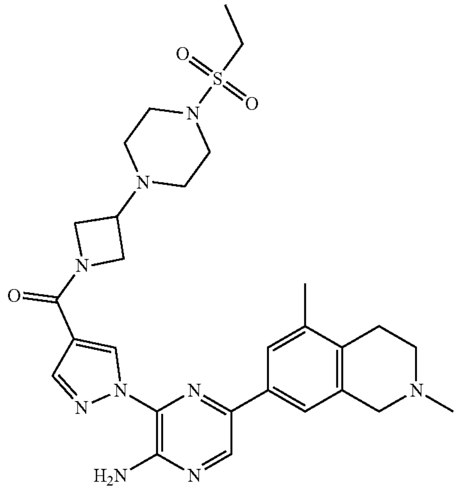
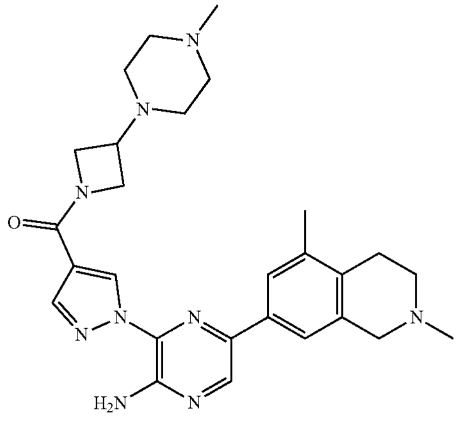
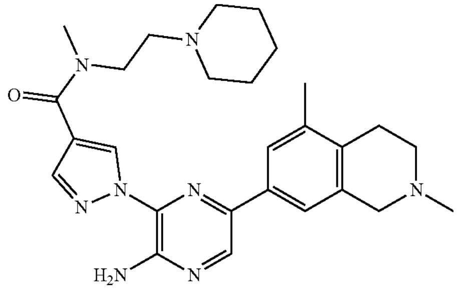
-continued
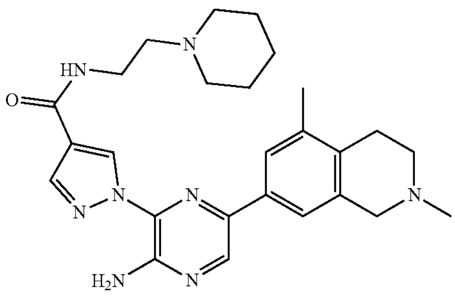
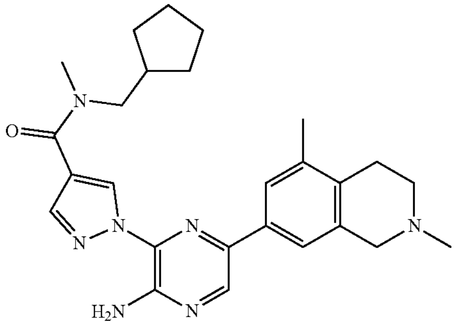
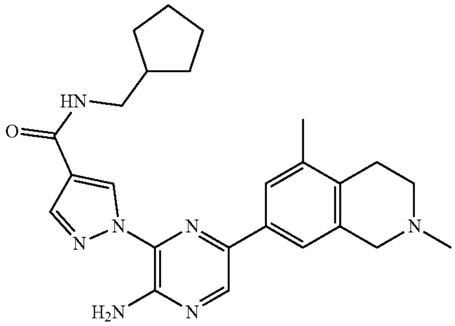
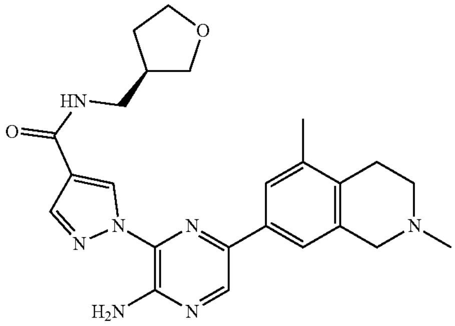
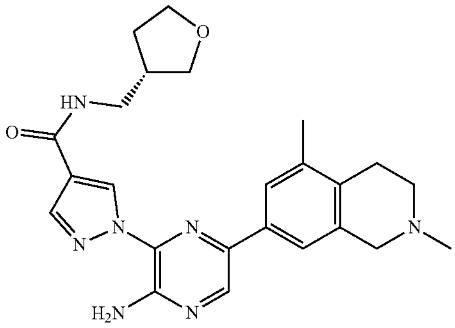

-continued
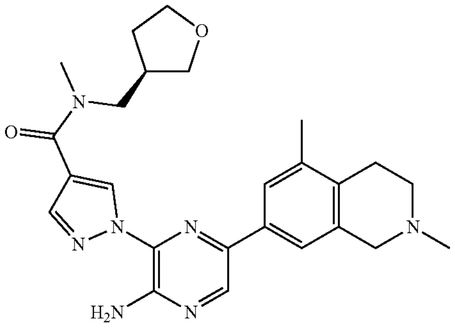
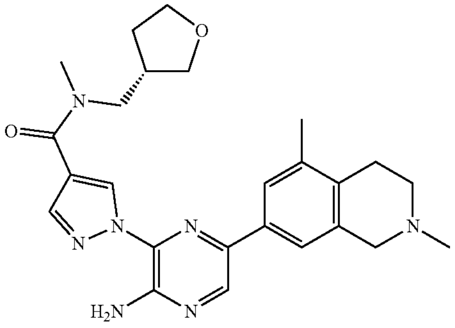
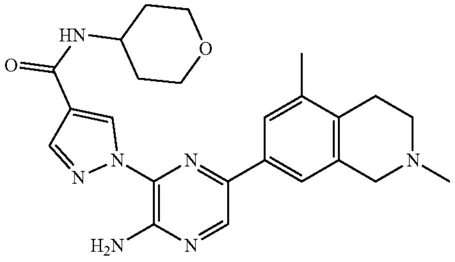
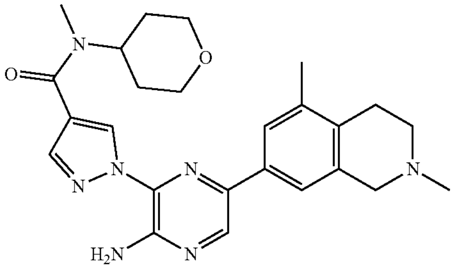
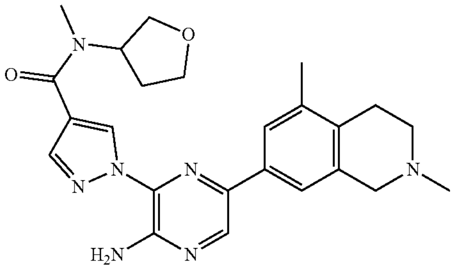
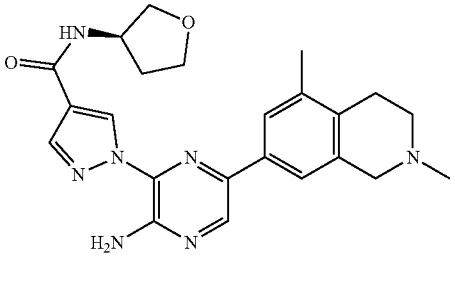
-continued
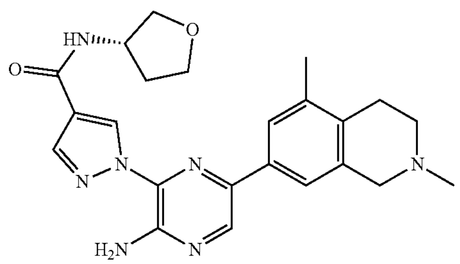
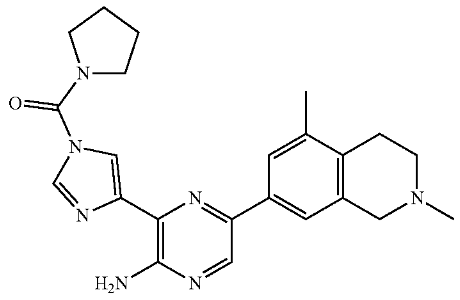
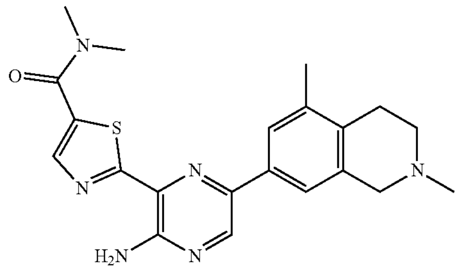
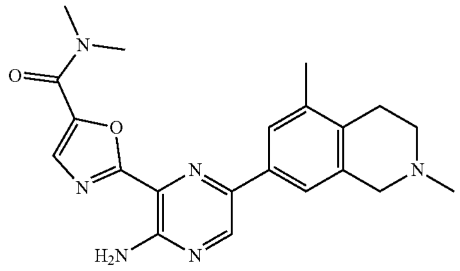
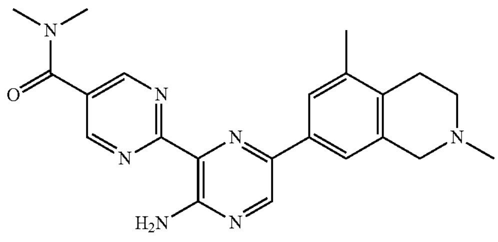
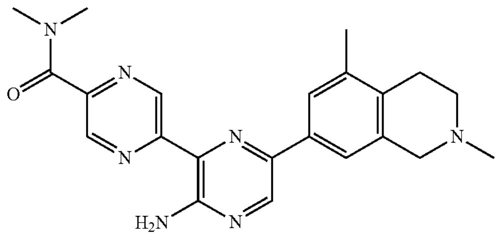

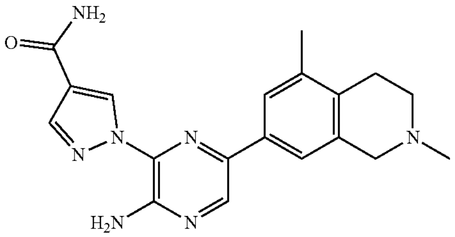
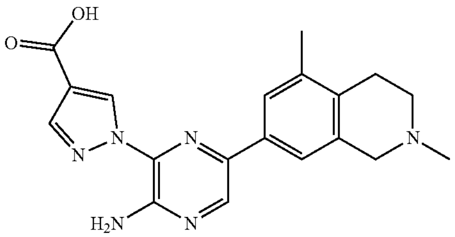
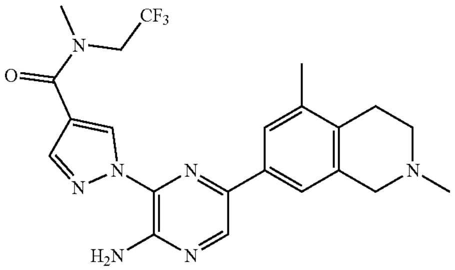
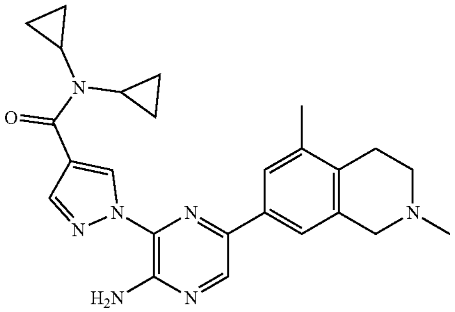
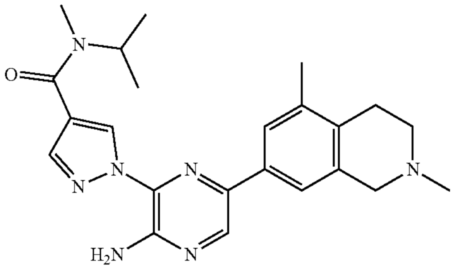
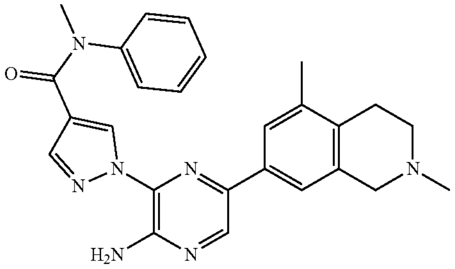
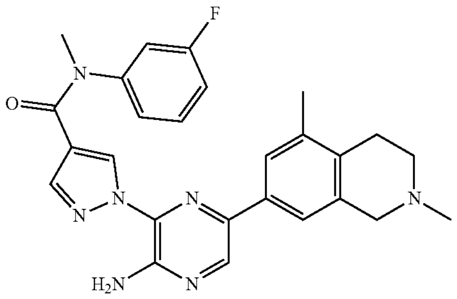
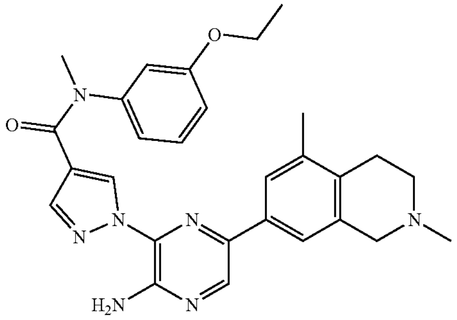
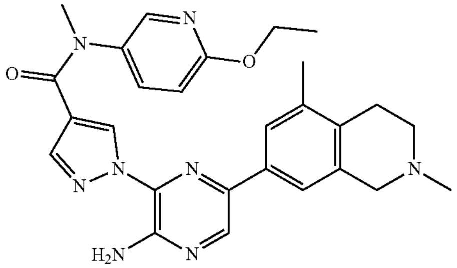
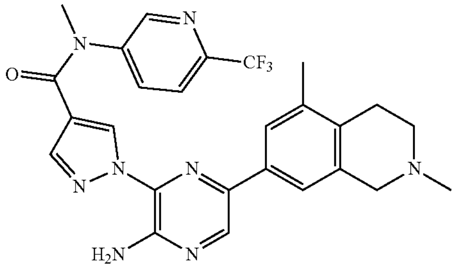
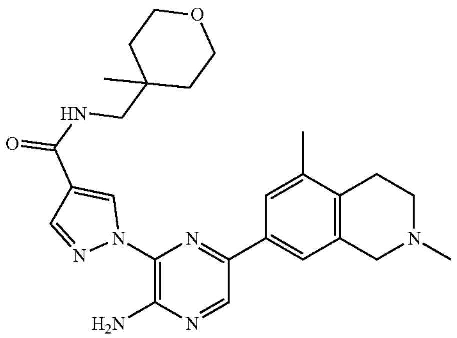

-continued
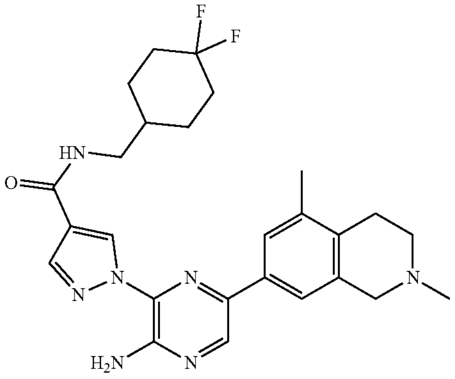
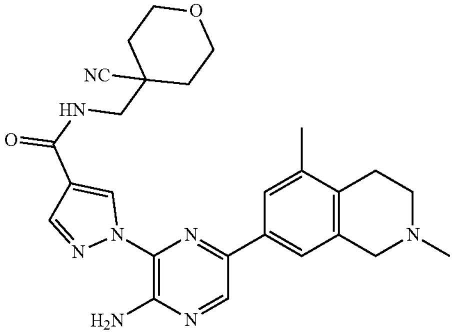
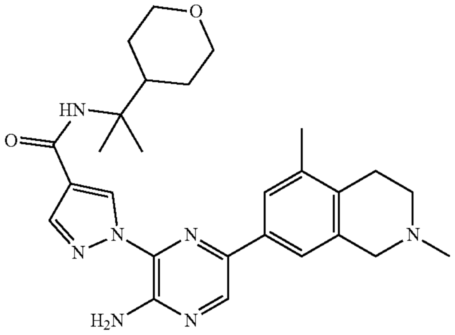
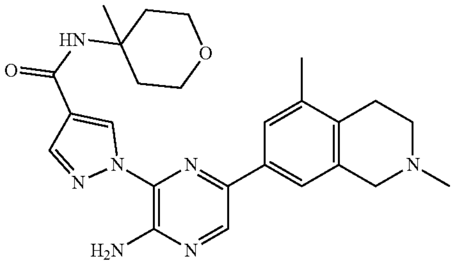
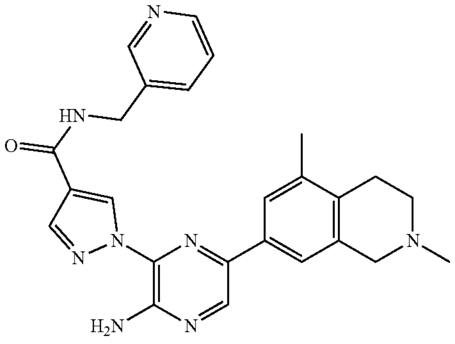
-continued
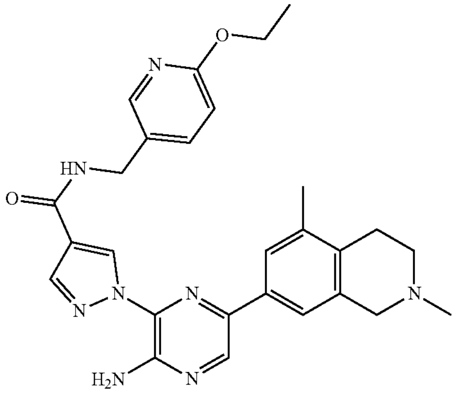
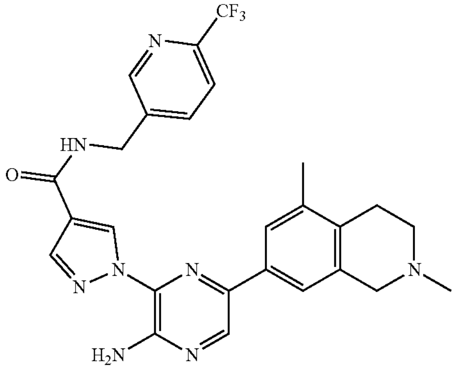
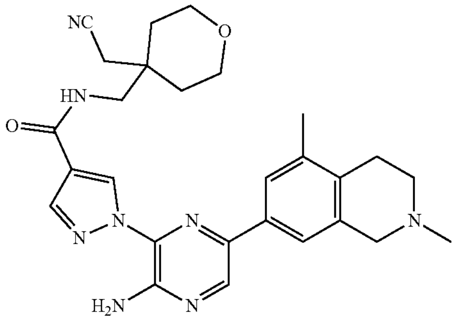
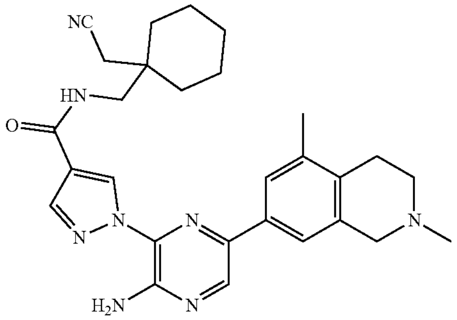
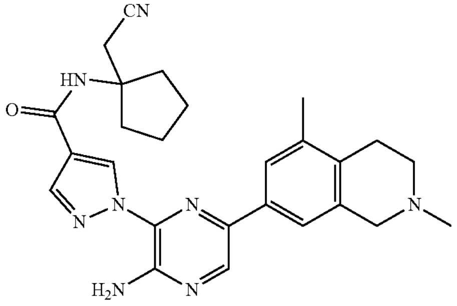

-continued
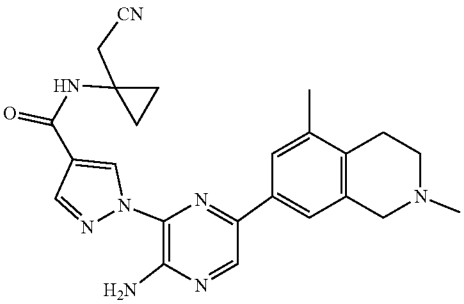
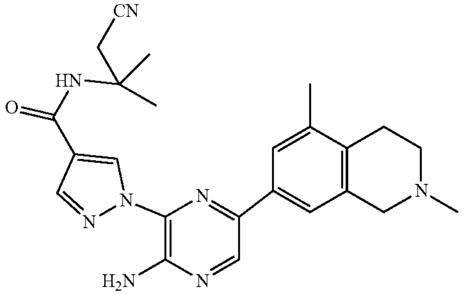
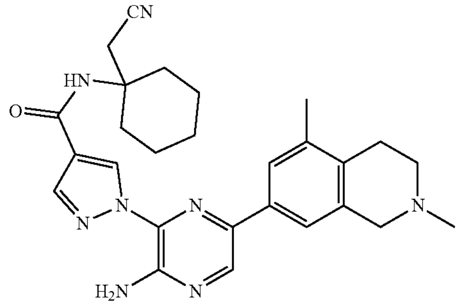
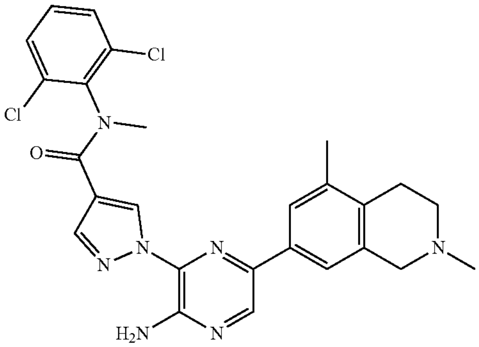
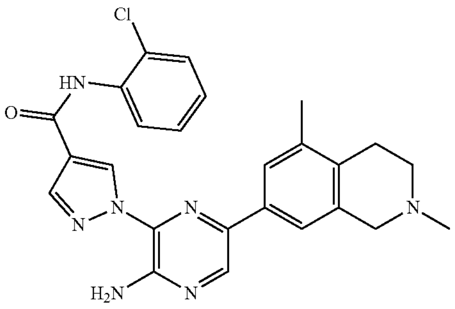
-continued
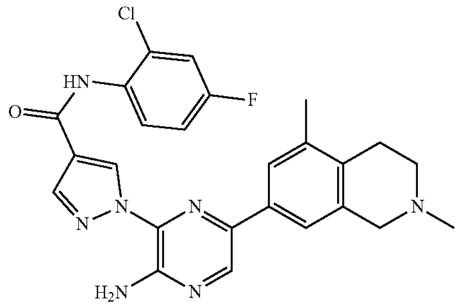
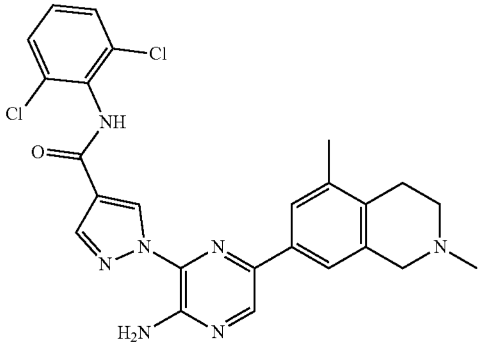
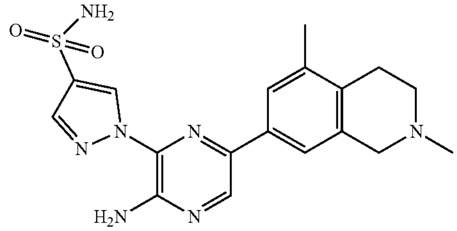
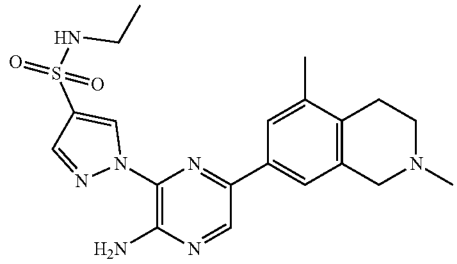
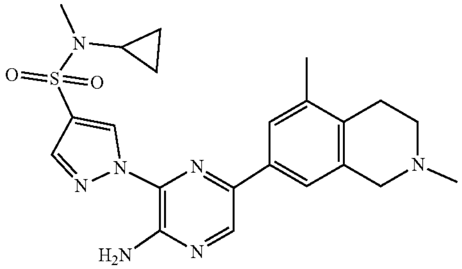
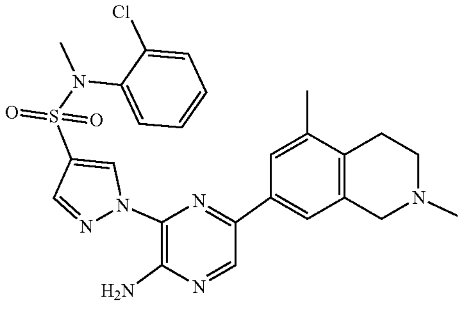

-continued
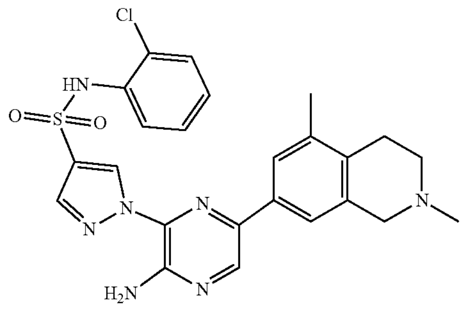
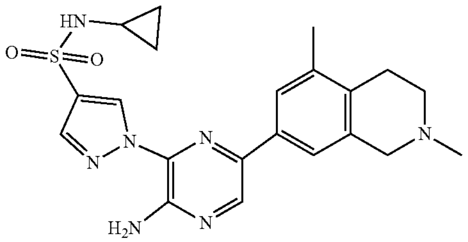
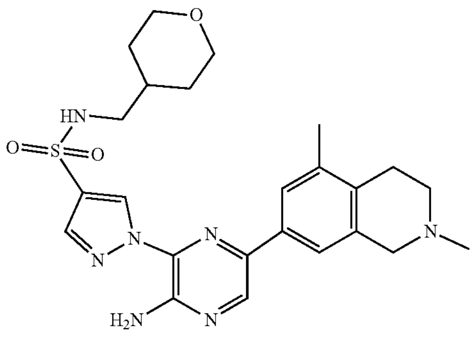
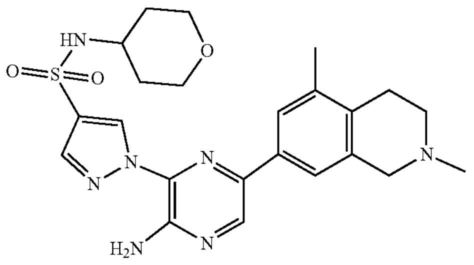
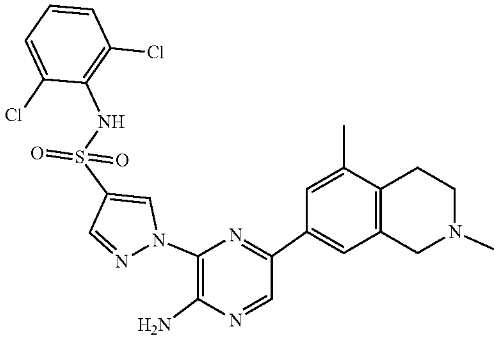
-continued
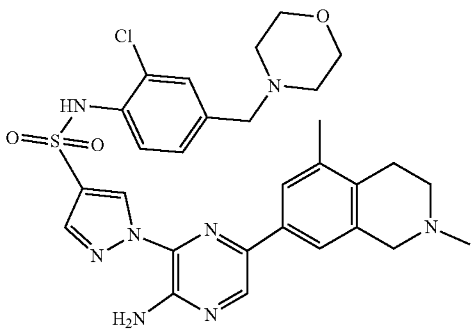
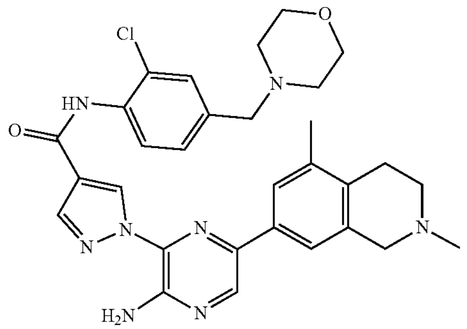
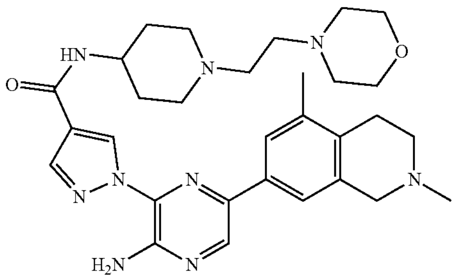
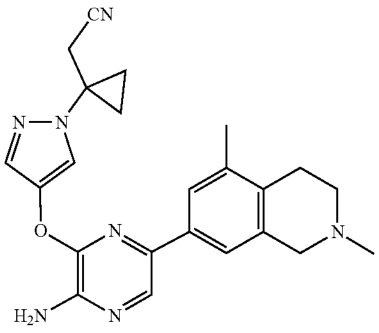
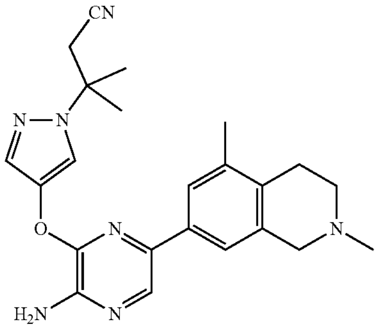

-continued
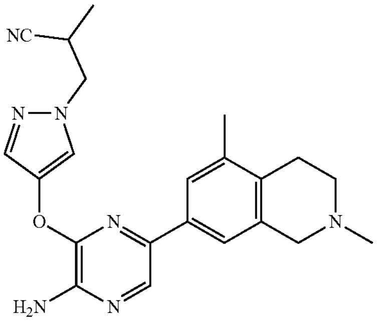
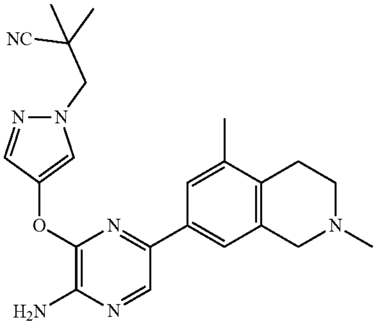
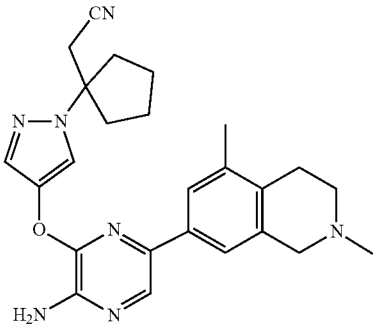
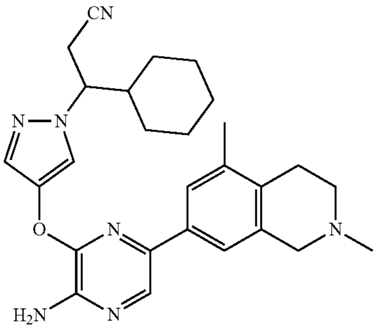
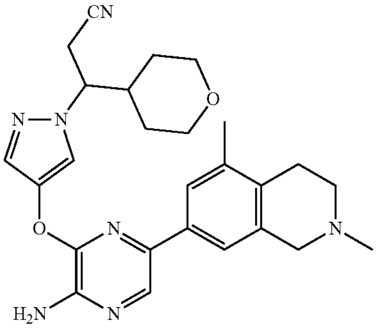
-continued
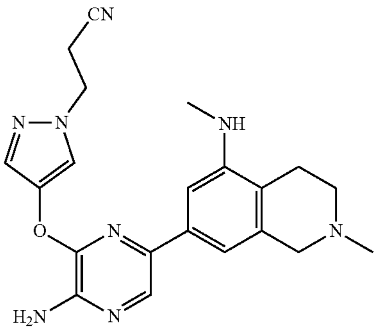
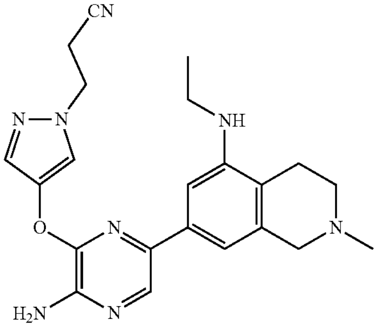
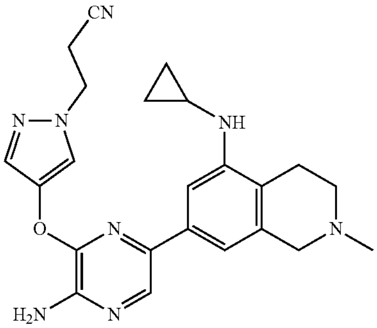
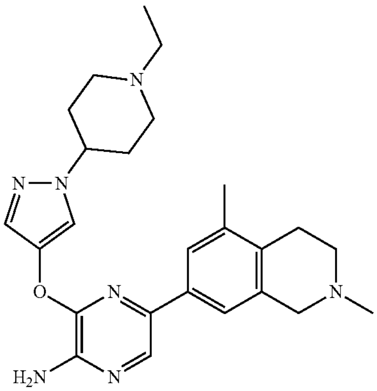

-continued
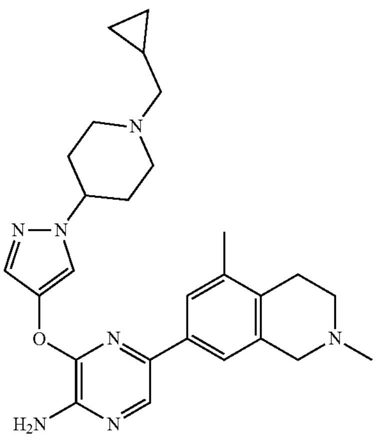
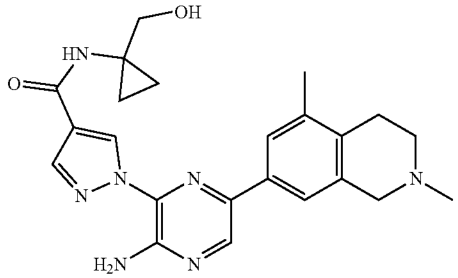
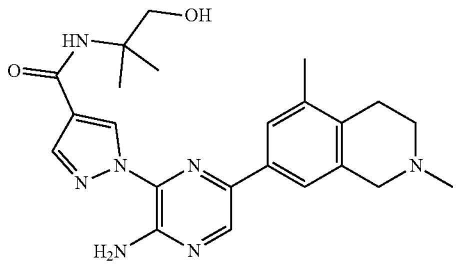
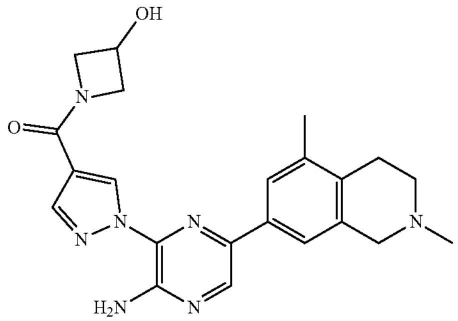
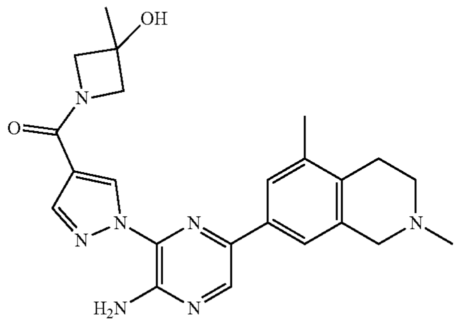
-continued
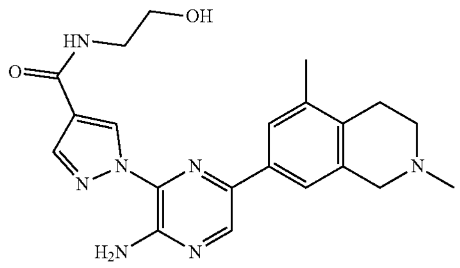
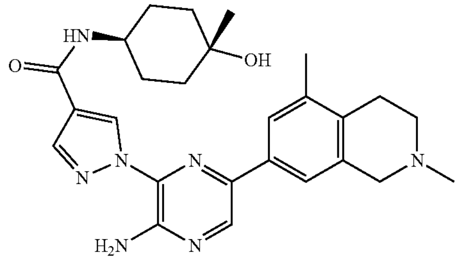
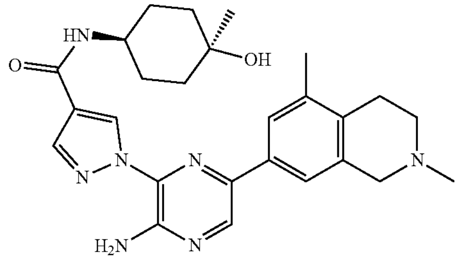
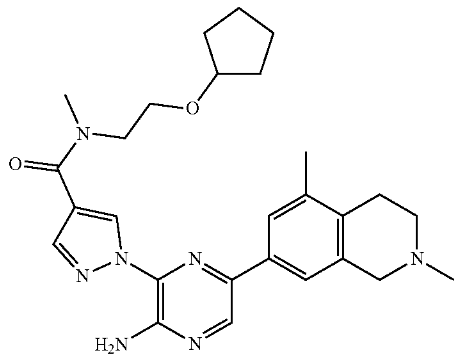
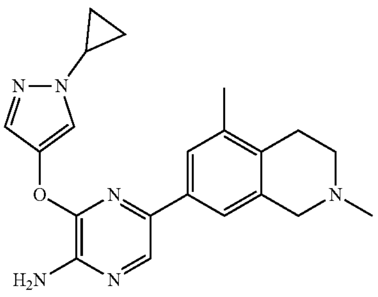

-continued

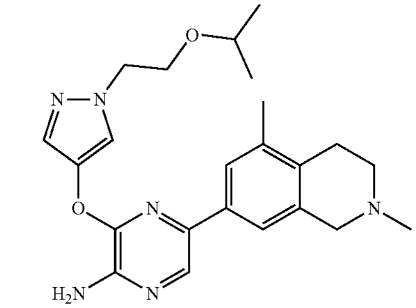

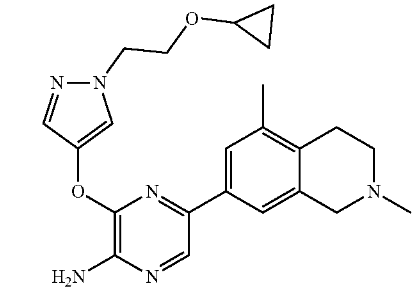

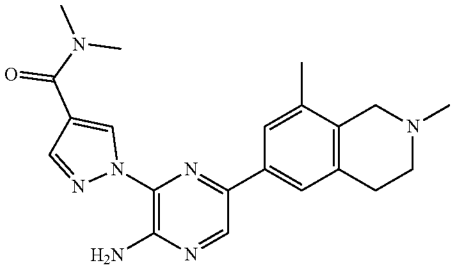

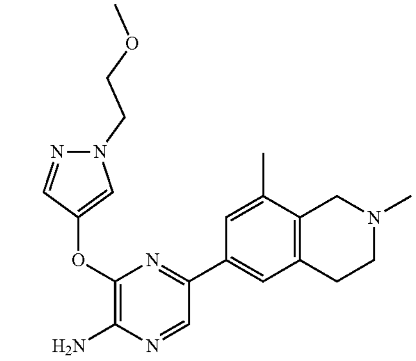

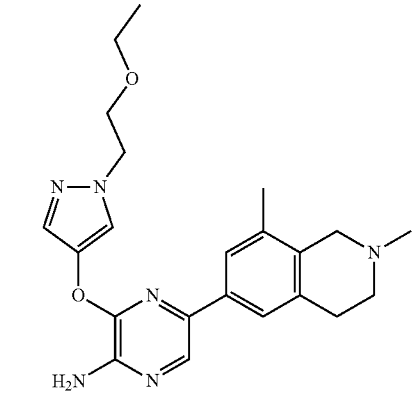

-continued

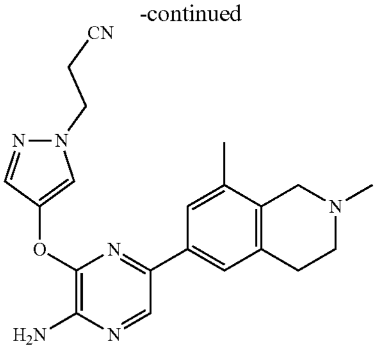

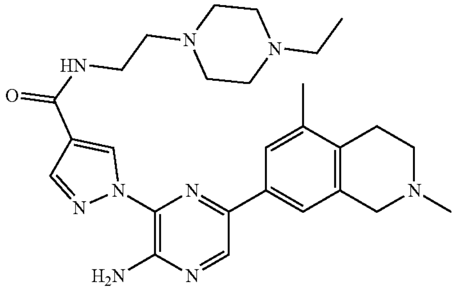

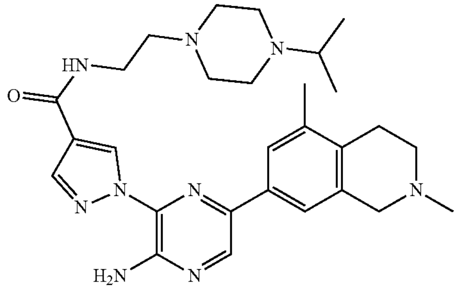

;

or a pharmaceutically acceptable salt thereof, or a stereoisomer thereof.

15. A pharmaceutical composition comprising the compound of claim 1 or a stereoisomer thereof, or a pharmaceutically acceptable salt thereof and a pharmaceutically acceptable excipient.

16. A method of treating cancer, comprising administering a subject in need thereof the compound of claim 1 or a stereoisomer thereof, or a pharmaceutically acceptable salt thereof.

17. The compound according to claim 12, wherein t=1 or 2; and each $R^4$ is independently selected from hydrogen, halogen, —$C_{1-8}$alkyl, —$C_{2-8}$alkynyl, cycloalkyl, heterocyclyl, oxo, —CN, —$OR^a$, —$CONR^aR^b$, —$NR^aCOR^b$, or —$NR^aR^b$, each of said —$C_{1-8}$alkyl, —$C_{2-8}$alkynyl, cycloalkyl or heterocyclyl is optionally substituted with at least one $R^d$.

18. The compound according to claim 17, wherein:

a) each $R^4$ is independently —$C_{1-8}$alkyl which is optionally substituted with at least one halogen or cyano;

b) each $R^4$ is independently cycloalkyl which is optionally substituted with cyano, —$C_{1-8}$alkyl or hydroxy;

c) each $R^4$ is heterocyclyl which is optionally substituted with halogen or —$C_{1-8}$alkyl;

d) each $R^4$ is —$C_{2-8}$alkynyl optionally substituted with at least one $R^d$; $R^d$ is each independently —$C_{1-8}$alkyl, cyclopropyl, cyclohexyl, aryl, pyridyl, pyrazlyl, or thiazolyl, —$SO_2R^f$ or —$CONR^fR^g$, each of said —$C_{1-8}$alkyl, cyclopropyl, cyclohexyl, aryl, pyridyl, pyrazlyl, or thiazolyl is optionally substituted with at least one substituent selected from halogen, —$C_{1-8}$alkyl, —$OR^i$, or —$NR^iR^j$; and $R^f$, $R^g$, $R^i$, and $R^j$ are each independently hydrogen or —$C_{1-8}$alkyl; or e) each $R^4$ is —$OR^a$, —$CONR^aR^b$, or —$NR^aR^b$, wherein $R^a$ and $R^b$ are each independently hydrogen, cycloalkyl, aryl, heterocyclyl, or —$C_{1-8}$alkyl which is optionally substituted with $R^e$; and $R^e$ is selected from cycloalkyl, aryl or heterocyclyl, each of cycloalkyl, aryl or heterocyclyl is optionally substituted with at least one —CO—$NR^iR^j$; and $R^i$, and $R^j$ are each independently hydrogen or —$C_{1-8}$alkyl; or wherein $R^a$ and $R^b$ together with the nitrogen atom to which they are attached, form a 3- to 12-membered ring, said ring comprising 0, 1 or 2 additional heteroatom(s) independently selected from nitrogen, oxygen or optionally oxidized sulfur as ring member(s), said ring is optionally substituted with at least one substituent $R^e$.

* * * * *